US008927576B2

(12) United States Patent
Gu

(10) Patent No.: US 8,927,576 B2
(45) Date of Patent: Jan. 6, 2015

(54) HCV INHIBITOR AND THERAPEUTIC AGENT COMBINATIONS

(75) Inventor: Zhengxian Gu, Princeton, NJ (US)

(73) Assignee: PTC Therpeutics, Inc., South Plainfield, NJ (US)

( * ) Notice: Subject to any disclaimer, the term of this patent is extended or adjusted under 35 U.S.C. 154(b) by 143 days.

(21) Appl. No.: 13/259,627

(22) PCT Filed: Apr. 6, 2010

(86) PCT No.: PCT/US2010/030077
§ 371 (c)(1),
(2), (4) Date: Sep. 23, 2011

(87) PCT Pub. No.: WO2010/118009
PCT Pub. Date: Oct. 14, 2010

(65) Prior Publication Data

US 2012/0027721 A1 Feb. 2, 2012

Related U.S. Application Data

(60) Provisional application No. 61/166,926, filed on Apr. 6, 2009.

(51) Int. Cl.

| | |
|---|---|
| ***A01N 43/42*** | (2006.01) |
| ***A61K 31/47*** | (2006.01) |
| ***A01N 43/38*** | (2006.01) |
| ***A61K 31/405*** | (2006.01) |
| ***C07D 215/00*** | (2006.01) |
| ***C07D 209/04*** | (2006.01) |
| ***C07F 9/572*** | (2006.01) |

(52) U.S. Cl.
CPC .................................... *C07F 9/5728* (2013.01)
USPC ............ 514/312; 514/415; 546/153; 548/469

(58) Field of Classification Search
USPC .................... 514/312, 415; 546/153; 548/469
See application file for complete search history.

(56) References Cited

U.S. PATENT DOCUMENTS

| | | | |
|---|---|---|---|
| 7,399,749 | B2 | 7/2008 | Arasappan et al. |
| 2005/0037018 | A1 | 2/2005 | Maertens et al. |
| 2007/0299069 | A1 | 12/2007 | Karp et al. |
| 2009/0068140 | A1 | 3/2009 | Bachand et al. |

FOREIGN PATENT DOCUMENTS

| | | | |
|---|---|---|---|
| WO | 0009543 | A2 | 2/2000 |
| WO | WO 02060926 | A2 * | 8/2002 |
| WO | WO 2006019831 | A1 * | 2/2006 |

OTHER PUBLICATIONS

Cole et. al., Journal of Medicinal Chemistry, 2003, American Chemical Society, vol. 46, pp. 207-209.*
Zhu et. al., Bioorganic and Medicinal Chemistry Letters, 2000, Pergamon, vol. 10, pp. 1121-1124.*
International Search Report for PCT/US10/30077 mailed Jun. 9, 2010.
Written Opinion for PCT/US10/30077 mailed Jun. 9, 2010.

* cited by examiner

*Primary Examiner* — Sarah Pihonak
(74) *Attorney, Agent, or Firm* — Hoffman & Baron, LLP

(57) ABSTRACT

The present invention is directed to a combination product for treating or ameliorating hepatitis C virus (HCV) infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

4 Claims, No Drawings

HCV INHIBITOR AND THERAPEUTIC AGENT COMBINATIONS

CROSS REFERENCE TO RELATED APPLICATIONS

This application is the National Stage of International Application No. PCT/US2010/030077, filed Apr. 5, 2010 which claims benefit of priority to provisional U.S. Ser. No. 61/166,926, filed Apr. 6, 2009, herein incorporated by reference in its entirety and for all purposes.

STATEMENT REGARDING FEDERALLY SPONSORED RESEARCH OR DEVELOPMENT

The research leading to the present invention was supported, at least in part, by grants from the National Institutes of Health (1R43AI054029010, 2R44AI054029020 and 5R44AI054029030). Accordingly, the Government may have certain rights in the invention.

FIELD OF THE INVENTION

The present invention is directed to a combination product for treating or ameliorating hepatitis C virus (HCV) infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

BACKGROUND OF THE INVENTION

HCV currently represents a major public health concern. The number of persons chronically infected with HCV in the world is estimated at 170 million to 200 million and hepatitis-C-related deaths at approximately 470 000 annually. Peak of incidence is expected to occur in 2025-2030 in developed countries.

HCV is a virus that has been implicated in progressive liver diseases such as fibrosis and cirrhosis of the liver and in induction of hepatocellular carcinoma, which are the prime reasons for liver transplants. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

The current standard of care for patients infected with the HCV genotype 1 is a combination of pegylated interferon alpha and ribavirin, a lengthy and often poorly tolerated therapy effective in 50% of patients that complete the therapy. In addition, a substantial number of patients never receive therapy.

Translation of the HCV RNA genome produces an approximately 3000 amino acid polyprotein that contains, from the amino terminus to the carboxy terminus, a nucleocapsid protein (C), envelope proteins (E1 and E2) and several non-structural proteins (P7, NS2, NS3, NS4a, NS4b, NS5a and NS5b).

The NS3 HCV protease necessary for polypeptide processing and viral replication has been identified, cloned and expressed. NS3 is an approximately 68 kda protein, encoded by approximately 1893 nucleotides of the HCV genome, and has two distinct domains: (a) a serine protease domain consisting of approximately 200 of the N-terminal amino acids; and (b) a RNA-dependent ATPase/helicase domain at the C-terminus of the protein.

The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA.

The HCV NS3 protease is responsible for proteolysis of the polypeptide (polyprotein) at the NS3/NS4a, NS4a/NS4b, NS4b/NS5a and NS5a/NS5b junctions and is thus responsible for generating five viral proteins during viral replication. This has made the HCV NS3 protease an attractive target for antiviral chemotherapy. Additionally, the NS4a protein, an approximately 6 kda polypeptide, has been determined to be a co-factor for the protease activity of NS3. Autocleavage of the NS3/NS4a junction by the NS3/NS4a protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys-Thr substitution at NS3/NS4a is postulated to account for the requirement of cis rather than trans processing at this junction (see, e.g., Pizzi et al., *Proc Natl Acad Sci* (*USA*), 1994, 91(3):888-892; Fulla et al., *Fold Des,* 1996, 1(1):35-42; Wang et al., *J Virol,* 2004, 78(2):700-709). The NS3/NS4a cleavage site is also more tolerant of mutagenesis than the other sites (see, e.g., Kolykhalov et al., *J Virol,* 1994, 68(11):7525-7533). It has also been found that acidic residues in the region upstream of the cleavage site are required for efficient cleavage (see, e.g., Komoda et al., *J Virol,* 1994, 68(11):7351-7357).

Thus, the conserved portions of the HCV RNA genome are likely targets for effective therapeutic intervention (see, e.g., McCaffrey et al., *Hepatology,* 2003, 38(2):503-508) using one or more HCV inhibitors.

Inhibitors of HCV protease that have been reported include antioxidants (see, International Patent Publication WO1998/14181), certain peptides and peptide analogs (see, International Patent Publication WO1998/17679, Landro et al., *Biochemistry,* 1997, 36(31):9340-9348; Ingallinella et al., *Biochemistry,* 1997, 37(25):8906-89 14; Llinas-Brunet et al., *Bioorg Med Chem Lett,* 1998, 8(13):1713-1718), inhibitors based on the 70-amino acid polypeptide eglin c (see, Martin et al., *Biochemistry,* 1998, 37(33):11459-11468), human pancreatic secretory trypsin (hPST1-C3) and minibody repertoire (MBip) inhibitors (see, Dimasi et al., *J Virol,* 1997, 71(10):7461-7469), antibodies and fragments thereof (such as $cV_HE2$, a "camelized" variable domain antibody fragment) (see, Martin et al., Protein Eng, 1997, 10(5):607-614) and α1-antichymotrypsin (ACT) (see, Elzouki et al., *J Hepat,* 1997, 27(1):42-48).

Combining various HCV protease inhibitors with an inhibitor of another target in the HCV life cycle including, but not limited to, HCV polymerase inhibitors, NS3 helicase or NS2/NS3 protease inhibitors as well as human immunodeficiency virus (HIV) and hepatitis B virus (HBV) inhibitors has been generally described.

U.S. patent application Ser. No. 12/281,022, filed Feb. 23, 2007 (having corresponding International Patent Application No. PCT/US2007/004721, filed Feb. 23, 2007) describes the use of certain indole and thienopyridine HCV inhibitor compounds and forms thereof in combination with at least one HCV protease inhibitor and, optionally at least one or more additional therapeutic agents, and is incorporated by reference herein in its entirety and for all purposes.

Additional HCV inhibitor compounds and forms thereof in combination with one or more anti-HCV agents have also been disclosed in U.S. patent application Ser. No. 11/653,450, filed Jan. 16, 2007 (having corresponding International Application No. PCT/US2007/00996, filed Jan. 16, 2007) and U.S. patent application Ser. No. 11/653,448, filed Jan. 16, 2007 (having corresponding International Application No. PCT/US2007/00923, filed Jan. 16, 2007), each of which is a continuation-in-part of U.S. patent application Ser. No. 11/331,180, filed Jan. 13, 2006, which is a continuation-in-part of U.S. patent application Ser. No. 11/180,961, filed Jul. 14, 2005 (having corresponding International Application No. PCT/US2005/024881, filed Jul. 14, 2005), each of which is incorporated herein by reference in their entirety and for all purposes.

United States Patent Publication 2006/0235028 discloses certain aryl and heteroaryl compounds as 11-beta-hydroxysteroid dehydrogenase type I inhibitors.

There continues to remain a strong need for new alternative approaches that work through multiple mechanisms of action, including combination products for use in treating or ameliorating HCV infection or disorders or symptoms associated therewith, and that modulate the processivity of viral replication and, in particular, the life cycle of the HCV polypeptide.

SUMMARY OF THE INVENTION

The present invention is directed to a combination product for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor or a pharmaceutically acceptable salt thereof disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which is incorporated herein by reference in their entirety and for all purposes.

In one embodiment, the HCV inhibitor is selected from a compound of the present invention or an enantiomer, stereoisomer, diastereomer, racemic, tautomeric, ester, prodrug, solvate, hydrate, isotopologue or salt form thereof.

Embodiments of the present invention include a HCV protease inhibitor selected from a NS2 protease inhibitor, a NS3 protease inhibitor, a peptide or dipeptide NS3 protease inhibitor or a NS4a protease cofactor inhibitor.

An embodiment of the present invention includes a HCV protease inhibitor selected from a HCV protease inhibitor of the present invention or an enantiomer, stereoisomer, diastereomer, racemic, tautomeric, ester, prodrug, solvate, hydrate, isotopologue or salt form thereof.

An embodiment of the present invention includes one or more different therapeutic agents selected from a HCV inhibitor, a HCV protease inhibitor, a nucleoside or non-nucleoside HCV polymerase inhibitor, a nonpegylated interferon, a pegylated interferon or another anti-HCV agent.

In one embodiment, one or more different HCV inhibitor therapeutic agents is selected from a HCV inhibitor compound of the present invention or a form thereof.

In one embodiment, one or more different HCV inhibitor therapeutic agents is selected from a HCV inhibitor other than a HCV inhibitor compound of the present invention or a form thereof.

In one embodiment, one or more different HCV protease inhibitor therapeutic agents is selected from a NS2 protease inhibitor, a NS3 protease inhibitor, a peptide or dipeptide NS3 protease inhibitor or a NS4a protease cofactor inhibitor.

In one embodiment, one or more different HCV protease inhibitor therapeutic agents is selected from a HCV protease inhibitor or a form thereof of the present invention.

In one embodiment, one or more different HCV protease inhibitor therapeutic agents is selected from a HCV protease inhibitor or a form thereof other than the HCV protease inhibitor or forms thereof of the present invention.

In one embodiment, one or more different nucleoside or non-nucleoside HCV polymerase inhibitor therapeutic agents selected from a NS5b polymerase inhibitor.

An embodiment of the present invention includes one or more different therapeutic agents selected from a NS4b inhibitor, NS5a inhibitor, IRES (internal ribosomal entry site) inhibitor, p7 inhibitor, entry inhibitor, fusion inhibitor, helicase inhibitor, ribavirin or a ribavirin analogue.

An embodiment of the present invention includes one or more different therapeutic agents selected from a Toll-like receptor (TLR) agonist, cyclophilin inhibitor, caspase or pan-caspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH (inosine monophosphate dehydrogenase) inhibitor, glycosidase inhibitor, glucosidase inhibitor, HCV therapeutic vaccine, A3 adenosine receptor (AR) agonist, polypeptide eglin c analog inhibitor, human pancreatic secretory trypsin and minibody repertoire inhibitor or a monoclonal antibody and fragment thereof.

Additional embodiments of the present invention include one or more different therapeutic agents selected from a HIV inhibitor, HBV inhibitor, RNA inhibitor, RNAi, anti-phospholipid therapy, protein therapeutic, botanical or non-specific pharmaceutical.

An embodiment of the present invention includes one or more different therapeutic agents selected from ribavirin and at least one or more of a nonpegylated interferon or a pegylated interferon.

The present invention is also directed to a method for treating or ameliorating HCV infection or disorders or symptoms associated therewith in a subject in need thereof comprising, administering an effective amount of a combination product to the subject, wherein the combination product is a HCV inhibitor and one or more therapeutic agents selected from either or both a HCV protease inhibitor and one or more different therapeutic agents administered in combination to the subject.

An embodiment of the present invention includes the use of a combination product comprising, a HCV inhibitor and one or more therapeutic agents selected from either or both a HCV protease inhibitor and one or more different therapeutic agents in the preparation of a medicament, pharmaceutical composition or pharmaceutical kit for treating or ameliorating HCV infection or disorders or symptoms associated therewith in a subject in need thereof.

DETAILED DESCRIPTION OF THE INVENTION

The present invention is directed to a combination product for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor or a pharmaceutically acceptable salt thereof disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which is incorporated herein by reference in their entirety and for all purposes.

In one embodiment, a representative HCV inhibitor is a compound of Formula (I):

(I)

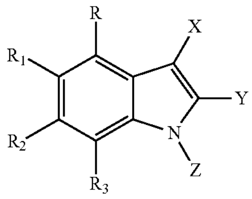

wherein:

X is:

-hydrogen;

-nitro;

-cyano;

—$COR_a$, where $R_a$ is:

- —$C_1$ to $C_6$ alkyl,
- —$C_3$ to $C_8$ cycloalkyl,
- -aryl optionally substituted with $C_1$ to $C_6$ alkoxy or halogen, or
- -di-$C_1$ to $C_6$ alkyl-amino;

—$COOR_x$, where $R_x$ is $C_1$ to $C_6$ alkyl or $C_3$ to $C_8$ cycloalkyl;

-formyl;

-aryl optionally substituted with $C_1$ to $C_6$ alkoxy; or

-5 or 6-membered heteroaryl optionally substituted with:

- —$C_1$ to $C_6$ alkyl,
- —$C_3$ to $C_8$ cycloalkyl,
- -aryl optionally substituted with $C_1$ to $C_6$ alkoxy or one or more halogen substituents, or

- -5 to 6 membered heteroaryl;

Y is:

-hydrogen;

—$C_1$ to $C_6$ haloalkyl;

-halogen;

-amino optionally substituted with one or more $C_1$ to $C_6$ alkyl or $C_3$ to $C_8$ cycloalkyl substituents;

-benzofuran;

-benzothiophene;

-dibenzofuran;

-dibenzothiophene;

-benzothiazole;

-naphthalene;

-indole, optionally substituted on the nitrogen with $C_1$ to $C_6$ alkyl or $C_3$ to $C_8$ cycloalkyl;

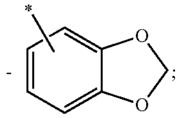

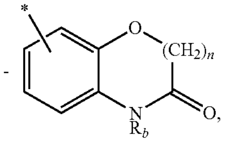

where $R_b$ is hydrogen, $C_1$ to $C_6$ alkyl or $C_3$ to $C_8$ cycloalkyl, and n is 0 or 1;

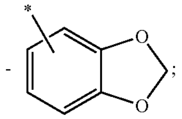

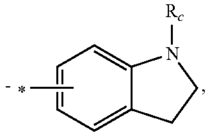

where $R_c$ is hydrogen, —$CONHR_x$, where $R_x$ is as defined above, or —$SO_2R_x$, where $R_x$ is as defined above;

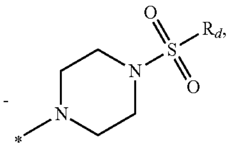

where $R_d$ is $C_1$ to $C_6$ alkyl, $C_3$ to $C_8$ cycloalkyl or aryl;

—$NHCOR_e$, where $R_e$ is:

- —$C_1$ to $C_6$ alkyl;
- —$C_3$ to $C_8$ cycloalkyl;
- -aryl optionally substituted with:
  - —$C_1$ to $C_6$ alkyl,
  - —$C_3$ to $C_8$ cycloalkyl,
  - —$C_1$ to $C_6$ alkoxy,
  - -cyano,
  - -nitro, or
  - -halogen;

—$NHCOOR_x$, where $R_x$ is as defined above;

—$CH_2O$—$R_f$, where $R_f$ is aryl;

—$NR_gR_h$, where $R_g$ is $C_1$ to $C_6$ alkyl, $C_3$ to $C_8$ cycloalkyl or hydrogen and $R_h$ is aryl optionally substituted with $C_1$ to $C_6$ alkoxy;

—$C_1$ to $C_6$ alkyl;

—$C_3$ to $C_8$ cycloalkyl;

-5 or 6 membered heteroaryl, optionally substituted with:

- —$C_1$ to $C_6$ alkyl, optionally substituted with aryl,
- —$C_3$ to $C_8$ cycloalkyl, optionally substituted with aryl,
- -aryl, optionally substituted with —$COOR_x$, where $R_x$ is as defined above, or -amino;

-5 or 6 membered heterocycle optionally substituted with:

- —$COOR_x$, where $R_x$ is as defined above, or
- —$NHCOOR_x$, where $R_x$ is as defined above;

-aryl, optionally substituted with one or more of the following:
—$C_1$ to $C_6$ alkoxy, optionally substituted with:
—$C_1$ to $C_6$ alkoxy,
-hydroxy,
-one or more halogen substituents,
-5 or 6 membered heterocycle, optionally substituted with:
—$C_1$ to $C_6$ alkyl,
—$C_3$ to $C_8$ cycloalkyl, or
-hydroxy,
-amino optionally substituted with one or more $C_1$ to $C_6$ alkyl or $C_3$ to $C_8$ cycloalkyl substituents,
—$NR_iSO_2R_x$, where $R_x$ is as defined above and $R_i$ is:
-hydrogen,
—$C_1$ to $C_6$ alkyl,
—$C_3$ to $C_8$ cycloalkyl,
—$COR_x$, where $R_x$ is as defined above,
—$C_1$ to $C_6$ haloalkyl, or
—$C_1$ to $C_6$ haloalkoxy,
—$NR_jCOR_k$, where $R_k$ is:
—$C_1$ to $C_6$ alkyl,
—$C_3$ to $C_8$ cycloalkyl,
-hydrogen, or
-amino optionally substituted with one or more $C_1$ to $C_6$ alkyl or $C_3$ to $C_8$ cycloalkyl substituents,
and $R_j$ is:
-hydrogen,
—$C_1$ to $C_6$ alkyl,
—$C_3$ to $C_8$ cycloalkyl,
—$COR_x$, where $R_x$ is as defined above,
—$C_1$ to $C_6$ haloalkyl, or
—$C_1$ to $C_6$ haloalkoxy,
—$N{=}N^+{=}N^-$, or
—$COR_l$, where $R_l$ is 5 or 6 membered heterocycle optionally substituted with hydroxy,
-amino optionally substituted with one or more $C_1$ to $C_6$ alkyl or $C_3$ to $C_8$ cycloalkyl substituents,
-nitro,
—$C_1$ to $C_6$ alkyl, optionally substituted with:
—$NHSO_2R_x$, where $R_x$ is as defined above, or
—$NR_xSO_2R_x$, where $R_x$ is as defined above,
—$C_3$ to $C_8$ cycloalkyl, optionally substituted with:
—$NHSO_2R_x$, where $R_x$ is as defined above, or
—$NR_xSO_2R_x$, where $R_x$ is as defined above,
—$C_1$ to $C_6$ haloalkoxy,
-halogen,
-hydroxy,
—$COOR_x$, where $R_x$ is as defined above,
—$COR_m$, where $R_m$ is:
-amino optionally substituted with one or more $C_1$ to $C_6$ alkyl or $C_3$ to $C_8$ cycloalkyl substituents, where the $C_1$ to $C_6$ alkyl or $C_3$ to $C_8$ cycloalkyl substituents are optionally substituted with:
-hydroxy
-5 or 6 membered heterocycle,
-amino optionally substituted with one or more $C_1$ to $C_6$ alkyl or $C_3$ to $C_8$ cycloalkyl substituents,
—$C_1$ to $C_6$ alkoxy,
-3 to 7 membered heterocycle, optionally substituted with $C_1$ to $C_6$ alkyl, optionally substituted with di-$C_1$ to $C_6$ alkyl-amino,
-3 to 7 membered heterocycle, optionally substituted with $C_3$ to $C_8$ cycloalkyl, optionally substituted with di-$C_1$ to $C_6$ alkyl-amino, —$NHR_n$, where $R_n$ is:
—$CH_2CONH_2$, or
-aryl optionally substituted with:
—$C_1$ to $C_6$ alkyl,
—$C_3$ to $C_8$ cycloalkyl,
-one or more halogen substituents,
-nitro, or
-one or more $C_1$ to $C_6$ alkoxy substituents,
—$NR_oCOR_p$, where $R_p$ is:
—$C_1$ to $C_6$ alkyl or $C_3$ to $C_8$ cycloalkyl optionally substituted with:
-halogen,
—$C_1$ to $C_6$ alkoxy, or
-aryl,
-5 or 6 membered heterocycle,
-aryl, optionally substituted with halogen,
-5 or 6 membered heteroaryl optionally substituted with one or more $C_1$ to $C_6$ alkyl or $C_3$ to $C_8$ cycloalkyl substituents,
-hydrogen,

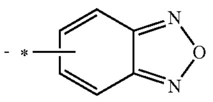
or
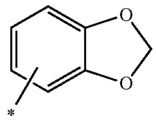
, and where $R_o$ is:
-hydrogen,
—$C_1$ to $C_6$ alkyl,
—$C_3$ to $C_8$ cycloalkyl,
—$COR_x$, where $R_x$ is as defined above,
—$C_1$ to $C_6$ haloalkyl, or
—$C_1$ to $C_6$ haloalkoxy,
—$NR_qCONR_qR_r$, where $R_q$ is:
-hydrogen,
—$C_1$ to $C_6$ alkyl,
—$C_3$ to $C_8$ cycloalkyl
—$C_1$ to $C_6$ haloalkyl,
—$C_1$ to $C_6$ haloalkoxy, or
—$COR_x$, where $R_x$ is as defined above,
and where $R_r$ is:
-aryl optionally substituted with:

-
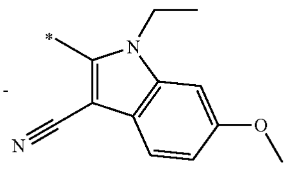
,

—$C_1$ to $C_6$ alkyl,
—$C_3$ to $C_8$ cycloalkyl,
—$C_1$ to $C_6$ haloalkyl,
—$OR_s$, where $R_s$ is aryl, or
—$COOR_x$, where $R_x$ is as defined above,
—$C_1$ to $C_6$ alkyl or $C_3$ to $C_8$ cycloalkyl optionally substituted with one or more of the following:
-halogen,
—$C_2$ to $C_6$ alkenyl,
-aryl, or
—$COOR_x$, where $R_x$ is as defined above,
—$COOR_x$, where $R_x$ is as defined above, —$NR_tCOOR_u$, where $R_u$ is:
- —$C_1$ to $C_{12}$ alkyl or $C_3$ to $C_8$ cycloalkyl, optionally substituted with:
  - -aryl optionally substituted with $C_1$ to $C_6$ alkyl, $C_3$ to $C_8$ cycloalkyl or $C_1$ to $C_6$ alkoxy,
  - —$C_2$ to $C_6$ alkenyl,
  - —$C_1$ to $C_6$ alkoxy,
  - -alkynyl,
  - -halogen, or
  - -5 or 6 membered heterocycle,
- -aryl, optionally substituted with:
  - —$C_1$ to $C_6$ alkoxy,
  - -halogen,
  - —$C_1$ to $C_6$ alkyl, or
  - —$C_3$ to $C_8$ cycloalkyl, or
- -5 or 6 membered heterocycle, and $R_t$ is:
- -hydrogen,
- —$C_1$ to $C_6$ alkyl,
- —$C_3$ to $C_8$ cycloalkyl,
- —$COR_x$, where $R_x$ is as defined above,
- —$C_1$ to $C_6$ haloalkyl, or
- —$C_1$ to $C_6$ haloalkoxy, —$NR_vSO_2R_w$, where $R_v$ is:
- -hydrogen,
- —$COR_x$, where $R_x$ is as defined above, or
- —$C_1$ to $C_6$ alkyl or $C_3$ to $C_8$ cycloalkyl, optionally substituted with:
  - -halogen,
  - —$COR_x$, where $R_x$ is as defined above,
  - —$OCOR_x$, where $R_x$ is as defined above,
  - -hydroxyl, or
  - —$C_1$ to $C_6$ alkoxy, and where $R_w$ is:
- —$C_1$ to $C_6$ alkyl or $C_3$ to $C_8$ cycloalkyl optionally substituted with:
  - -halogen,
  - —$C_1$ to $C_6$ haloalkyl,
  - -aryl, or
  - -5 or 6 membered heterocycle,
- —$C_2$ to $C_6$ alkenyl,
- —$C_1$ to $C_6$ alkyl- or di-$C_1$ to $C_6$ alkyl-amino optionally substituted with halogen,
- -5 or 6 membered heterocycle, or
- -5 or 6 membered heteroaryl optionally substituted with:
  - —$C_1$ to $C_6$ alkyl,
  - —$C_3$ to $C_8$ cycloalkyl,
  - -5 or 6 membered heterocycle, or

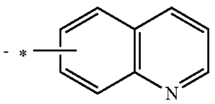

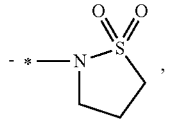

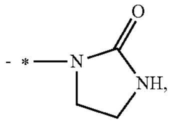

-continued

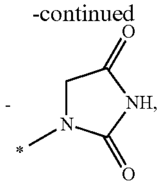

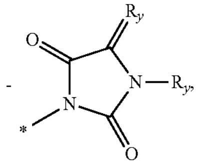

optionally substituted with $C_1$ to $C_6$ alkyl or $C_3$ to $C_8$ cycloalkyl, where $R_y$ is $C_1$ to $C_6$ alkyl, $C_3$ to $C_8$ cycloalkyl or hydrogen,

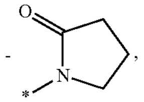

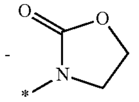

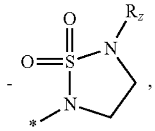

where $R_z$ is hydrogen, $C_1$ to $C_6$ alkyl or $C_3$ to $C_8$ cycloalkyl, where the $C_1$ to $C_6$ alkyl or $C_3$ to $C_8$ cycloalkyl substituents are optionally substituted with aryl,
- —$SR_x$, where $R_x$ is as defined above,
- —$SO_2R_{aa}$, where $R_{aa}$ is:
  - —$C_1$ to $C_6$ alkyl,
  - —$C_3$ to $C_8$ cycloalkyl,
  - -amino,
  - —$C_1$ to $C_6$ alkyl- or di-$C_1$ to $C_6$ alkyl-amino optionally substituted with hydroxy or —$COOR_x$, where $R_x$ is as defined above,
  - -5 or 6 membered heteroaryl,
  - -aryl, or
  - —$NHR_{bb}$, where $R_{bb}$ is:

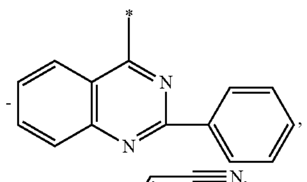

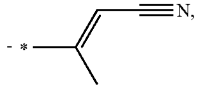

- —C(═S)$NH_2$, or
- —$PO(OR_x)_2$, where $R_x$ is as defined as above;

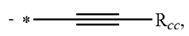

where $R_{cc}$ is:
- -naphthalene,
- -5 or 6 membered heteroaryl,

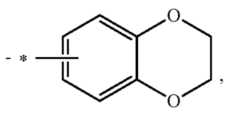

- -aryl, optionally substituted with one or more of the following:
  - —$C_1$ to $C_6$ alkoxy,
  - -hydroxy,
  - -halogen,
  - —$C_1$ to $C_6$ alkyl, optionally substituted with cyano,
  - —$C_3$ to $C_8$ cycloalkyl, optionally substituted with cyano,
  - -amino optionally substituted with one or more $C_1$ to $C_6$ alkyl or $C_3$ to $C_8$ cycloalkyl substituents,
  - —$NHPOR_xR_x$, where $R_x$ is as defined above,
  - —$NR_{ee}CONR_{ff}R_{ff}$, where $R_{ee}$ is hydrogen, $C_1$ to $C_6$ alkyl or $C_3$ to $C_8$ cycloalkyl, where the $C_1$ to $C_6$ alkyl or $C_3$ to $C_8$ cycloalkyl substituents are optionally substituted with halogen, and $R_{ff}$ is:
    - -hydrogen,
    - —$C_1$ to $C_6$ haloalkyl,
    - —$C_1$ to $C_6$ haloalkoxy,
    - —$C_1$ to $C_6$ alkyl,
    - —$C_3$ to $C_8$ cycloalkyl, or
    - —$COR_x$, where $R_x$ is as defined above,
  - —$NR_{gg}COR_{hh}$, where $R_{hh}$ is:
    - -hydrogen,
    - —$C_1$ to $C_6$ alkyl or $C_3$ to $C_8$ cycloalkyl, where the $C_1$ to $C_6$ alkyl or $C_3$ to $C_8$ cycloalkyl substituents are optionally substituted with:
      - —$C_1$ to $C_6$ alkoxy,
      - -halogen, or
      - -amino optionally substituted with one or more $C_1$ to $C_6$ alkyl or $C_3$ to $C_8$ cycloalkyl substituents,
    - -amino optionally substituted with one or more $C_1$ to $C_6$ alkyl or $C_3$ to $C_8$ cycloalkyl substituents, where alkyl or cycloalkyl is optionally substituted with halogen,
    - -5 or 6 membered heterocycle,
    - -5 or 6 membered heteroaryl,
  - and $R_{gg}$ is:
    - -hydrogen,
    - —$C_1$ to $C_6$ alkyl,
    - —$C_3$ to $C_8$ cycloalkyl,
    - —$C_1$ to $C_6$ haloalkyl,
    - —$C_1$ to $C_6$ haloalkoxy, or
    - —$COR_x$, where $R_x$ is as defined above,
  - —$C_1$ to $C_6$ haloalkyl,
  - -5 or 6 membered heterocycle,
  - -amino optionally substituted with one or more $C_1$ to $C_6$ alkyl or $C_3$ to $C_8$ cycloalkyl substituents,
  - —$NR_{ii}SO_2R_x$, where $R_x$ is as defined above, and $R_{ii}$ is:
    - -hydrogen,
    - —$C_1$ to $C_6$ alkyl,
    - —$C_3$ to $C_8$ cycloalkyl,
    - —$C_1$ to $C_6$ haloalkyl,
    - —$C_1$ to $C_6$ haloalkoxy,
    - —$COR_x$, where $R_x$ is as defined above;

Z is:
- -hydrogen;
- —$C_1$ to $C_6$ alkyl or $C_3$ to $C_8$ cycloalkyl optionally substituted with:
  - —$C_1$ to $C_6$ alkoxy,
  - -one or more halogen substituents, or
  - -aryl;
- —$C_2$ to $C_6$ alkenyl;
- -aryl optionally substituted with $C_1$ to $C_6$ alkoxy or one or more $C_1$ to $C_6$ alkyl or $C_3$ to cycloalkyl substituents;
- —$COOR_x$, where $R_x$ is as defined above; or

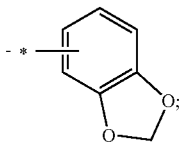

R is hydrogen, halogen or $C_1$ to $C_6$ alkoxy;

$R_1$ is:
- -hydrogen;
- -hydroxy;
- -halogen;
- —$C_1$ to $C_6$ haloalkyl;
- -nitro;
- -5 or 6 membered heteroaryl;
- -5 or 6 membered heterocycle;
- —$C_1$ to $C_6$ alkoxy optionally substituted with:
  - -one or more halogen substituents,
  - -aryl, or
  - -5 or 6 membered heterocycle;
- -aryl optionally substituted with $C_1$ to $C_6$ alkoxy;
- —$COR_x$, where $R_x$ is as defined above;
- —$C_1$ to $C_6$ alkyl or $C_3$ to $C_8$ cycloalkyl, where the $C_1$ to $C_6$ alkyl or $C_3$ to $C_8$ cycloalkyl substituents are optionally substituted with di-$C_1$ to $C_6$ alkyl-amino or 5 or 6 membered heterocycle; or $R_1$ joins together with $R_2$ to form:

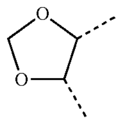 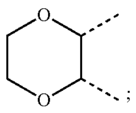 ;

$R_2$ is:
- -nitro;
- -hydrogen;
- -halogen;
- -hydroxy;
- —$C_1$ to $C_6$ alkyl or $C_3$ to $C_8$ cycloalkyl, where the $C_1$ to $C_6$ alkyl or $C_3$ to $C_8$ cycloalkyl substituents are optionally substituted with one or more halogen substituents;
- -amino;
- —$C_1$ to $C_6$ alkoxy optionally substituted with:
  - -one or more halogen substituents,
  - —$OCOR_x$, where $R_x$ is as defined above,
  - -di-$C_1$ to $C_6$ alkyl-amino optionally substituted with $C_1$ to $C_6$ alkoxy,
  - -5 or 6 membered heterocycle optionally substituted with $C_1$ to $C_6$ alkyl or $C_3$ to $C_8$ cycloalkyl, -5 or 6 membered heteroaryl, or -aryl;

—$COOR_x$, where $R_x$ is as defined above;

—$C_1$ to $C_6$ haloalkyl;

-amide optionally substituted with:

-hydroxy, or

-aryl;

-5 or 6 membered heteroaryl;

—$OCOR_x$, where $R_x$ is as defined above;

—$NHCOR_{jj}$, where $R_{jj}$ is:

—$C_1$ to $C_6$ alkoxy, or

-amino optionally substituted with one or more $C_1$ to $C_6$ alkyl or $C_3$ to $C_8$ cycloalkyl substituents;

—$OR_{kk}$, where $R_{kk}$ is 5 to 6 membered heteroaryl;

—$NHSO_2R_x$, where $R_x$ is as defined above; or $R_2$ joins together with $R_1$ to form:

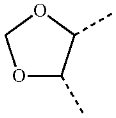

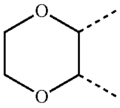

; and, $R_3$ is:

-hydrogen; or

—$CH_2OCOR_x$, and $R_x$, is as defined above, or an enantiomer, stereoisomer, diastereomer, racemic, tautomeric, ester, prodrug, solvate, hydrate, isotopologue or salt form thereof.

In one embodiment, a representative HCV inhibitor is a compound selected from:

1

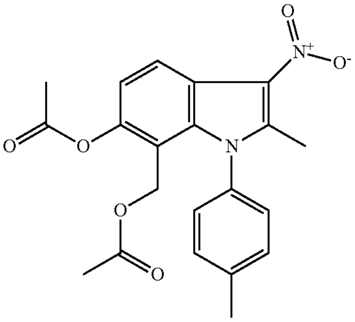

2

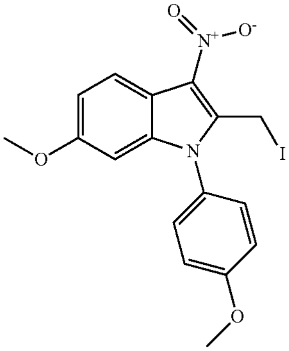

-continued

3

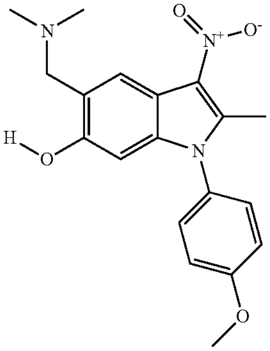

4

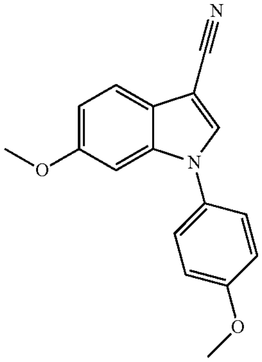

5

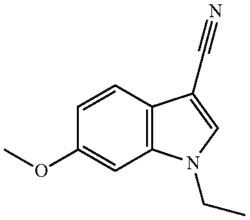

6

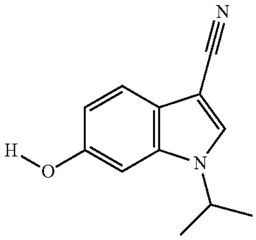

7

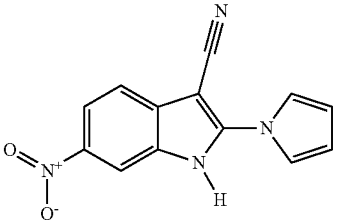

-continued
8
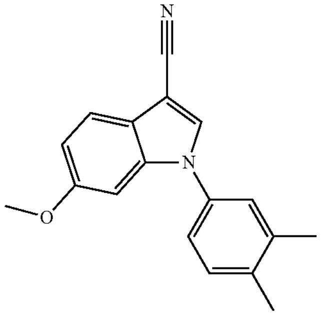
9
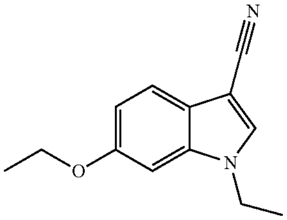
10
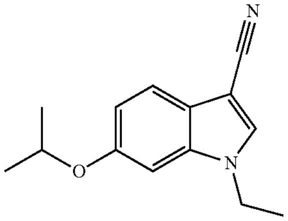
11
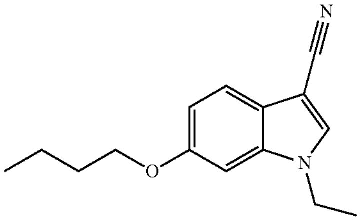
12
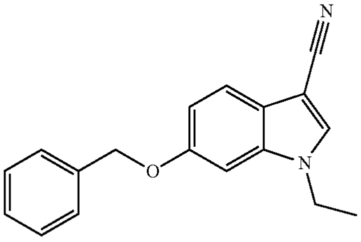
13
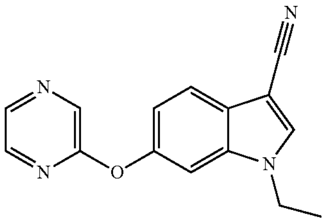
-continued
14
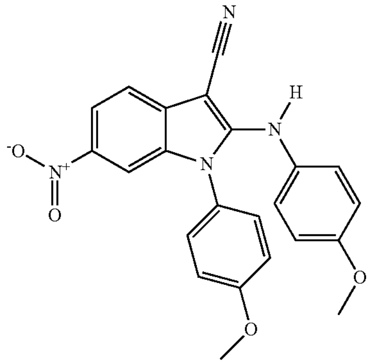
15
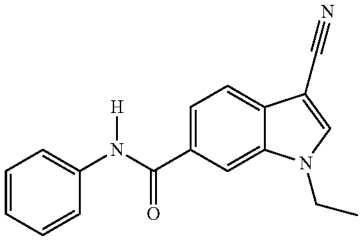
16
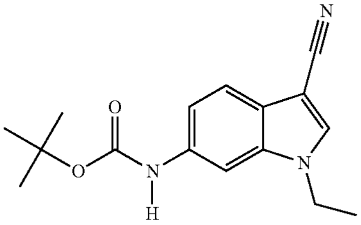
17
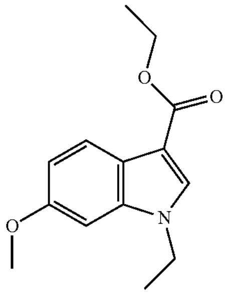
18
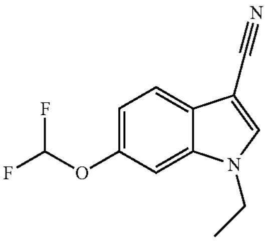
19
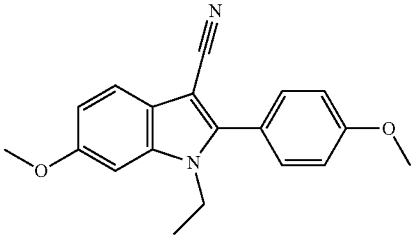

-continued
20
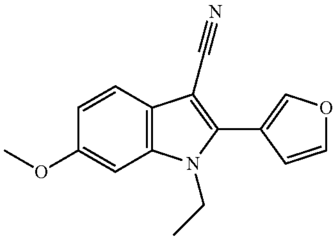
21
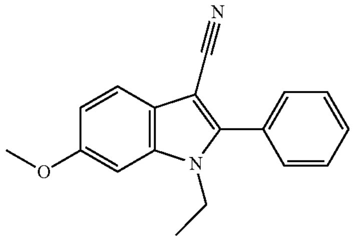
22
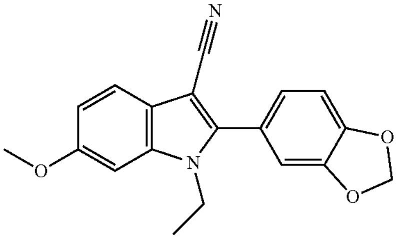
23
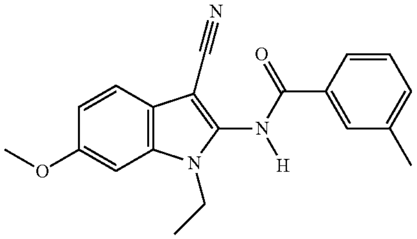
24
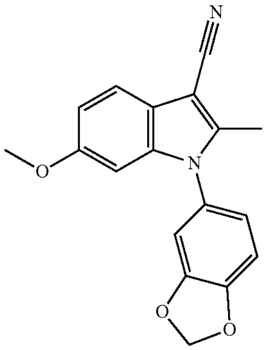
25
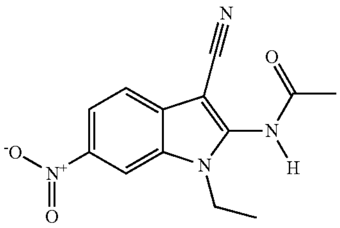
-continued
26
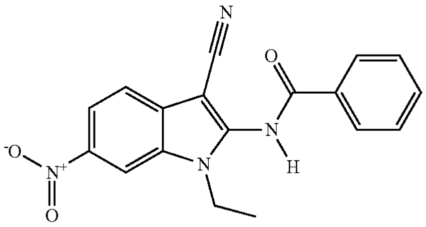
27
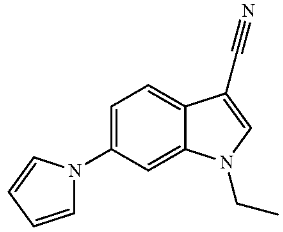
28
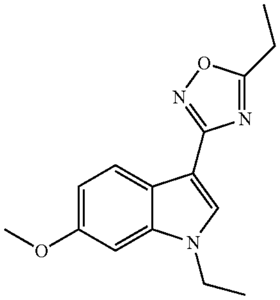
29
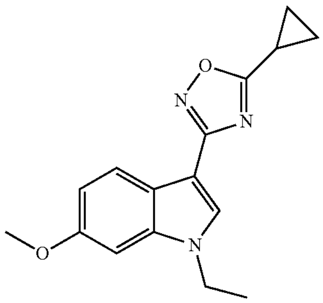
30
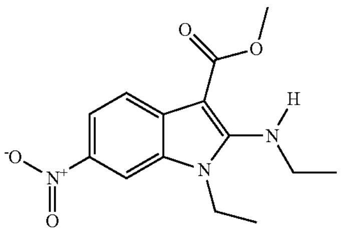
31
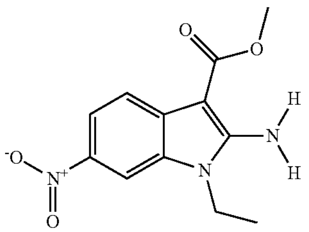

-continued
32
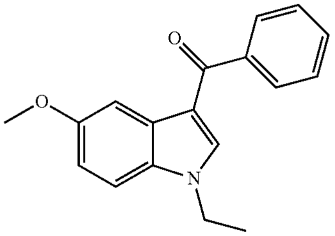
33
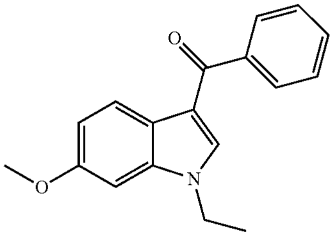
34
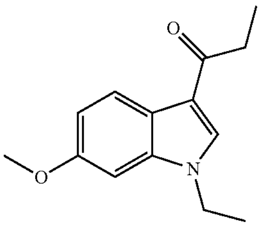
35
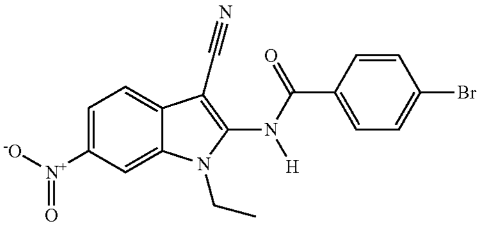
36
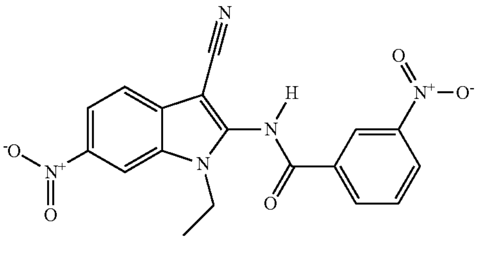
37
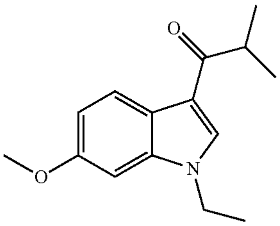
-continued
38
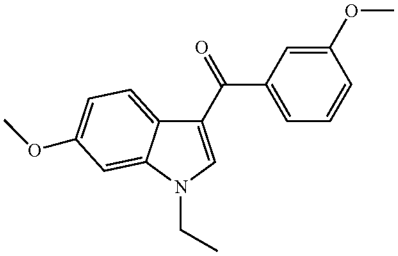
39
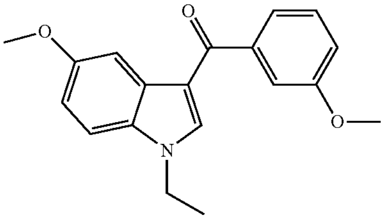
40
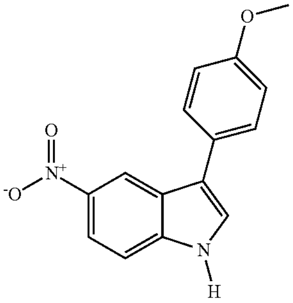
41
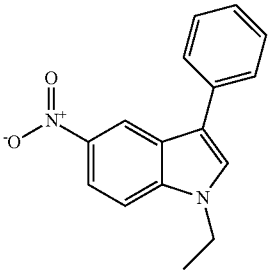
42
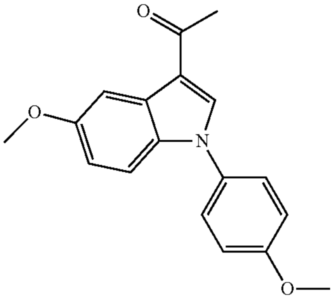
43
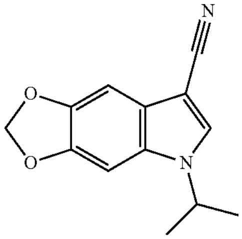

-continued
44
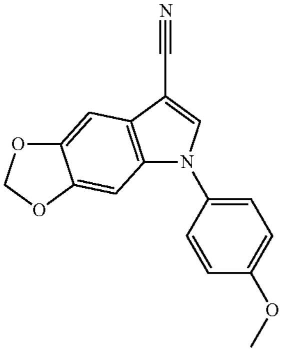
45
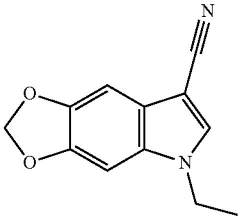
46
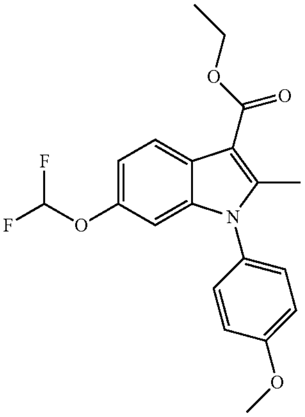
47
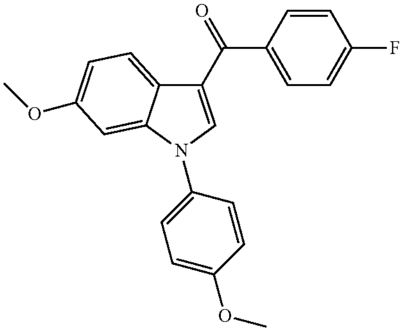
48
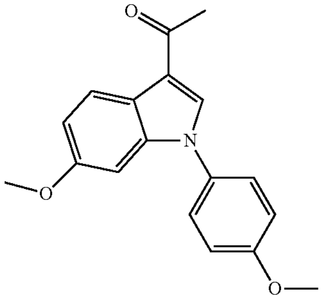
-continued
49
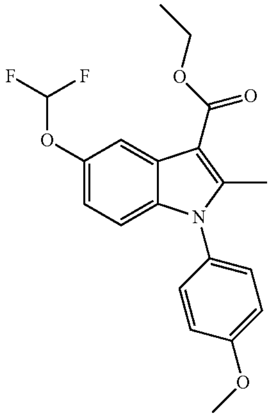
50
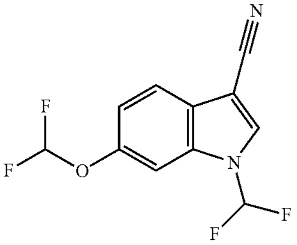
51
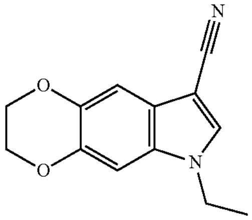
52
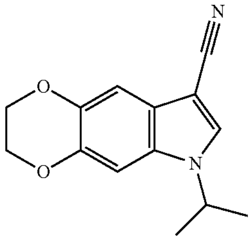
53
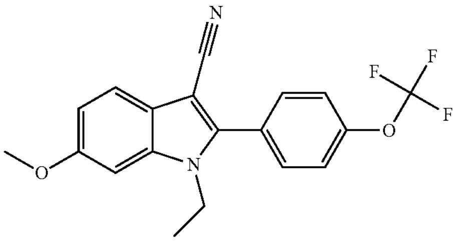

-continued
54
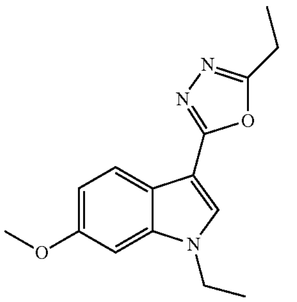
55
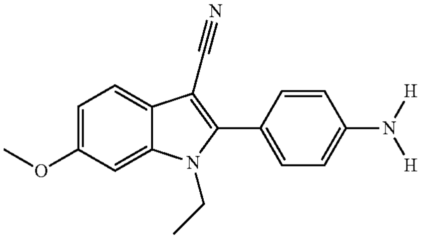
56
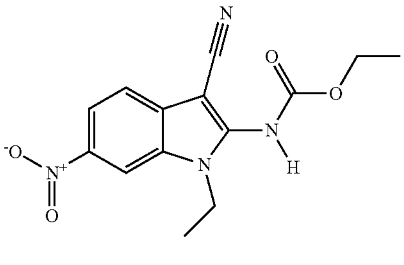
57
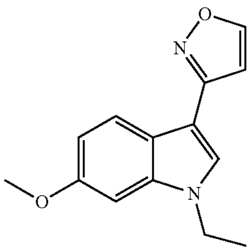
58
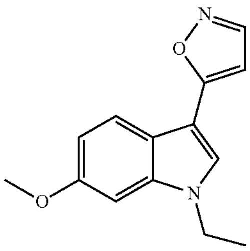
59
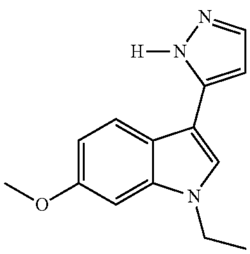
-continued
60
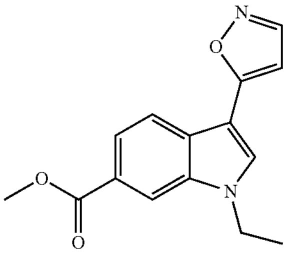
61
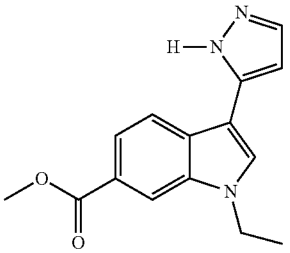
62
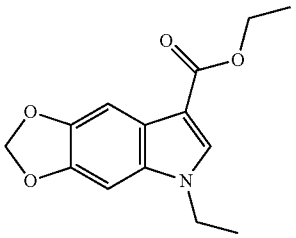
63
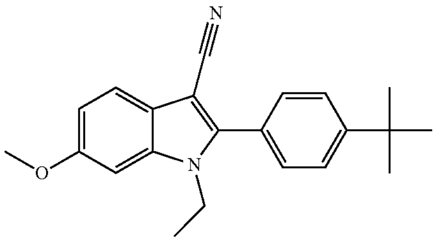
64
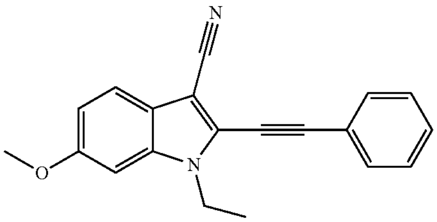
65
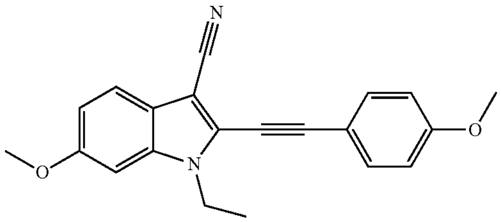

-continued
66
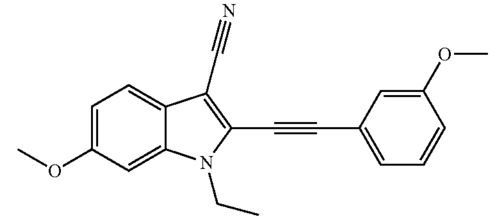
67
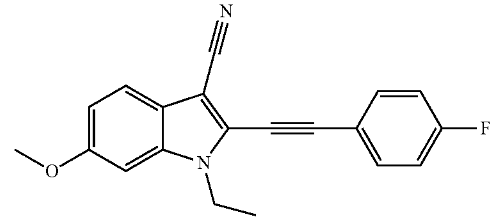
68
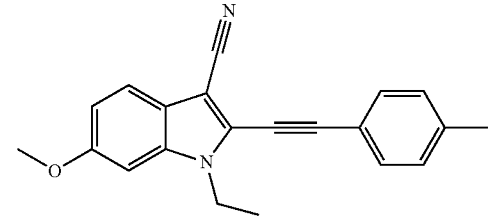
69
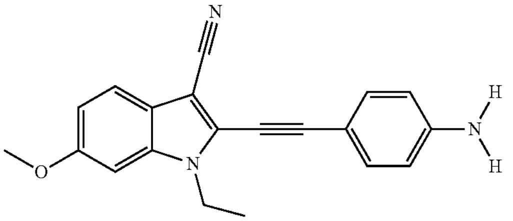
70
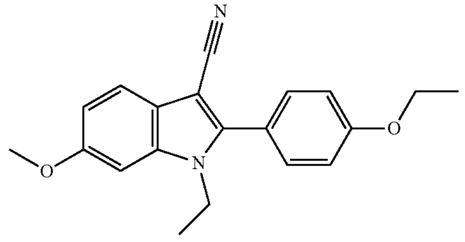
71
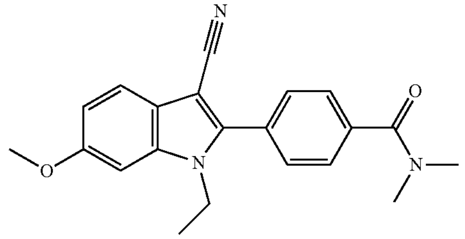
-continued
72
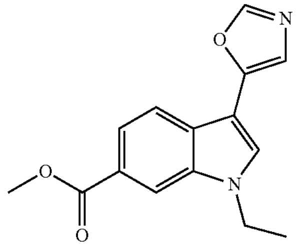
73
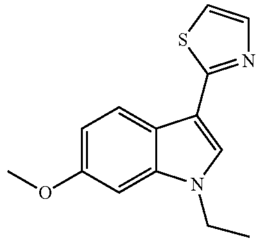
74
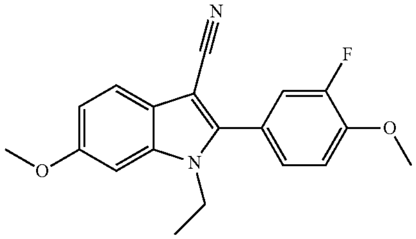
75
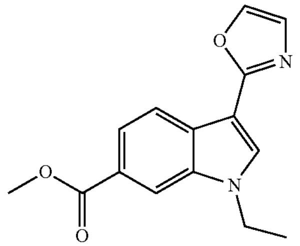
76
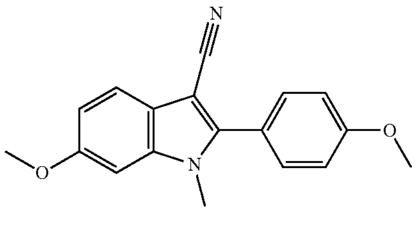
77
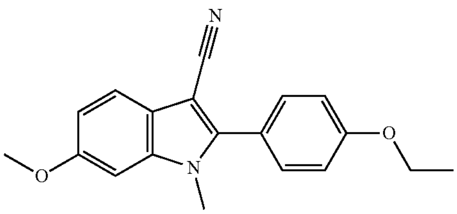

-continued
78
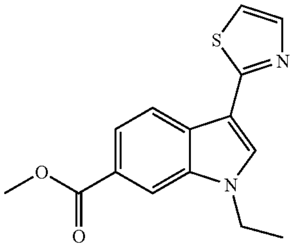
79
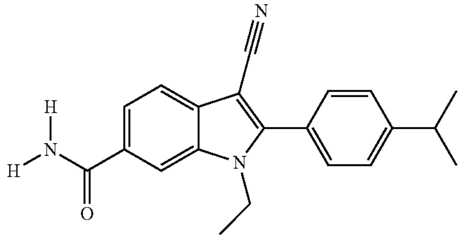
80
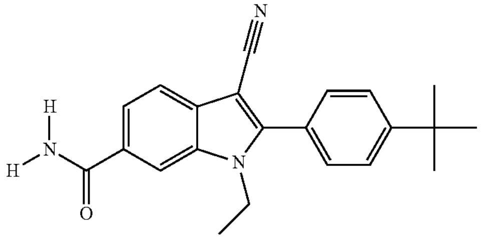
81
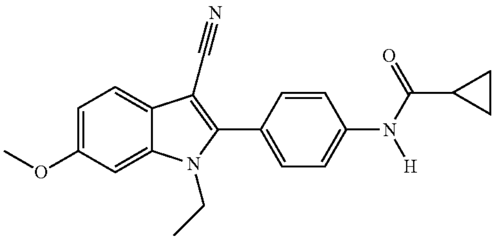
82
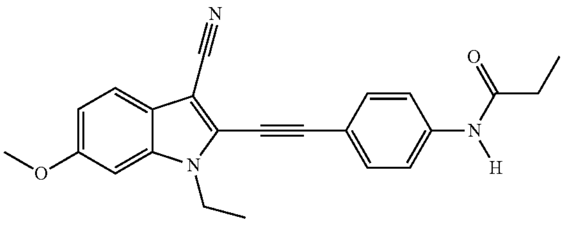
83
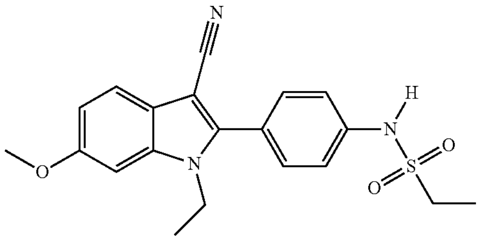
-continued
84
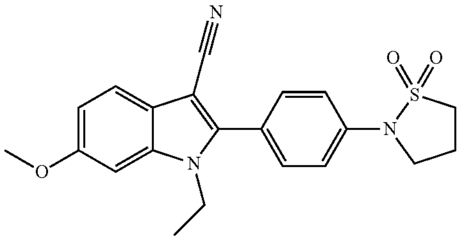
85
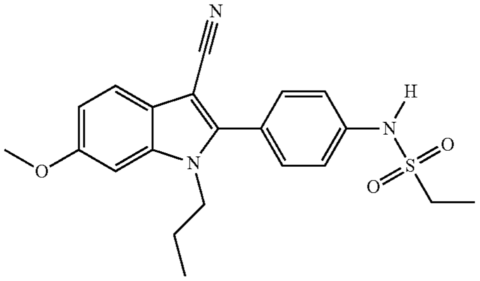
86
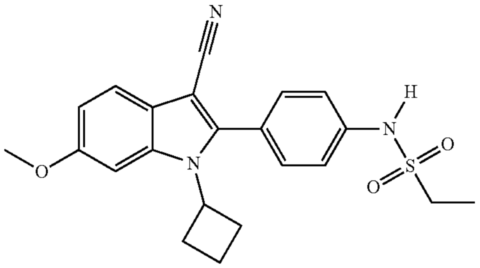
87
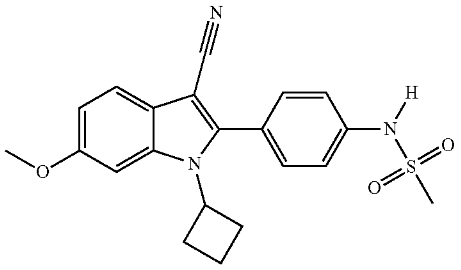
88
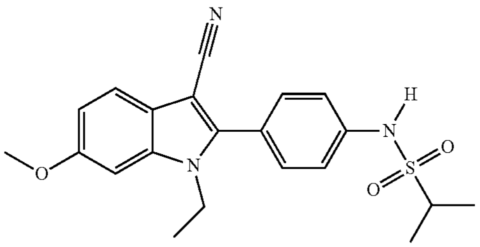

-continued
89
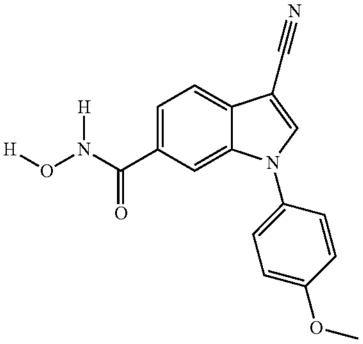
90
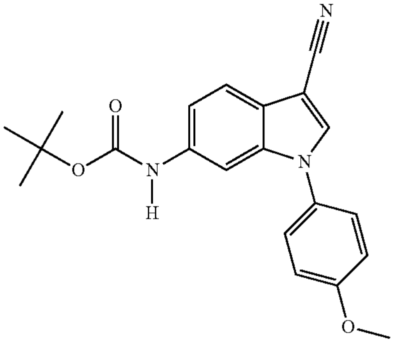
91
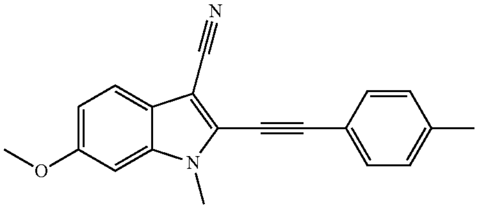
92
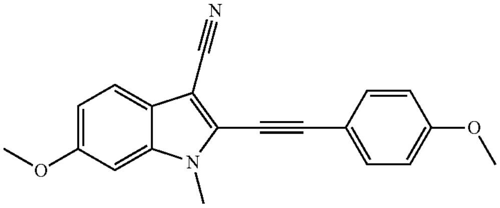
93
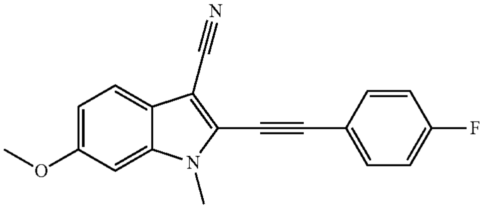
94
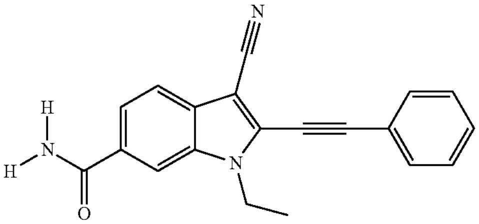
-continued
95
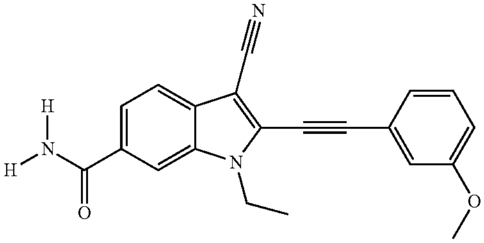
96
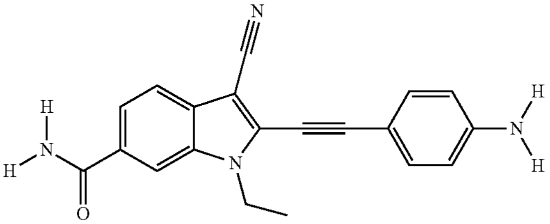
97
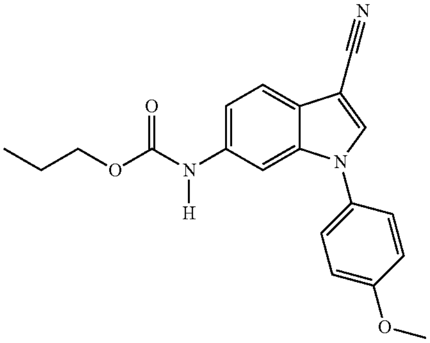
98
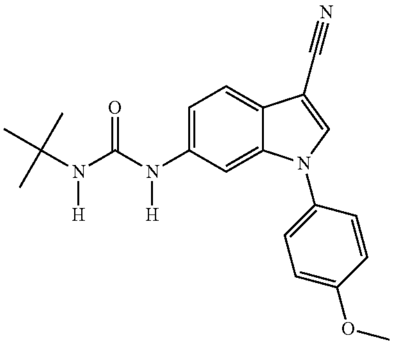
99
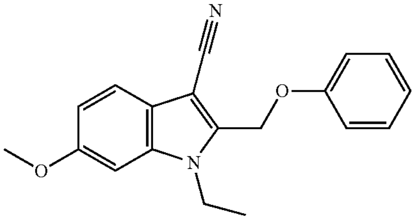
100
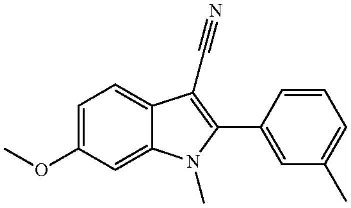

-continued
101
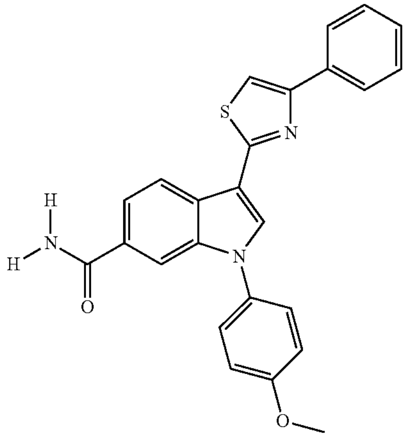
102
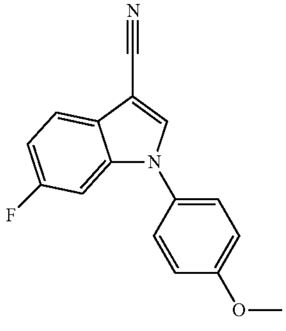
103
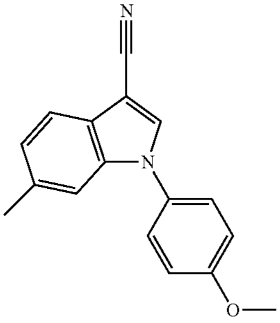
104
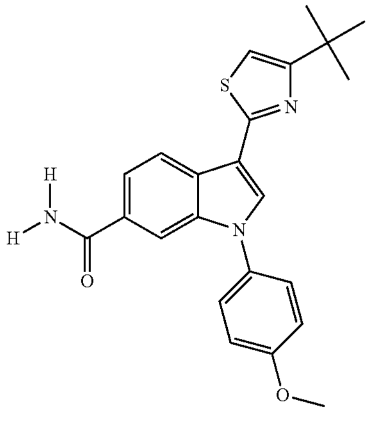
-continued
105
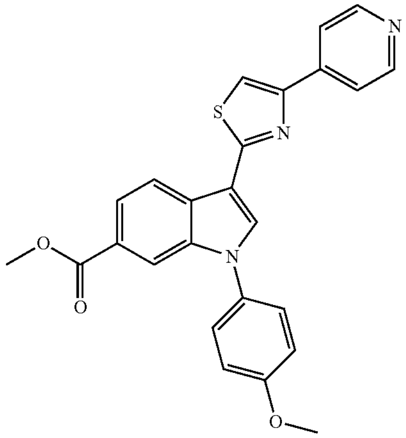
106
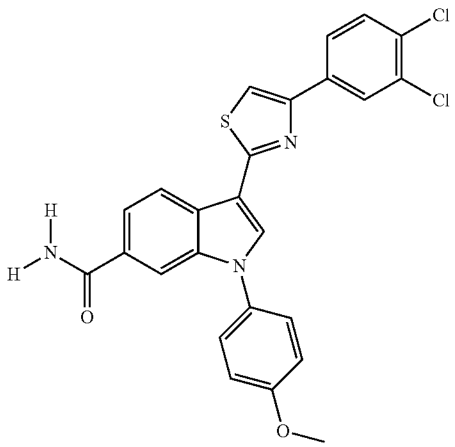
107
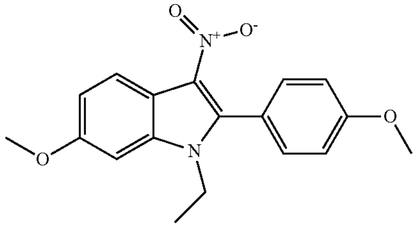
108
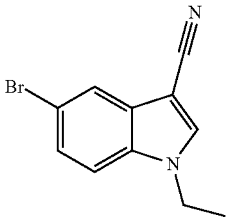
109
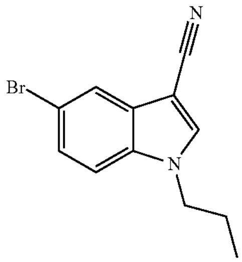

-continued
110
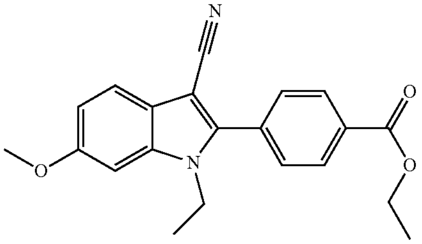
111
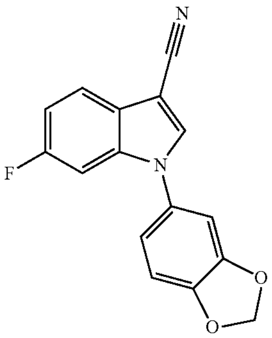
112
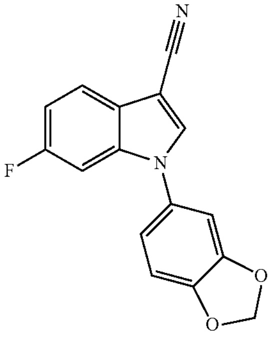
113
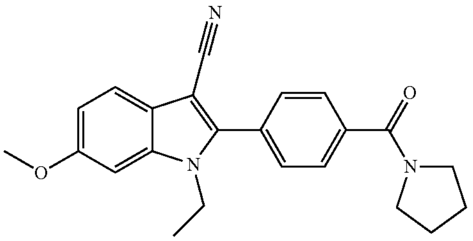
114
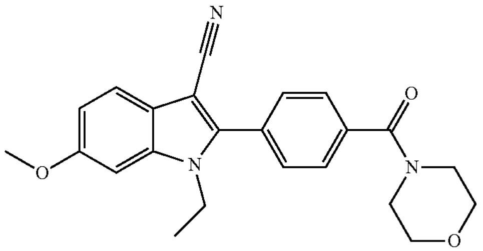
-continued
115
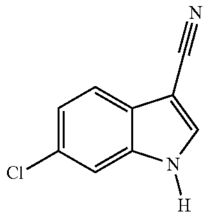
116
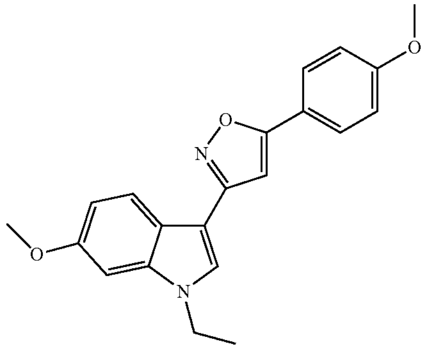
117
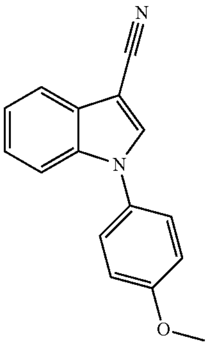
118
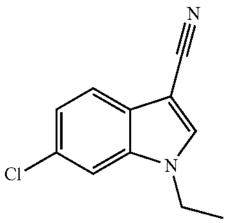
119
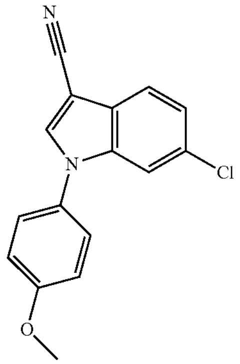

-continued
120
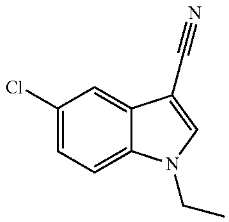
121
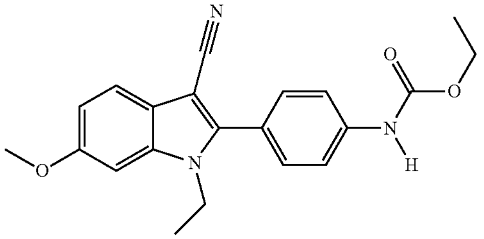
122
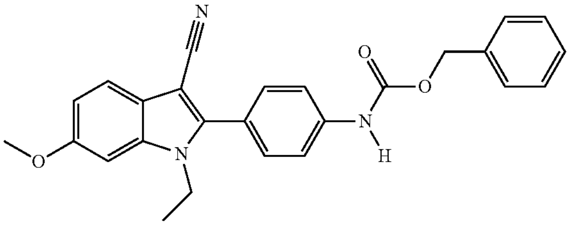
123
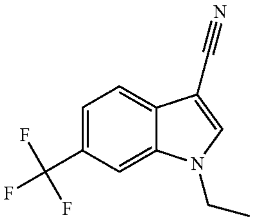
124
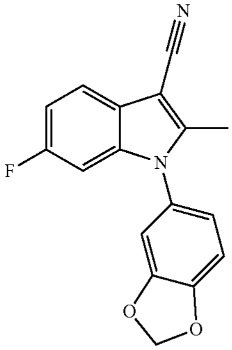
-continued
125
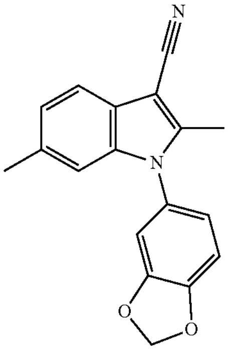
126
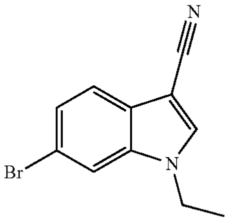
127
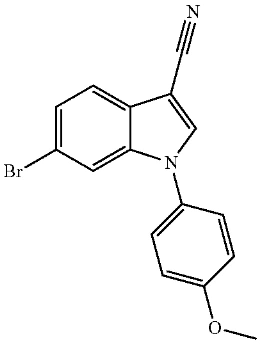
128
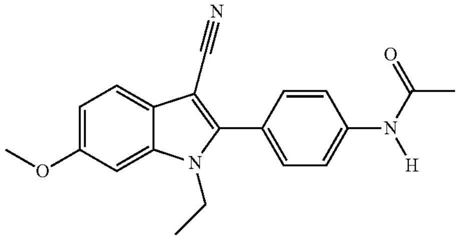
129
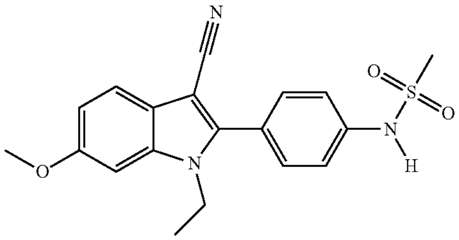

-continued
130
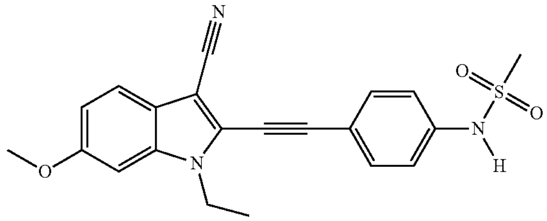
131
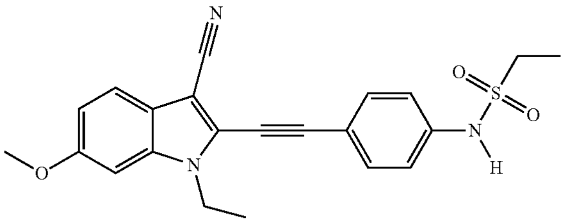
132
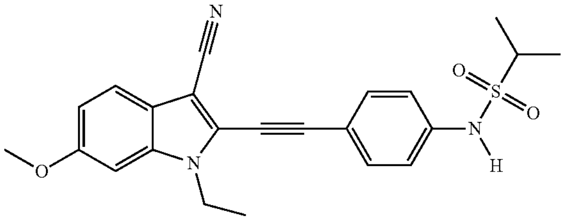
133
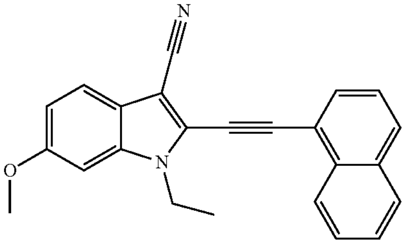
134
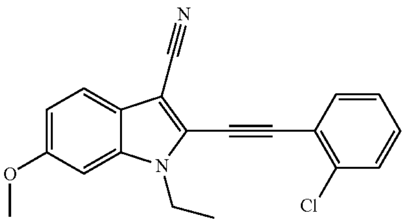
135
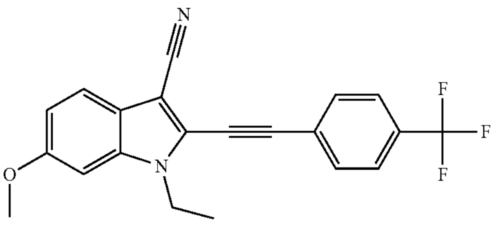
-continued
136
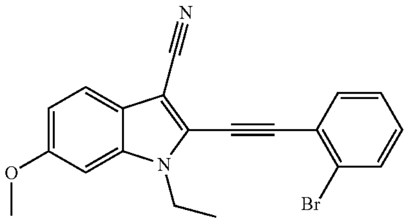
137
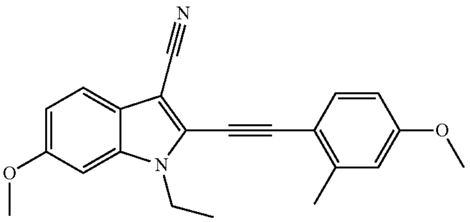
138
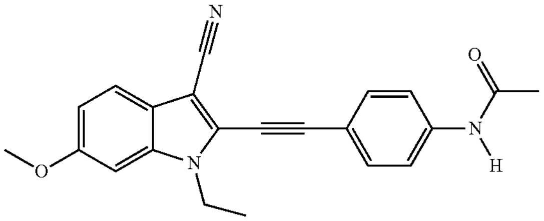
139
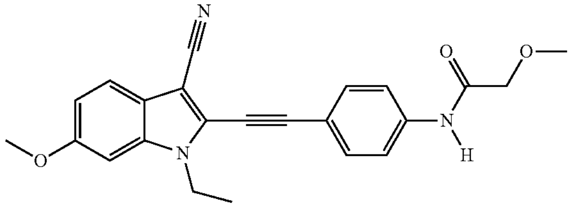
140
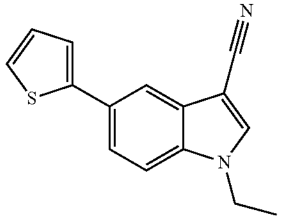
141
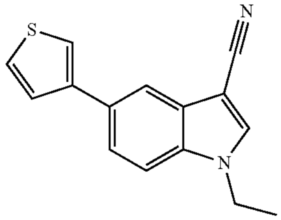
142
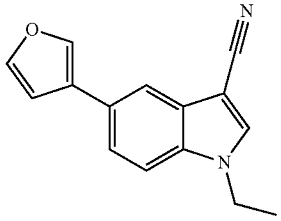

-continued
143
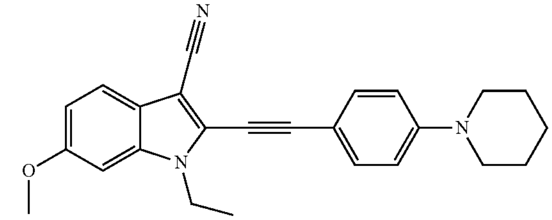
144
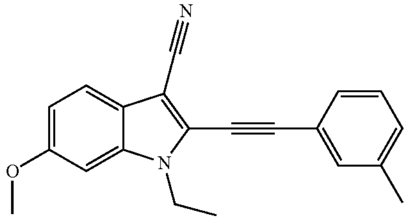
145
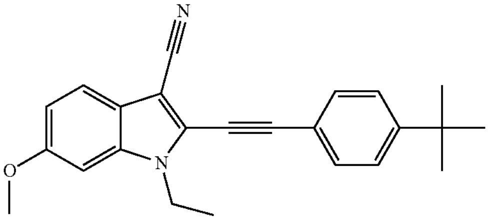
146
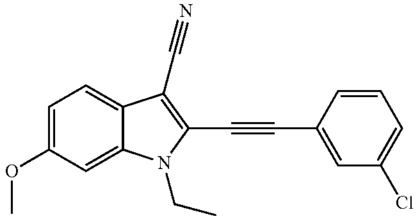
147
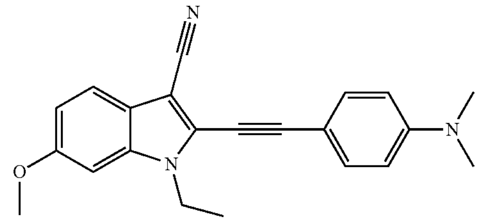
148
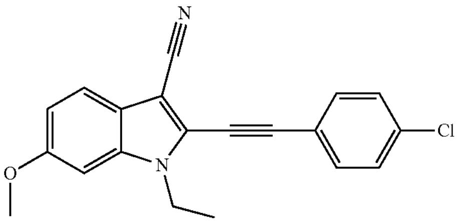
149
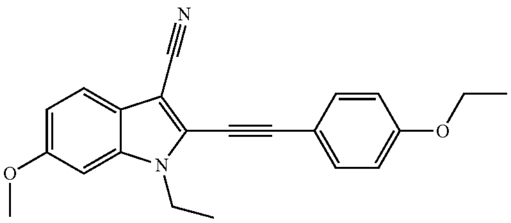
-continued
150
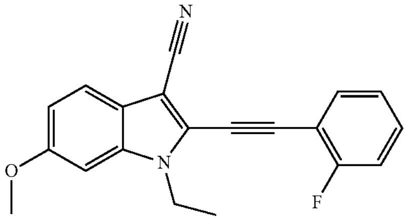
151
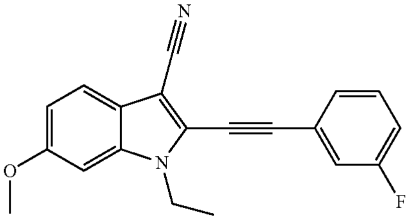
152
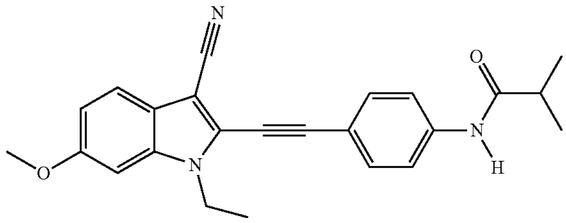
153
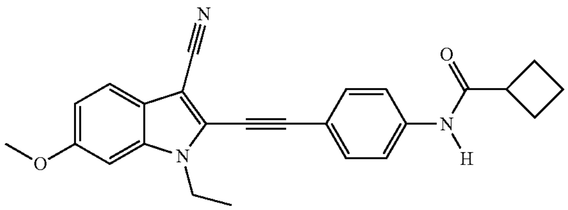
154
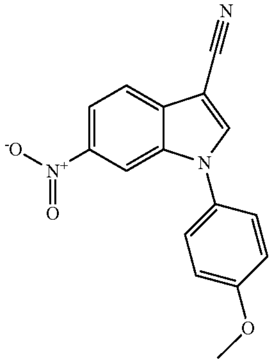
155
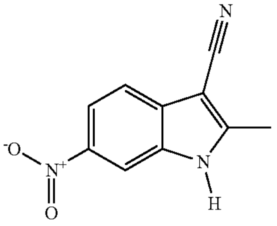

-continued
156
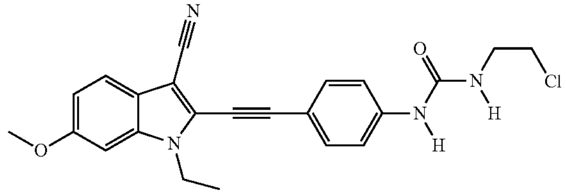
157
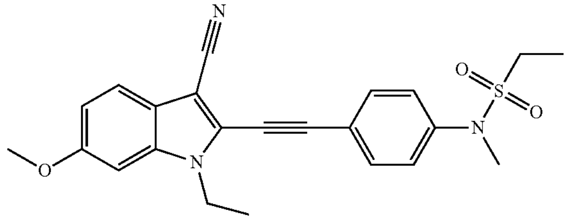
158
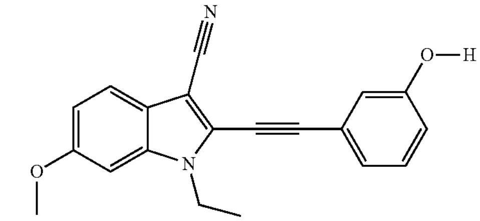
159
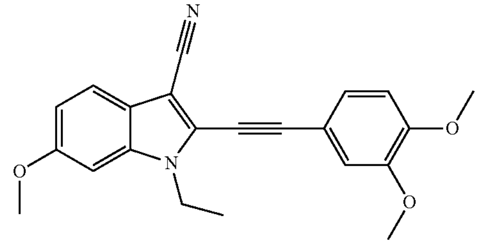
160
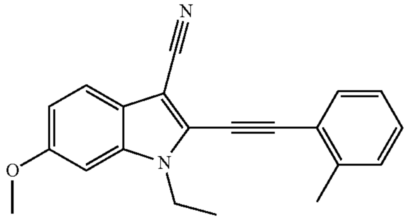
161
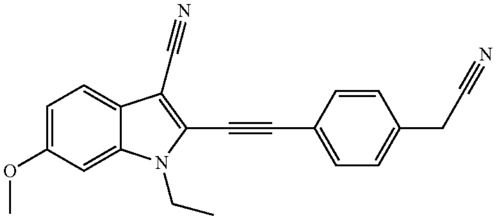
162
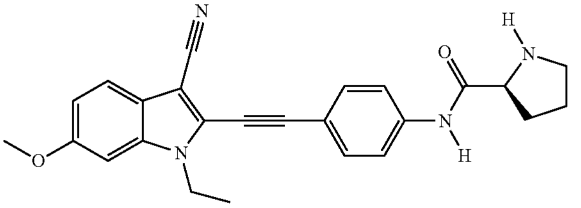
-continued
163
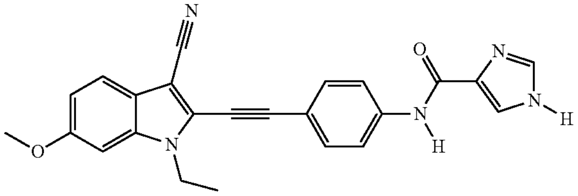
164
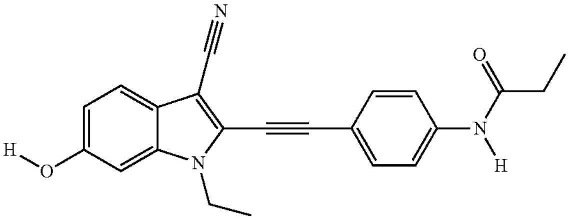
165
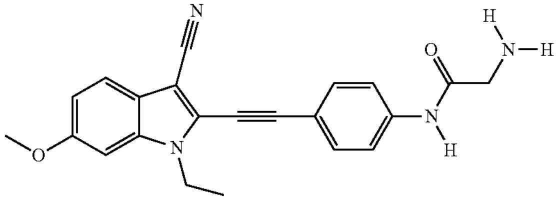
166
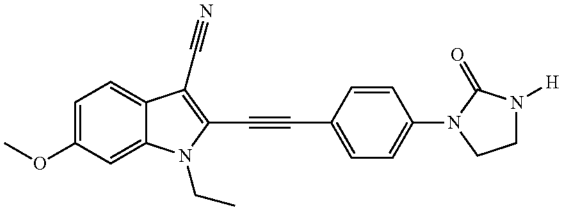
167
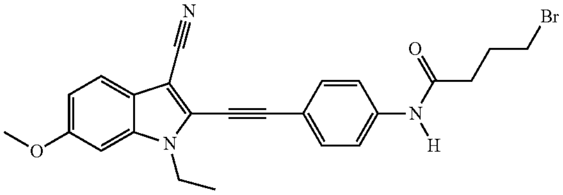
168
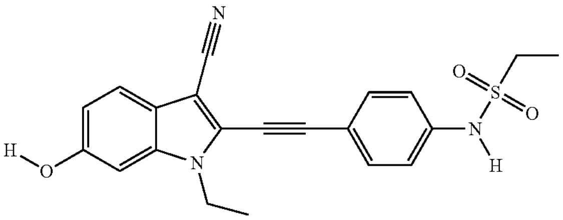

-continued
169
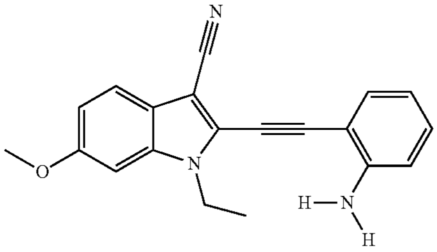
170
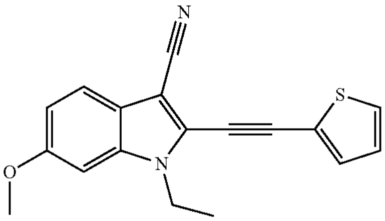
171
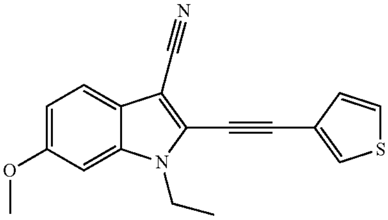
172
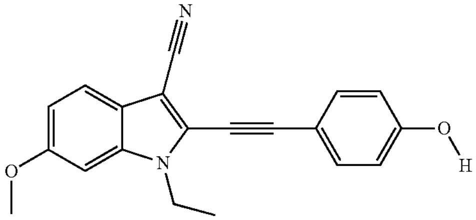
173
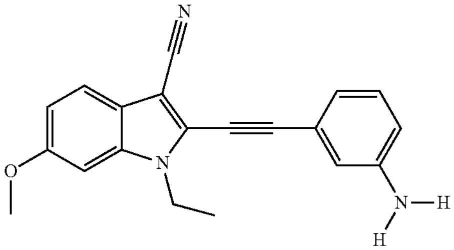
174
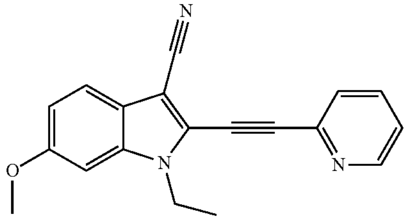
-continued
175
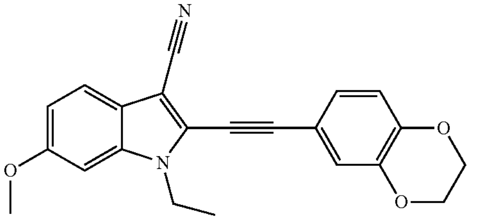
176
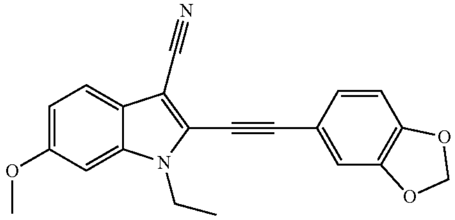
177
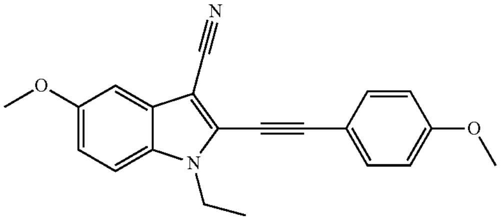
178
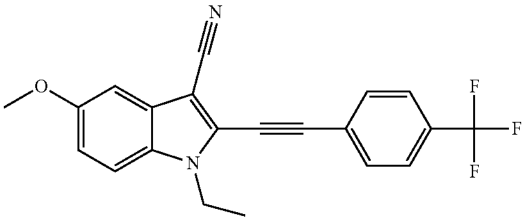
179
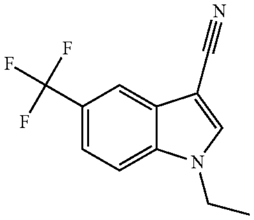
180
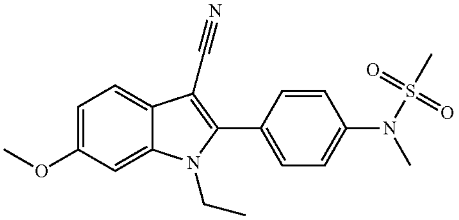
181
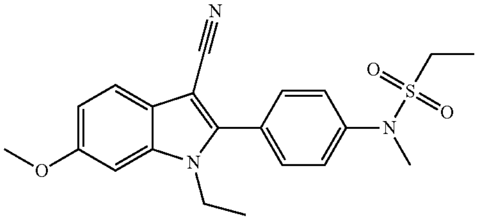

-continued
182
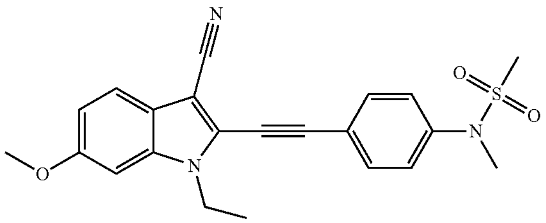
183
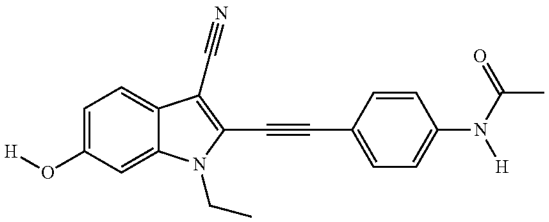
184
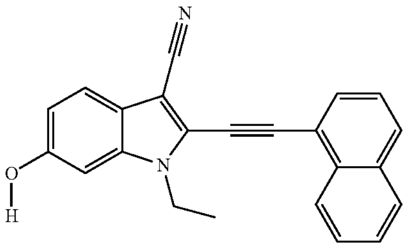
185
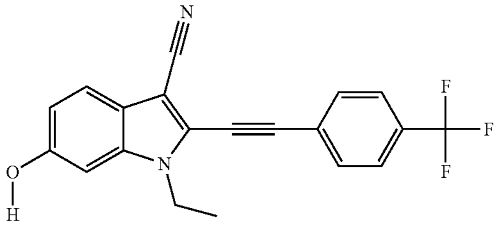
186
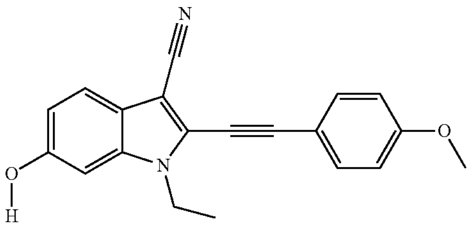
187
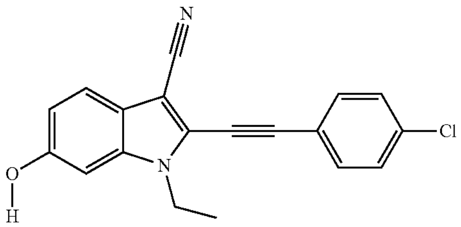
-continued
188
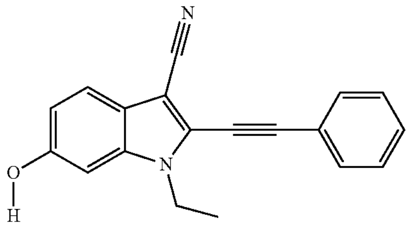
189
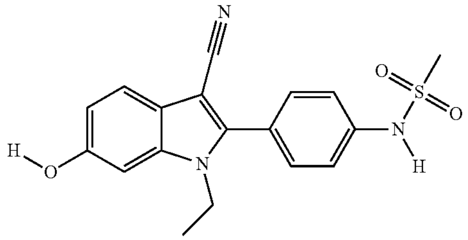
190
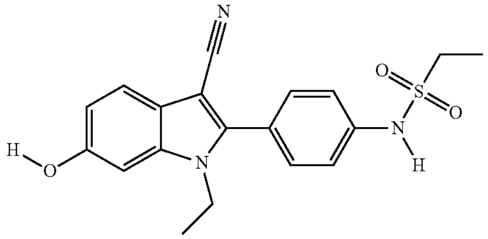
191
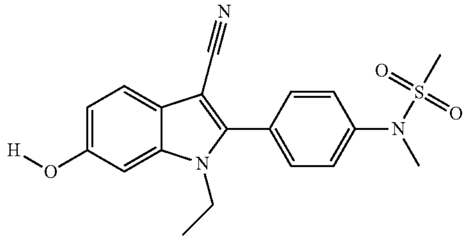
192
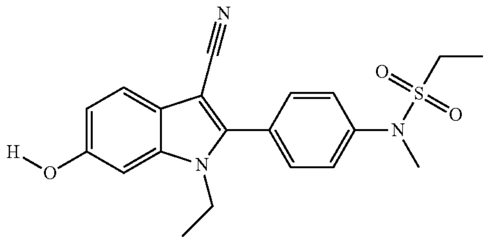
193
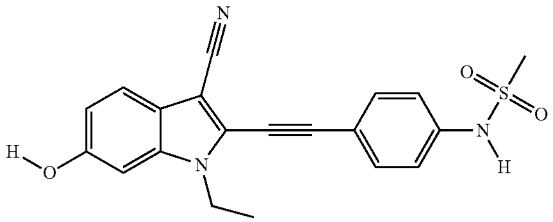

-continued
194
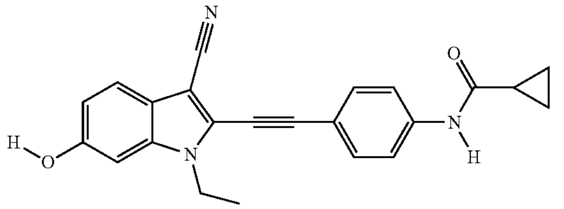
195
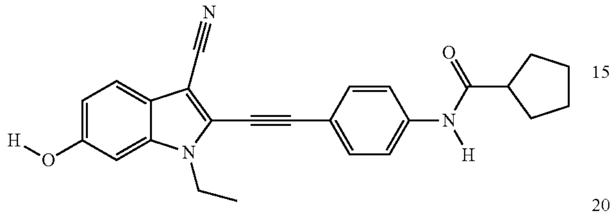
196
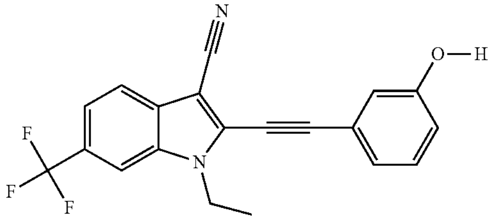
197
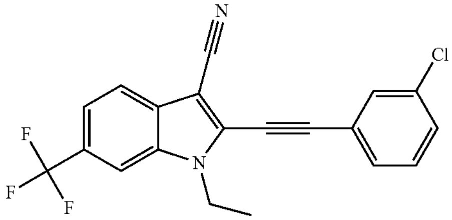
198
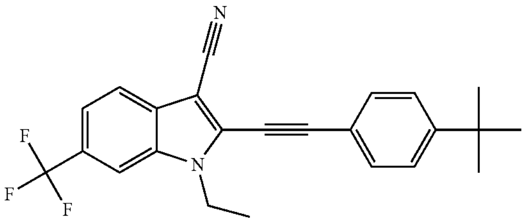
199
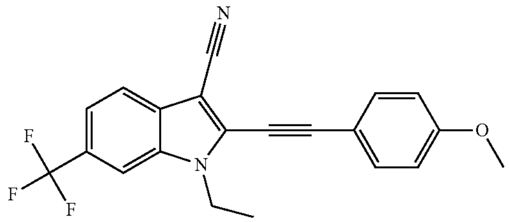
200
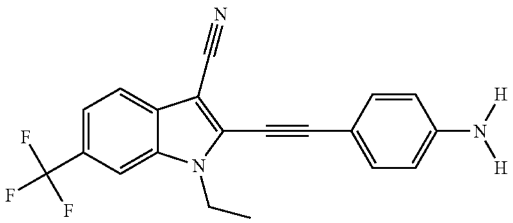
-continued
201
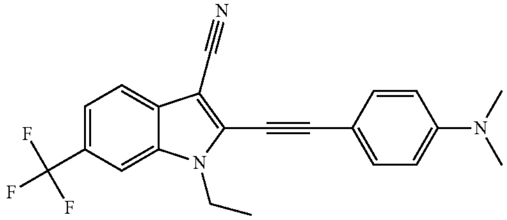
202
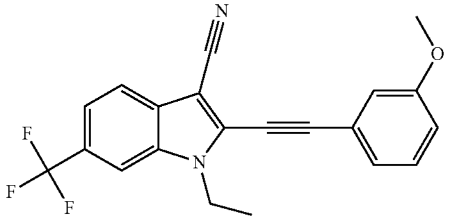
203
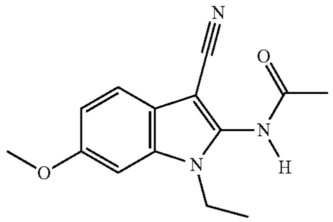
204
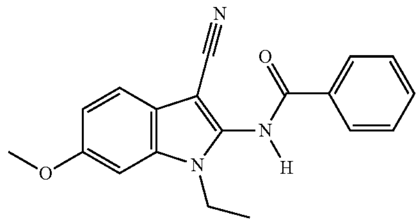
205
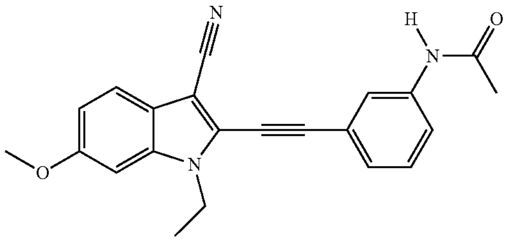
206
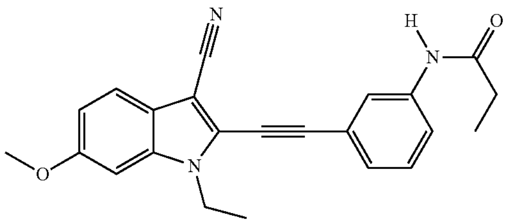

-continued
207
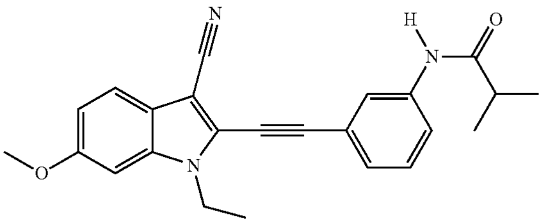
208
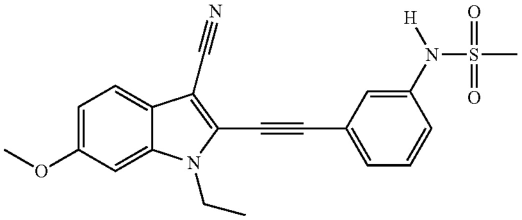
209
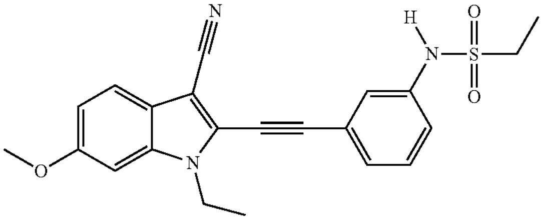
210
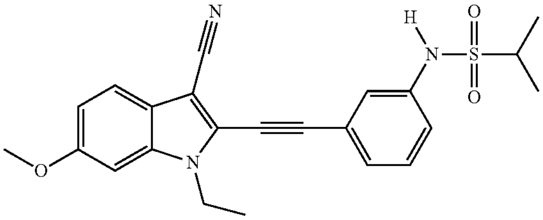
211
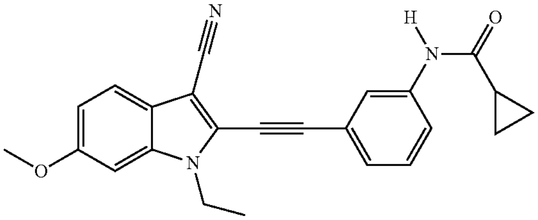
212
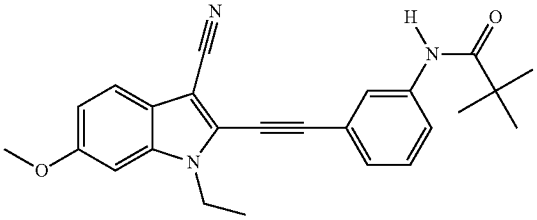
-continued
213
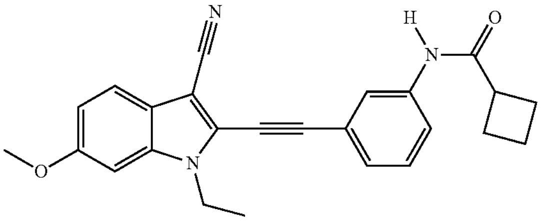
214
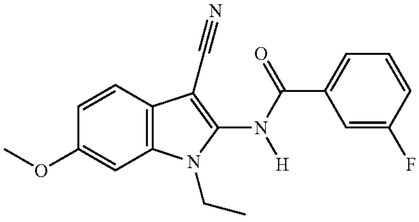
215
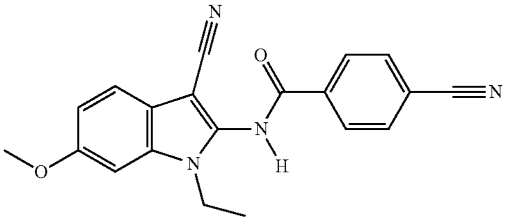
216
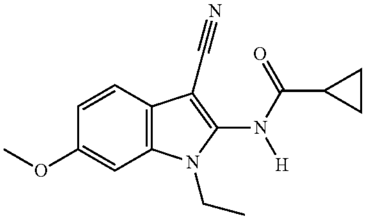
217
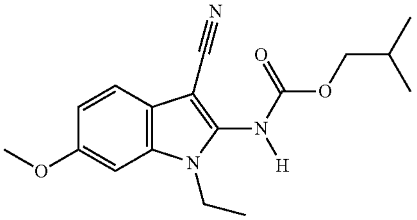
218
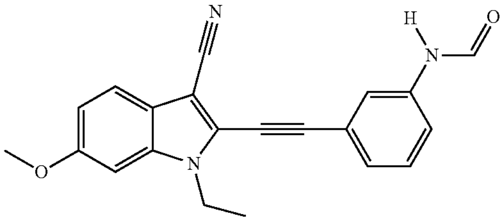
219
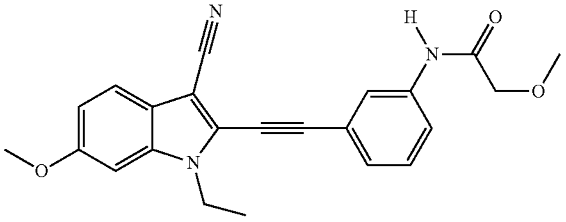

-continued
220
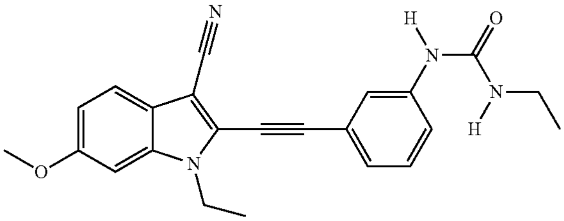
221
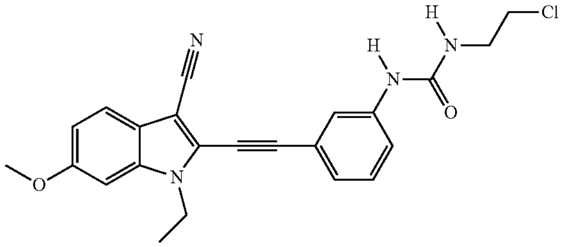
222
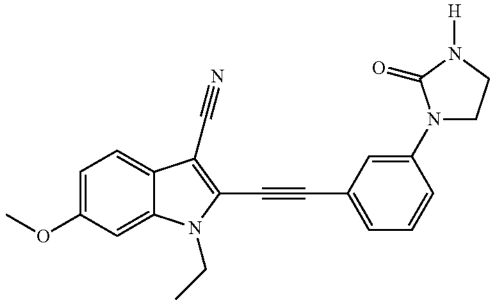
223
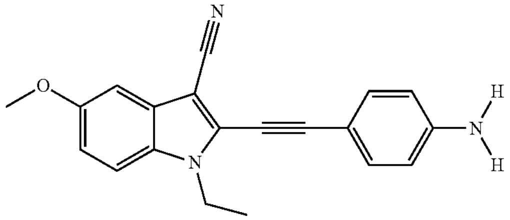
224
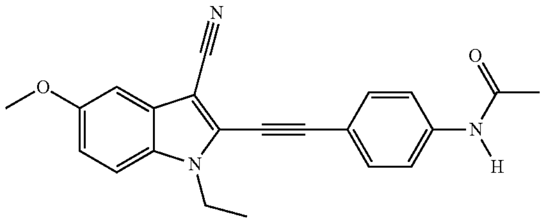
225
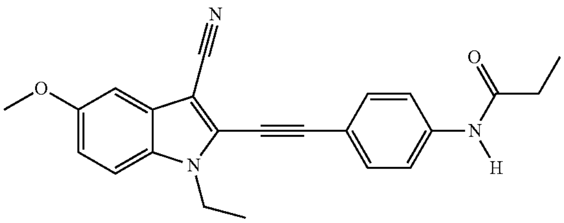
-continued
226
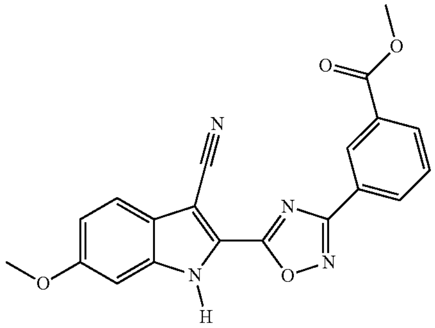
227
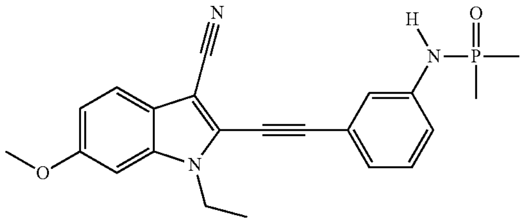
228
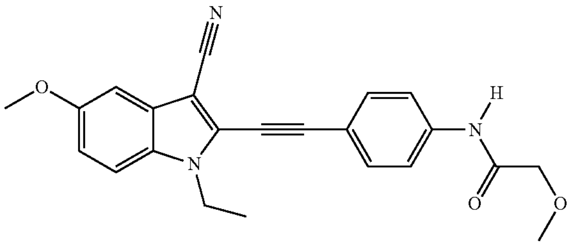
229
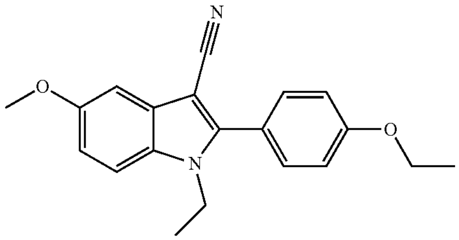
230
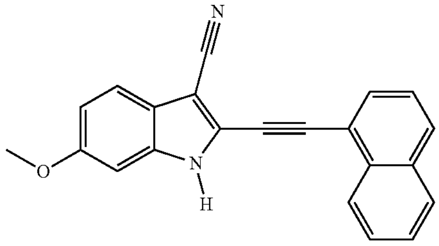
231
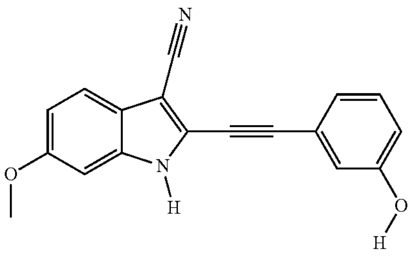

-continued
232
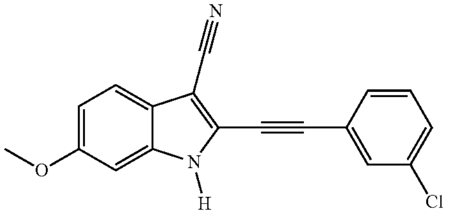
233
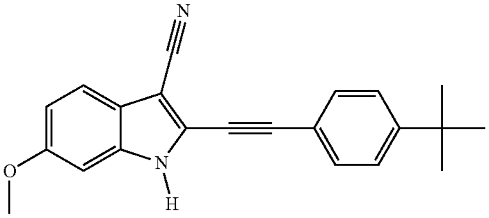
234
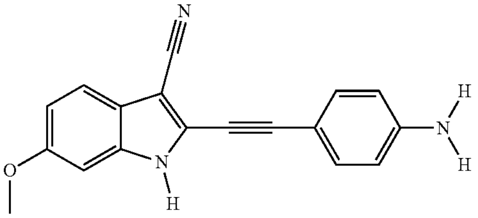
235
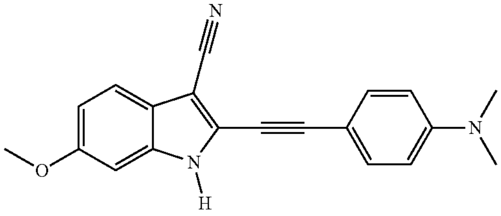
236
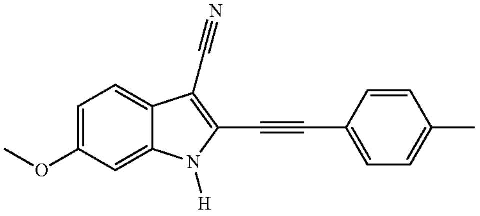
237
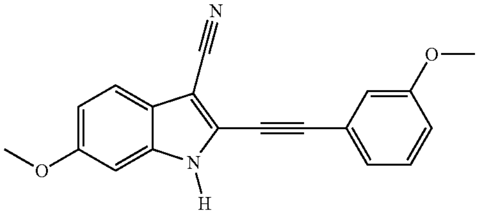
238
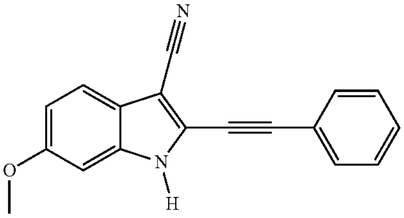
-continued
239
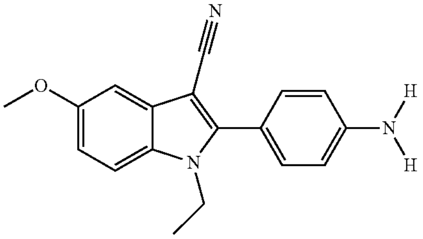
240
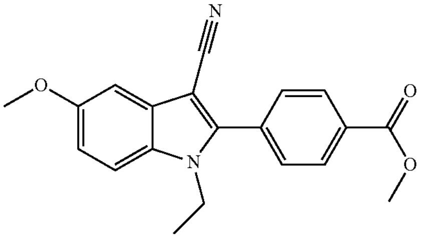
241
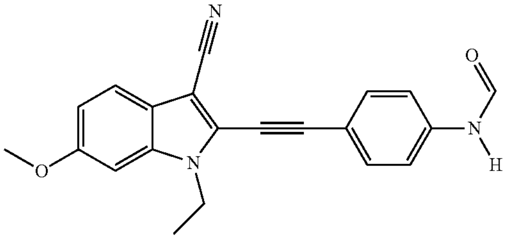
242
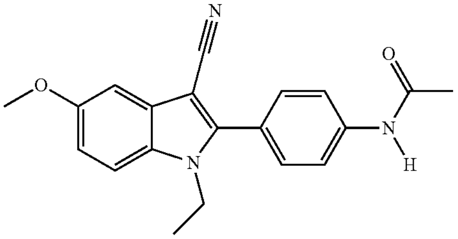
243
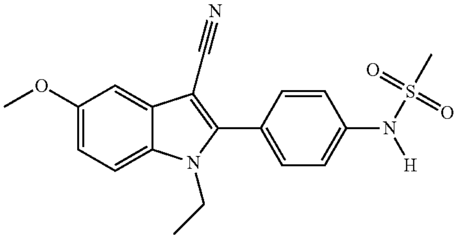
244
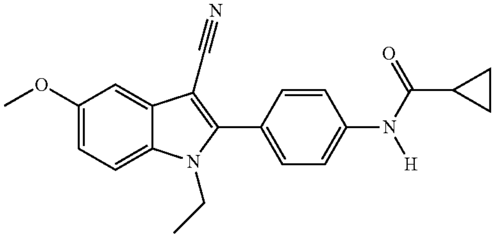

-continued
245
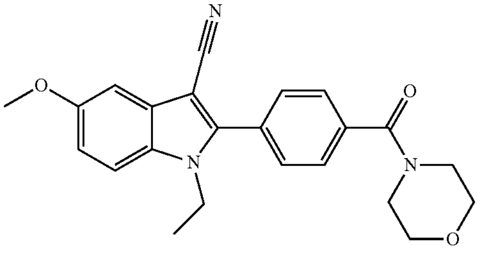
246
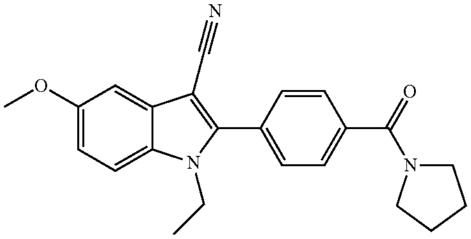
247
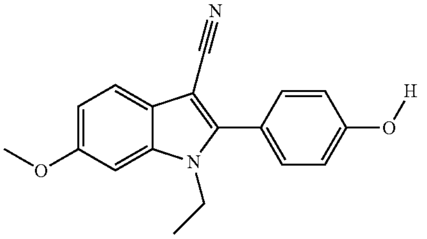
248
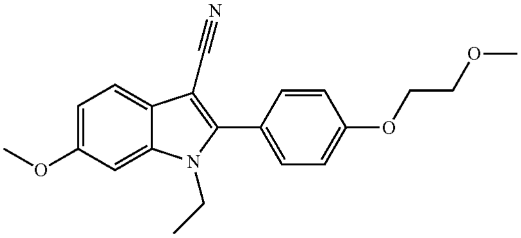
249
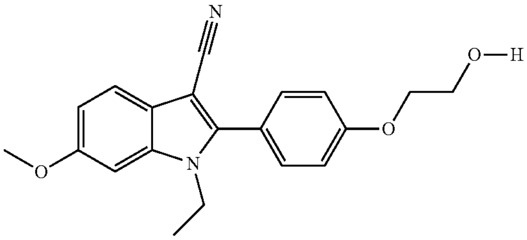
250
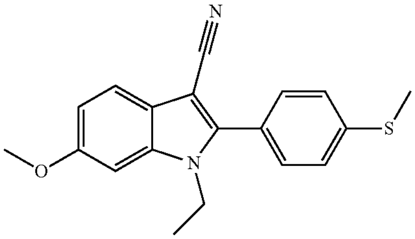
-continued
251
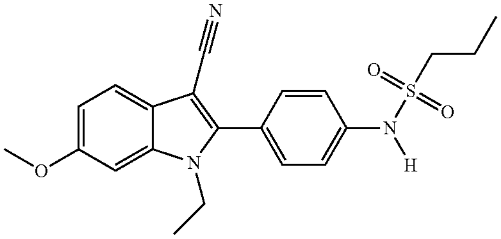
252
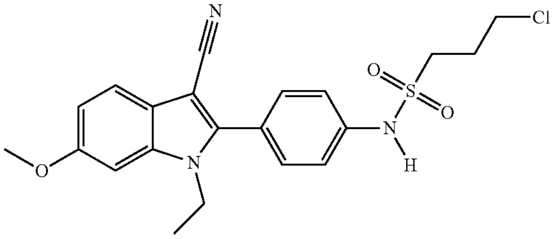
253
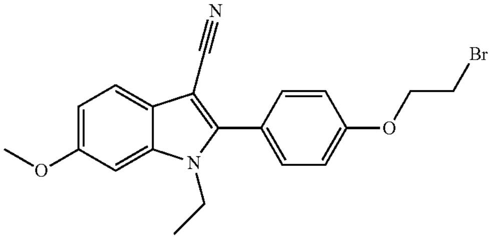
254
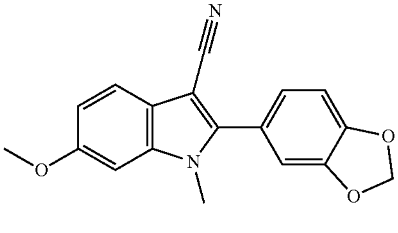
255
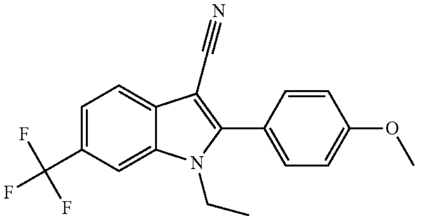
256
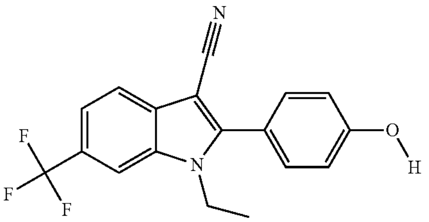

-continued
257
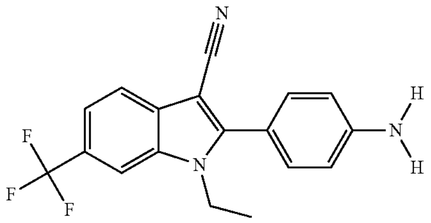
258
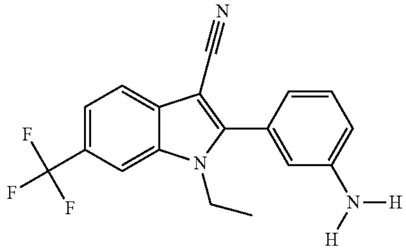
259
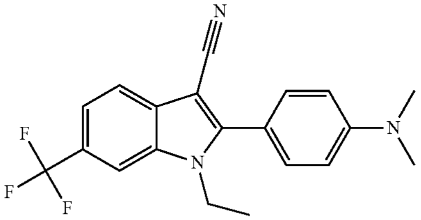
260
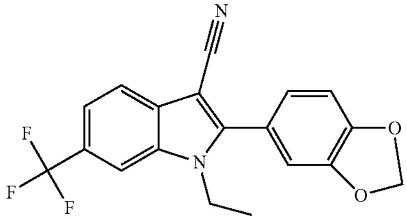
261
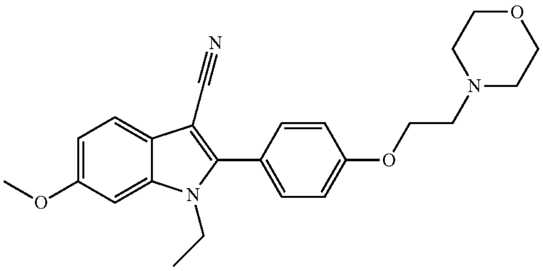
262
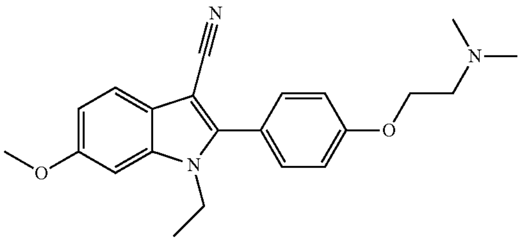
-continued
263
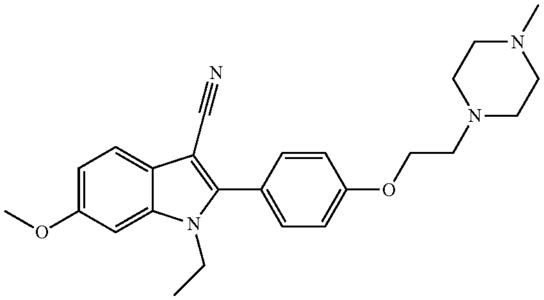
264
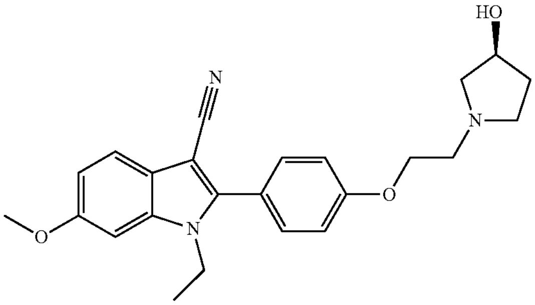
265
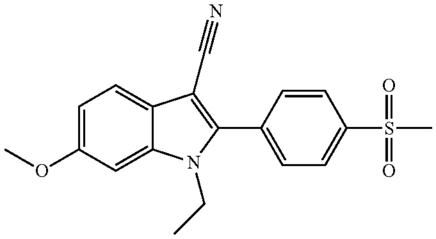
266
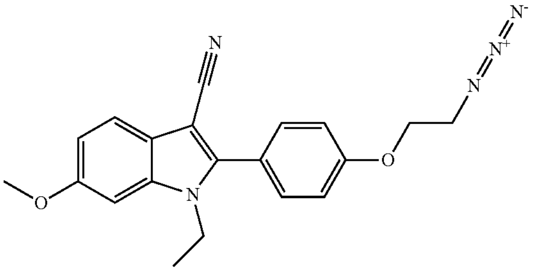
267
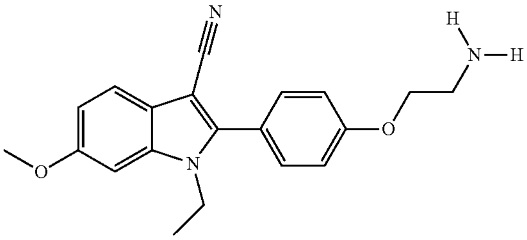

-continued
268
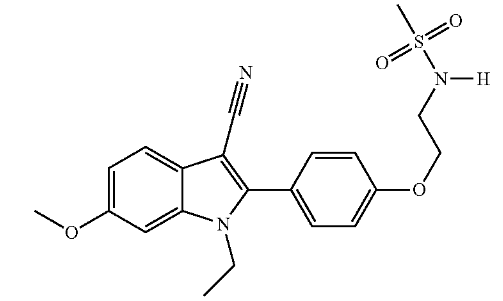
269
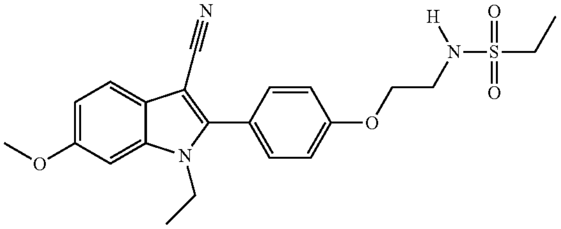
270
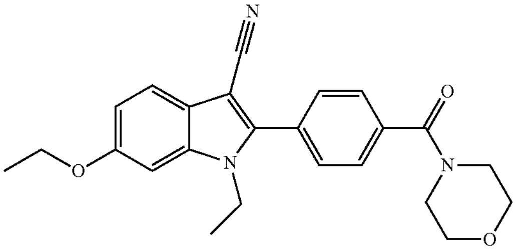
271
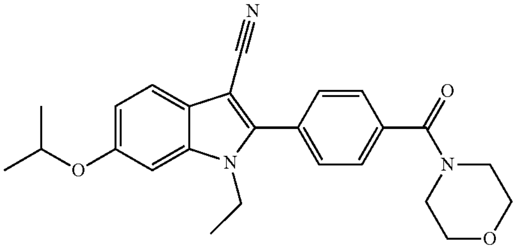
272
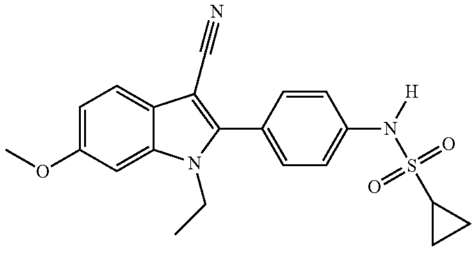
273
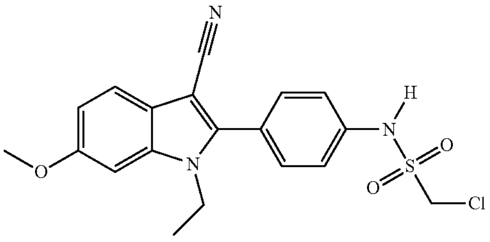
-continued
274
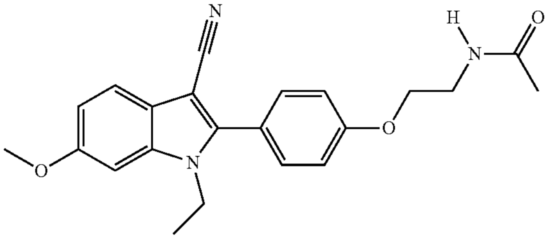
275
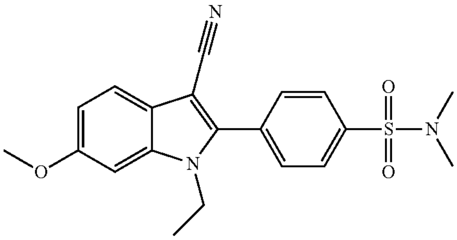
276
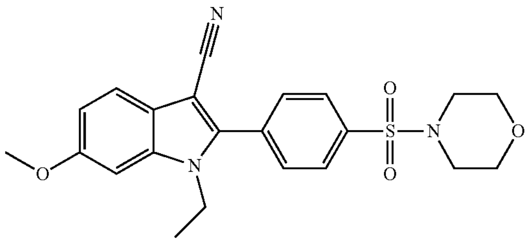
277
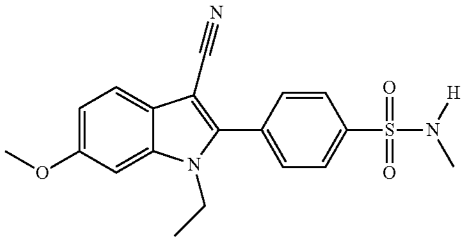
278
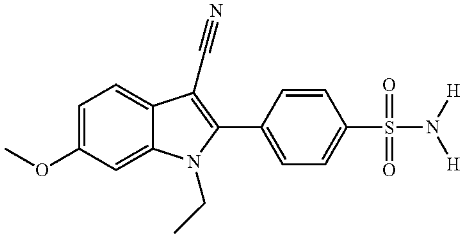
279
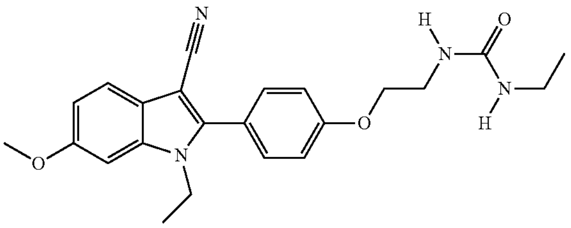

-continued
280
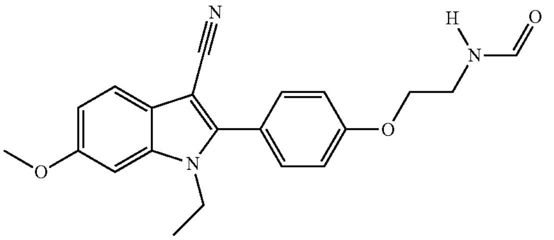
281
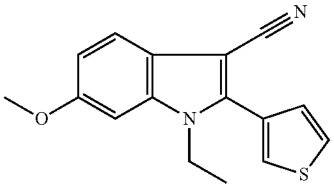
282
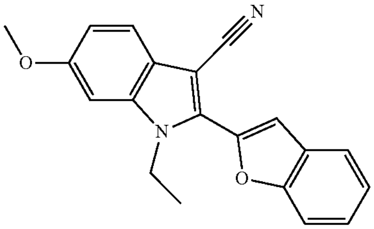
283
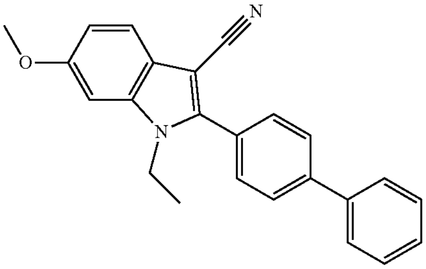
284
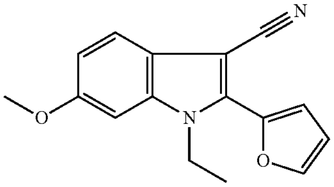
285
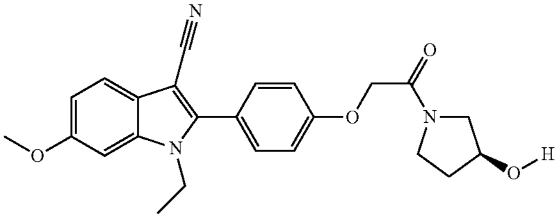
-continued
286
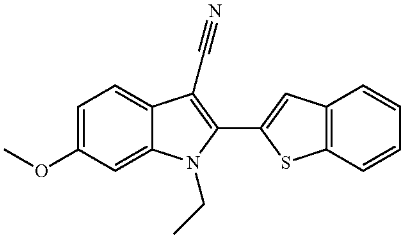
287
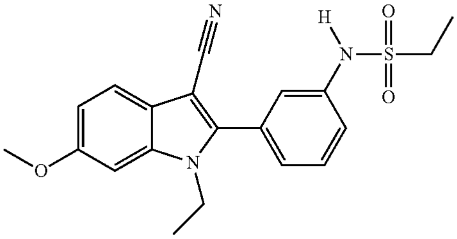
288
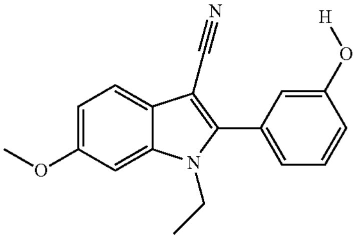
289
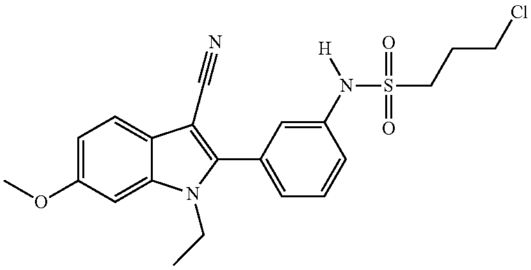
290
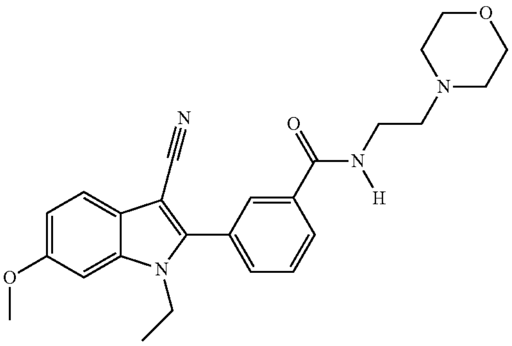
291
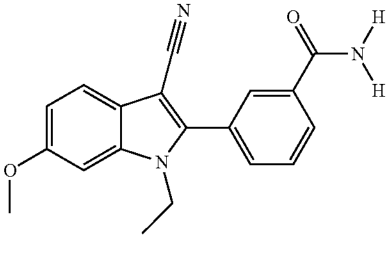

-continued
292
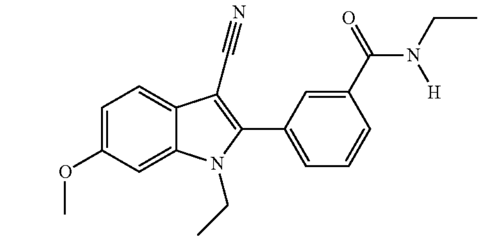
293
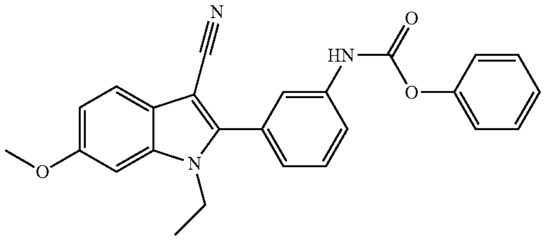
294
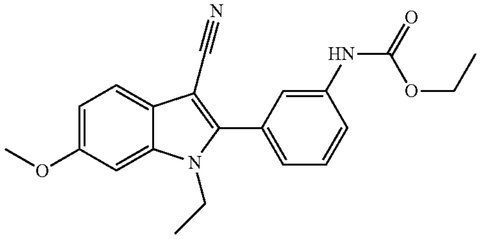
295
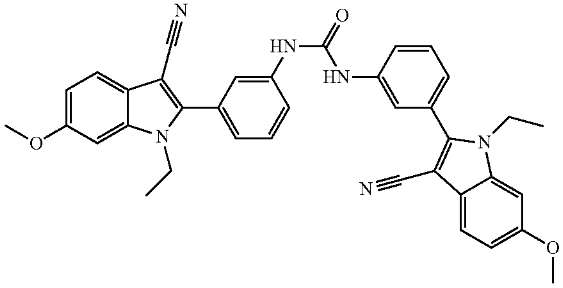
296
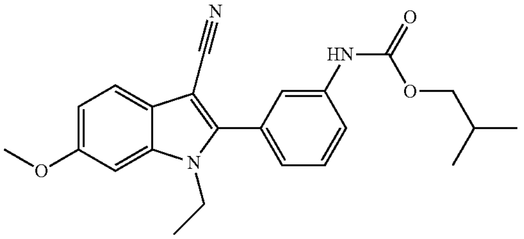
297
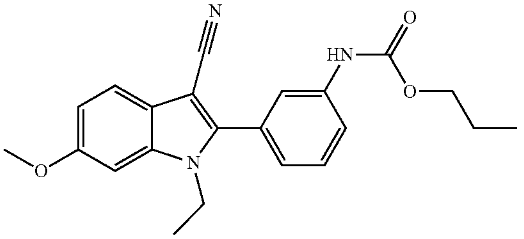
-continued
298
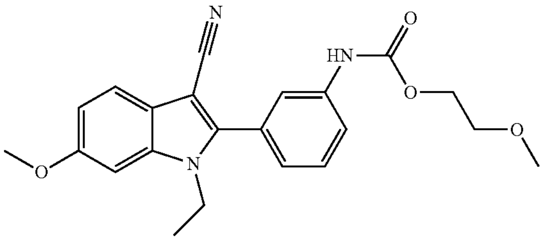
299
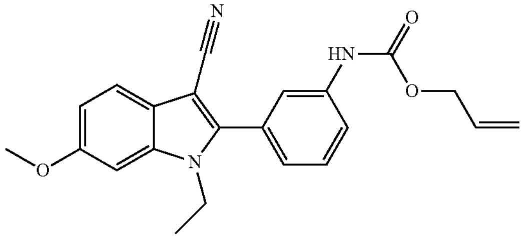
300
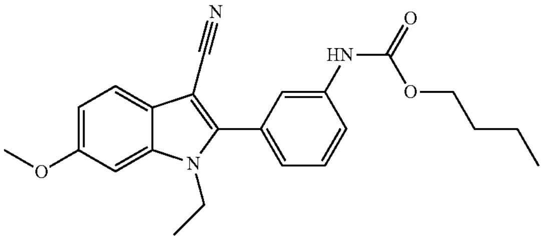
301
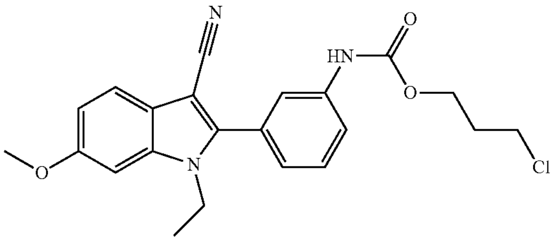
302
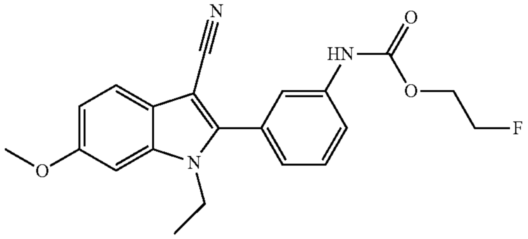
303
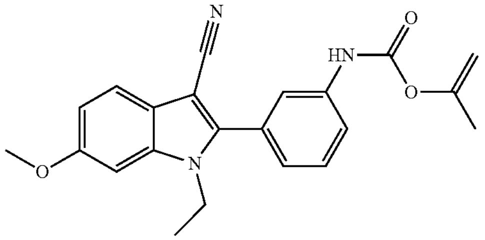

-continued
304
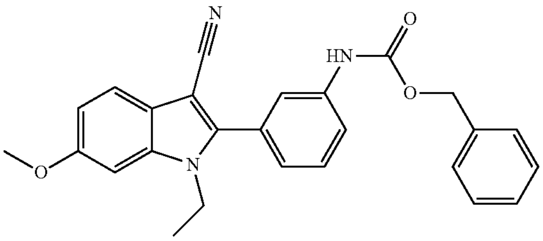
305
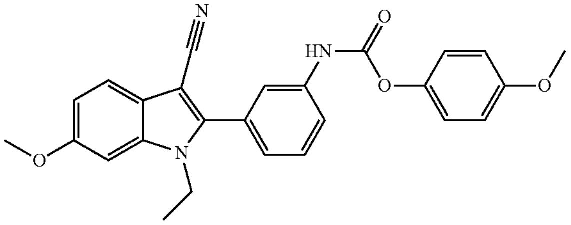
306
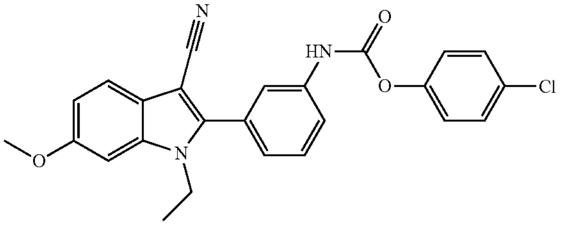
307
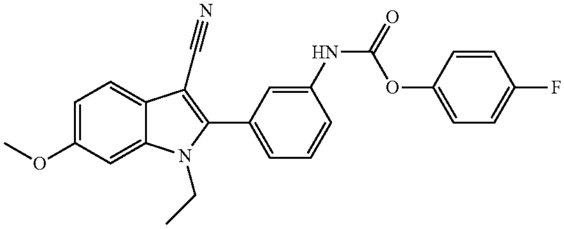
308
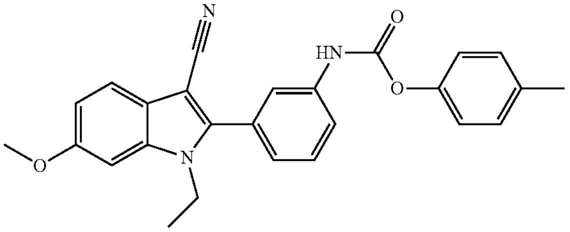
309
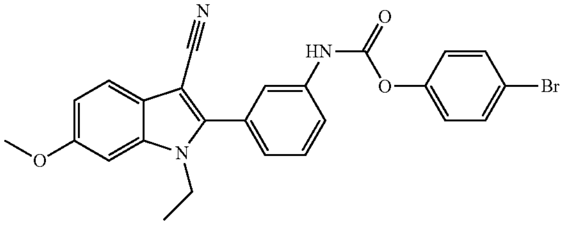
-continued
310
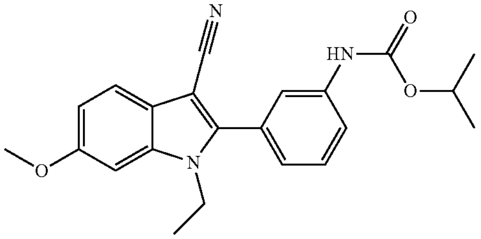
311
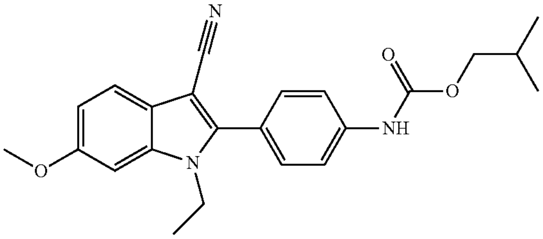
312
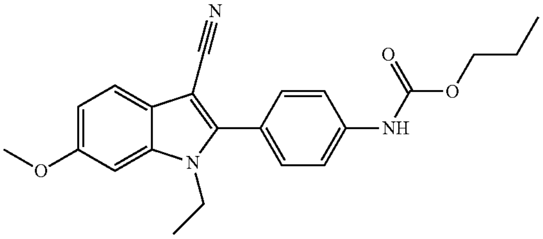
313
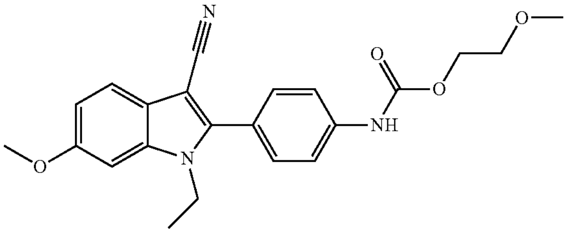
314
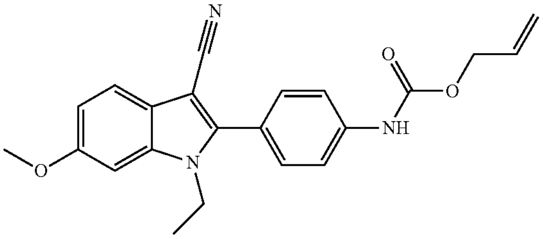
315
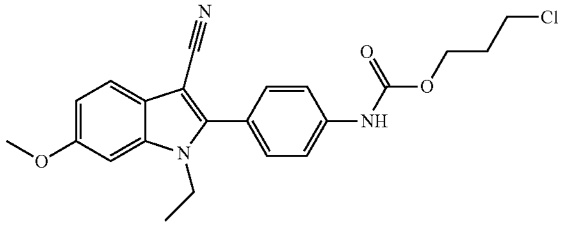

-continued
316
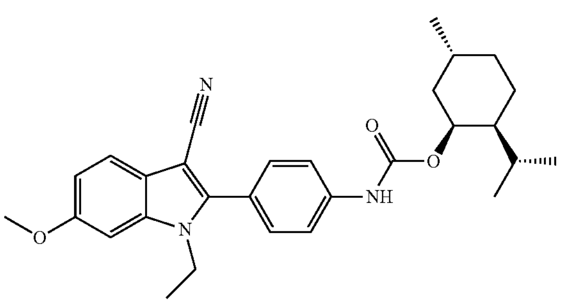
317
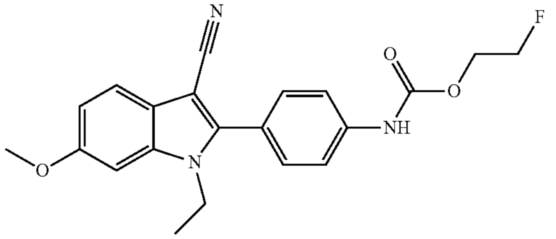
318
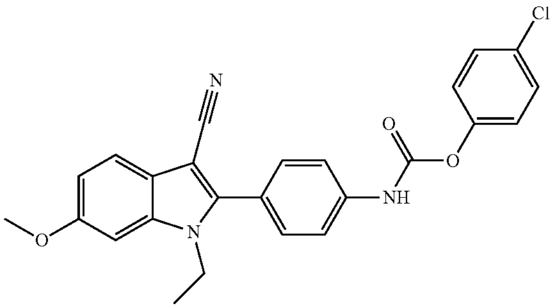
319
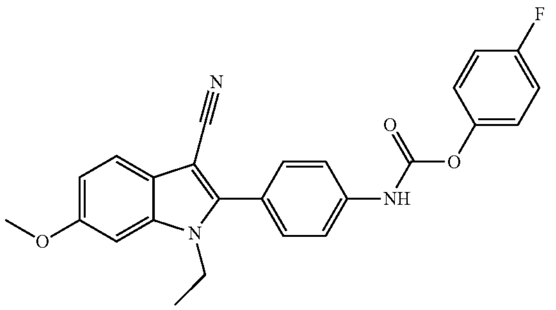
320
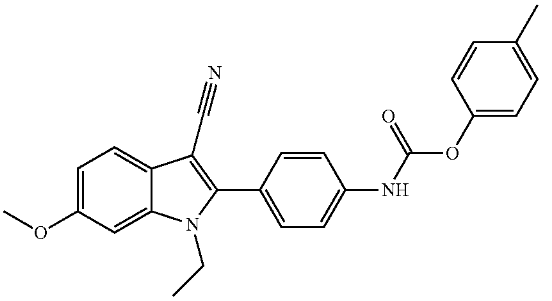
-continued
321
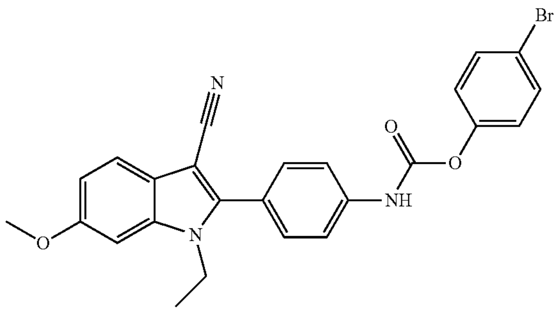
322
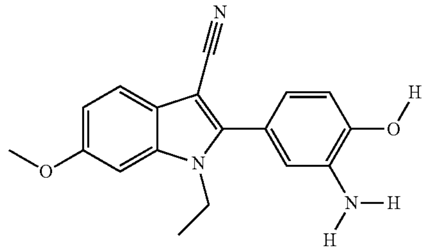
323
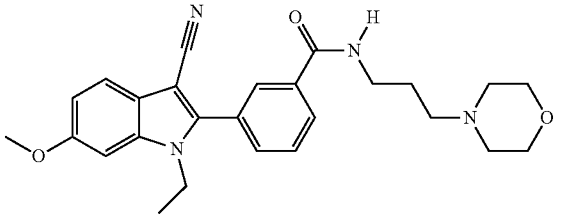
324
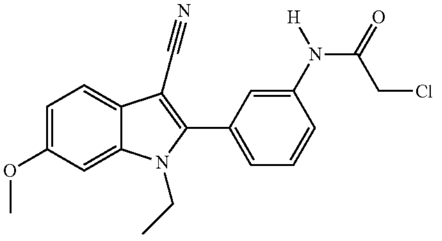
325
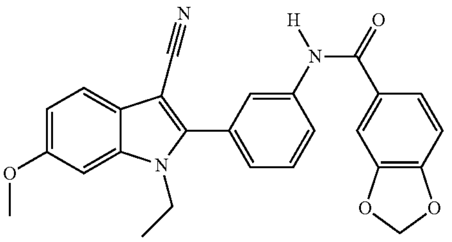
326
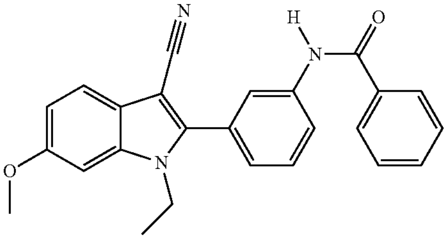

-continued
327
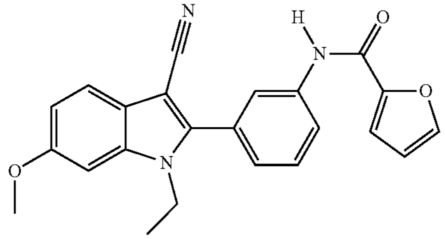
328
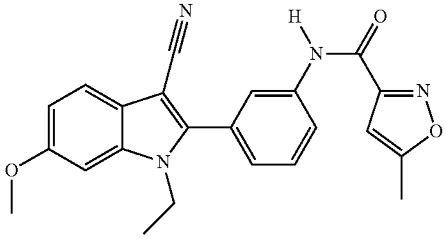
329
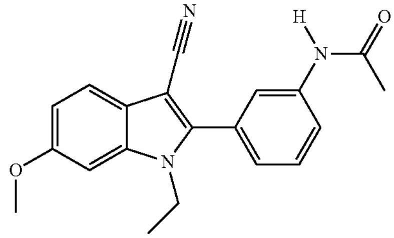
330
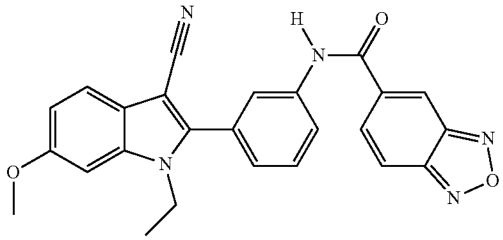
331
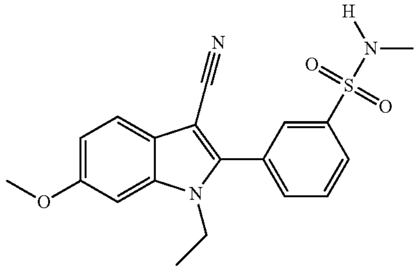
332
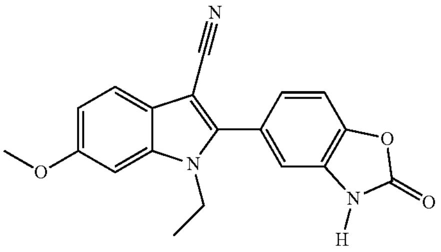
-continued
333
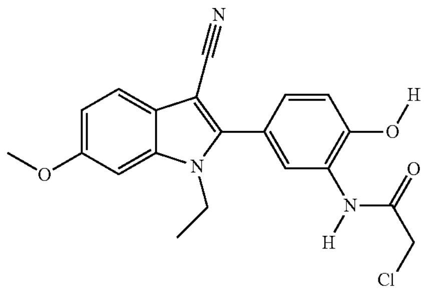
334
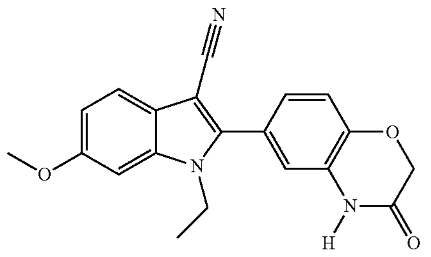
335
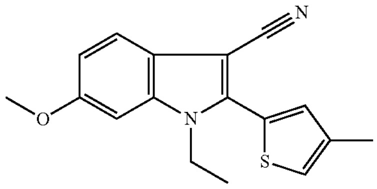
336
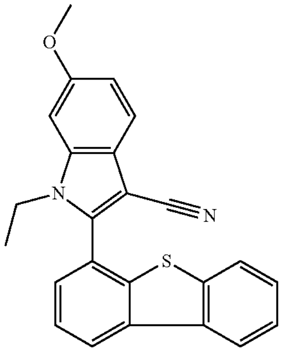
337
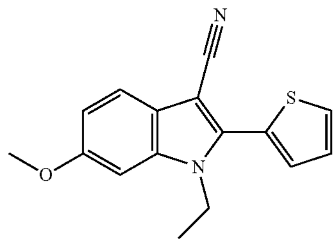

-continued
338
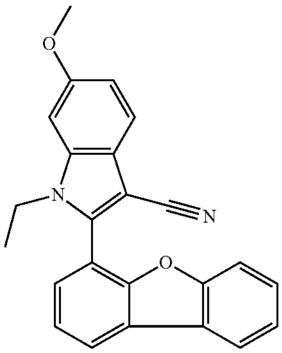
339
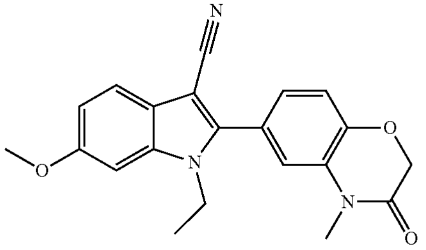
340
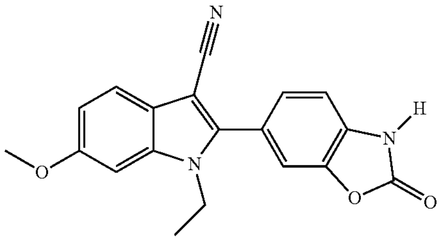
341
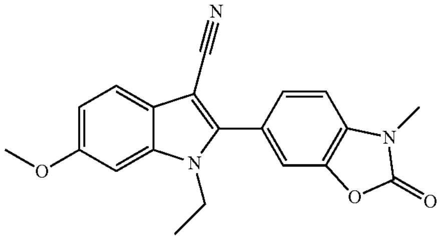
342
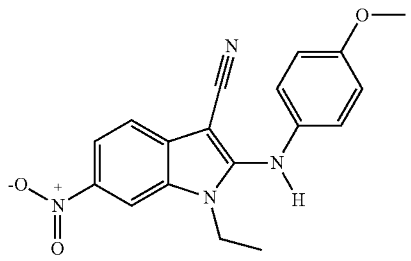
343
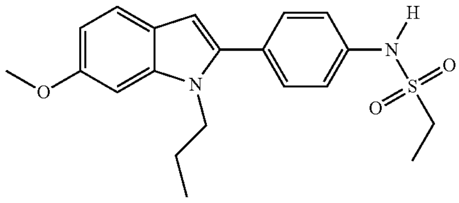
-continued
344
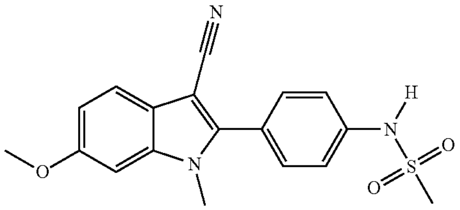
345
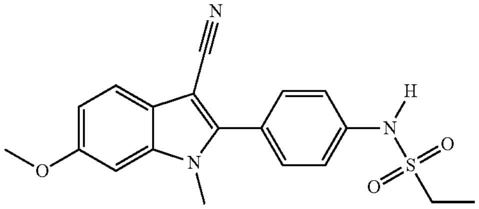
346
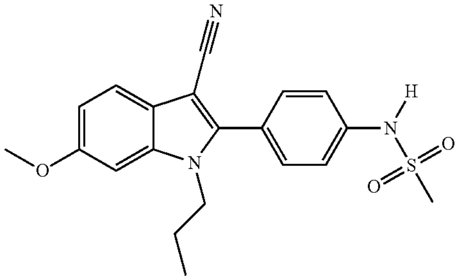
347
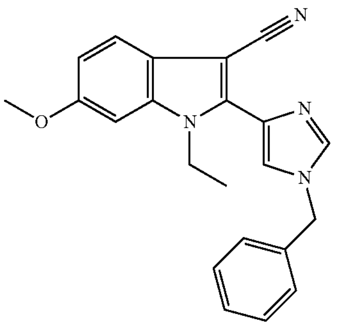
348
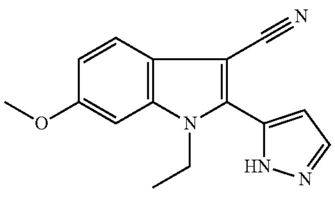
349
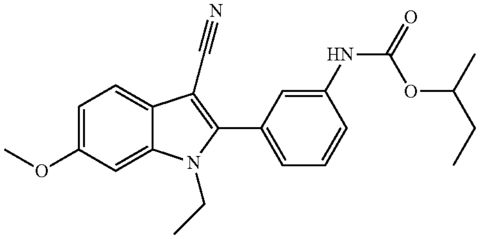

-continued
350
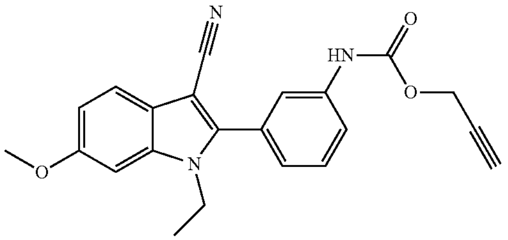
351
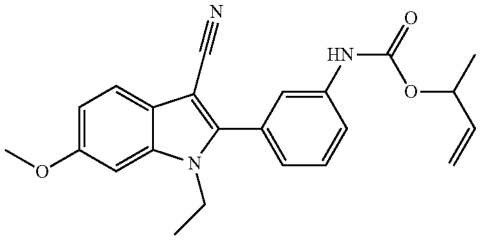
352
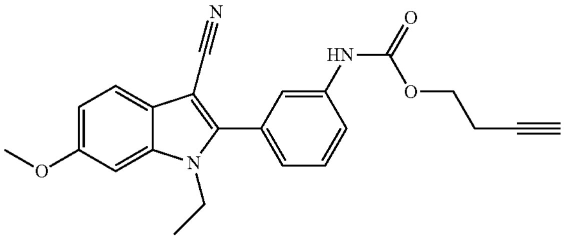
353
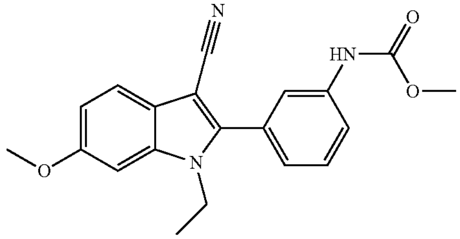
354
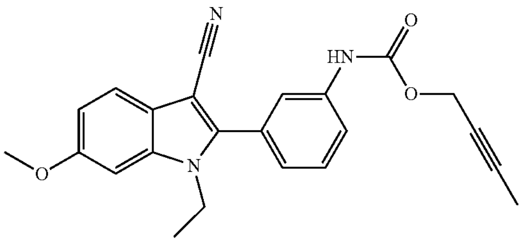
355
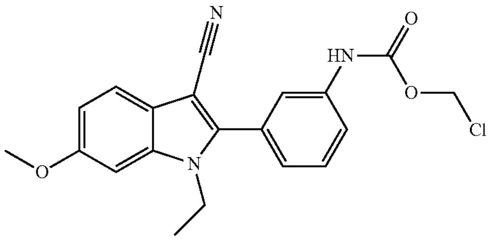
-continued
356
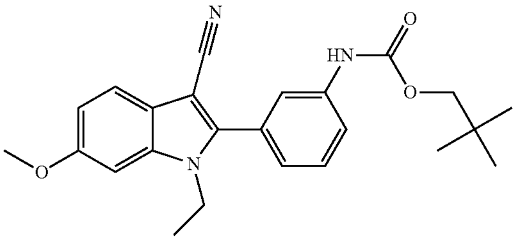
357
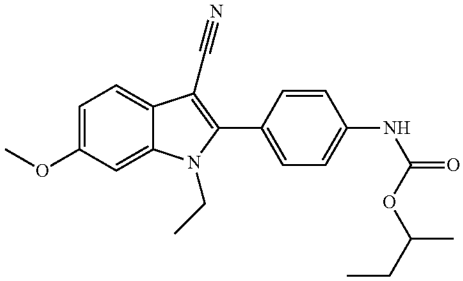
358
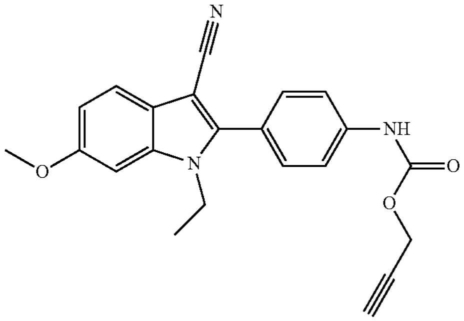
359
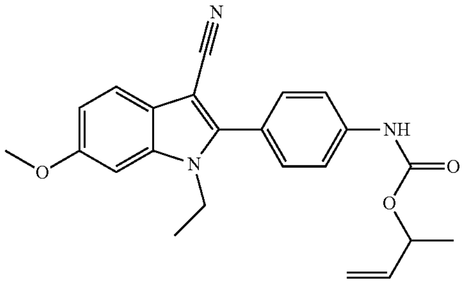
360
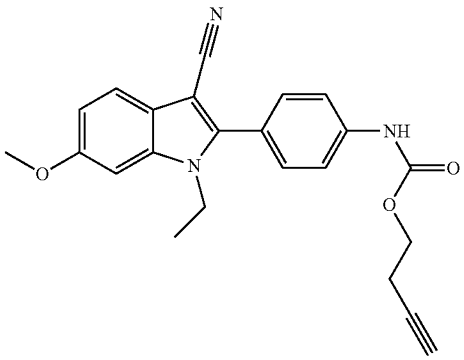

361
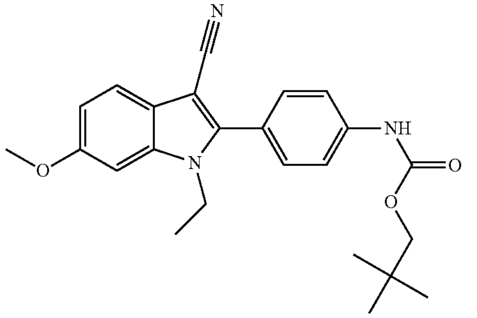
362
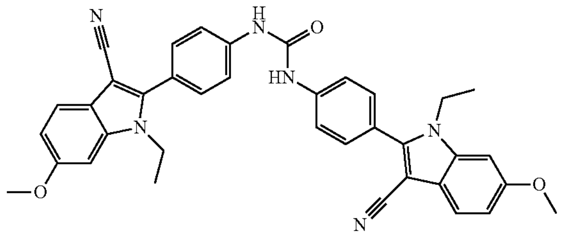
363
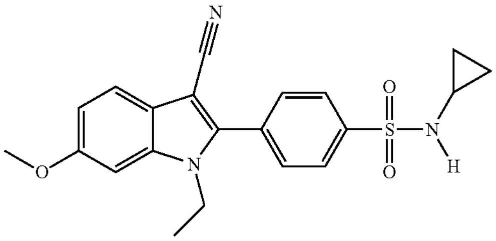
364
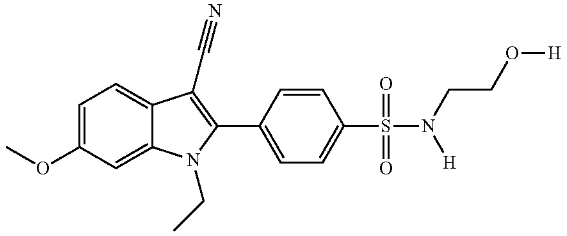
365
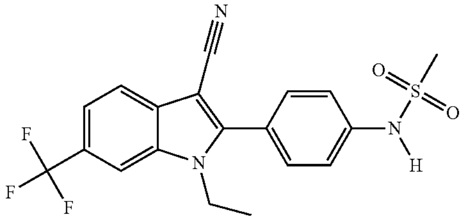
366
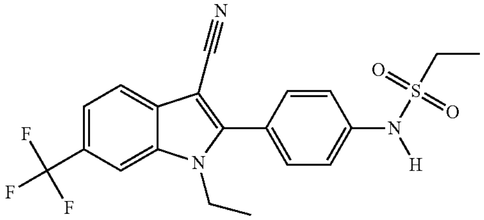
367
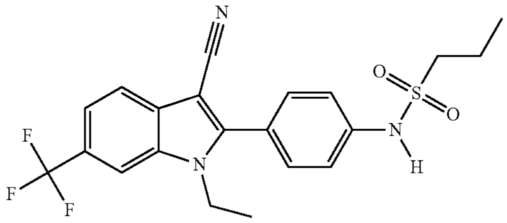
368
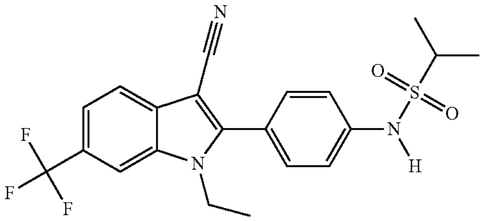
369
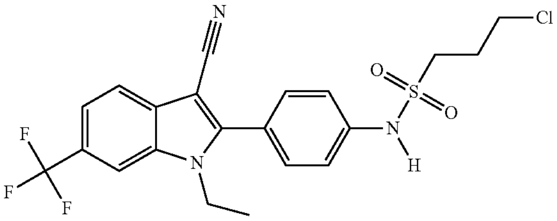
370
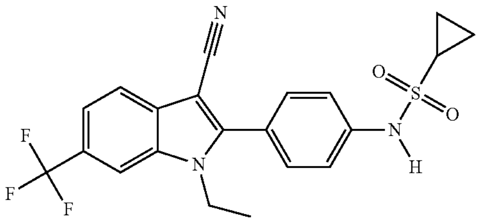
371
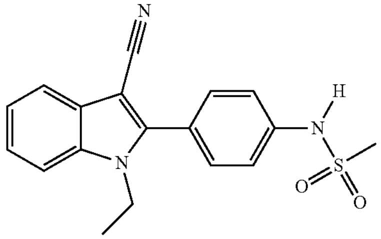
372
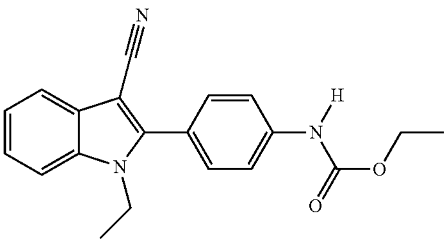

-continued
373
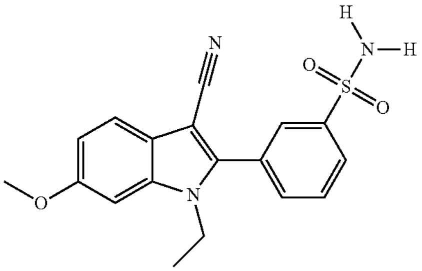
374
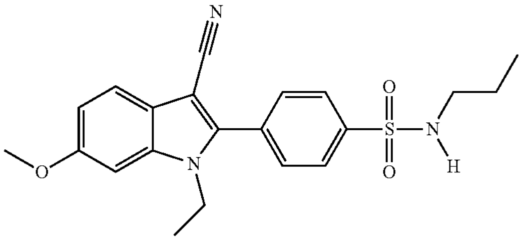
375
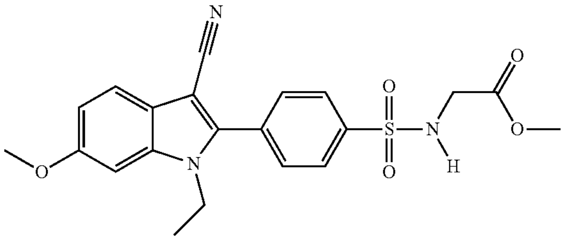
376
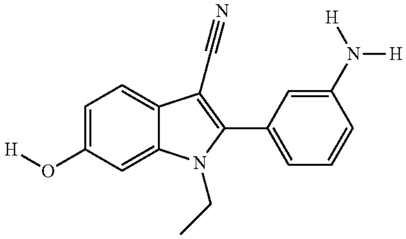
377
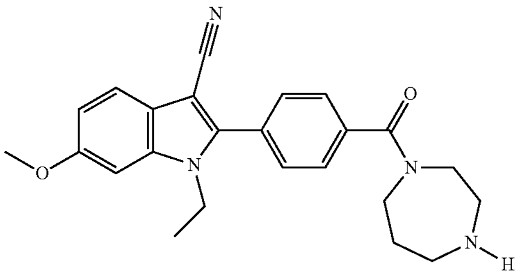
-continued
378
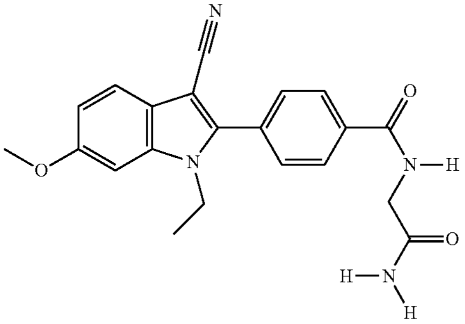
379
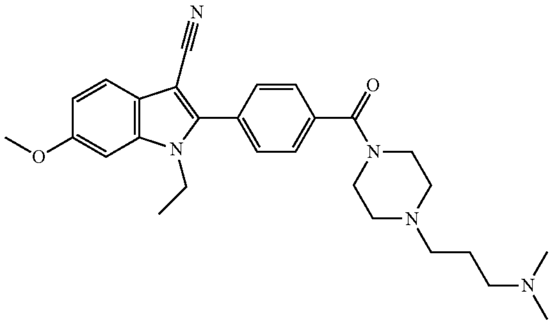
380
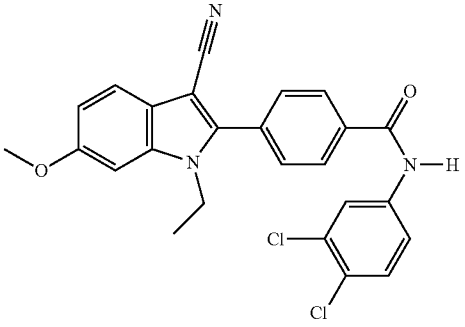
381
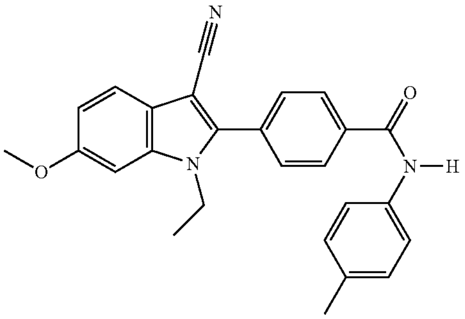

-continued
382
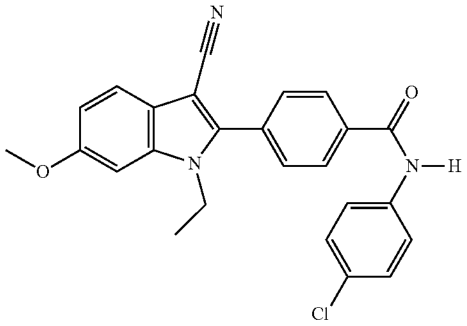
383
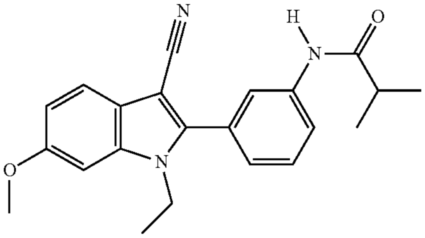
384
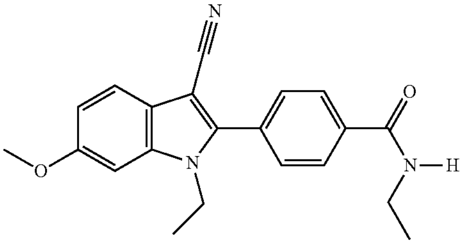
385
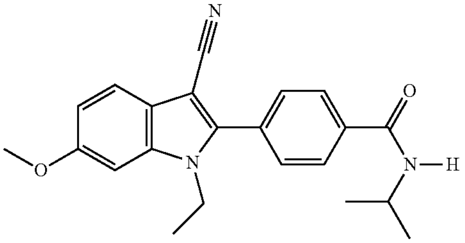
386
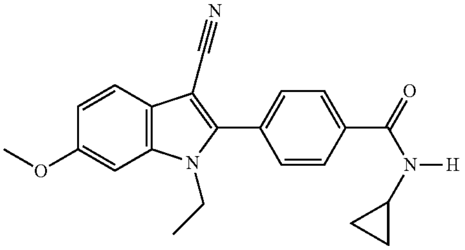
387
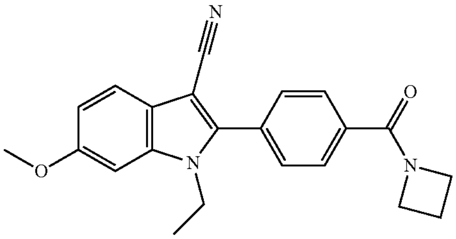
-continued
388
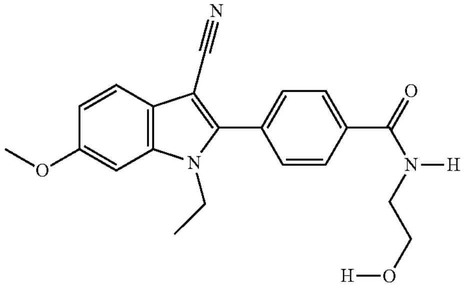
389
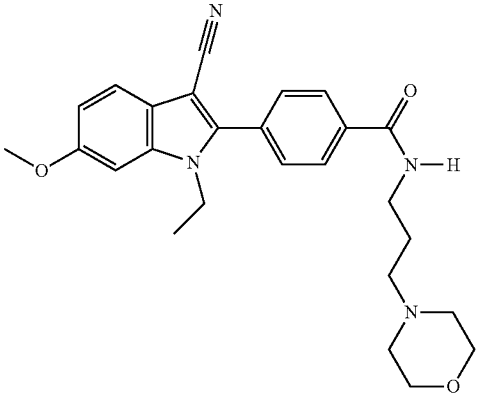
390
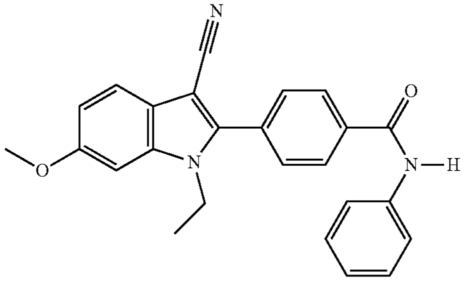
391
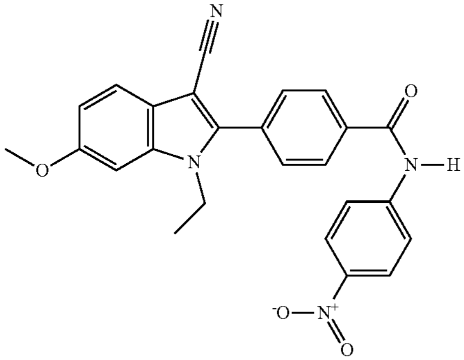

-continued
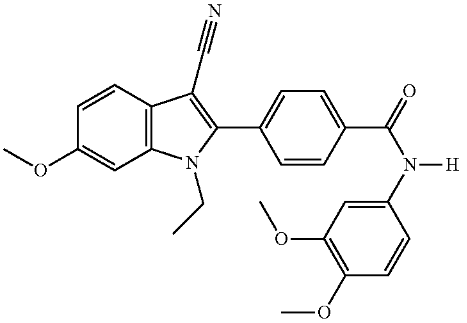
392
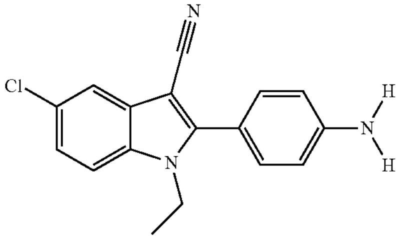
393
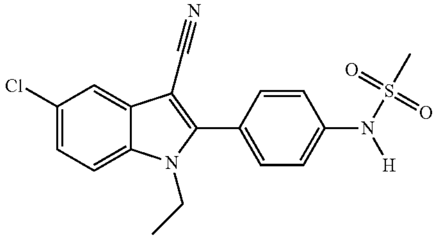
394
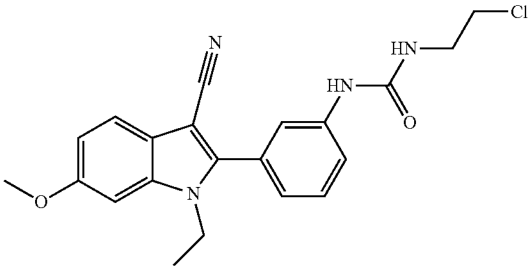
395
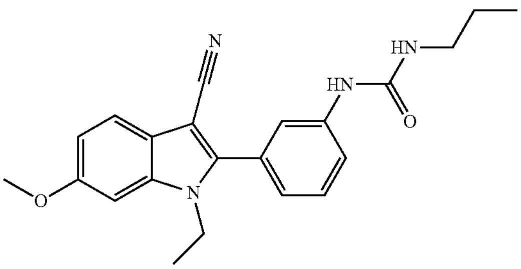
396
-continued
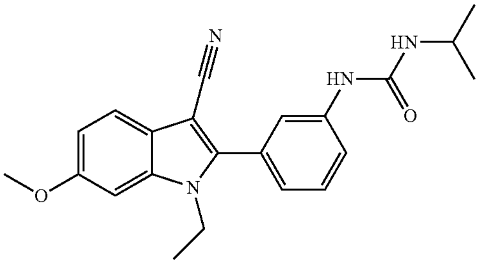
397
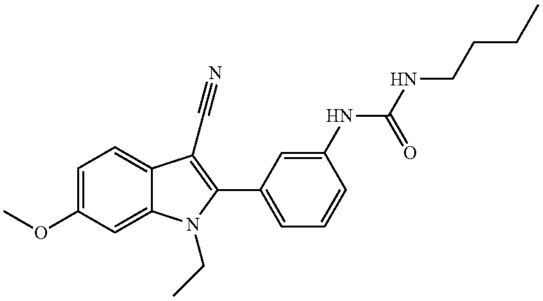
398
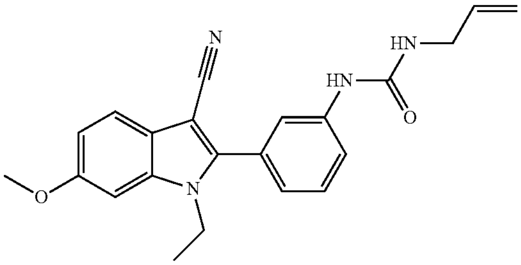
399
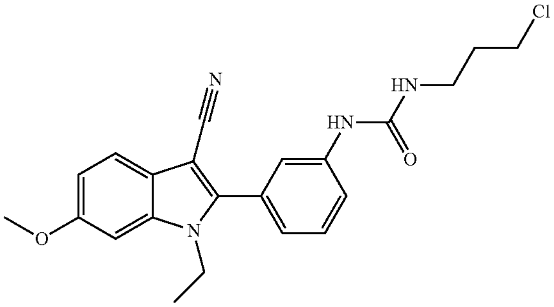
400
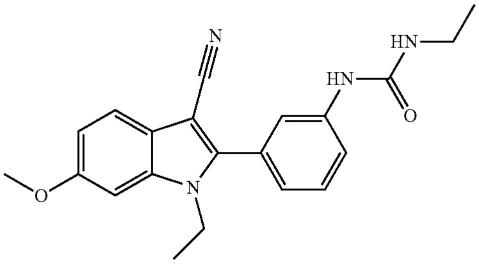
401

-continued
402
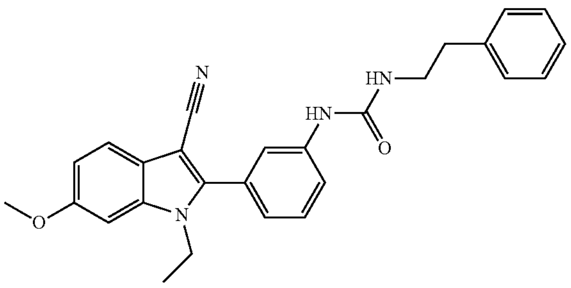
403
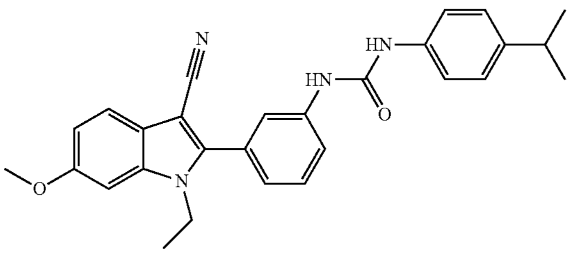
404
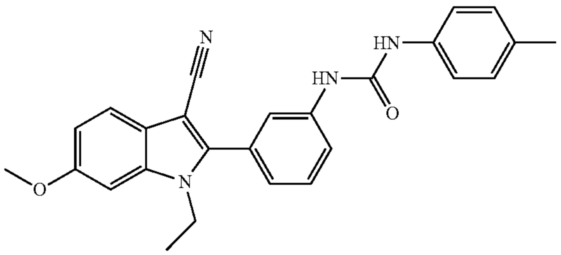
405
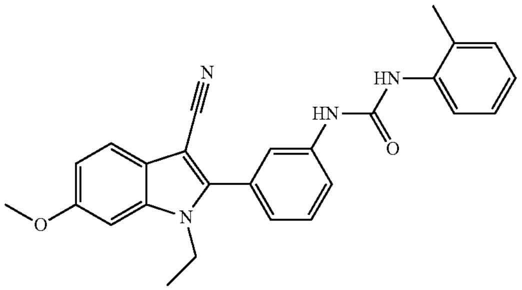
406
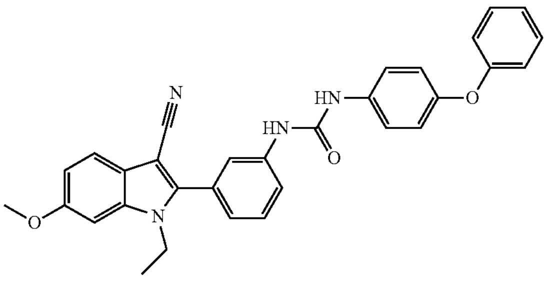
-continued
407
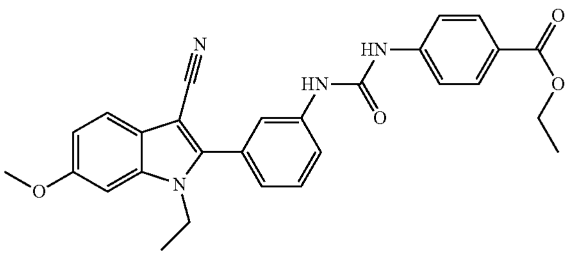
408
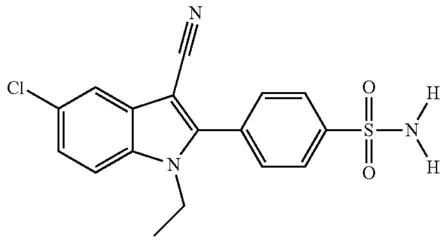
409
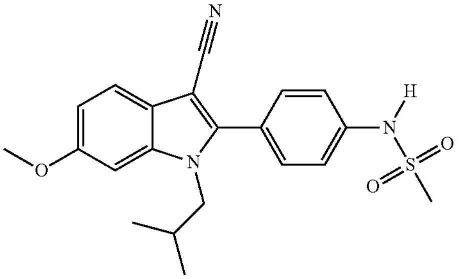
410
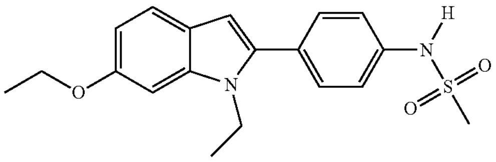
411
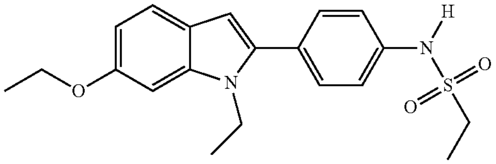
412
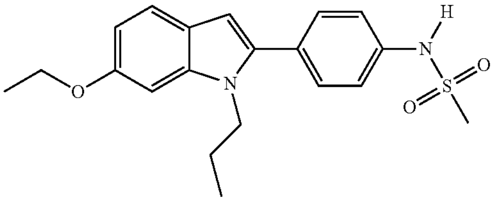
413
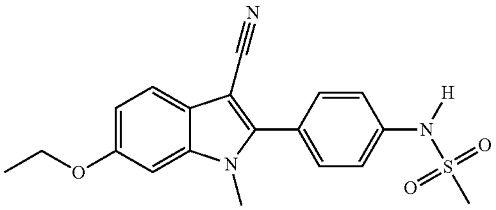

-continued
414
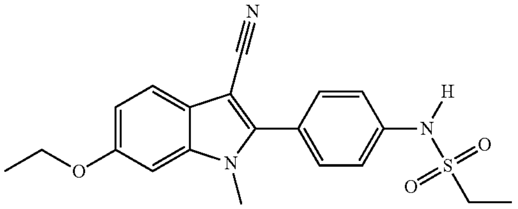
415
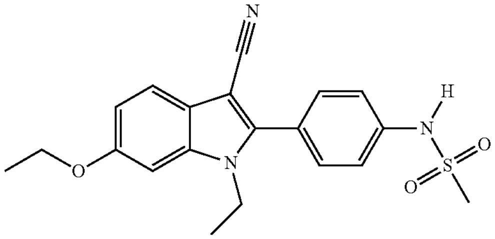
416
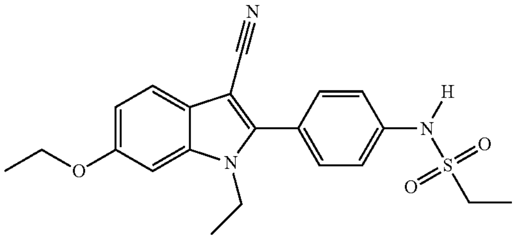
417
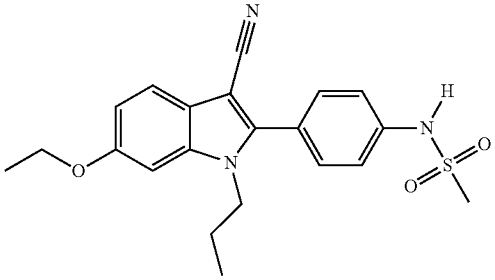
418
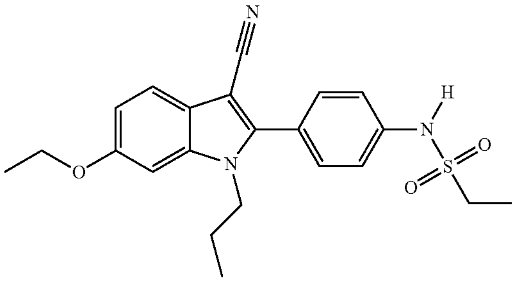
419
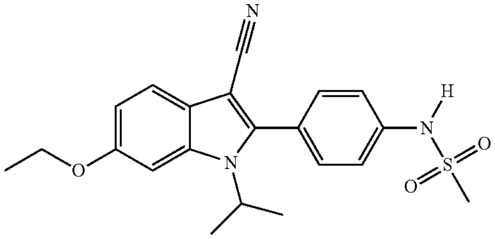
-continued
420
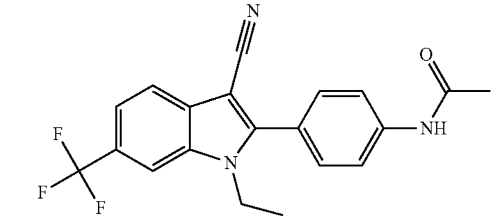
421
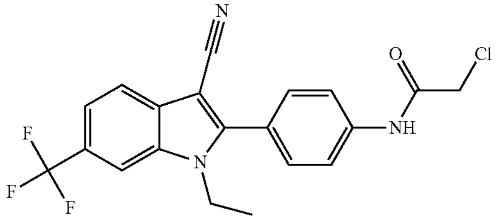
422
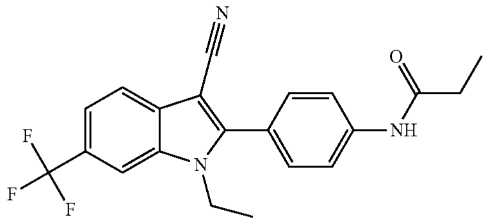
423
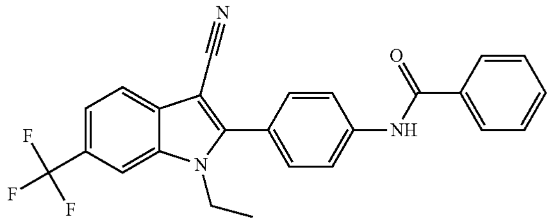
424
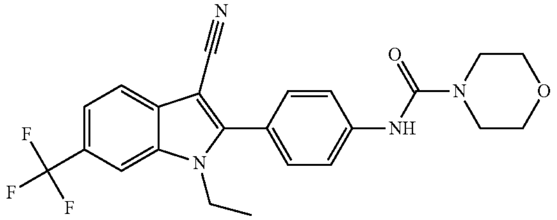
425
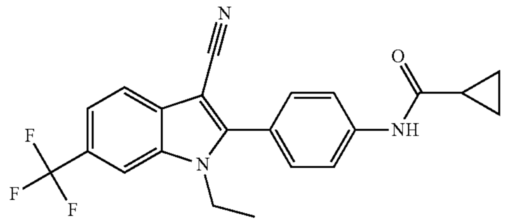
426
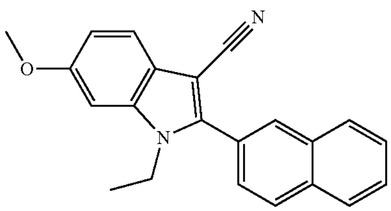

-continued
427
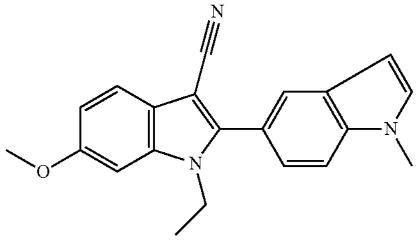
428
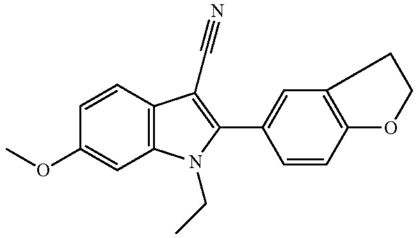
429
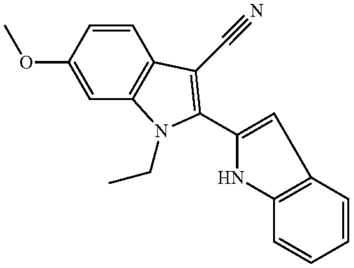
430
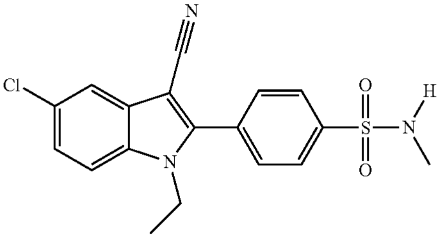
431
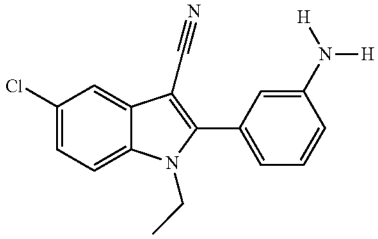
432
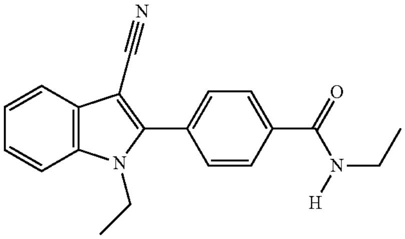
-continued
433
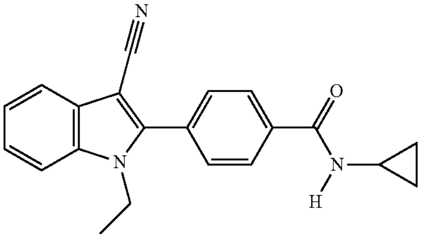
434
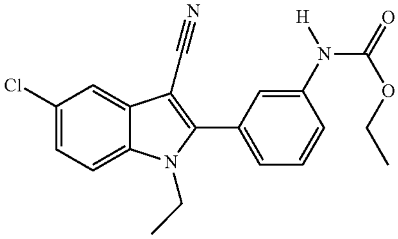
435
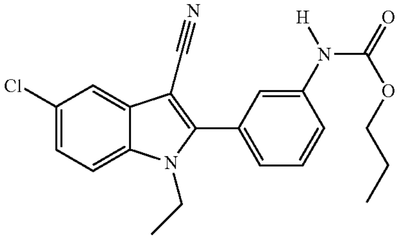
436
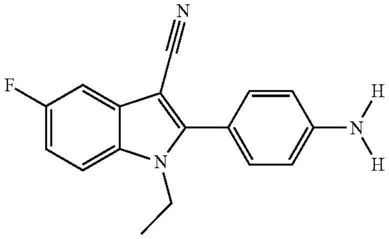
437
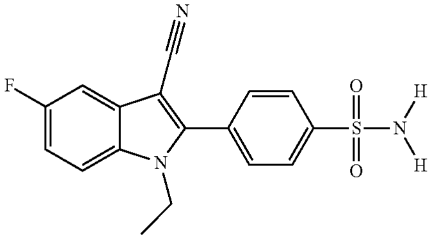
438
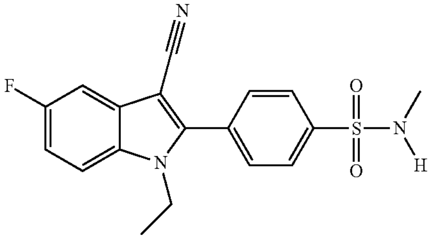

-continued
439
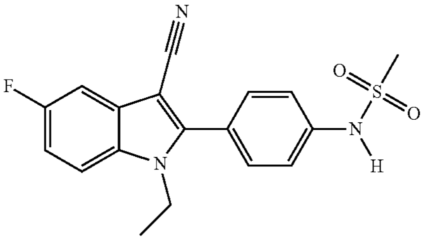
440
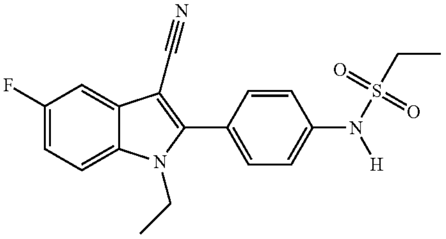
441
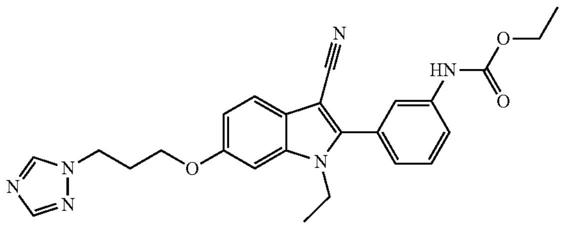
442
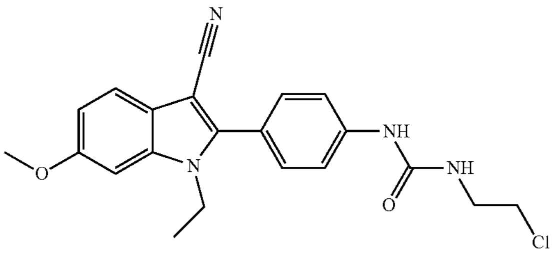
443
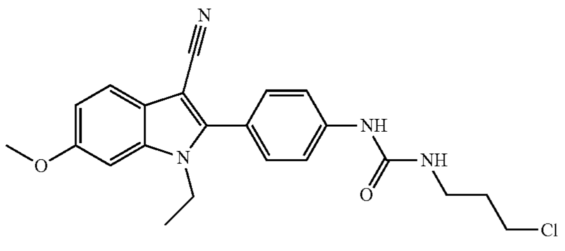
444
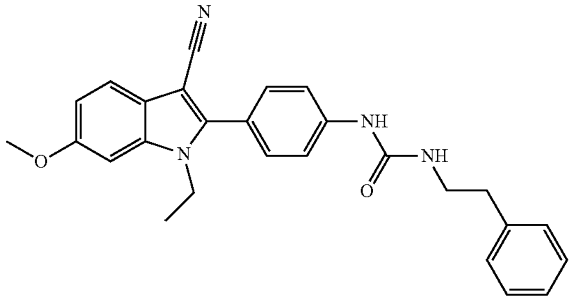
-continued
445
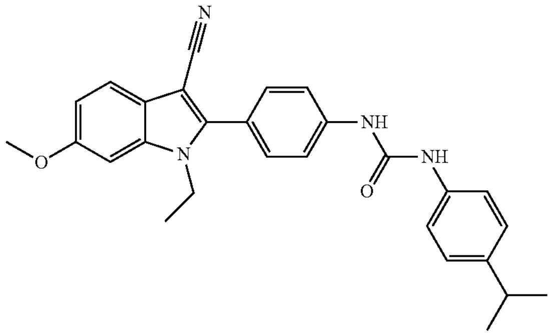
446
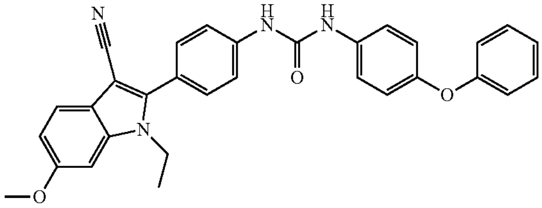
447
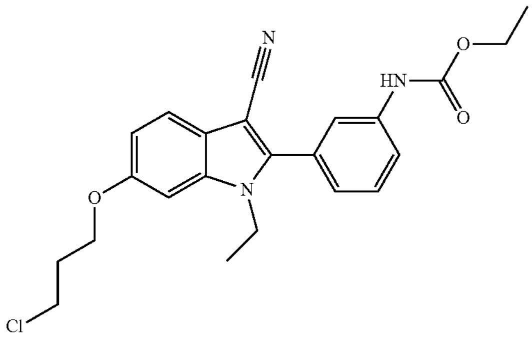
448
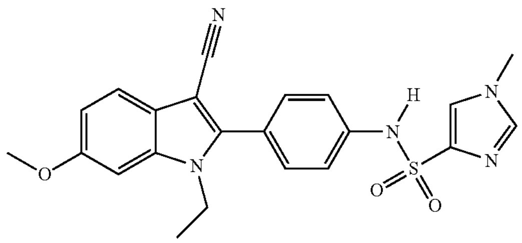
449
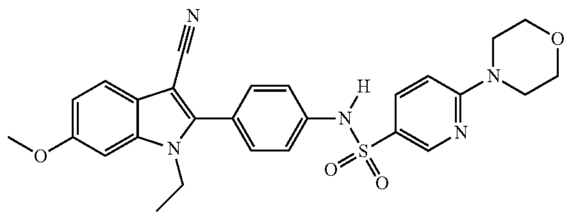

-continued
450
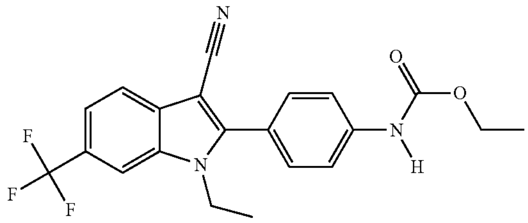
451
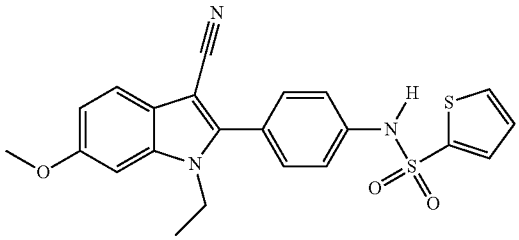
452
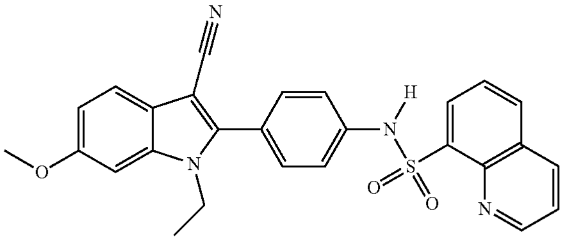
453
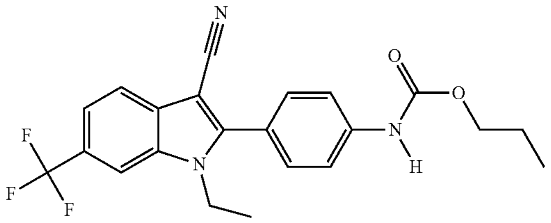
454
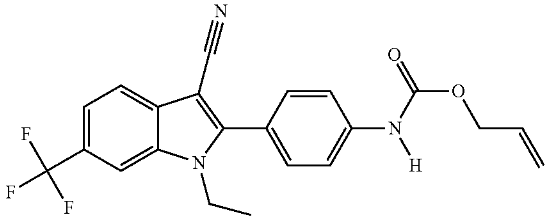
455
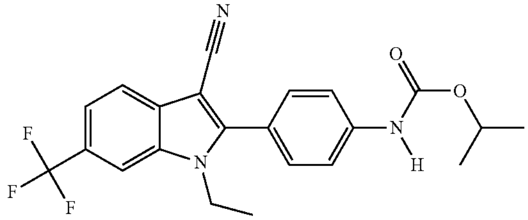
-continued
456
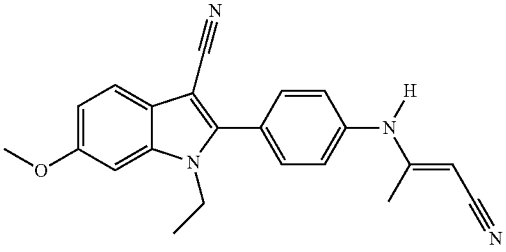
457
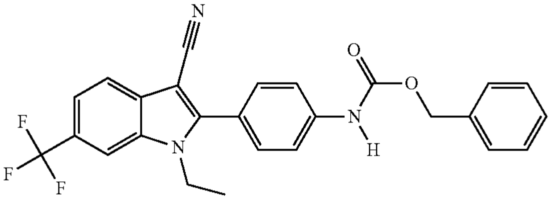
458
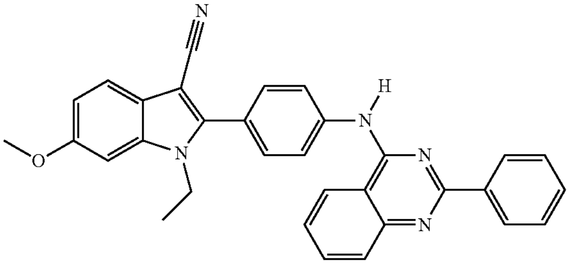
459
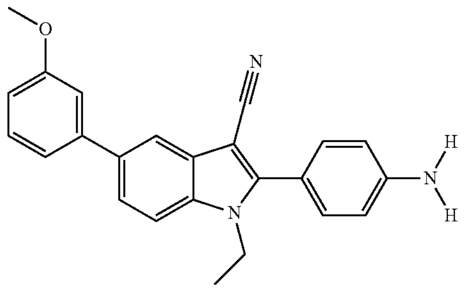
460
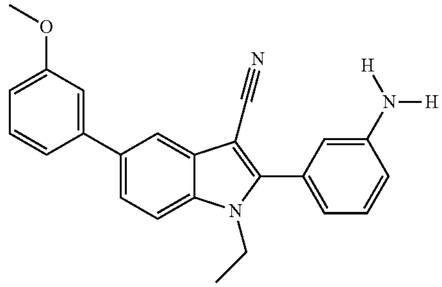

-continued
461
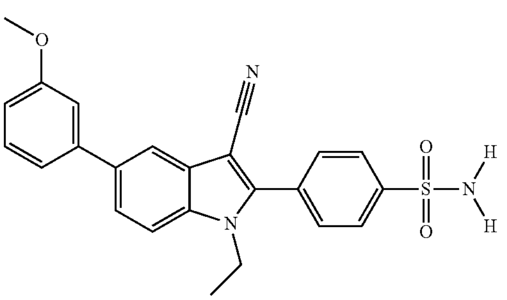
462
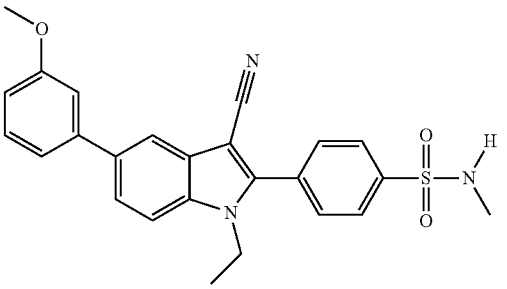
463
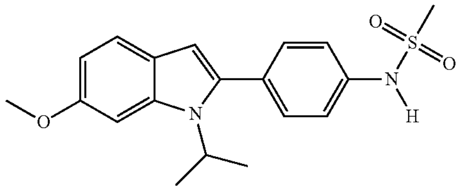
464
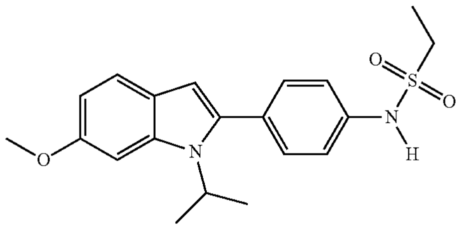
465
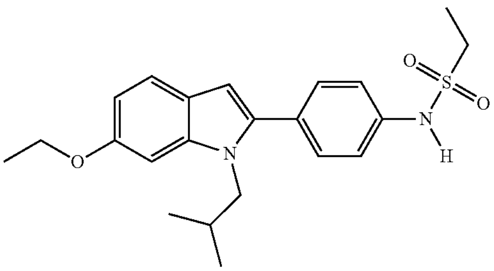
466
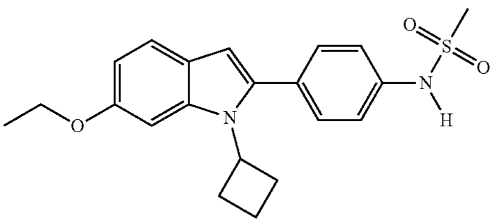
-continued
467
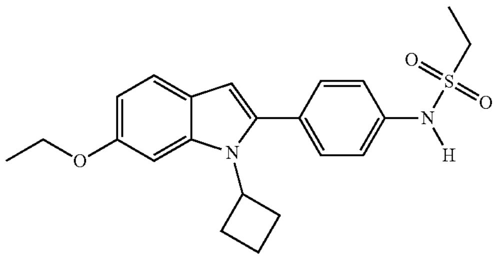
468
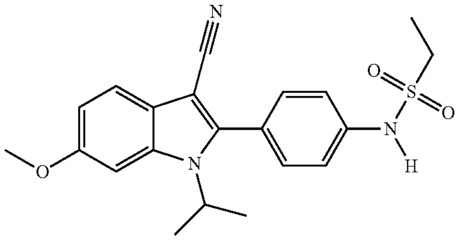
469
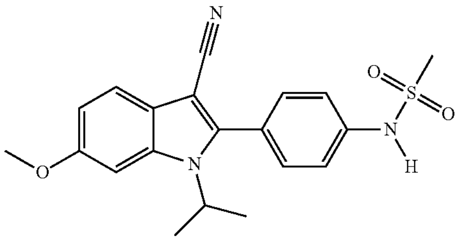
470
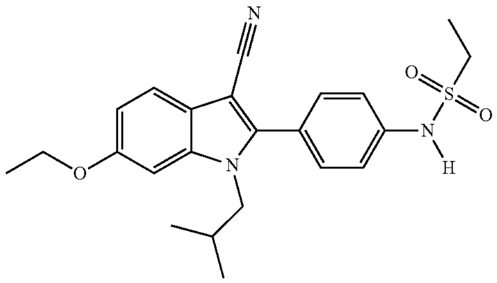
471
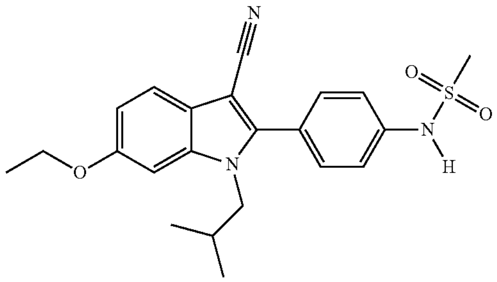
472
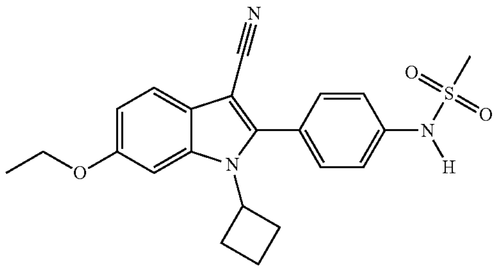

-continued
473
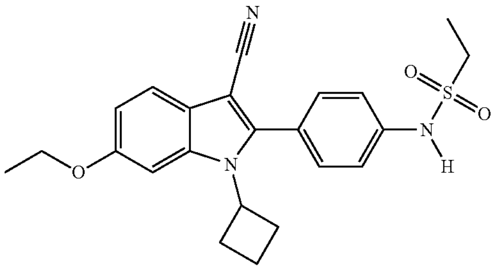
474
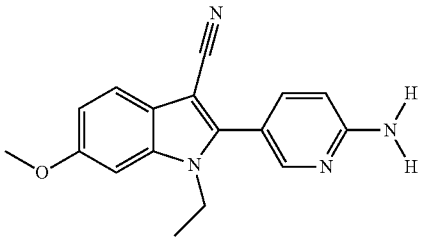
475
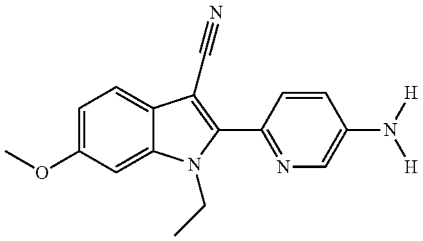
476
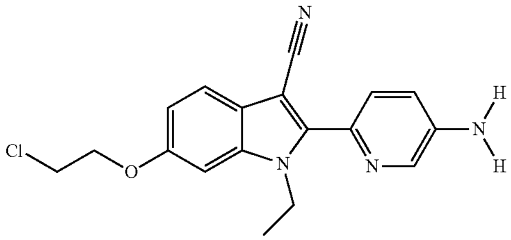
477
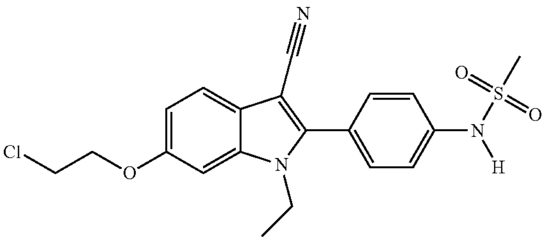
478
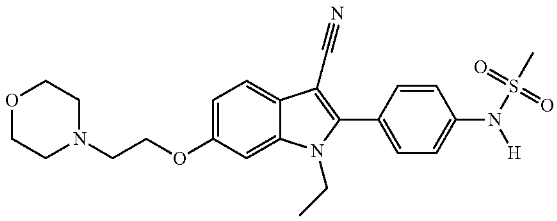
-continued
479
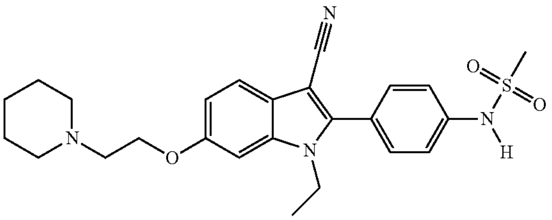
480
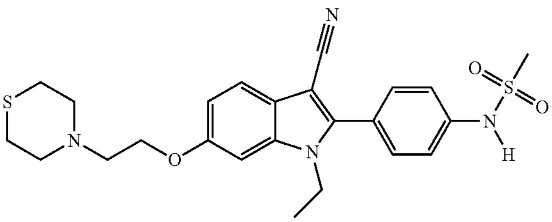
481
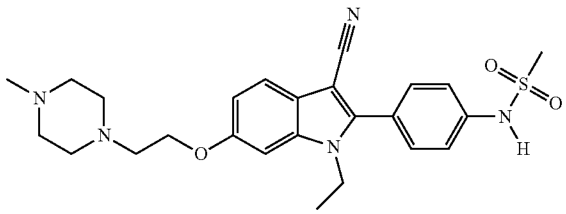
482
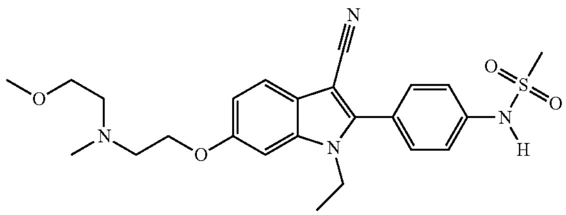
483
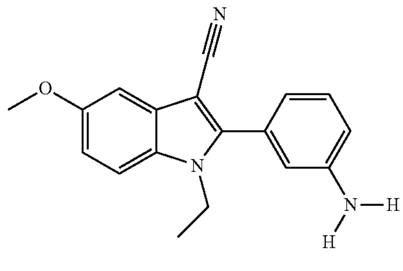
484
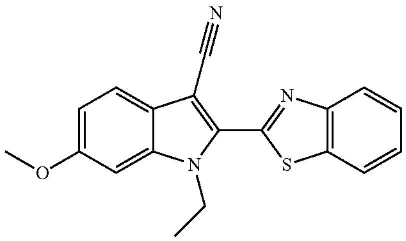

-continued
485
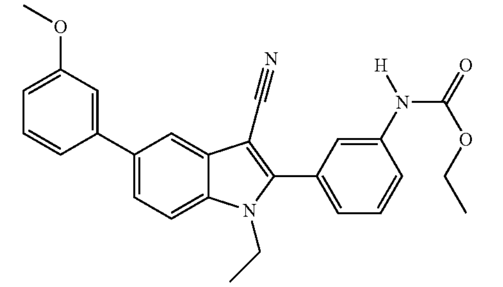
486
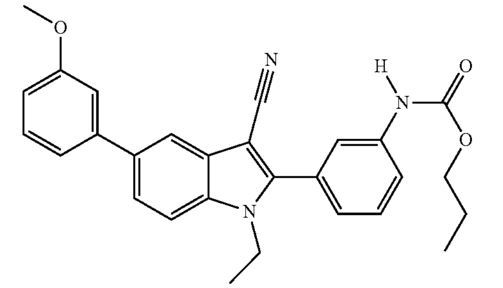
487
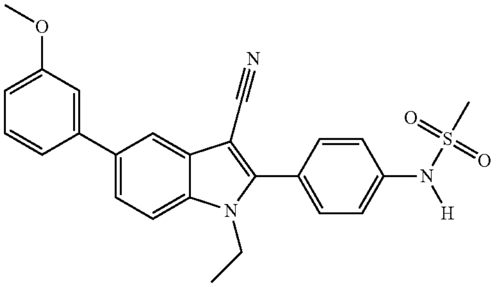
488
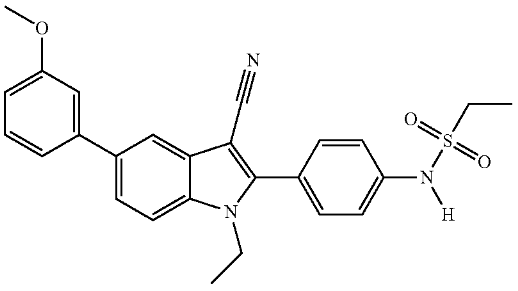
489
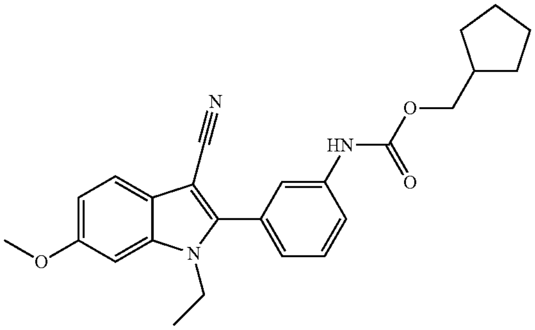
-continued
490
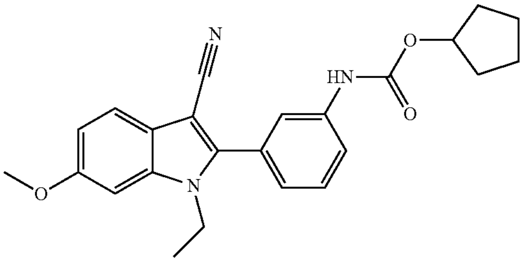
491
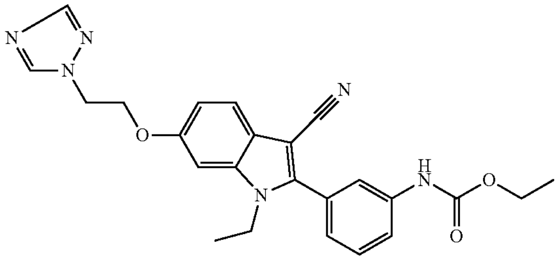
492
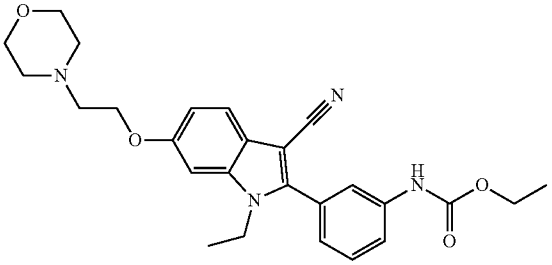
493
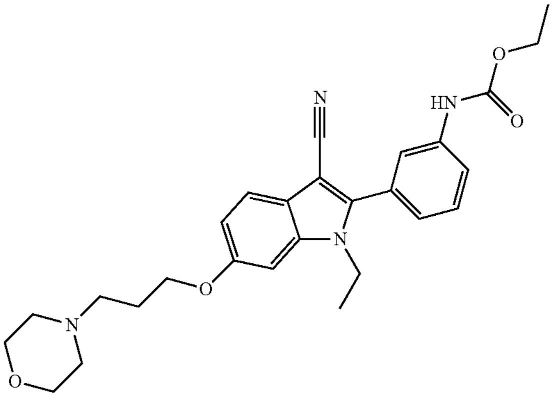
494
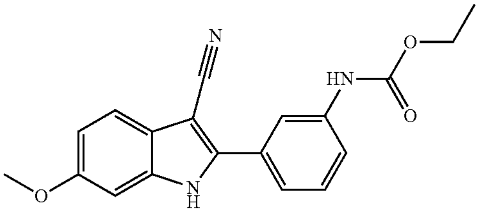

-continued
495
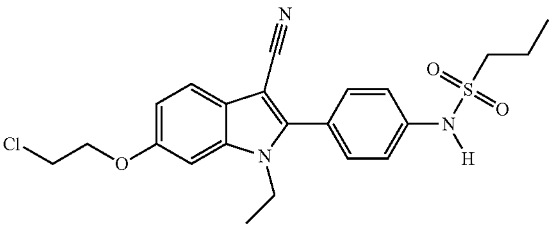
496
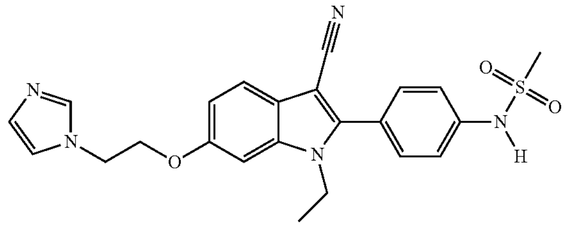
497
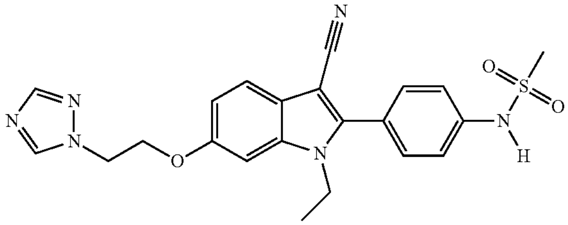
498
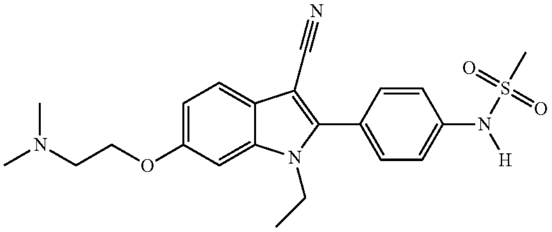
499
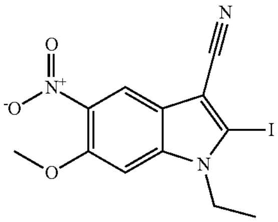
500
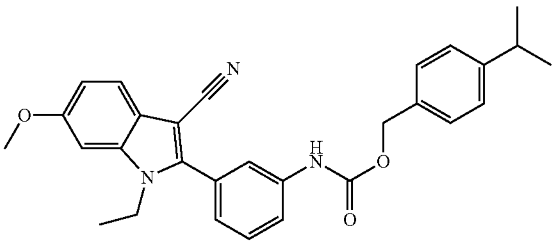
-continued
501
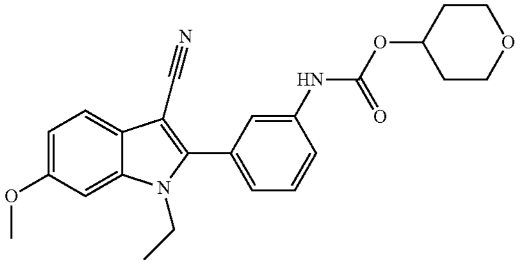
502
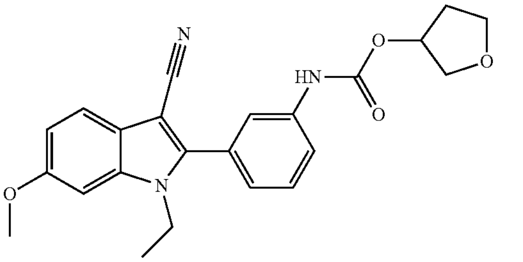
503
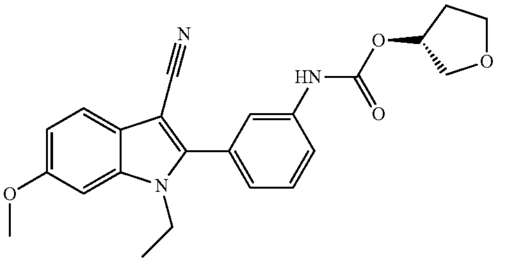
504
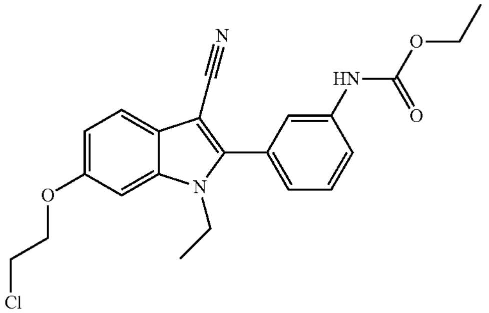
505
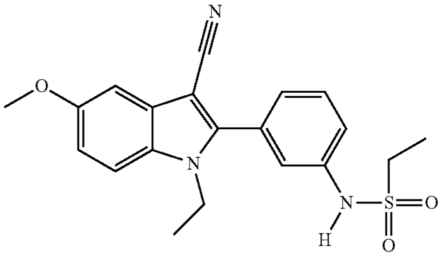
506
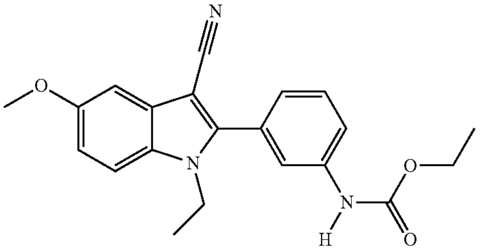

-continued
507
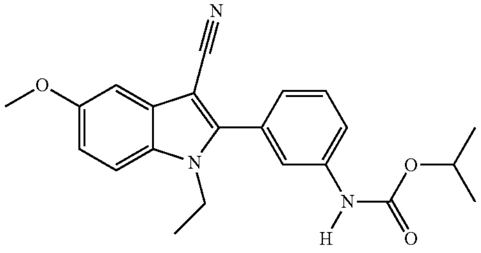
508
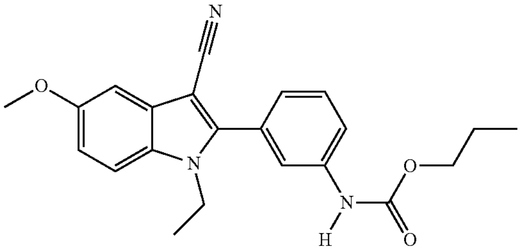
509
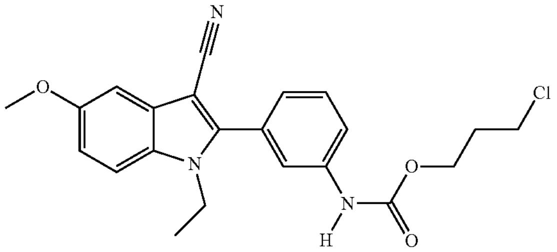
510
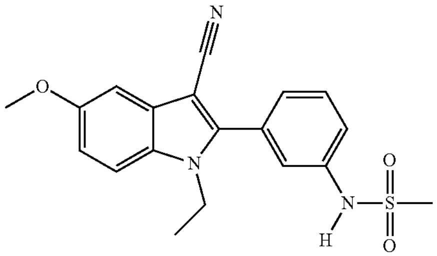
511
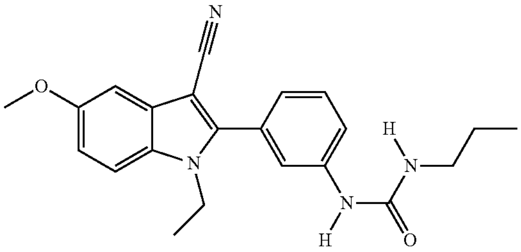
512
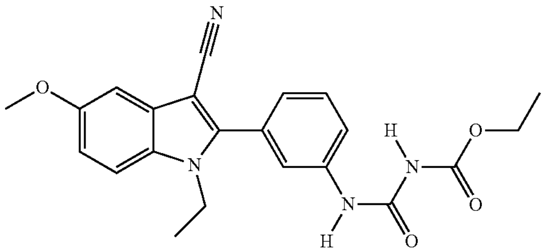
-continued
513
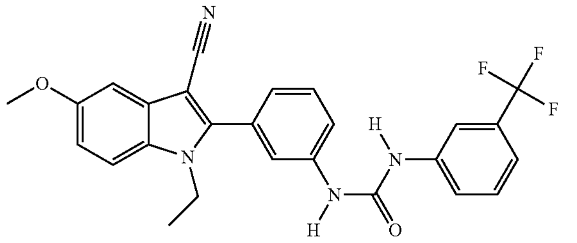
514
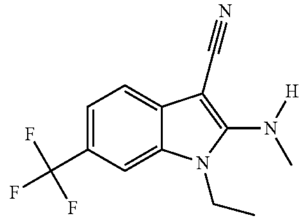
515
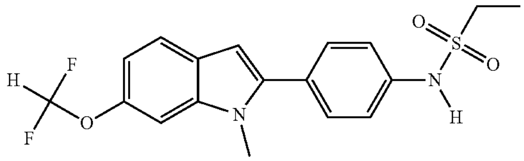
516
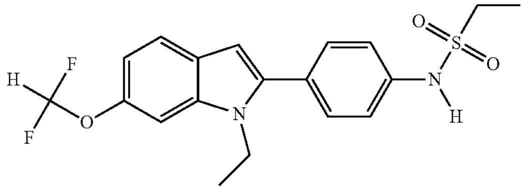
517
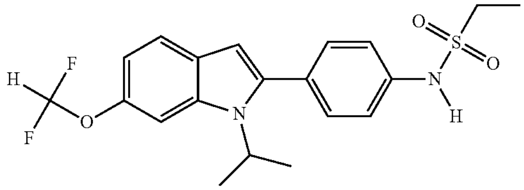
518
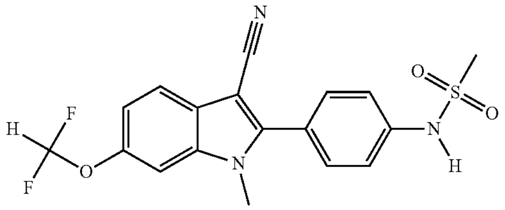
519
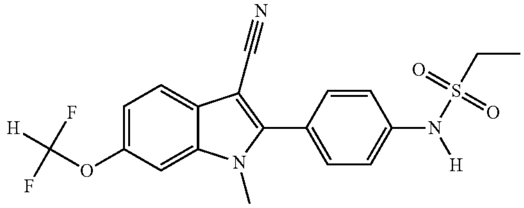

-continued
520
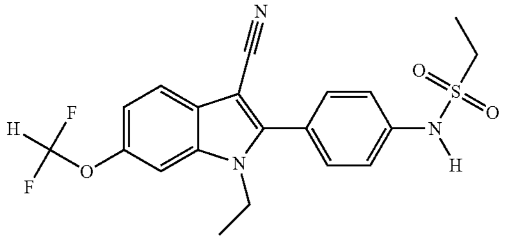
521
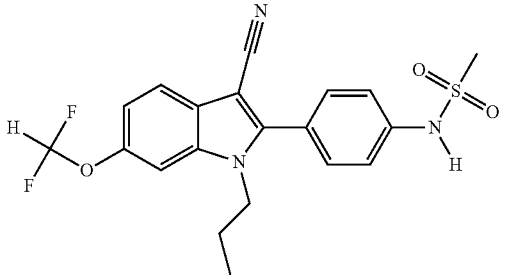
522
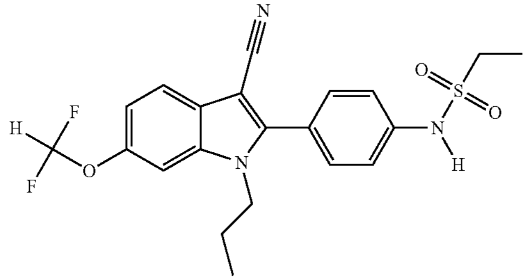
523
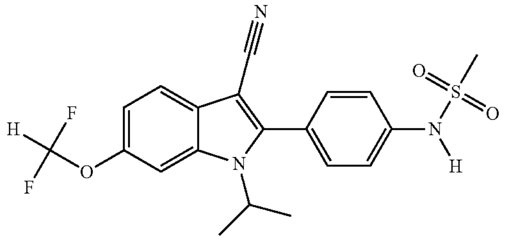
524
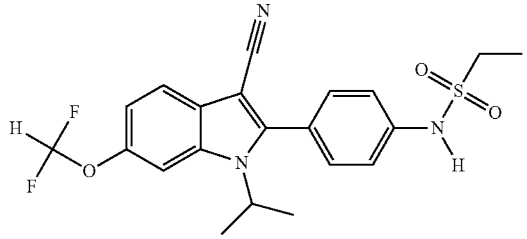
-continued
525
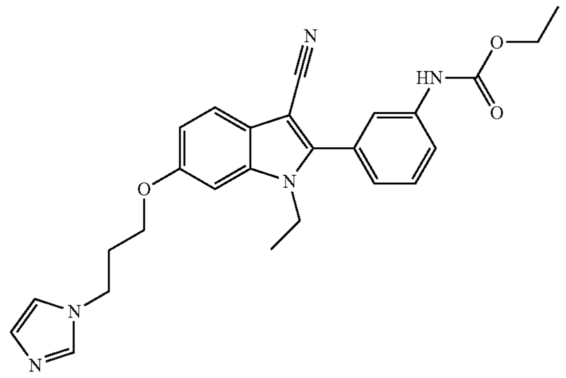
526
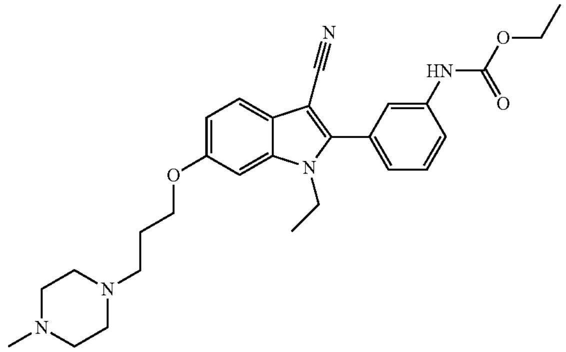
527
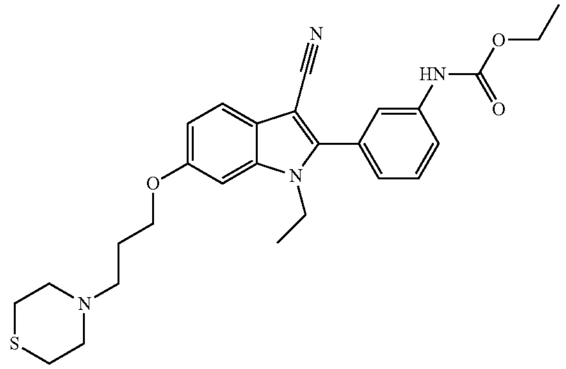
528
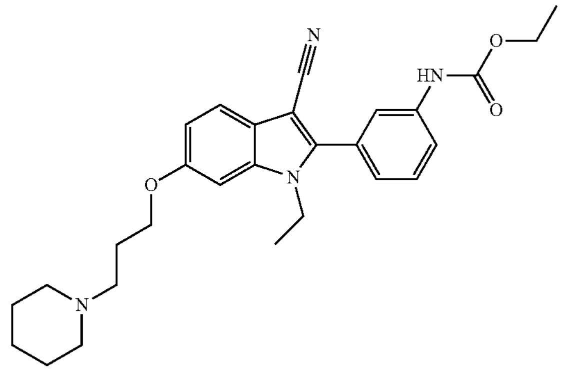

-continued
529
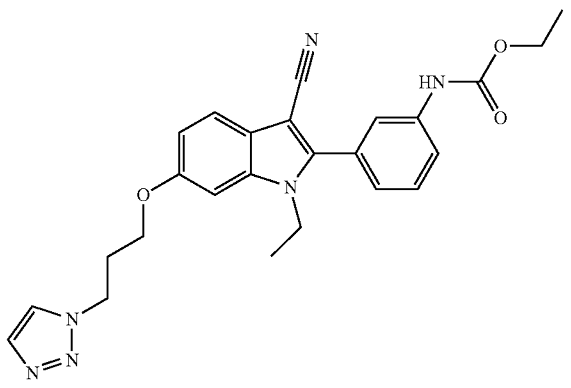
530
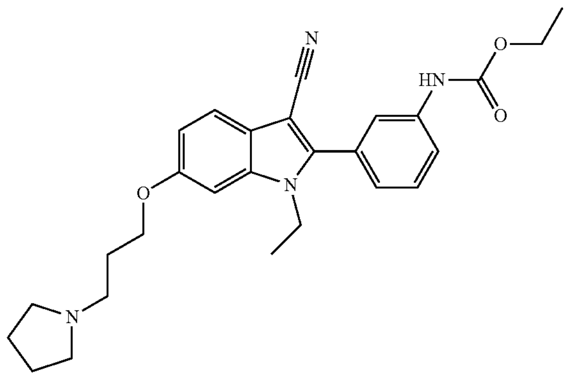
531
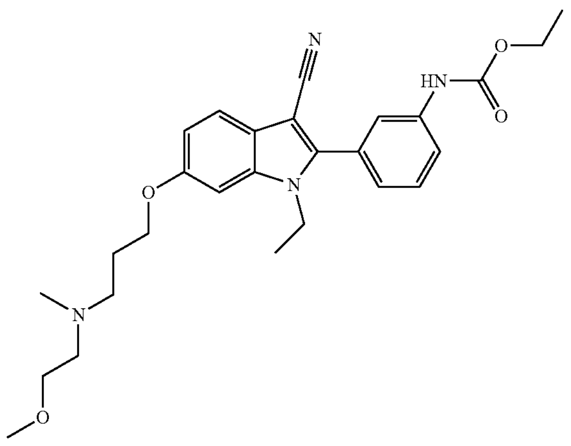
532
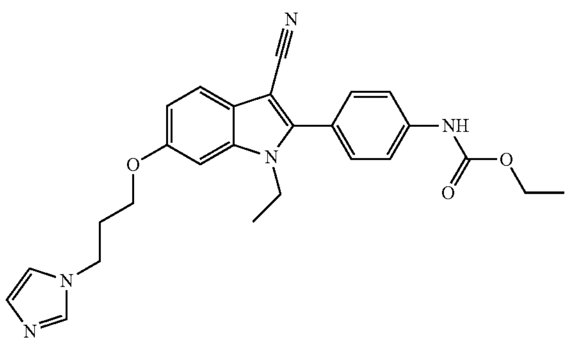
-continued
533
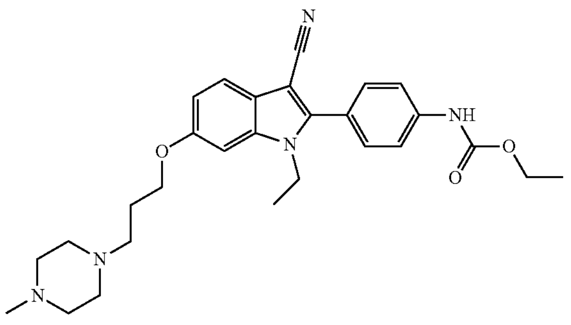
534
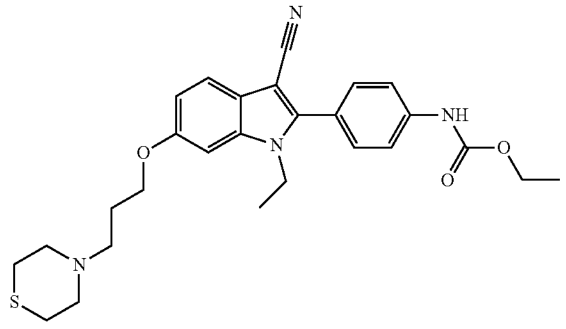
535
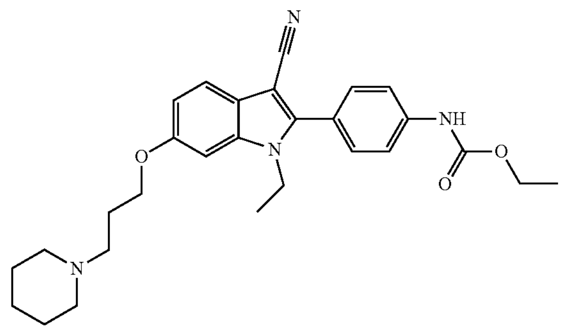
536
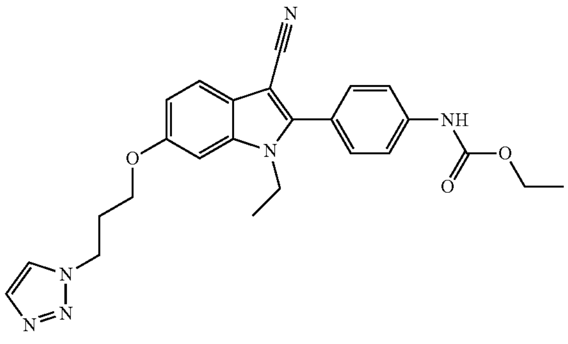

-continued
537
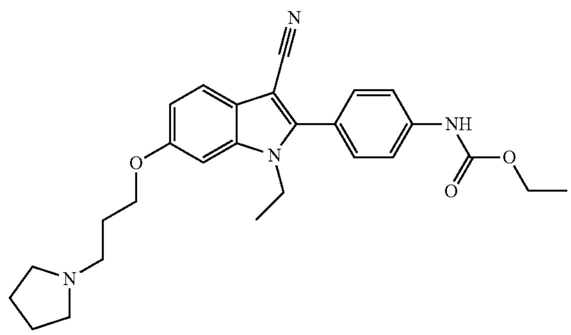
538
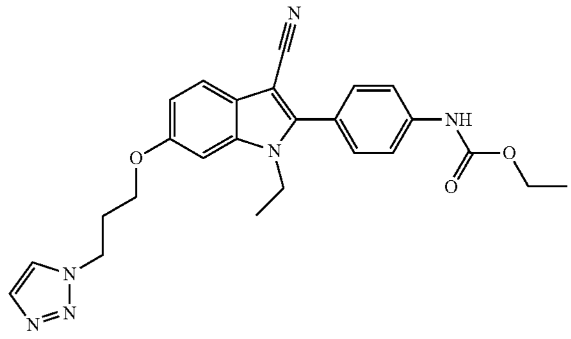
539
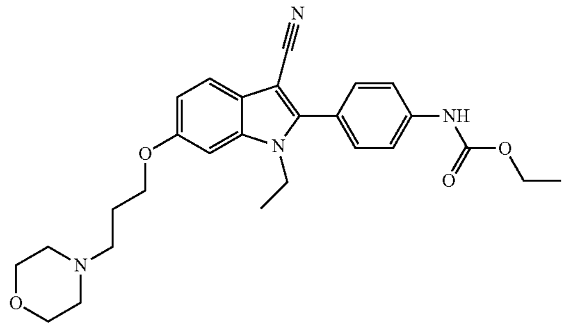
540
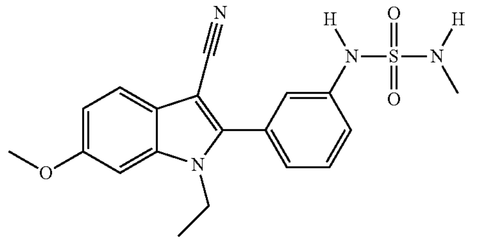
541
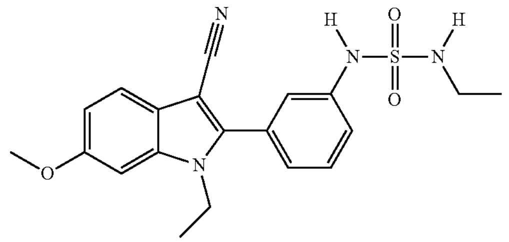
-continued
542
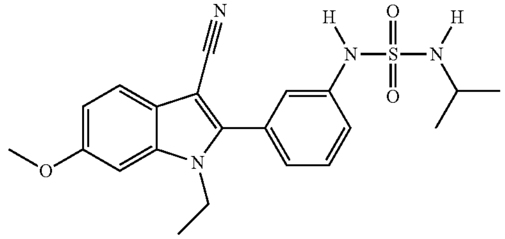
543
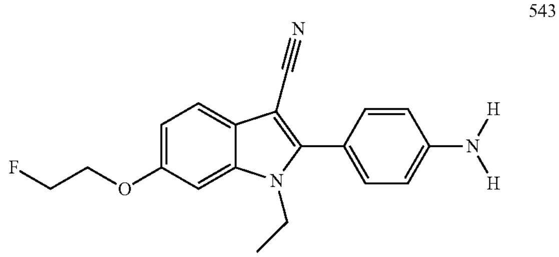
544
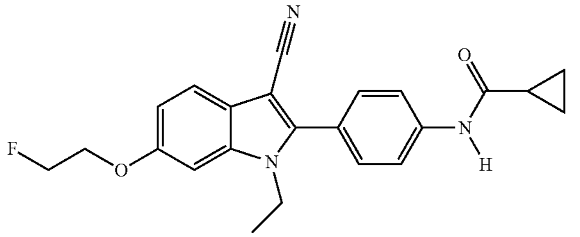
545
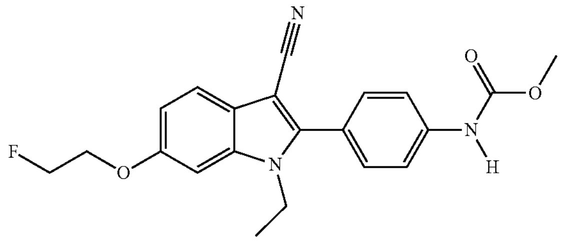
546
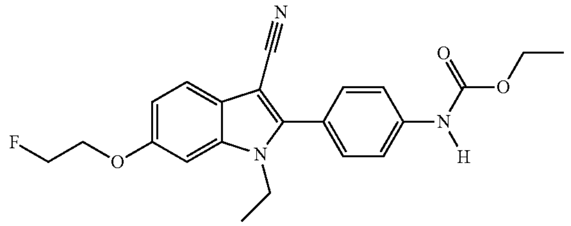
547
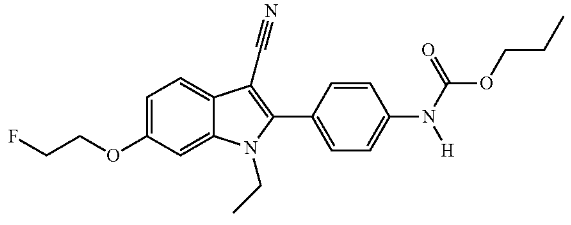

-continued
548
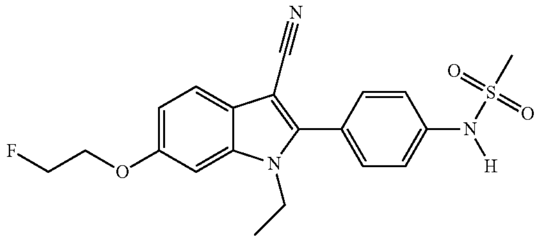
549
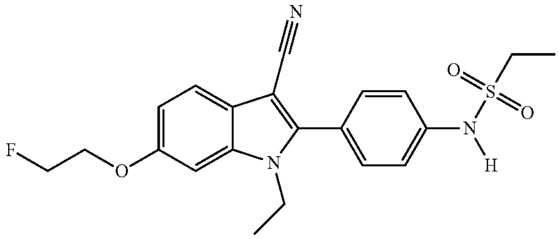
550
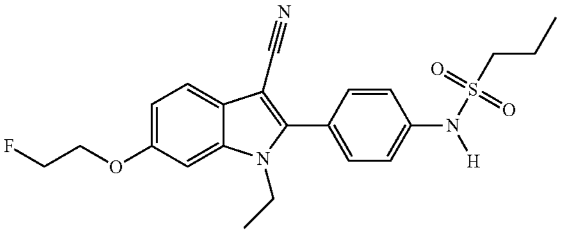
551
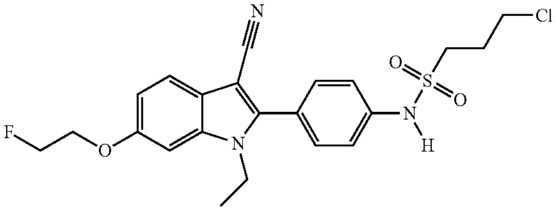
552
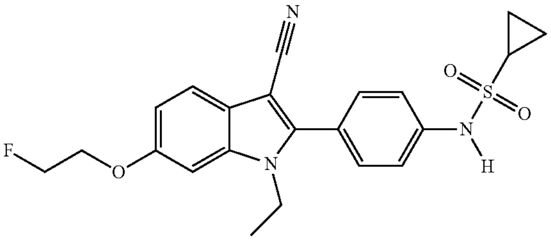
553
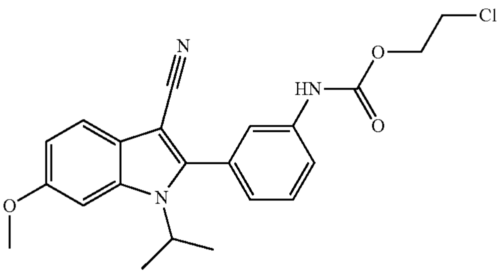
-continued
554
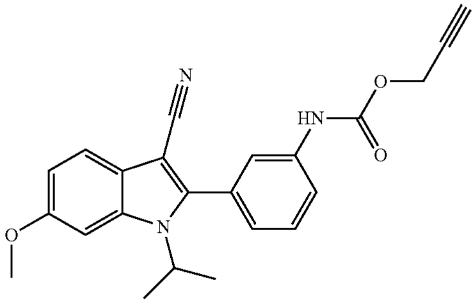
555
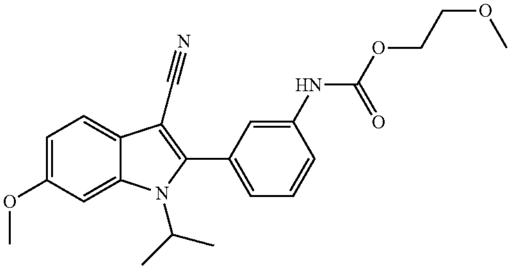
556
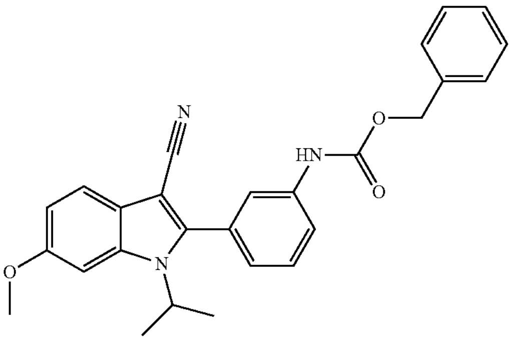
557
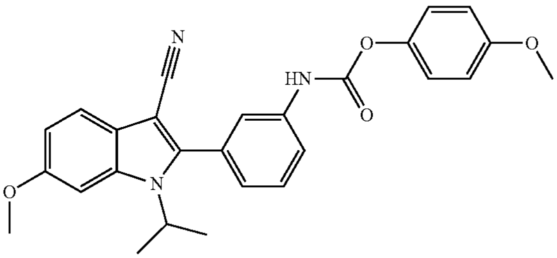
558
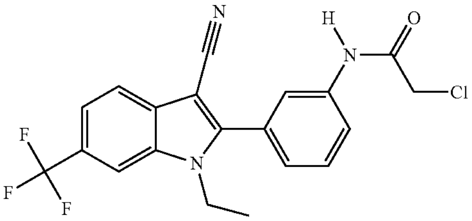

-continued
559
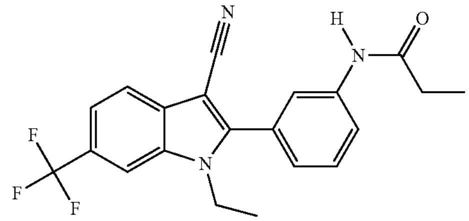
560
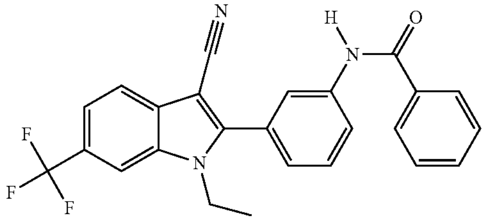
561
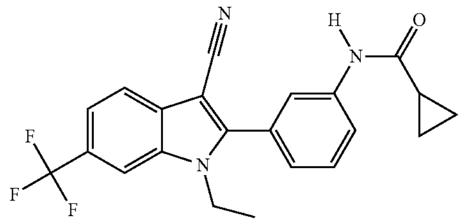
562
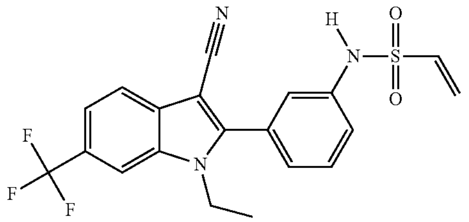
563
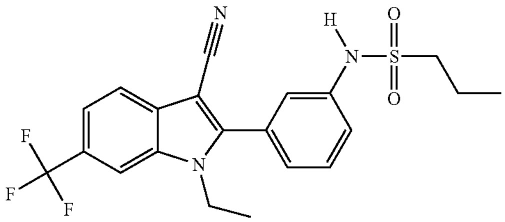
564
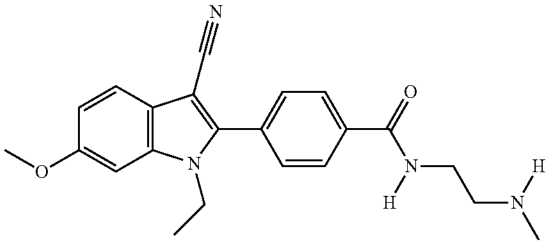
-continued
565
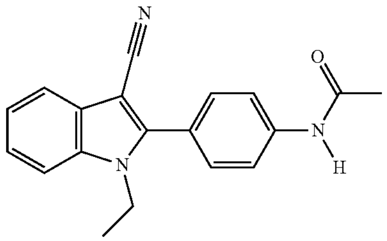
566
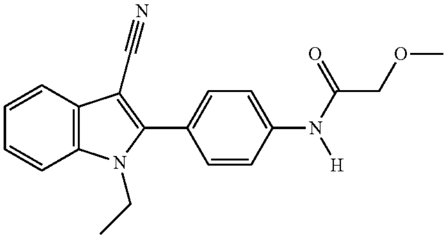
567
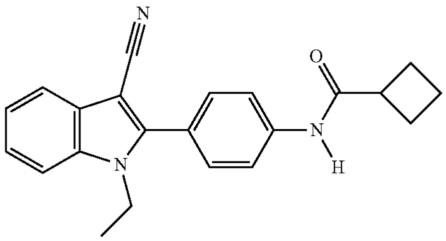
568
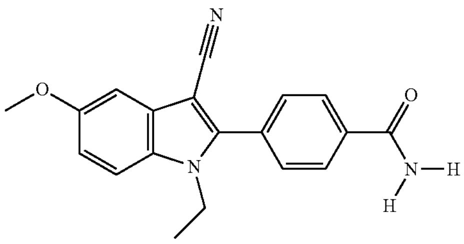
569
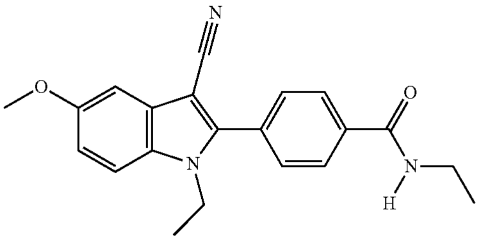
570
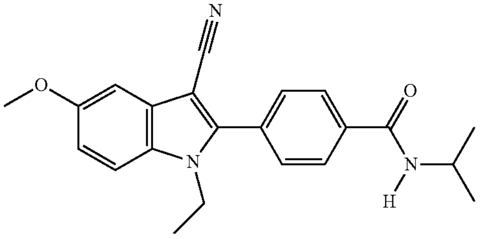

-continued
571
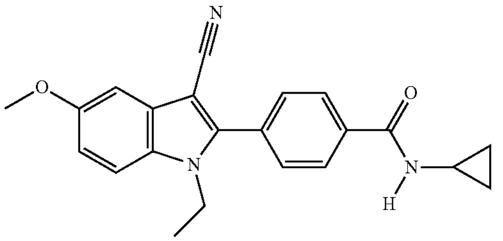
572
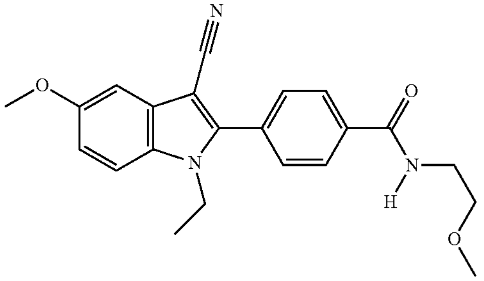
573
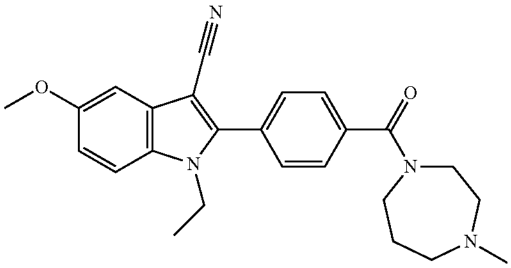
574
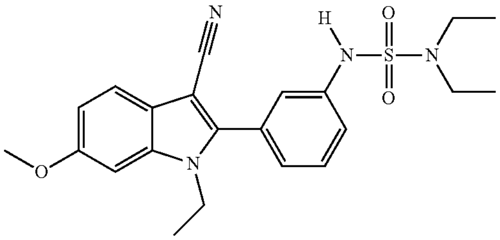
575
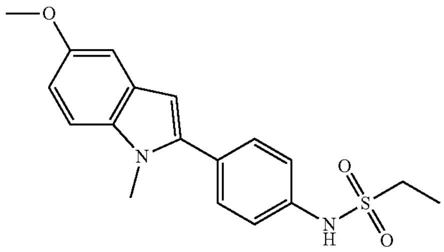
576
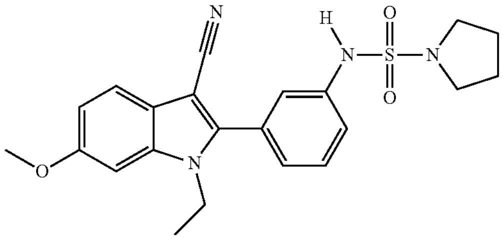
-continued
577
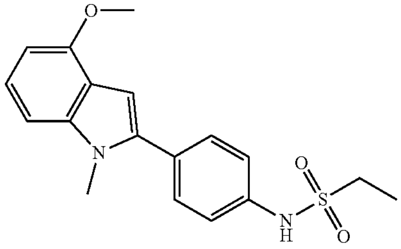
578
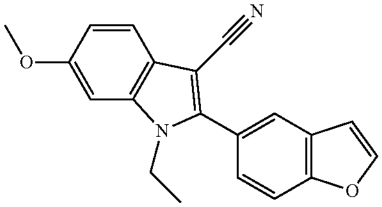
579
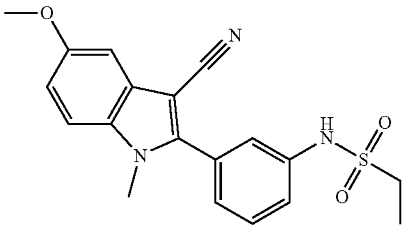
580
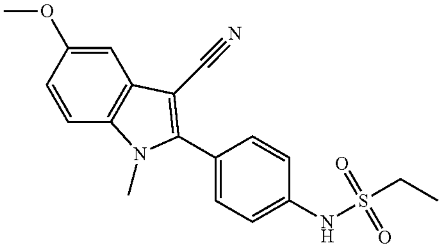
581
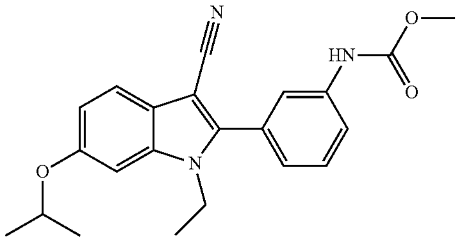
582
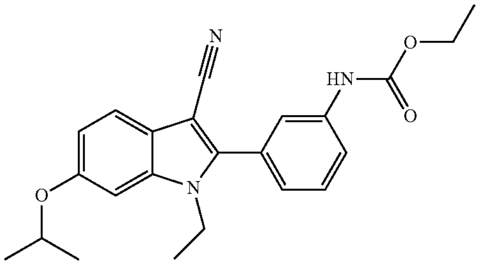

-continued
583
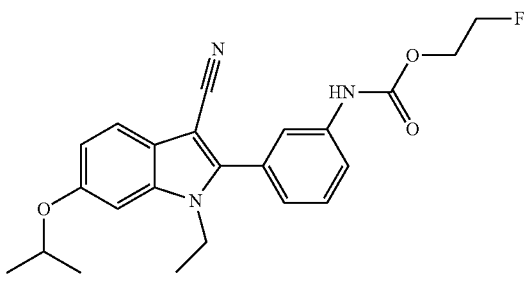
584
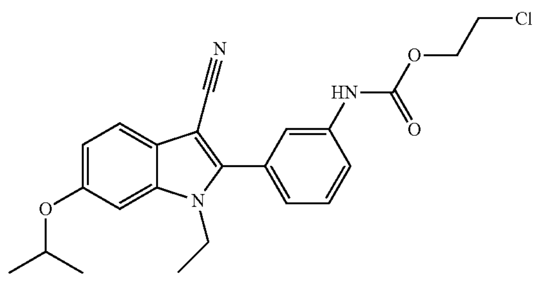
585
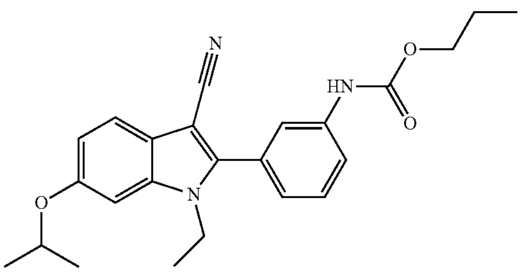
586
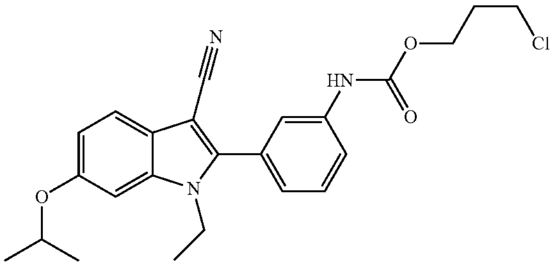
587
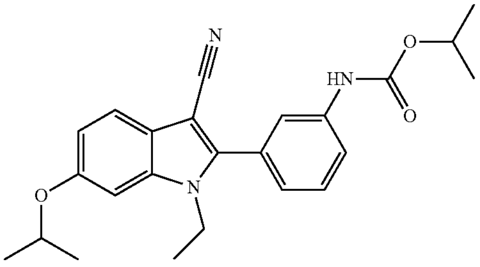
-continued
588
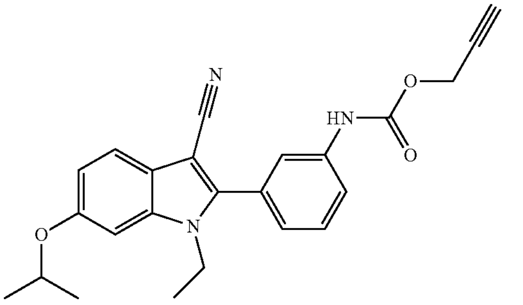
589
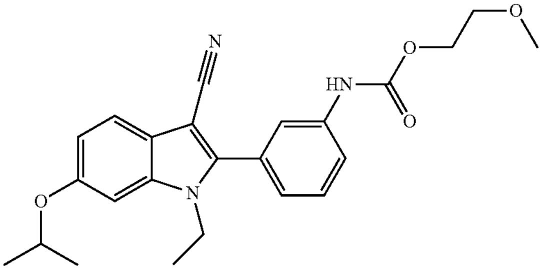
590
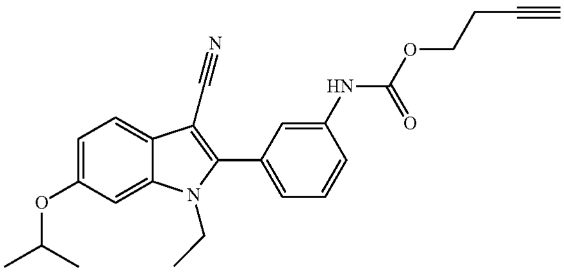
591
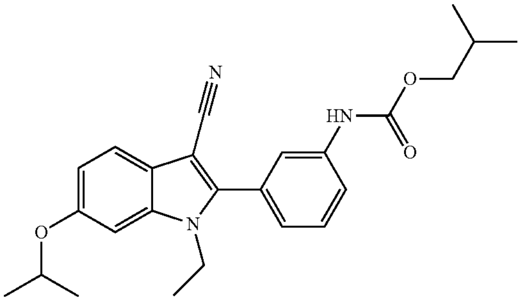
592
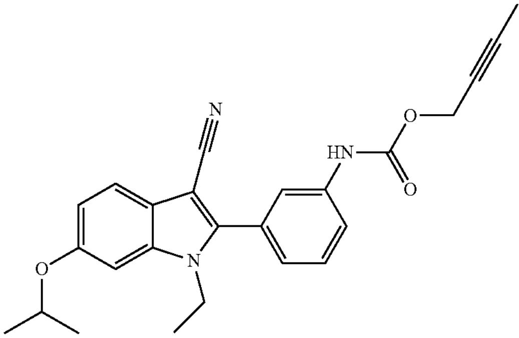

-continued
593
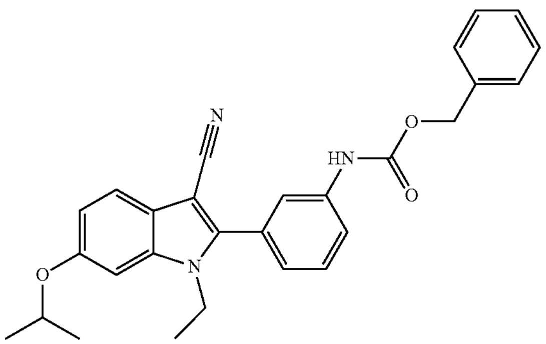
594
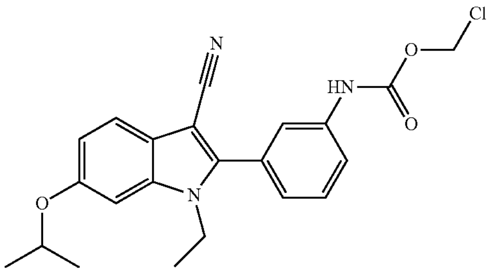
595
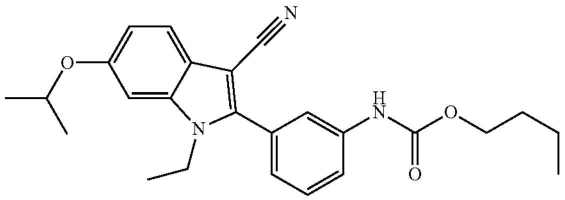
596
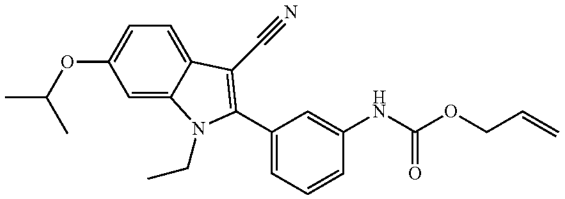
597
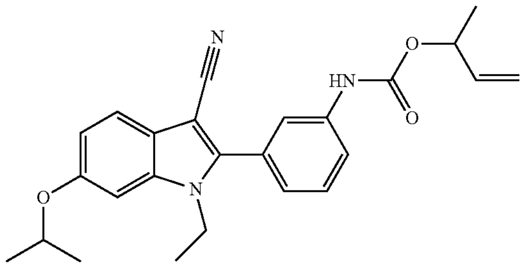
598
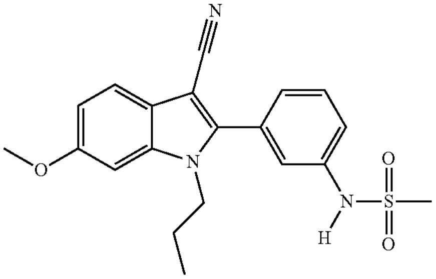
-continued
599
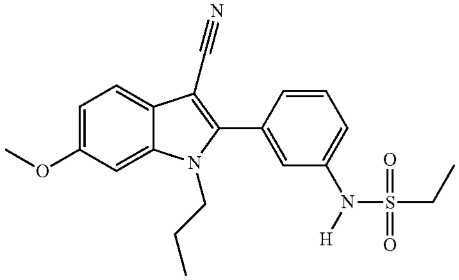
600
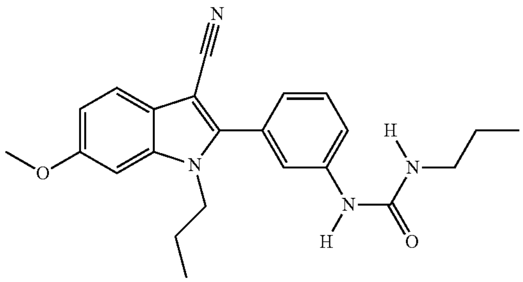
601
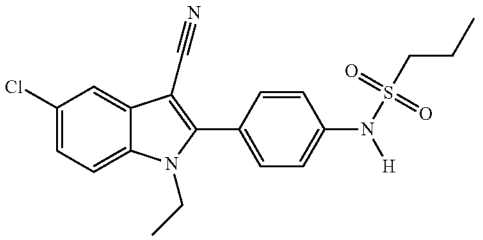
602
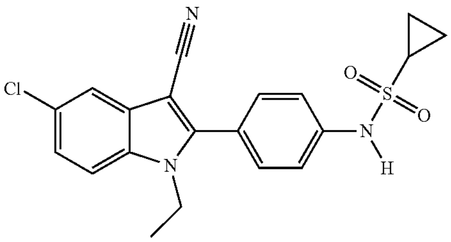
603
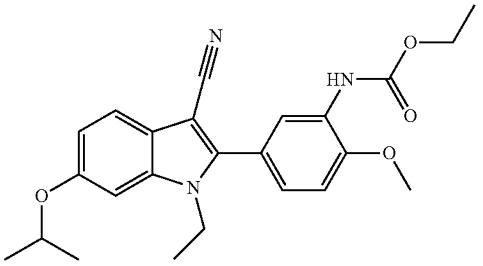
604
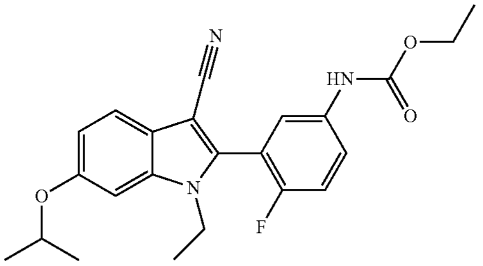

605
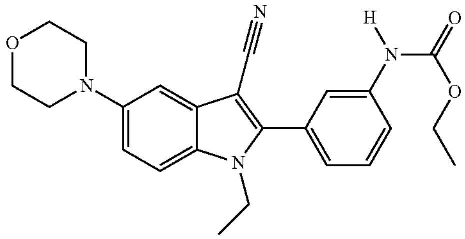
606
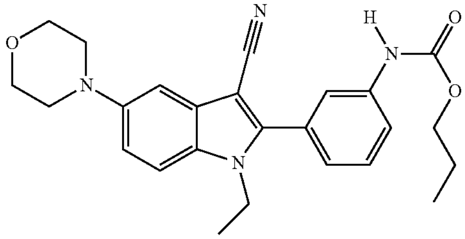
607
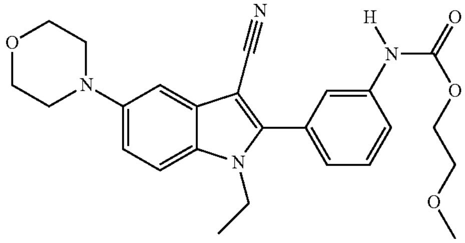
608
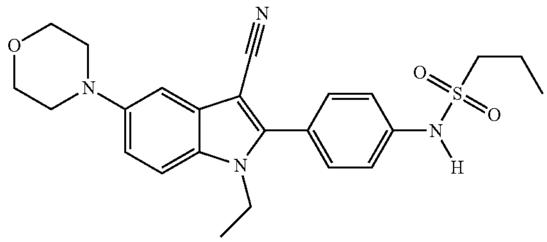
609
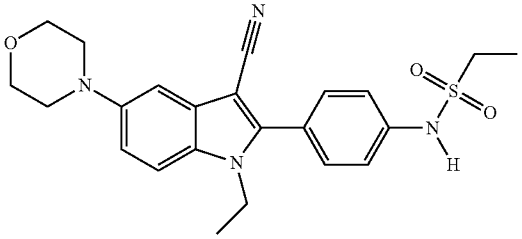
610
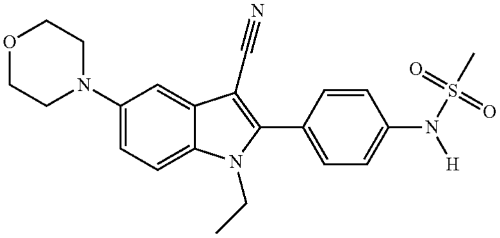
611
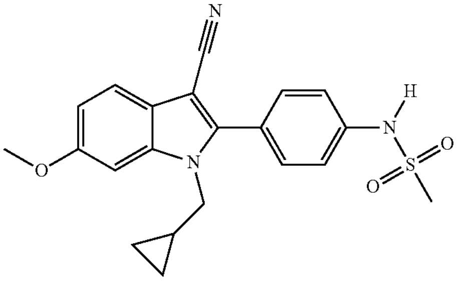
612
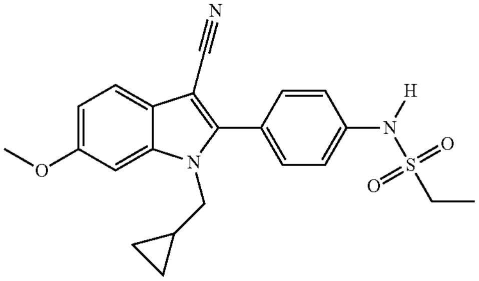
613
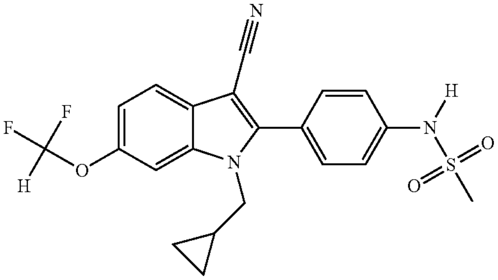
614
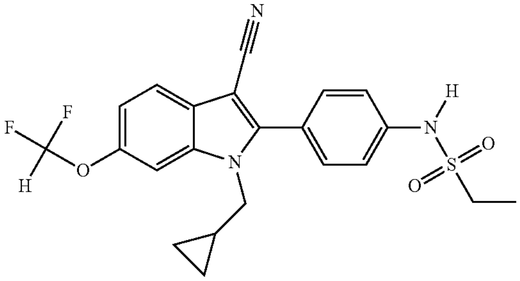
615
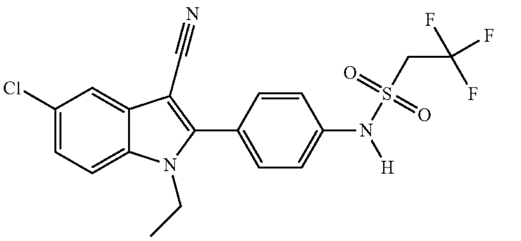

-continued
616
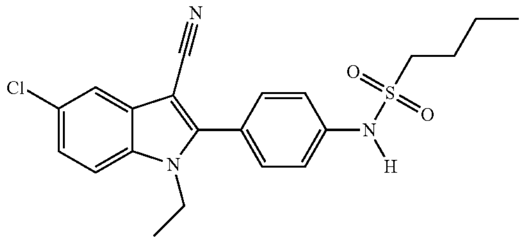
617
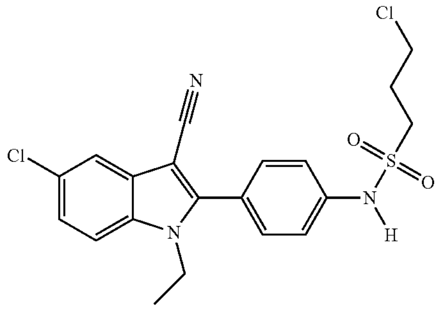
618
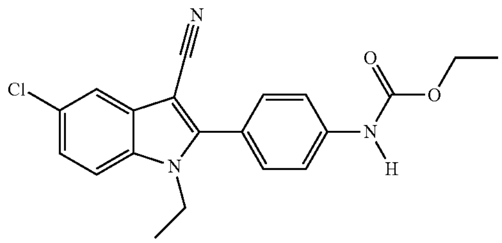
619
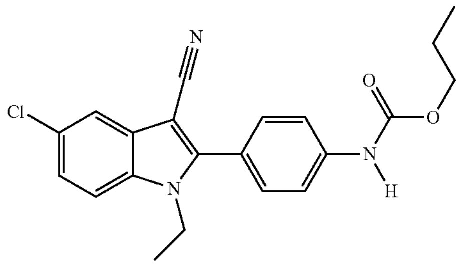
620
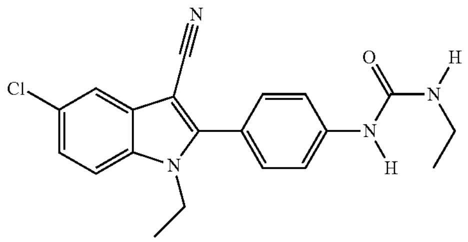
-continued
621
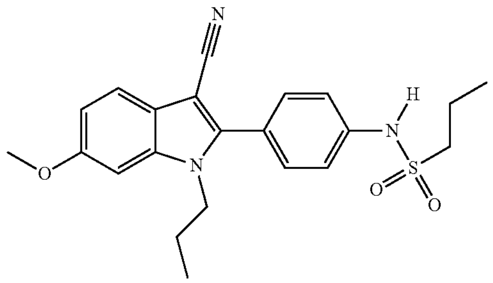
622
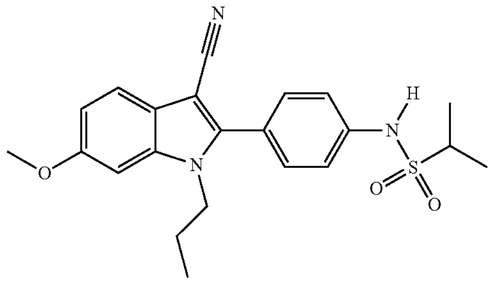
623
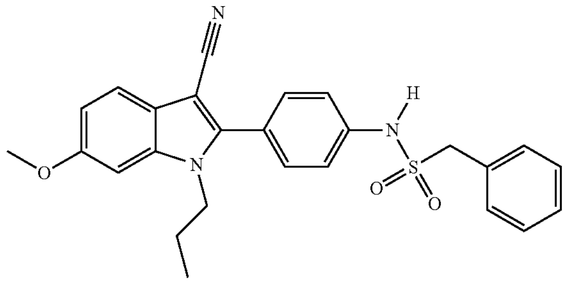
624
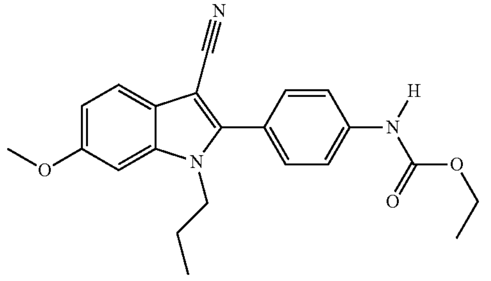
625
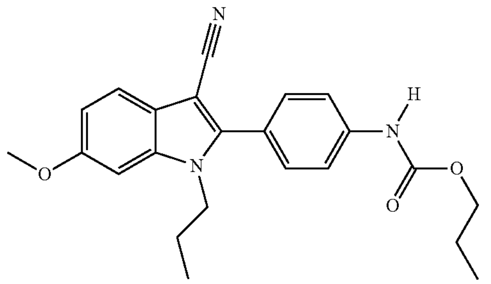

-continued
626
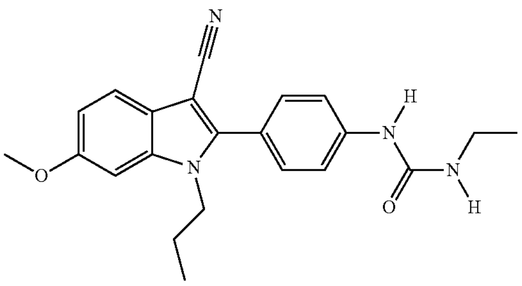
627
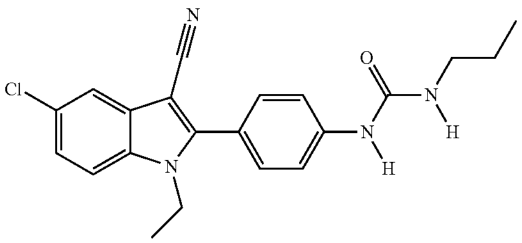
628
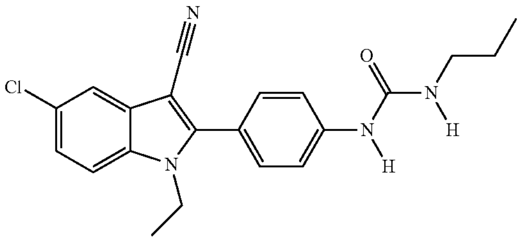
629
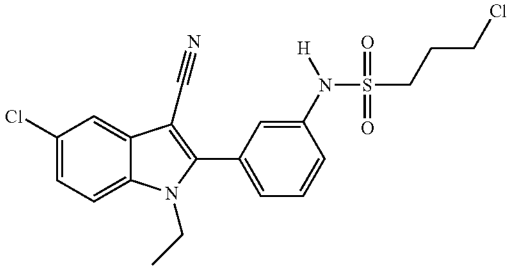
630
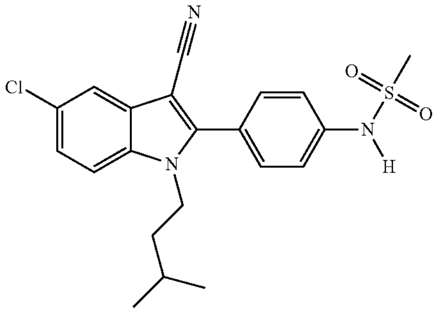
-continued
631
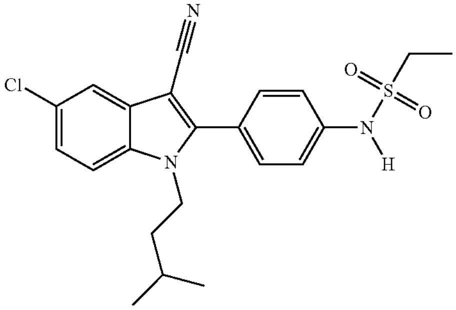
632
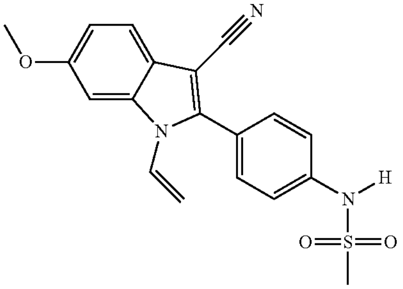
633
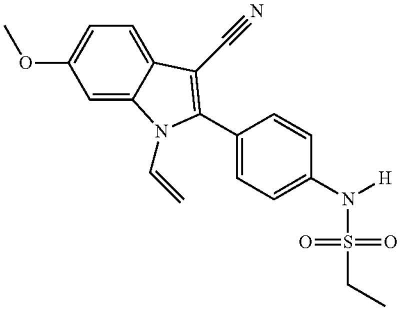
634
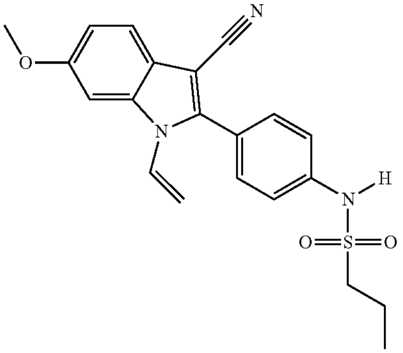
635
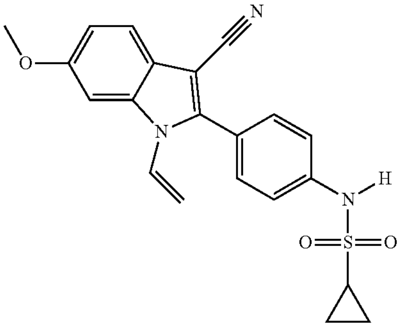

-continued
636
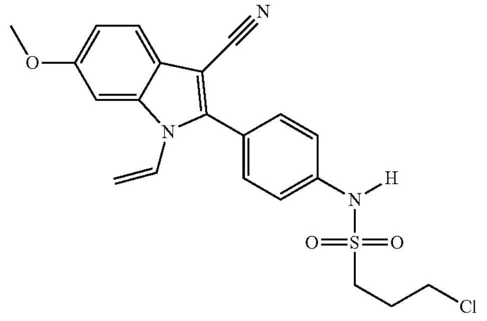
637
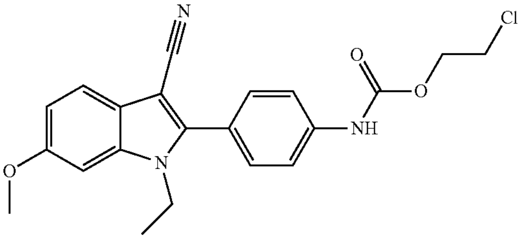
638
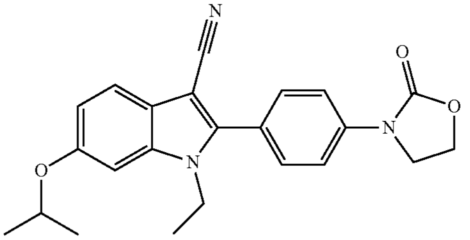
639
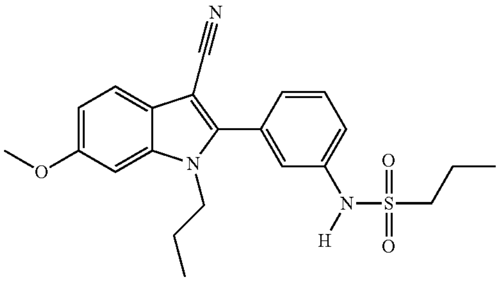
640
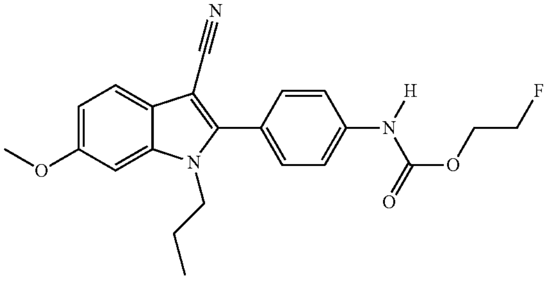
-continued
641
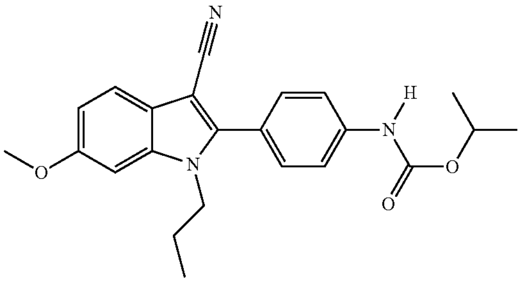
642
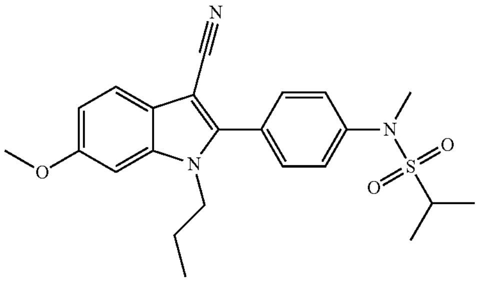
643
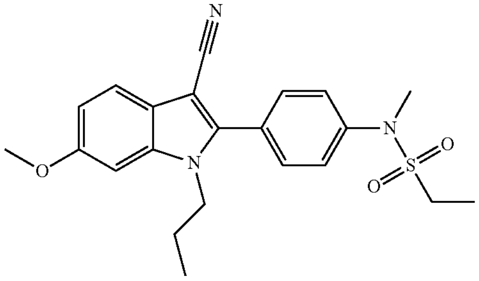
644
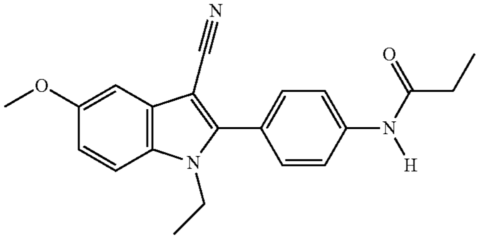
645
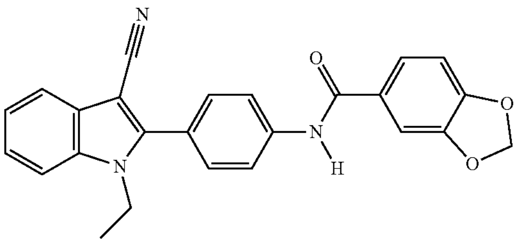
646
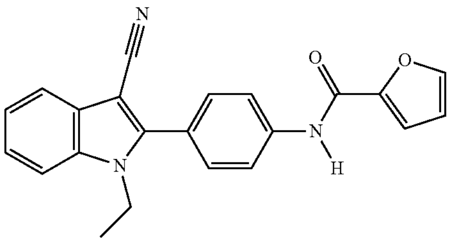

-continued
647
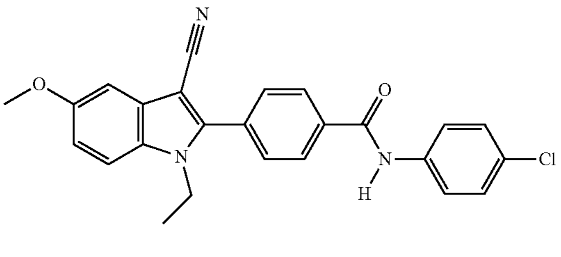
648
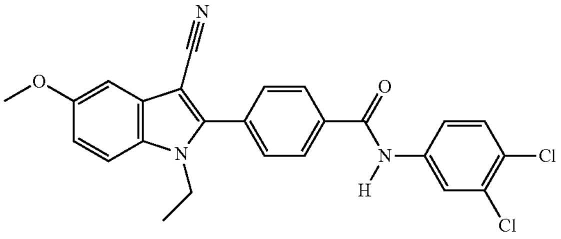
649
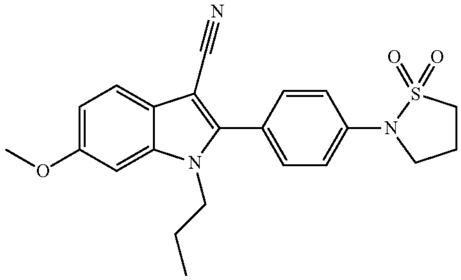
650
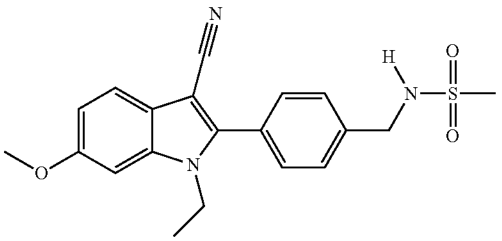
651
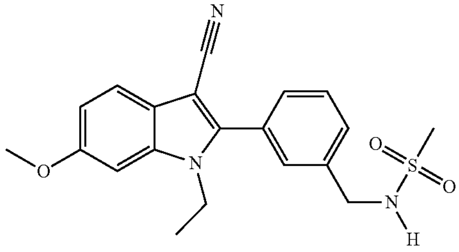
652
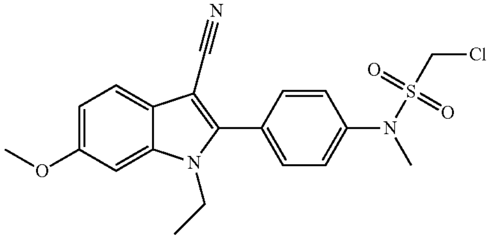
-continued
653
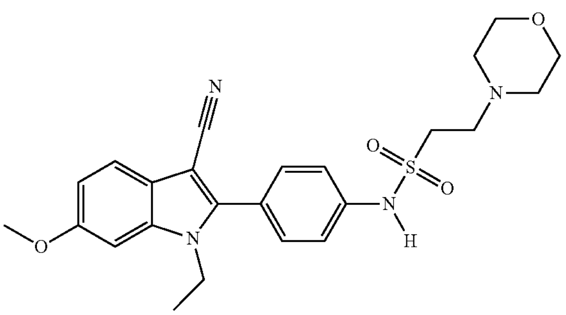
654
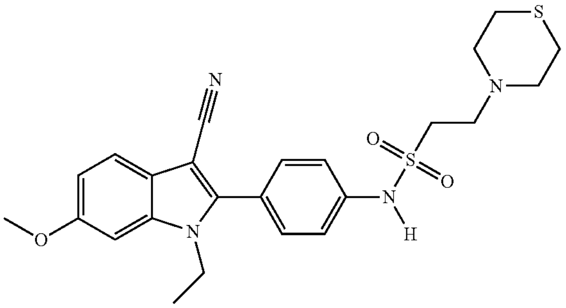
655
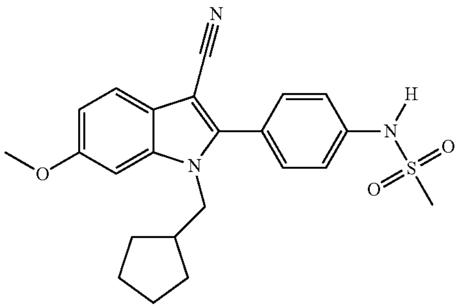
656
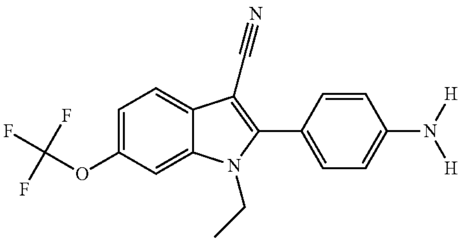
657
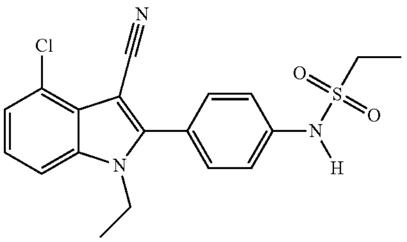

-continued
658
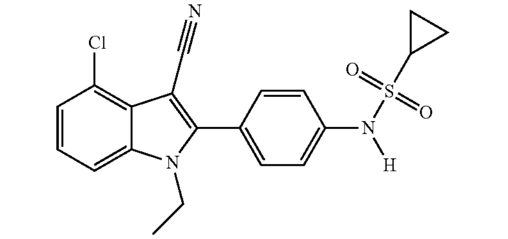
659
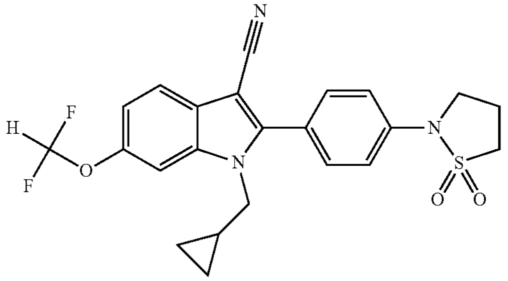
660
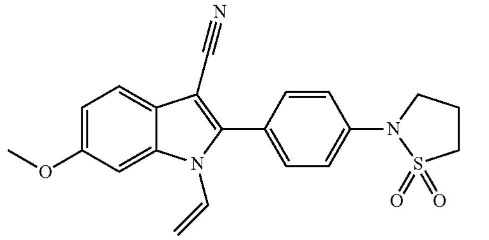
661
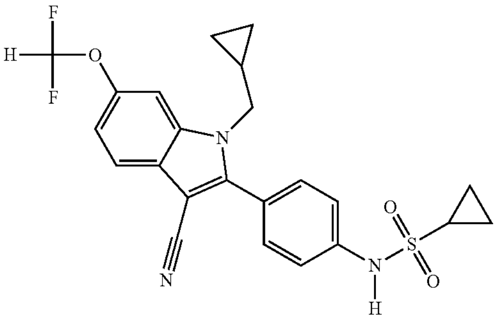
662
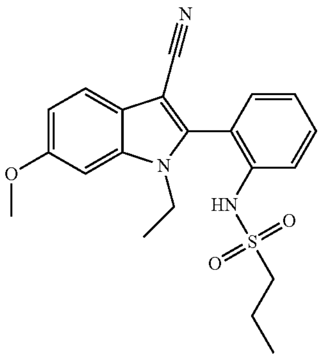
-continued
663
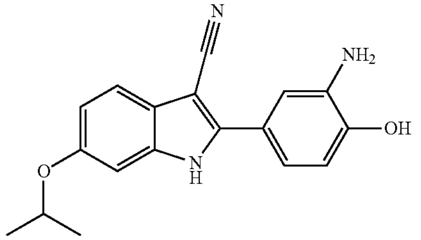
664
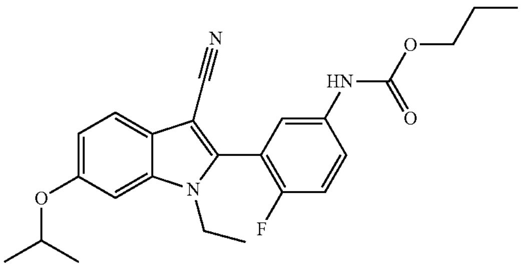
665
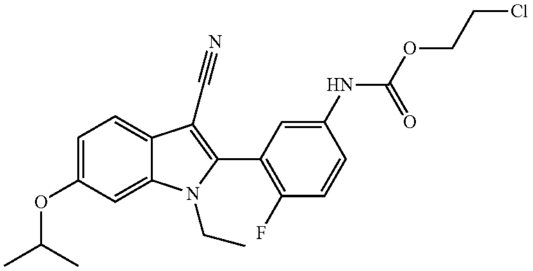
666
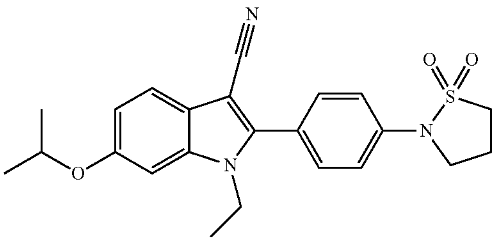
667
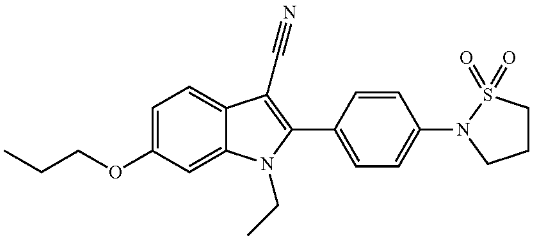

-continued
668
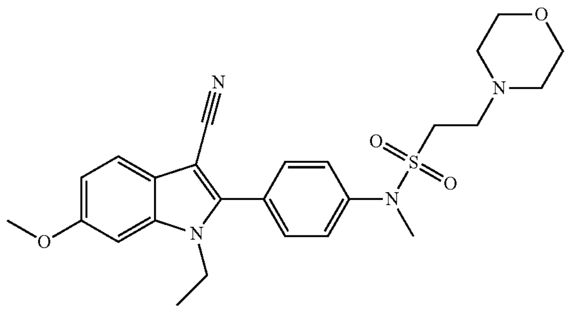
669
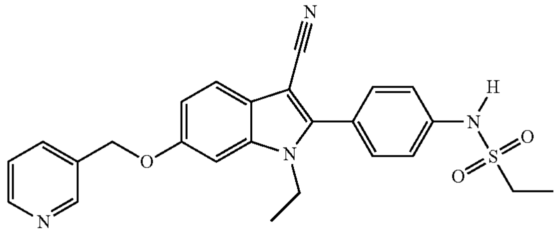
670
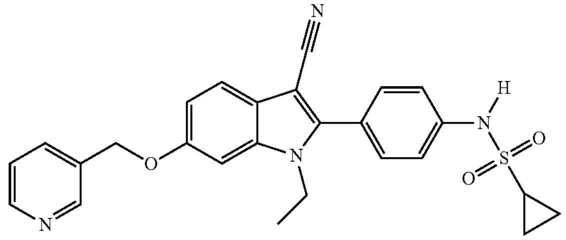
671
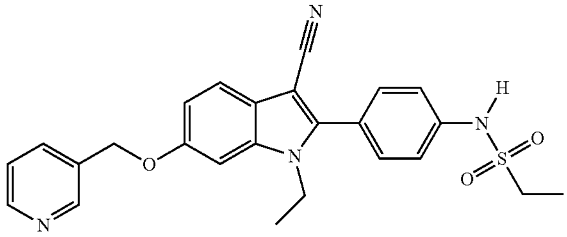
672
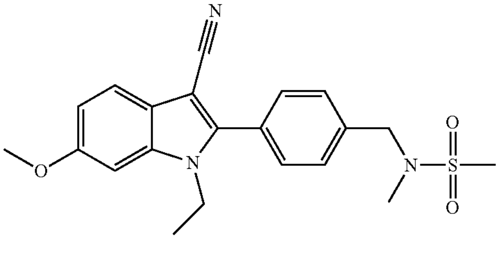
673
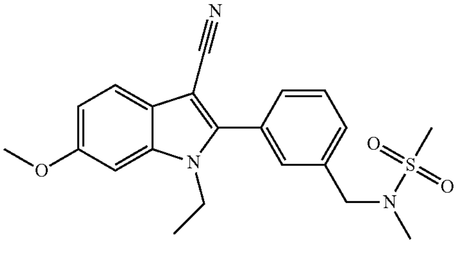
-continued
674
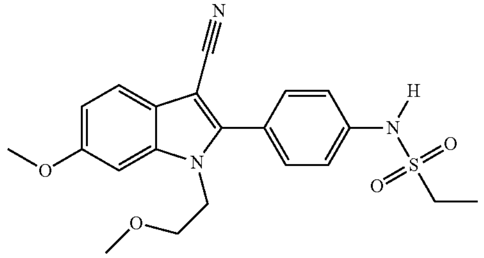
675
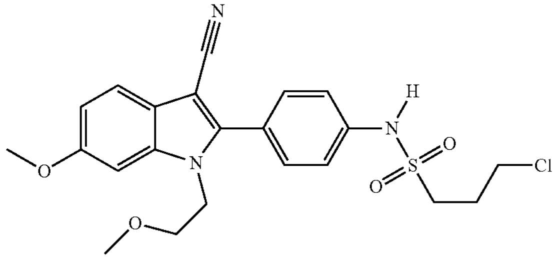
676
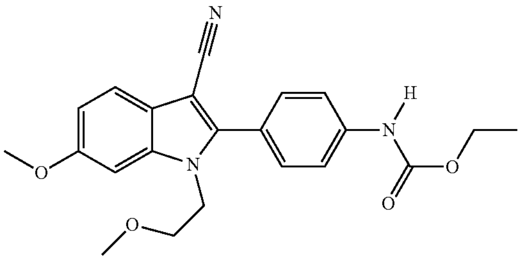
677
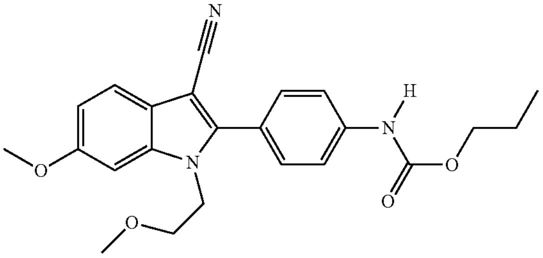
678
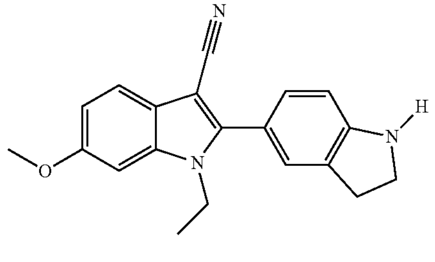
679
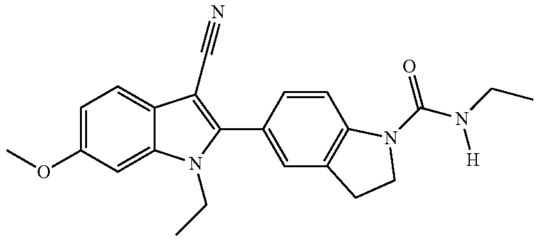

-continued
680
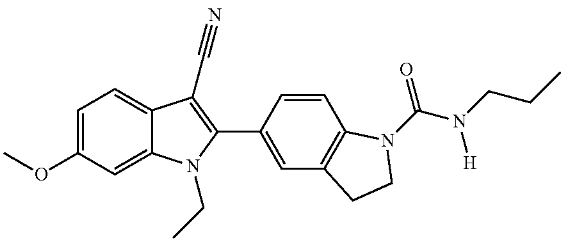
681
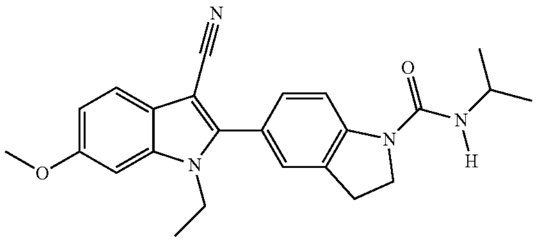
682
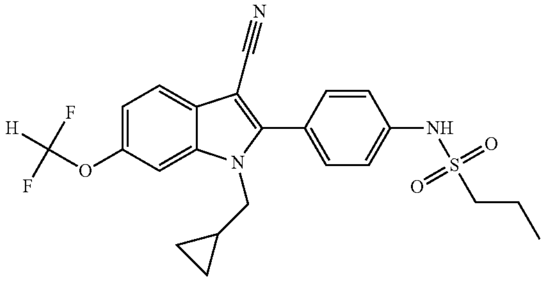
683
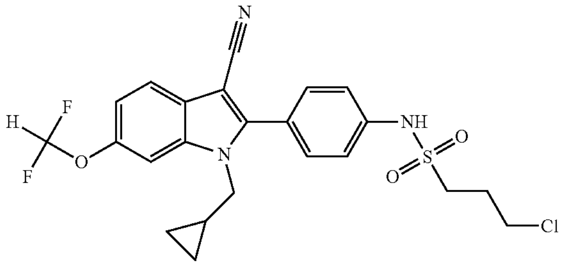
684
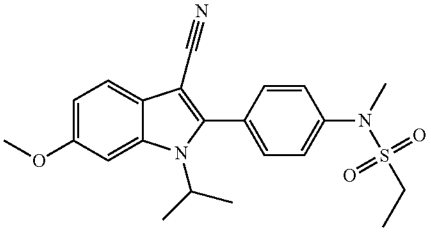
685
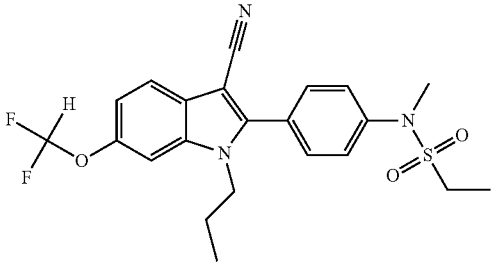
-continued
686
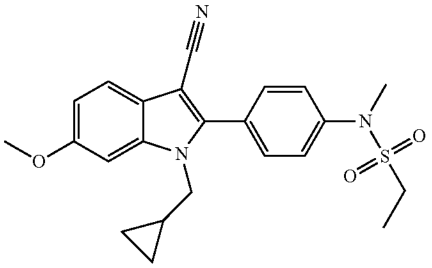
687
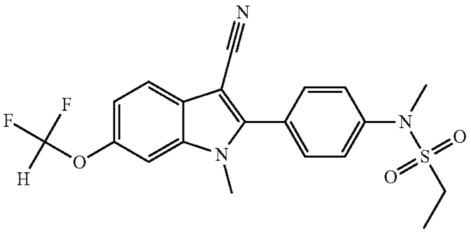
688
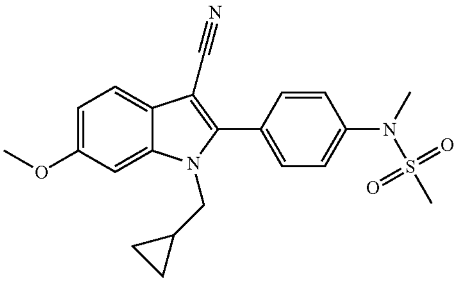
689
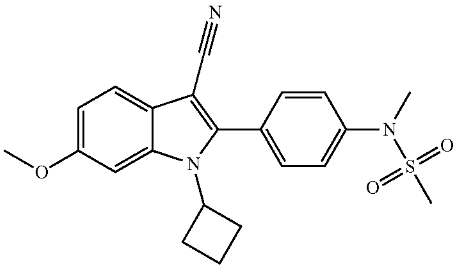
690
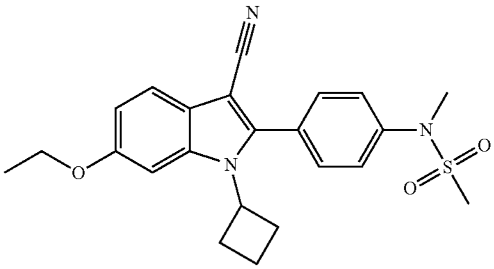
691
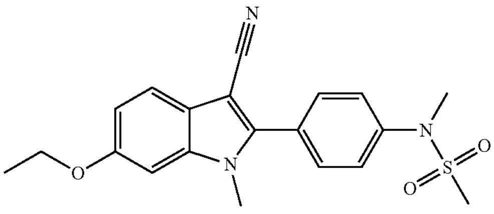

-continued
692
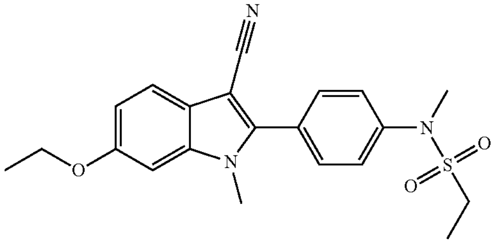
693
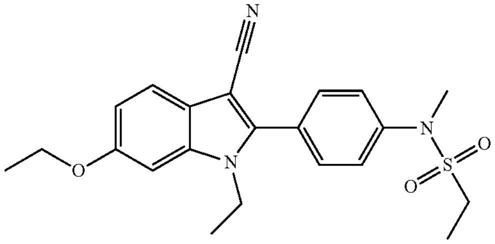
694
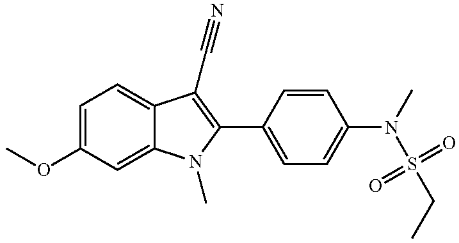
695
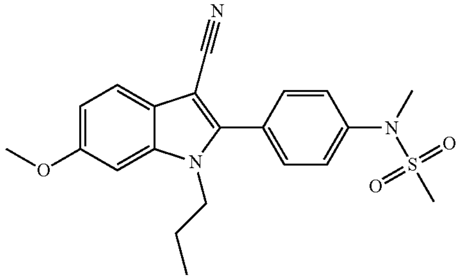
696
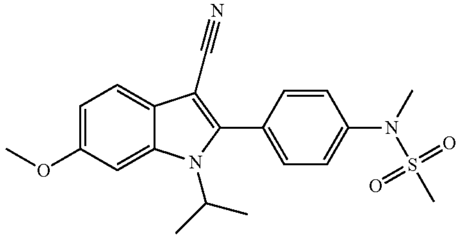
697
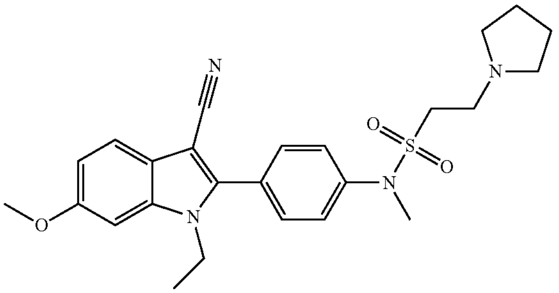
-continued
698
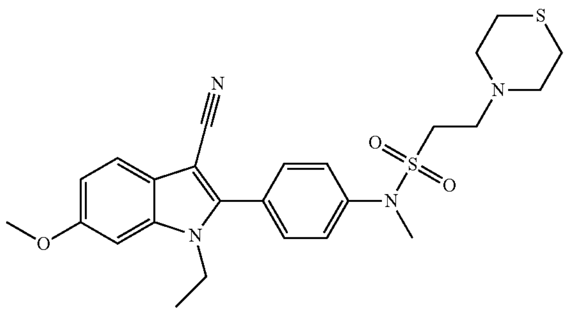
699
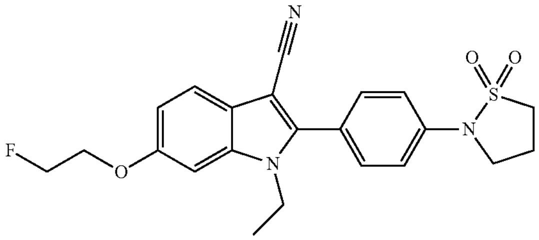
701
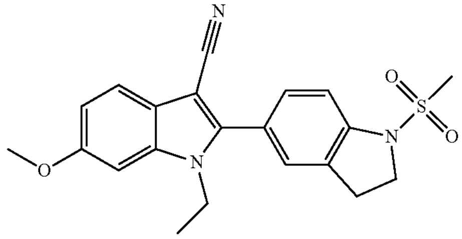
702
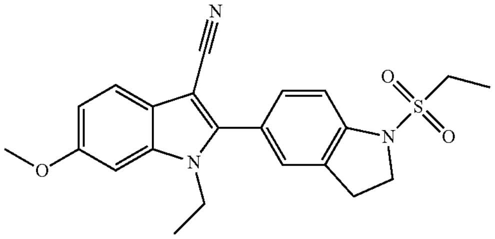
703
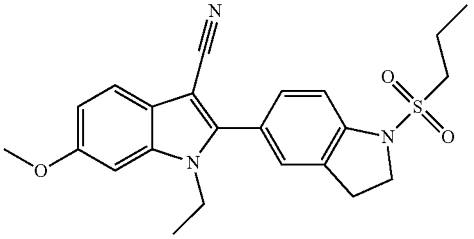
704
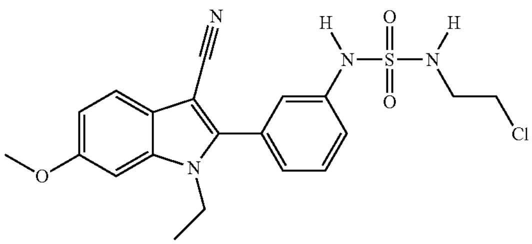

-continued
705
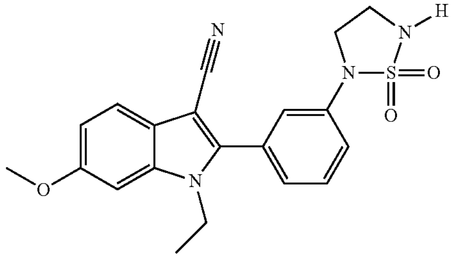
706
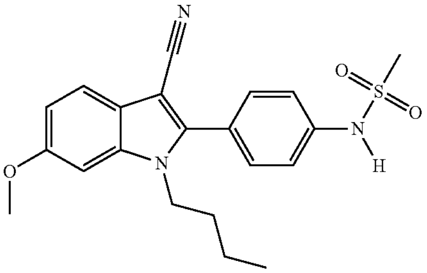
707
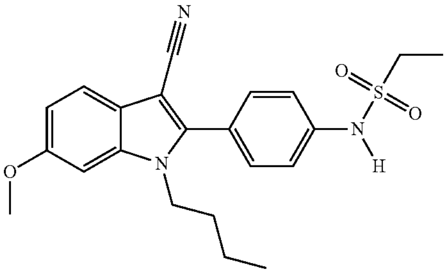
708
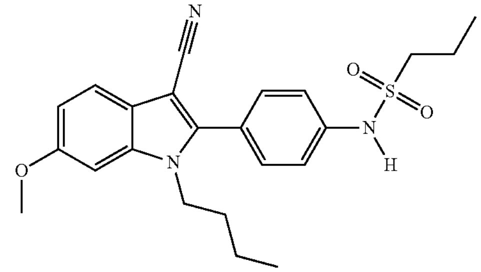
709
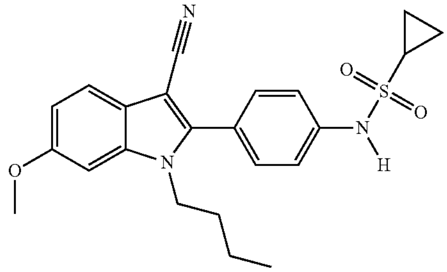
-continued
710
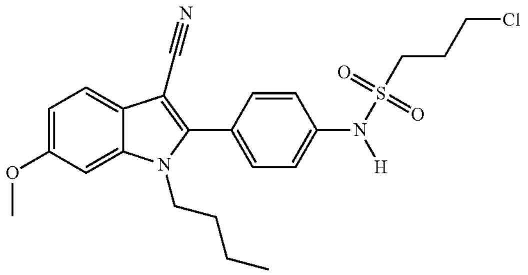
711
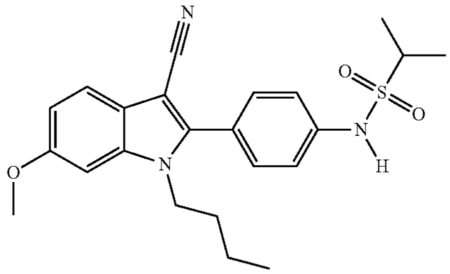
712
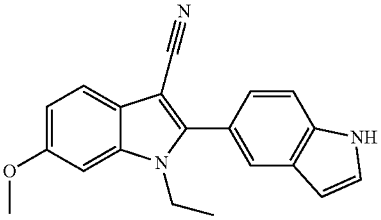
713
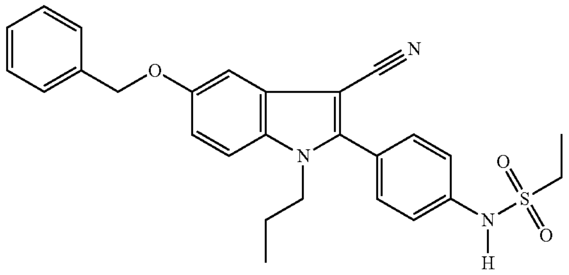
714
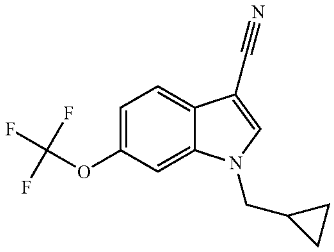
715
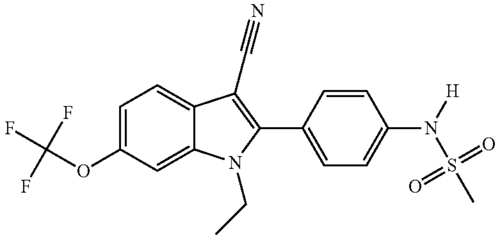

-continued
716
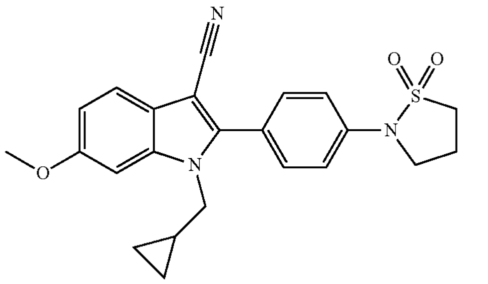
717
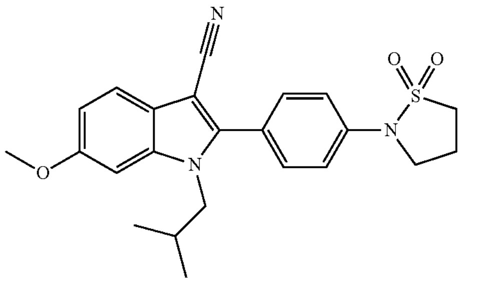
718
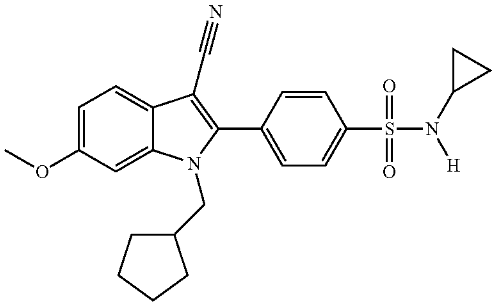
719
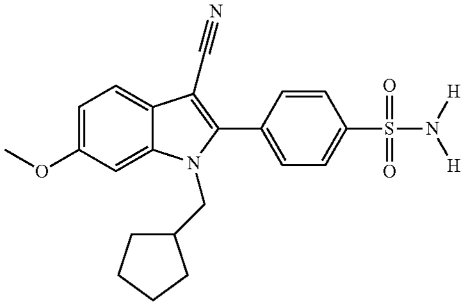
720
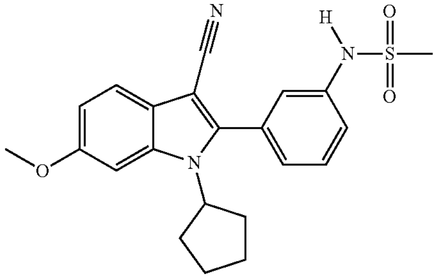
-continued
721
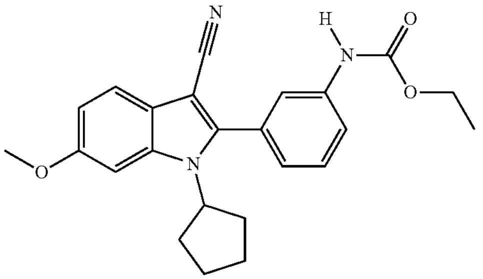
722
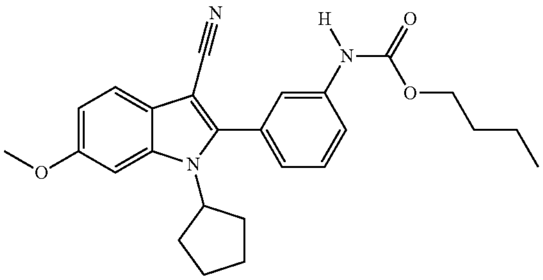
723
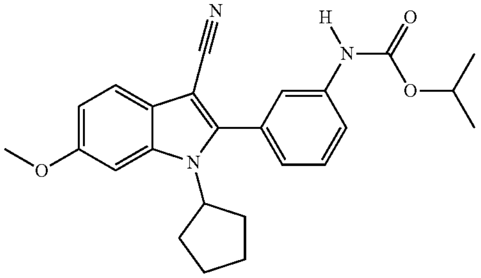
724
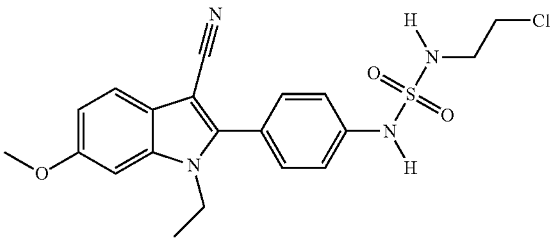
725
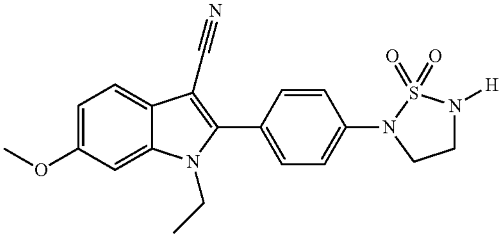
726
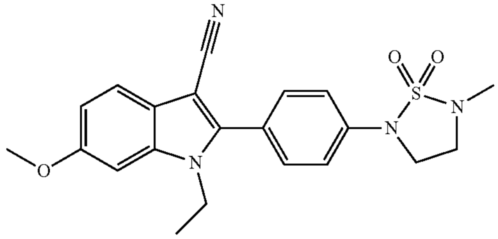

-continued
727
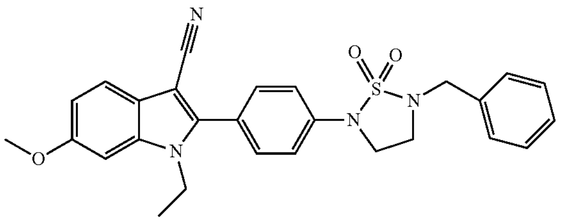
728
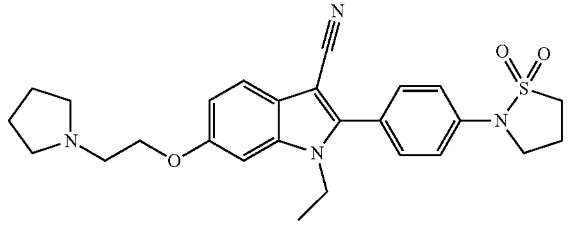
729
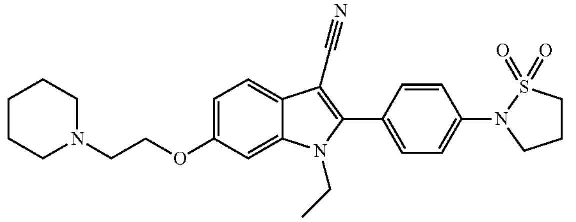
730
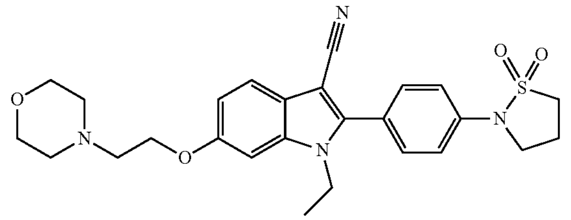
731
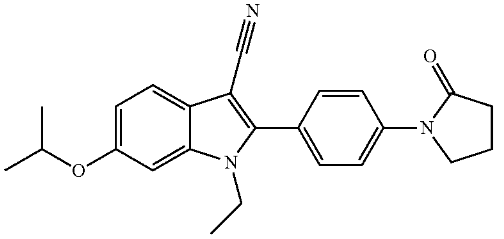
732
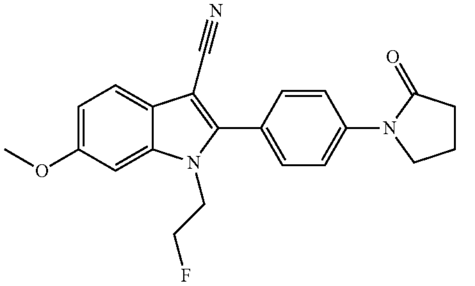
-continued
733
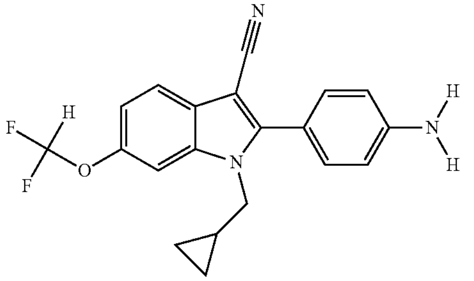
734
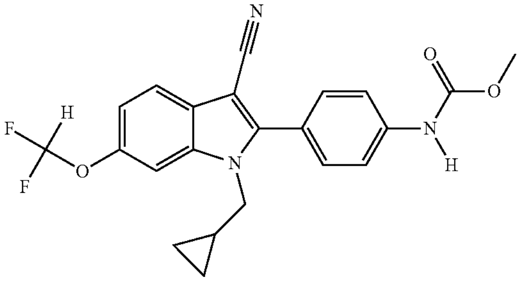
735
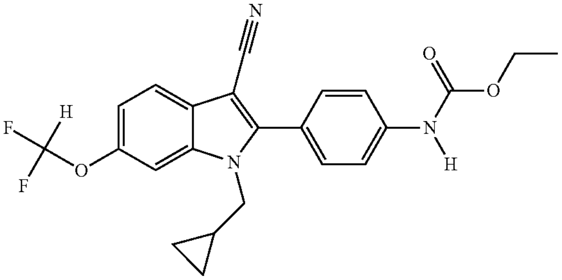
736
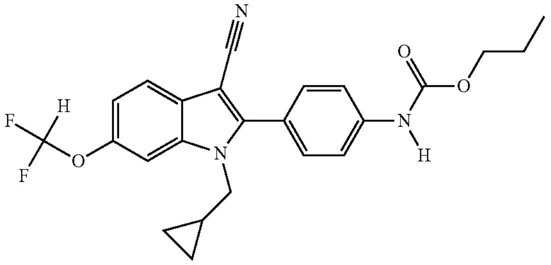
737
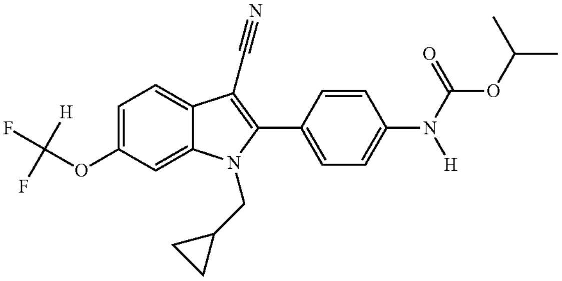

-continued
738
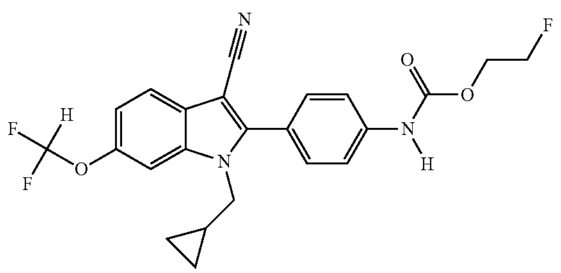
739
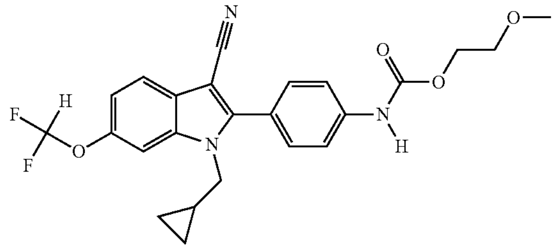
740
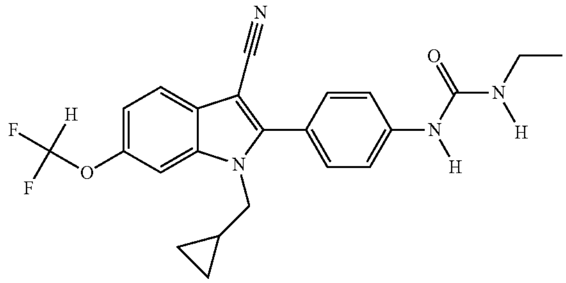
741
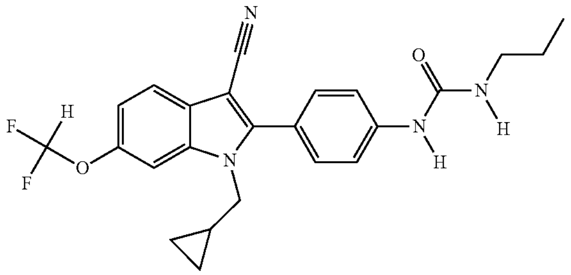
742
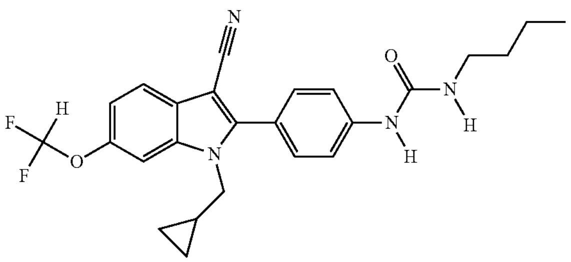
-continued
743
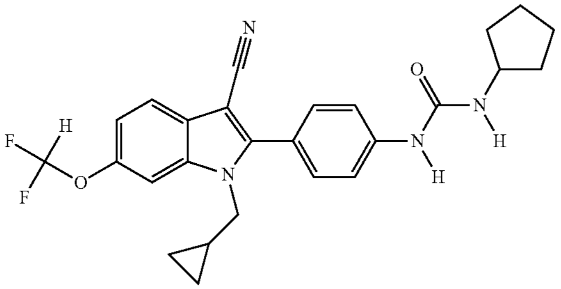
744
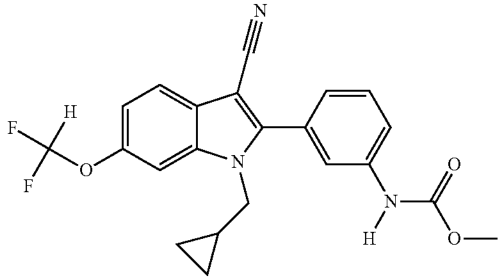
745
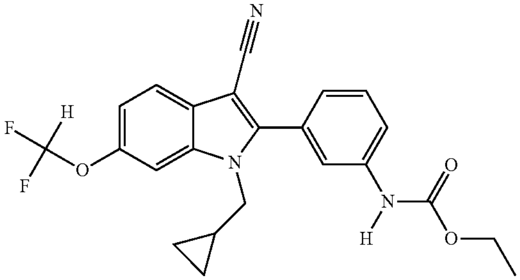
746
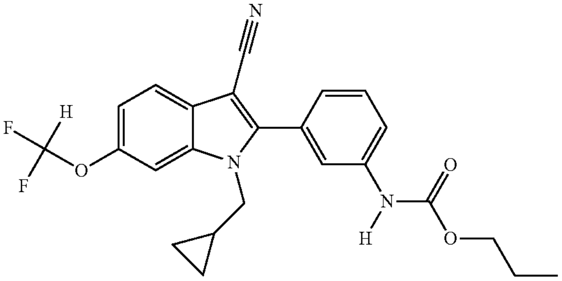
747
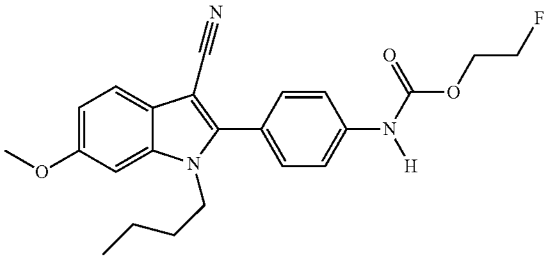

-continued
748
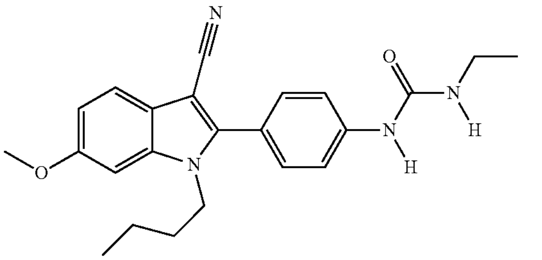
749
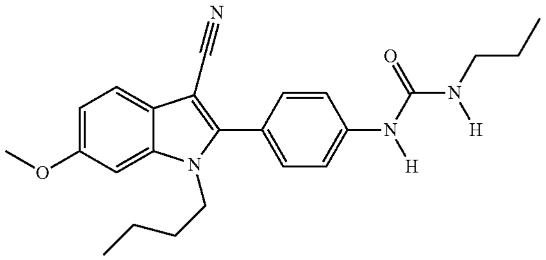
750
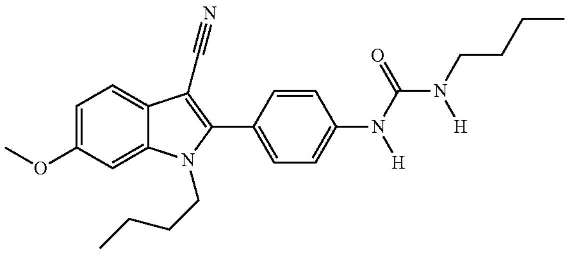
751
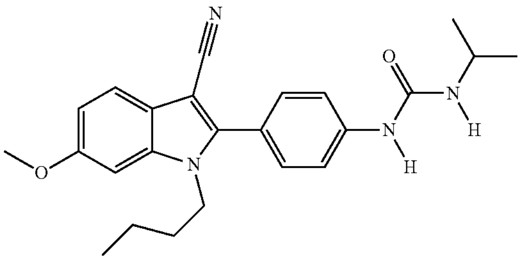
752
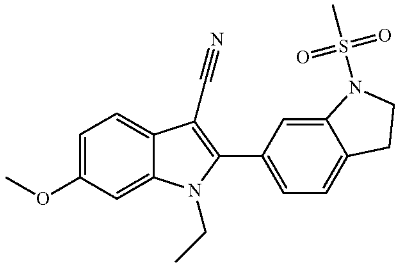
-continued
753
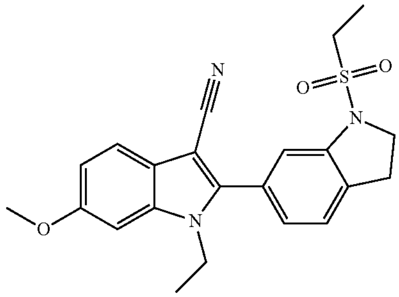
754
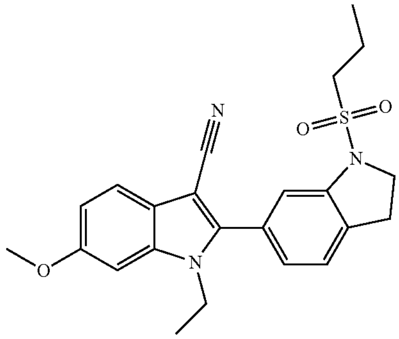
755
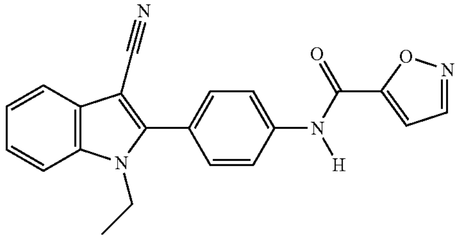
756
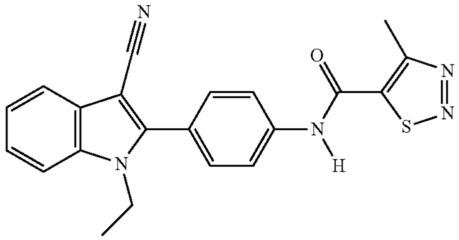
757
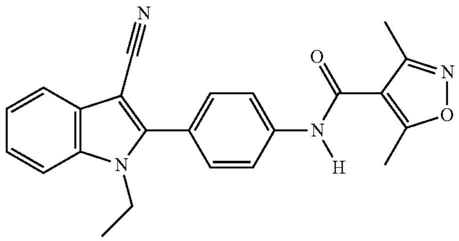
758
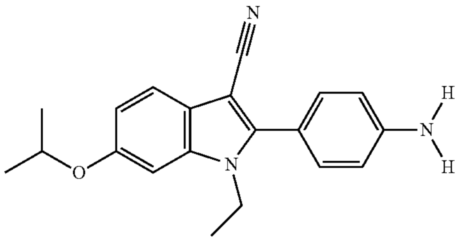

-continued
759
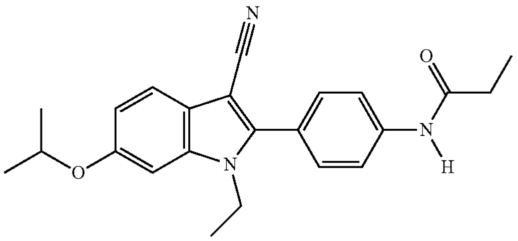
760
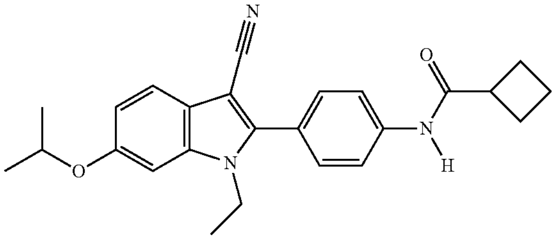
761
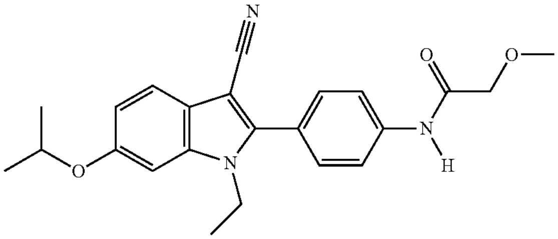
762
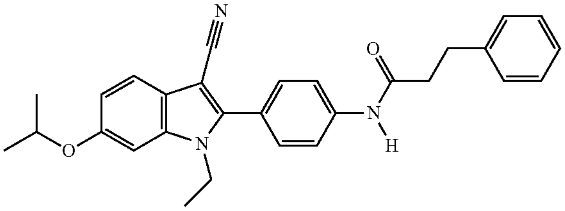
763
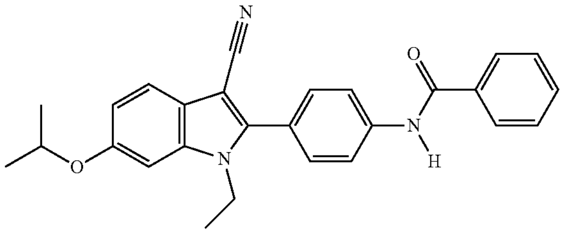
764
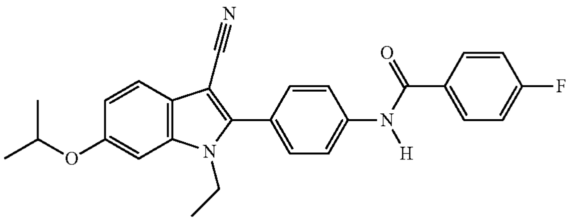
-continued
765
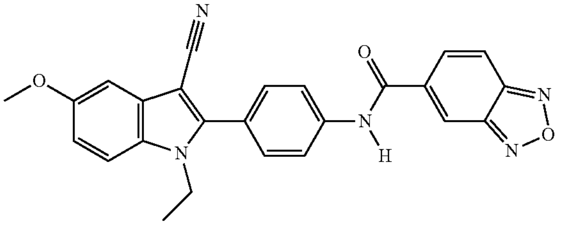
766
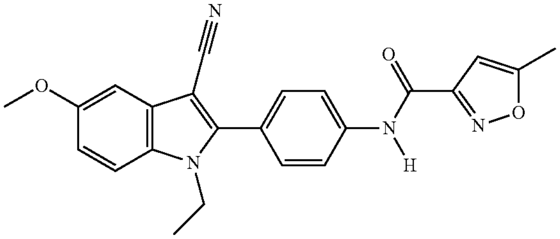
767
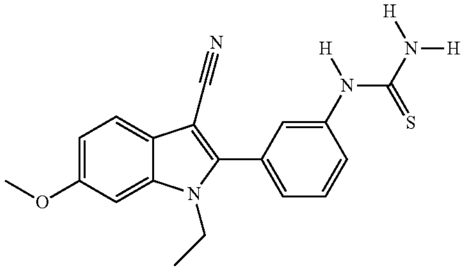
768
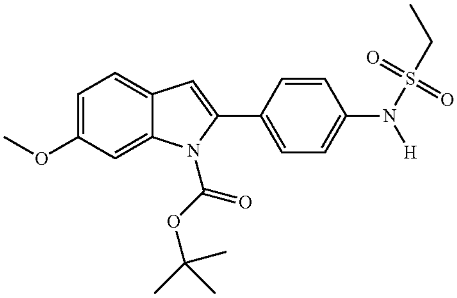
769
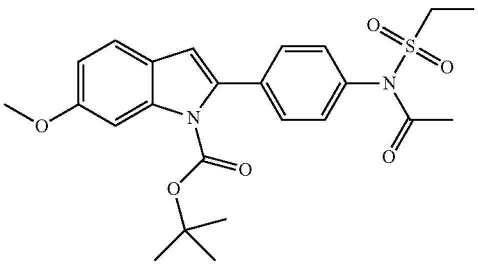
770
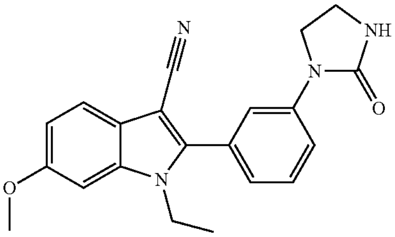

-continued
771
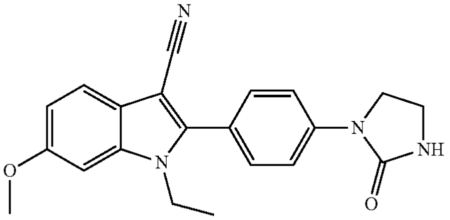
772
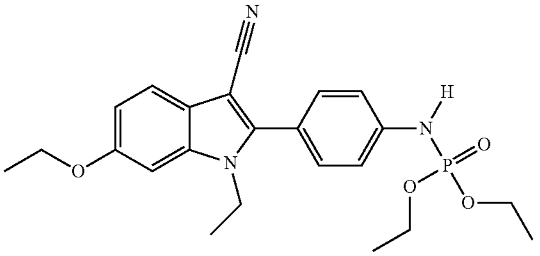
773
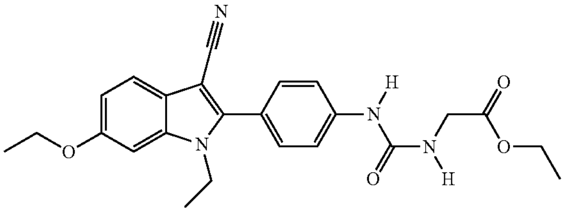
774
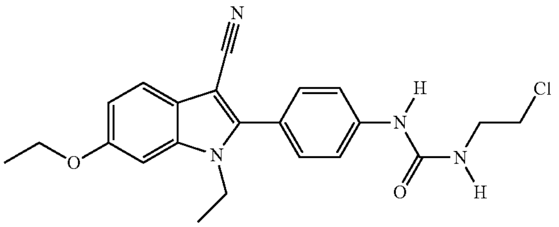
775
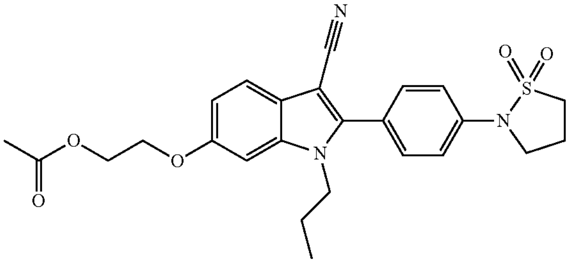
776
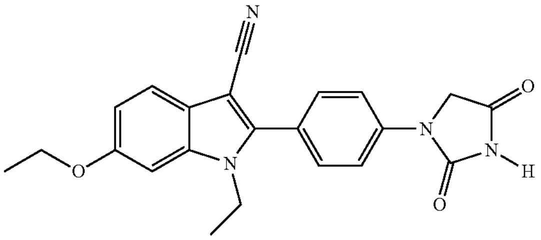
-continued
777
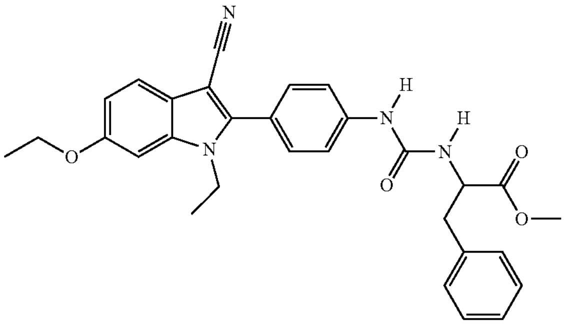
778
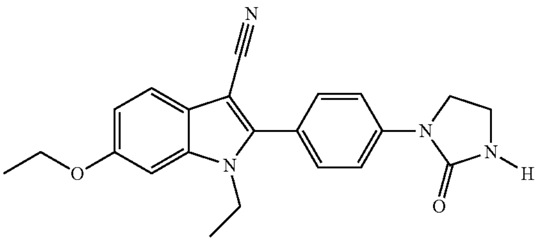
779
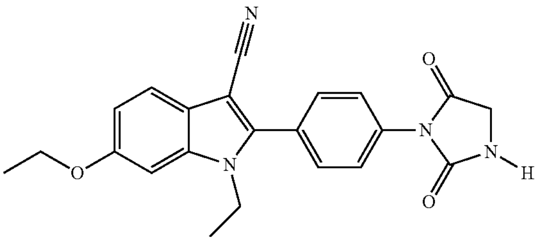
780
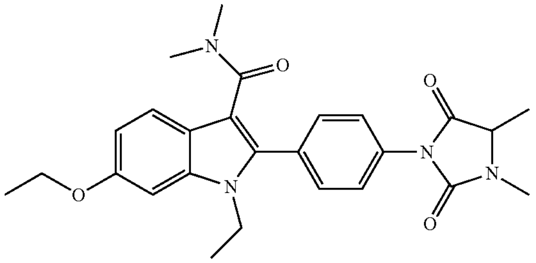
781
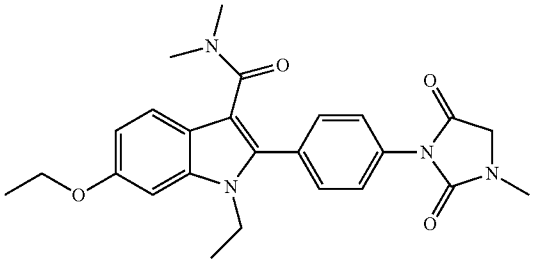

-continued
782
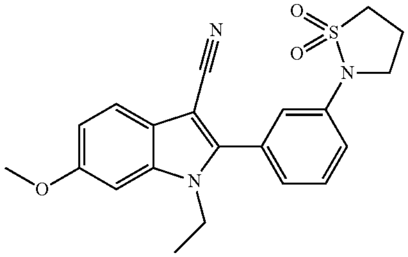
783
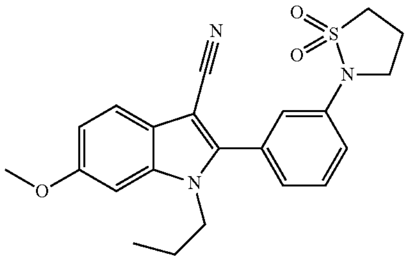
784
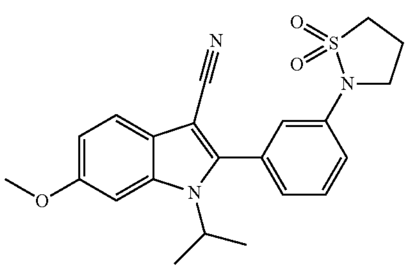
785
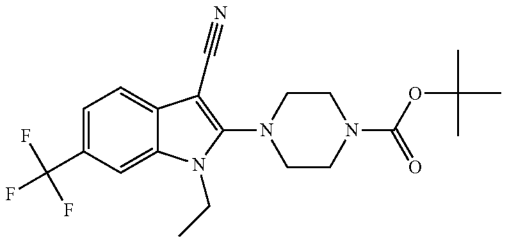
786
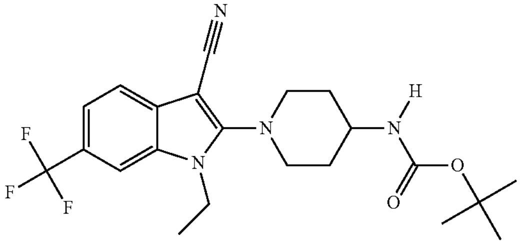
787
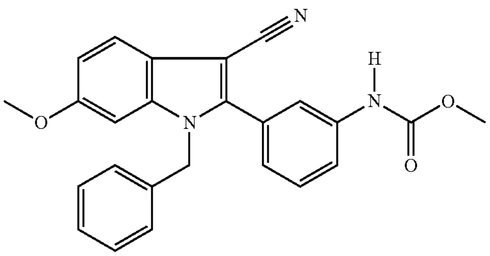
-continued
788
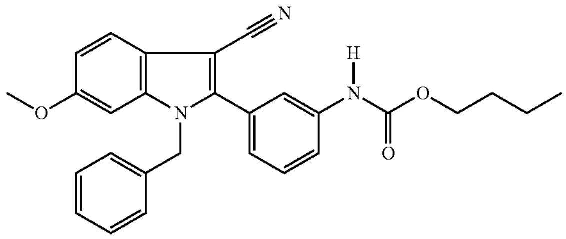
789
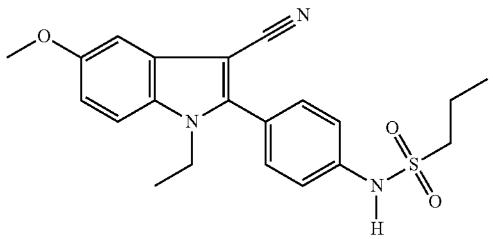
790
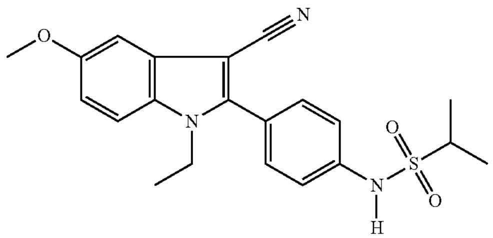
791
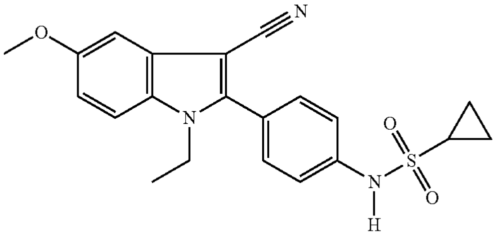
792
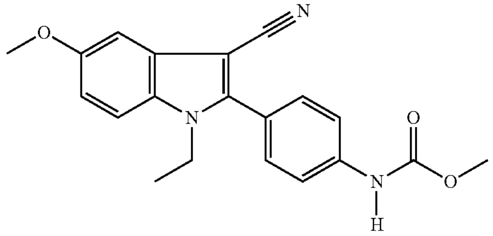
793
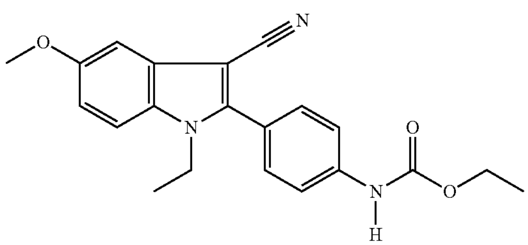

-continued
794
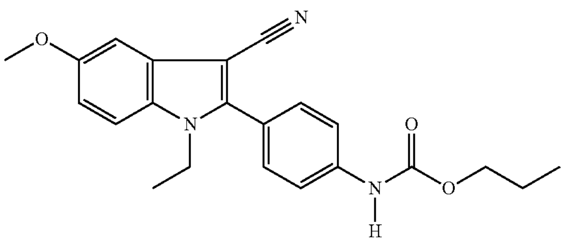
795
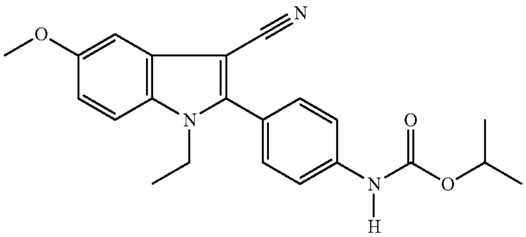
796
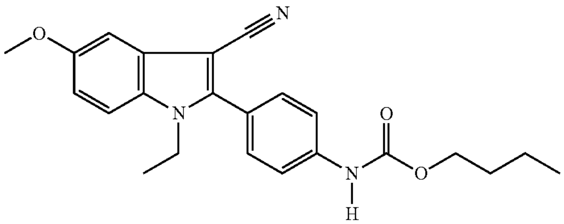
797
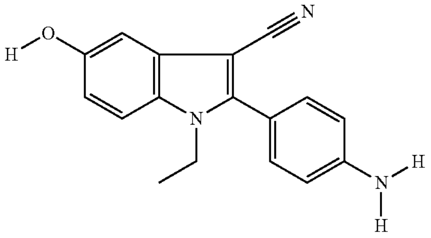
798
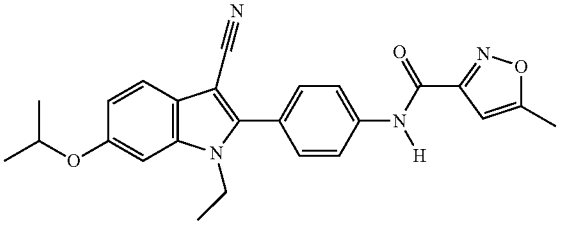
799
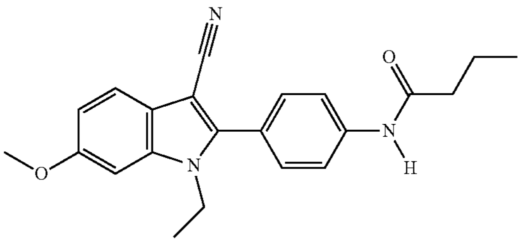
-continued
801
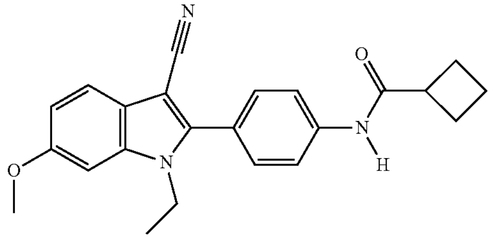
802
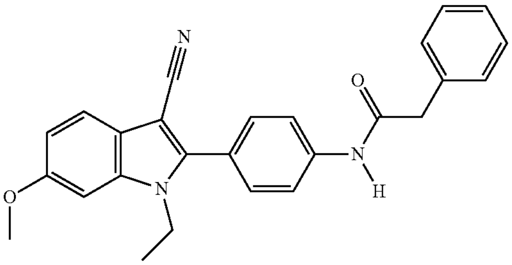
803
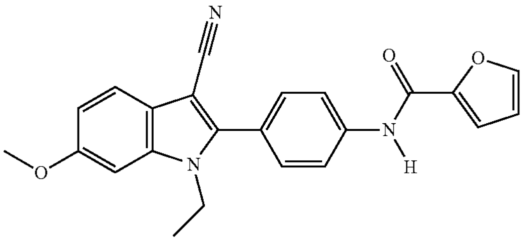
804
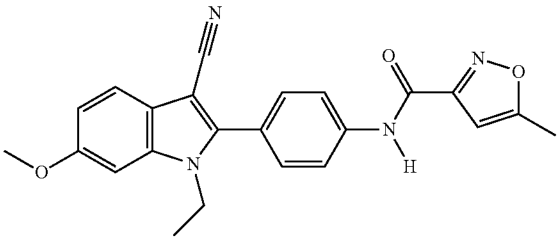
805
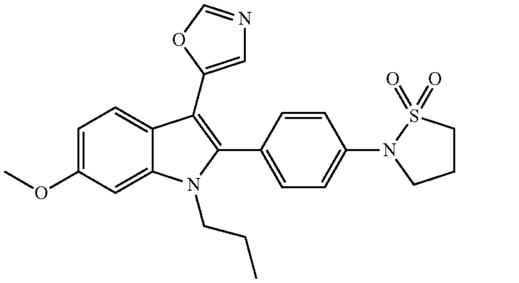
806
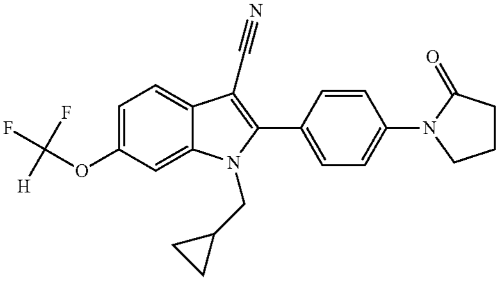

-continued
807
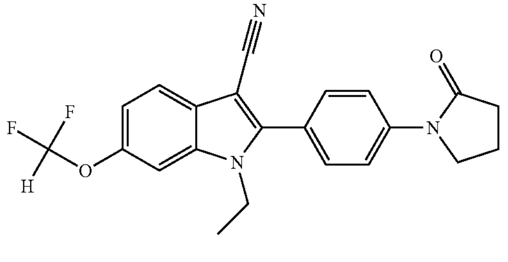
808
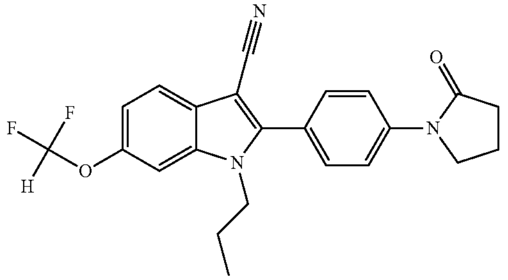
809
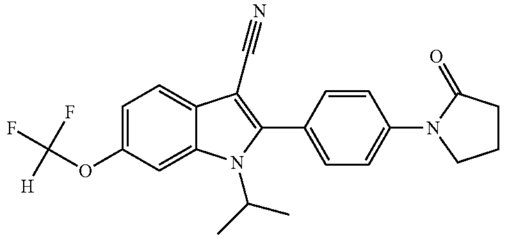
810
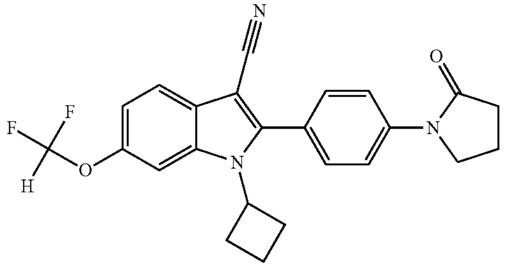
811
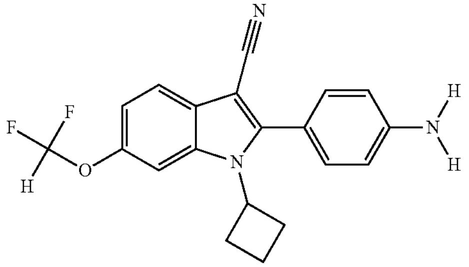
812
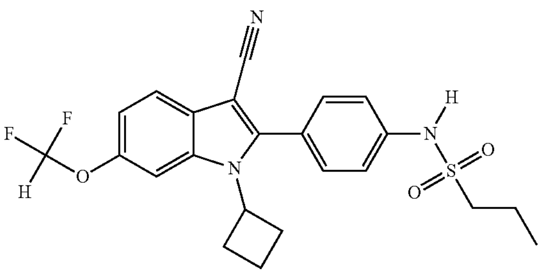
-continued
813
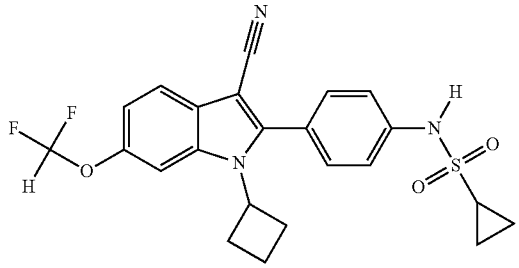
814
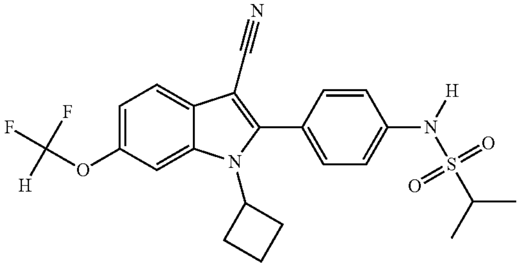
815
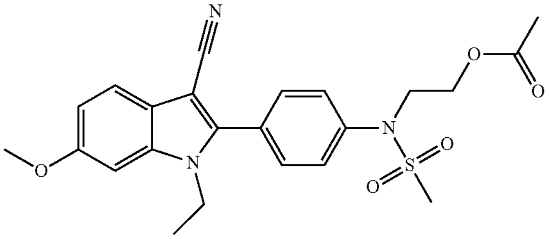
816
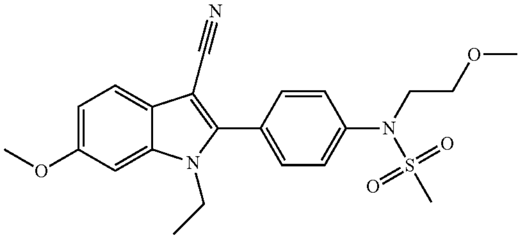
817
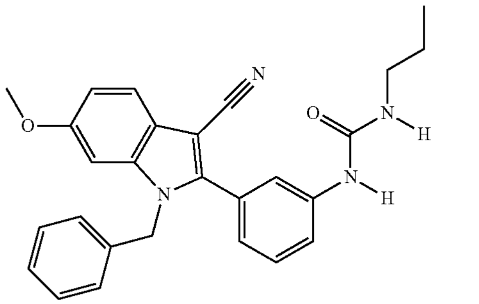

818
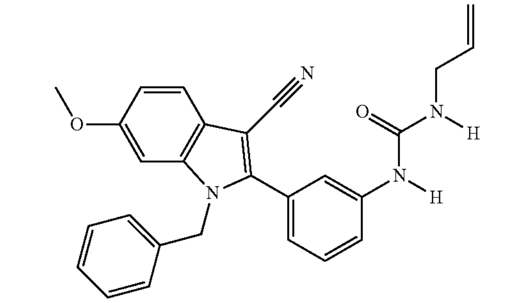
819
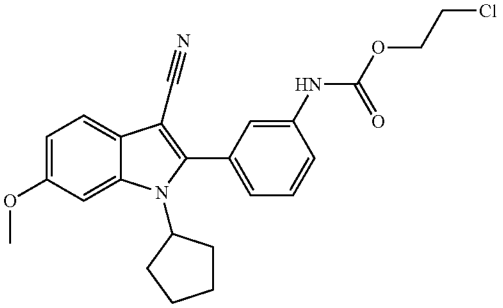
820
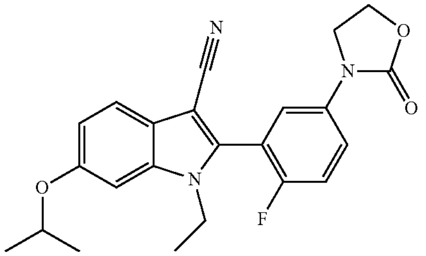
821
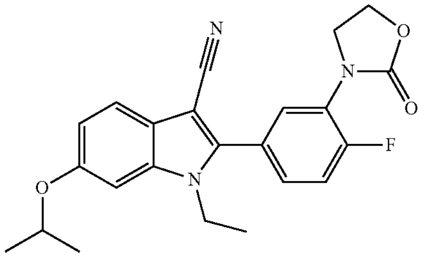
822
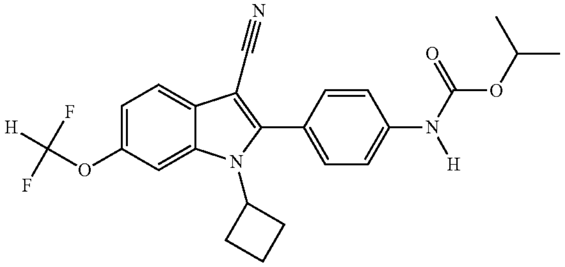
823
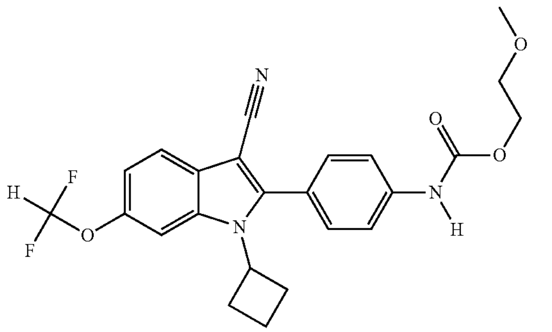
824
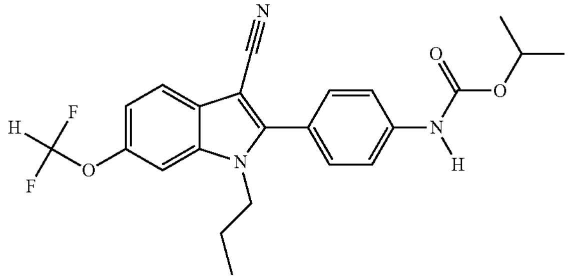
825
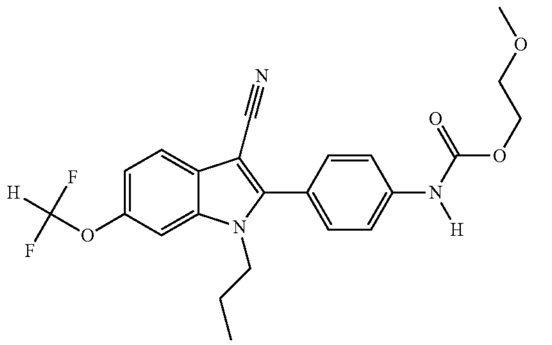
826
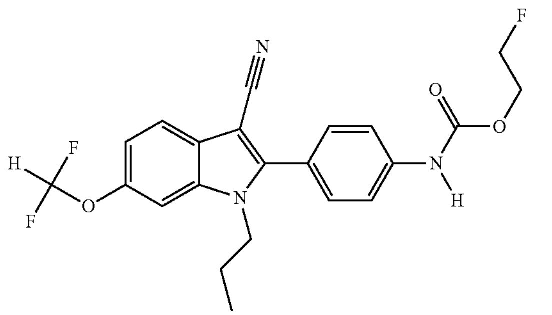

-continued
827
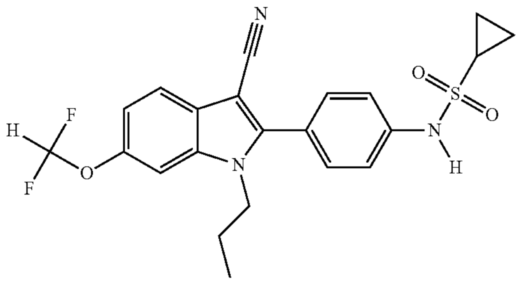
828
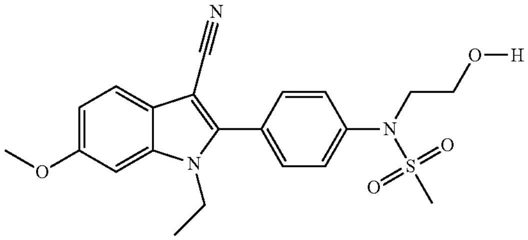
829
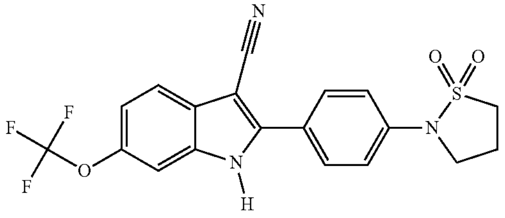
830
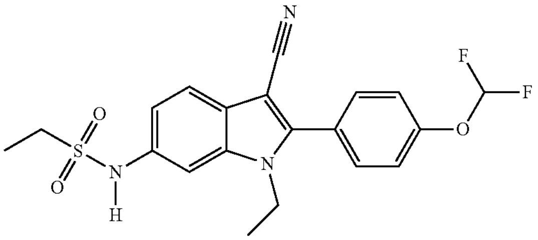
831
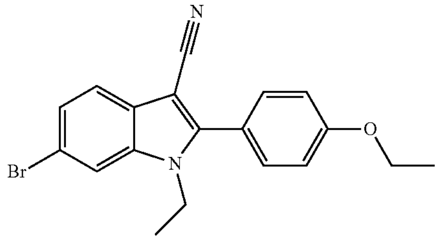
832
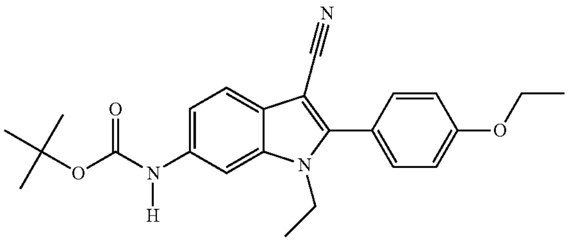
-continued
833
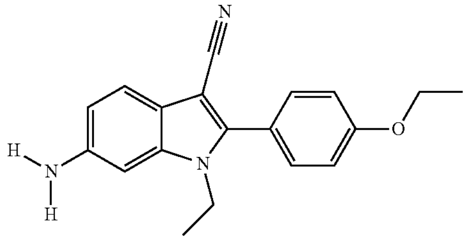
834
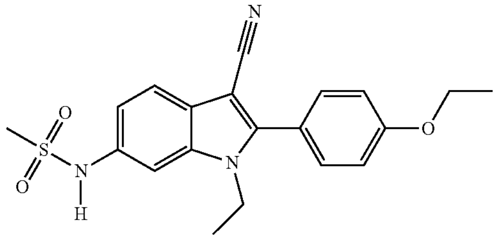
835
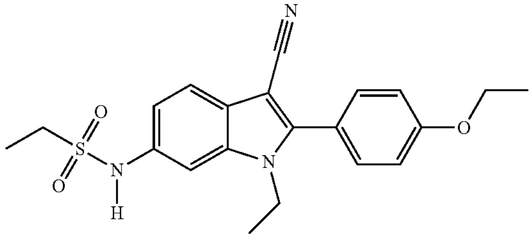
836
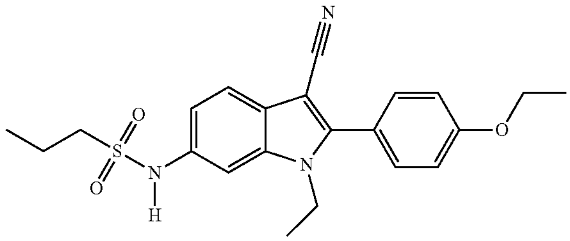
837
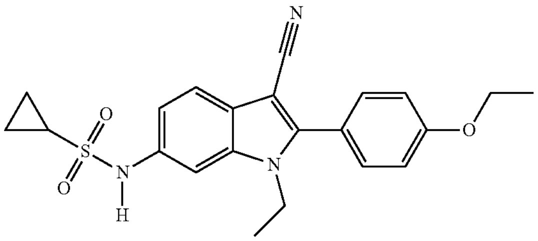
838
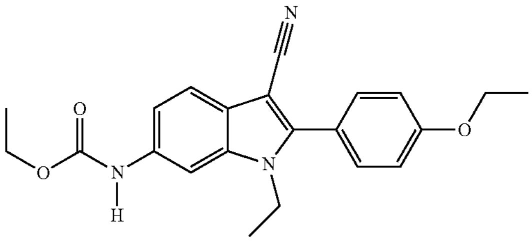

-continued
839
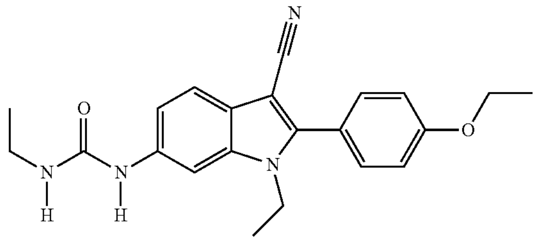
840
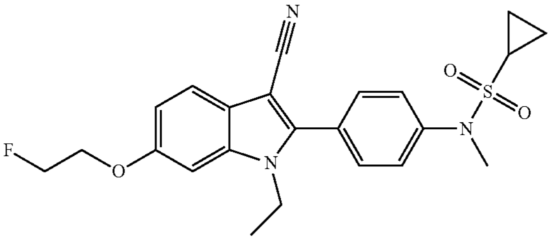
841
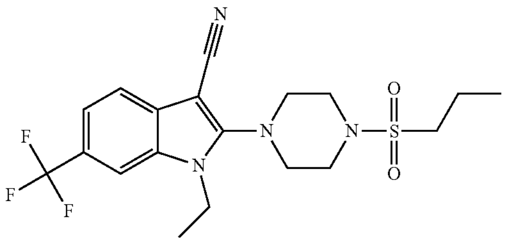
842
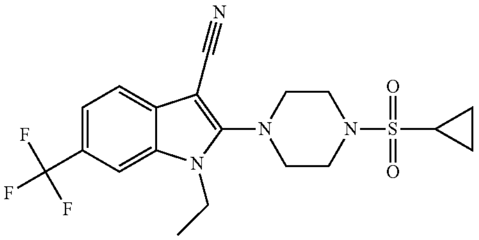
843
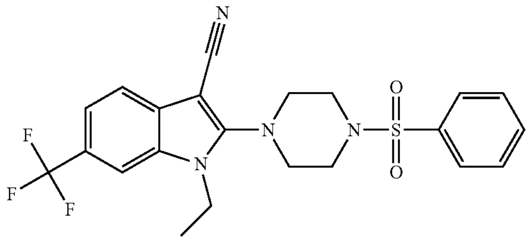
844
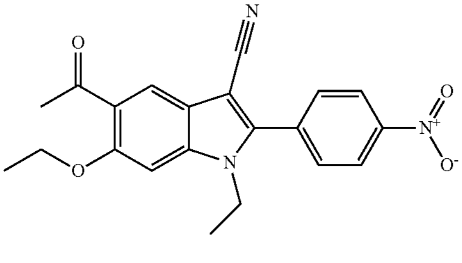
-continued
845
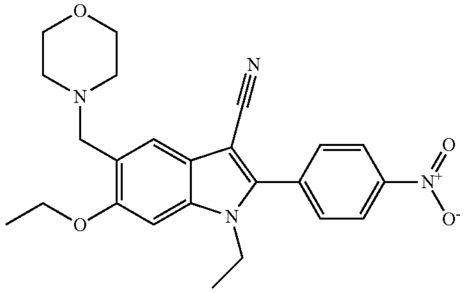
846
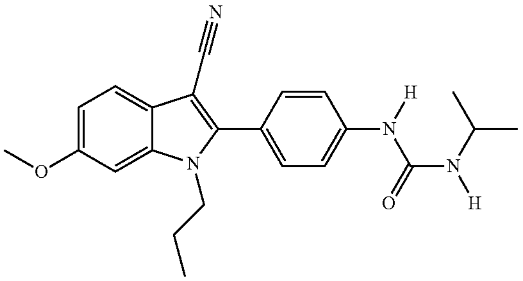
847
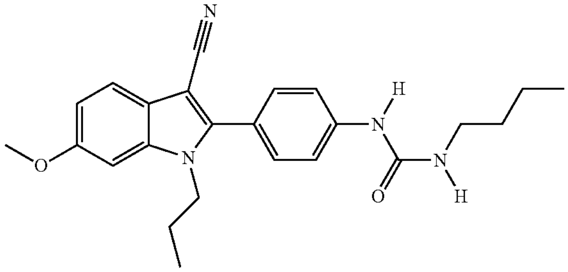
848
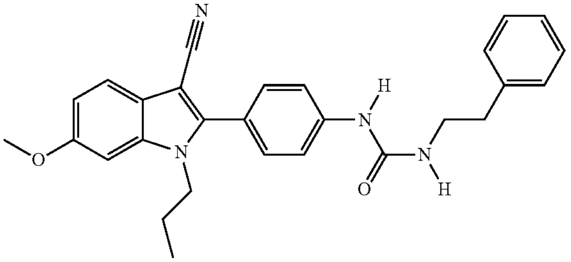
849
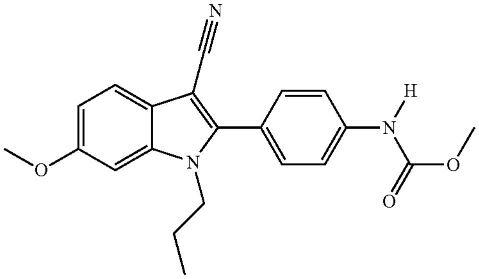

-continued
850
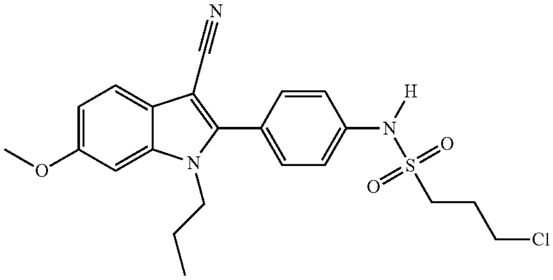
851
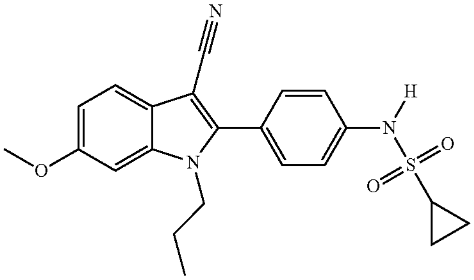
852
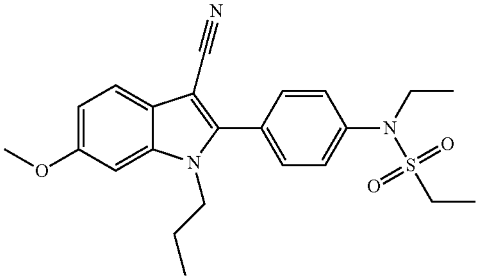
853
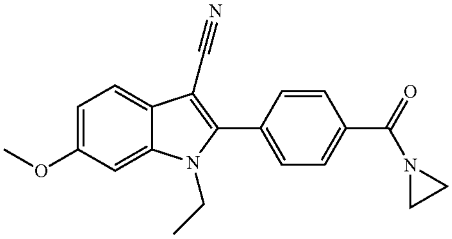
854
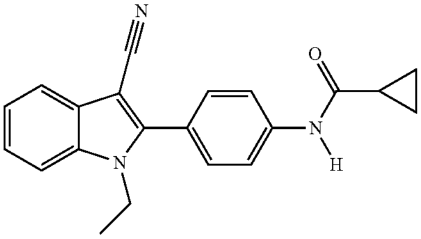
855
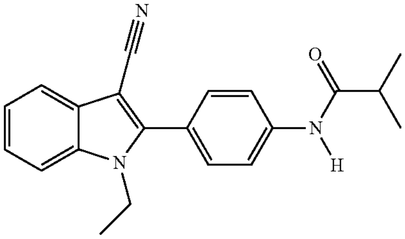
-continued
856
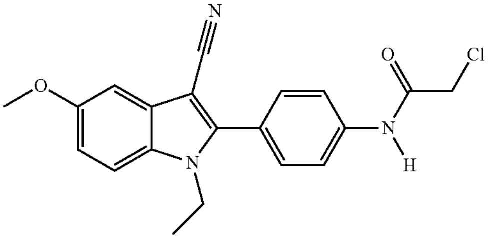
857
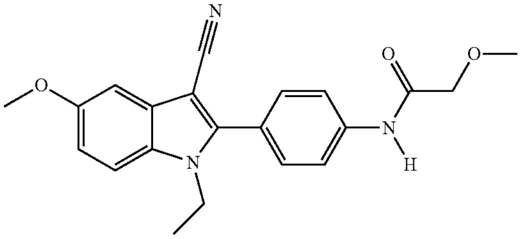
858
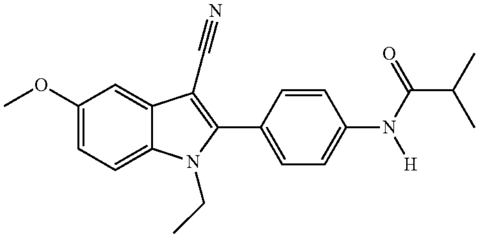
859
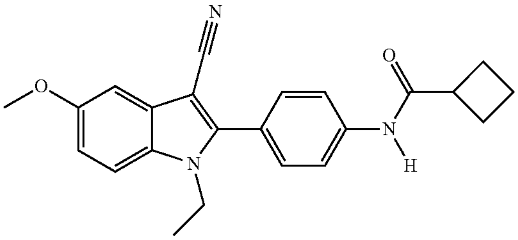
860
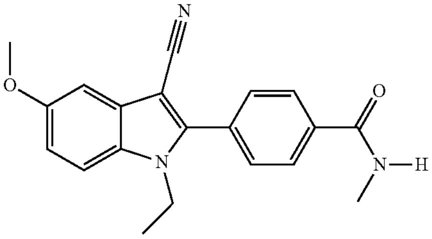
861
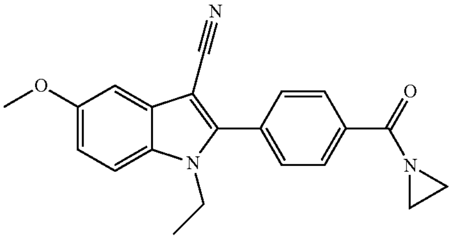

-continued

862

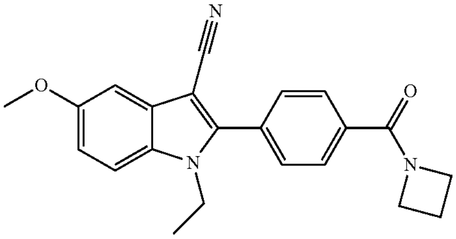

863

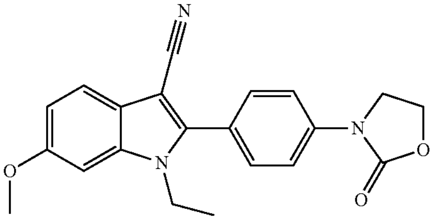

864

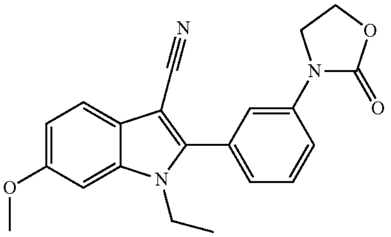

865

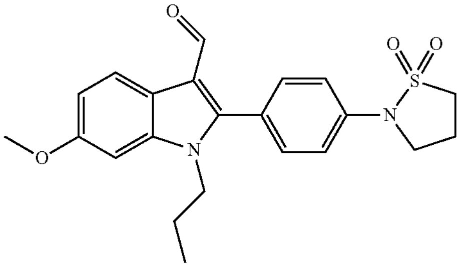

or an enantiomer, stereoisomer, diastereomer, racemic, tautomeric, ester, prodrug, solvate, hydrate, isotopologue or salt form thereof. Such compounds and pharmaceutically acceptable salts thereof were disclosed in U.S. patent application Ser. No. 11/180,961.

In one embodiment, a representative HCV inhibitor is a compound of Formula (I):

I

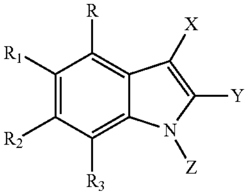

wherein:

X is:

-hydrogen;

-nitro;

-cyano;

—$COR_a$, where $R_a$ is:

—$C_1$ to $C_6$ alkyl,

—$C_3$ to $C_8$ cycloalkyl,

—$C_6$ to $C_8$ aryl optionally substituted with alkoxy or halogen, or

-dialkyl-amino;

—$COOR_x$, where $R_x$ is $C_1$ to $C_6$ alkyl or $C_3$ to $C_8$ cycloalkyl;

-formyl;

-aryl optionally substituted with alkoxy; or

-5 or 6-membered heteroaryl optionally substituted with:

—$C_1$ to $C_6$ alkyl,

—$C_3$ to $C_8$ cycloalkyl,

-aryl optionally substituted with alkoxy or one or more halogen(s), or

-5 to 6 membered heteroaryl;

Y is:

-hydrogen;

-haloalkyl;

-halogen;

-benzofuran;

-benzothiophene;

-dibenzofuran;

-dibenzothiophene;

-benzothiazole;

-naphthalene;

-indole, optionally substituted on the nitrogen with $C_1$ to $C_6$ alkyl or $C_3$ to $C_8$ cycloalkyl;

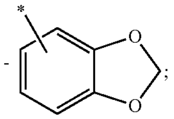

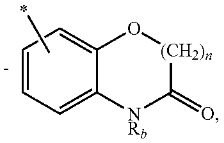

where $R_b$ is hydrogen or $C_1$ to $C_6$ alkyl or $C_3$ to $C_8$ cycloalkyl, and n is 0 or 1;

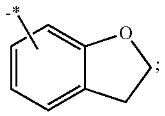

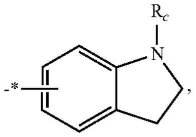

where $R_c$ is hydrogen, —$CONHR_x$, where $R_x$ is as defined above, or —$SO_2R_x$, where $R_x$ is as defined above; or

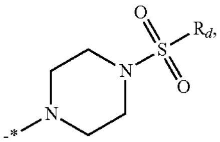

where $R_d$ is $C_1$ to $C_6$ alkyl, $C_3$ to $C_8$ cycloalkyl or aryl;

—$NHCOR_e$, where $R_e$ is:

—$C_1$ to $C_6$ alkyl;

—$C_3$ to $C_8$ cycloalkyl;

-aryl optionally substituted with:
—$C_1$ to $C_6$ alkyl,
—$C_3$ to $C_8$ cycloalkyl,
-alkoxy,
-cyano,
-nitro, or
-halogen;
—$NHCOOR_x$, where $R_x$ is as defined above;
—$CH_2O$—$R_f$, where $R_f$ is aryl;
—$NR_gR_h$, where $R_g$ is hydrogen, $C_1$ to $C_6$ alkyl or $C_3$ to $C_8$ cycloalkyl and $R_h$ is hydrogen or aryl optionally substituted with alkoxy;
—$C_1$ to $C_6$ alkyl;
—$C_3$ to $C_8$ cycloalkyl;
-5 or 6 membered heteroaryl, optionally substituted with:
—$C_1$ to $C_6$ alkyl, optionally substituted with aryl,
—$C_3$ to $C_8$ cycloalkyl, optionally substituted with aryl,
-aryl, optionally substituted with —$COOR_x$, where $R_x$ is as defined above, or
-amino;
-5 or 6 membered heterocycle optionally substituted with:
—$COOR_x$, where $R_x$ is as defined above, or
—$NHCOOR_x$, where $R_x$ is as defined above;
-aryl, optionally substituted with one or more of the following:
-alkoxy, optionally substituted with:
-alkoxy,
-hydroxy,
-one or more halogen(s),
-5 or 6 membered heterocycle, optionally substituted with:
—$C_1$ to $C_6$ alkyl,
—$C_3$ to $C_8$ cycloalkyl, or
-hydroxy,
-amino optionally substituted with one or more $C_1$ to $C_6$ alkyl(s) or one or more $C_3$ to $C_8$ cycloalkyl(s),
—$NR_iSO_2R_x$, where $R_x$ is as defined above and $R_i$ is:
-hydrogen,
—$C_1$ to $C_6$ alkyl,
—$C_3$ to $C_8$ cycloalkyl,
—$COR_x$, where $R_x$ is as defined above,
-haloalkyl, or
-haloalkoxy,
—$NR_jCOR_k$, where $R_k$ is:
—$C_1$ to $C_6$ alkyl,
—$C_3$ to $C_8$ cycloalkyl,
-hydrogen, or
-amino optionally substituted with one or more $C_1$ to $C_6$ alkyl(s) or one or more $C_3$ to $C_8$ cycloalkyl(s),
and $R_1$ is:
-hydrogen,
—$C_1$ to $C_6$ alkyl,
—$C_3$ to $C_8$ cycloalkyl,
—$COR_x$, where $R_x$ is as defined above,
-haloalkyl, or
-haloalkoxy,
—$N{=}N^{30}{=}N^{-}$, or
—$COR_l$, where $R_l$ is 5 or 6 membered heterocycle optionally substituted with hydroxy,
-amino optionally substituted with one or more $C_1$ to $C_6$ alkyl(s) or one or more $C_3$ to $C_8$ cycloalkyl(s),
—$C_1$ to $C_6$ alkyl, optionally substituted with:
—$NHSO_2R_x$, where $R_x$ is as defined above, or
—$NR_xSO_2R_x$, where $R_x$ is as defined above,
—$C_3$ to $C_8$ cycloalkyl, optionally substituted with:
—$NHSO_2R_x$, where $R_x$ is as defined above, or
—$NR_xSO_2R_x$, where $R_x$ is as defined above, -haloalkoxy,
-halogen,
-hydroxy,
—$COOR_x$, where $R_x$ is as defined above,
—$COR_m$, where $R_m$ is:
-amino optionally substituted with one or more $C_1$ to $C_6$ alkyl(s) or one or more $C_3$ to $C_8$ cycloalkyl(s), where the one or more $C_1$ to $C_6$ alkyl(s) or one or more $C_3$ to $C_8$ cycloalkyl(s) is/are optionally substituted with:
-hydroxy
-5 or 6 membered heterocycle,
-amino optionally substituted with one or more $C_1$ to $C_6$ alkyl(s) or one or more $C_3$ to $C_8$ cycloalkyl(s),
-alkoxy,
-3 to 7 membered heterocycle, optionally substituted with $C_1$ to $C_6$ alkyl or $C_3$ to $C_8$ cycloalkyl, where $C_1$ to $C_6$ alkyl or $C_3$ to $C_8$ cycloalkyl are optionally substituted with dialkyl-amino,
—$NHR_n$, where $R_n$ is:
—$CH_2CONH_2$, or
-aryl optionally substituted with:
-alkyl,
-one or more halogen(s),
-nitro, or
-one or more alkoxy(s),
—$NR_oCOR_p$, where $R_p$ is:
—$C_1$ to $C_6$ alkyl or $C_3$ to $C_8$ cycloalkyl, where $C_1$ to $C_6$ alkyl or $C_3$ to $C_8$ cycloalkyl are optionally substituted with:
-halogen,
-alkoxy, or
-aryl,
-5 or 6 membered heterocycle,
-aryl, optionally substituted with halogen,
-5 or 6 membered heteroaryl optionally substituted with one or more $C_1$ to $C_6$ alkyl(s) or one or more $C_3$ to $C_8$ cycloalkyl,
-hydrogen,

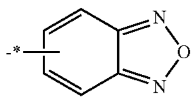

or

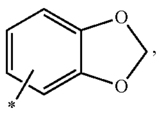

, and where $R_o$ is:
-hydrogen,
—$C_1$ to $C_6$ alkyl,
—$C_3$ to $C_8$ cycloalkyl,
—$COR_x$, where $R_x$ is as defined above,
-haloalkyl, or
-haloalkoxy,
—$NR_qCONR_qR_r$, where $R_q$ is:
-hydrogen,
—$C_1$ to $C_6$ alkyl,
—$C_3$ to $C_8$ cycloalkyl,
-haloalkyl,
-haloalkoxy, or
—$COR_x$, where $R_x$ is as defined above, and where $R_r$ is:

-aryl optionally substituted with:

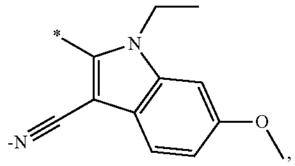

—$C_1$ to $C_6$ alkyl,

—$C_3$ to $C_8$ cycloalkyl,

-haloalkyl,

—$OR_S$, where $R_s$ is aryl, or

—$COOR_x$, where $R_x$ is as defined above,

—$C_1$ to $C_6$ alkyl or $C_3$ to $C_8$ cycloalkyl, where $C_1$ to $C_6$ alkyl or $C_3$ to $C_8$ cycloalkyl are optionally substituted with one or more of the following:

-halogen,

-alkenyl,

-aryl, and/or

—$COOR_x$, where $R_x$ is as defined above,

—$COOR_x$, where $R_x$ is as defined above,

—$NRCOOR_u$, where $R_u$ is:

—$C_1$ to $C_{12}$ alkyl or $C_3$ to $C_8$ cycloalkyl, optionally substituted with:

-aryl optionally substituted with $C_1$ to $C_6$ alkyl, $C_3$ to $C_8$ cycloalkyl, or alkoxy, -alkenyl, -alkoxy, -alkynyl, -halogen, or -5 or 6 membered heterocycle, -aryl, optionally substituted with:

-alkoxy,

-halogen,

—$C_1$ to $C_6$ alkyl, or

—$C_3$ to $C_8$ cycloalkyl, or

-5 or 6 membered heterocycle, and $R_t$ is:

-hydrogen,

—$C_1$ to $C_6$ alkyl,

—$C_3$ to $C_8$ cycloalkyl,

—$COR_x$, where $R_x$ is as defined above,

-haloalkyl, or

-haloalkoxy,

—$NR_vSO_2R_w$, where $R_v$ is:

-hydrogen,

—$COR_x$, where $R_x$ is as defined above, or

—$C_1$ to $C_6$ alkyl or $C_3$ to $C_8$ cycloalkyl, where $C_1$ to $C_6$ alkyl or $C_3$ to $C_8$ cycloalkyl are optionally substituted with:

-halogen,

—$COR_x$, where $R_x$ is as defined above,

—$OCOR_x$, where $R_x$ is as defined above,

-hydroxy, or

-alkoxy, and where $R_w$ is:

—$C_1$ to $C_6$ alkyl or $C_3$ to $C_8$ cycloalkyl, where $C_1$ to $C_6$ alkyl or $C_3$ to $C_8$ cycloalkyl are optionally substituted with:

-halogen,

-haloalkyl,

-aryl, or

-5 or 6 membered heterocycle,

—$C_2$ to $C_6$ alkenyl,

-alkyl- or dialkyl-amino optionally substituted with halogen,

-5 or 6 membered heterocycle, or

-5 or 6 membered heteroaryl optionally substituted with:

—$C_1$ to $C_6$ alkyl,

—$C_3$ to $C_8$ cycloalkyl,

-5 or 6 membered heterocycle, or

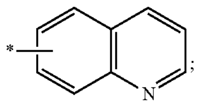;
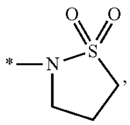,
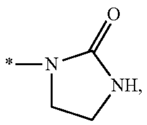,
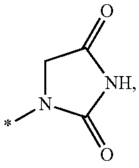,
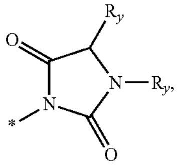, optionally substituted with $C_1$ to $C_6$ alkyl or $C_3$ to $C_8$ cycloalkyl, where $R_y$ is $C_1$ to $C_6$ alkyl, $C_3$ to $C_8$ cycloalkyl, or hydrogen,

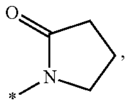,
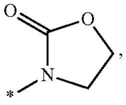,
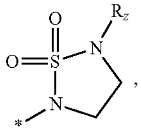, where $R_z$ is hydrogen, $C_1$ to $C_6$ alkyl or $C_3$ to $C_8$ cycloalkyl, where $C_1$ to $C_6$ alkyl or $O_3$ to $C_8$ cycloalkyl are optionally substituted with aryl, —$SR_x$, where $R_x$ is as defined above, —$SO_2R_{aa}$, where $R_{aa}$ is:

—$C_1$ to $C_6$ alkyl,

—$C_3$ to $C_8$ cycloalkyl,

-amino,

-alkyl- or dialkyl-amino optionally substituted with hydroxy or —$COOR_x$, where $R_x$ is as defined above, -5 or 6 membered heteroaryl, -aryl, and/or —$NHR_{bb}$, where $R_{bb}$ is:

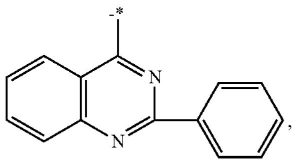,
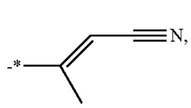

—$C(=S)NH_2$, or

—$PO(OR_x)_2$, where $R_x$ is as defined above;

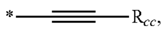

where $R_{cc}$ is:

-naphthalene,

-5 or 6 membered heteroaryl,

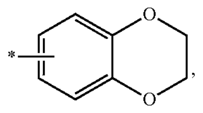

-aryl, optionally substituted with one or more of the following:

-alkoxy,

-hydroxy,

-halogen,

—$C_1$ to $C_6$ alkyl or $C_3$ to $C_8$ cycloalkyl, where $C_1$ to $C_6$ alkyl or $C_3$ to $C_8$ cycloalkyl are optionally substituted with cyano, -amino optionally substituted with one or more $C_1$ to $C_6$ alkyl(s) or one or more $C_3$ to $C_8$ cycloalkyl(s), —$NHPOR_xR_x$, where $R_x$ is as defined above, —$NR_{ee}CONR_{ff}R_{ff}$, where $R_{ee}$ is hydrogen, $C_1$ to $C_6$ alkyl or $C_3$ to $C_8$ cycloalkyl, where $C_1$ to $C_6$ alkyl or $C_3$ to $C_8$ cycloalkyl are optionally substituted with halogen, and $R_{ff}$ is:

-hydrogen,

-haloalkyl,

-haloalkoxy,

—$C_1$ to $C_6$ alkyl,

—$C_3$ to $C_8$ cycloalkyl, or

—$COR_x$, where $R_x$ is as defined above,

—$NR_{gg}COR_{hh}$, where $R_{hh}$ is:

-hydrogen,

—$C_1$ to $C_6$ alkyl or $C_3$ to $C_8$ cycloalkyl, where $C_1$ to $C_6$ alkyl or $C_3$ to $C_8$ cycloalkyl are optionally substituted with:

-alkoxy,

-halogen, or

-amino optionally substituted with one or more $C_1$ to $C_6$ alkyl(s) or one or more $C_3$ to $C_8$ cycloalkyl(s), -amino optionally substituted with one or more $C_1$ to $C_6$ alkyl(s) or one or more $C_3$ to $C_8$ cycloalkyl(s), where the one or more $C_1$ to $C_6$ alkyl(s) or one or more $C_3$ to $C_8$ cycloalkyl(s) is/are optionally substituted with halogen, -5 or 6 membered heterocycle, -5 or 6 membered heteroaryl, and $R_{gg}$ is:

-hydrogen,

—$C_1$ to $C_6$ alkyl,

—$C_3$ to $C_8$ cycloalkyl,

-haloalkyl,

-haloalkoxy, or

—$COR_x$, where $R_x$ is as defined above,

-haloalkyl,

-5 or 6 membered heterocycle,

-amino optionally substituted with one or more $C_1$ to $C_6$ alkyl(s) or one or more $C_3$ to $C_8$ cycloalkyl(s), and/or —$NR_{ii}SO_2R_x$, where $R_x$ is as defined above, and is:

-hydrogen,

—$C_1$ to $C_6$ alkyl,

—$C_3$ to $C_8$ cycloalkyl,

-haloalkyl,

-haloalkoxy,

—$COR_x$, where $R_x$ is as defined above;

Z is:

-hydrogen;

—$C_1$ to $C_6$ alkyl or $C_3$ to $C_8$ cycloalkyl, where $C_1$ to $C_6$ alkyl or $C_3$ to $C_8$ cycloalkyl are optionally substituted with:

-alkoxy,

-one or more halogen(s), or

-aryl;

—$C_2$ to $C_6$ alkenyl;

-aryl optionally substituted with alkoxy or one or more $C_1$ to $C_6$ alkyl(s) or one or more $C_3$ to $C_8$ cycloalkyl(s);

—$COOR_x$, where $R_x$ is as defined above; or

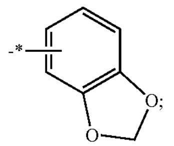

R is hydrogen, halogen or alkoxy;

$R_1$ is:

-hydrogen;

-hydroxy;

-halogen;

-haloalkyl;

-nitro;

-5 or 6 membered heteroaryl;

-5 or 6 membered heterocycle;

-alkoxy optionally substituted with:

-one or more halogen(s),

-aryl, or

-5 or 6 membered heterocycle;

-aryl optionally substituted with alkoxy;

—$COR_x$, where $R_x$ is as defined above;

—$C_1$ to $C_6$ alkyl or $C_3$ to $C_8$ cycloalkyl, where $C_1$ to $C_6$ alkyl or $C_3$ to $C_8$ cycloalkyl are optionally substituted with dialkyl-amino or 5 or 6 membered heterocycle; or $R_1$ joins together with $R_2$ to form:

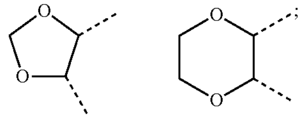

$R_2$ is:

-nitro;

-hydrogen;

-halogen;

-hydroxy;

—$C_1$ to $C_6$ alkyl or $C_3$ to $C_8$ cycloalkyl, where $C_1$ to $C_6$ alkyl or $C_3$ to $C_8$ cycloalkyl are optionally substituted with one or more halogen(s);

-amino;

-alkoxy optionally substituted with:

-one or more halogen(s),

—$OCOR_x$, where $R_x$ is as defined above,

-dialkyl-amino optionally substituted with alkoxy,

-5 or 6 membered heterocycle optionally substituted with $C_1$ to $C_6$ alkyl or $C_3$ to $C_8$ cycloalkyl, -5 or 6 membered heteroaryl, or -aryl;

—$COOR_x$, where $R_x$ is as defined above;

-haloalkyl;

-amide optionally substituted with:

-hydroxy, or

-aryl;

-5 or 6 membered heteroaryl;

—$OCOR_x$, where $R_x$ is as defined above;

—$NHCOR_{jj}$, where $R_{jj}$ is:

-alkoxy, or

-amino optionally substituted with one or more $C_1$ to $C_6$ alkyl(s) or one or more $C_3$ to $C_8$ cycloalkyl(s);

—$OR_{kk}$, where $R_{kk}$ is 5 to 6 membered heteroaryl;

—$NHSO_2R_x$, where $R_x$ is as defined above; or $R_2$ joins together with $R_1$ to form:

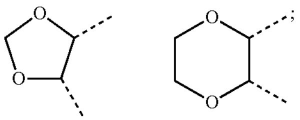

$R_3$ is:

-hydrogen; or

—$CH_2OCOR_x$, and $R_x$ is as defined above;

or an enantiomer, stereoisomer, diastereomer, racemic, tautomeric, ester, prodrug, solvate, hydrate, isotopologue or salt form thereof;

provided that when X is phenyl substituted with alkoxy, Y is phenyl, R is hydrogen, $R_1$ is halogen, $R_2$ is hydrogen, and $R_3$ is hydrogen, and provided that when X is phenyl, hydroxyphenyl or pyridyl, Y is alkyl or cycloalkyl, R is hydrogen, $R_1$ is hydrogen or hydroxy, $R_2$ is hydrogen or hydroxy, and $R_3$ is hydrogen, then Z is:

—$C_1$ to $C_6$ alkyl or $C_3$ to $C_8$ cycloalkyl, where $C_1$ to $C_6$ alkyl or $C_3$ to $C_8$ cycloalkyl are substituted with:

-alkoxy,

-one or more halogen(s), or

-aryl;

—$C_2$ to $C_6$ alkenyl;

-aryl optionally substituted with alkoxy or one or more $C_1$ to $C_6$ alkyl(s) or one or more $C_3$ to $C_8$ cycloalkyl(s);

—$COOR_x$, where $R_x$ is as defined above; or

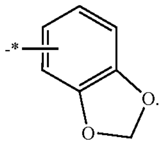

In one embodiment, a representative HCV inhibitor is a compound selected from:

1497

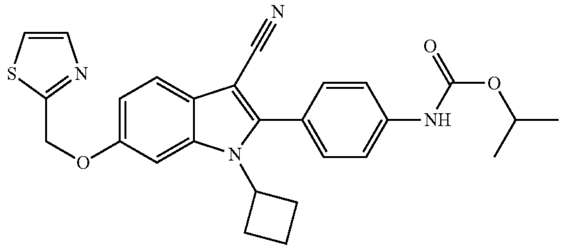

1506

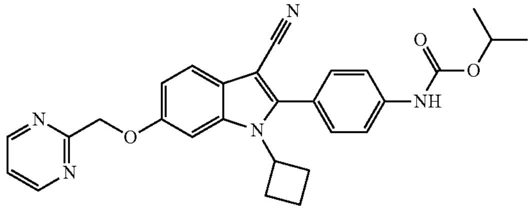

1507

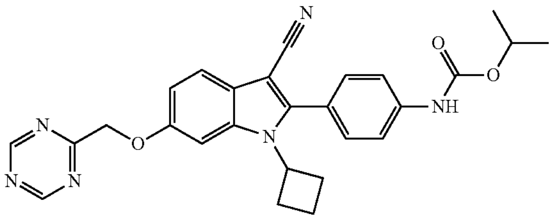

1510

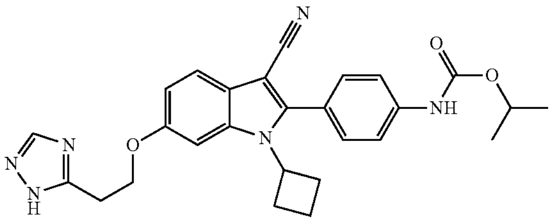

1511

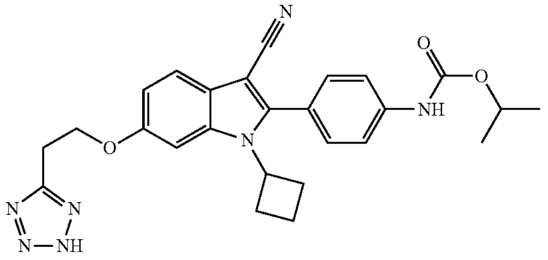

1512

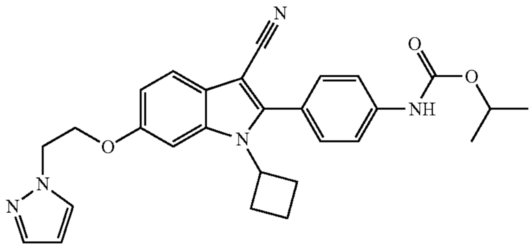

-continued
1513
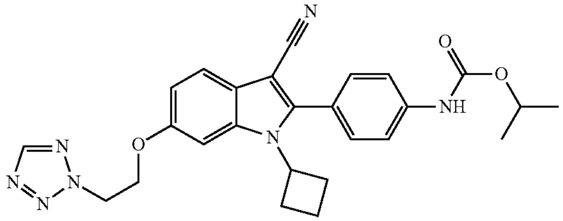
1514
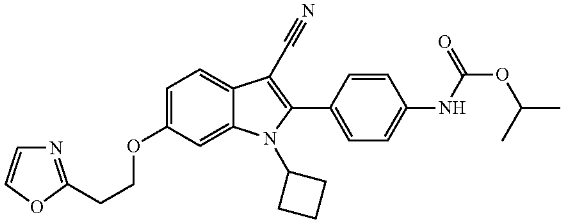
1517
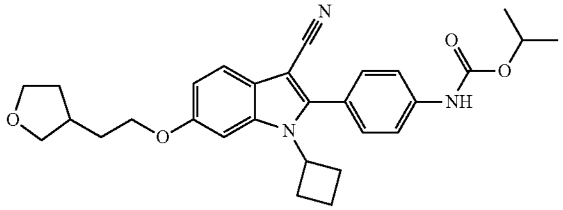
1518
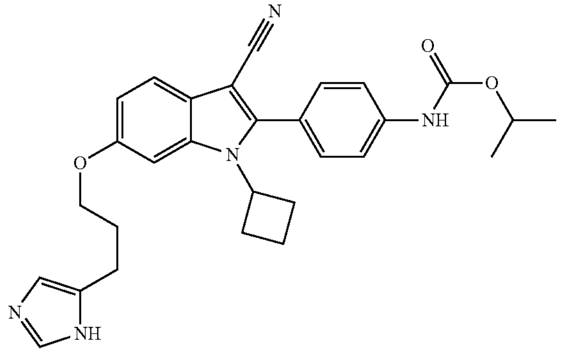
1519
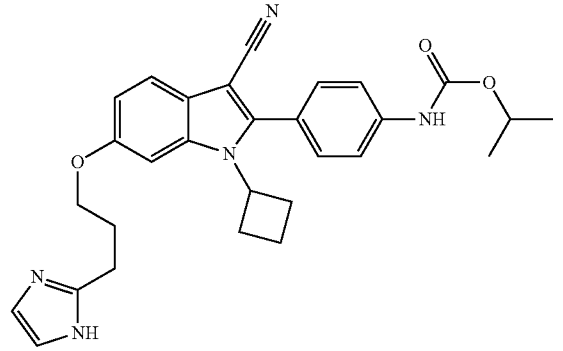
-continued
1520
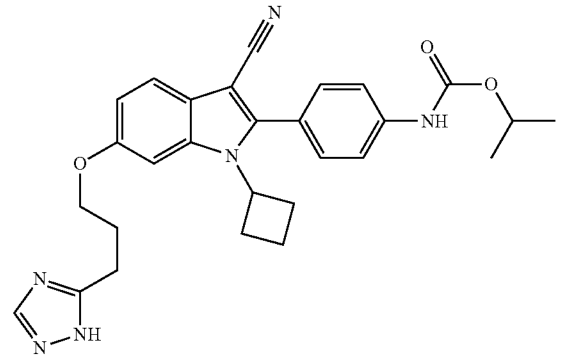
1521
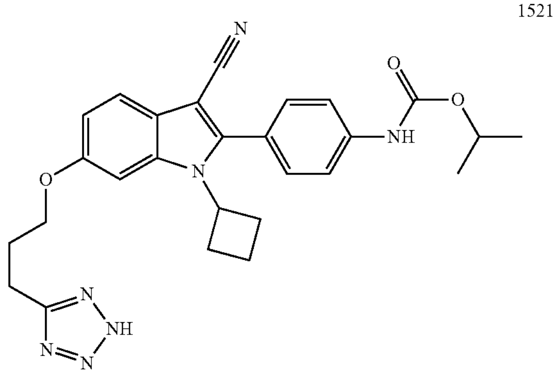
1522
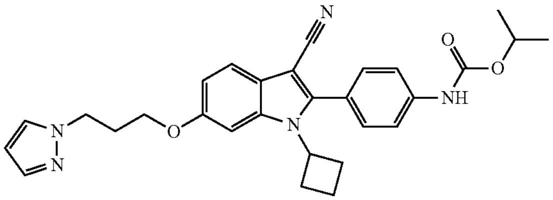
1523
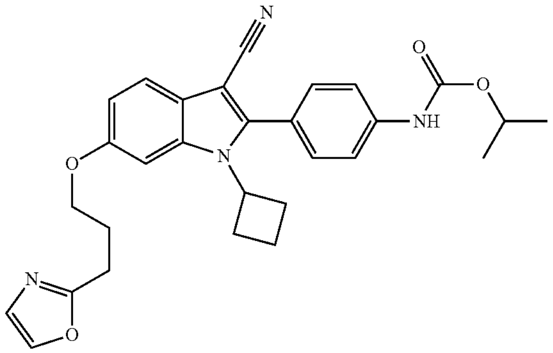
1540
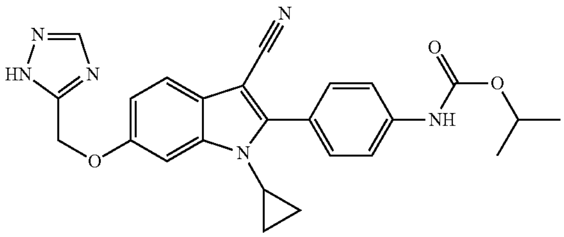

-continued
1541
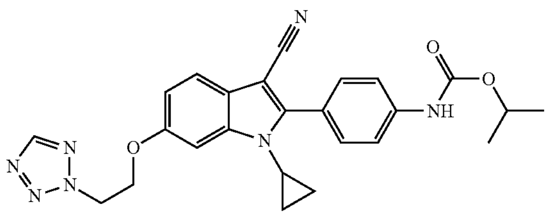
1542
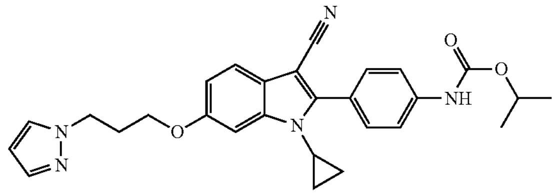
1556
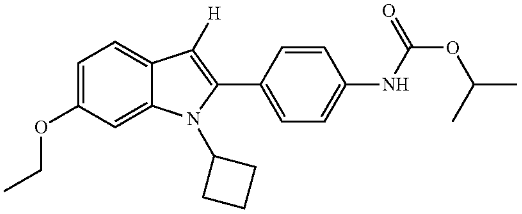
1574
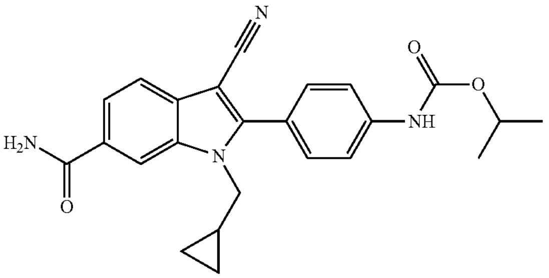
1581
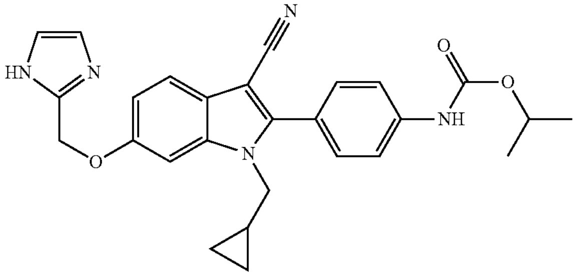
1582
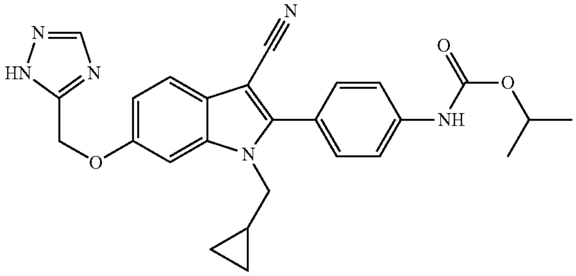
-continued
1583
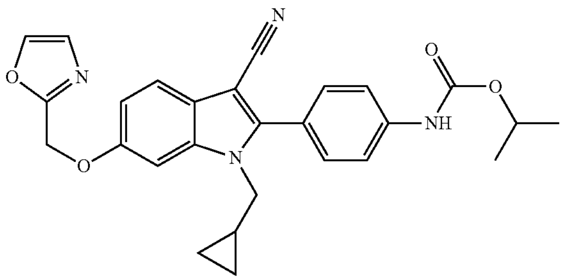
1584
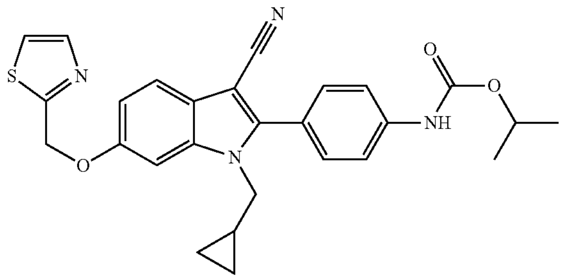
1590
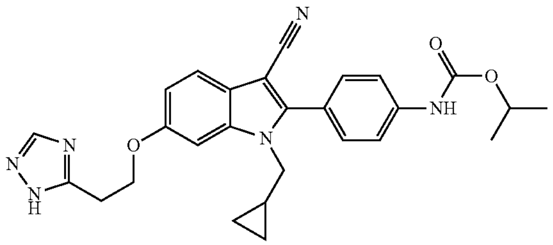
1591
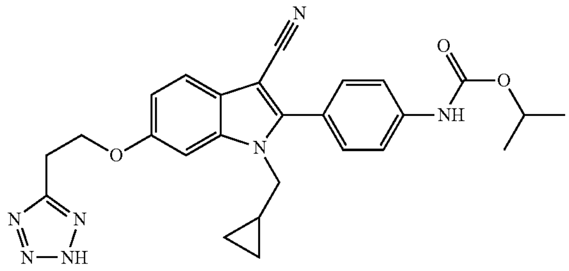
1592
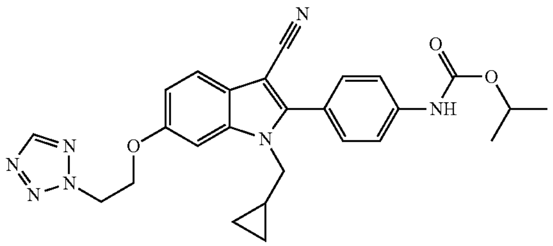

1593
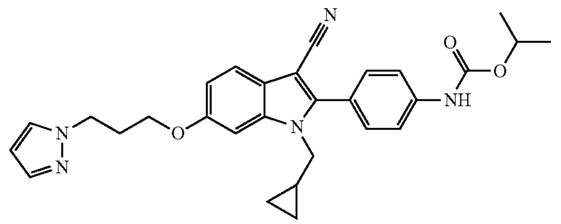
1610
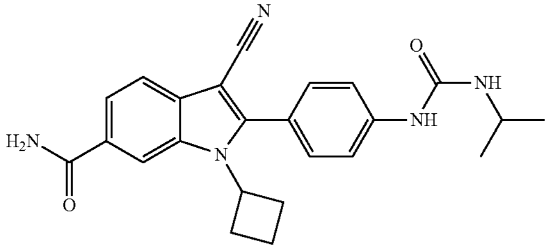
1617
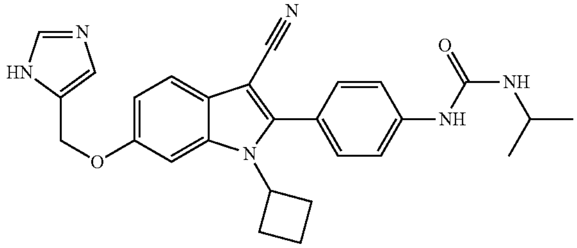
1618
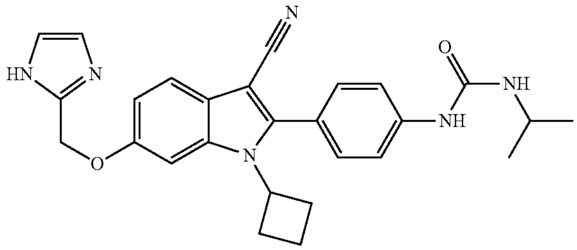
1619
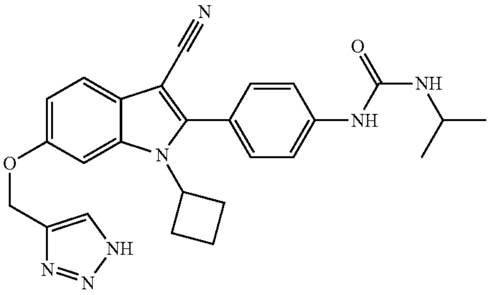
1620
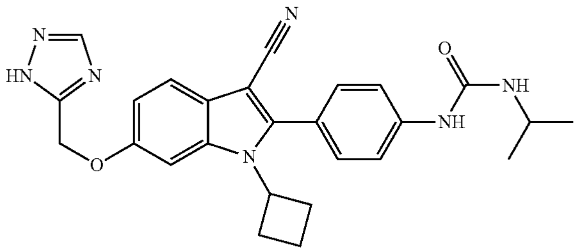
1621
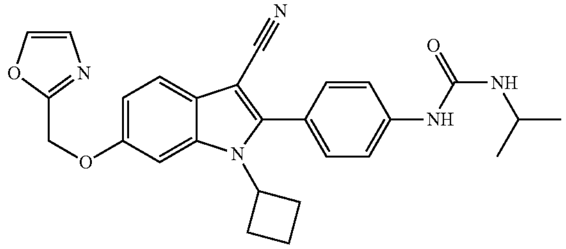
1622
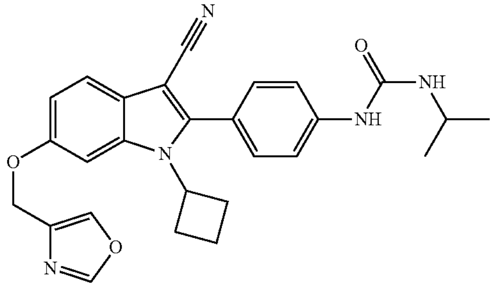
1623
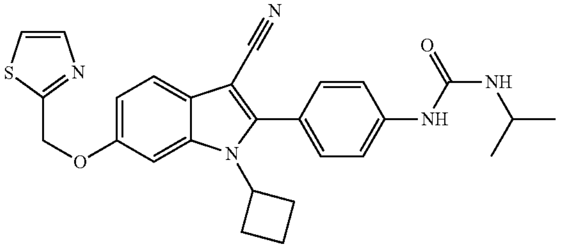
1632
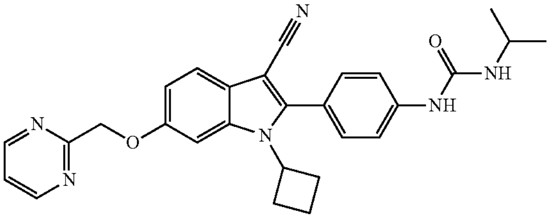
1633
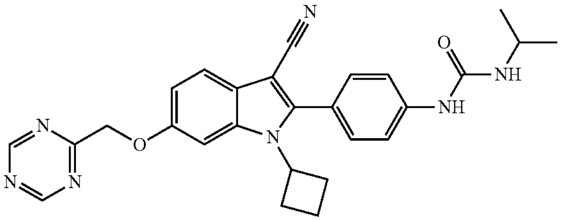

-continued
1636
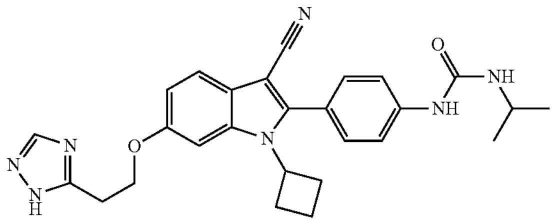
1637
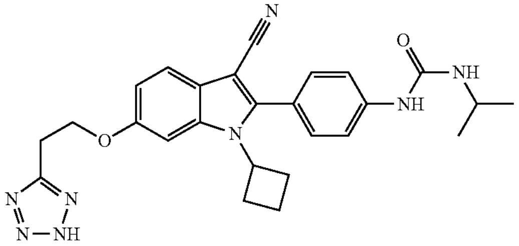
1638
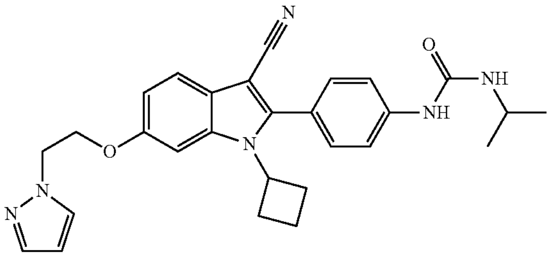
1639
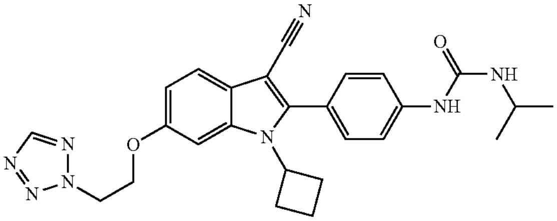
1640
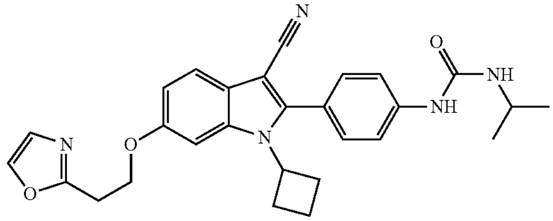
1643
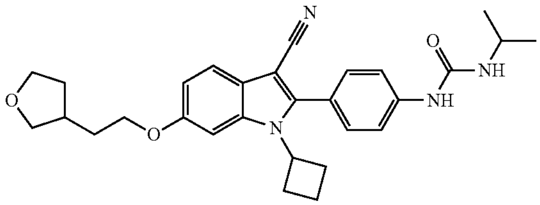
-continued
1644
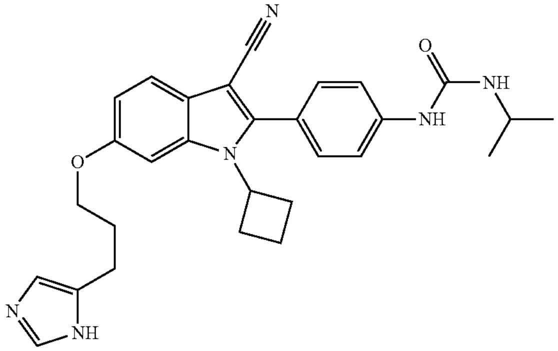
1645
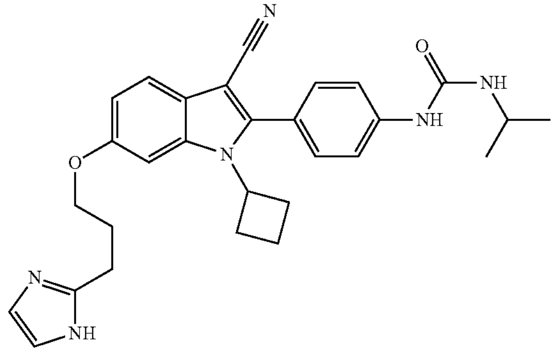
1646
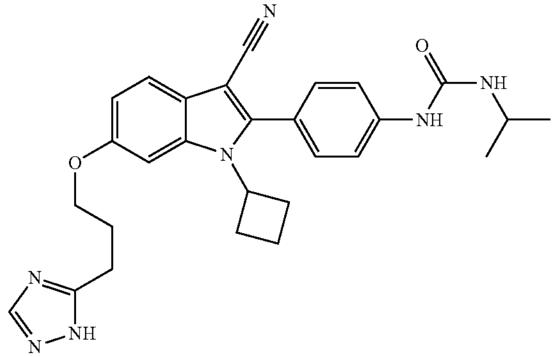
1647
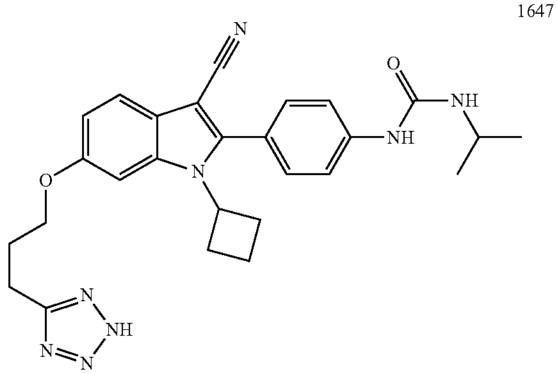

-continued
1648
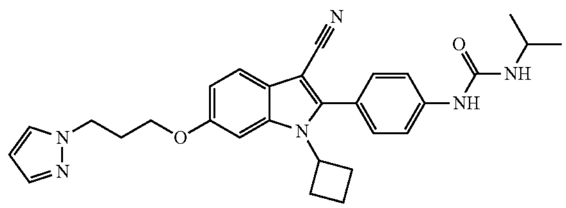
1649
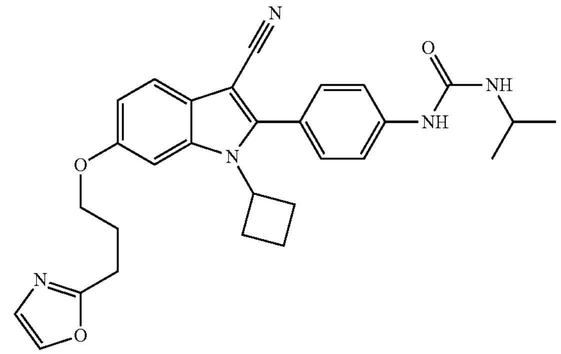
1667
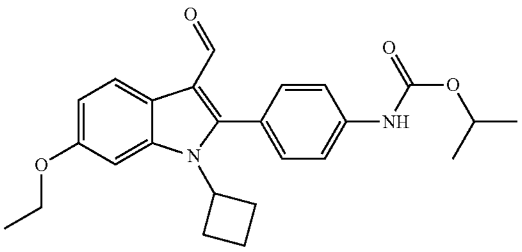
1687
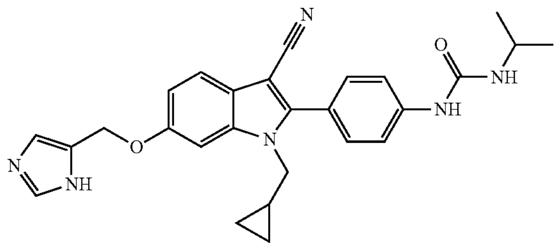
1688
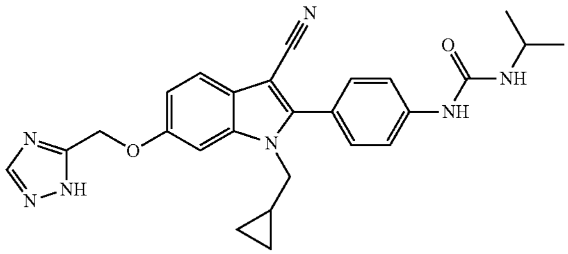
-continued
1689
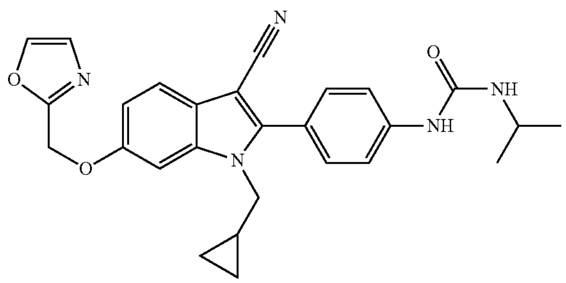
1690
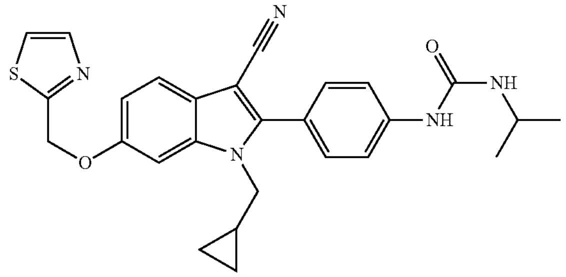
1695
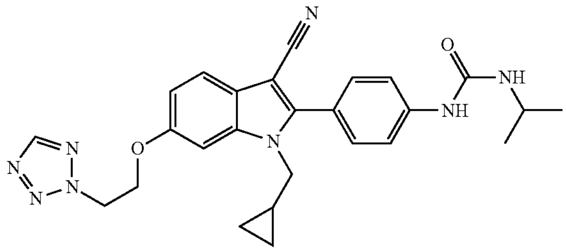
1702
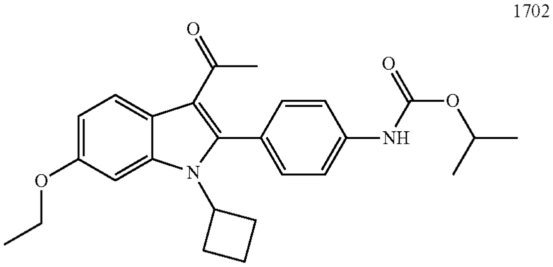
1720
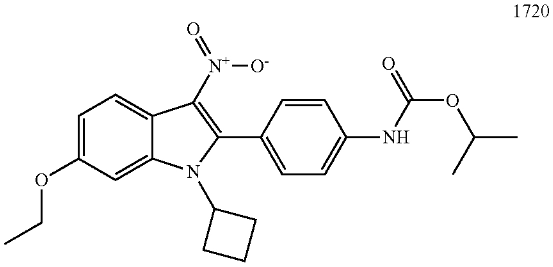

-continued
1726
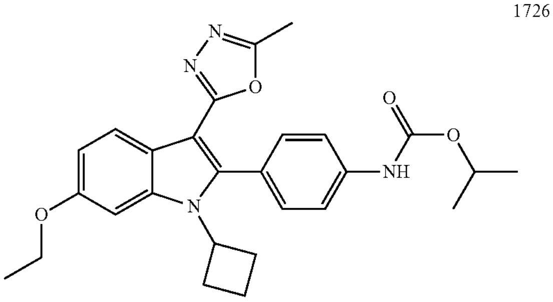
1728
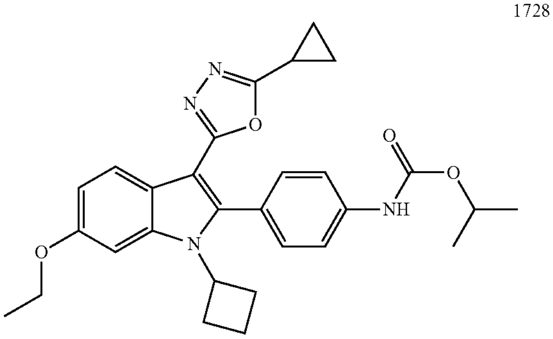
1730
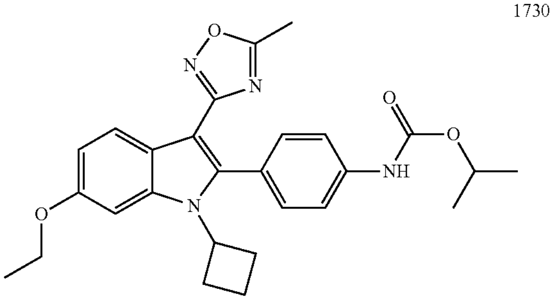
1732
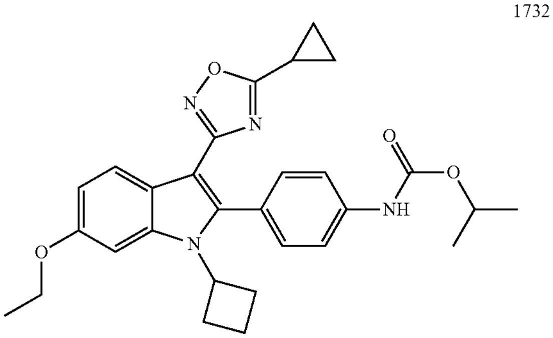
1734
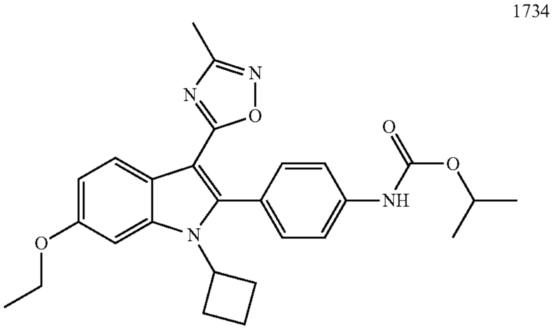
-continued
1736
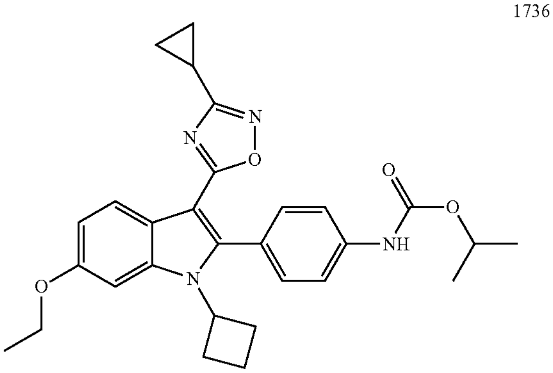
1738
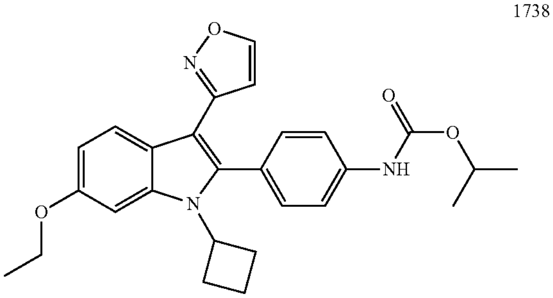
1740
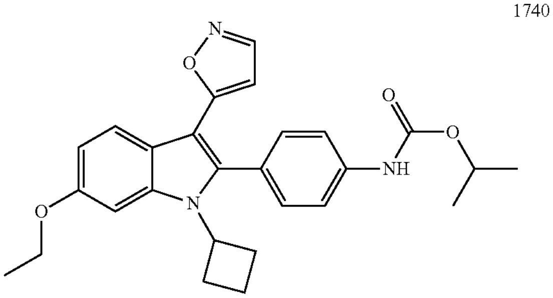
1749
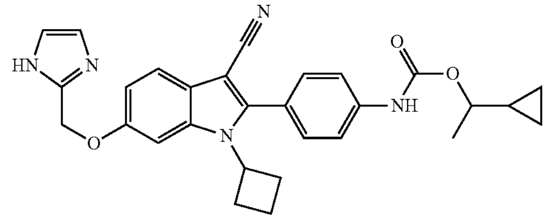
1750
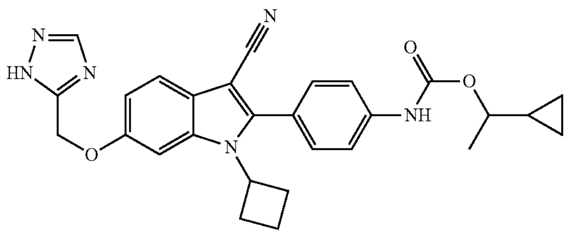

-continued
1751
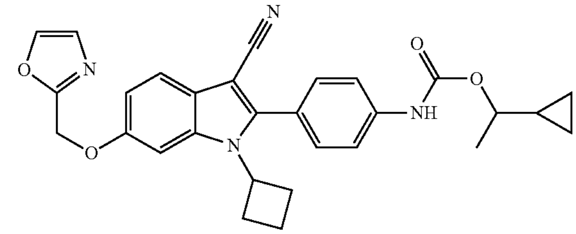
1752
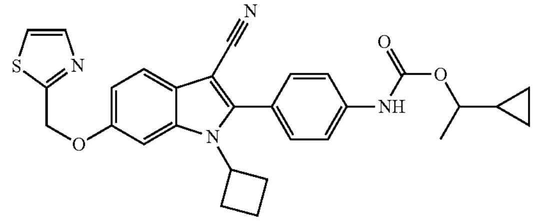
1759
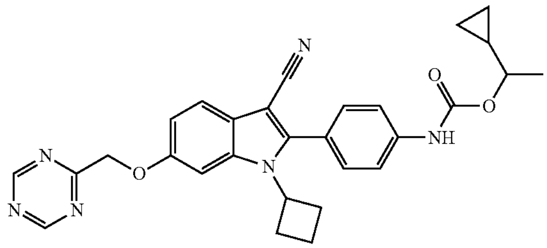
1761
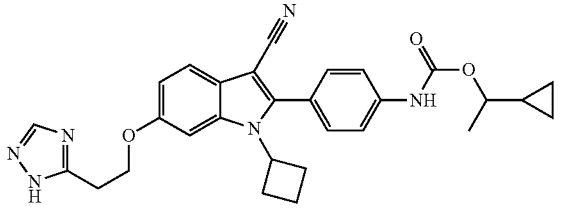
1762
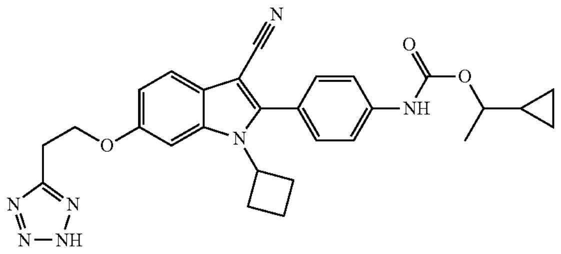
1763
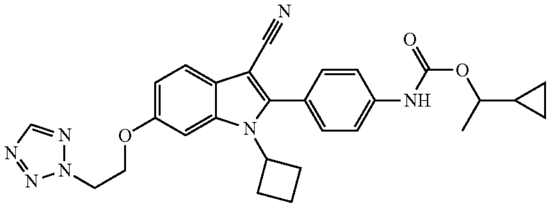
-continued
1765
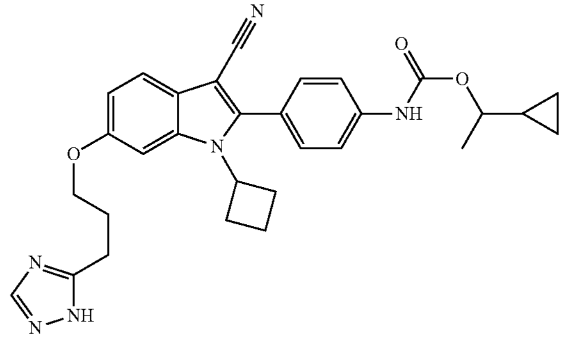
1766
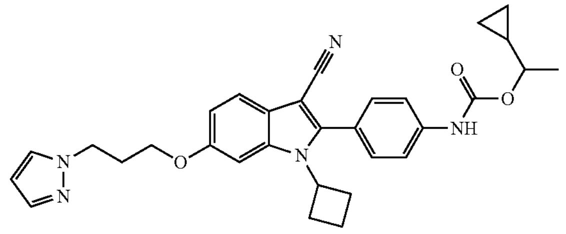
1771
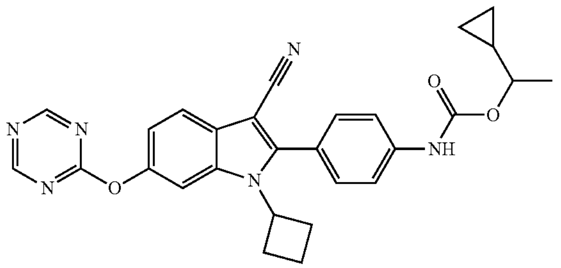
1778
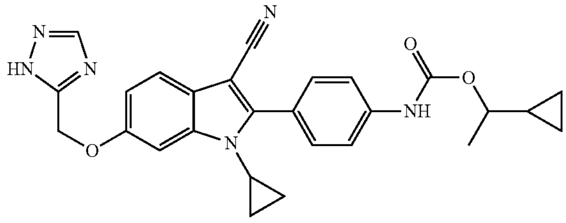
1783
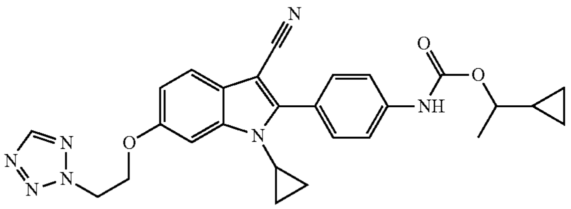

-continued
1784
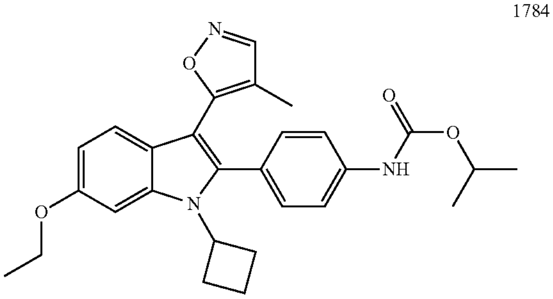
1785
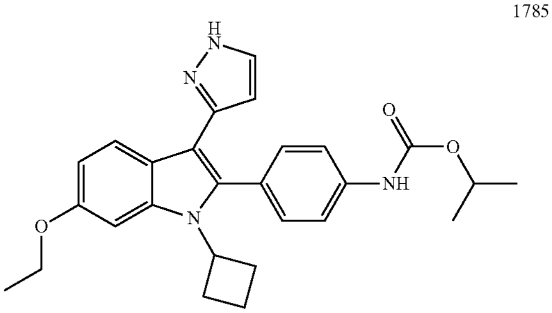
1787
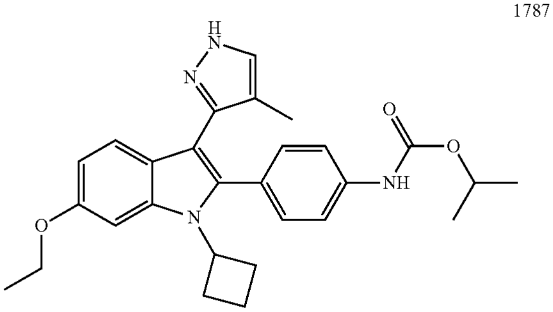
1789
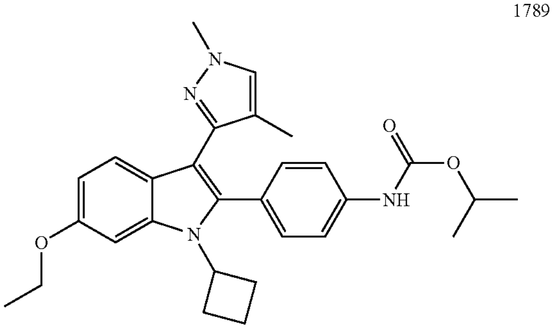
1791
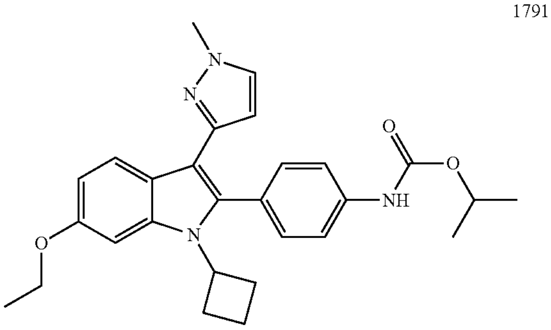
-continued
1793
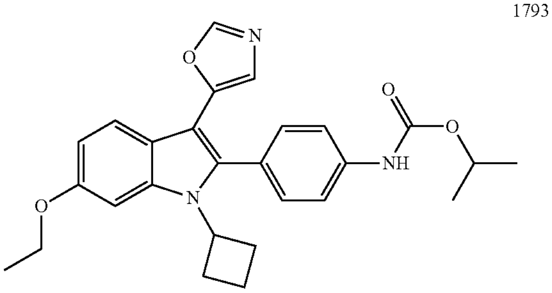
1795
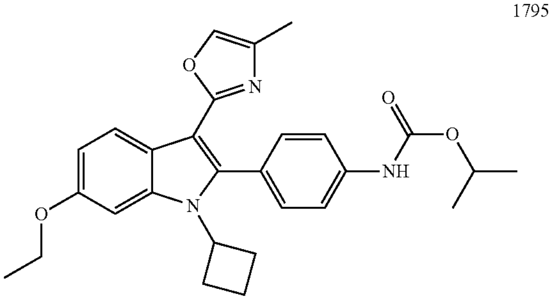
1799
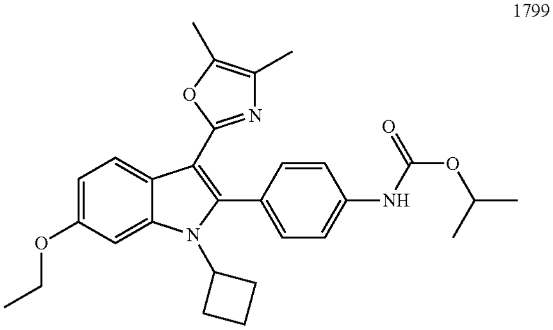
1801
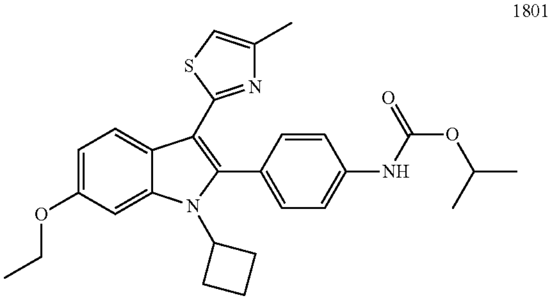
1803
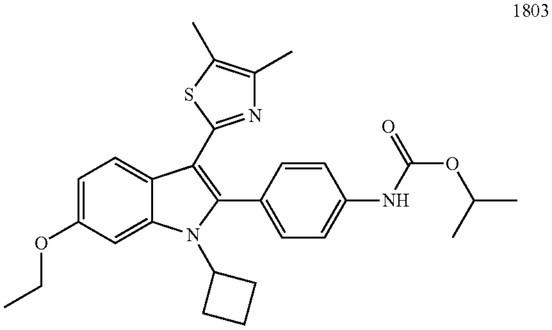

-continued
1807
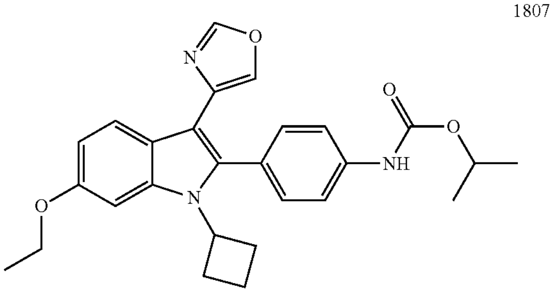
1809
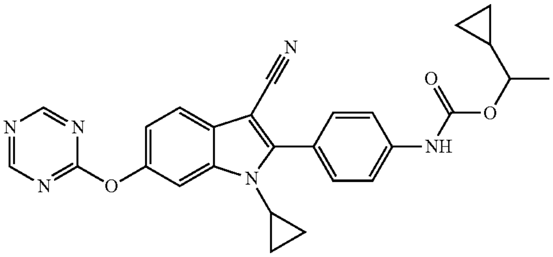
1812
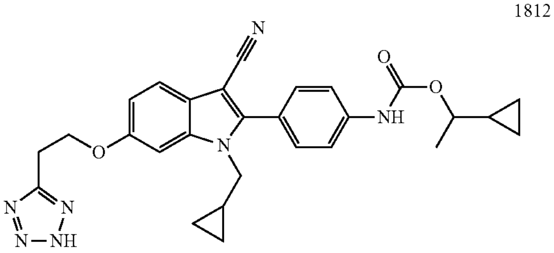
1813
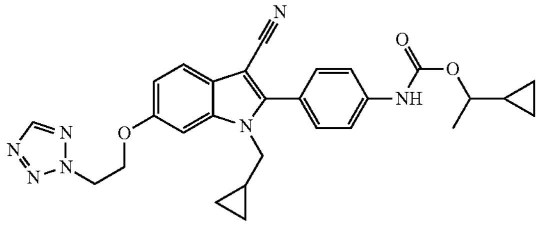
1816
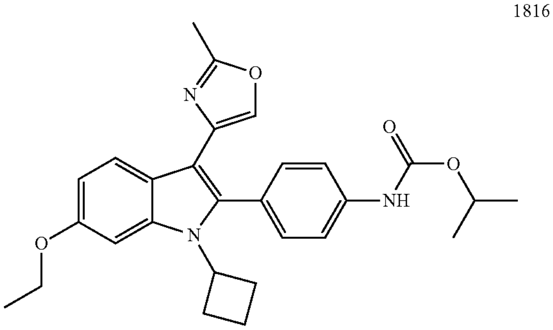
-continued
1818
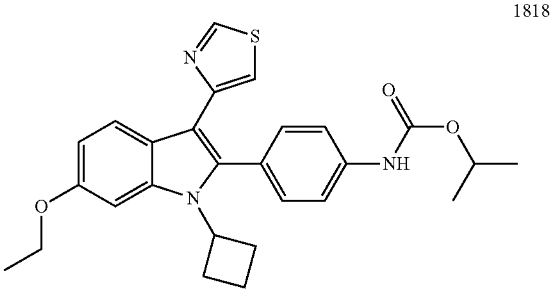
1820
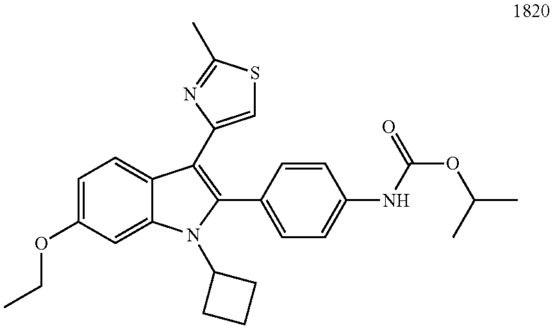
1830
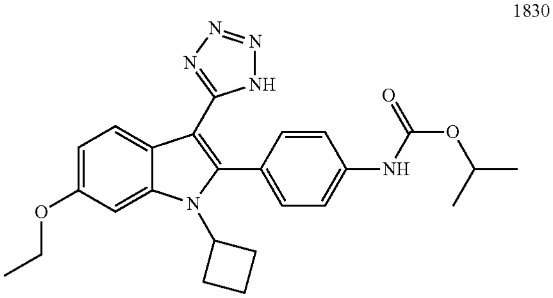
1832
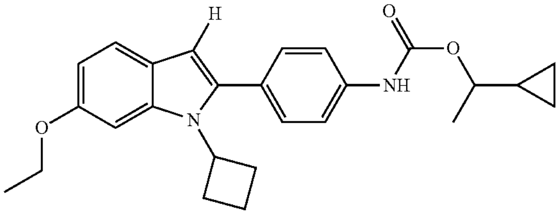
1856
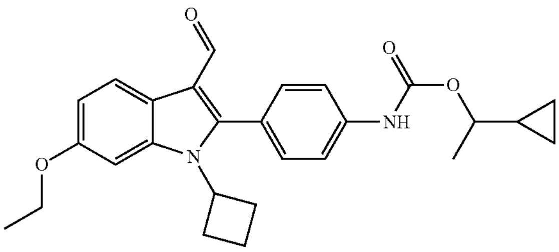

-continued
1862
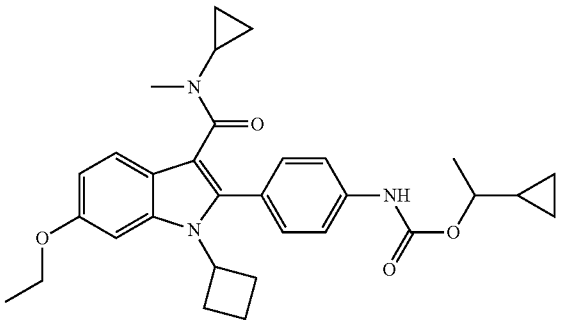
1872
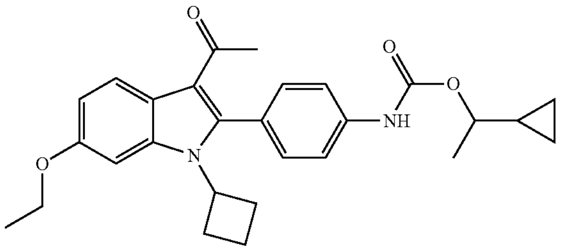
1885
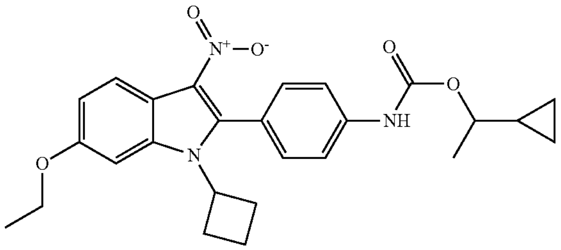
1891
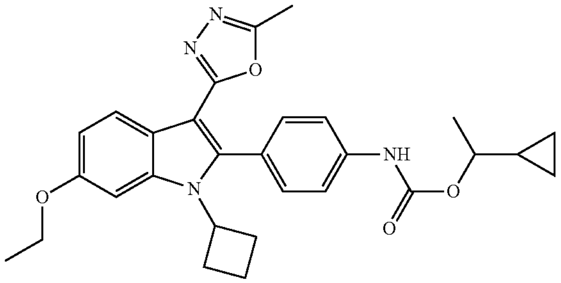
1893
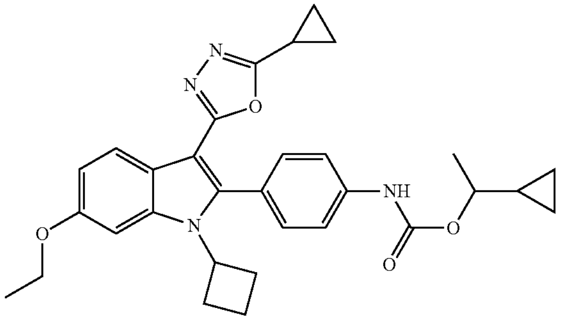
-continued
1895
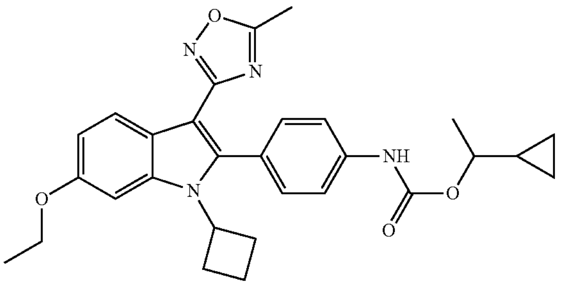
1897
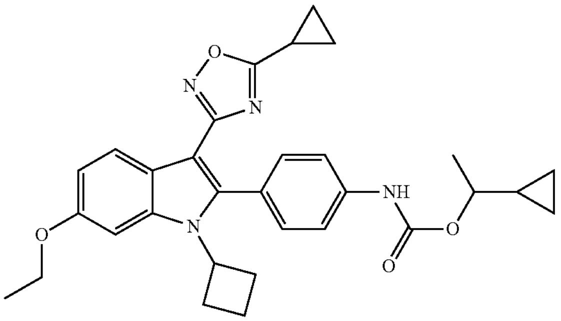
1899
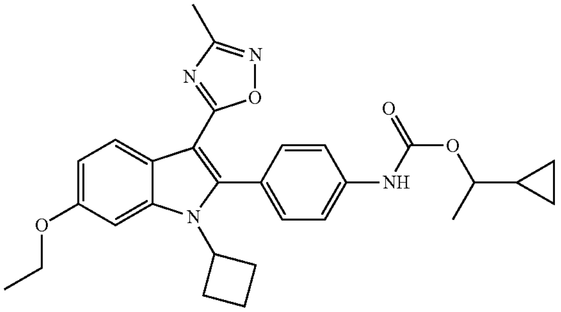
1901
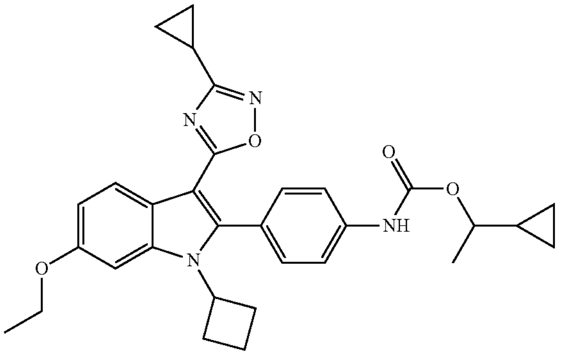

-continued
1903
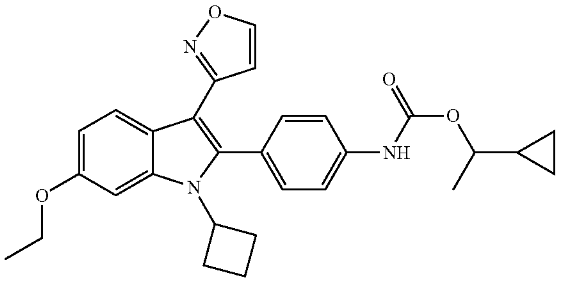
1905
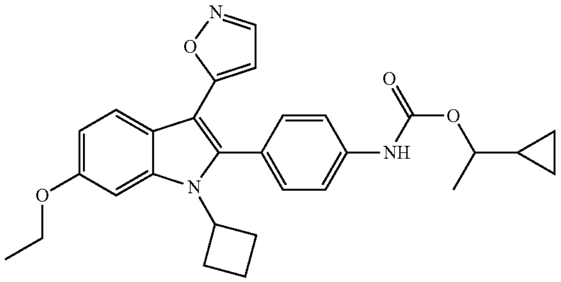
1907
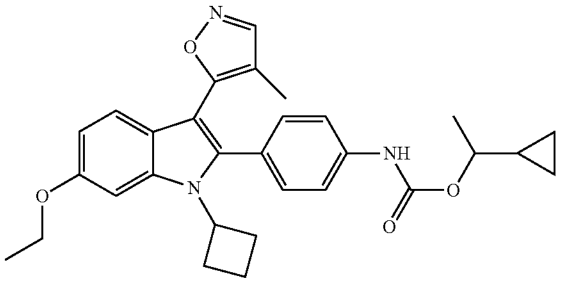
1909
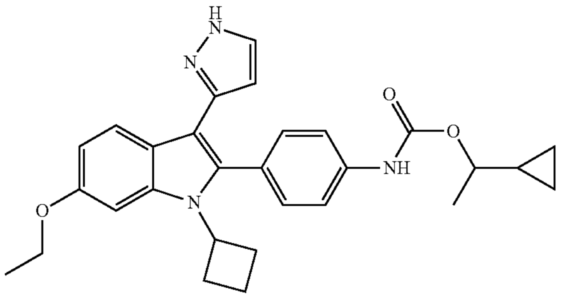
1911
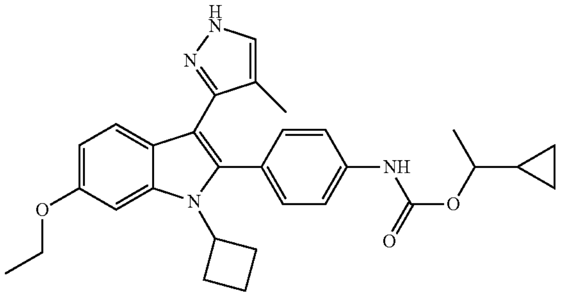
-continued
1913
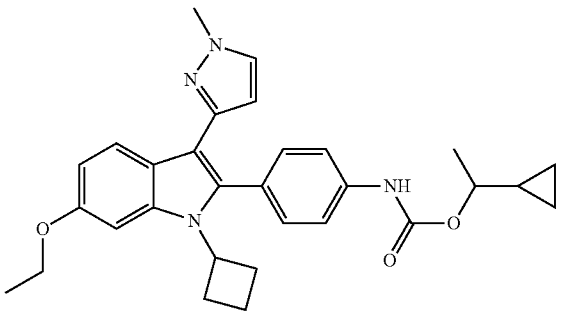
1915
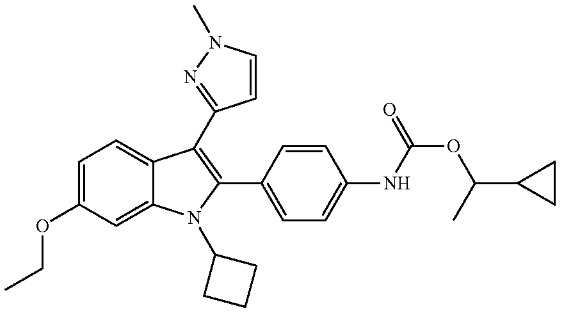
1925
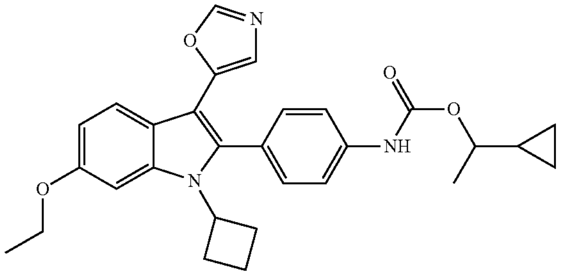
1927
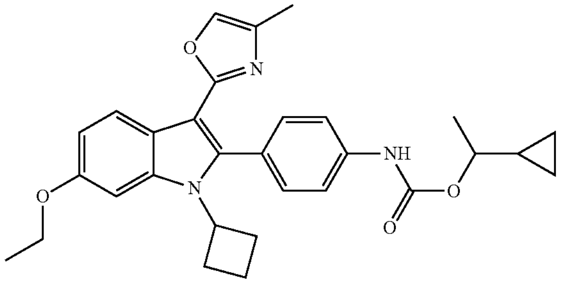
1929
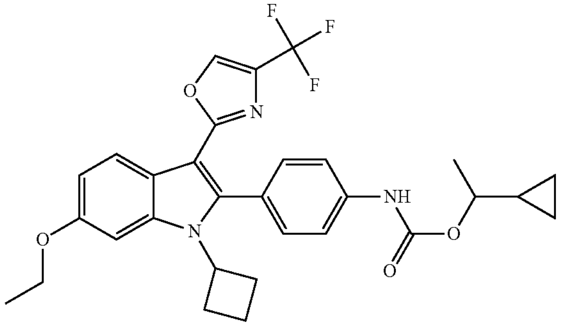

-continued
1931
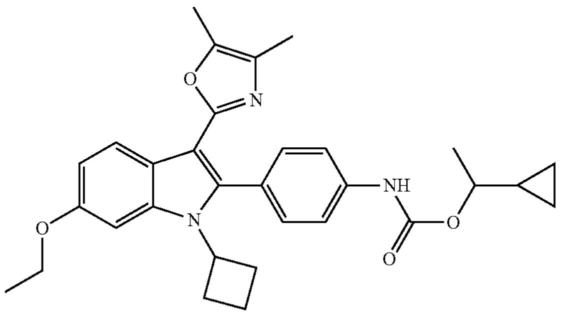
1933
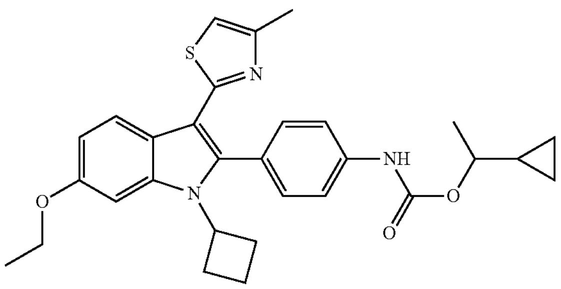
1935
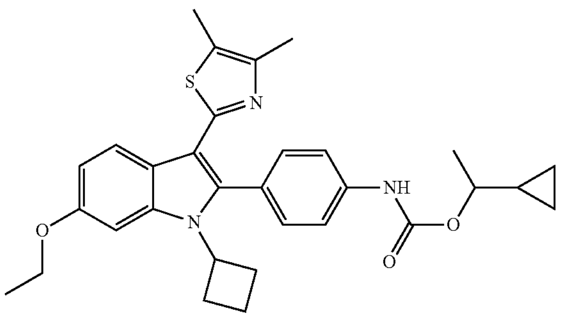
1939
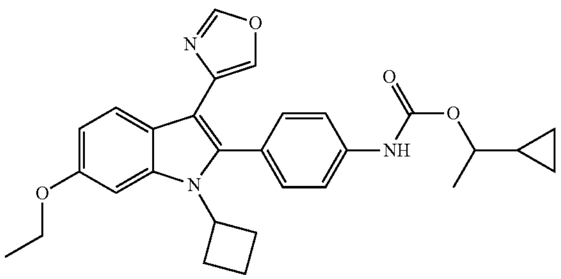
1941
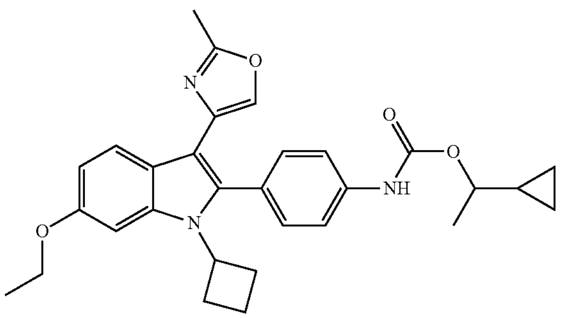
-continued
1943
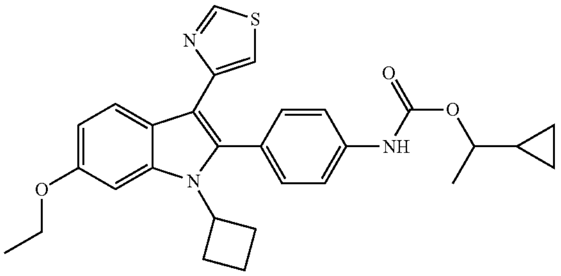
1945
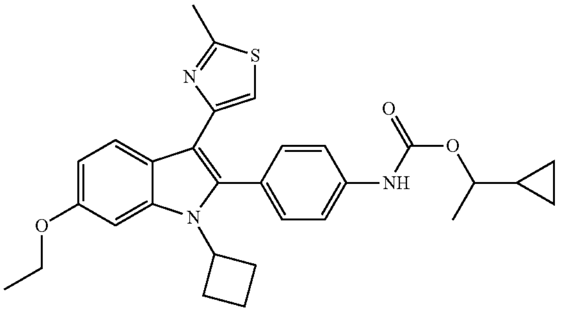
1955
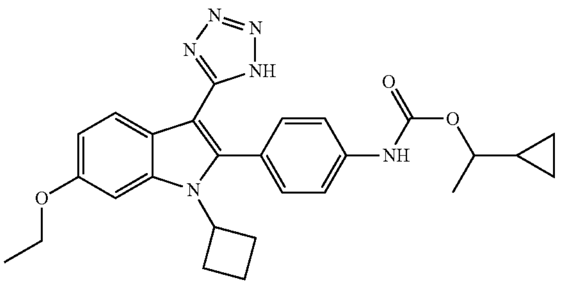
1957
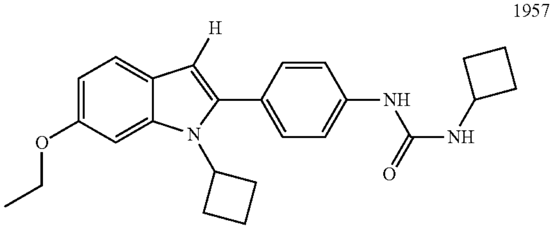
1967
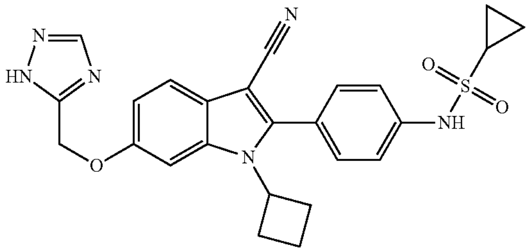

-continued
1968
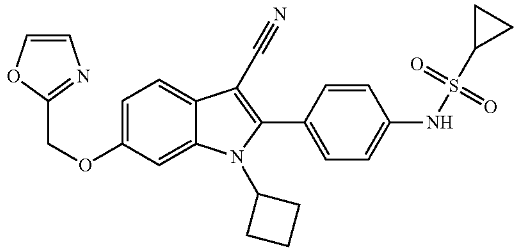
1969
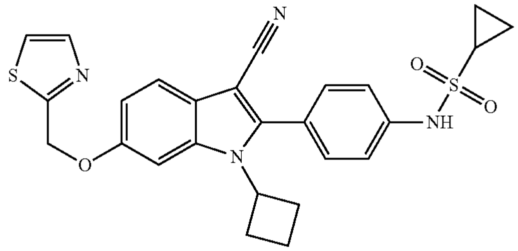
1994
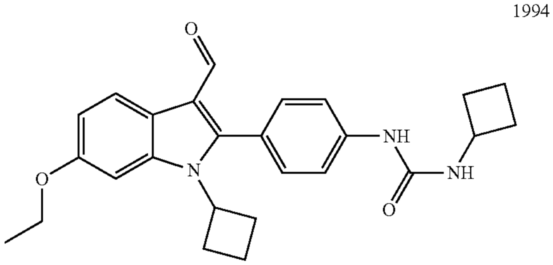
2000
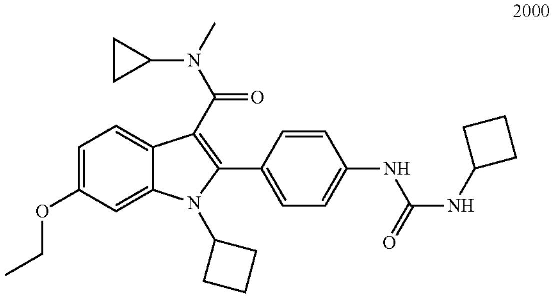
2002
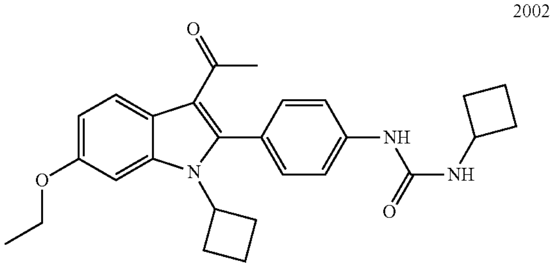
2015
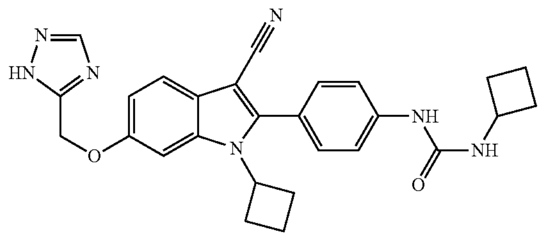
-continued
2016
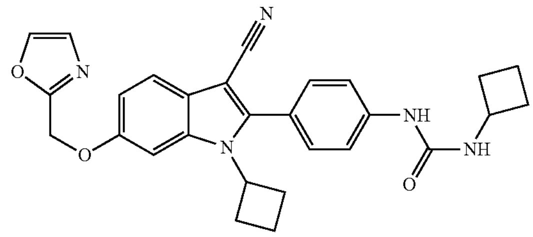
2017
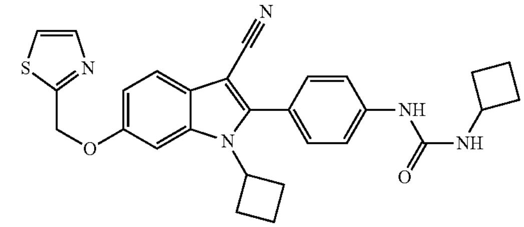
2022
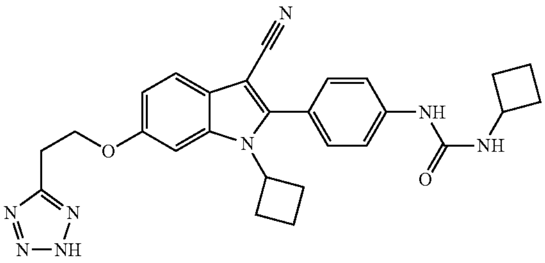
2023
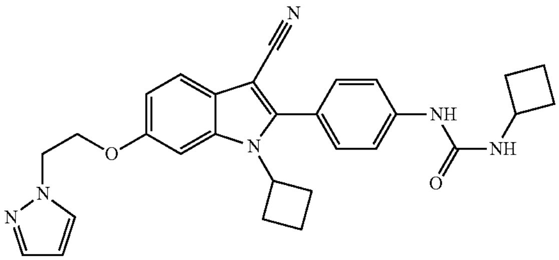
2024
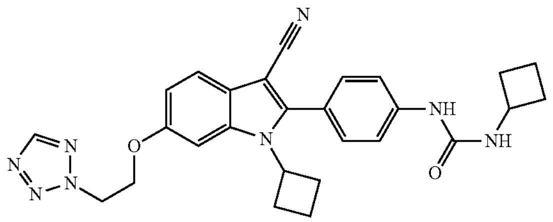
2034
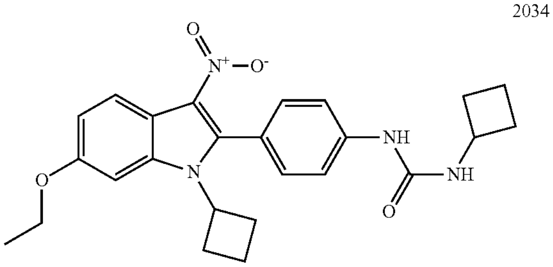

-continued
2040
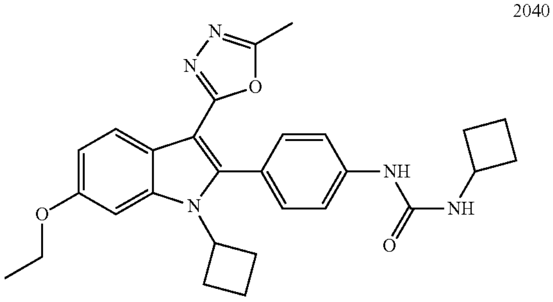
2042
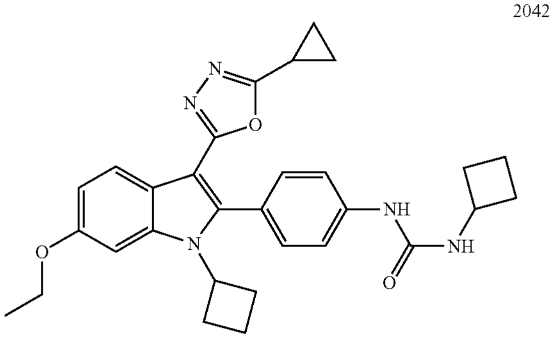
2044
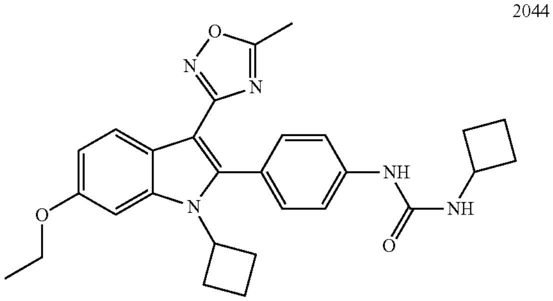
2046
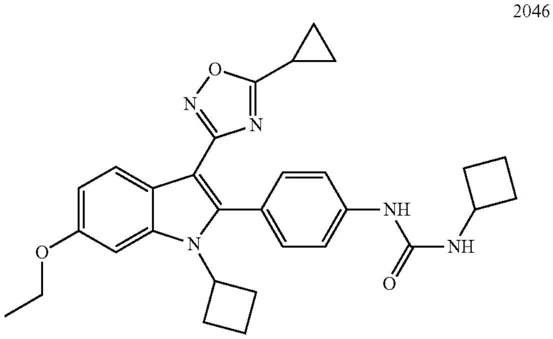
2048
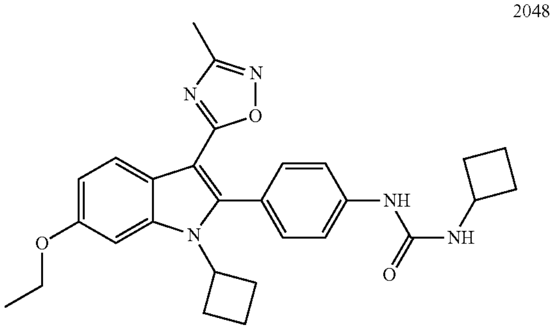
-continued
2050
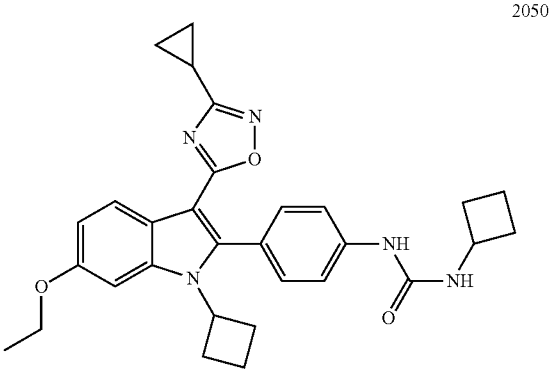
2056
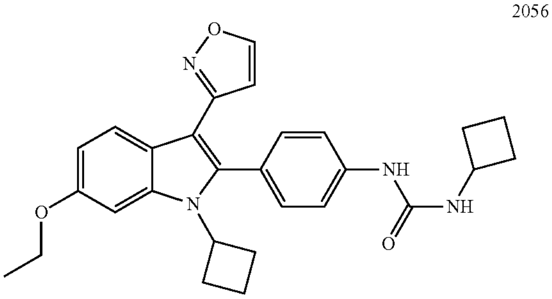
2058
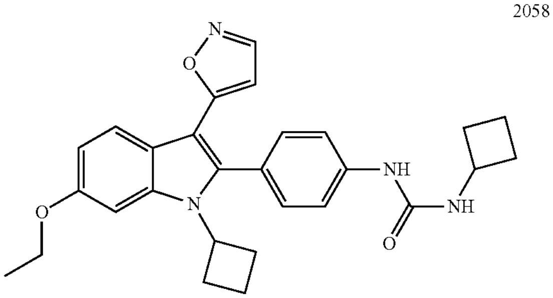
2060
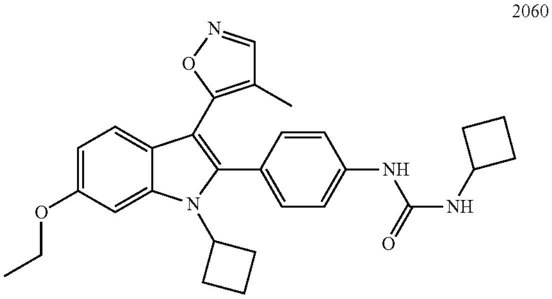
2062
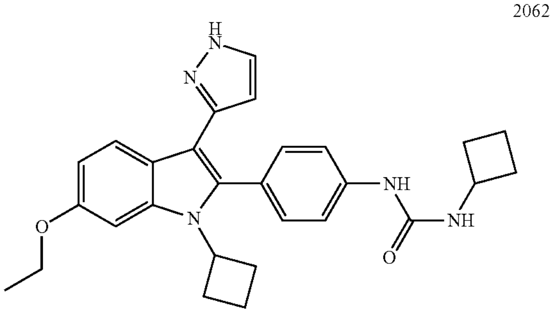

-continued
2064
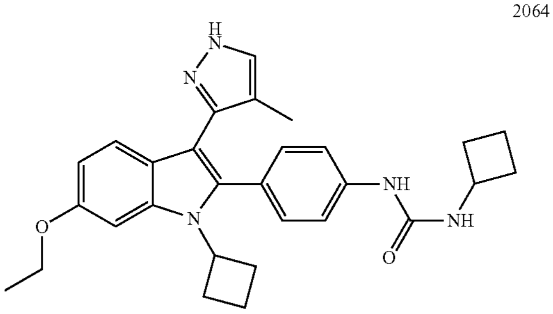
2066
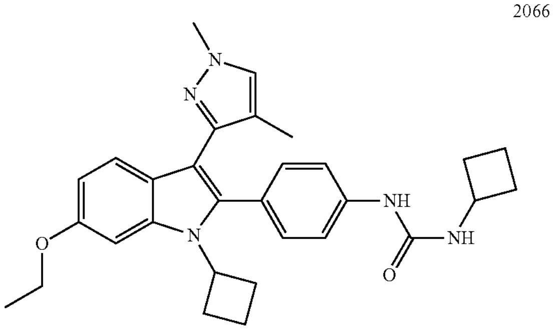
2068
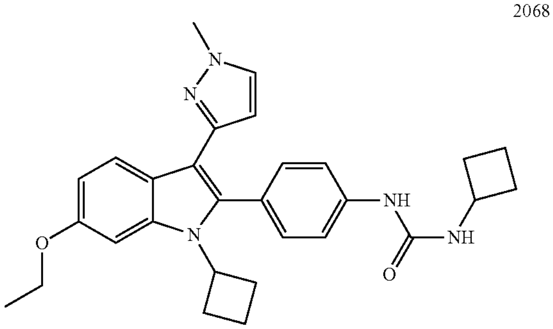
2070
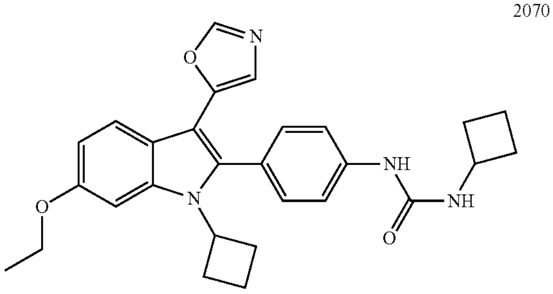
2072
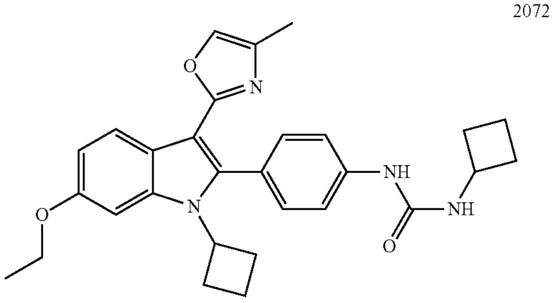
-continued
2076
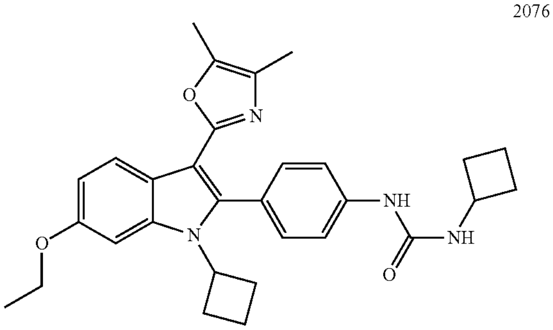
2078
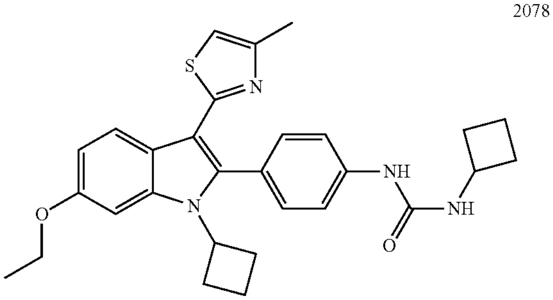
2080
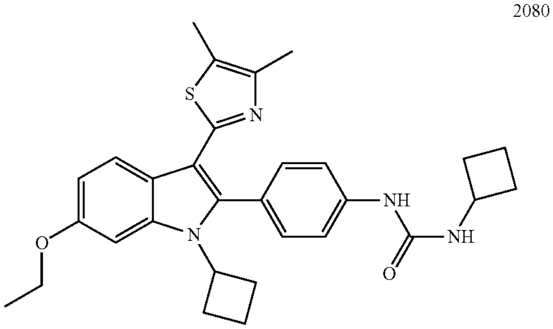
2084
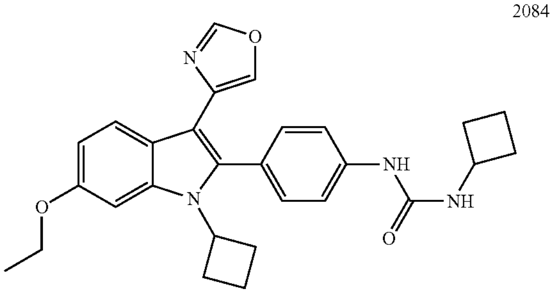
2086
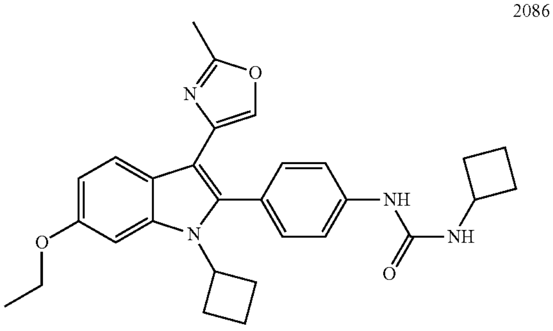

-continued

2088

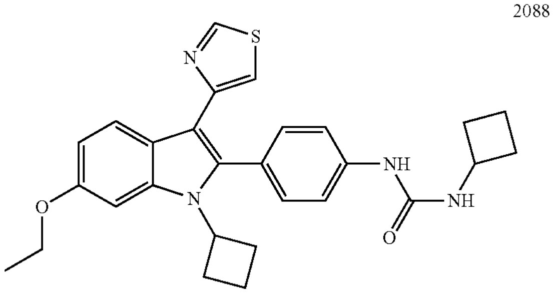

2090

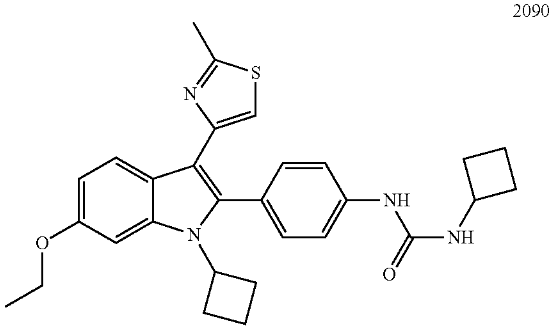

2105

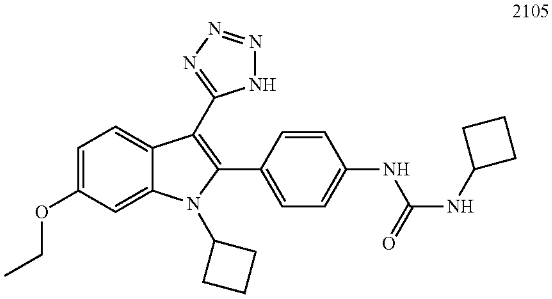

2127

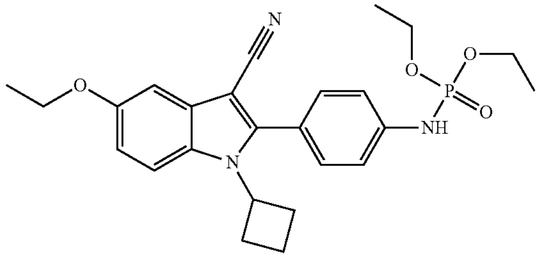

or an enantiomer, stereoisomer, diastereomer, racemic, tautomeric, ester, prodrug, solvate, hydrate; isotopologue or salt form thereof. Such compounds and pharmaceutically acceptable salts thereof were disclosed in U.S. patent application Ser. No. 11/331,180.

In one embodiment, a representative HCV inhibitor is a compound of Formula (I):

(I)

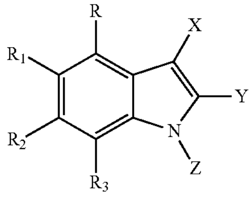

wherein:

X is: (a) -cyano; (b) -nitro; (c) -formyl; (d) —COOH; (e) —$COR_x$, wherein $R_x$ is $C_1$ to $C_6$ alkyl or $C_3$ to $C_8$ cycloalkyl; (f) —CH═N—($C_1$ to $C_6$ alkoxy); (g) —CH═N-(amino optionally substituted with one or more $C_1$ to $C_6$ alkyl(s) or one or more $C_3$ to $C_8$ cycloalkyl(s); (h) -halo; (i) -alkyl or cycloalkyl optionally substituted with one or more halos; (j) -alkynyl optionally substituted with $C_1$ to $C_6$ alkyl or $C_3$ to $C_8$ cycloalkyl, which alkyl or cycloalkyl is optionally substituted with one or more independently selected halos or cyanos; (k) -oximyl; (l) —$SO_2R_x$; (m) —$SO_2NH_2$; (n) —$SO_2NH(R_x)$; (o) —$SO_2N(R_x)_2$; (p) -amino optionally substituted with one or more $C_1$ to $C_6$ alkyls, one or more $C_3$ to $C_8$ cycloalkyl(s), —C(O)—$C_1$ to $C_6$ alkyls and/or —C(O)—$C_3$ to $C_8$ cycloalkyls; (q) -amido optionally substituted with one or more independently selected $C_1$ to $C_6$ alkyls or one or more independently selected $C_3$ to $C_8$ cycloalkyl(s); (r)-5 or 6 membered heterocyclo; (s) -5 or 6 membered heteroaryl optionally substituted with one or more $C_1$ to $C_6$ alkyl(s) or one or more $C_3$ to $C_8$ cycloalkyl(s), which alkyl(s) or cycloalkyl(s) are optionally substituted with one or more halos; or (t)-aryl optionally substituted with one or more substituents independently selected from: (1) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with one or more halos; (2) -halo; and (3) -cyano;

Y is: (a) -benzothiazolyl optionally substituted with amino, which amino is optionally substituted with one or more $C_1$ to $C_6$ alkyls or one or more $C_3$ to $C_8$ cycloalkyl(s);

(b) -indolyl optionally substituted on the nitrogen with —$SO_2R_x$;

(c) -aryl optionally substituted with one or more substituents independently selected from: (1) -halos; (2) —$C_1$ to $C_6$ alkyl or $C_3$ to $C_8$ cycloalkyl; (3) -alkoxy optionally substituted with one or more substituents independently selected from: (i) -one or more halos; and (ii) -5 or 6 membered heterocyclo; (4) -hydroxy; (5) -amino optionally substituted with one or more substituents independently selected from: (i) —$SO_2R_x$; (ii) —$C_1$ to $C_6$ alkyl or —$C_3$ to $C_8$ cycloalkyl, where —$C_1$ to $C_6$ alkyl or —$C_3$ to $C_8$ cycloalkyl are optionally and independently substituted with one or more 5 or 6 membered heteroaryls; and (iii) —$PO_2R_x$; (6) —OC(O)$NHR_x$; (7) —OC(O)$N(R_x)_2$; (8) —OC(O)NH($OR_x$); (9) —OC(O)$NR_x(OR_x)$; (10) —OC(O)$N(OR_x)_2$; (11) —OC(O)$R_{ab}$, wherein $R_{ab}$ is 5 or 6 membered heterocyclo; (12) —$NR_oCOR_p$, wherein $R_p$ is: (i) —$C_1$ to $C_6$ alkyl or —$C_3$ to $C_8$ cycloalkyl; (ii) -amino optionally substituted with one or more $C_1$ to $C_6$ alkyl(s) or one or more $C_3$ to $C_8$ cycloalkyl(s), which alkyl(s) or cycloalkyl(s) are optionally and independently substituted with one or more aryl and/or alkoxy; or -(iii) 5 or 6 membered heterocyclo optionally substituted with one or more $C_1$ to $C_6$ alkyls or one or more $C_3$ to $C_8$ cycloalkyl(s) and/or aryl; and wherein $R_o$ is: -hydrogen; —$C_1$ to $C_6$ alkyl; or $C_3$ to $C_8$ cycloalkyl; (13) —$NR_qCONR_qR_r$, wherein $R_q$ is hydrogen; and wherein $R_r$ is: (i) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with one or more substituents independently selected from: -halo; -hydroxy; -alkoxy; -5 or 6 membered heterocyclo; -5 or 6 membered heteroaryl; and aryl optionally substituted with one or more halos; (ii) —$C_2$ to $C_6$ alkenyl optionally substituted with one or more halos; (iii) —$C_1$ to $C_6$ alkoxy; or (iv) 5 or 6 membered heterocyclo; (14) —$SO_2R_{aa}$, wherein $R_{aa}$ is: (i) -5 or 6 heterocyclo optionally substituted with hydroxy; (ii) —$C_1$ to $C_6$ alkoxy; or (iii) —$C_1$ to $C_6$ alkyl or —$C_3$ to $C_8$ cycloalkyl; (15) —$COR_m$, wherein $R_m$ is: (i) -amino optionally substituted with one or more $C_1$ to $C_6$ alkyl(s) or one or more $C_3$ to $C_8$ cycloalkyl(s), wherein the $C_1$ to $C_6$ alkyl(s) or $C_3$ to $C_8$ cycloalkyl(s) are optionally substituted with a 5 or 6 membered heterocyclo; or (ii) -3 to 7 membered heterocyclo optionally substituted with $C_1$ to $C_6$ alkyl or $C_3$ to $C_8$ cycloalkyl, which alkyl or cycloalkyl is optionally substituted with dialkyl-amino; (16) —$NR_tCOOR_u$, wherein $R_t$ is hydrogen, and wherein $R_u$ is: (i) —$C_1$ to $C_{12}$ alkyl or —$C_3$ to $C_8$ cycloalkyl optionally substituted with one or more substituents independently selected from: aryl optionally substituted with one or more halos and/or haloalkyls; -alkoxy optionally substituted with one or more alkoxys; -amino optionally substituted with one or more $C_1$ to $C_6$ alkyl(s) or one or more $C_3$ to $C_8$ cycloalkyl(s); -halo; -5 or 6 membered heteroaryl; and -5 or 6 membered heterocyclo; (ii) —$C_2$ to $C_6$ alkenyl; or (iii) aryl optionally substituted with halo; (17) —$NHR_{bb}$, wherein $R_{bb}$ is: —C(═S)$NH_2$; or —PO$(OR_x)_2$; (18) —$NR_vSO_2R_w$, wherein $R_v$ is hydrogen, and wherein $R_w$ is: —$C_1$ to $C_6$ alkyl or —$C_3$ to $C_8$ cycloalkyl; or -alkyl-amino or -dialkyl-amino optionally substituted with halo;

(19) -

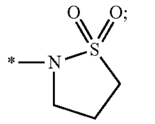

(20) -

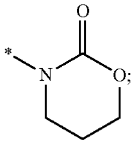

Z is: —$C_1$ to $C_6$ alkyl or —$C_3$ to $C_8$ cycloalkyl

R is hydrogen;

$R_1$ is: (a) -hydrogen;

(b) -5 or 6 membered heterocyclo;

(c) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with one or more substituents independently selected from: (1) -amino optionally substituted with heterocyclo; (2) -amido optionally substituted with $C_1$ to $C_6$ alkyl or $C_3$ to $C_8$ cycloalkyl; (3) -5 or 6 membered heterocyclo optionally substituted with $C_1$ to $C_6$ alkyl or $C_3$ to $C_8$ cycloalkyl; (4) -5 or 6 membered heteroaryl; and (5) aryl;

(d) —$C_1$ to $C_6$ alkoxy optionally substituted with one or more substituents independently selected from: (1) -amino optionally substituted with heterocyclo; (2) -amido optionally substituted with $C_1$ to $C_6$ alkyl or $C_3$ to $C_8$ cycloalkyl; (3) -5 or 6 membered heterocyclo optionally substituted with $C_1$ to $C_6$ alkyl or $C_3$ to $C_8$ cycloalkyl; (4) -5 or 6 membered heteroaryl; and (5) aryl;

(e) —(O)-5 or 6 membered heterocyclo;

(f) —(O)-5 or 6 membered heteroaryl;

(g) —$SO_2R_x$ optionally substituted with one or more substituents independently selected from: (1) -5 or 6 membered heterocyclo; (2) aryl; and (3) -5 or 6 membered heteroaryl; or (h) -alkylthio optionally substituted with one or more substituents independently selected from: (1) -5 or 6 membered heterocyclo; (2) aryl; and (3) -5 or 6 membered heteroaryl;

$R_2$ is: (a) —$C_1$ to $C_6$ alkyl or $C_3$ to $C_8$ cycloalkyl, where —$C_1$ to $C_6$ alkyl or $C_3$ to $C_8$ cycloalkyl are optionally substituted with one or more substituents independently selected from: (1)-5 or 6 membered heterocyclo; (2) -5 or 6 membered heteroaryl; (3) aryl; (4) -amido optionally substituted with $C_1$ to $C_6$ alkyl or $C_3$ to $C_8$ cycloalkyl; and (5) -amino optionally substituted with one or more substituents independently selected from (i) heterocyclo, (ii) alkoxy and (iii) alkyl or $C_3$ to $C_8$ cycloalkyl, which alkyl or cycloalkyl is optionally substituted with one or more alkoxys;

(b) -alkylthio optionally substituted with 5 or 6 membered heteroaryl, which heteroaryl is optionally substituted with alkyl or $C_3$ to $C_8$ cycloalkyl;

(c) -alkylthio optionally substituted with 5 or 6 membered heterocyclo;

(d) -alkylthio optionally substituted with aryl;

(e) -alkylthio optionally substituted with $C_1$ to $C_6$ alkyl or $C_3$ to $C_8$ cycloalkyl;

(f) —$SO_2R_x$ optionally substituted with 5 or 6 membered heteroaryl, which heteroaryl is optionally substituted with one or more $C_1$ to $C_6$ alkyl(s) or one or more $C_3$ to $C_8$ cycloalkyl(s);

(g) —$SO_2R_x$ optionally substituted with 5 or 6 membered heterocyclo;

(h) —$SO_2R_x$ optionally substituted with aryl;

(i) —$SO_2R_x$ optionally substituted with $C_1$ to $C_6$ alkyl or $C_3$ to $C_8$ cycloalkyl;

(j) —$S(O)R_x$ optionally substituted with 5 or 6 membered heteroaryl;

(k) —$S(O)R_x$ optionally substituted with 5 or 6 membered heterocyclo;

(l) —$S(O)R_x$ optionally substituted with aryl;

(m) —$S(O)R_x$ optionally substituted with $C_1$ to $C_6$ alkyl or $C_3$ to $C_8$ cycloalkyl;

(n) -alkoxy optionally substituted with one or more substituents independently selected from: (1) -halo; (2) -hydroxy; (3) -alkoxy optionally substituted with alkoxy; (4) -amino optionally substituted with one or more substituents independently selected from 5 or 6 membered heteroaryl, 5 or 6 membered heterocyclo and alkyl or $C_3$ to $C_8$ cycloalkyl, which alkyl or cycloalkyl are optionally substituted with one or more substituents independently selected from: -5 or 6 membered heterocyclo; and -amino optionally substituted with one or more alkyl(s) or one or more $C_3$ to $C_8$ cycloalkyl(s); (5) -amido optionally substituted with $C_1$ to $C_6$ alkyl or $C_3$ to $C_8$ cycloalkyl; (6) —S-5 or 6 membered heterocyclo; (7) —S-5 or 6 membered heteroaryl optionally substituted with $C_1$ to $C_6$ alkyl or $C_3$ to $C_8$ cycloalkyl; (8) —S—$C_1$ to $C_6$ alkyl or —S—$C_3$ to $C_8$ cycloalkyl; (9) —S-aryl; (10) -sulfinyl-5 or 6 membered heterocyclo; (11) -sulfinyl-5 or 6 membered heteroaryl; (12) -sulfinyl-$C_1$ to $C_6$ alkyl or -sulfinyl-$C_3$ to $C_8$ cycloalkyl; (13) -sulfinyl-aryl; (14) -sulfonyl-5 or 6 membered heterocyclo; (15) -sulfonyl-5 or 6 membered heteroaryl optionally substituted with $C_1$ to $C_6$ alkyl or $C_3$ to $C_8$ cycloalkyl; (16) -sulfonyl-$C_1$ to $C_6$ alkyl or -sulfonyl-$C_3$ to $C_8$ cycloalkyl; (17) -sulfonyl-aryl; (18) -5 to 7 membered heterocyclo optionally substituted with one or more substituents independently selected from hydroxy and $C_1$ to $C_6$ alkyl or $C_3$ to $C_8$ cycloalkyl, which alkyl or cycloalkyl is optionally substituted with one or more $C_1$ to $C_6$ alkoxys; (19) -5 or 6 membered heteroaryl optionally substituted with one or more $C_1$ to $C_6$ alkyl(s) or one or more $C_3$ to $C_8$ cycloalkyl(s); and (20) aryl;

(o) aryl;

(p) —(O)-5 or 6 membered heteroaryl optionally substituted with one or more independently selected $C_1$ to $C_6$ alkyls or one or more independently selected $C_3$ to $C_8$ cycloalkyls;

(q) —C(O)-5 or 6 membered heterocyclo optionally substituted with one or more aryl;

(r) —C(O)-aryl;

(s) -5 or 6 membered heteroaryl optionally substituted with one or more substituents independently selected from: —$C_1$ to $C_6$ alkyl or $C_3$ to $C_8$ cycloalkyl;

(t) -5 or 6 membered heterocyclo optionally substituted with one or more substituents independently selected from: (1) -hydroxy; (2) —$C_1$ to $C_6$ alkyl or $C_3$ to $C_8$ cycloalkyl; (3) —$SO_2R_x$; (4) —C(O)-aryl; and (5) —$C(O)OR_x$; or (u) —$OR_{kk}$, wherein $R_{kk}$ is: (1) aryl; (2) -5 or 6 membered heterocyclo optionally substituted with $C_1$ to $C_6$ alkyl or $C_3$ to $C_8$ cycloalkyl, which alkyl or cycloalkyl is optionally substituted with aryl; (3) -5 or 6 membered heteroaryl optionally substituted with one or more substituents independently selected from halo, $C_1$ to $C_6$ alkyl, $C_3$ to $C_8$ cycloalkyl, $C_1$ to $C_6$ alkoxy, and $C_1$ to $C_6$ haloalkyl; (4) —$SO_2R_x$; or (5) —$Si(R_x)_3$; and $R_3$ is hydrogen;

or an enantiomer, stereoisomer, diastereomer, racemic, tautomeric, ester, prodrug, solvate, hydrate, isotopologue or salt form thereof;

with the proviso that at least one of X, Y, $R_1$, and $R_2$ is selected from the following:

X is: (a) —COOH; (b) —CH═N—($C_1$ to $C_6$ alkoxy); (c) —CH═N-(amino optionally substituted with one or more $C_1$ to $C_6$ alkyl(s) or one or more $C_3$ to $C_8$ cycloalkyl(s); (d) -halo; (e) -alkyl or cycloalkyl optionally substituted with one or more halos; (f) -alkynyl optionally substituted with $C_1$ to $C_6$ alkyl or $C_3$ to $C_8$ cycloalkyl, which alkyl or cycloalkyl is optionally substituted with one or more halos and/or cyanos; (g) -oximyl; (h) —$SO_2R_x$; (i) —$SO_2NH_2$; (j) —$SO_2NH(R_x)$; (k) —$SO_2N(R_x)_2$; (l) -amino optionally substituted with one or more $C_1$ to $C_6$ alkyl(s), one or more $C_3$ to $C_8$ cycloalkyl(s), —C(O)—$C_1$ to $C_6$ alkyl(s) and/or —C(O)—$C_3$ to $C_8$ cycloalkyl(s); (m) -amido optionally substituted with one or more independently selected $C_1$ to $C_6$ alkyls or one or more independently selected $C_3$ to $C_8$ cycloalkyl; (n) -5 or 6 membered heterocyclo; (o) -5 or 6 membered heteroaryl substituted with one or more $C_1$ to $C_6$ alkyl(s) or $C_3$ to $C_8$ cycloalkyl(s), which alkyl(s) or cycloalkyl(s) are substituted with one or more halos; or (p) aryl substituted with one or more substituents independently selected from: (1) —$C_1$ to $C_6$ alkyl or $C_3$ to $C_8$ cycloalkyl optionally substituted with one or more halos; (2) -halo; and (3) -cyano;

Y is: (a) -benzothiazolyl substituted with amino, which amino is optionally substituted with one or more $C_1$ to $C_6$ alkyl(s) or one or more $C_3$ to $C_8$ cycloalkyl(s);

(b) -indolyl substituted on the nitrogen with $SO_2R_x$; or (c) -aryl substituted with one or more substituents independently selected from:

(1) -amino optionally substituted with one or more substituents independently selected from: —$SO_2R_x$, and —$C_1$ to $C_6$ alkyl or —$C_3$ to $C_8$ cycloalkyl, where —$C_1$ to $C_6$ alkyl or —$C_3$ to $C_8$ cycloalkyl are substituted with one or more 5 or 6 membered heteroaryls; (2) —OC(O)$NHR_x$; (3) —$OC(O)N(R_x)_2$; (4) —$OC(O)NH(OR_x)$; (5) —$OC(O)NR_x(OR_x)$; (6) —$OC(O)N(OR_x)_2$; (7) —OC(O)$R_{ab}$, wherein $R_{ab}$ is 5 or 6 membered heterocyclo; (8) —$NR_oCOR_p$, wherein $R_p$ is: (i) -amino optionally substituted with one or more $C_1$ to $C_6$ alkyls or $C_3$ to $C_8$ cycloalkyl(s), which alkyl(s) or cycloalkyl(s) are optionally and independently substituted with one or more aryl and/or alkoxys, or (ii) -5 or 6 membered heterocyclo substituted with one or more $C_1$ to $C_6$ alkyl(s) or one or more $C_3$ to $C_8$ cycloalkyl(s) and/or aryl; (9) —$NR_q$-$CONR_qR_r$, wherein $R_r$ is: (i) —$C_1$ to $C_6$ alkyl or —$C_3$ to $C_8$ cycloalkyl, where —$C_1$ to $C_6$ alkyl or —$C_3$ to $C_8$ cycloalkyl are substituted with one or more substituents independently selected from: hydroxy; -alkoxy; -5 or 6 membered heterocyclo; -5 or 6 membered heteroaryl; and aryl substituted with one or more halos; (ii) —$C_2$ to $C_6$ alkenyl; (iii) —$C_1$ to $C_6$ alkoxy; or (iv) -5 or 6 membered heterocyclo; (10) —$NR_tCOOR_u$, wherein $R_u$ is: (i) —$C_1$ to $C_{12}$ alkyl or —$C_3$ to $C_8$ cycloalkyl, where —$C_1$ to $C_6$ alkyl or —$C_3$ to $C_8$ cycloalkyl are substituted with one or more substituents independently selected from: -alkoxy substituted with one or more alkoxys; -amino optionally substituted with one or more $C_1$ to $C_6$ alkyl(s) or $C_3$ to $C_8$ cycloalkyl(s); and -5 or 6 membered heteroaryl; or (ii) —$C_2$ to $C_6$ alkenyl; and

(19) -

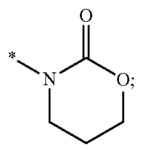

$R_1$ is: (a) —$C_1$ to $C_6$ alkyl or —$C_3$ to $C_8$ cycloalkyl, where —$C_1$ to $C_6$ alkyl or —$C_3$ to $C_8$ cycloalkyl are substituted with: (1) -amido optionally substituted with $C_1$ to $C_6$ alkyl or $C_3$ to $C_8$ cycloalkyl; and/or (2) -5 or 6 membered heteroaryl;

(b) —$C_1$ to $C_6$ alkoxy substituted with: (1) -amino optionally substituted with heterocyclo; (2) -amido optionally substituted with $C_1$ to $C_6$ alkyl or $C_3$ to $C_8$ cycloalkyl; (3) -5 or 6 membered heterocyclo substituted with $C_1$ to $C_6$ alkyl or $C_3$ to $C_8$ cycloalkyl; and/or (4) -5 or 6 membered heteroaryl;

(c) —(O)-5 or 6 membered heterocyclo;

(d) —(O)-5 or 6 membered heteroaryl;

(e) —$SO_2R_x$ optionally substituted with: (1)-5 or 6 membered heterocyclo; (2) aryl; and/or (3) -5 or 6 membered heteroaryl; or (f) -alkylthio optionally substituted with: (1)-5 or 6 membered heterocyclo; (2) aryl; and/or (3) -5 or 6 membered heteroaryl;

$R_2$ is: (a) —$C_1$ to $C_6$ alkyl or $C_3$ to $C_8$ cycloalkyl, where $C_1$ to $C_6$ alkyl or $C_3$ to $C_8$ cycloalkyl are substituted with one or more substituents independently selected from: (1) -5 or 6 membered heterocyclo; (2) -5 or 6 membered heteroaryl; (3) aryl; (4) -amido optionally substituted with $C_1$ to $C_6$ alkyl or $C_3$ to $C_8$ cycloalkyl; and (5) -amino optionally substituted with one or more substituents independently selected from heterocyclo, alkoxy and alkyl or $C_3$ to $C_8$ cycloalkyl, which alkyl or $C_3$ to $C_8$ cycloalkyl are optionally substituted with one or more alkoxys;

(b) -alkylthio optionally substituted with 5 or 6 membered heteroaryl, which heteroaryl is optionally substituted with alkyl or $C_3$ to $C_8$ cycloalkyl;

(c) -alkylthio optionally substituted with 5 or 6 membered heterocyclo;

(d) -alkylthio optionally substituted with aryl;

(e) -alkylthio optionally substituted with $C_1$ to $C_6$ alkyl or $C_3$ to $C_8$ cycloalkyl;

(f) —$SO_2R_x$ optionally substituted with 5 or 6 membered heteroaryl, which heteroaryl is optionally substituted with one or more $C_1$ to $C_6$ alkyl(s) or one or more $C_3$ to $C_8$ cycloalkyl(s);

(g) —$SO_2R_x$ optionally substituted with 5 or 6 membered heterocyclo;

(h) —$SO_2R_x$ optionally substituted with aryl;

(i) —$SO_2R_x$ optionally substituted with $C_1$ to $C_6$ alkyl or $C_3$ to $C_8$ cycloalkyl;

(j) —S(O)$R_x$ optionally substituted with 5 or 6 membered heteroaryl;

(k) —S(O)$R_x$ optionally substituted with 5 or 6 membered heterocyclo;

(l) —S(O)$R_x$ optionally substituted with aryl;

(m) —S(O)$R_x$ optionally substituted with $C_1$ to $C_6$ alkyl or $O_3$ to $C_8$ cycloalkyl;

(n) -alkoxy substituted with: (1) -alkoxy; (2) -amino substituted with one or more substituents independently selected from 5 or 6 membered heteroaryl, 5 or 6 membered heterocyclo and alkyl or $C_3$ to $C_8$ cycloalkyl, which alkyl or $C_3$ to $C_8$ cycloalkyl is optionally substituted with one or more substituents independently selected from: -5 or 6 membered heterocyclos; and -amino optionally substituted with one or more alkyl(s) or $C_3$ to $C_8$ cycloalkyl(s); (3) -amido optionally substituted with $C_1$ to $C_6$ alkyl or $C_3$ to $C_8$ cycloalkyl; (4) —S-5 or 6 membered heterocyclo; (5) —S-5 or 6 membered heteroaryl optionally substituted with $C_1$ to $C_6$ alkyl or $C_3$ to $C_8$ cycloalkyl; (6) —S—$C_1$ to $C_6$ alkyl or —S—$C_3$ to $C_8$ cycloalkyl; (7) —S-aryl; (8) -sulfinyl-5 or 6 membered heterocyclo; (9) -sulfinyl-5 or 6 membered heteroaryl; (10) -sulfinyl-$C_1$ to $C_6$ alkyl or -sulfinyl-$C_3$ to $C_8$ cycloalkyl; (11) -sulfinyl-aryl; (12) -sulfonyl-5 or 6 membered deterocyclo; (13) -sulfonyl-5 or 6 membered heteroaryl optionally substituted with $C_1$ to $C_6$ alkyl or $C_3$ to $C_8$ cycloalkyl; (14) -sulfonyl-$C_1$ to $C_6$ alkyl or -sulfonyl-$C_3$ to $C_8$ cycloalkyl; (15) -sulfonyl-aryl; (16) 5 to 7 membered heterocyclo substituted with one or more substituents independently selected from hydroxy and $C_1$ to $C_6$ alkyl or $C_3$ to $C_8$ cycloalkyl, which alkyl or cycloalkyl is substituted with one or more $C_1$ to $C_6$ alkoxys; (17) -5 or 6 membered heteroaryl substituted with one or more $C_1$ to $C_6$ alkyl(s) or one or more $C_3$ to $C_8$ cycloalkyl(s); or (18) aryl;

(o) —C(O)-5 or 6 membered heterocyclo optionally substituted with one or more aryl;

(p) —C(O)-aryl;

(q) -5 or 6 membered heterocyclo substituted with one or more substituents independently selected from: (1) -hydroxy; (2) —$C_1$ to $C_6$ alkyl or $C_3$ to $C_8$ cycloalkyl; (3) —$SO_2R_x$; (4) —C(O)-aryl; and (5) —C(O)O$R_x$;

(r) —O$R_{kk}$, wherein $R_{kk}$ is:

(1) aryl; (2) -5 or 6 membered heterocyclo optionally substituted with $C_1$ to $C_6$ alkyl, $C_3$ to $C_8$ cycloalkyl and/or aryl; or (3) —Si$(R_x)_3$;

(s) —(O)-5 or 6 membered heterocyclo optionally substituted with one or more independently selected $C_1$ to $C_6$ alkyl(s) or one or more independently selected $C_3$ to $C_8$ cycloalkyl(s); or (t) —(O)-5 or 6 membered heteroaryl optionally substituted with one or more independently selected $C_1$ to $C_6$ alkyl(s) or one or more independently selected $C_3$ to $C_8$ cycloalkyl(s).

In one embodiment, a representative HCV inhibitor is a compound of Formula (I):

(I)

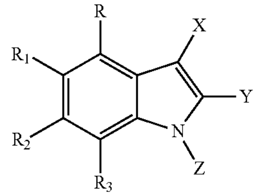

wherein:

X is:

(a) -nitro;

(b) -cyano;

(c) —$COR_a$, where $R_a$ is: (1) —$C_1$ to $C_6$ alkyl or —$C_3$ to $C_8$ cycloalkyl, (2) aryl optionally substituted with alkoxy or halogen, or (3) -dialkyl-amino;

(d) —$COOR_x$, where $R_x$ is $C_1$ to $C_6$ alkyl or —$C_3$ to $C_8$ cycloalkyl;

(e) -formyl;

(f) aryl optionally substituted with alkoxy; or (g) -5 or 6-membered heteroaryl optionally substituted with: (1) —$C_1$ to $C_6$ alkyl or —$C_3$ to $C_8$ cycloalkyl, (2) aryl optionally substituted with alkoxy or one or more halogen(s), or (3) -5 to 6 membered heteroaryl;

Y is:

(a) -haloalkyl;

(b) -halogen;

(c) -benzofuran;

(d) -benzothiophene;

(e) -dibenzofuran;

(f) -dibenzothiophene;

(g) -benzothiazole;

(h) -naphthalene;

(i) -indole, optionally substituted on the nitrogen with $C_1$ to $C_6$ alkyl or —$C_3$ to $C_8$ cycloalkyl;

(j) -

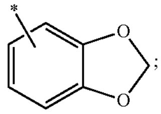

;

(k) -

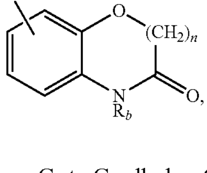

, where $R_b$ is hydrogen, $C_1$ to $C_6$ alkyl or $C_3$ to $C_8$ cycloalkyl, and n is 0 or 1;

(l) -

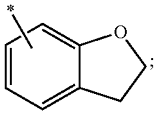

;

-continued (m) -

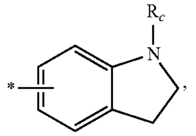

where $R_c$ is hydrogen, —CONH$R_x$, where $R_x$ is as defined above, or —$SO_2R_x$, where $R_x$ is as defined above; or (n) -

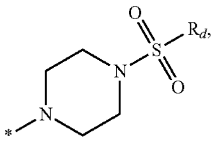

where $R_d$ is $C_1$ to $C_6$ alkyl, $C_3$ to $C_8$ cycloalkyl or aryl;

(o) —NHCO$R_e$, where $R_e$ is: (1) —$C_1$ to $C_6$ alkyl or —$C_3$ to $C_8$ cycloalkyl; (2) aryl optionally substituted with: (i) —$C_1$ to $C_6$ alkyl or —$C_3$ to $C_8$ cycloalkyl, (ii) -alkoxy, (iii) -cyano, (iv) -nitro, or (v) -halogen;

(p) —NHCOO$R_x$, where $R_x$ is as defined above;

(q) —$CH_2O$—$R_f$, where $R_f$ is aryl;

(r) —N$R_gR_h$, where $R_g$ is hydrogen, $C_1$ to $C_6$ alkyl or $C_3$ to $C_8$ cycloalkyl and $R_h$ is hydrogen or aryl optionally substituted with alkoxy;

(s) —$C_1$ to $C_6$ alkyl or —$C_3$ to $C_8$ cycloalkyl;

(t) -5 or 6 membered heteroaryl, optionally substituted with: (1) —$C_1$ to $C_6$ alkyl or —$C_3$ to $C_8$ cycloalkyl, optionally substituted with aryl, (2) -aryl, optionally substituted with —COO$R_x$, where $R_x$ is as defined above, or (3) -amino;

(u) -5 or 6 membered heterocycle optionally substituted with: (1) —COO$R_x$, where $R_x$ is as defined above, or (2) —NHCOO$R_x$, where $R_x$ is as defined above;

(v) -aryl, optionally substituted with one or more of the following:

(1) -alkoxy optionally substituted with: (i) -alkoxy, (ii) -hydroxy, (iii) -one or more halogen(s), (iv) -5 or 6 membered heterocycle, optionally substituted with: —$C_1$ to $C_6$ alkyl, —$C_3$ to $C_8$ cycloalkyl or -hydroxy, (v) -amino optionally substituted with one or more $C_1$ to $C_6$ alkyl(s) or one or more $C_3$ to $C_8$ cycloalkyl(s), (vi) —N$R$SO$_2R_x$, where $R_x$ is as defined above and $R_j$ is: hydrogen, —$C_1$ to $C_6$ alkyl, —$C_3$ to $C_8$ cycloalkyl, —CO$R_x$, where $R_x$ is as defined above, -haloalkyl, or -haloalkoxy, (vii) —N$R_j$CO$R_k$, where $R_k$ is: —$C_1$ to $C_6$ alkyl, —$C_3$ to $C_8$ cycloalkyl, -hydrogen, or -amino optionally substituted with one or more $C_1$ to $C_6$ alkyl(s) or one or more $C_3$ to $C_8$ cycloalkyl(s), and $R_j$ is: -hydrogen, —$C_1$ to $C_6$ alkyl, —$C_3$ to $C_8$ cycloalkyl, —CO$R_x$, where $R_x$ is as defined above, -haloalkyl, or -haloalkoxy, —N═$N^+$═$N^-$, or (ix) —CO$R_l$, where $R_l$ is 5 or 6 membered heterocycle optionally substituted with hydroxy, (2) -amino optionally substituted with one or more $C_1$ to $C_6$ alkyl(s) or one or more —$C_3$ to $C_8$ cycloalkyl(s), (3) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with: —NHSO$_2R_x$, where $R_x$ is as defined above, or —N$R_x$SO$_2R_x$, where $R_x$ is as defined above, (4) -haloalkoxy, (5) -halogen, (6) -hydroxy, (7) —COO$R_x$, where $R_x$ is as defined above, (8) —CO$R_m$, where $R_m$ is: (i) -amino optionally substituted with one or more $C_1$ to $C_6$ alkyl(s) or one or more $C_3$ to $C_8$ cycloalkyl(s), where the one or more $C_1$ to $C_6$ alkyl(s) or one or more $C_3$ to $C_8$ cycloalkyl(s) are optionally substituted with: hydroxy, -5 or 6 membered heterocycle, -amino optionally substituted with one or more $C_1$ to $C_6$ alkyl(s), one or more $C_3$ to $C_8$ cycloalkyl(s), or -alkoxy, (ii) -3 to 7 membered heterocycle, optionally substituted with $C_1$ to $C_6$ alkyl or $C_3$ to $C_8$ cycloalkyl, optionally substituted with dialkyl-amino, or (iii) —NH$R_n$, where $R_n$ is: —$CH_2CONH_2$, or aryl optionally substituted with: -alkyl, -one or more halogen(s), -nitro, or -one or more alkoxy(s), (9) —N$R_o$CO$R_p$, where $R_p$ is: (i) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with: -halogen, -alkoxy, or aryl, (ii) -5 or 6 membered heterocycle, (iii) aryl, optionally substituted with halogen, (iv) -5 or 6 membered heteroaryl optionally substituted with one or more $C_1$ to $C_6$ alkyl(s) or one or more $C_3$ to $C_8$ cycloalkyl(s), (v) -hydrogen, or (vi) -

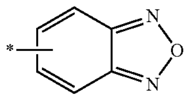

or

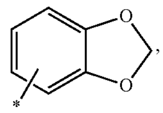

, and where $R_o$ is: (i) -hydrogen, (ii) —$C_1$ to $C_6$ alkyl or —$C_3$ to $C_8$ cycloalkyl, (iii) —CO$R_x$, where $R_1$ is as defined above, (iv) -haloalkyl, or (v) -haloalkoxy,

(10) —N$R_q$CON$R_qR_r$, where $R_q$ is: (i) -hydrogen, (ii) —$C_1$ to $C_6$ alkyl or —$C_3$ to $C_8$ cycloalkyl, -haloalkyl, (iv) -haloalkoxy, or (v) —CO$R_x$, where $R_x$ is as defined above, and where $R_r$ is: (i) aryl optionally substituted with:

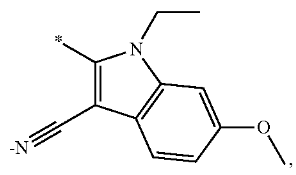

,

—$C_1$ to $C_6$ alkyl, —$C_3$ to $C_8$ cycloalkyl, -haloalkyl, —O$R_s$, where $R_s$ is aryl, or —COO$R_x$, where $R_x$ is as defined above, (ii) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with one or more of the following: -halogen, -alkenyl, aryl, and/or —COO$R_x$, where $R_x$ is as defined above, or (iii) —COO$R_x$, where $R_x$ is as defined above,

(11) —N$R_t$COO$R_u$, where $R_u$ is: (i) —$C_1$ to $C_{1\text{-}2}$ alkyl or —$C_3$ to $C_8$ cycloalkyl, optionally substituted with: aryl optionally substituted with $C_1$ to $C_6$ alkyl or $C_3$ to $C_8$ cycloalkyl, or alkoxy, -alkenyl, -alkoxy-alkynyl, -halogen, or -5 or 6 membered heterocycle, (ii) aryl, optionally substituted with: -alkoxy, -halogen, —$C_1$ to $C_6$ alkyl, or —$C_3$ to $C_8$ cycloalkyl, or (iii) -5 or 6 membered heterocycle, and $R_t$ is: (i) -hydrogen, (ii) —$C_1$ to $C_6$ alkyl or —$C_3$ to $C_8$ cycloalkyl, (iii) —$COR_x$, where $R_x$ is as defined above, (iv) -haloalkyl, or (v) -haloalkoxy,

(12) —$NR_vSO_2R_w$, where $R_v$ is: (i) -hydrogen, (ii) —$COR_x$, where $R_x$ is as defined above, or (iii) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with: -halogen, —$COR_x$, where $R_x$ is as defined above, —$OCOR_x$, where $R_x$ is as defined above, -hydroxy, or -alkoxy, and where $R_w$ is: (i) —$C_1$ to $C_6$ alkyl or —$C_3$ to $C_8$ cycloalkyl, where to $C_6$ alkyl or —$C_3$ to $C_8$ cycloalkyl are optionally substituted with: -halogen, -haloalkyl, aryl, or -5 or 6 membered heterocycle, (ii) —$C_2$ to $C_6$ alkenyl, (iii) -alkyl-amino or dialkyl-amino optionally substituted with halogen, (iv) -5 or 6 membered heterocycle, or (v) -5 or 6 membered heteroaryl optionally substituted with: —$C_1$ to $C_6$ alkyl or —$C_3$ to $C_8$ cycloalkyl, -5 or 6 membered heterocycle, or

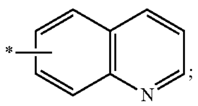

(13) -

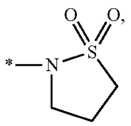

(14) -

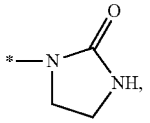

(15) -

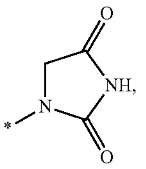

(16) -

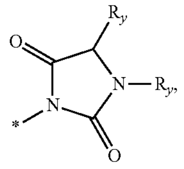

optionally substituted with $C_1$ to $C_6$ alkyl or $C_3$ to cycloalkyl, where $R_y$ is $C_1$ to $C_6$ alkyl, $C_3$ to $C_8$ cycloalkyl or hydrogen, (17)

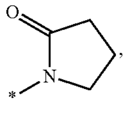

(18)

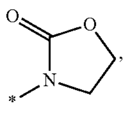

-continued (19)

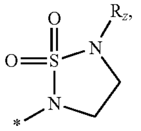

where $R_z$ is hydrogen, $C_1$ to $C_6$ alkyl or $C_3$ to $C_8$ cycloalkyl, where $C_1$ to $C_6$ alkyl or $C_3$ to $C_8$ cycloalkyl are optionally substituted with aryl,

(20) —$SR_x$, where $R_x$ is as defined above,

(21) —$SO_2R_{aa}$, where $R_{aa}$ is: (i) —$C_1$ to $C_6$ alkyl or —$C_3$ to $C_8$ cycloalkyl, (ii) -amino, (iii) -alkyl-amino or dialkyl-amino optionally substituted with hydroxy or —$COOR_x$, where $R_x$ is as defined above, or (iv) -5 or 6 membered heteroaryl,

(22) aryl, and/or (i)

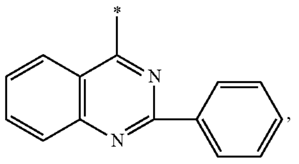

(ii)

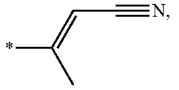

(23) —$NHR_{bb}$, where $R_{bb}$ is:

(iii) —$C(=S)NH_2$, or (iv) —$PO(OR_x)_2$, where $R_x$ is as defined above;

(w) -

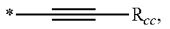

where $R_{cc}$ is:

(1) -naphthalene, (2) -5 or 6 membered heteroaryl, (3) -

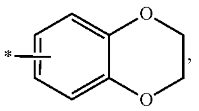

(4) aryl, optionally substituted with one or more of the following: (i) -alkoxy, (ii) -hydroxy, (iii) -halogen, (iv) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with cyano, (v) -amino optionally substituted with one or more $C_1$ to $C_6$ alkyl(s) or one or more $C_3$ to $C_8$ cycloalkyl(s), (vi) —$NHPOR_xR_x$, where $R_x$ is as defined above, (vii) —$NR_{ee}CONR_{ff}R_{ff}$, where $R_{ee}$ is hydrogen, $C_1$ to $C_6$ alkyl $C_3$ to $C_8$ cycloalkyl, where $C_1$ to $C_6$ alkyl or $C_3$ to $C_8$ cycloalkyl are optionally substituted with halogen, and $R_{ff}$ is: -hydrogen, -haloalkyl, -haloalkoxy, —$C_1$ to $C_6$ alkyl, —$C_3$ to $C_8$ cycloalkyl, or —$COR_x$, where $R_x$ is as defined above, (viii) —$NR_{gg}COR_{hh}$, where $R_{hh}$ is: -hydrogen, —$C_1$ to $C_6$ alkyl —$C_3$ to $C_8$ cycloalkyl, where —$C_1$ to $C_6$ alkyl or —$C_3$ to $C_8$ cycloalkyl are optionally substituted with: -alkoxy, -halogen, or -amino optionally substituted with one or more $C_1$ to $C_6$ alkyl(s) or one or more $C_3$ to $C_8$ cycloalkyl(s), -amino optionally substituted with one or more $C_1$ to $C_6$ alkyl(s), where the one or more $C_1$ to $C_6$ alkyl(s) or one or more $C_3$ to $C_8$ cycloalkyl(s), where alkyl or cycloalkyl are optionally substituted with halogen, -5 or 6 membered heterocycle, -5 or 6 membered heteroaryl, and $R_{gg}$ is -hydrogen, —$C_1$ to $C_6$ alkyl, —$C_3$ to $C_8$ cycloalkyl, -haloalkyl, -haloalkoxy, or —$COR_x$, where $R_x$ is as defined above, -haloalkyl, (ix) -5 or 6 membered heterocycle, (x) -amino optionally substituted with one or more $C_1$ to $C_6$ alkyl(s) or one or more $C_3$ to $C_8$ cycloalkyl(s), and/or (xi) —$NR_{ii}SO_2R_x$, where $R_x$ is as defined above, and $R_{ii}$ is: -hydrogen, —$C_1$ to $C_6$ alkyl, or —$C_3$ to $C_8$ cycloalkyl, -haloalkyl, -haloalkoxy, —$COR_x$, where $R_x$ is as defined above;

Z is:

(a) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with: (1) -alkoxy, (2) -one or more halogen(s), or (3) aryl;

(b) —$C_2$ to $C_6$ alkenyl;

(c) aryl optionally substituted with alkoxy or one or more $C_1$ to $C_6$ alkyl(s) or one or more $C_3$ to $C_8$ cycloalkyl(s);

(d) —$COOR_x$, where $R_x$ is as defined above; or (e) -

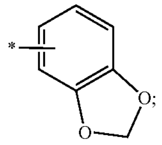

R is hydrogen, halogen or alkoxy;

$R_1$ is:

(a) -hydrogen;

(b) -hydroxy;

(c) -halogen;

(d) -haloalkyl;

(e) -nitro;

(f) -5 or 6 membered heteroaryl;

(g) -5 or 6 membered heterocycle;

(h) -alkoxy optionally substituted with: (1) -one or more halogen(s), (2) aryl, or (3) -5 or 6 membered heterocycle;

(i) aryl optionally substituted with alkoxy;

(j) —$COR_x$, where $R_x$ is as defined above;

(k) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with dialkyl-amino or 5 or 6 membered heterocycle; or $R_1$ joins together with $R_2$ to form:

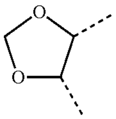

or

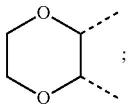

;

$R_2$ is:

(a) -nitro;

(b) -hydrogen;

(c) -halogen;

(d) -hydroxy;

(e) —$C_1$ to $C_6$ alkyl or —$C_3$ to $C_8$ cycloalkyl, where —$C_1$ to $C_6$ alkyl or —$C_3$ to $C_8$ cycloalkyl are optionally substituted with one or more halogen(s);

(f) -amino;

(g) -alkoxy optionally substituted with: (1) -one or more halogen(s), (2) —$OCOR_x$, where $R_x$ is as defined above, (3) -dialkyl-amino optionally substituted with alkoxy, (4) -5 or 6 membered heterocycle optionally substituted with $C_1$ to $C_6$ alkyl or $C_3$ to $C_8$ cycloalkyl, (5) -5 or 6 membered heteroaryl, or (6) aryl;

(h) —$COOR_x$, where $R_x$ is as defined above;

(i) -haloalkyl;

(j) -amide optionally substituted with: (1) -hydroxy, or (2) aryl;

(k) -5 or 6 membered heteroaryl;

(l) —$OCOR_x$, where $R_x$ is as defined above;

(m) —$NHCOR_{jj}$, where $R_{jj}$ is: (1) -alkoxy, or (2) -amino optionally substituted with one or more $C_1$ to $C_6$ alkyl(s) or one or more $C_3$ to $C_8$ cycloalkyl(s);

(n) —$OR_{kk}$, where $R_{kk}$ is 5 to 6 membered heteroaryl;

(o) —$NHSO_2R_x$, where $R_x$ is as defined above; or $R_2$ joins together with $R_1$ to form:

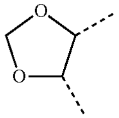

or

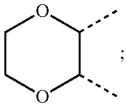

;

$R_3$ is:

(a) -hydrogen; or (b) —$CH_2OCOR_x$, and $R_x$ is as defined above;

or an enantiomer, stereoisomer, diastereomer, racemic, tautomeric, ester, prodrug, solvate, hydrate, isotopologue or salt form thereof;

provided that when X is phenyl substituted with alkoxy, Y is phenyl, R is hydrogen, $R_1$ is halogen, $R_2$ is hydrogen, and $R_3$ is hydrogen, and provided that when X is phenyl, hydroxyphenyl or pyridyl, Y is alkyl or $C_3$ to $C_8$ cycloalkyl, R is hydrogen, $R_1$ is hydrogen or hydroxy, $R_2$ is hydrogen or hydroxy, and $R_3$ is hydrogen, then Z is:

(a) —$C_1$ to $C_6$ alkyl or —$C_3$ to $C_8$ cycloalkyl, where —$C_1$ to $C_6$ alkyl or —$C_3$ to $C_8$ cycloalkyl are substituted with: (1) -alkoxy, (2) -one or more halogen(s), or (3) aryl;

(b) —$C_2$ to $C_6$ alkenyl;

(c) -aryl optionally substituted with alkoxy or one or more $C_1$ to $C_6$ alkyl(s) or one or more $C_3$ to $C_8$ cycloalkyl(s);

(d) —$COOR_x$, where $R_x$ is as defined above; or (e)

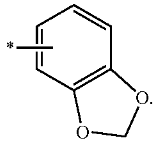

In one embodiment, a representative HCV inhibitor is a compound selected from:

866
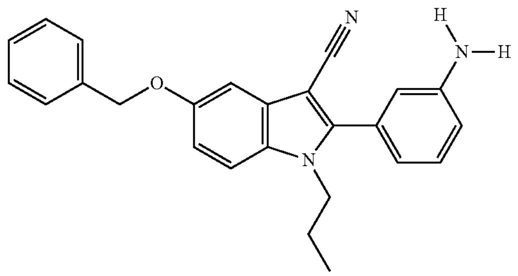
867
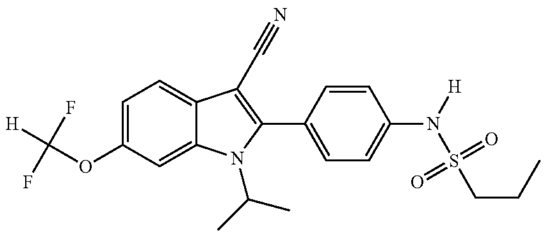
868
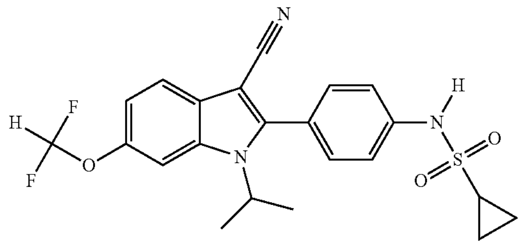
869
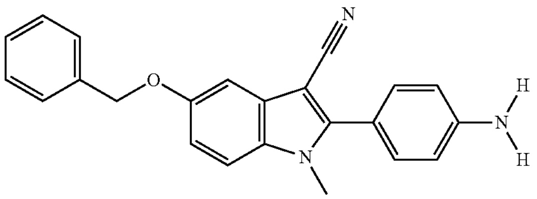
870
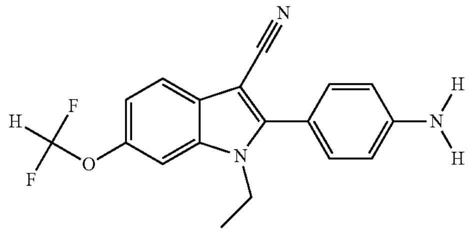
871
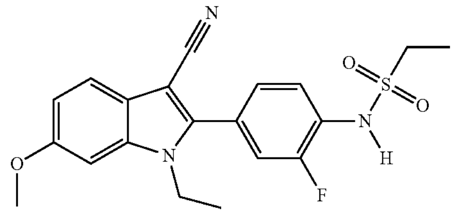
872
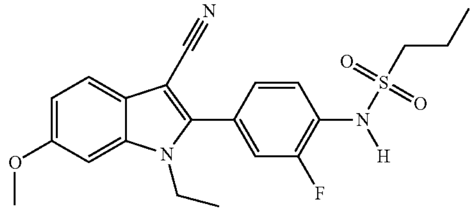
873
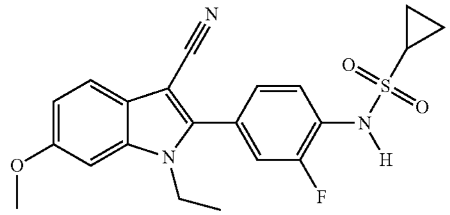
874
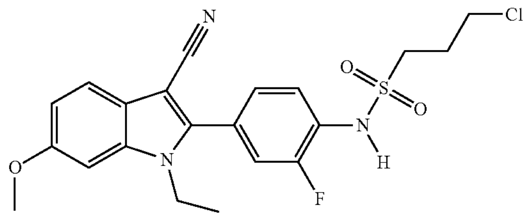
875
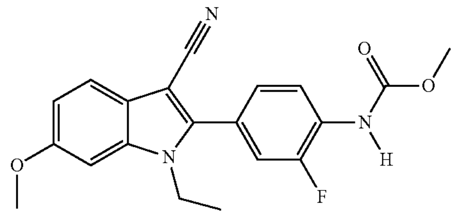
876
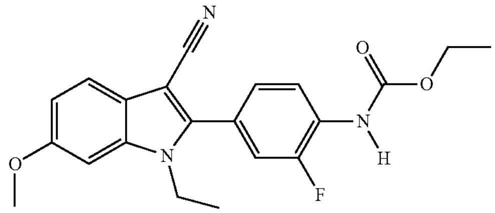
877
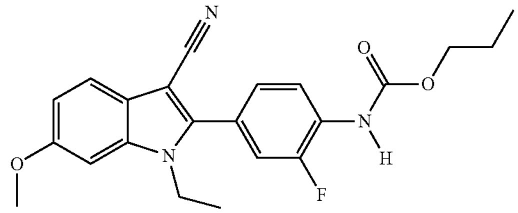

-continued
878
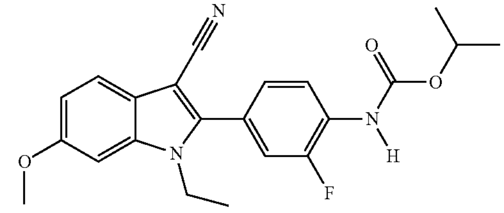
879
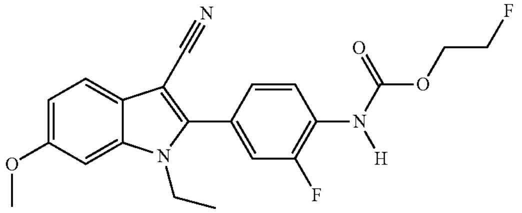
880
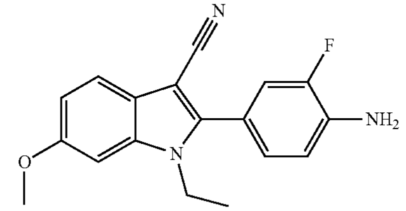
881
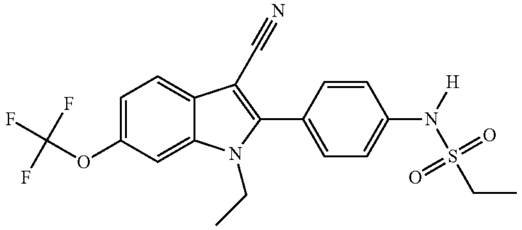
882
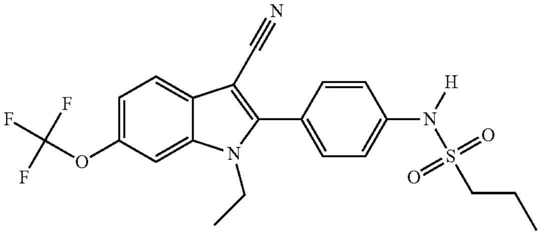
883
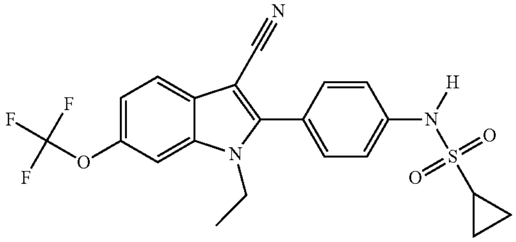
884
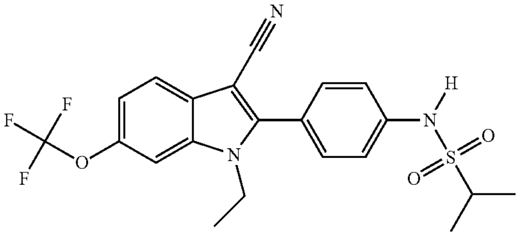
885
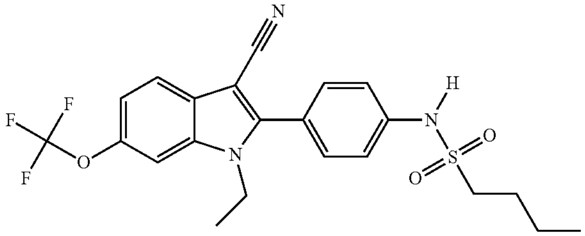
886
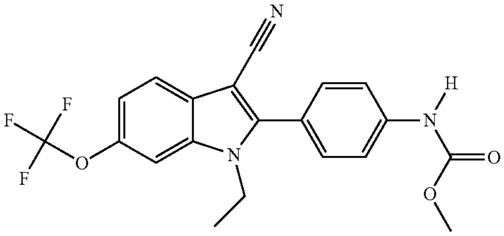
887
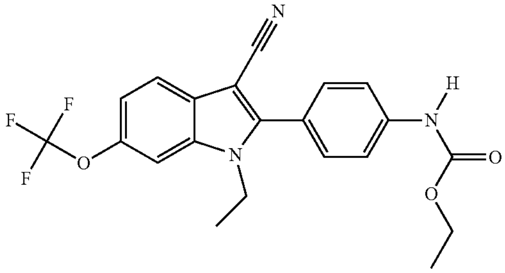
888
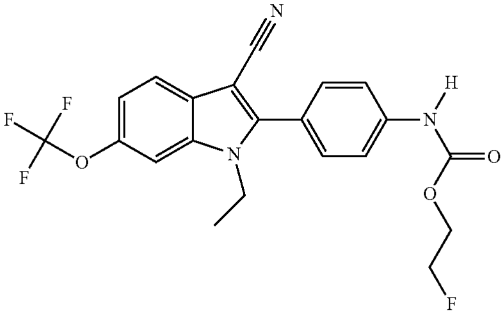
889
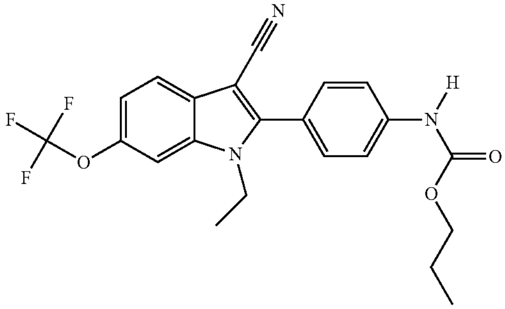

-continued
890
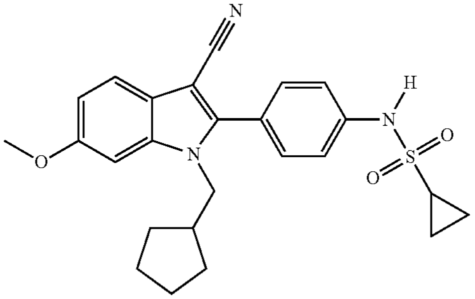
891
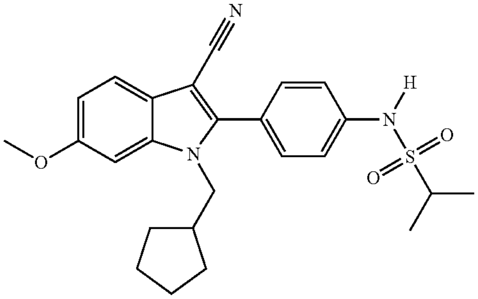
892
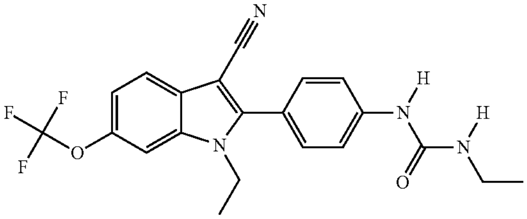
893
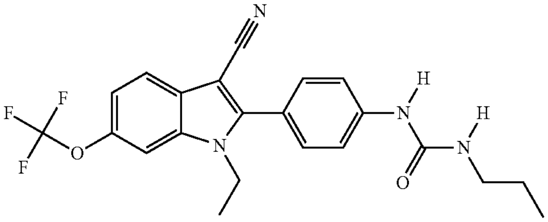
894
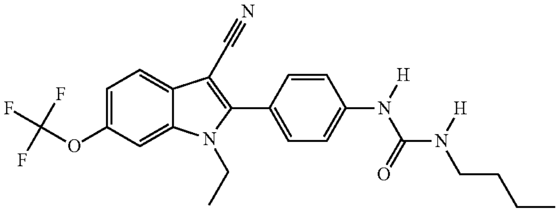
895
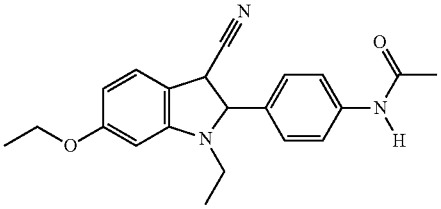
896
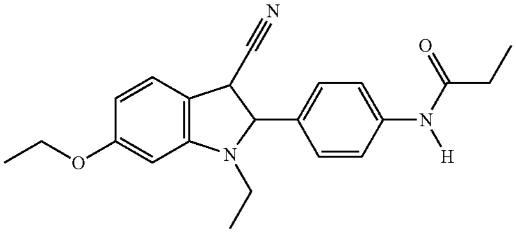
897
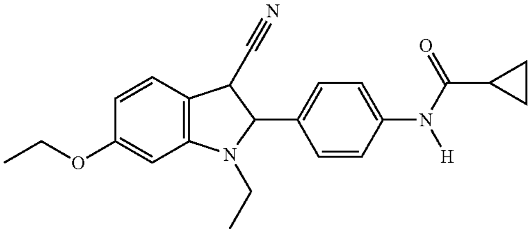
898
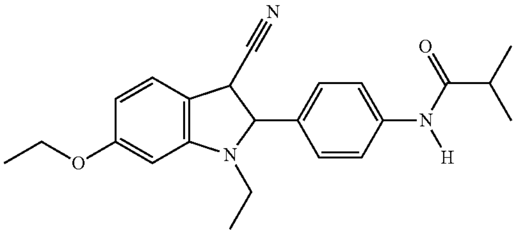
899
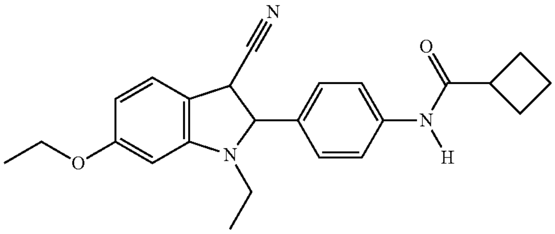
900
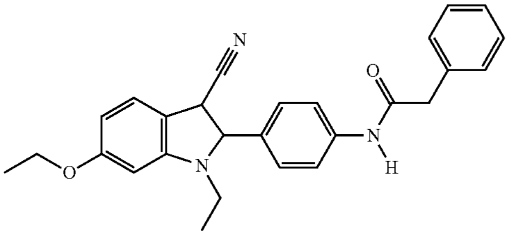
901
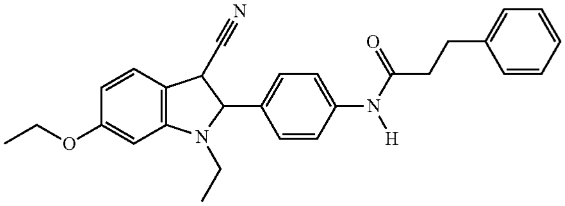

-continued
902
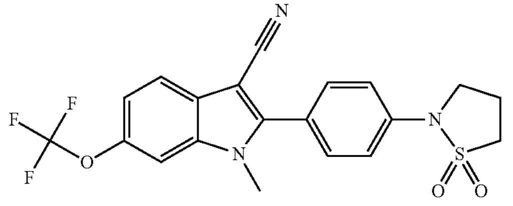
903
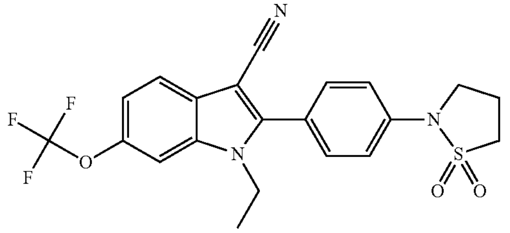
904
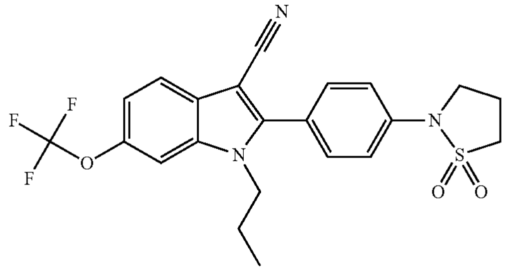
905
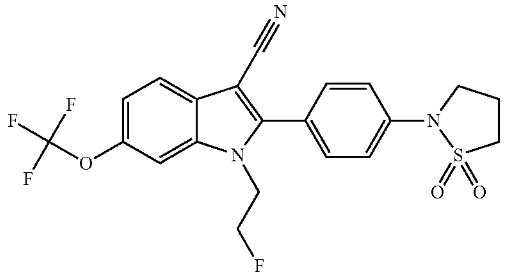
906
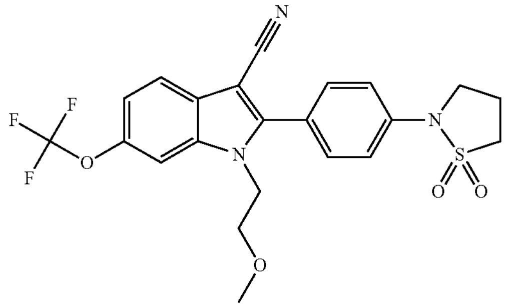
907
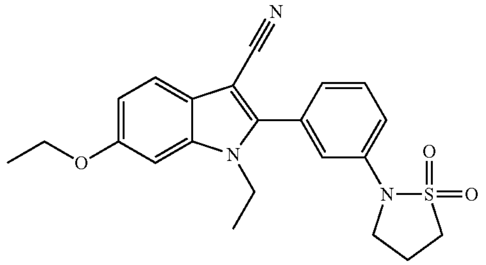
908
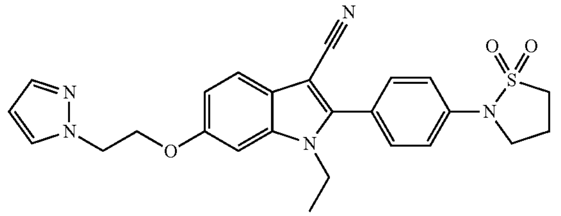
909
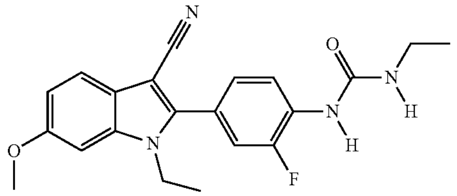
910
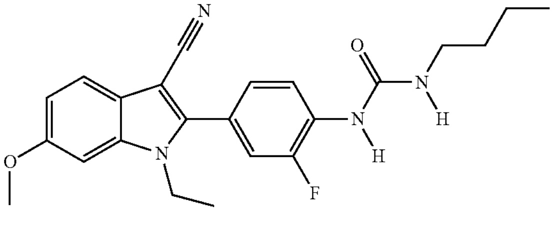
911
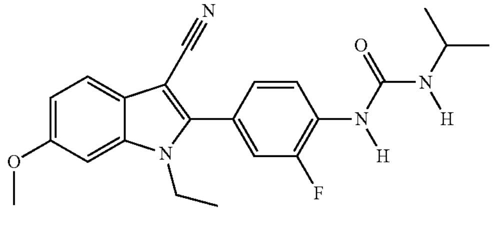
912
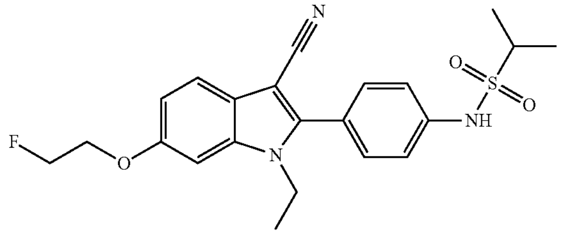
913
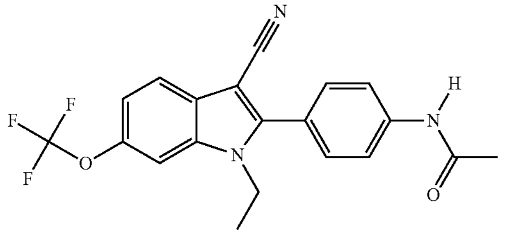

-continued
914
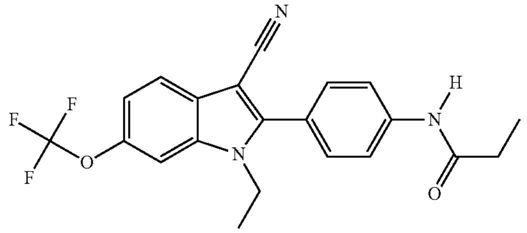
915
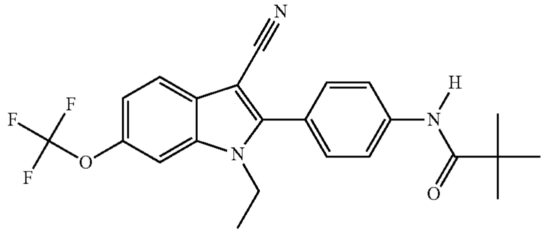
916
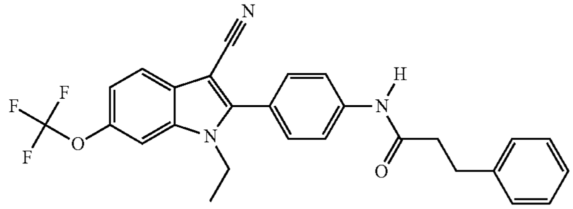
917
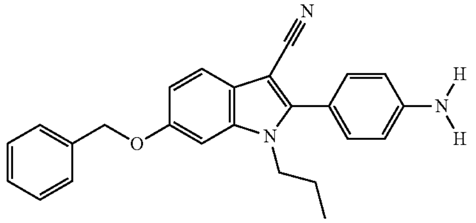
918
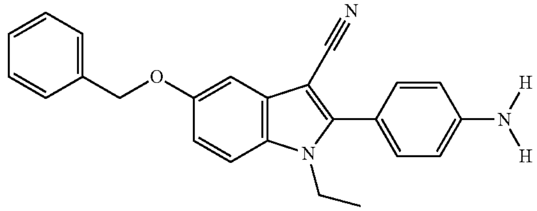
919
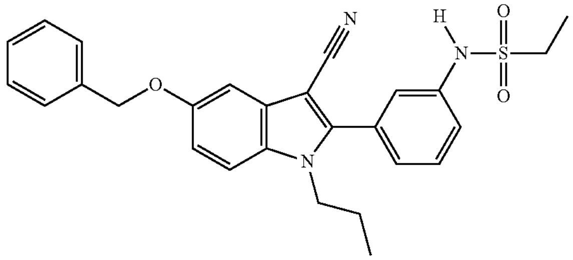
920
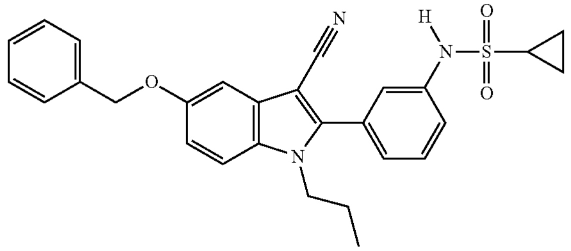
921
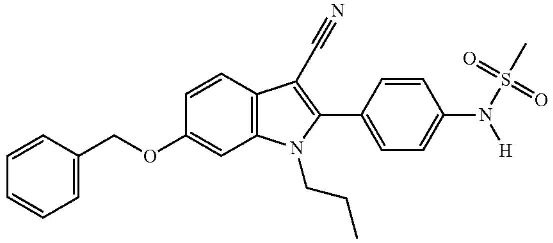
922
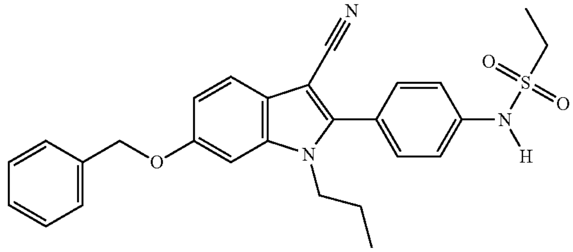
923
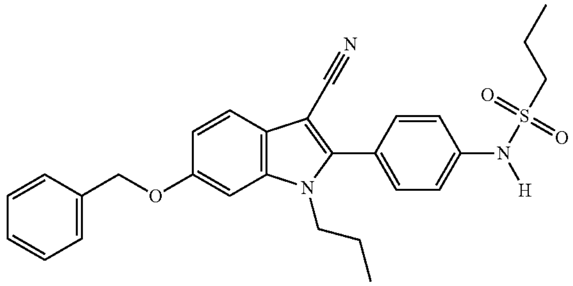
924
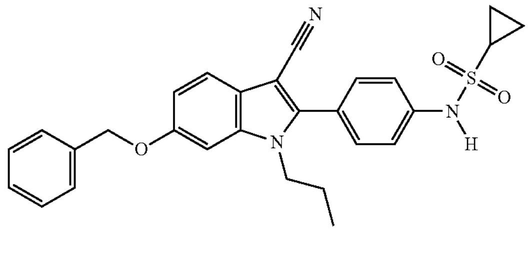
925
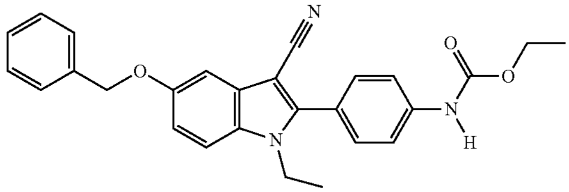

-continued
926
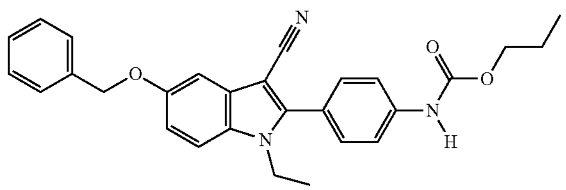
927
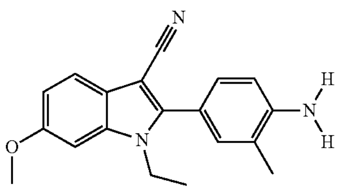
928
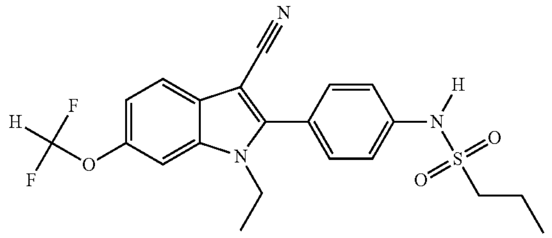
929
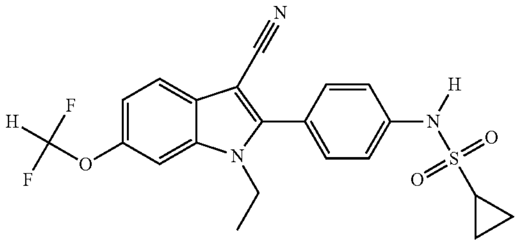
930
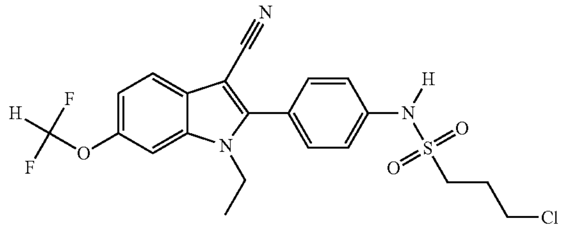
931
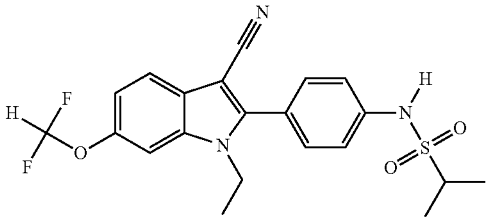
932
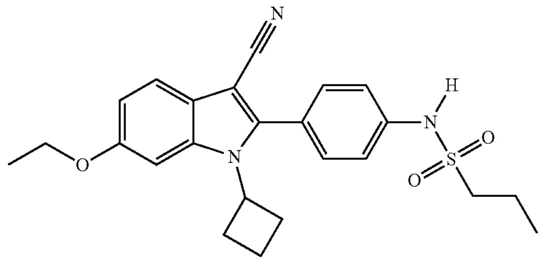
933
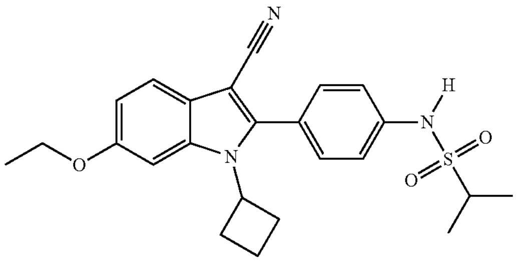
934
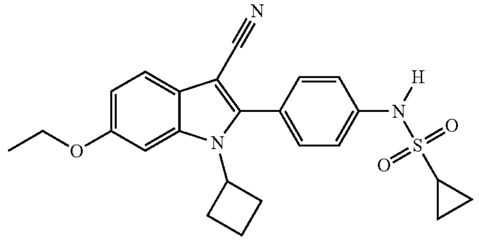
935
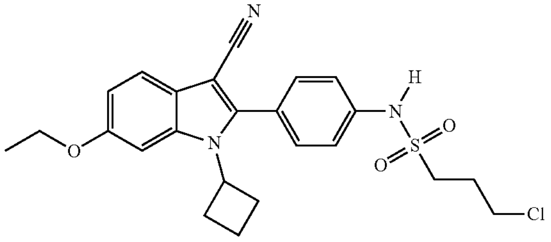
936
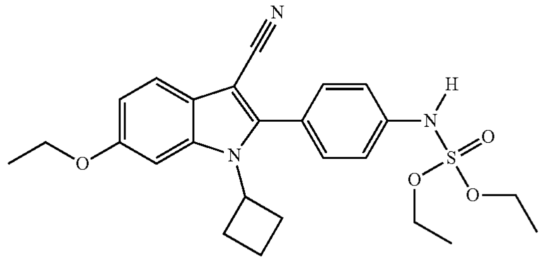
937
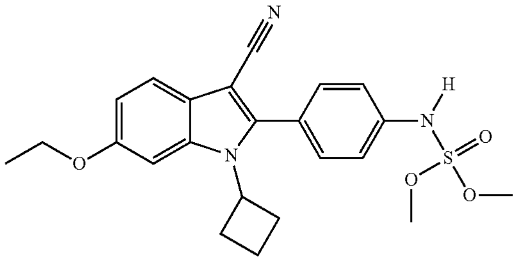

-continued
938
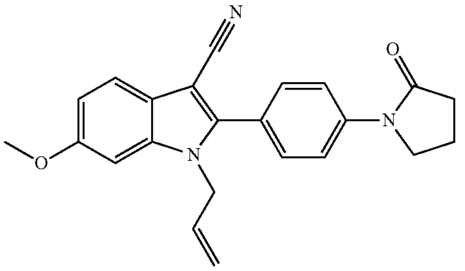
939
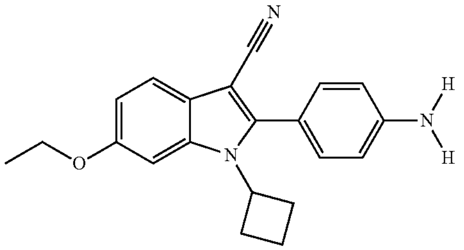
940
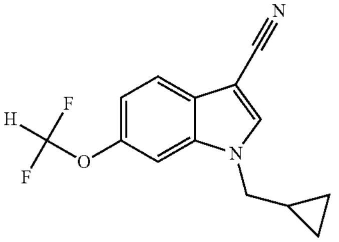
941
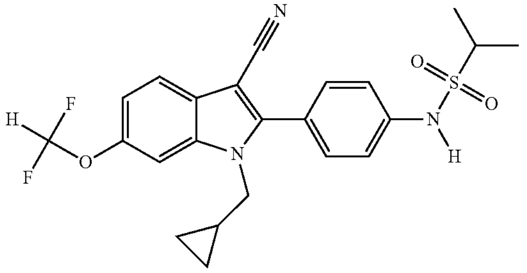
942
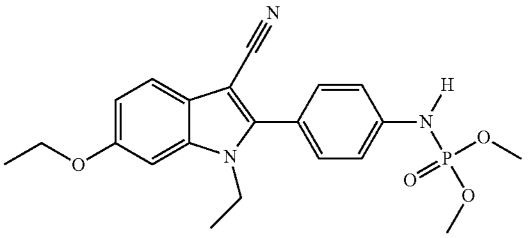
943
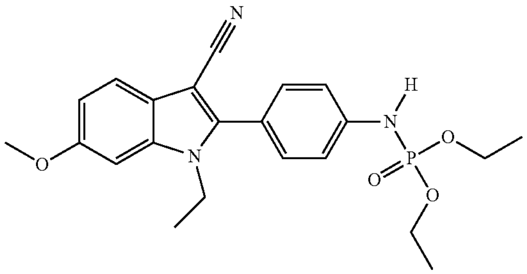
944
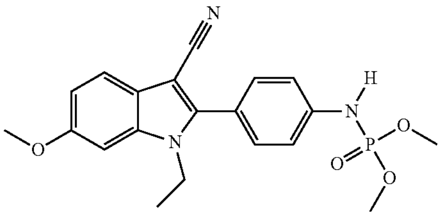
945
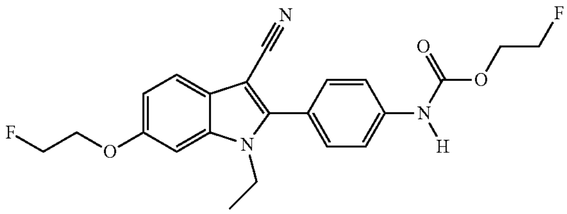
946
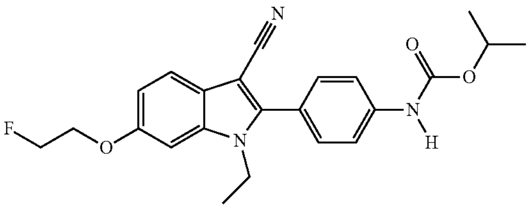
947
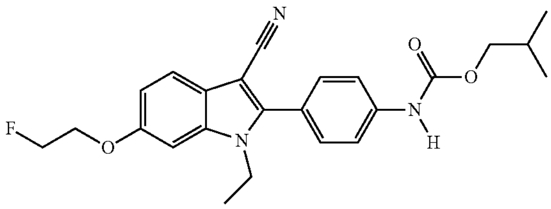
948
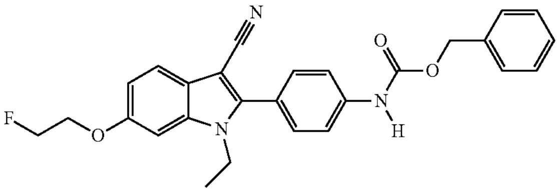
949
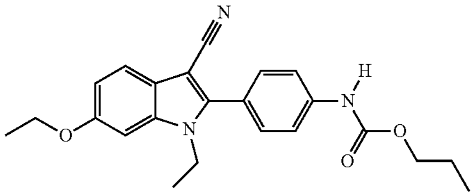

-continued
950
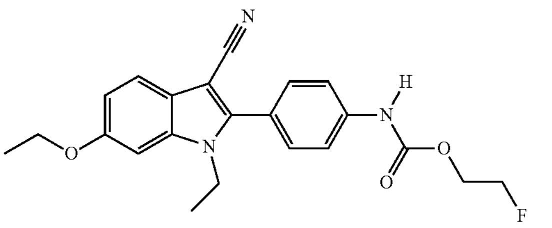
951
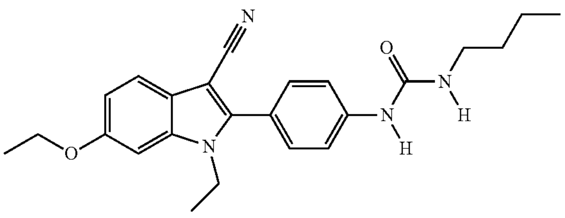
952
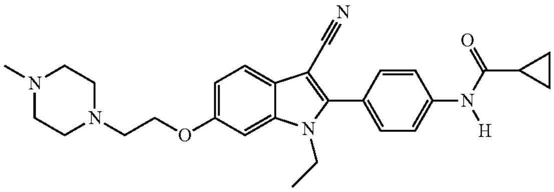
953
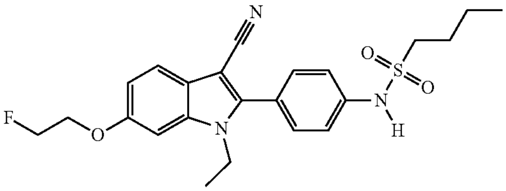
954
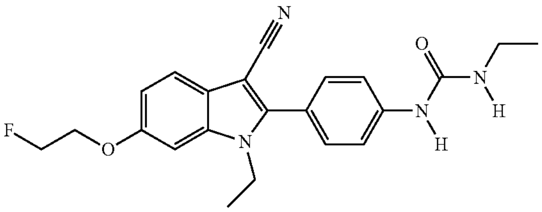
955
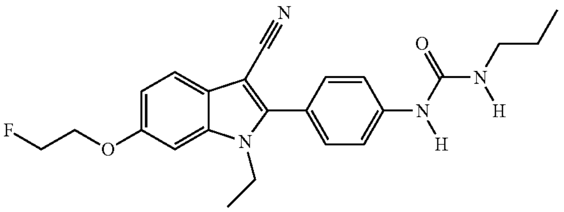
956
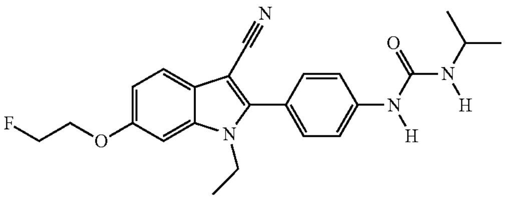
957
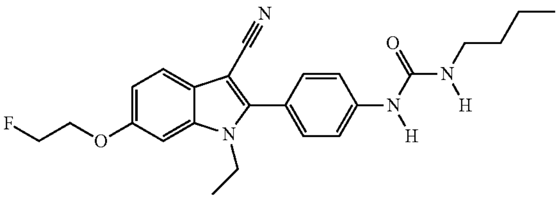
958
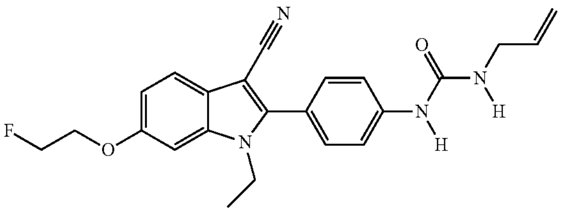
959
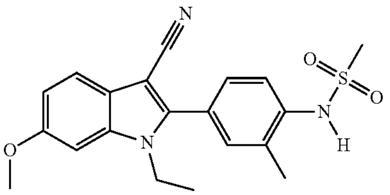
960
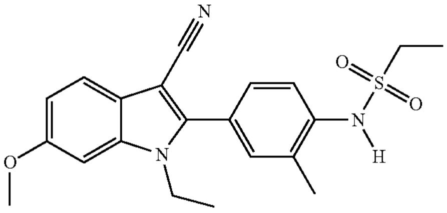
961
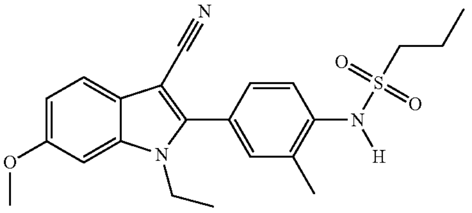
962
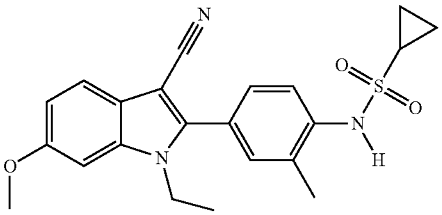
963
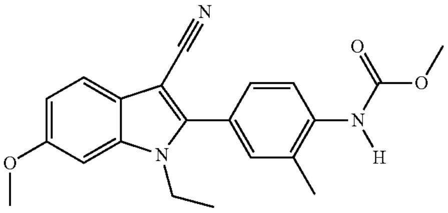

-continued
964
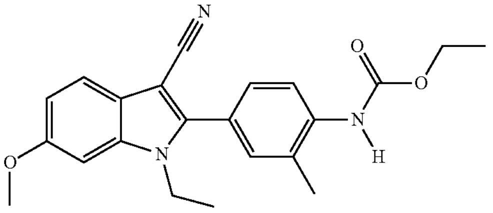
965
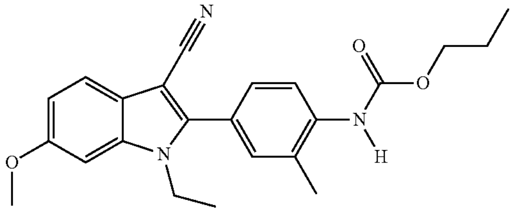
966
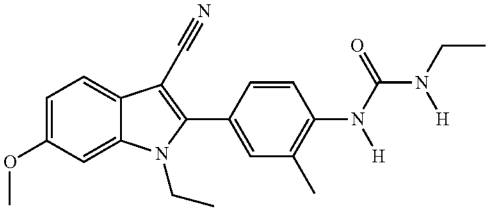
967
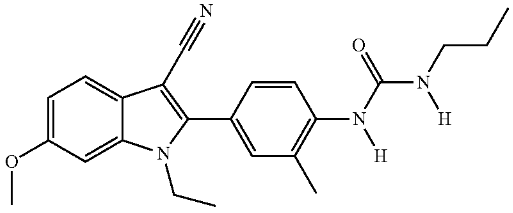
968
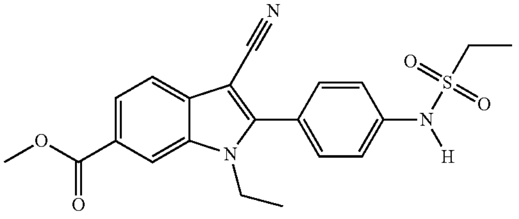
969
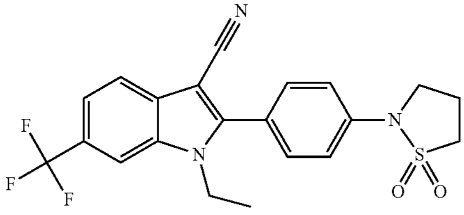
970
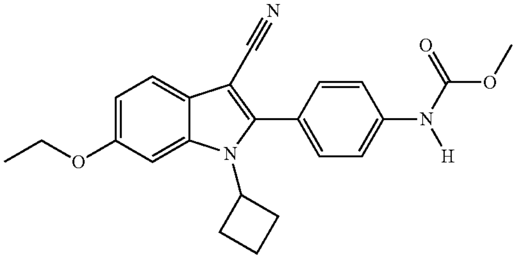
971
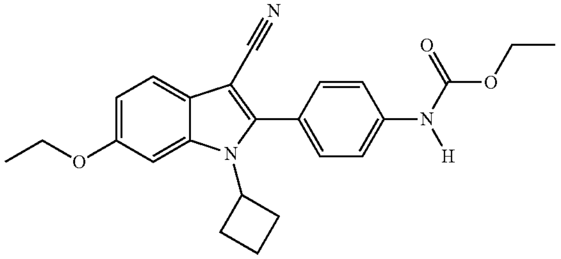
972
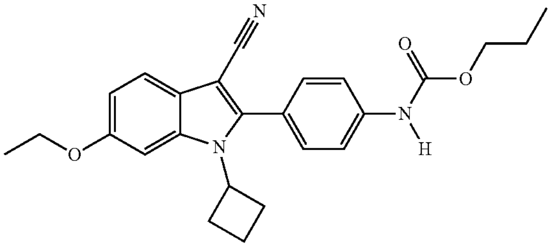
973
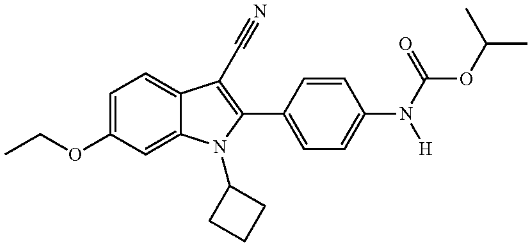
974
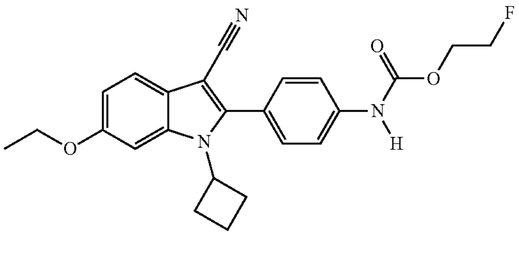
975
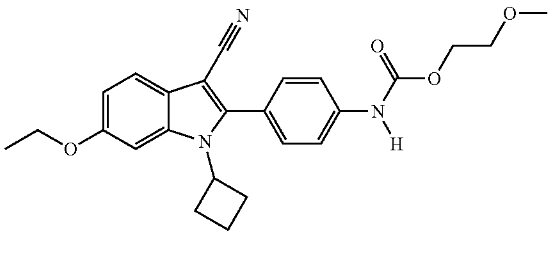

-continued
976
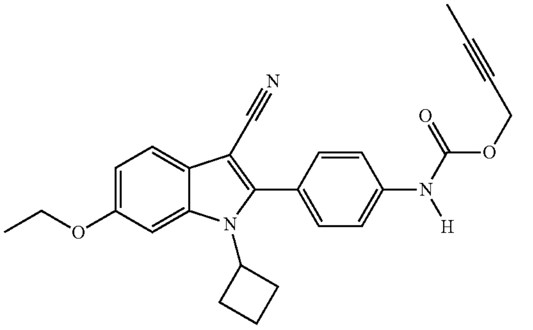
977
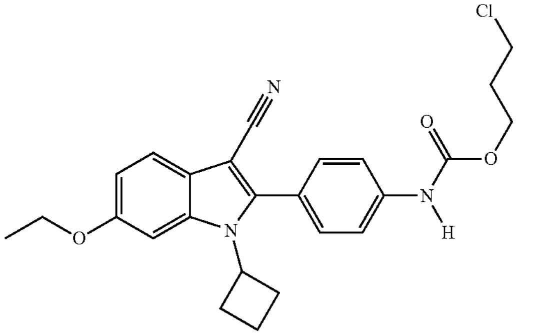
978
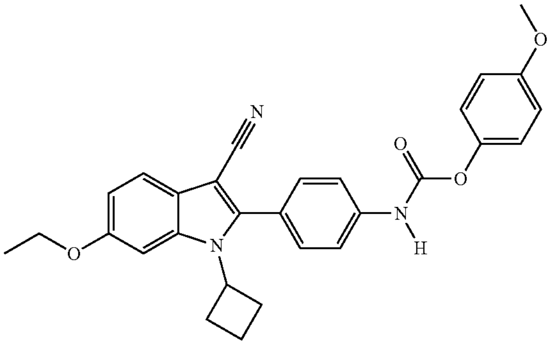
979
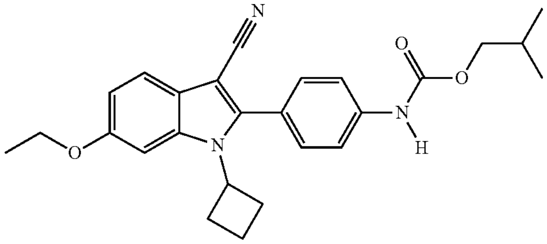
980
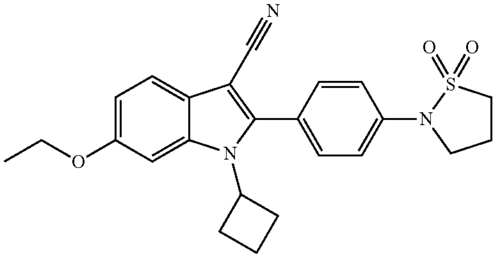
981
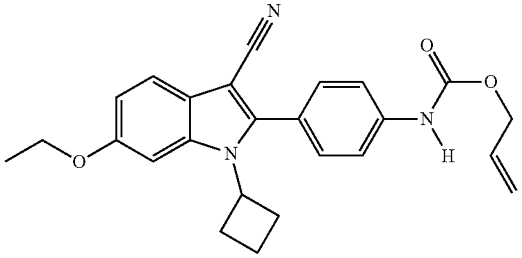
982
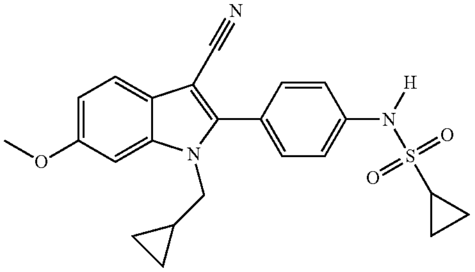
983
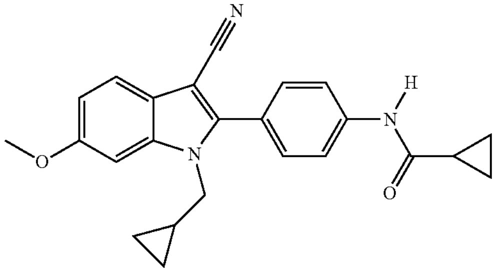
984
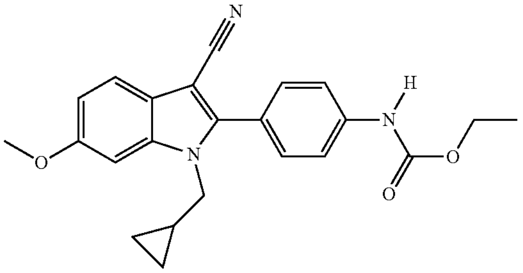
985
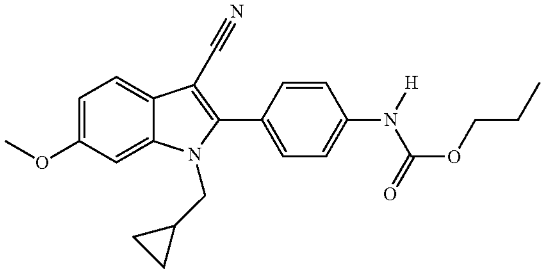

-continued
986
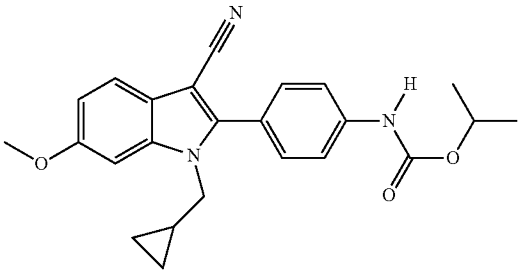
987
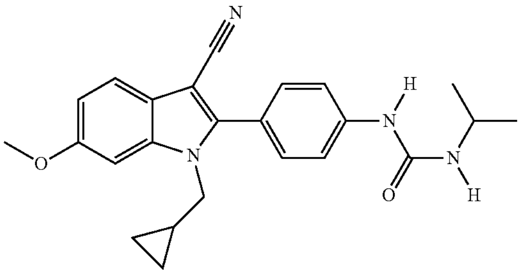
988
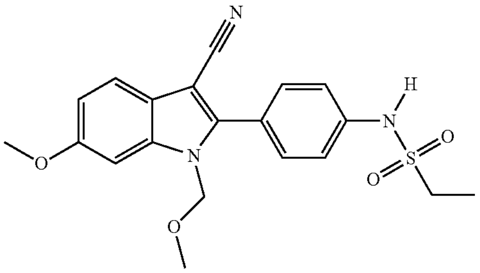
989
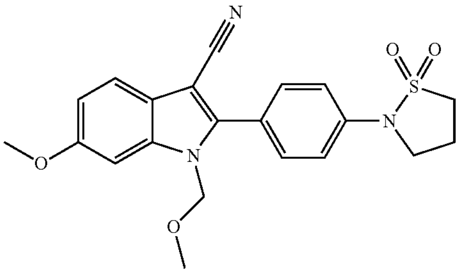
990
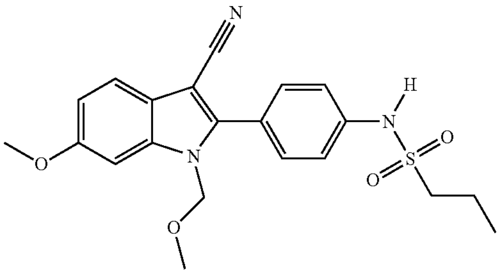
991
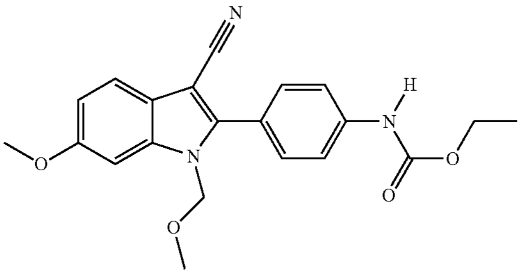
992
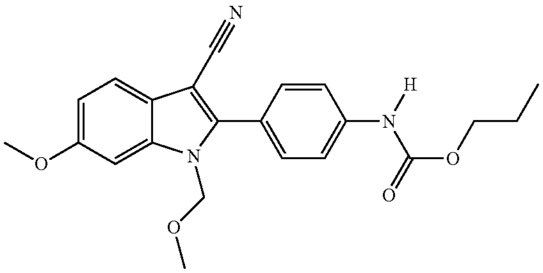
993
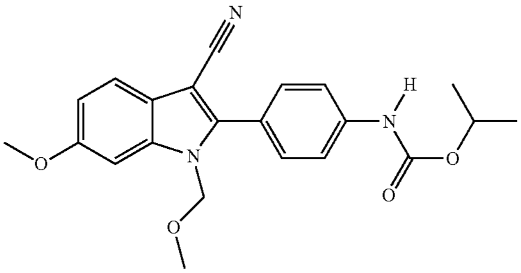
994
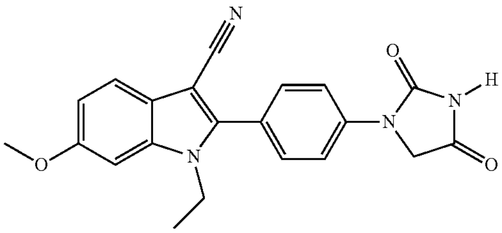
995
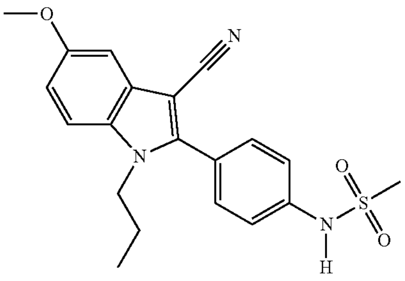

-continued
996
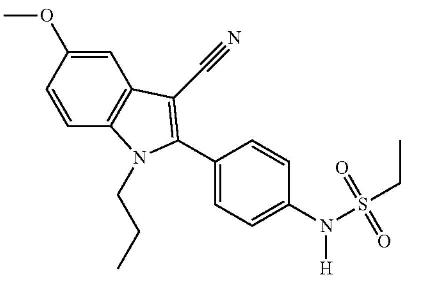
997
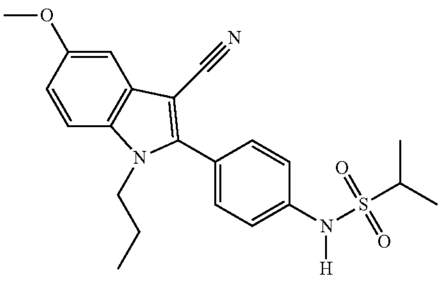
998
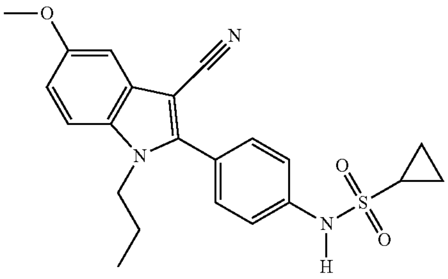
999
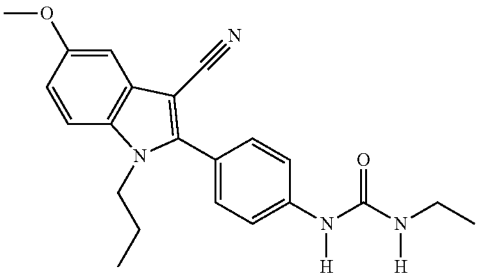
1000
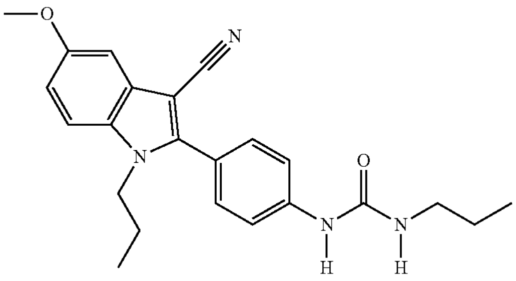
1001
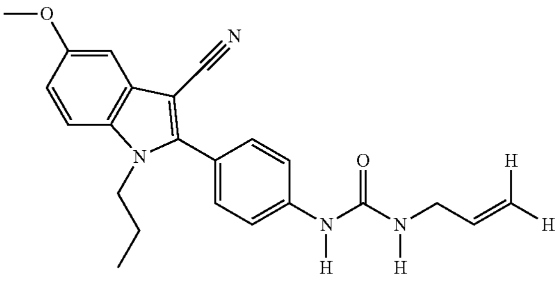
1002
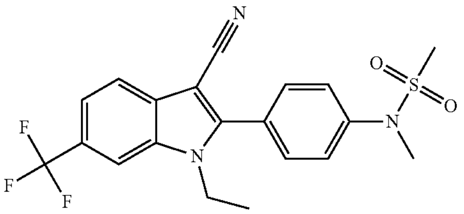
1003
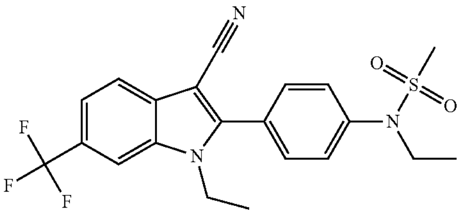
1004
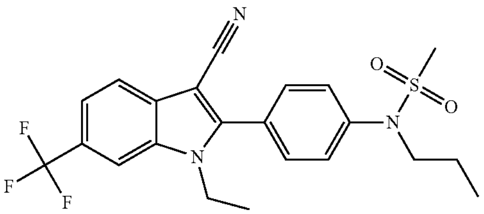
1005
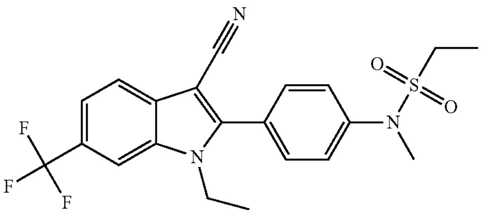
1006
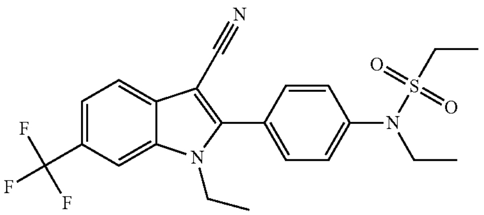
1007
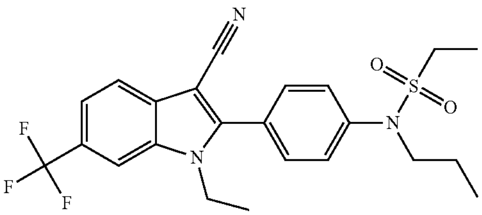

-continued
1008
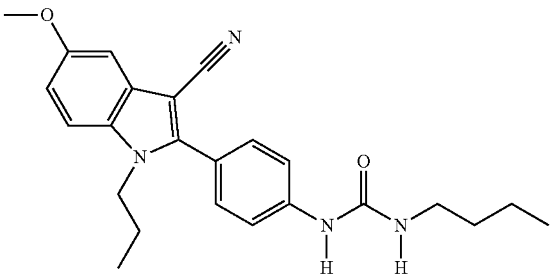
1009
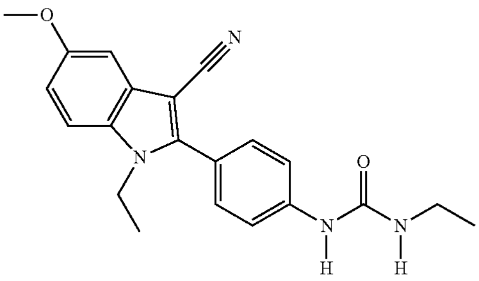
1010
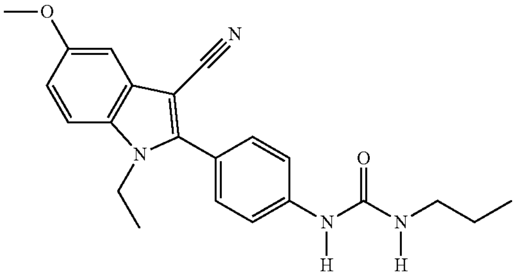
1011
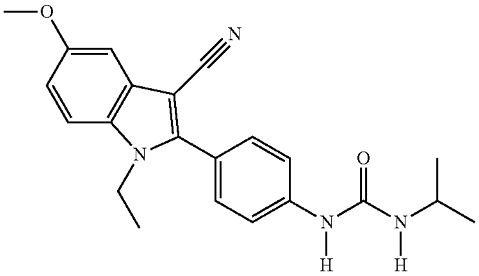
1012
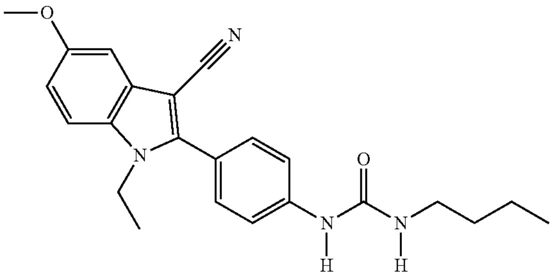
1013
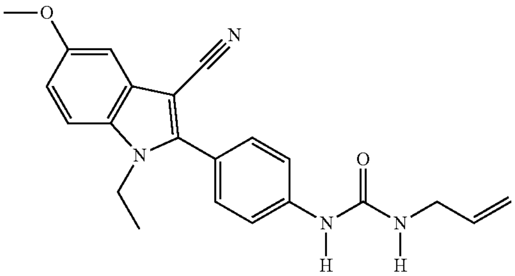
1014
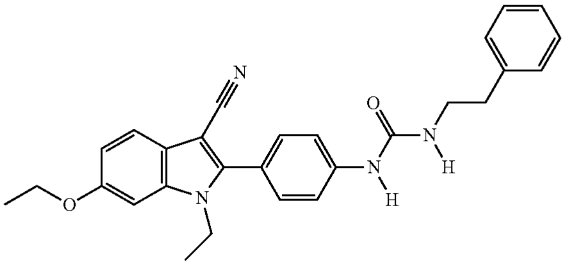
1015
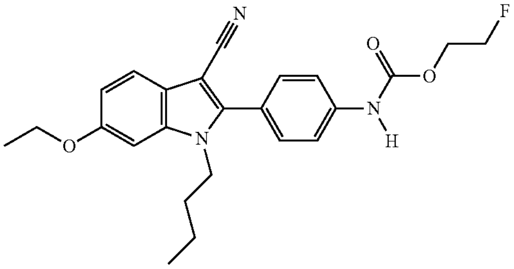
1016
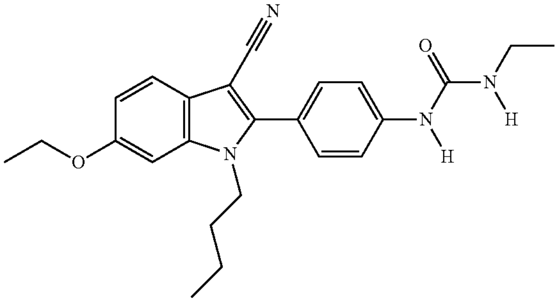
1017
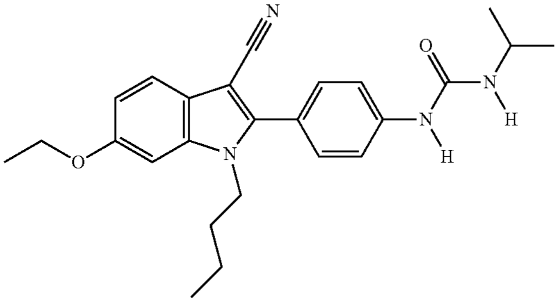

-continued
1018
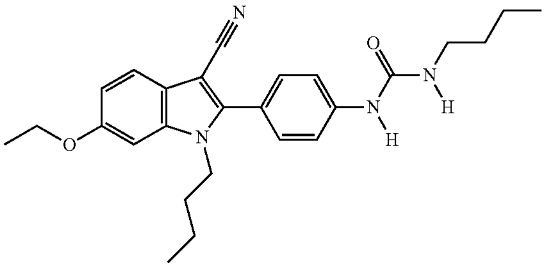
1019
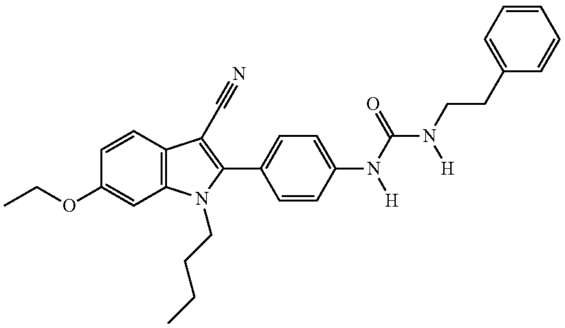
1020
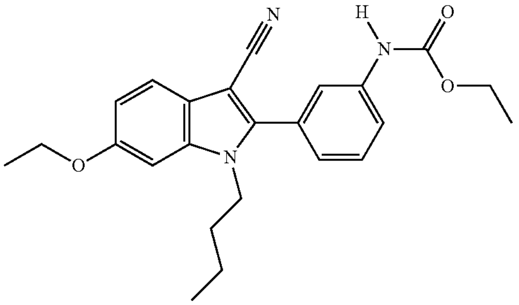
1021
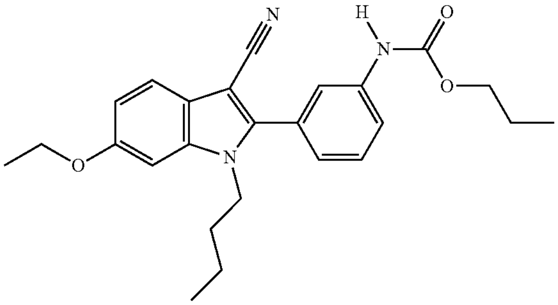
1022
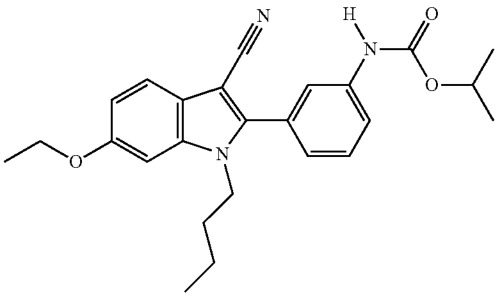
1023
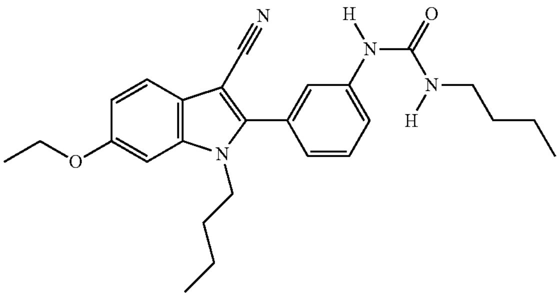
1024
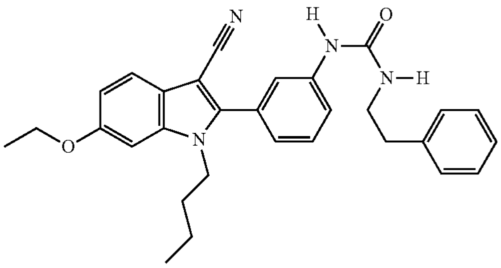
1025
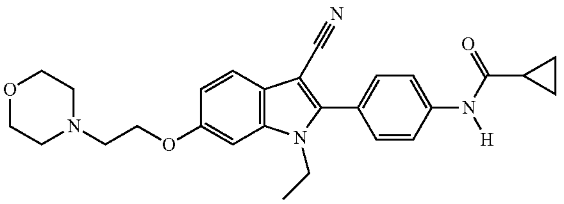
1026
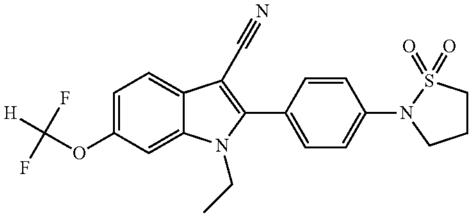
1027
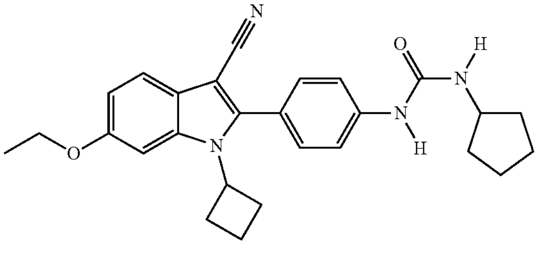

-continued
1028
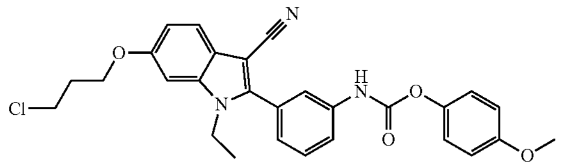
1029
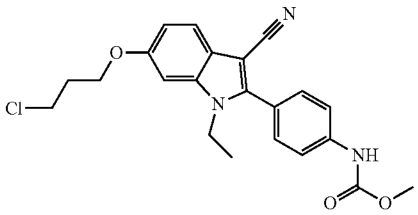
1030
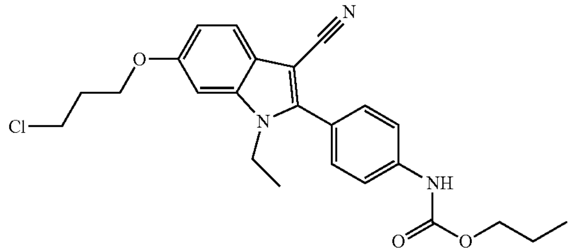
1031
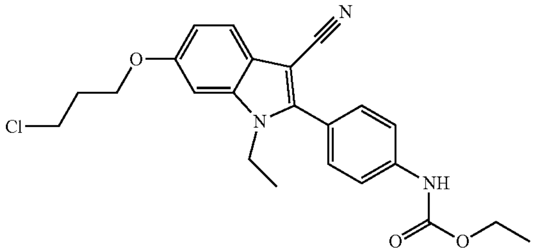
1032
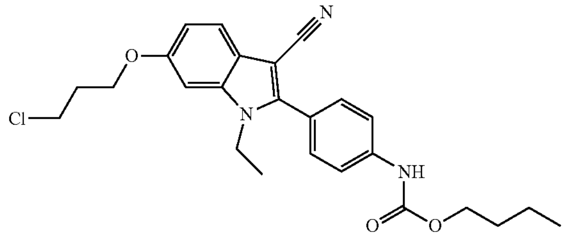
1033
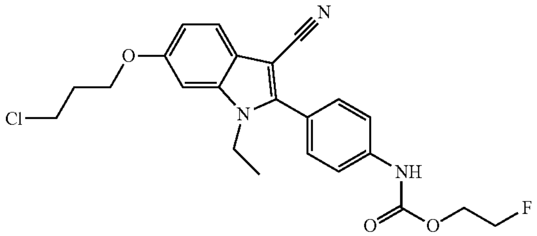
1034
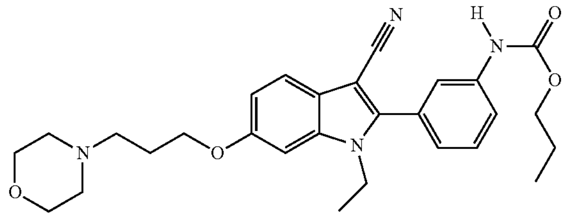
1035
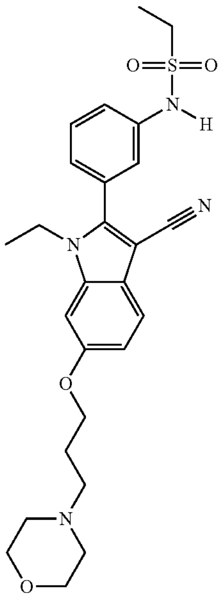

-continued
1036
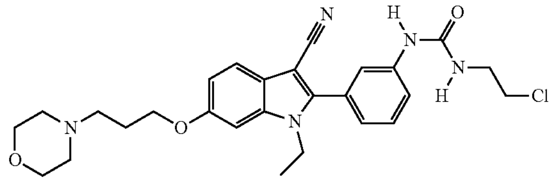
1037
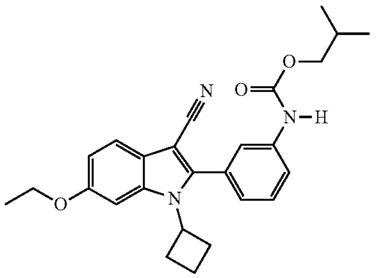
1038
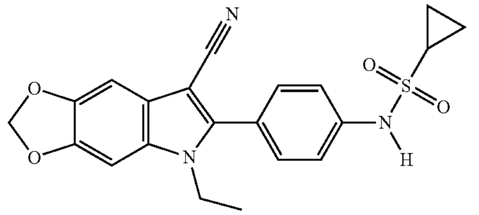
1039
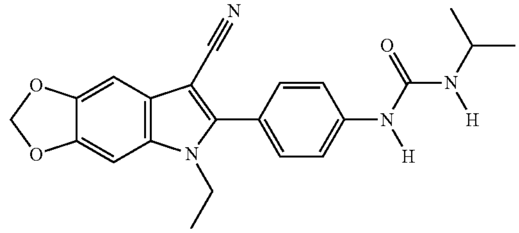
1040
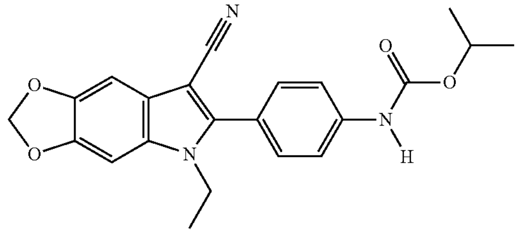
1041
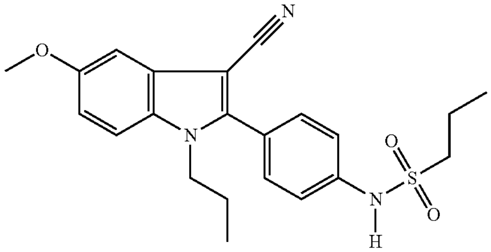
1042
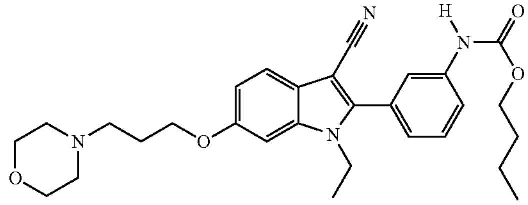
1043
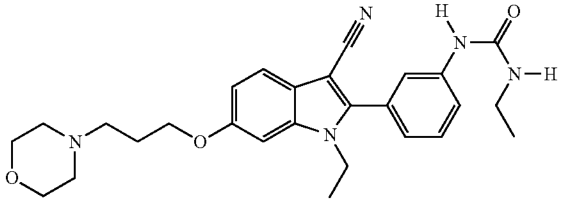
1044
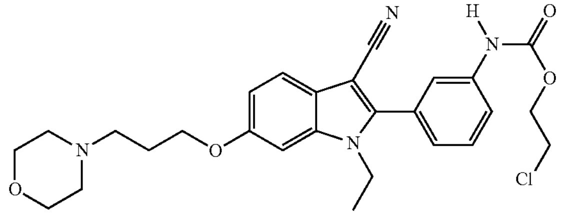
1045
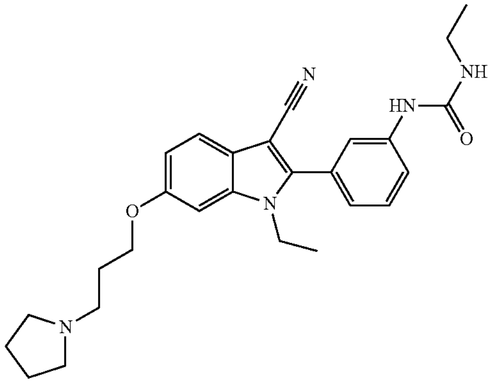

-continued
1046
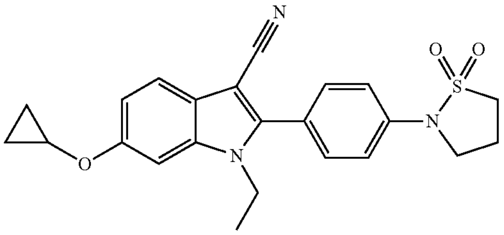
1047
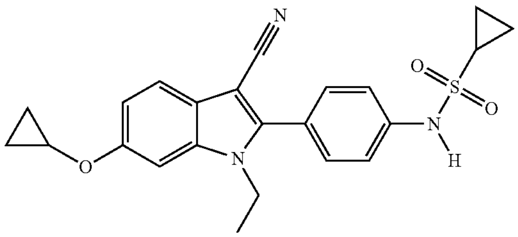
1048
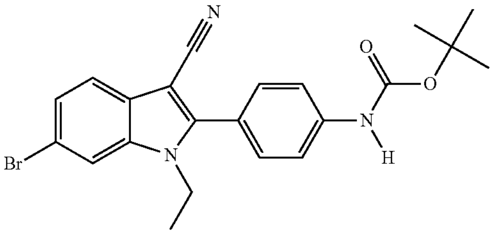
1049
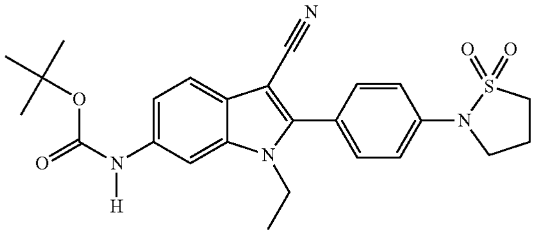
1050
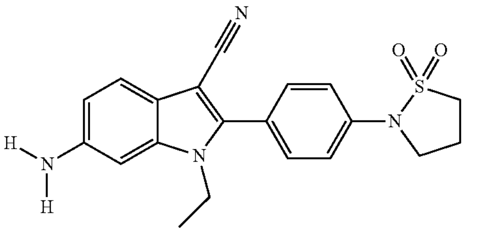
1051
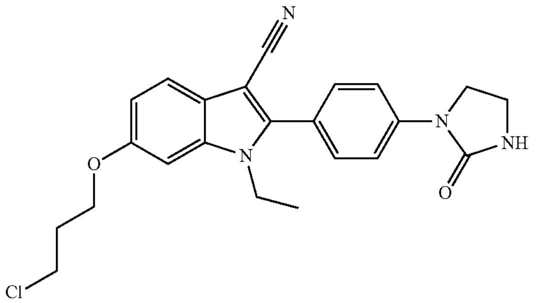
1052
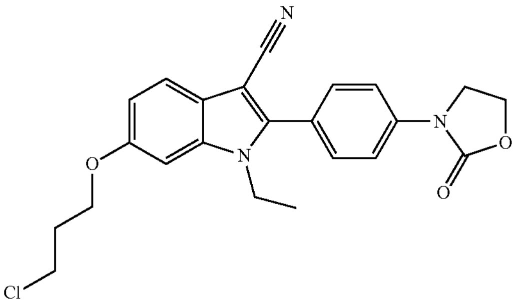
1053
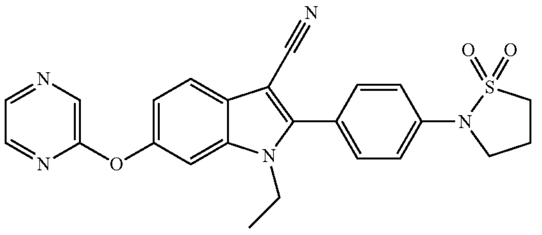
1054
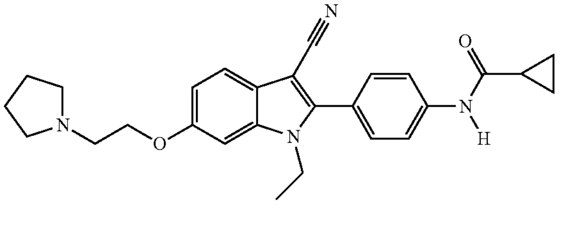
1055
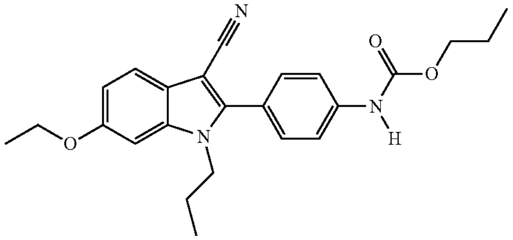

-continued
1056
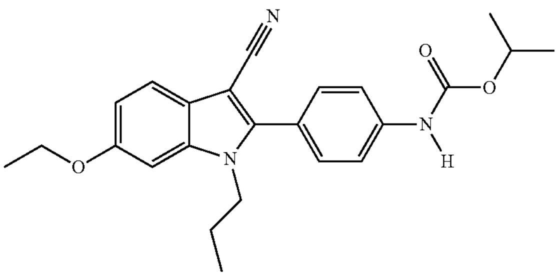
1057
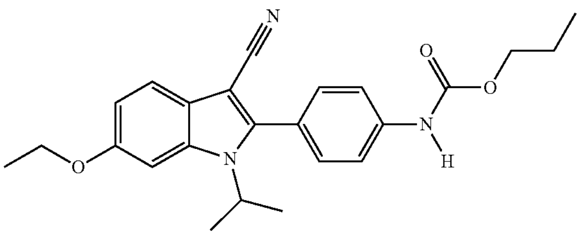
1058
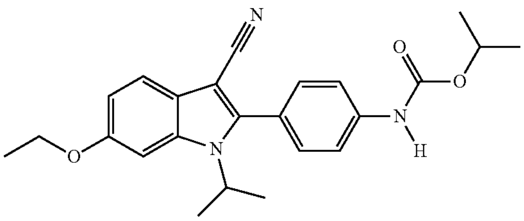
1059
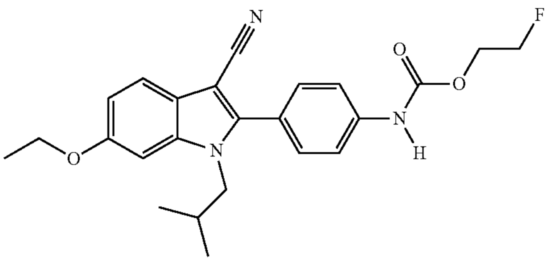
1060
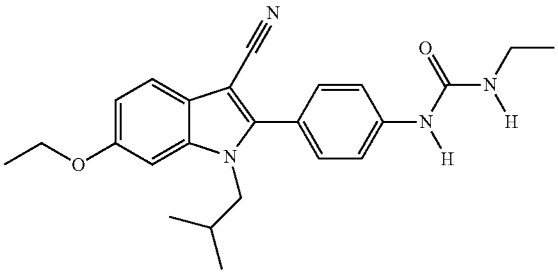
1061
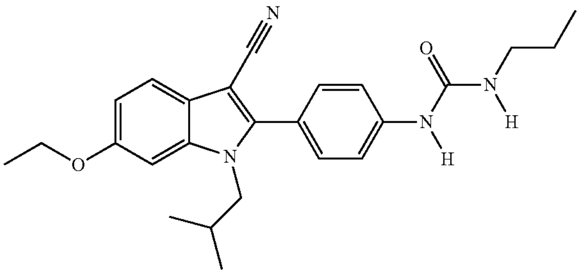
1062
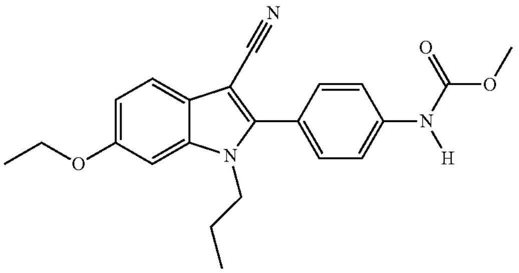
1063
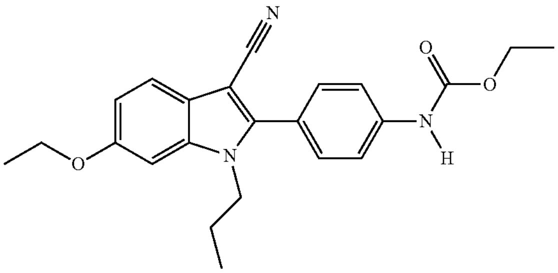
1064
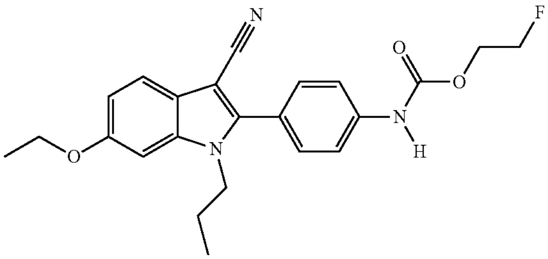
1065
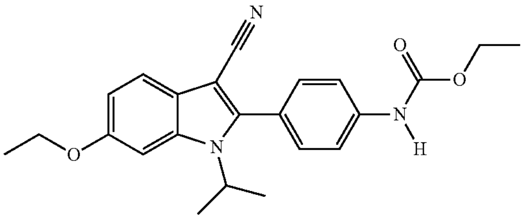

-continued
1066
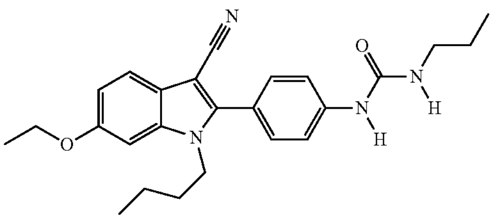
1067
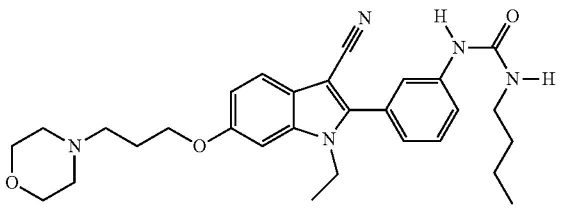
1068
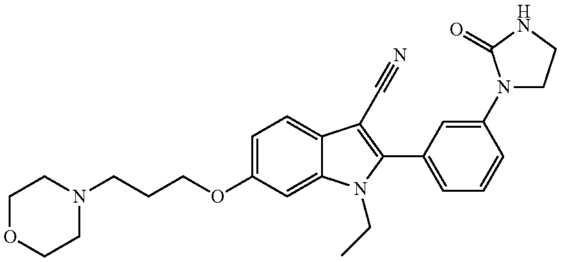
1069
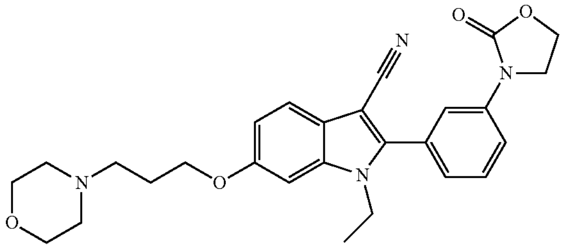
1070
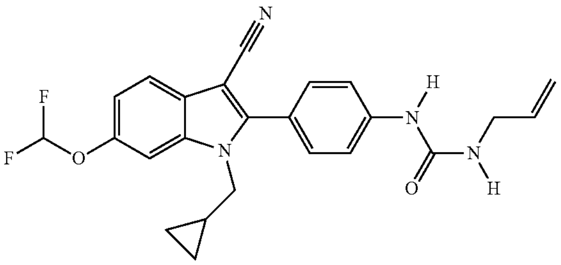
1071
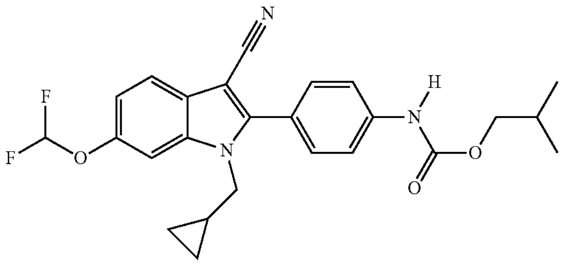
1072
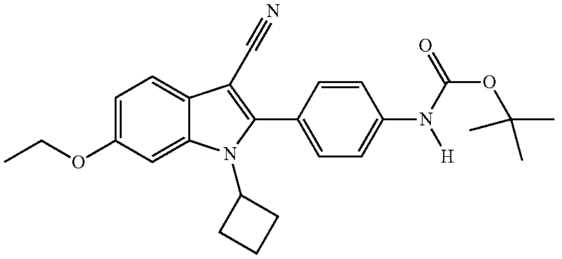
1073
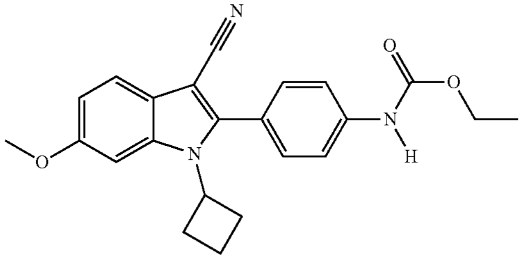
1074
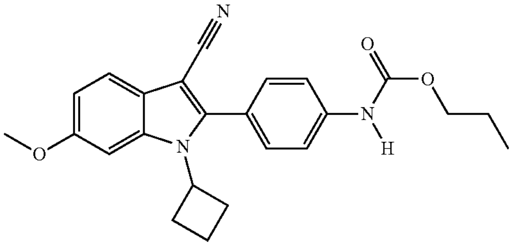
1075
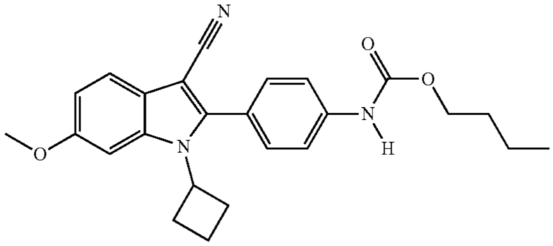

-continued
1076
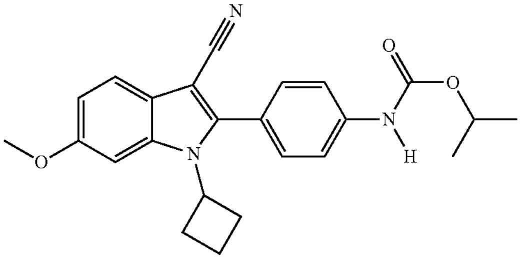
1077
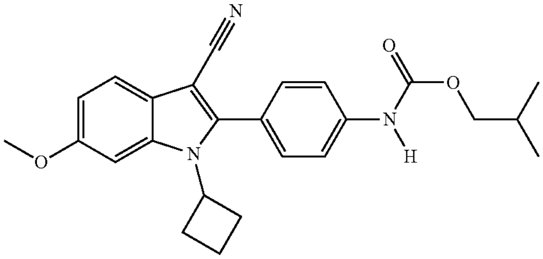
1078
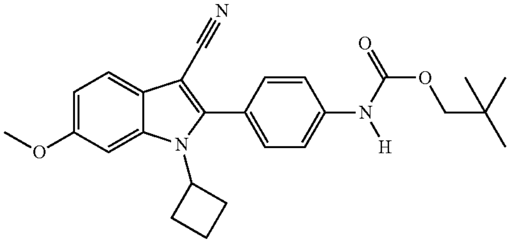
1079
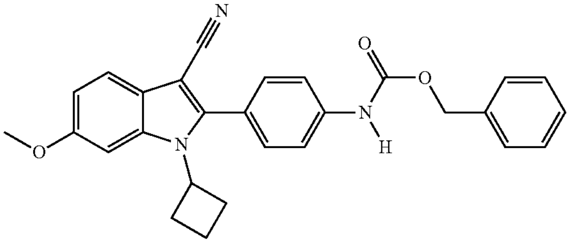
1080
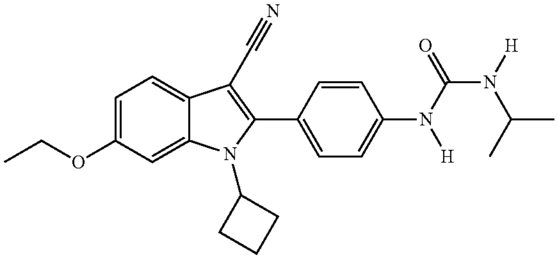
1081
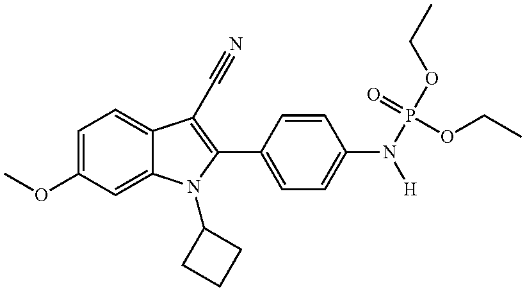
1082
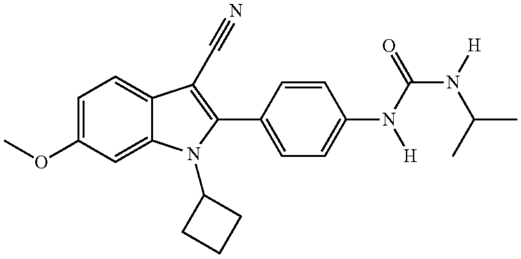
1083
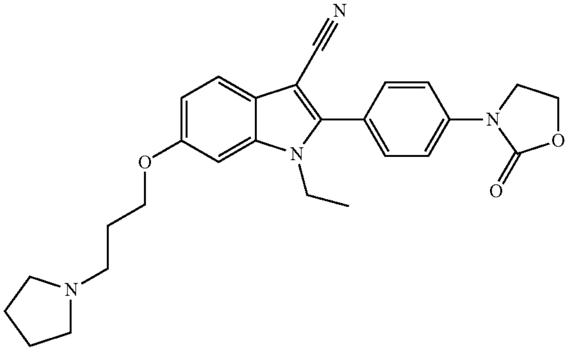
1084
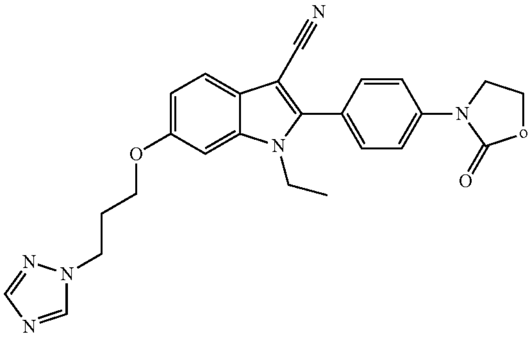
1085
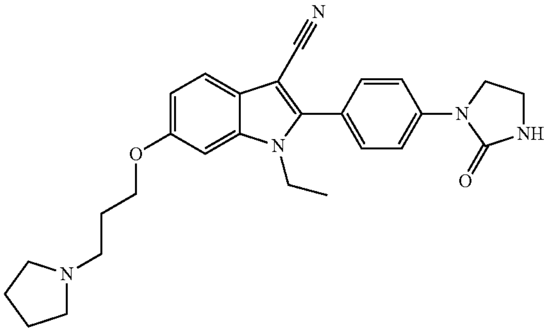

-continued
1086
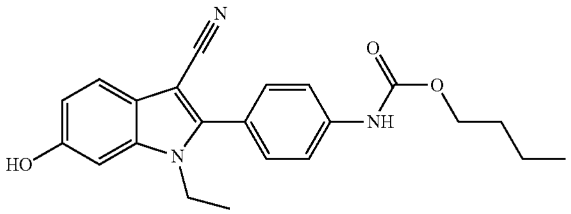
1087
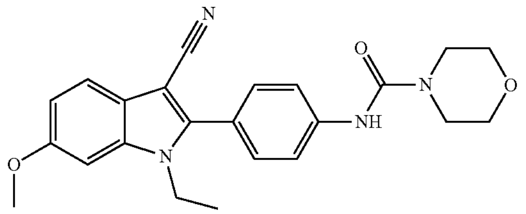
1088
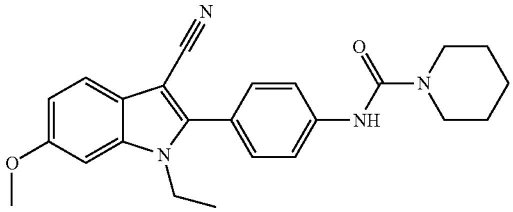
1089
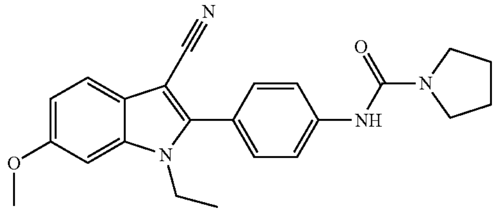
1090
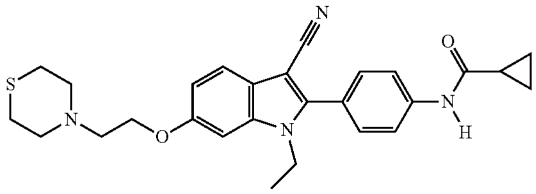
1091
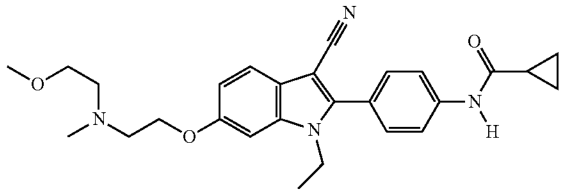
1092
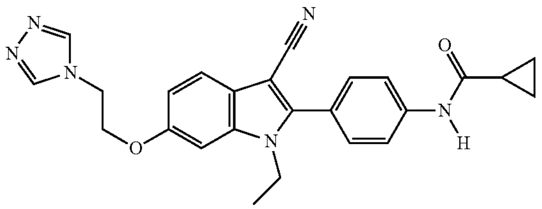
1093
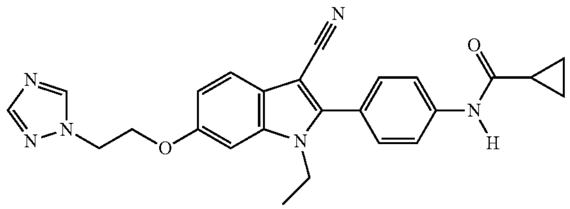
1094
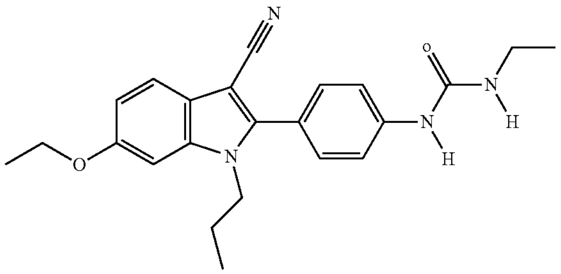
1095
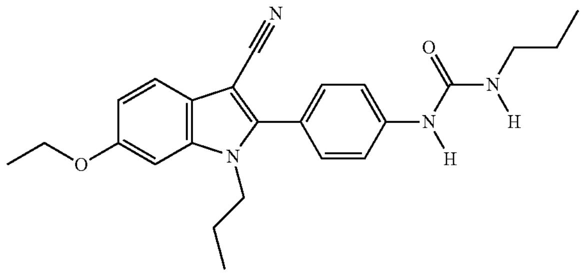
1096
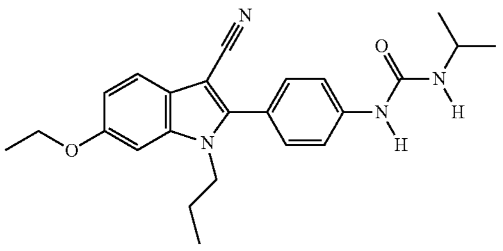
1097
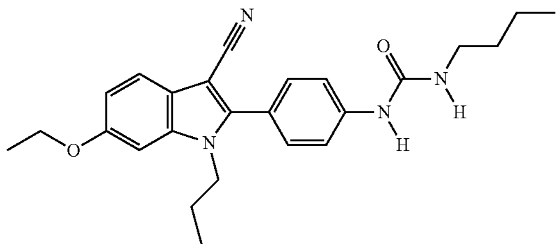

-continued
1098
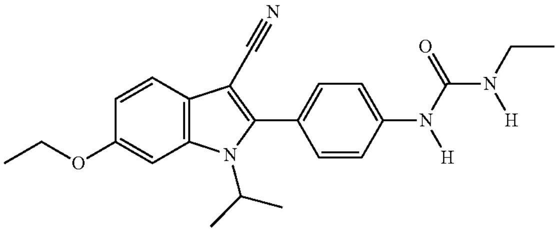
1099
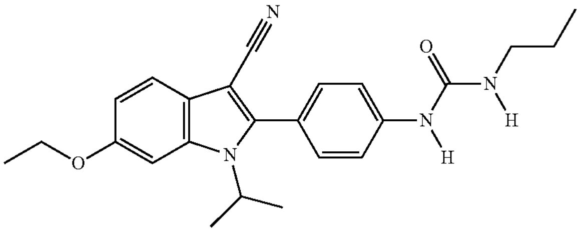
1100
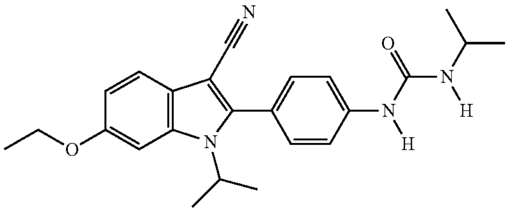
1101
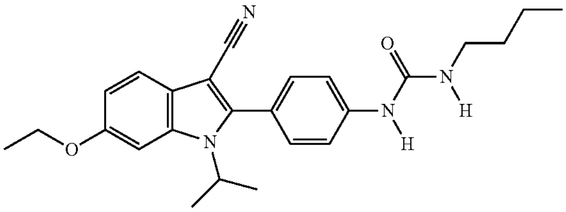
1102
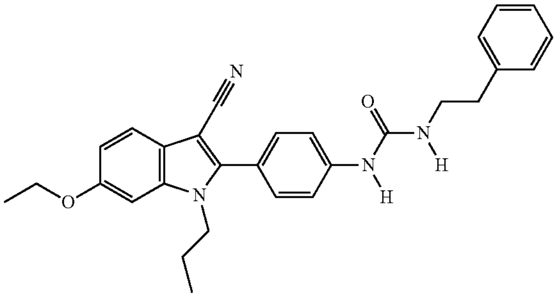
1103
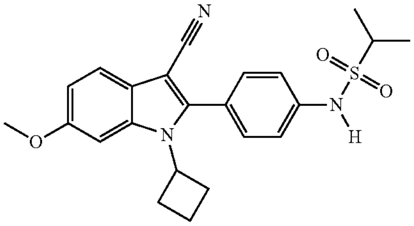
1104
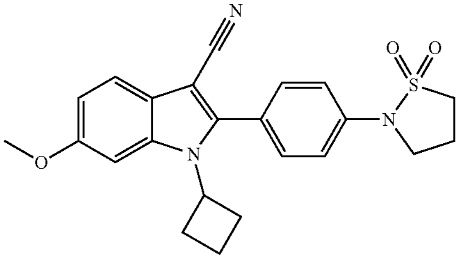
1105
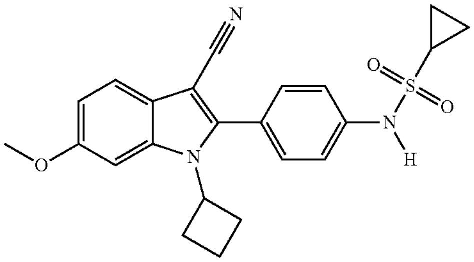
1106
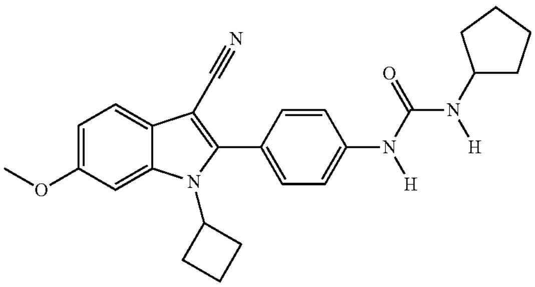
1107
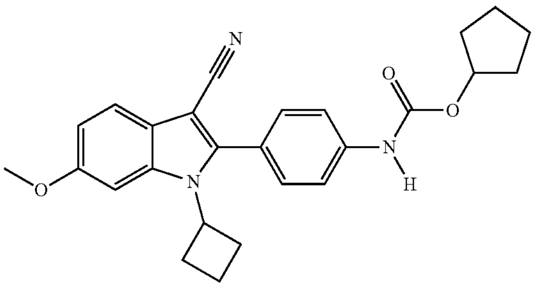

-continued
1108
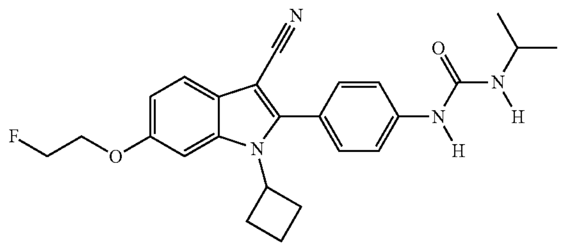
1109
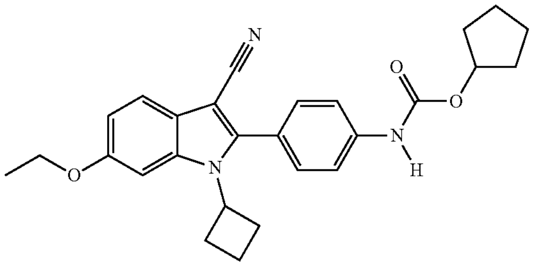
1110
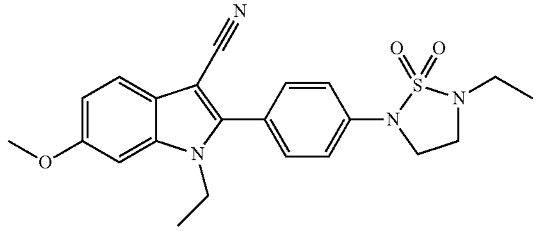
1111
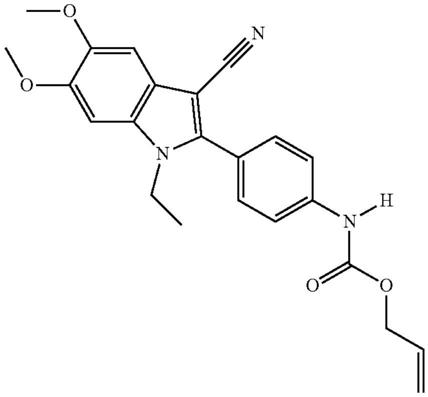
1112
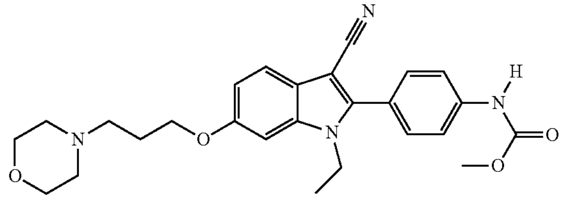
1113
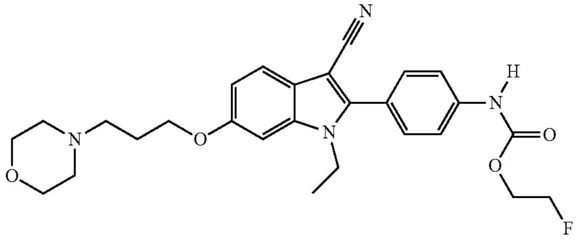
1114
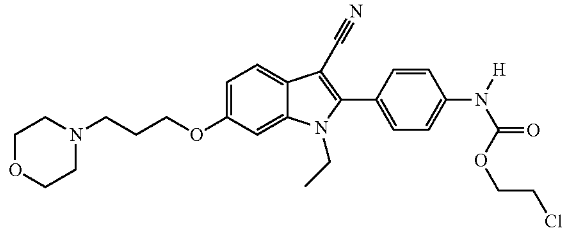
1115
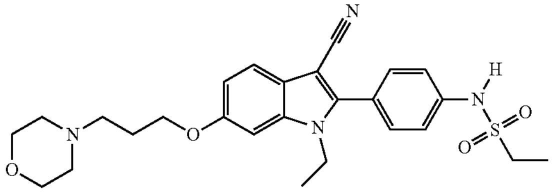
1116
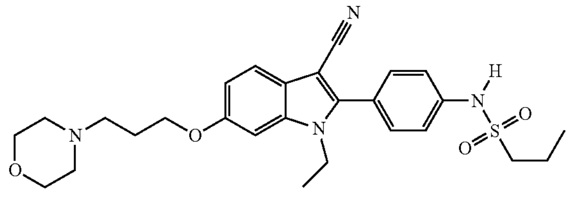
1117
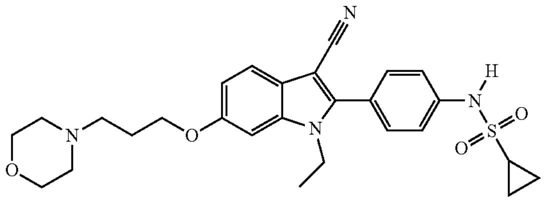

-continued
1118
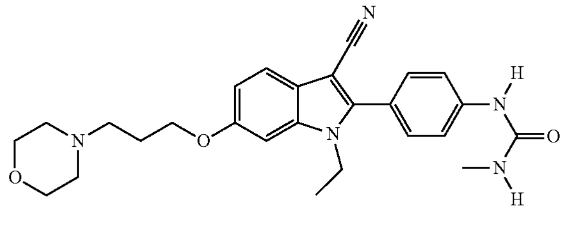
1119
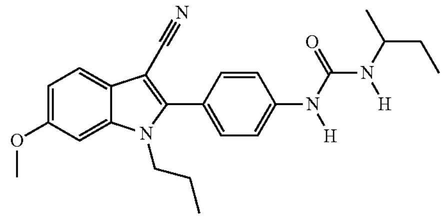
1120
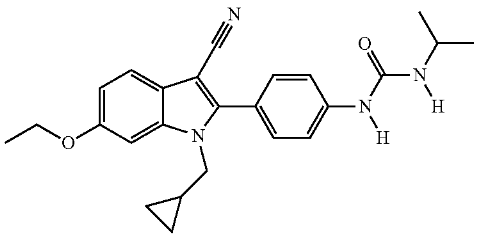
1121
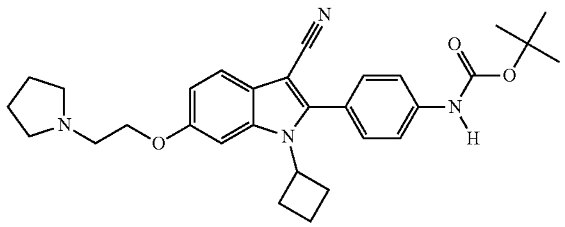
1122
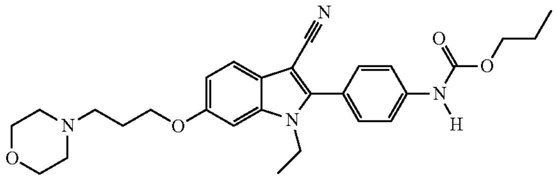
1123
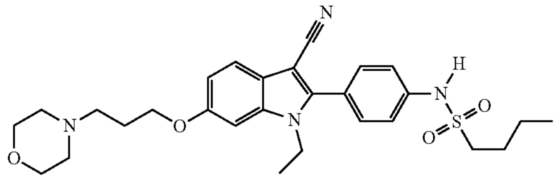
1124
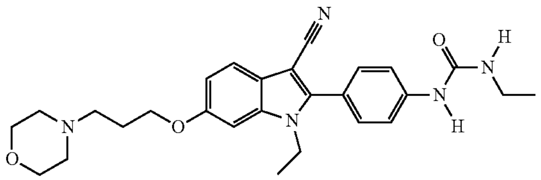
1125
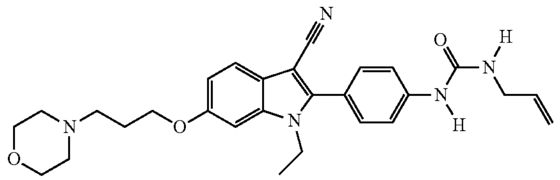
1126
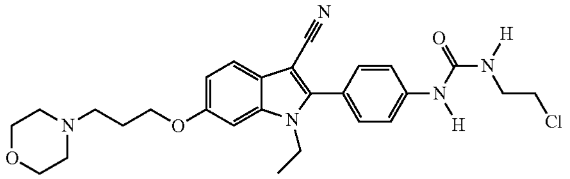
1127
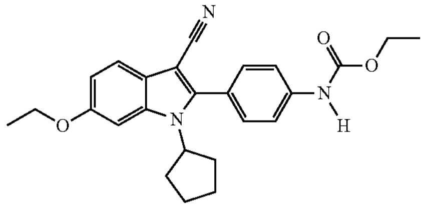
1128
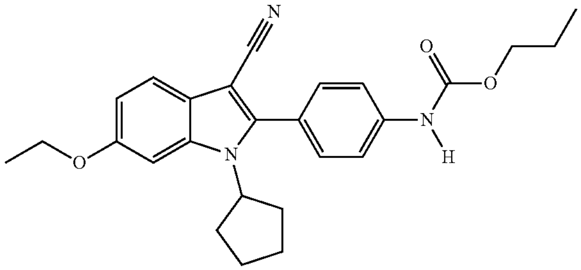
1129
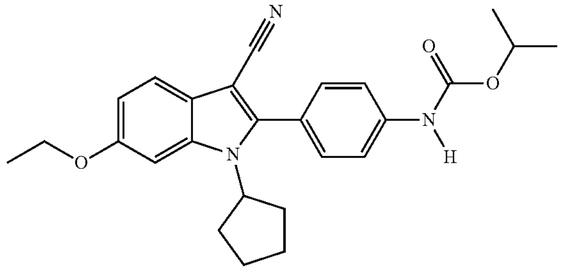

-continued
1130
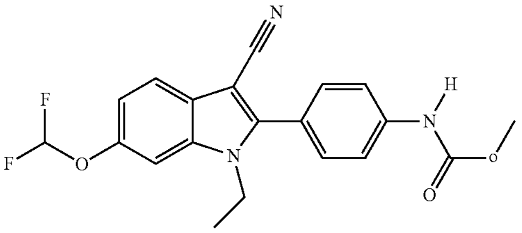
1131
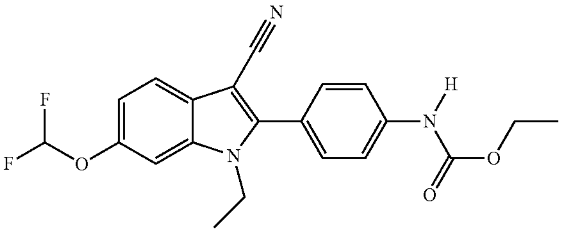
1132
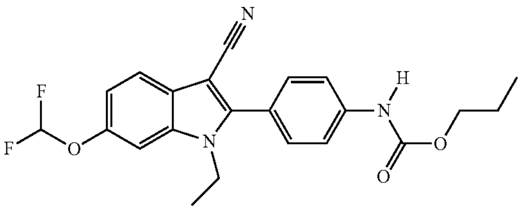
1133
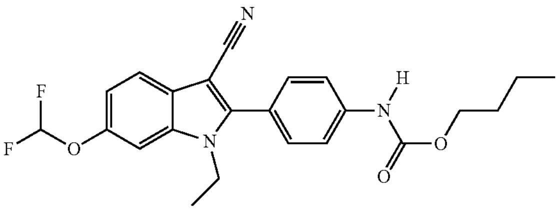
1134
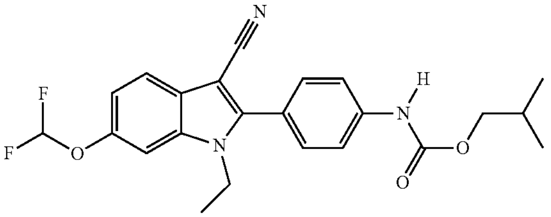
1135
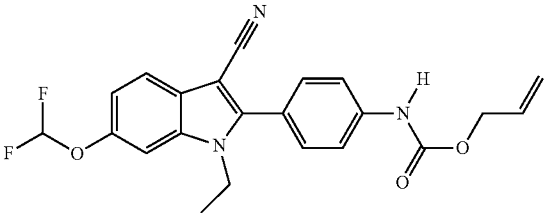
1136
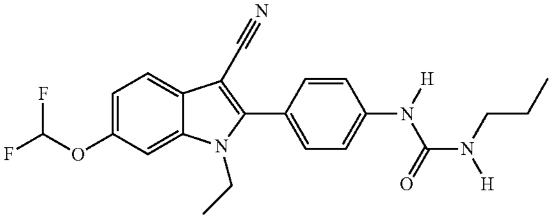
1137
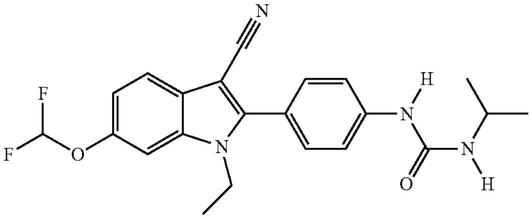
1138
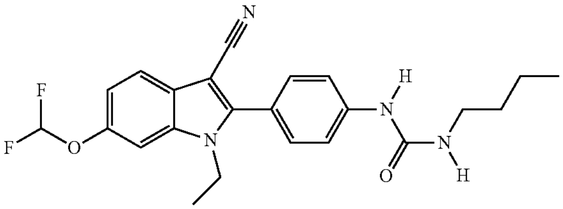
1139
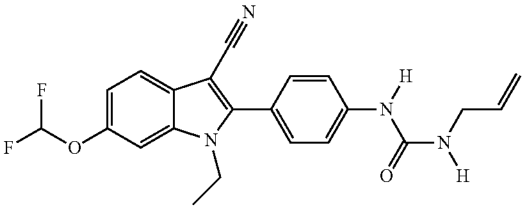
1140
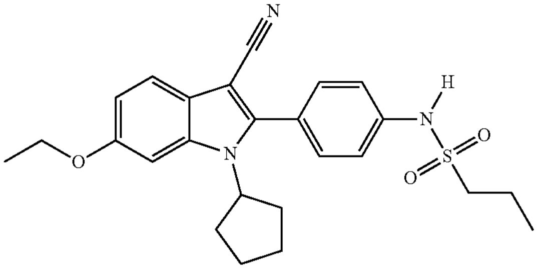
1141
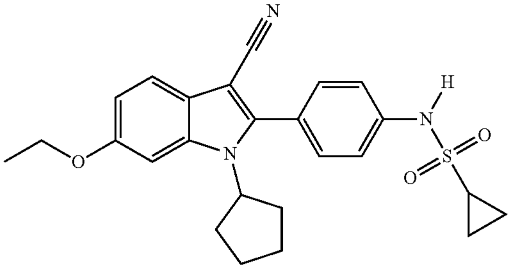

-continued
1142
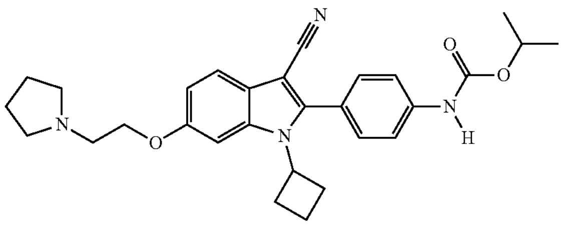
1143
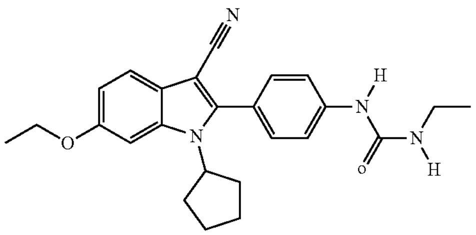
1144
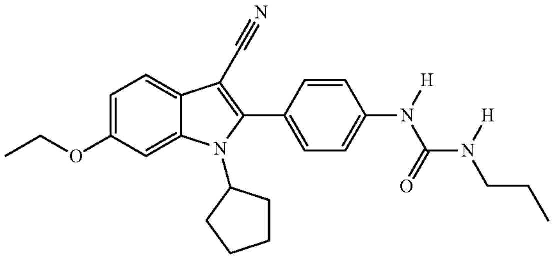
1145
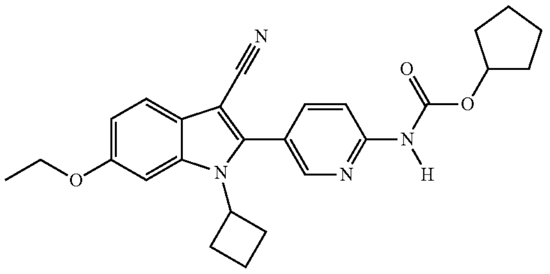
1146
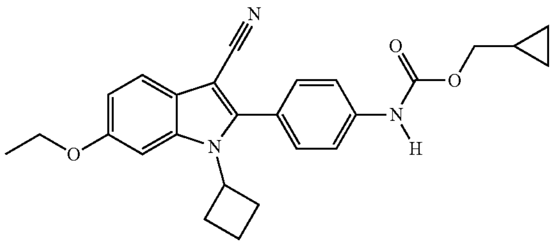
1147
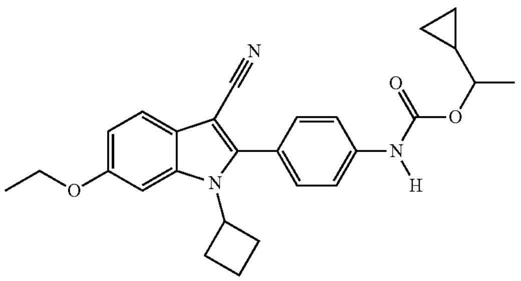
1148
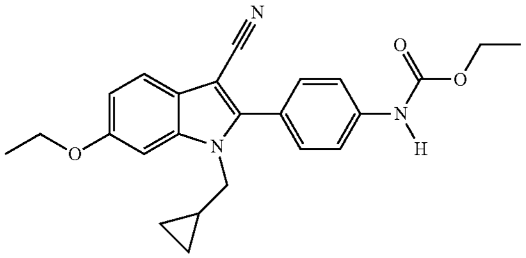
1149
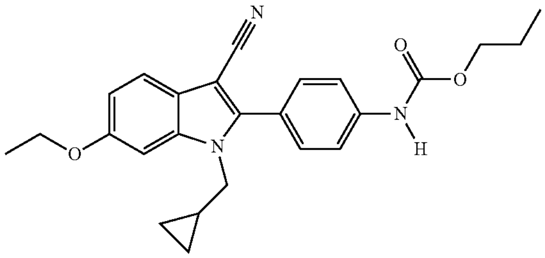
1150
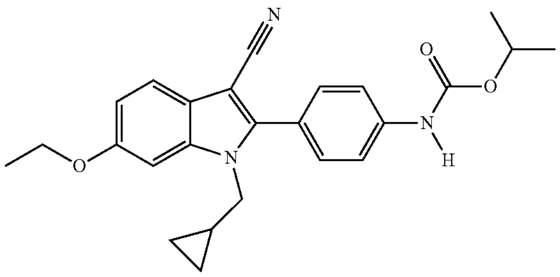
1151
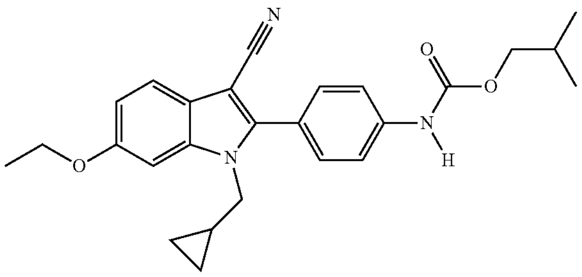

-continued
1152
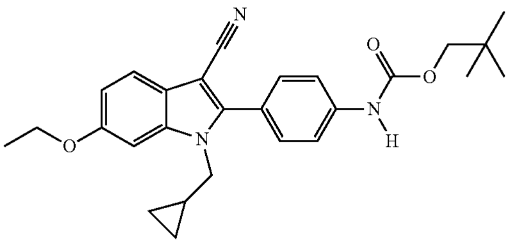
1153
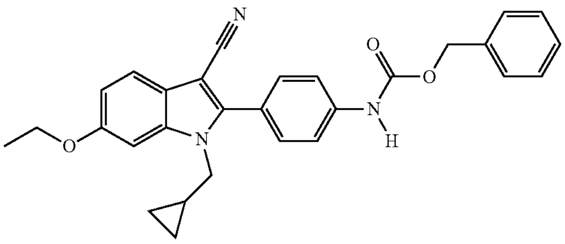
1154
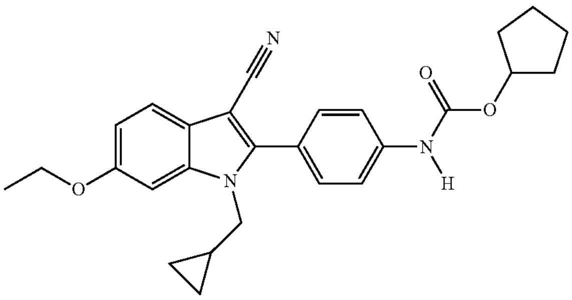
1155
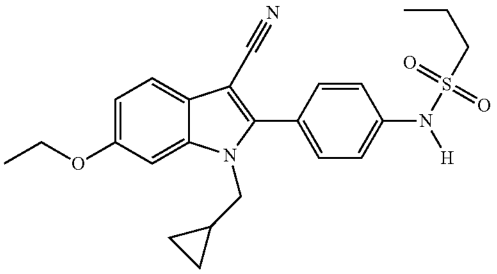
1156
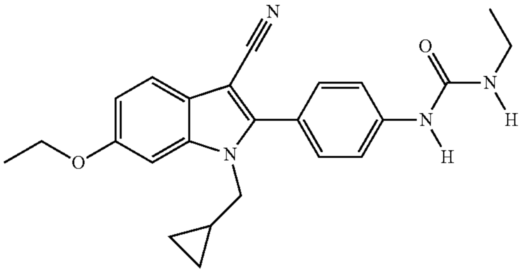
1157
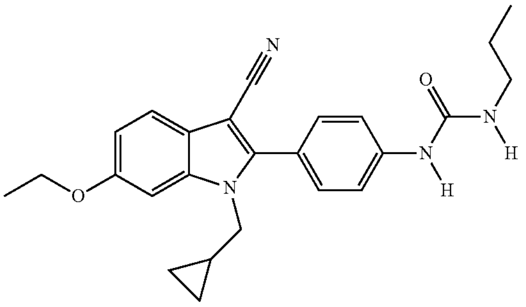
1158
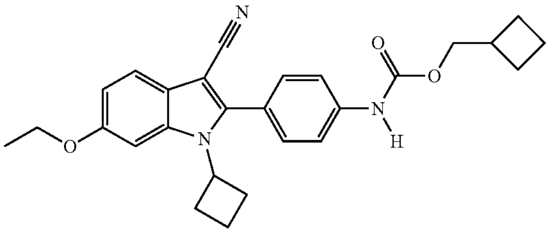
1159
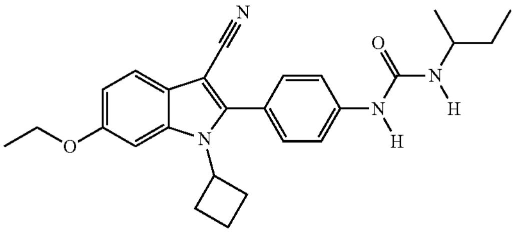
1160
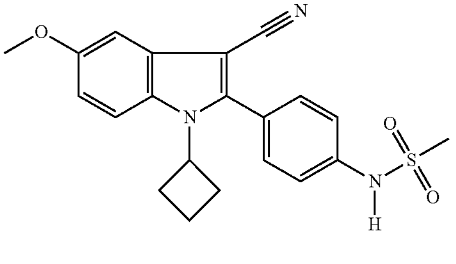
1161
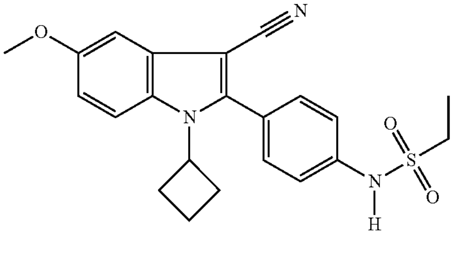

-continued
1162
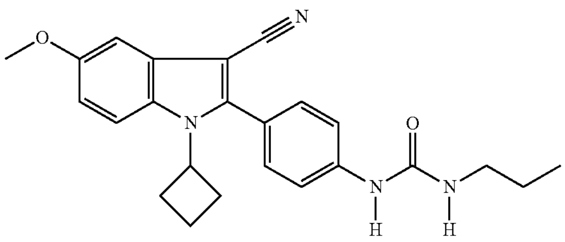
1163
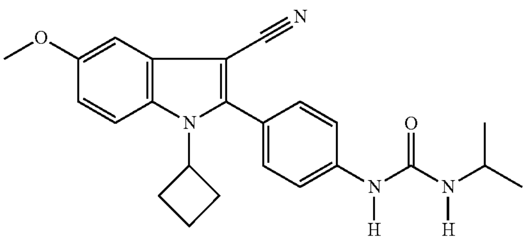
1164
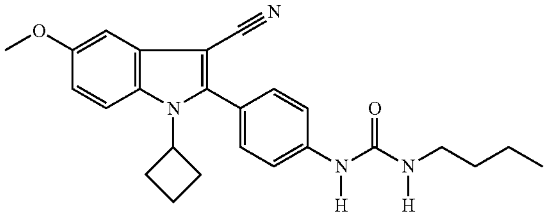
1165
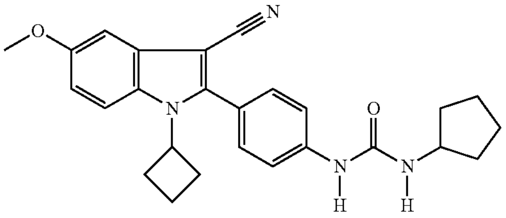
1166
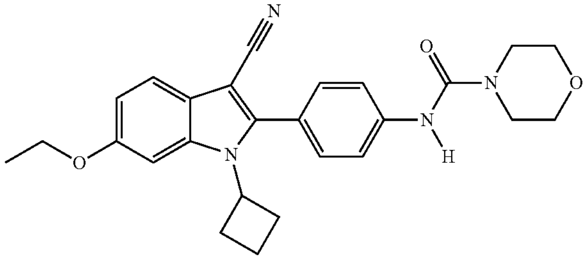
1167
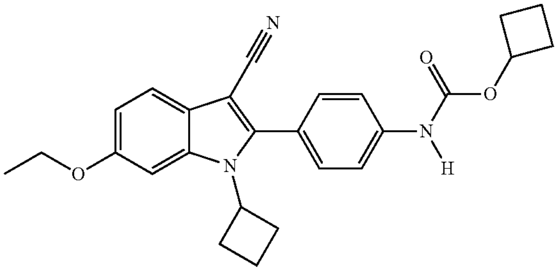
1168
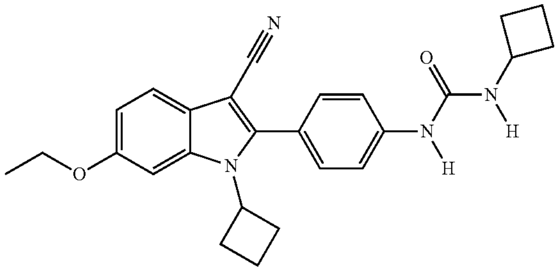
1169
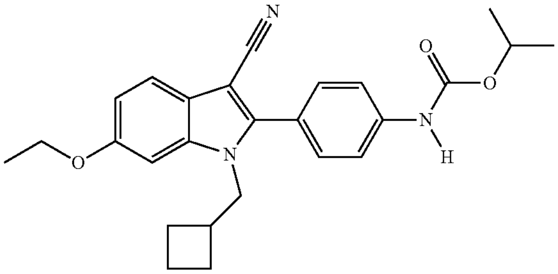
1170
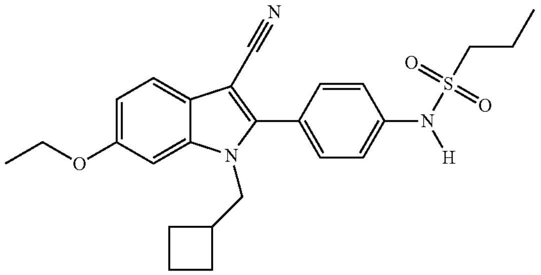
1171
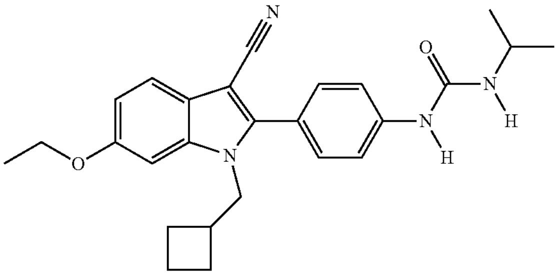

-continued
1172
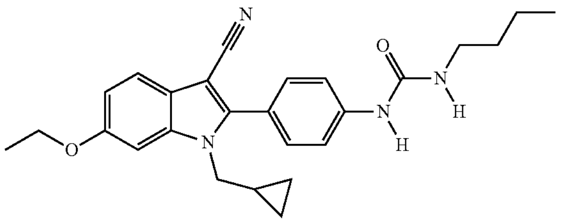
1173
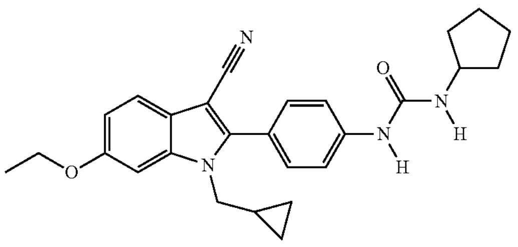
1174
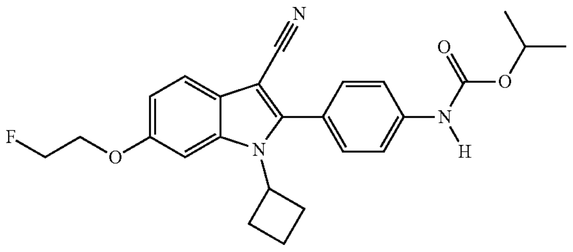
1175
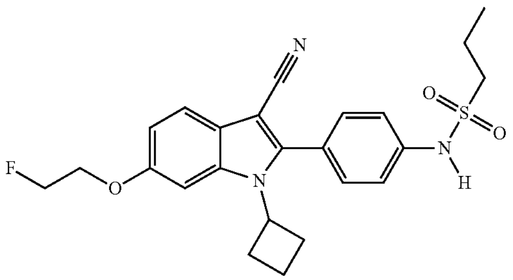
1176
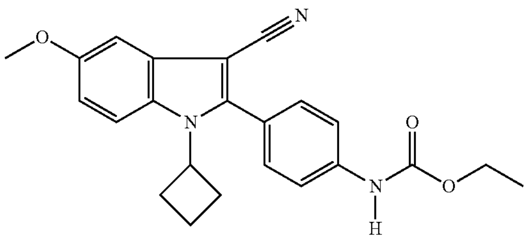
1177
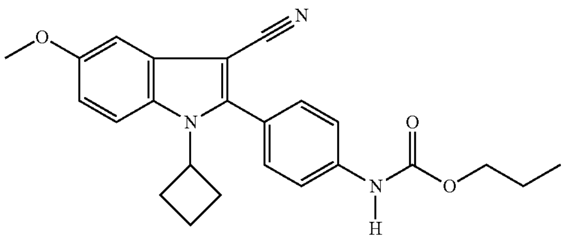
1178
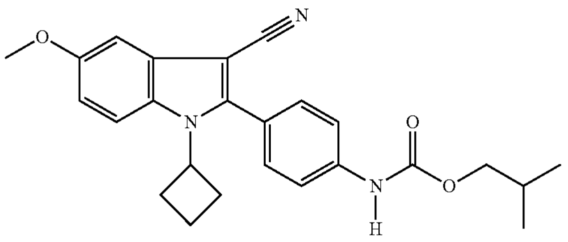
1179
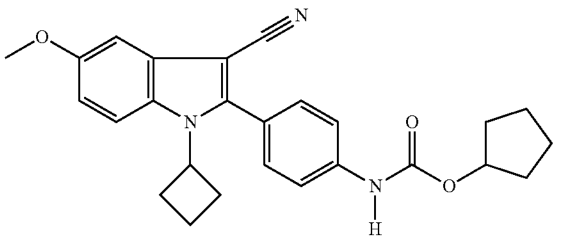
1180
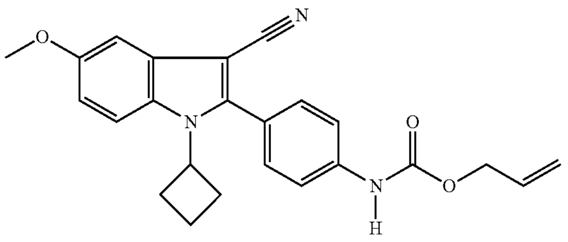
1181
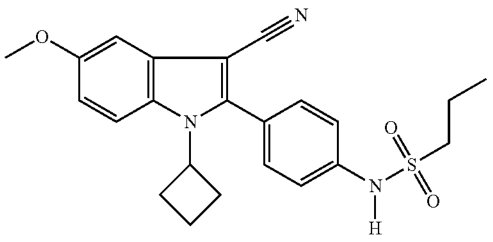
1182
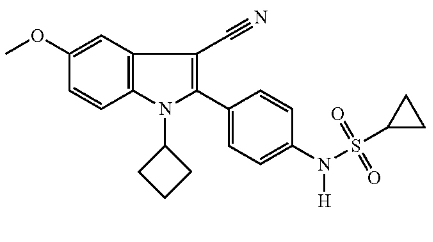
1183
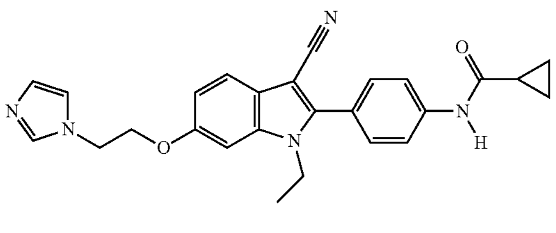

-continued
1184
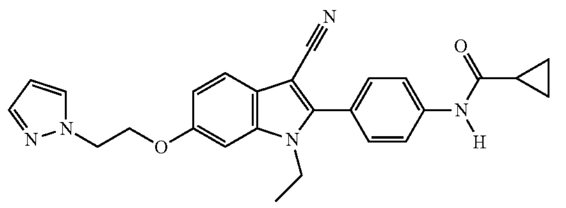
1185
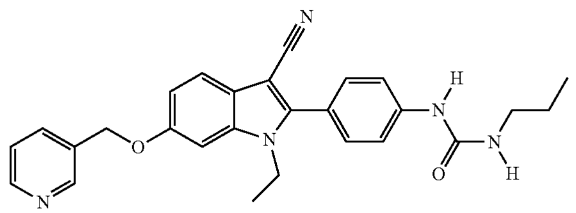
1186
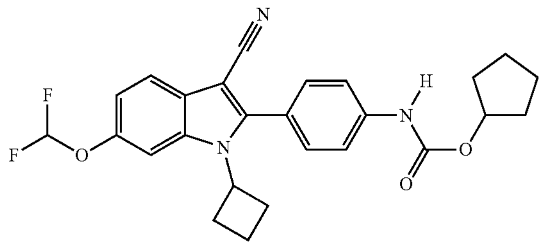
1187
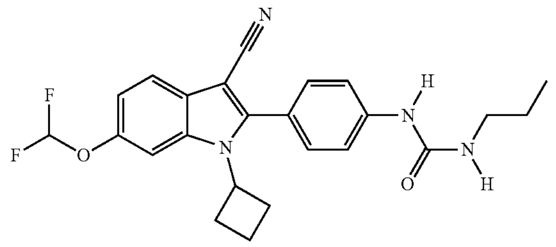
1188
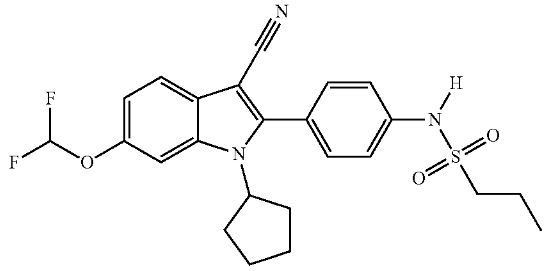
1189
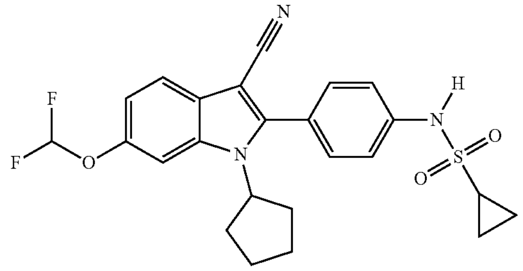
1190
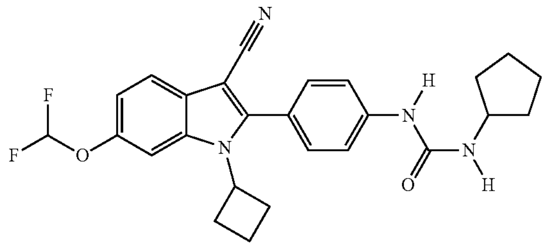
1191
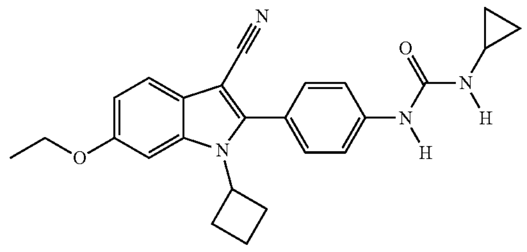
1192
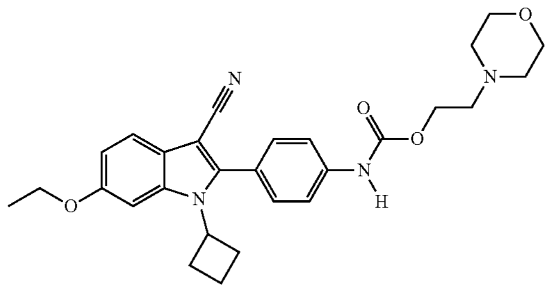
1193
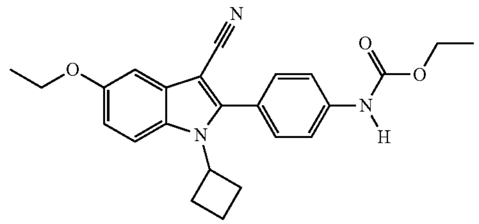

-continued
1194
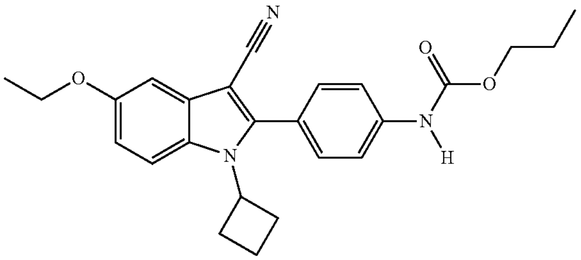
1195
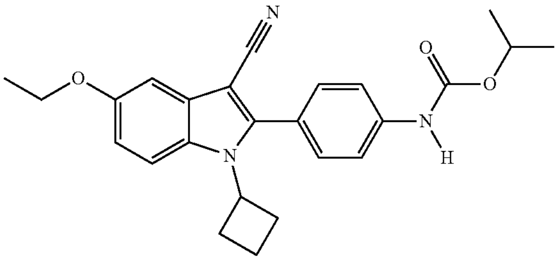
1196
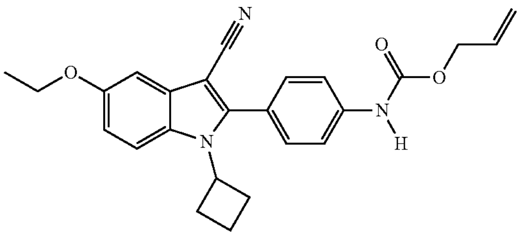
1197
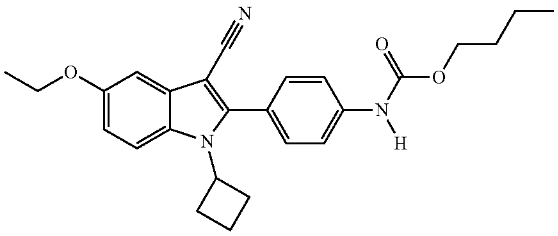
1198
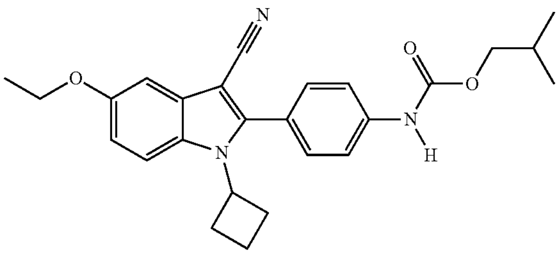
1199
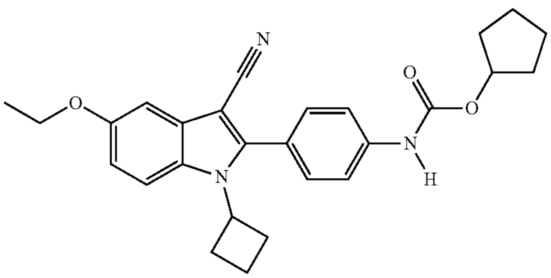
1200
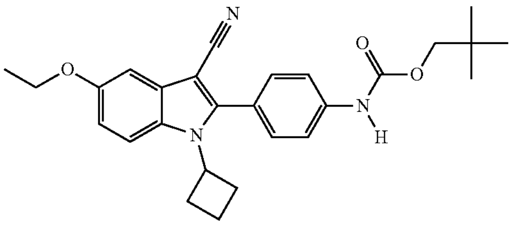
1201
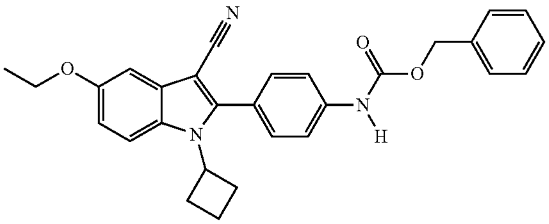
1202
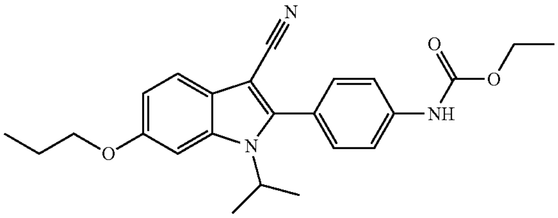
1203
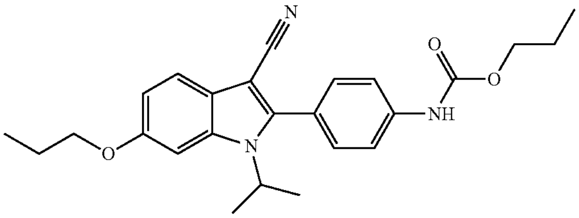
1204
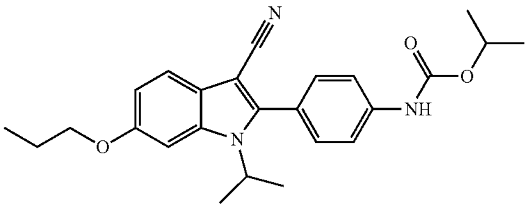
1205
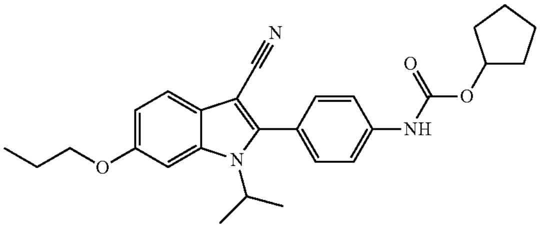

-continued
1206
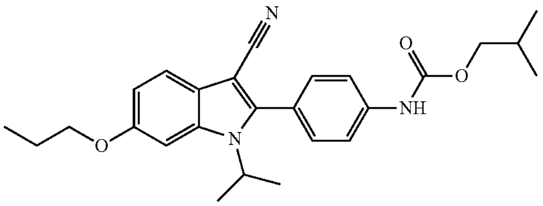
1207
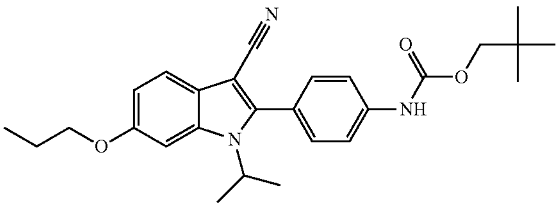
1208
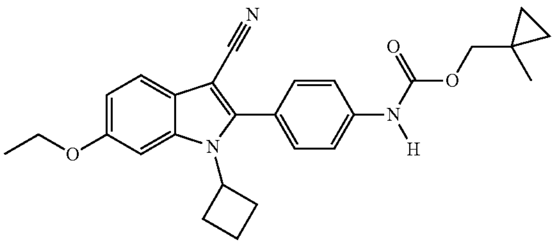
1209
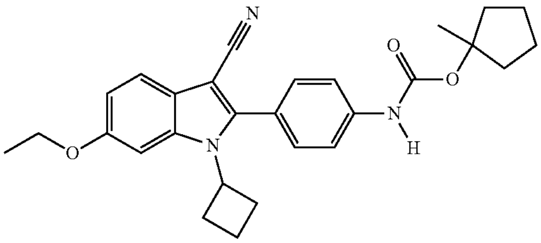
1210
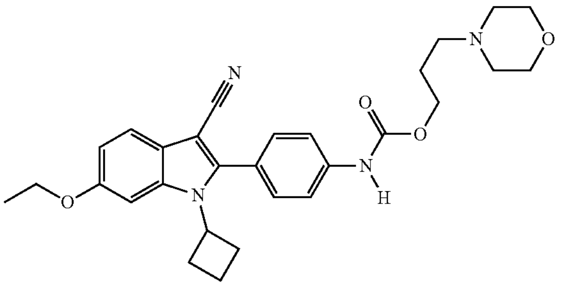
1211
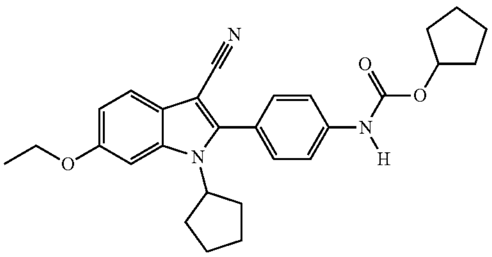
1212
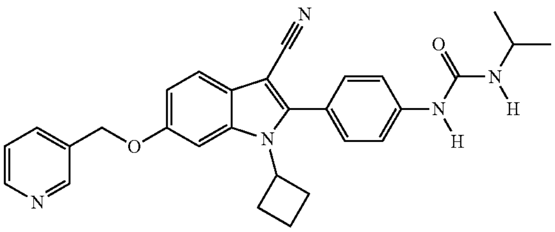
1213
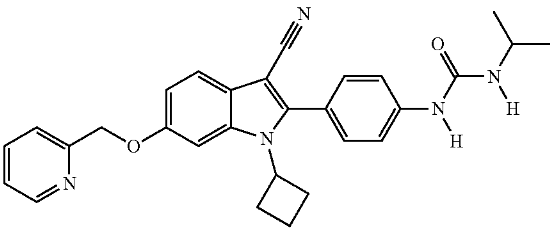
1214
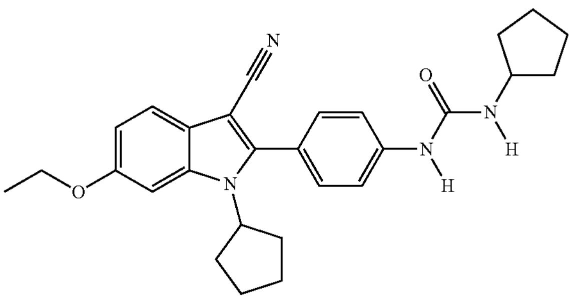
1215
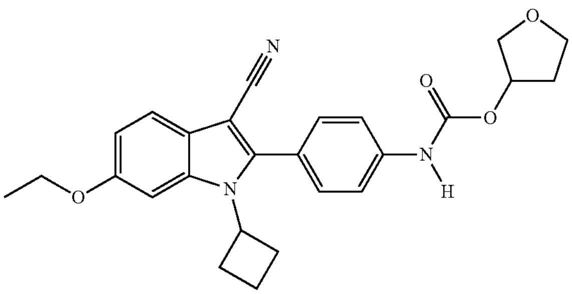

-continued
1216
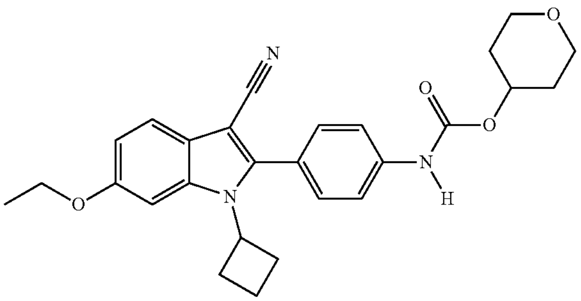
1217
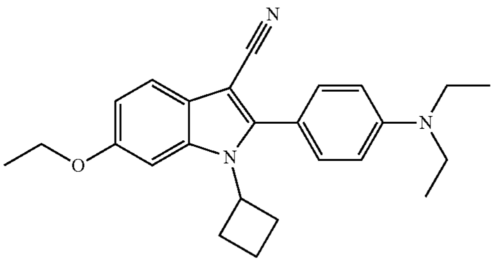
1218
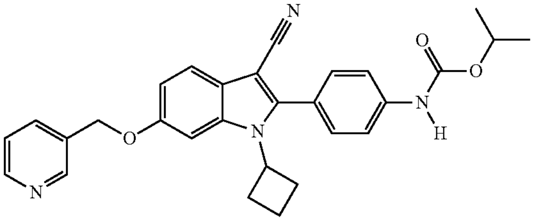
1219
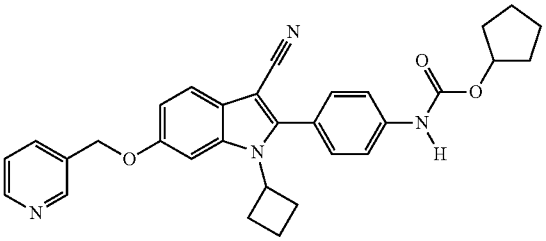
1220
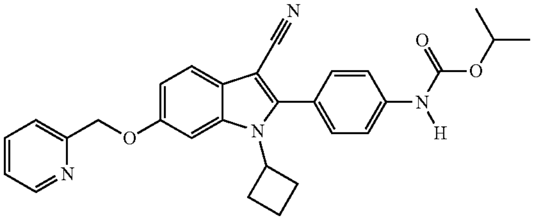
1221
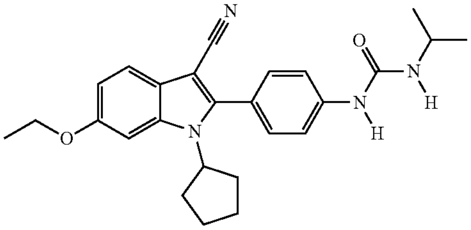
1222
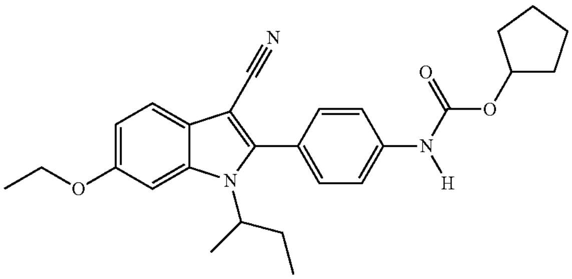
1223
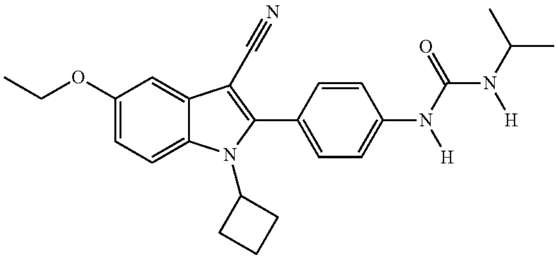
1224
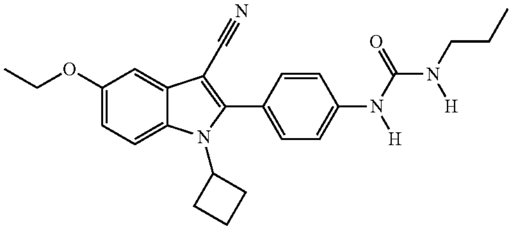
1225
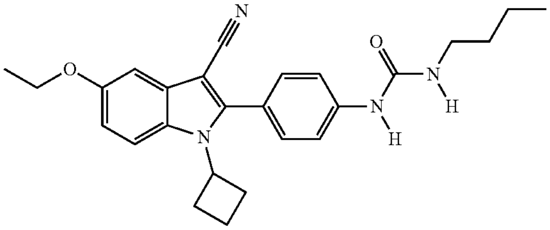

-continued
1226
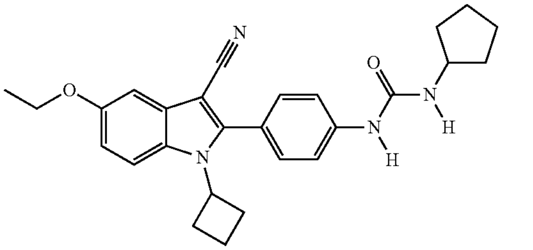
1227
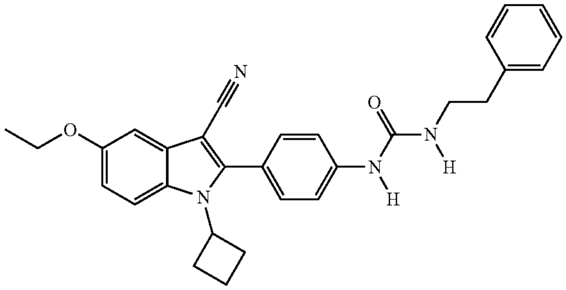
1228
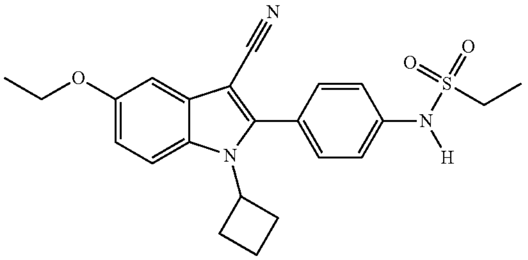
1229
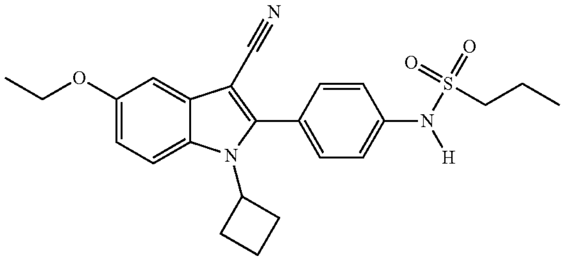
1230
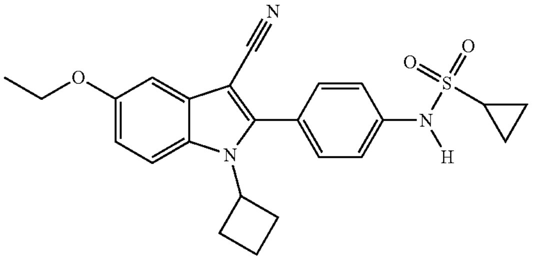
1231
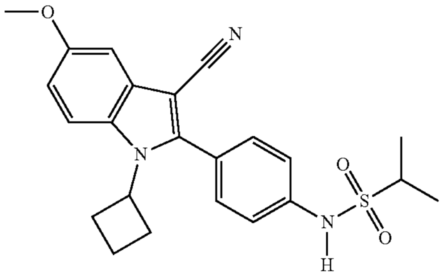
1232
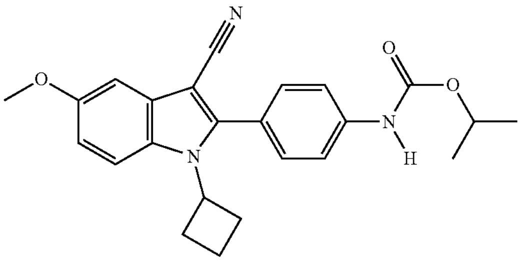
1233
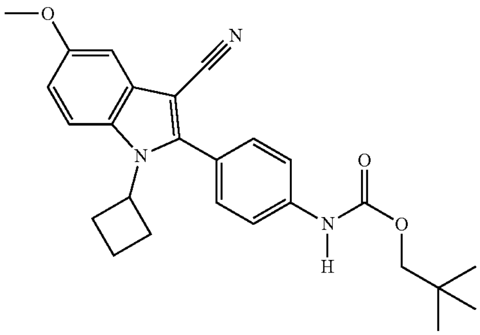
1234
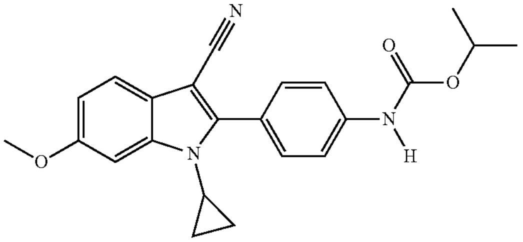
1235
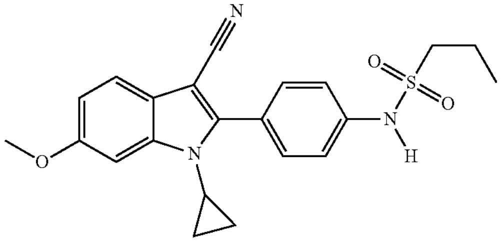

-continued
1236
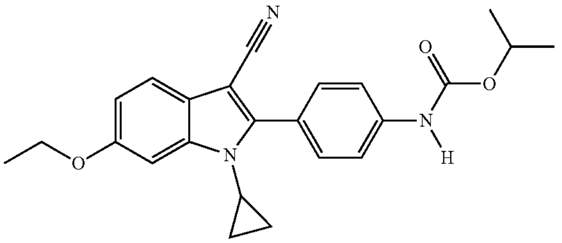
1237
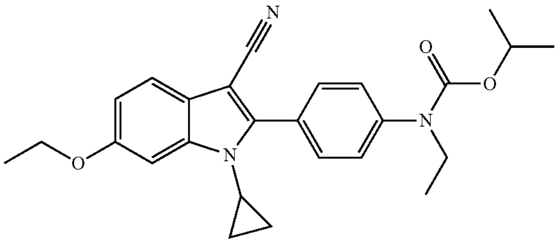
1238
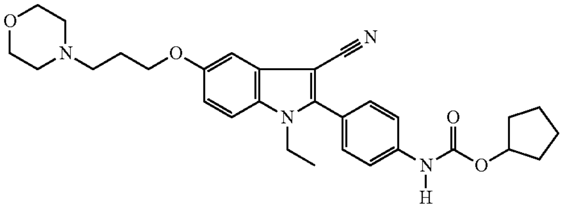
1239
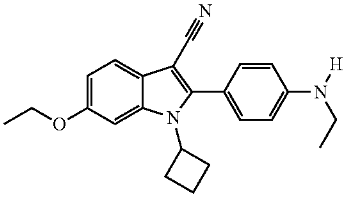
1240
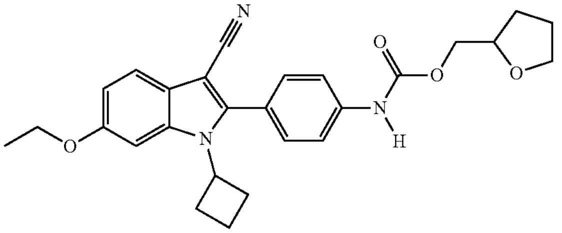
1241
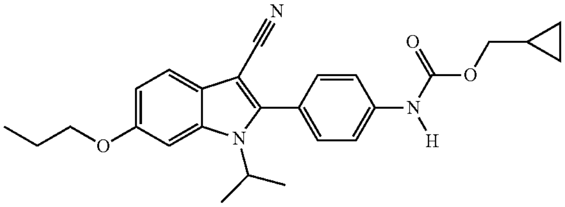
1242
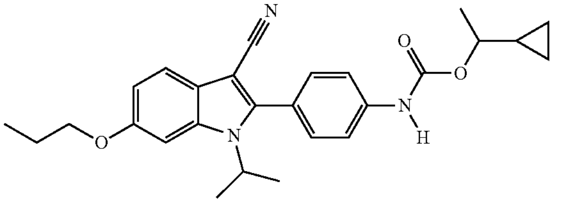
1243
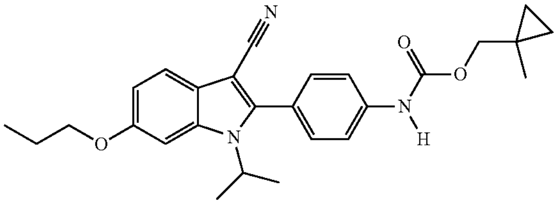
1244
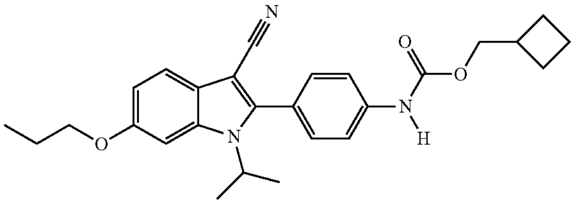
1245
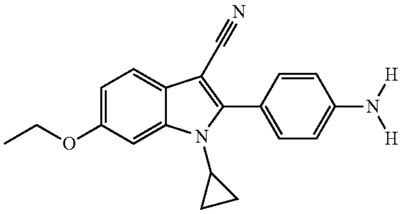
1246
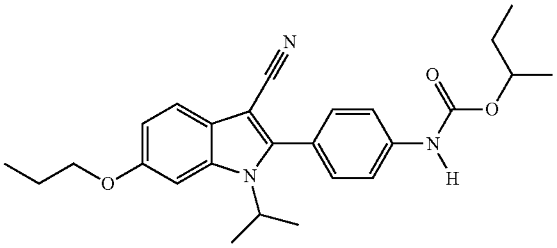
1247
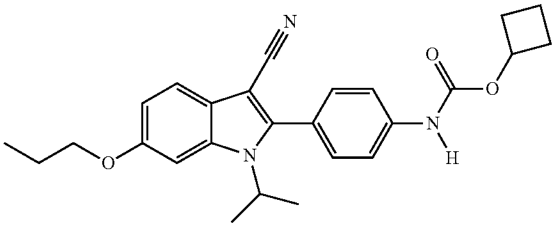

-continued
1248
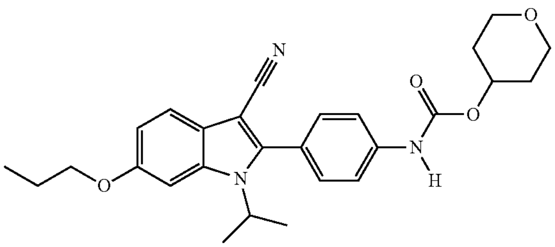
1249
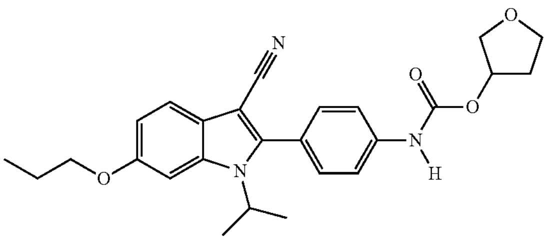
1250
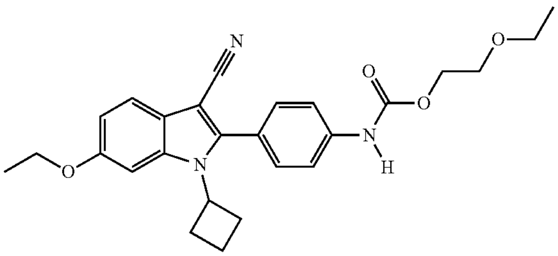
1251
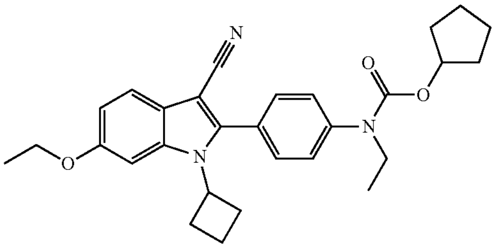
1252
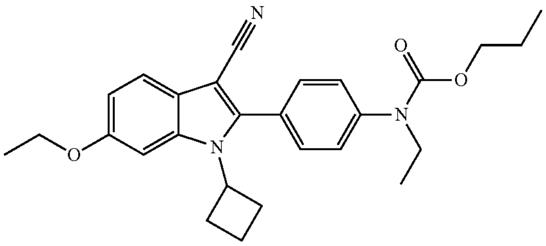
1253
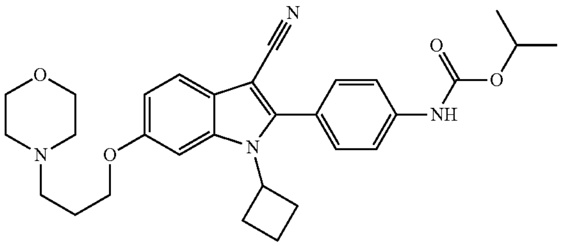
1254
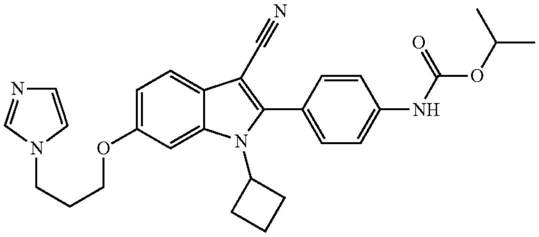
1255
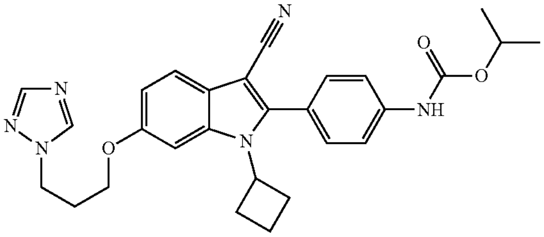
1256
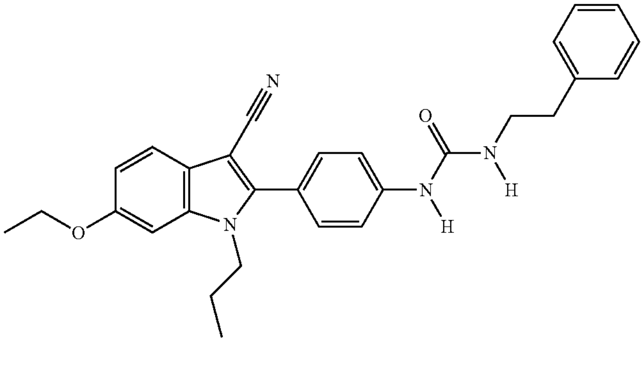

-continued
1257
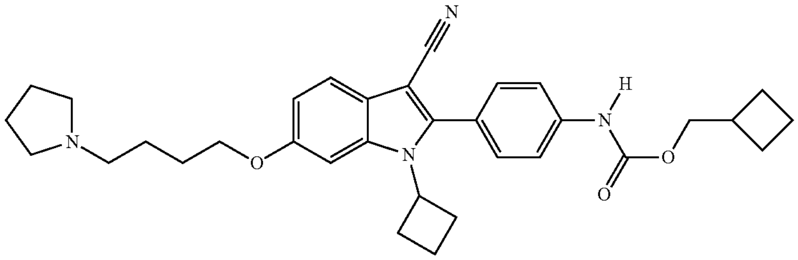
1258
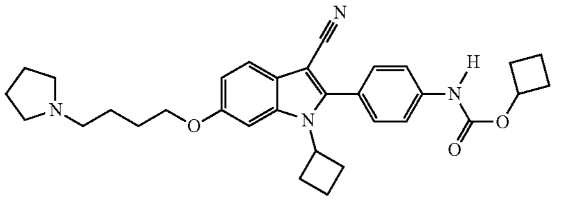
1259
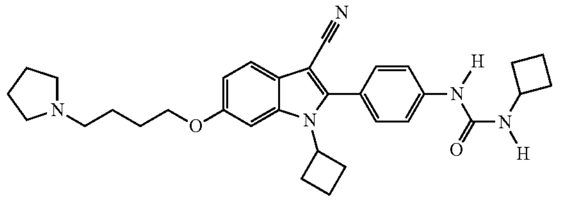
1260
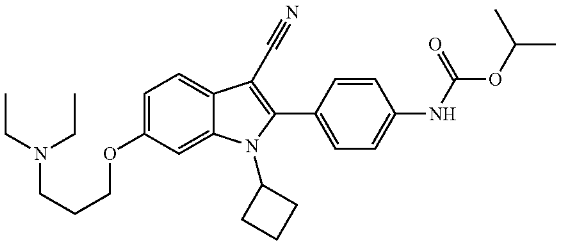
1261
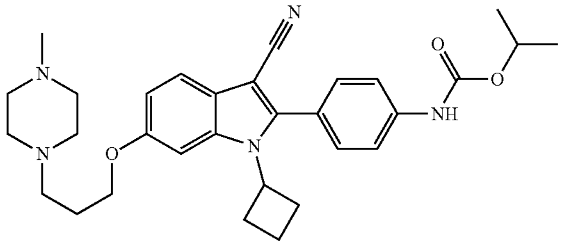
1262
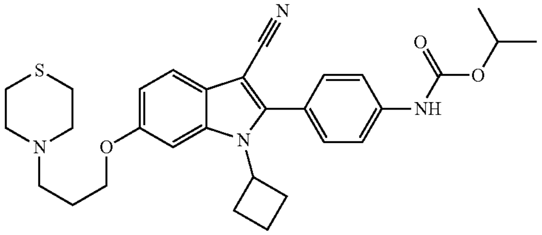
1263
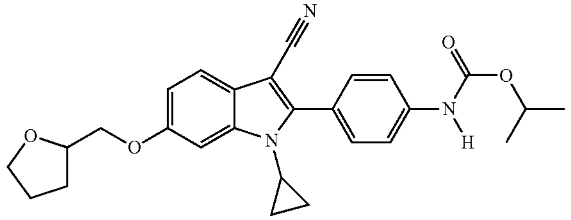
1264
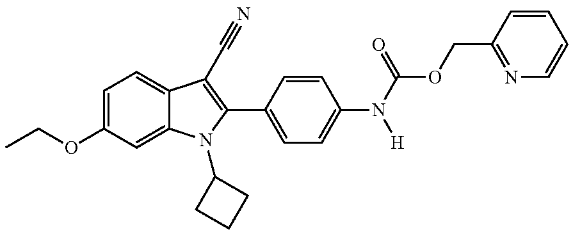
1265
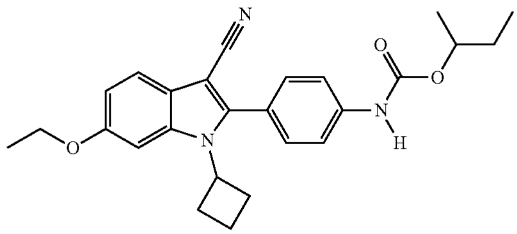
1266
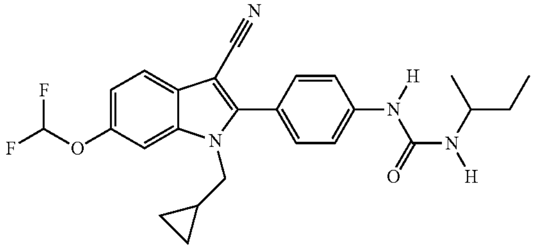
1267
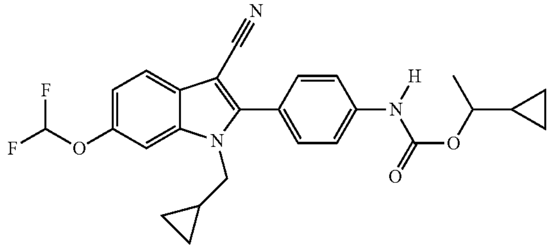

-continued
1268
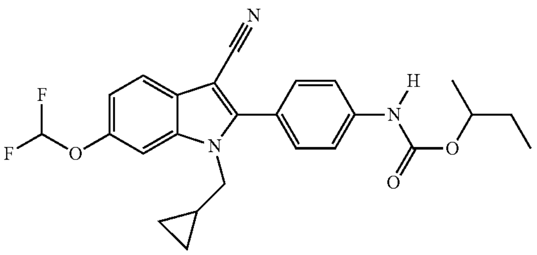
1269
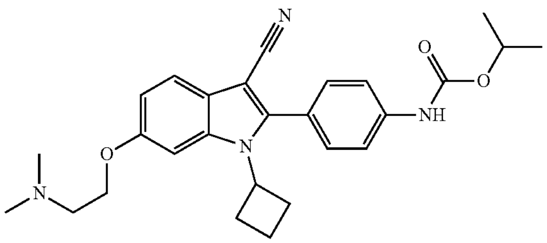
1270
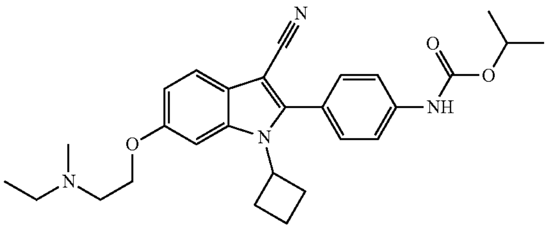
1271
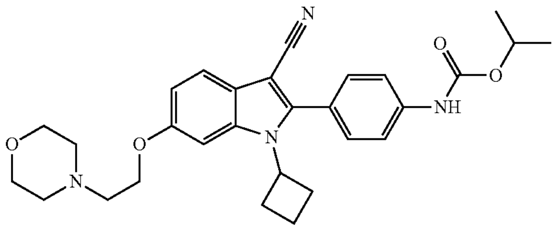
1272
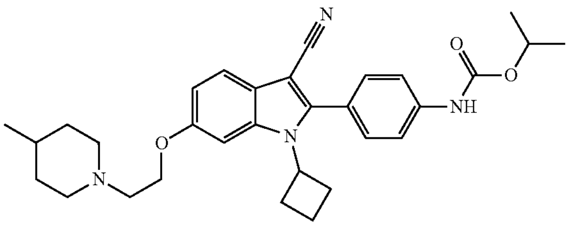
1273
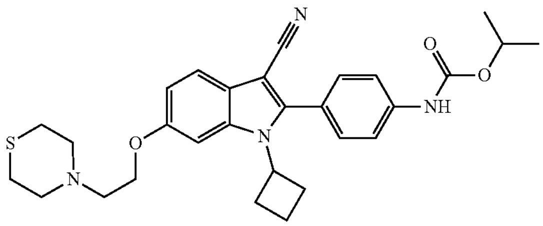
1274
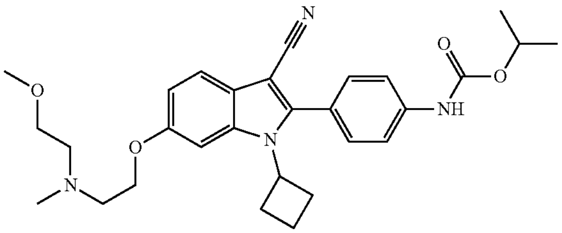
1275
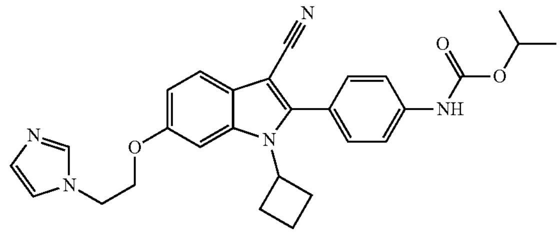
1276
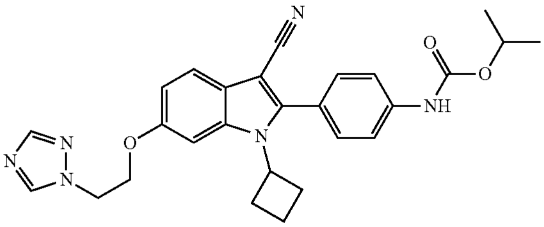
1277
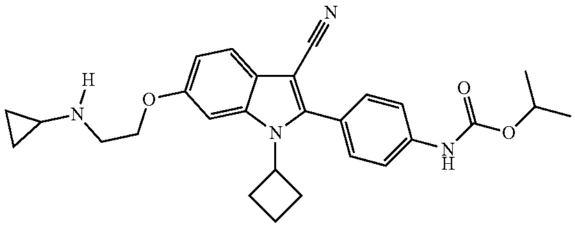
1278
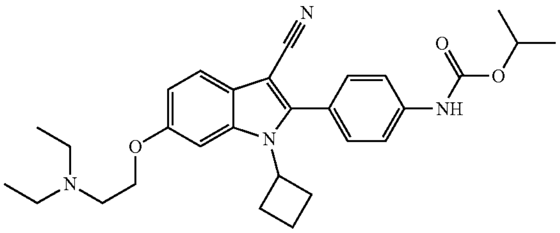
1279
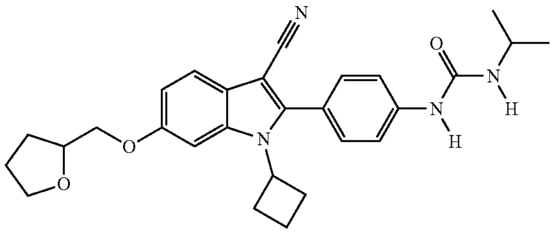

-continued
1280
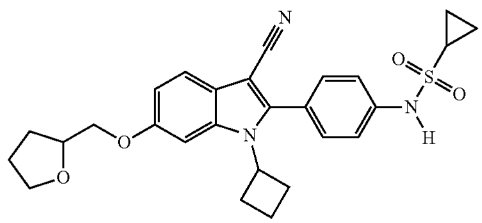
1281
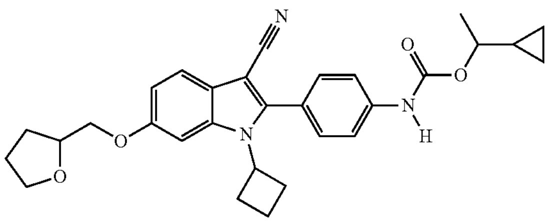
1282
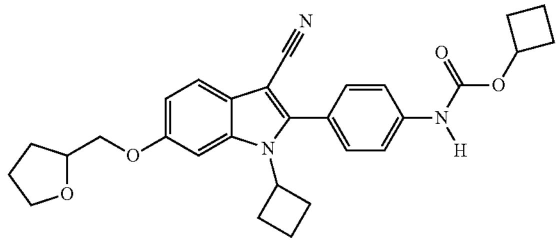
1283
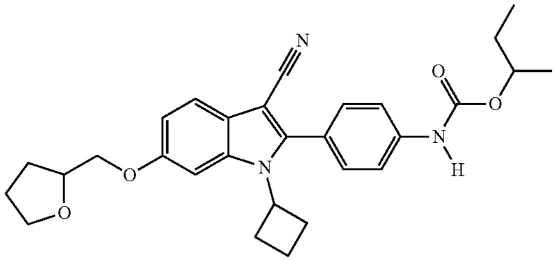
1284
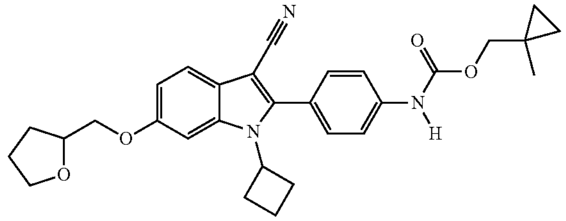
1285
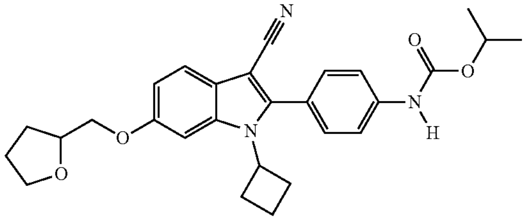
1286
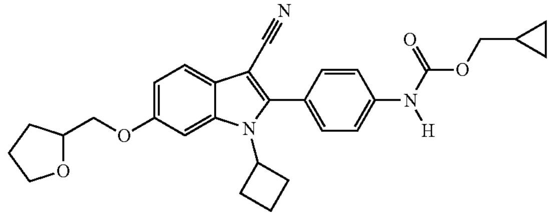
1287
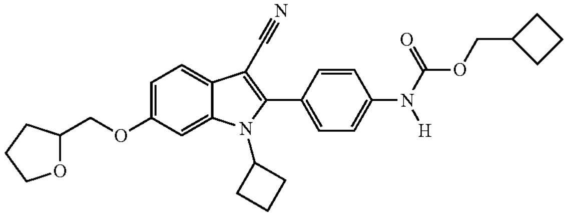
1288
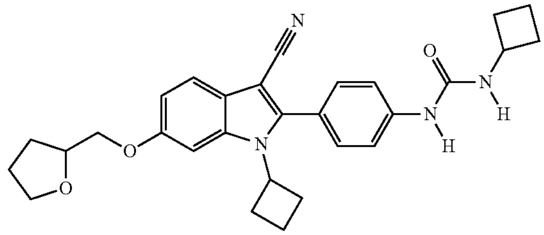
1289
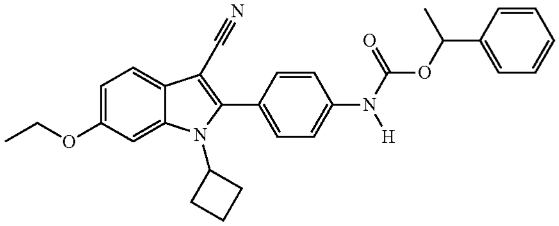
1290
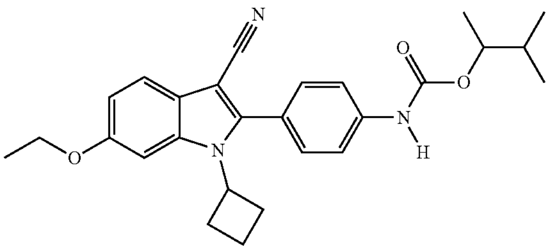
1291
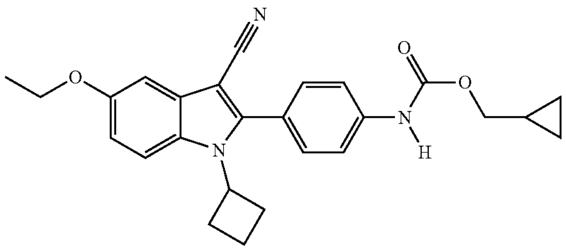

-continued
1292
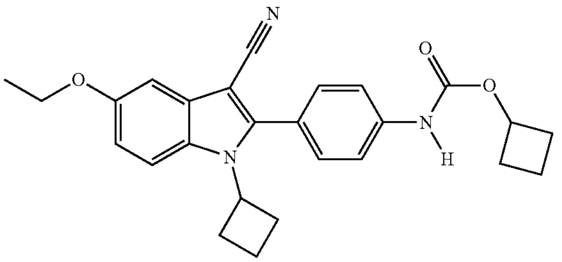
1293
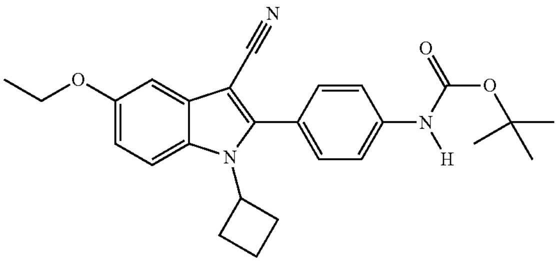
1294
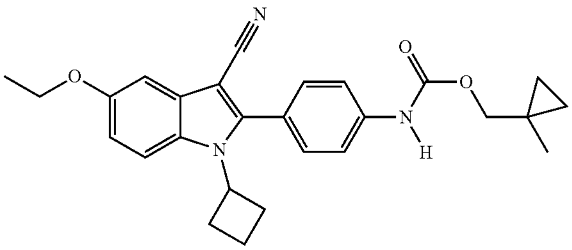
1295
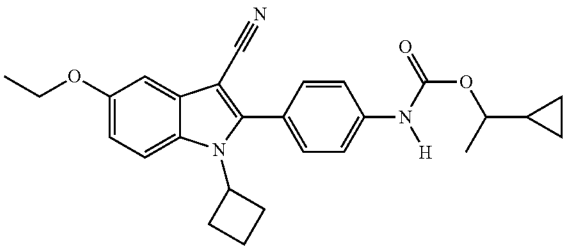
1296
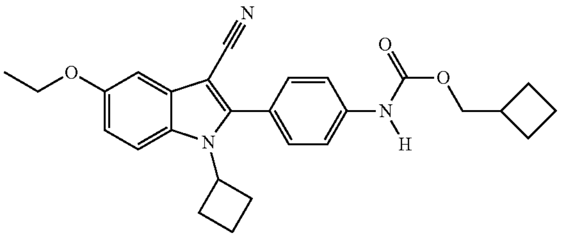
1297
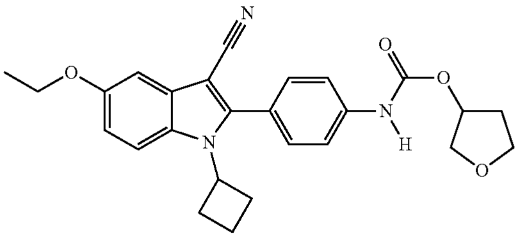
1298
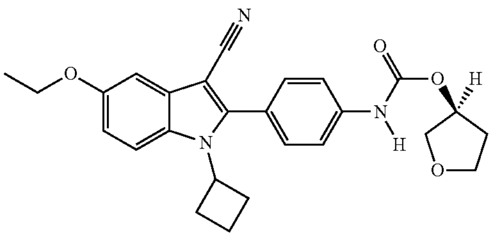
1299
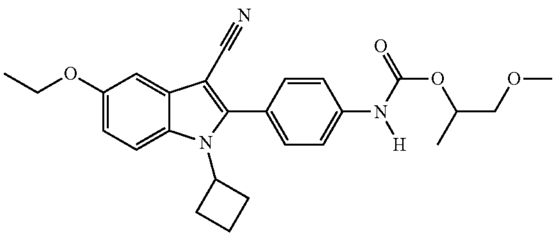
1300
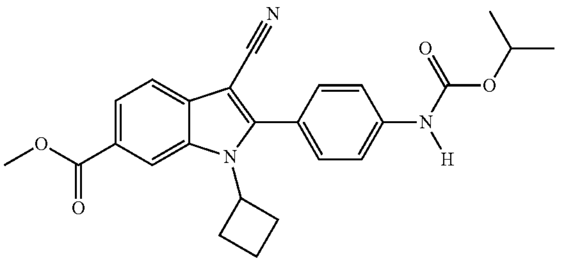
1301
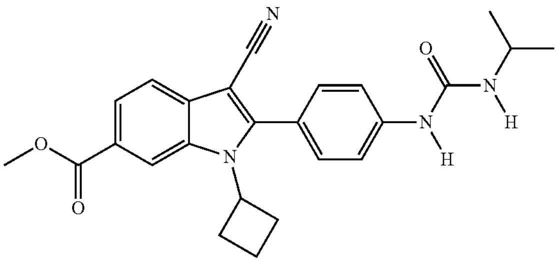
1302
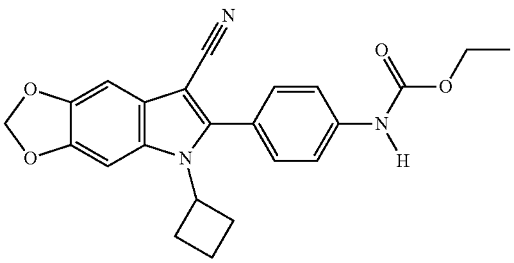
1303
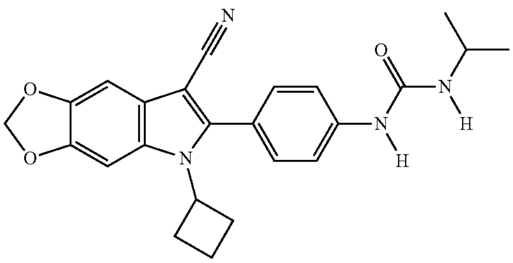

-continued
1304
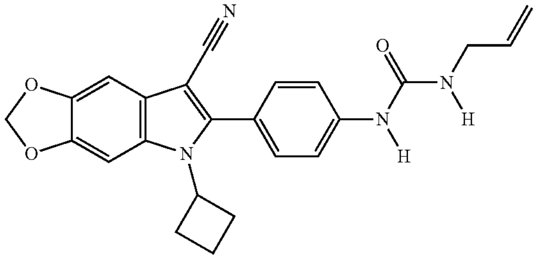
1305
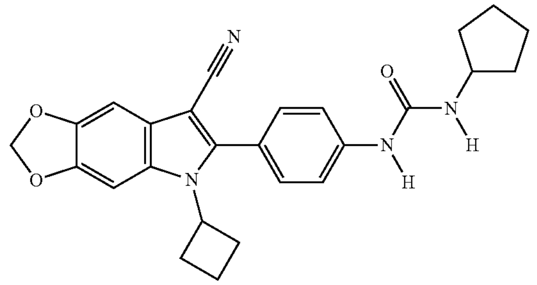
1306
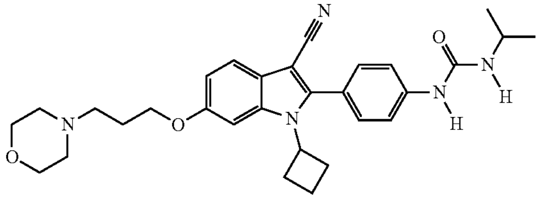
1307
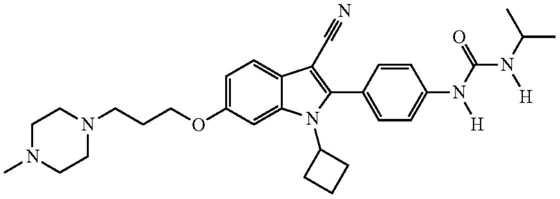
1308
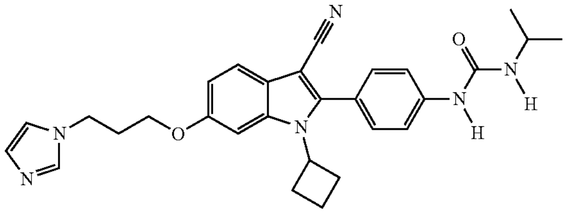
1309
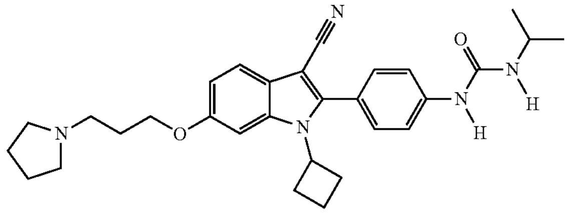
1310
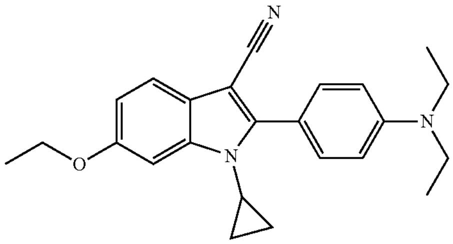
1311
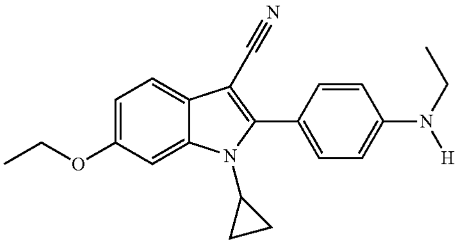
1312
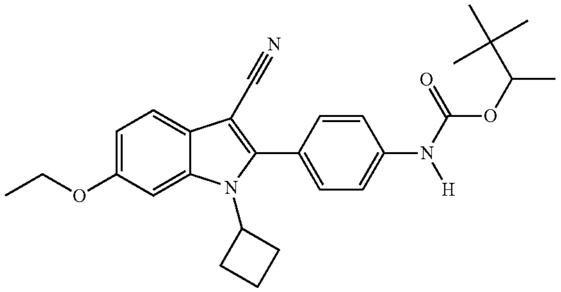
1313
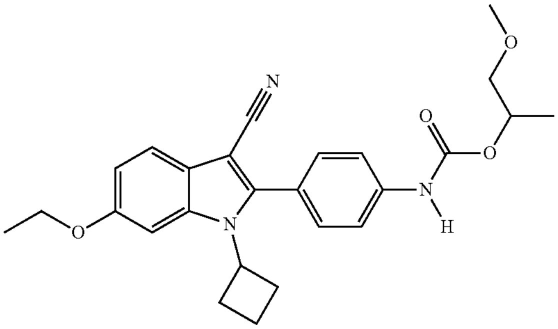
1314
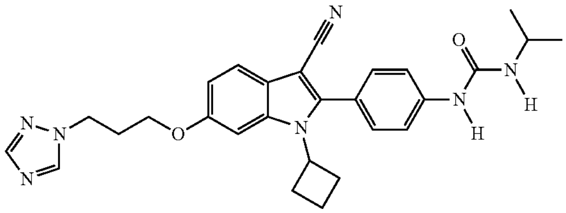
1315
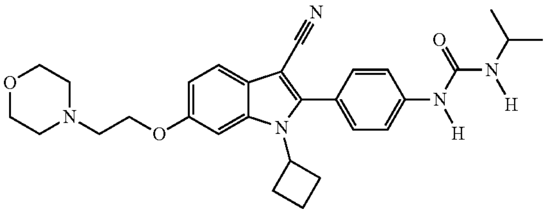

-continued
1316
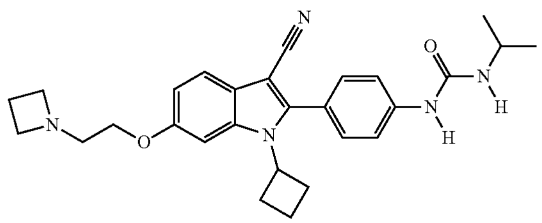
1317
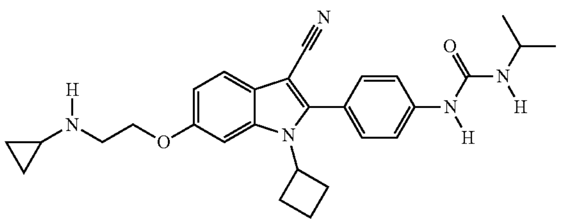
1318
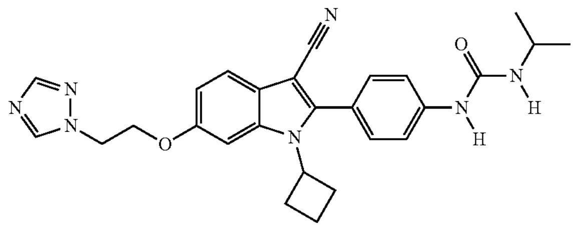
1319
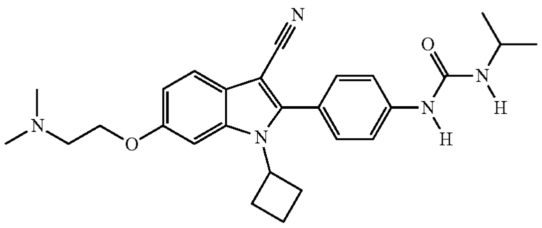
1320
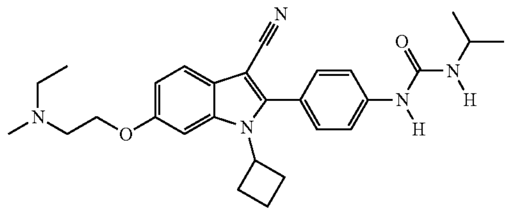
1321
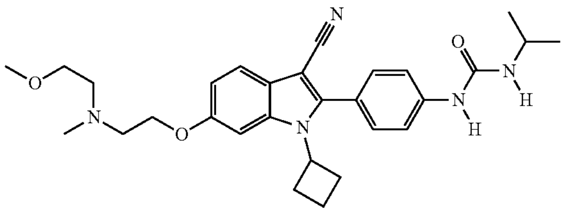
1322
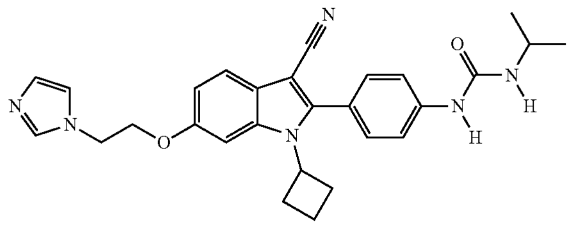
1323
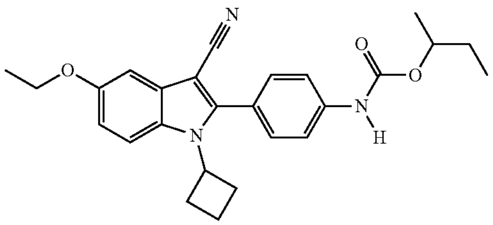
1324
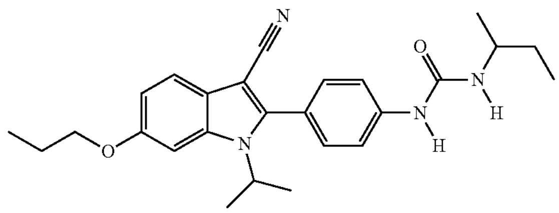
1325
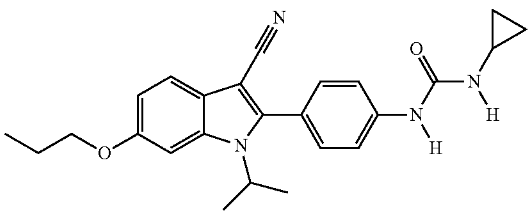
1326
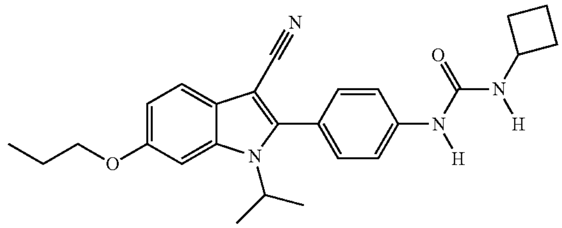
1327
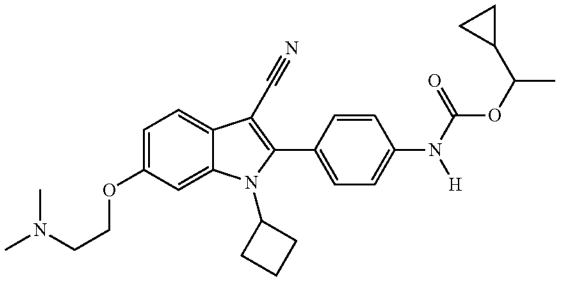

-continued
1328
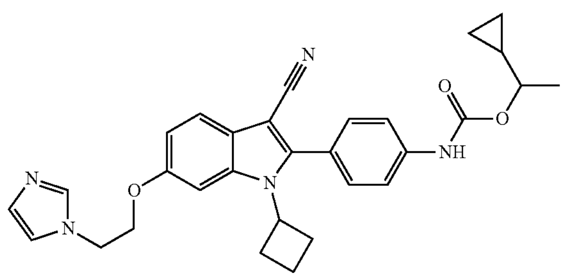
1329
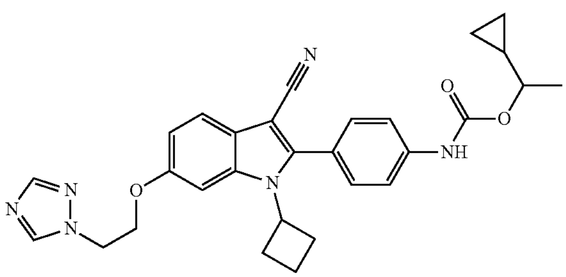
1330
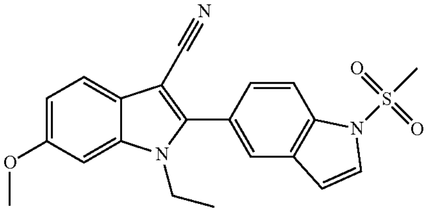
1331
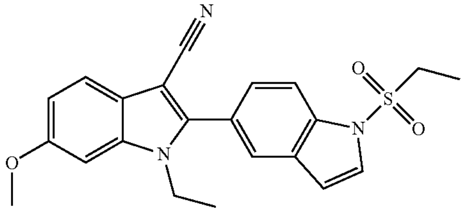
1332
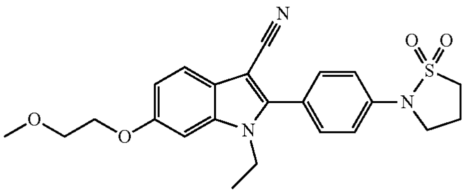
1333
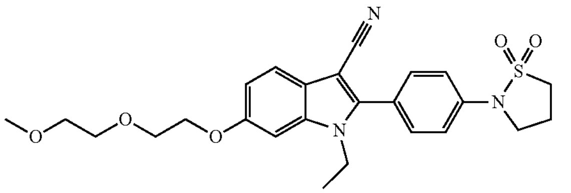
1334
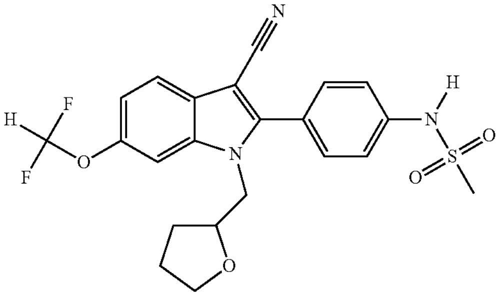
1335
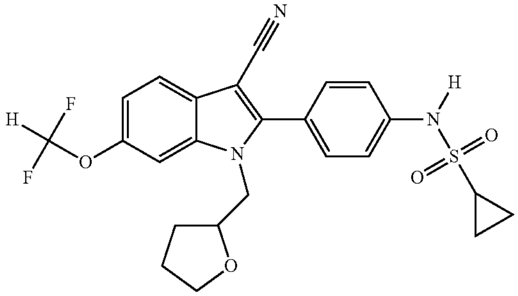
1336
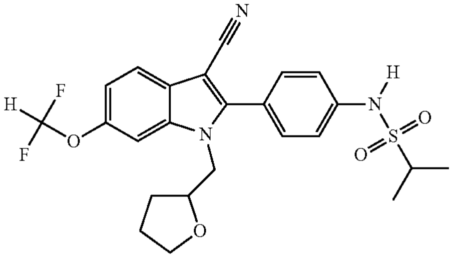
1337
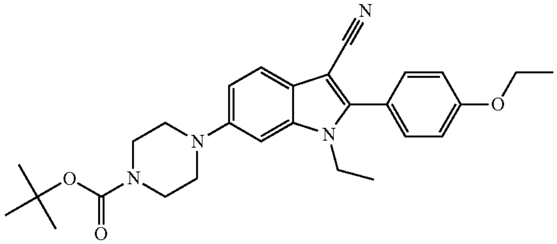
1338
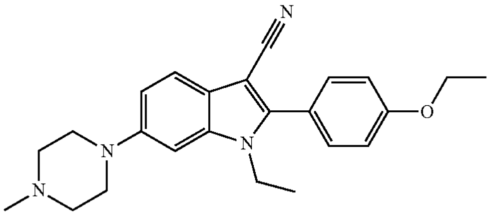
1339
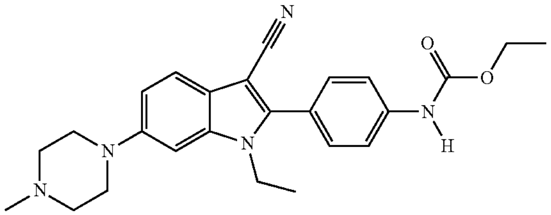

-continued
1340
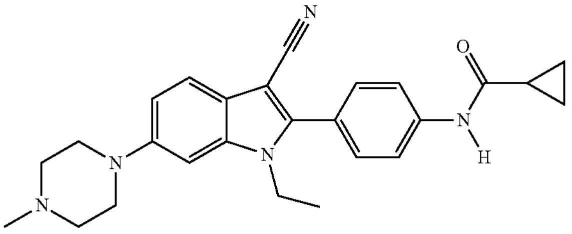
1341
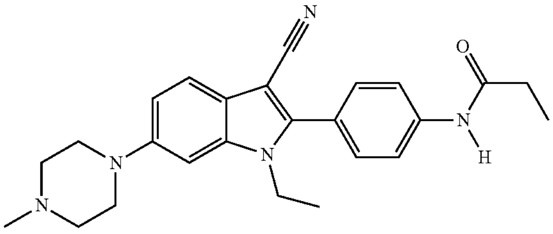
1342
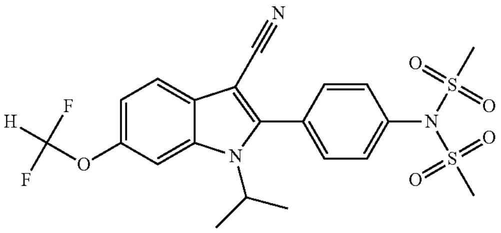
1343
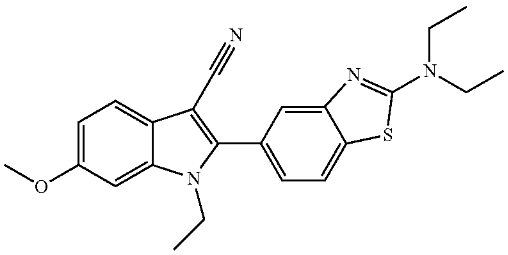
1344
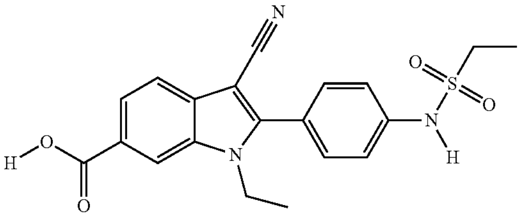
1345
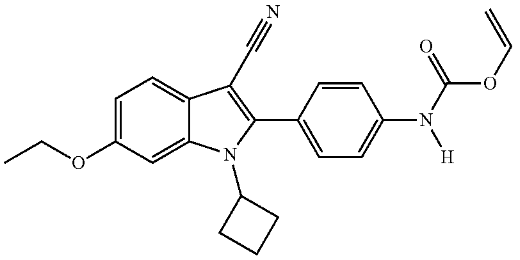
1346
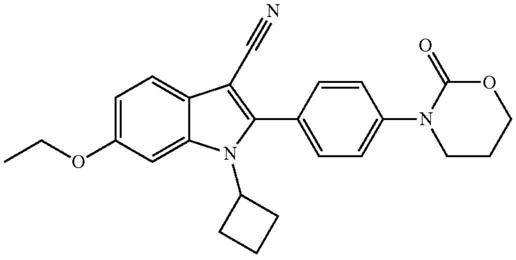
1347
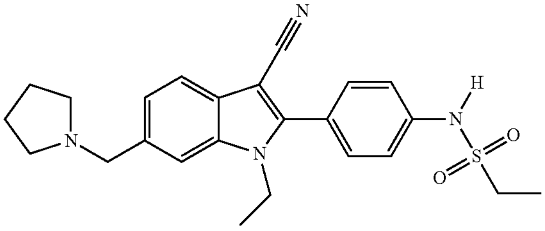
1348
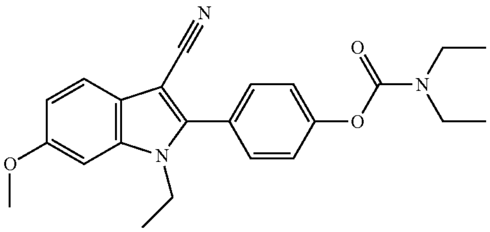
1349
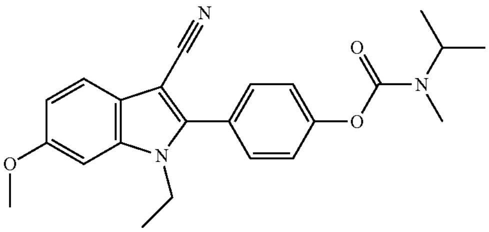
1350
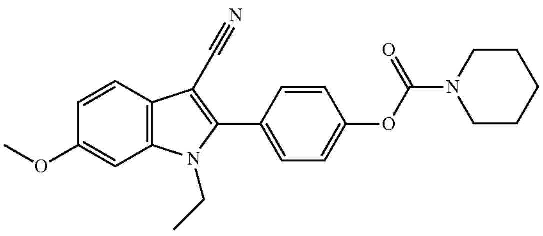
1351
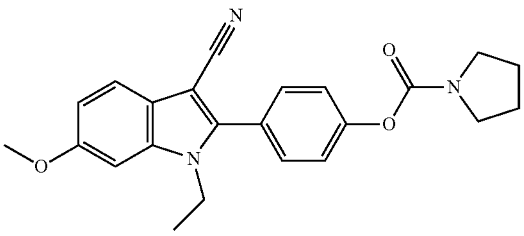

-continued
1352
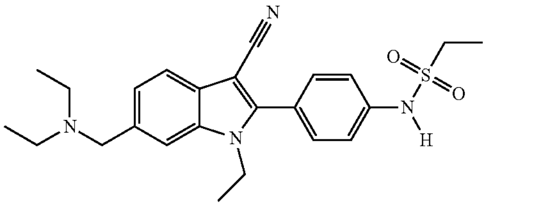
1353
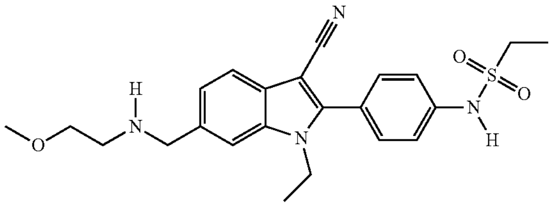
1354
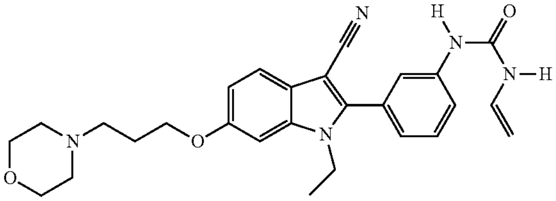
1355
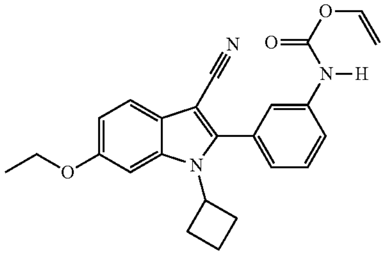
1356
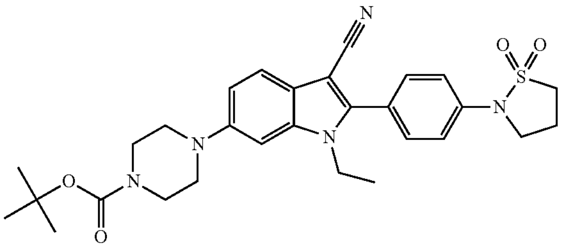
1357
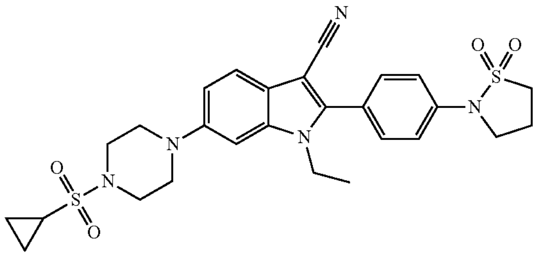
1358
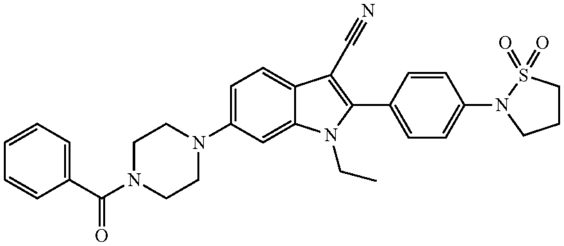
1359
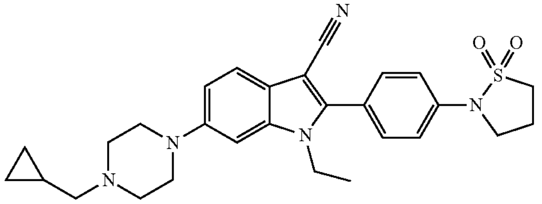
1360
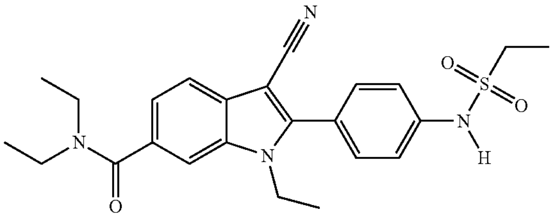
1361
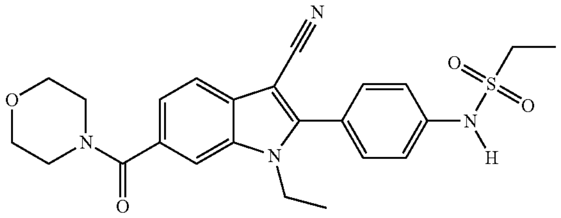
1362
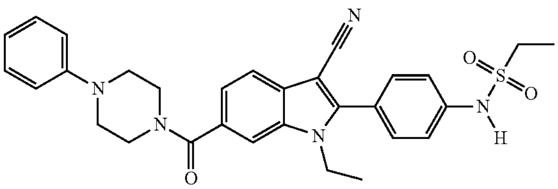
1363
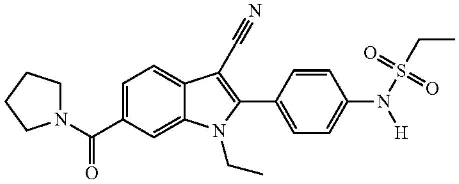

-continued
1364
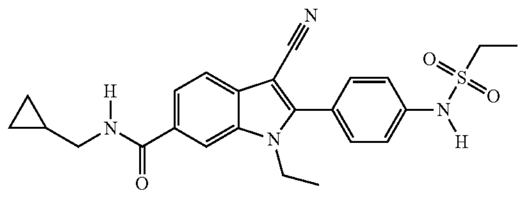
1365
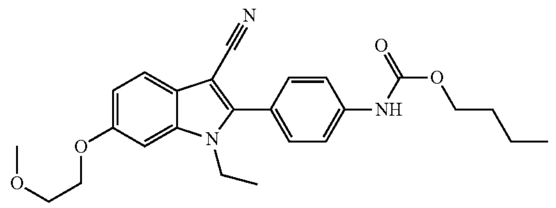
1366
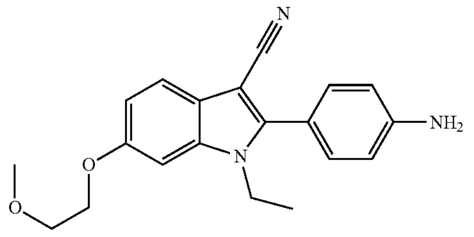
1367
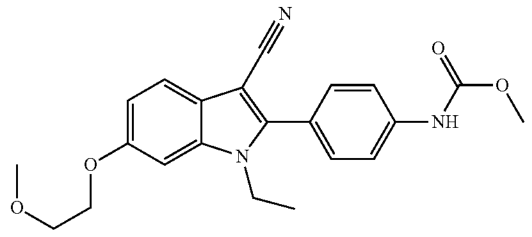
1368
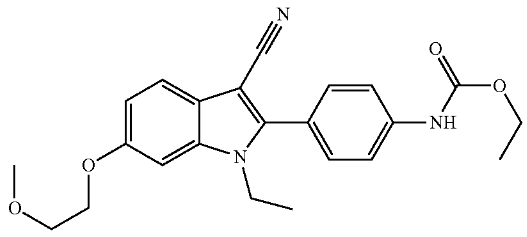
1369
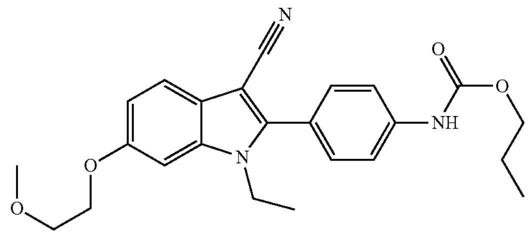
1370
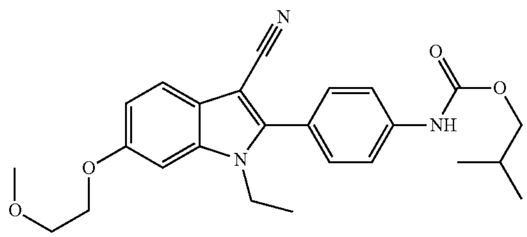
1371
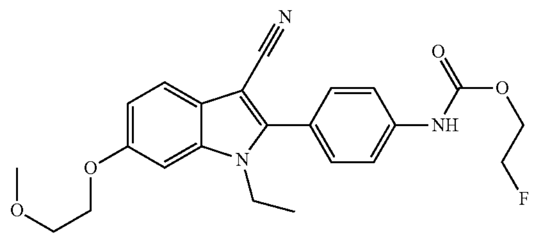
1372
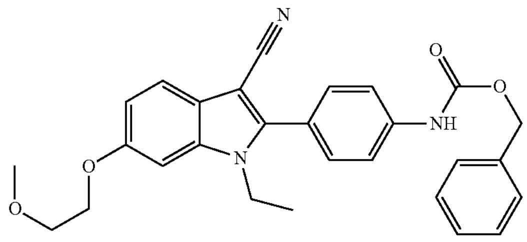
1373
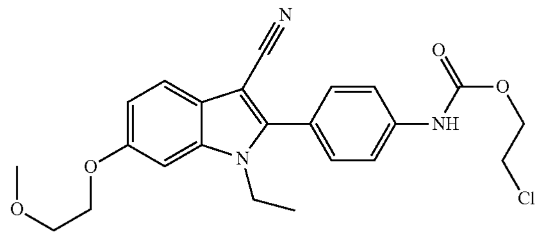
1374
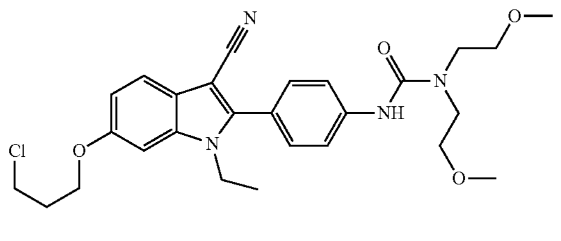
1375
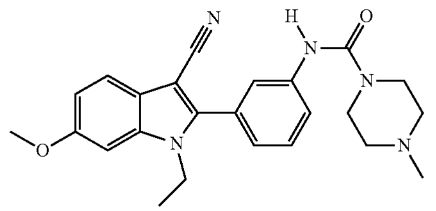

-continued
1376
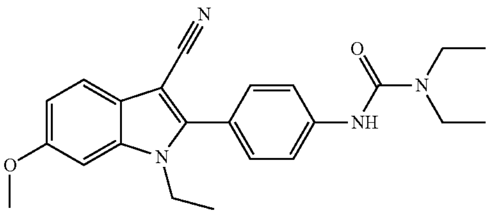
1377
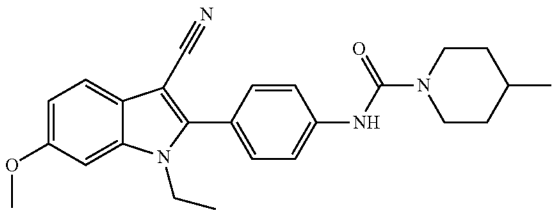
1378
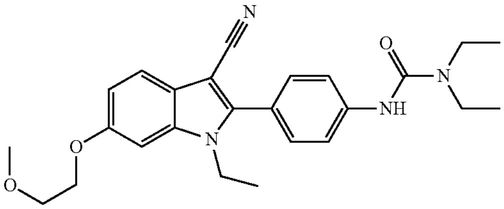
1379
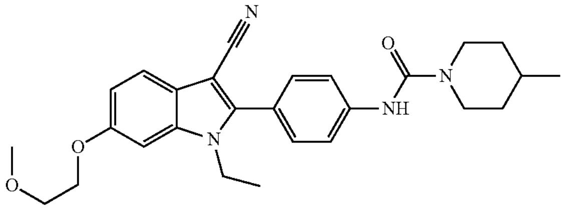
1380
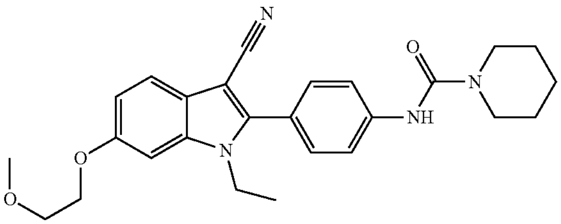
1381
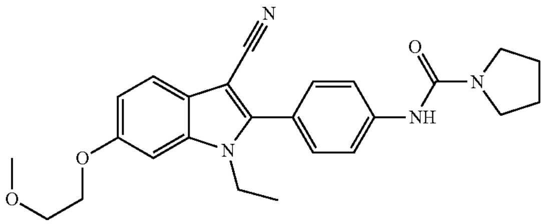
1382
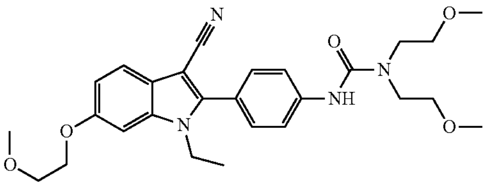
1383
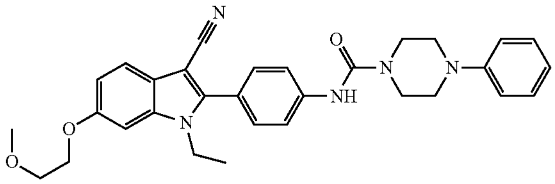
1384
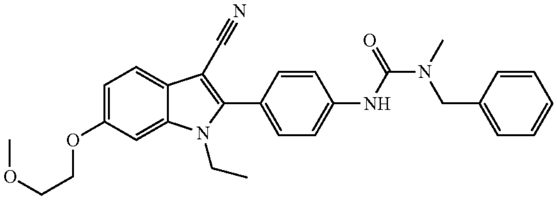
1385
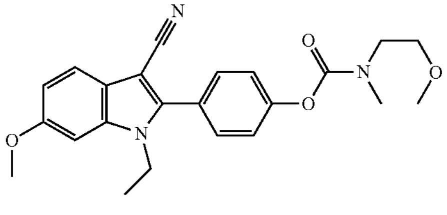
1386
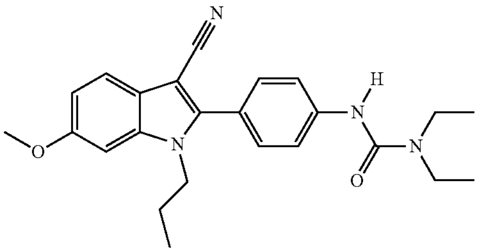
1387
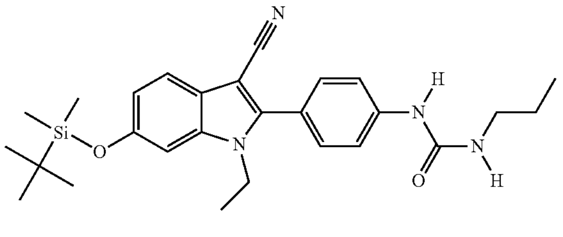

-continued
1388
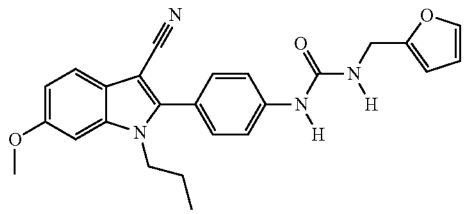
1389
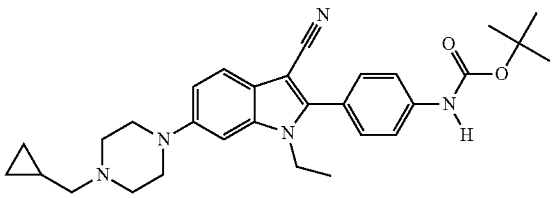
1390
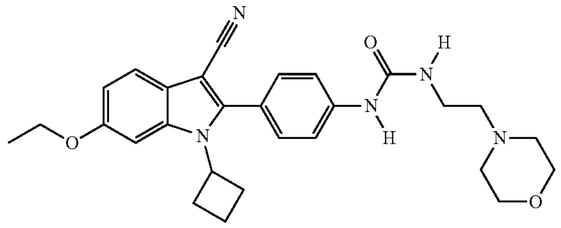
1391
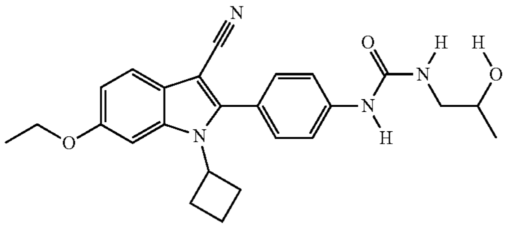
1392
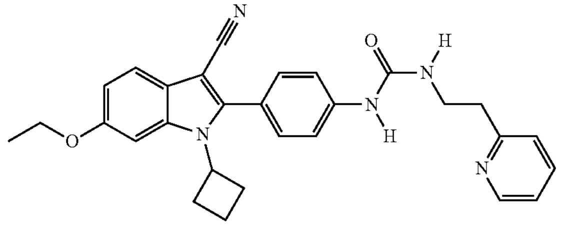
1393
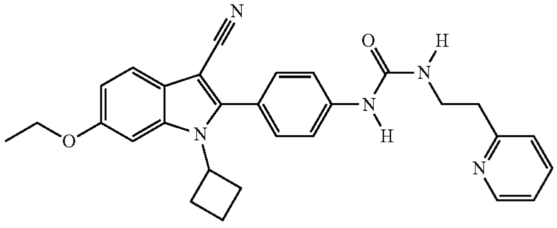
1394
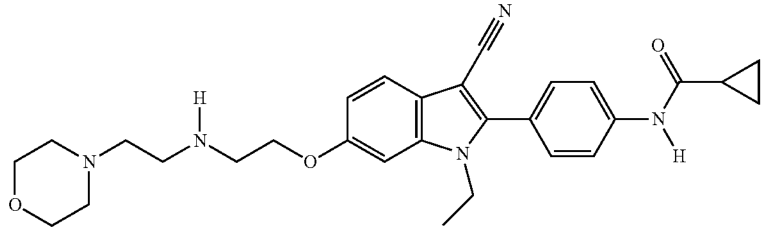
1395
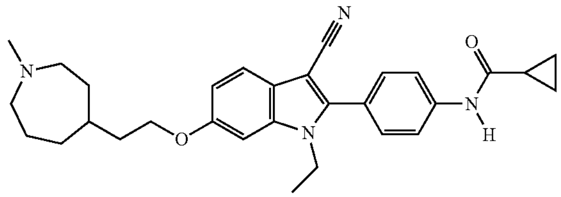
1396
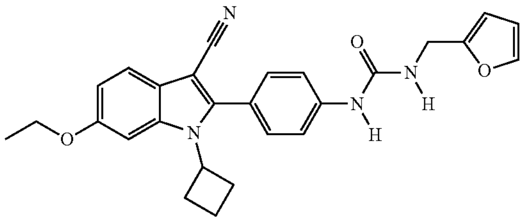
1397
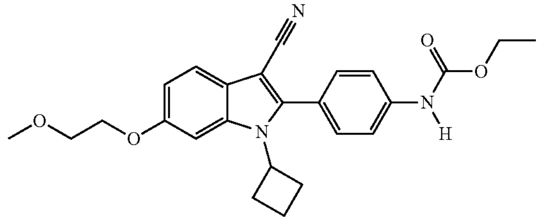
1398
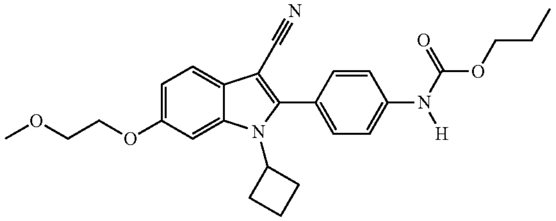

-continued
1399
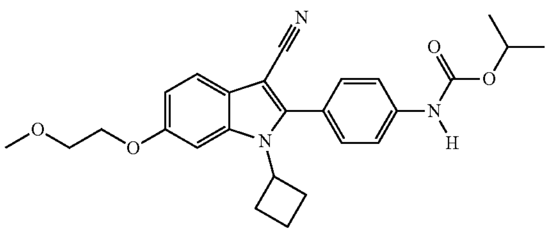
1400
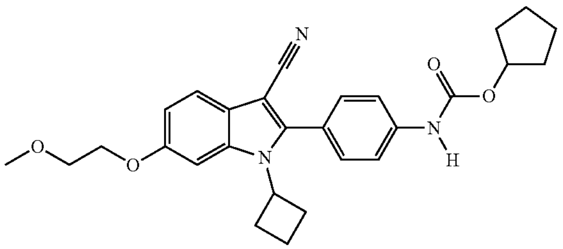
1401
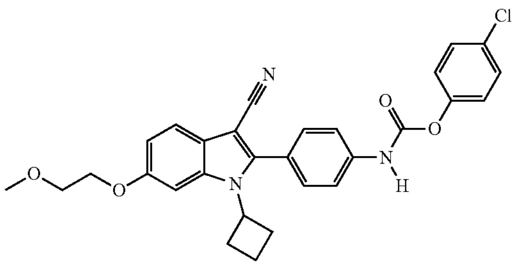
1402
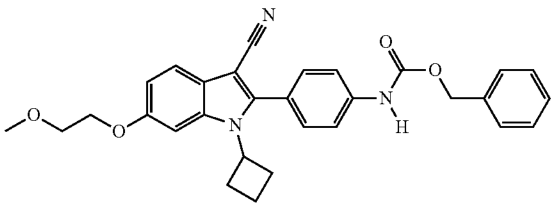
1403
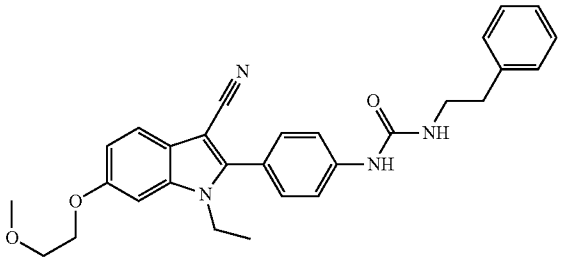
1404
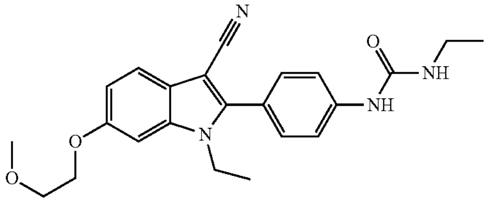
1405
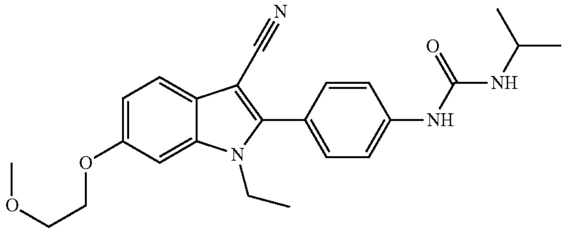
1406
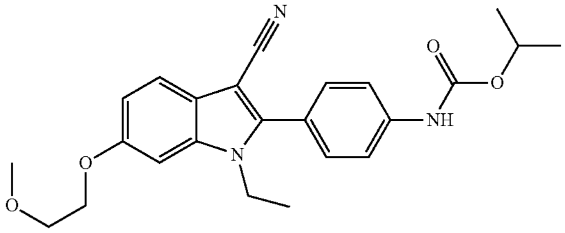
1407
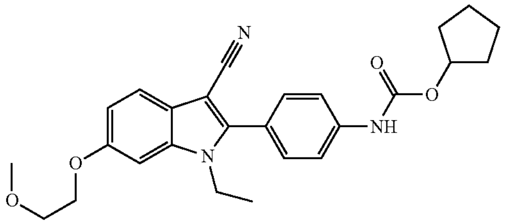
1408
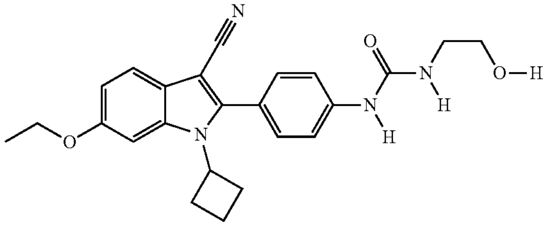
1409
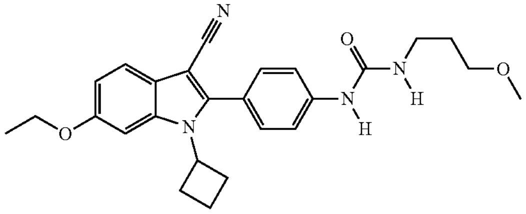
1410
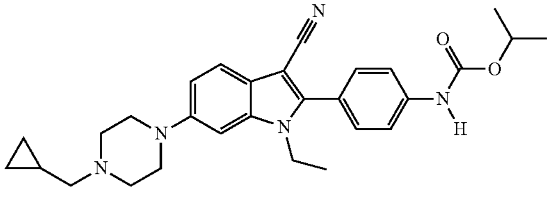

-continued
1411
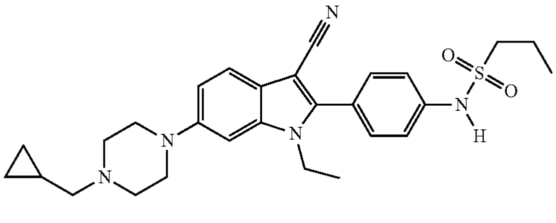
1412
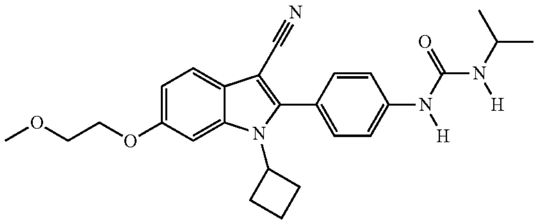
1413
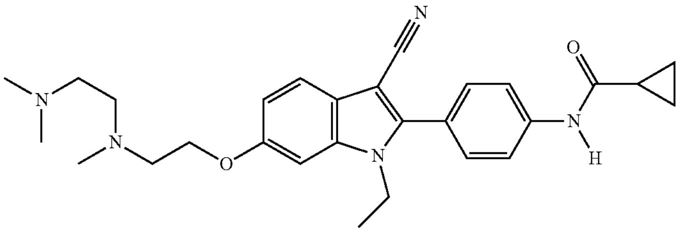
1414
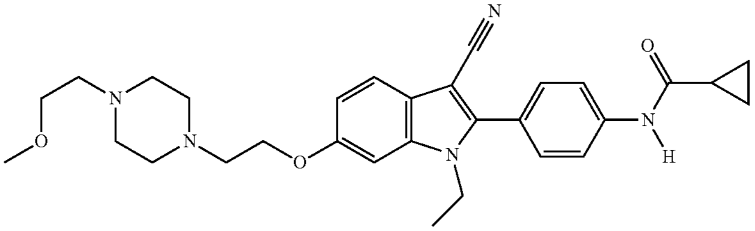
1415
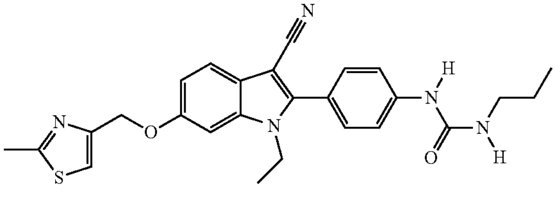
1416
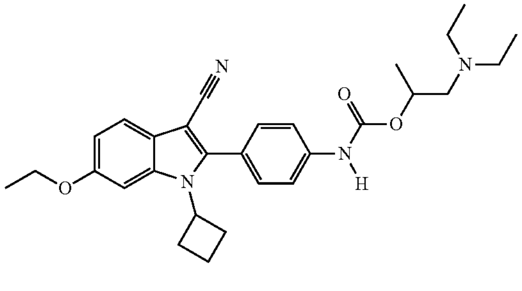
1417
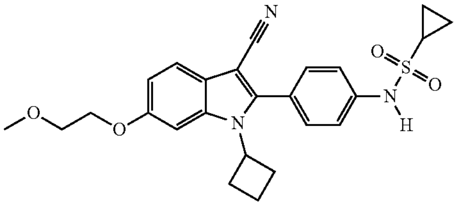
1418
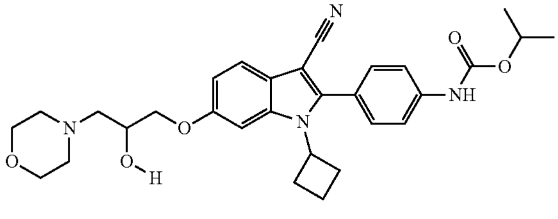
1419
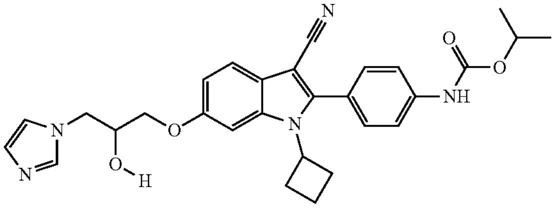
1420
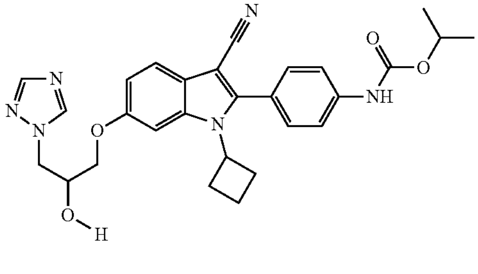

-continued
1421
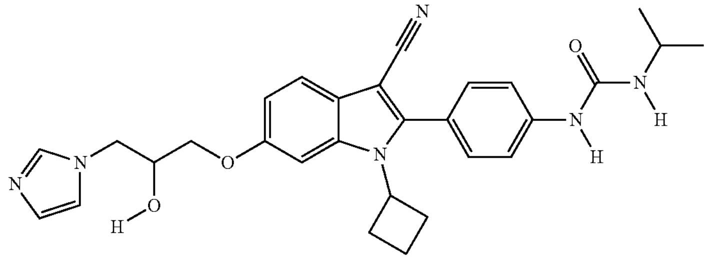
1422
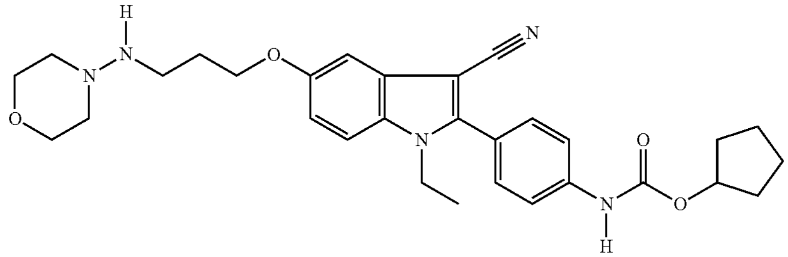
1423
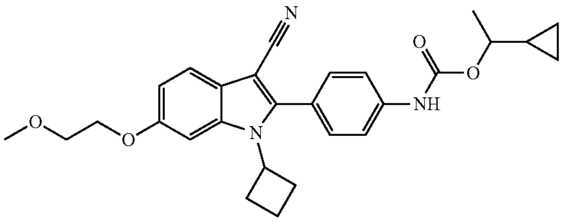
1424
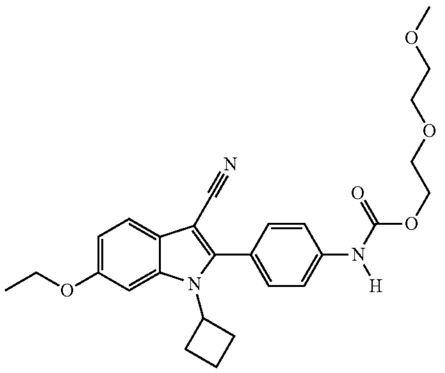
1425
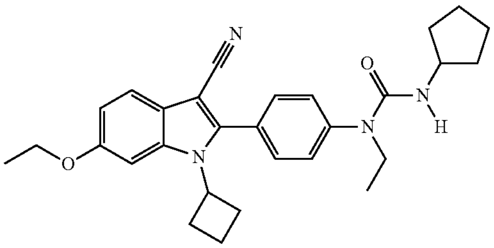
1426
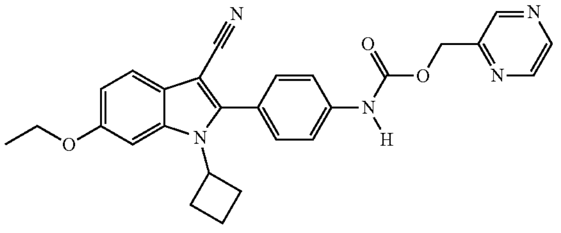
1427
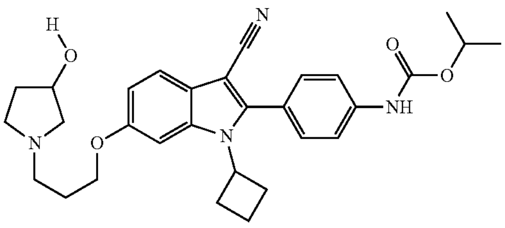
1428
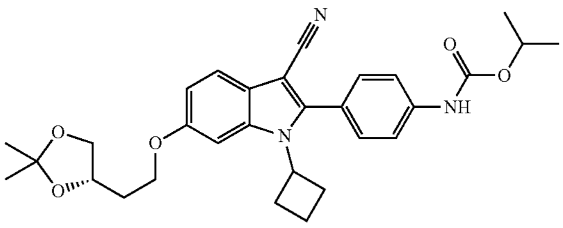

-continued
1429
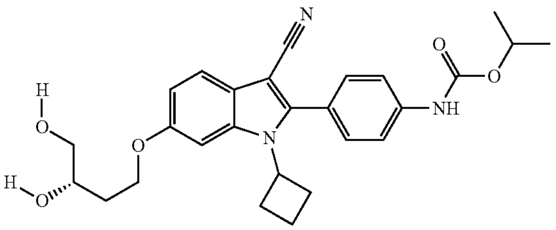
1430
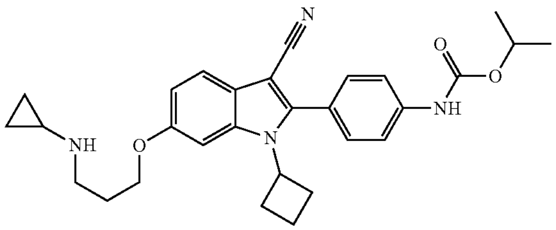
1431
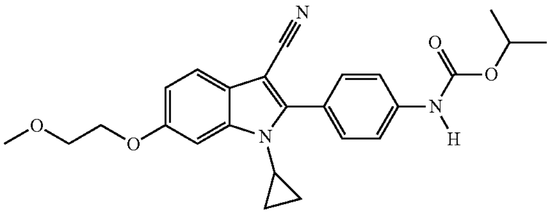
1432
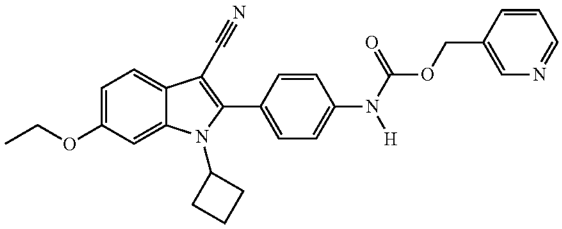
1433
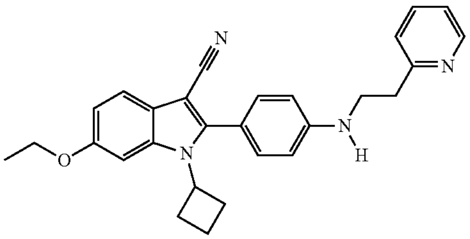
1434
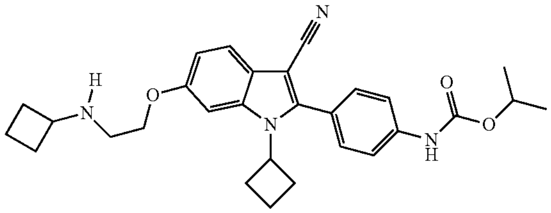
1435
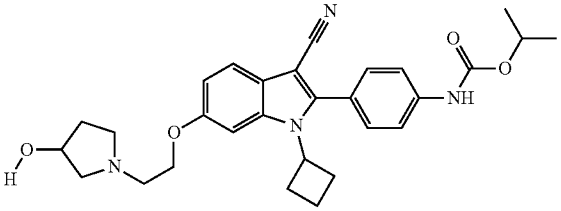
1436
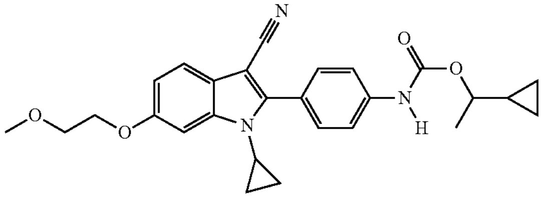
1437
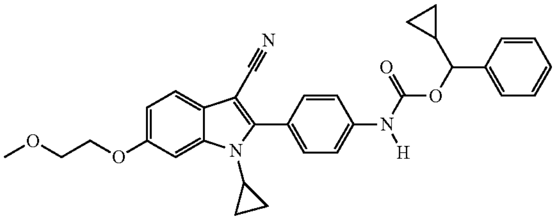
1438
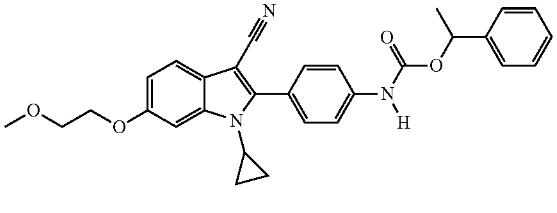
1439
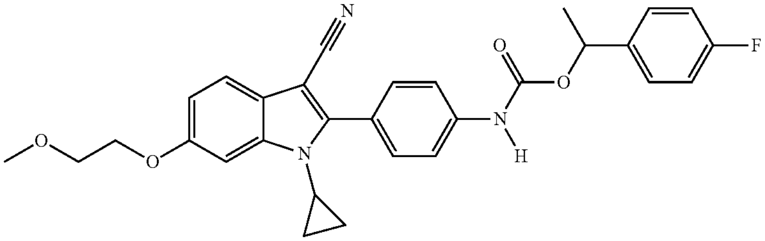

-continued
1440
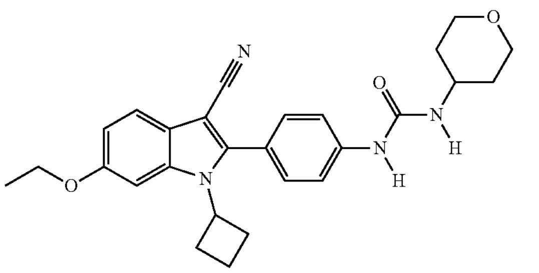
1441
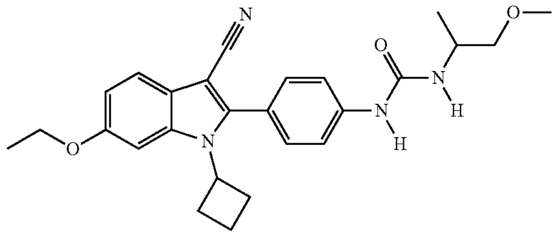
1442
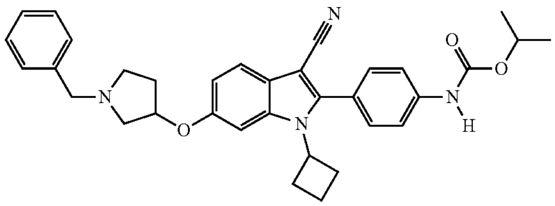
1443
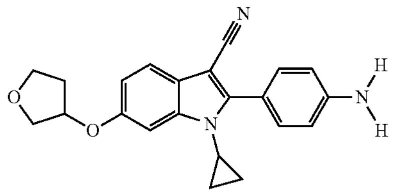
1444
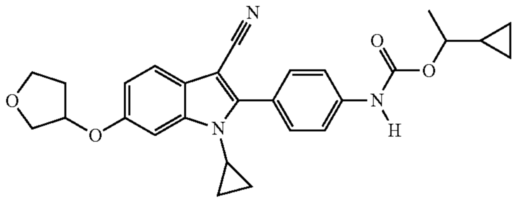
1445
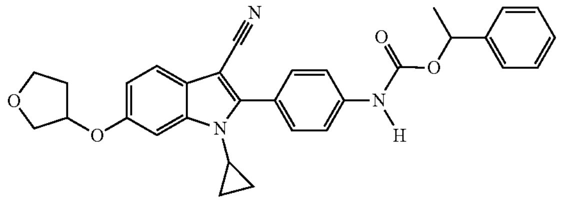
1446
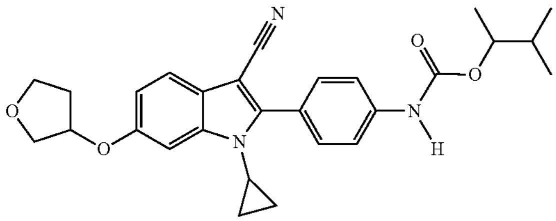
1447
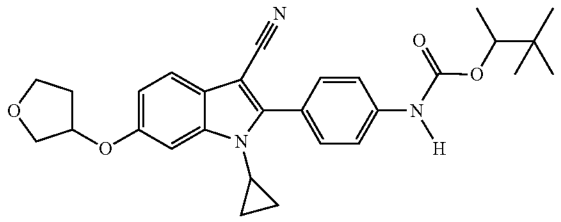
1448
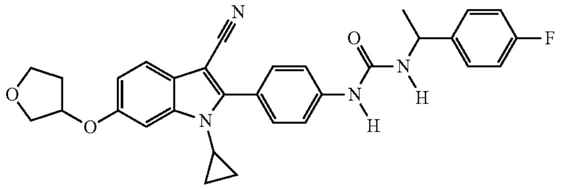
1449
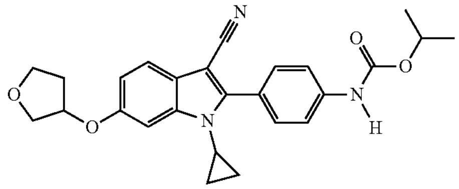
1450
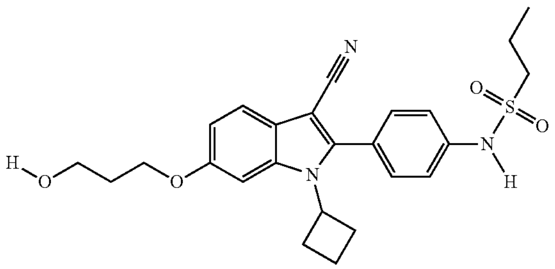
1451
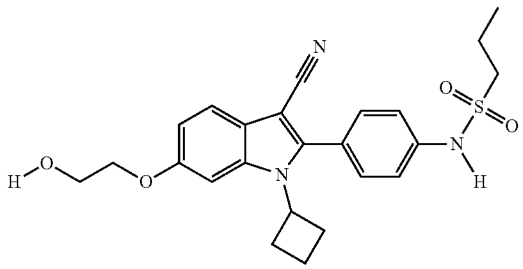

-continued
1452
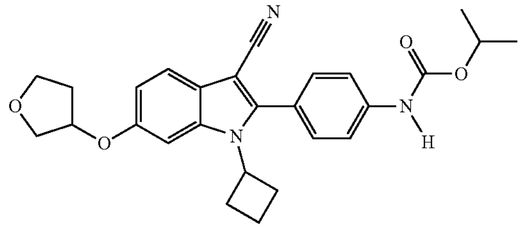
1453
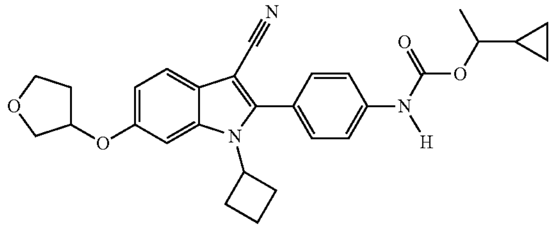
1454
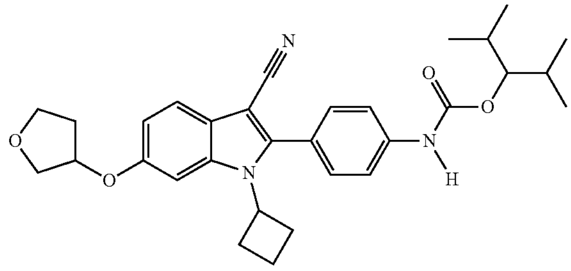
1455
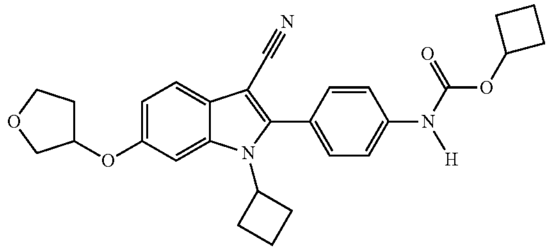
1456
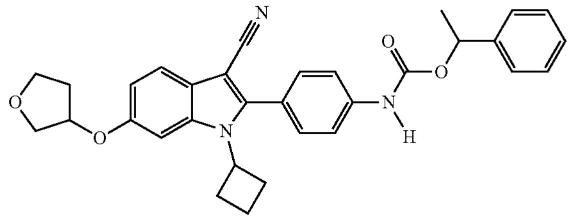
1457
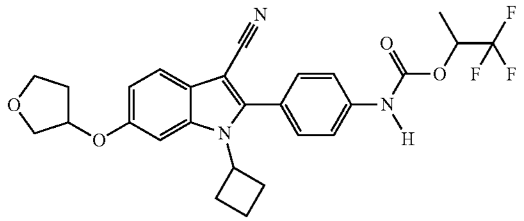
1458
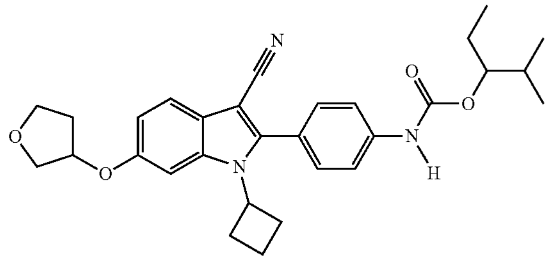
1459
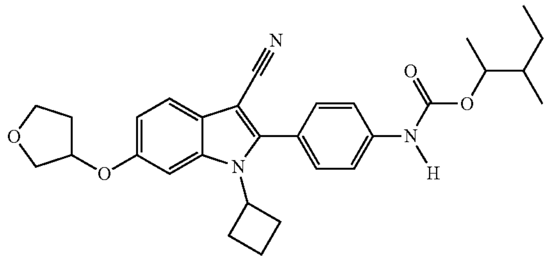
1460
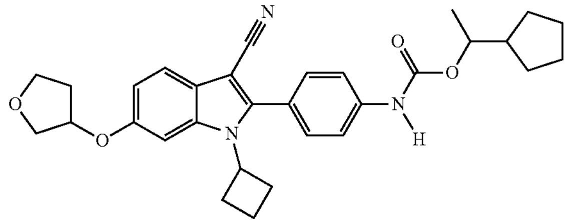
1461
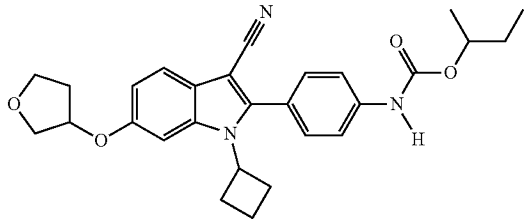
1462
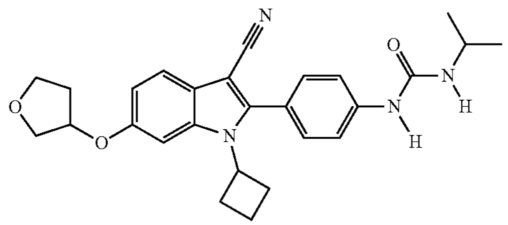
1463
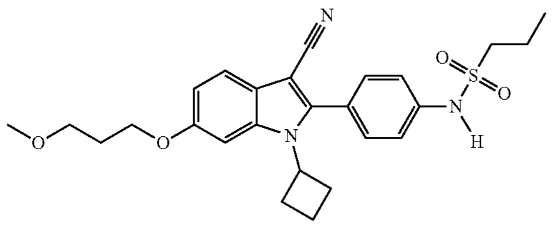

-continued

1464

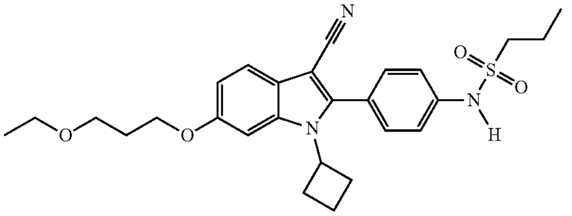

1465

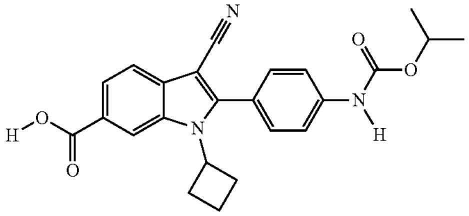

1466

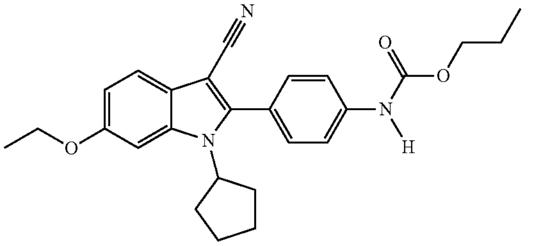

1467

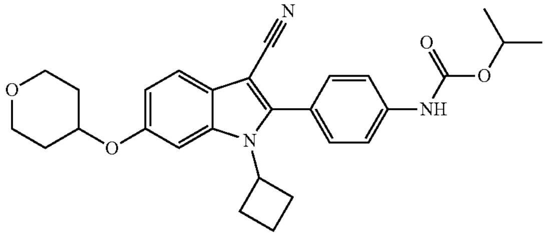

1468

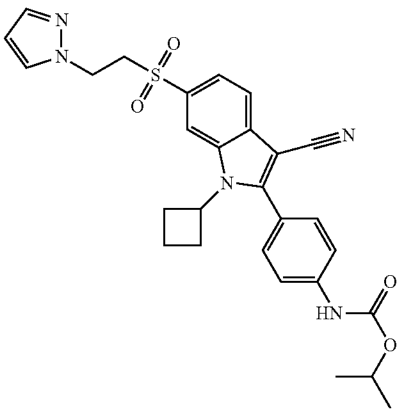

1469

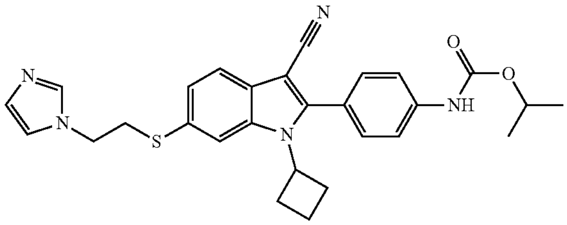

or an enantiomer, stereoisomer, diastereomer, racemic, tautomeric, ester, prodrug, solvate, hydrate, isotopologue or salt form thereof. Such compounds and pharmaceutically acceptable salts thereof were disclosed in U.S. patent application Ser. No. 11/653,450 and U.S. patent application Ser. No. 11/653,448).

In one embodiment, a HCV protease inhibitor or an enantiomer, stereoisomer, diastereomer, racemic, tautomeric, ester, prodrug, solvate, hydrate, isotopologue or salt form thereof is selected from:

Cpd 1p

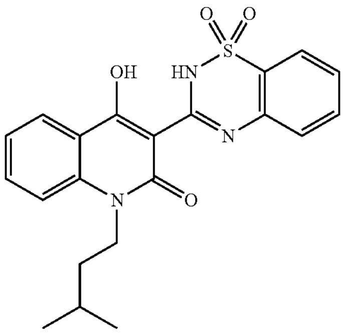

-continued

Cpd 2p

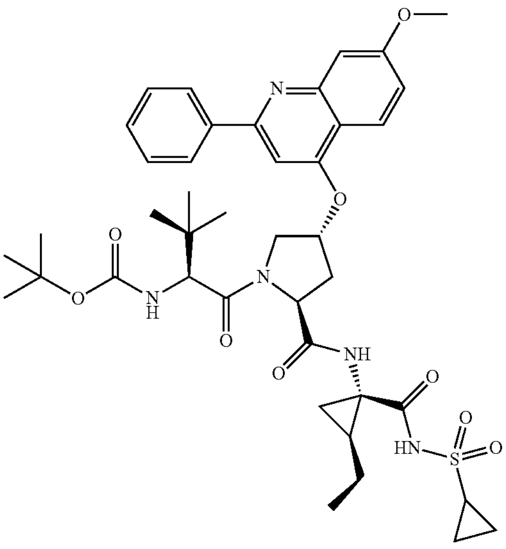

In another embodiment, the HCV protease inhibitor or an enantiomer, stereoisomer, diastereomer, racemic, tautomeric, ester, prodrug, solvate, hydrate, isotopologue or salt form thereof is a compound selected from:

| Cpd | Name |
|---|---|
| 1p | 3-(1,1-dioxido-2H-1,2,4-benzothiadiazin-3-yl)-4-hydroxy-1-(3-methylbutyl)quinolin-2(1H)-one, |
| 2p | N-(tert-butoxycarbonyl)-3-methyl-L-valyl-(4R)-N-{(1S,2R)-1-[(cyclopropylsulfonyl)carbamoyl]-2-ethenylcyclopropyl}-4-[(7-methoxy-2-phenylquinolin-4-yl)oxy]-L-prolinamide, |

The chemical terms used above and throughout the description of the invention, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-6}$alkyl and the like. A $C_{1-8}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indole, indazolyl, isoindolyl, benzofuranyl, benzothienyl, benzimidazolyl, benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical may be optionally substituted on a carbon or nitrogen atom ring member where allowed by available valences.

As used herein, the term "amino" refers to a radical of the formula: —$NH_2$.

As used herein, the term "halo" or "halogen" generally refers to a halogen atom radical, including fluoro, chloro, bromo and iodo.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. It should also be noted that any carbon as well as heteroatom with valences that appear to be unsatisfied as described or shown herein is assumed to have a sufficient number of hydrogen atom(s) to satisfy the valences described or shown.

For the purposes of this invention, where one or more substituent variables for a compound structure encompass functionalities incorporated into a compound of the present invention, each functionality appearing at any location within the disclosed compound may be independently selected, and as appropriate, independently and/or optionally substituted.

As used herein, the terms "independently selected," or "each selected" refer to functional variables in a substituent list that may occur more than once on a compound structure, the pattern of substitution at each occurrence is independent of the pattern at any other occurrence. Further, the use of a generic substituent variable on any formula or structure for a compound of the present invention is understood to include the replacement of the generic substituent with species substituents that are included within the particular genus, e.g., aryl may be replaced with phenyl or naphthalenyl and the like, and that the resulting compound is to be included within the scope of the compounds representative of the present invention.

As used herein, the reference to carbon atoms may appear as either "$C_{1-8}$" or as "$C_1$ to $C_8$," wherein either of such references is the equivalent of the other.

As used herein, the term "each instance of" when used in a phrase such as " . . . aryl, Aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$ alkyl.

As used herein, the term "optionally substituted" means optional substitution with specified substituent variables, groups, radicals or moieties.

As used herein, the terms "stable compound' or "stable structure" mean a compound that is sufficiently robust to survive isolation to a useful degree of purity from a reaction mixture and formulations thereof into an efficacious therapeutic agent.

Compound names used herein were obtained using ACD Labs Index Name software Version 10.0, provided by ACD Labs; and/or, were provided using the Autonom function of ChemDraw Ultra 10.0.4, provided by CambridgeSoft. When the compound name disclosed herein conflicts with the structure depicted, the structure shown will supercede the use of the name to define the compound intended.

Compound Forms

As used herein, the term "form" means a compound isolated for use selected from a free acid, free base, salt, hydrate, solvate, clathrate, isotopologue, racemate, enantiomer, diastereomer, stereoisomer, polymorph or tautomer form thereof.

As used herein, the term "isolated" means the physical state of a compound of after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group substituent on a compound is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Prodrugs and solvates of the compounds of the invention are also contemplated herein.

As used herein, the term "prodrug" means a form of an instant compound (e.g., a drug precursor) that is transformed in vivo to yield an active compound. The transformation may occur by various mechanisms (e.g., by metabolic and/or non-metabolic chemical processes), such as, for example, through hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound contains a carboxylic acid functional group, a prodrug can comprise an ester formed by the replacement of the hydrogen atom of the acid group with a functional group such as alkyl and the like. In another example, when a compound contains an alcohol functional group, a prodrug can be formed by the replacement of the hydrogen atom of the alcohol group with a functional group such as alkyl or carbonyloxy and the like. In another example, when a compound contains an amine functional group, a prodrug can be formed by the replacement of one or more amine hydrogen atoms with a functional group such as alkyl or substituted carbonyl.

One or more compounds of the invention may exist in unsolvated as well as solvated forms with pharmaceutically acceptable solvents such as water, ethanol, and the like, and it is intended that the invention embrace both solvated and unsolvated forms.

As used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of the invention may optionally be converted to a solvate. Preparation of solvates is generally known. The Preparation of solvates of the antifungal fluconazole in ethyl acetate as well as from water has been described (see, M. Caira et al, *J. Pharmaceutical Sci.,* 93(3), 601-611 (2004)). Similar preparations of solvates, hemisolvate, hydrates and the like have also been described (see, E. C. van Tonder et al, *AAPS PharmSciTech.,* 5(1), article 12 (2004); and A. L. Bingham et al, *Chem. Commun.,* 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of the present invention can form salts which are also within the scope of this invention. Reference to a compound of the present invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a instant compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of the present invention may be formed, for example, by reacting the compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: carboxylic acid esters, sulfonate esters, amino acid esters phosphonate esters and mono-, di- or triphosphate esters.

Compounds of the present invention and salts, solvates, esters and prodrugs thereof, may further exist in their tautomeric form (for example, as an amide or imino ether). All such tautomeric forms are contemplated herein as part of the present invention.

The instant compounds may contain asymmetric or chiral centers, and, therefore, exist in different stereoisomeric forms. It is intended that all stereoisomeric forms of said compounds as well as mixtures thereof, including racemic mixtures, form part of the present invention.

The compounds of the invention may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of the invention are (S) isomers and may exist as enantiomerically pure compositions substantially comprising only the (S) isomer. In another embodiment, the compounds of the invention are (R) isomers and may exist as enantiomerically pure compositions substantially comprising only the (R) isomer. As one of skill in the art will recognize, when more than one chiral center is present, the compounds of the invention may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the invention, a compound of the present invention is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the invention, a compound of the present invention is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present invention embraces all geometric and positional isomers. For example, if a compound of the present invention incorporates a double bond or a fused ring, both the and trans-forms, as well as mixtures, are embraced within the scope of the invention. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds may be atropisomers (e.g., substituted biaryls) and are considered as part of this invention.

It is also possible that the compounds of the present invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound incorporates a double bond or a fused ring, both the cis- and trans-forms, as well as mixtures thereof, are embraced within the scope of the invention. Also, for example, all keto-enol and imine-enamine forms of the compounds are included in the invention. Individual stereoisomers of the compounds of the invention may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this invention.

Certain isotopically-enriched compounds of the present invention (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances. Isotopically-enriched compounds can generally be prepared by following procedures known to those skilled in the art by substituting an appropriate isotopically-enriched reagent for a non-isotopically-enriched reagent.

Polymorphic crystalline and amorphous forms of the compounds of the present invention, and of the salts, solvates, esters and prodrugs thereof are further intended to be included in the present invention.

Methods of Use

The combination product of the present invention comprising a HCV inhibitor and one or more therapeutic agents selected from either or both a HCV protease inhibitor and one or more different therapeutic agents administered in combination in an effective amount to the subject has demonstrated activity to inhibit viral replication.

Accordingly, the combination product of the present invention is useful for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor or an enantiomer, stereoisomer, diastereomer, racemic, tautomeric, ester, prodrug, solvate, hydrate, isotopologue or salt form thereof disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which is incorporated herein by reference in their entirety and for all purposes.

In one embodiment, the HCV inhibitor is selected from a compound of the present invention or an enantiomer, stereoisomer, diastereomer, racemic, tautomeric, ester, prodrug, solvate, hydrate, isotopologue or salt form thereof.

Embodiments of the present invention include a HCV protease inhibitor selected from a NS2 protease inhibitor, a NS3 protease inhibitor, a peptide or dipeptide NS3 protease inhibitor or a NS4a protease cofactor inhibitor.

An embodiment of the present invention includes a HCV protease inhibitor selected from a HCV protease inhibitor of the present invention or an enantiomer, stereoisomer, diastereomer, racemic, tautomeric, ester, prodrug, solvate, hydrate, isotopologue or salt form thereof.

An embodiment of the present invention includes one or more different therapeutic agents selected from a HCV inhibitor, a HCV protease inhibitor, a nucleoside or non-nucleoside HCV polymerase inhibitor, a nonpegylated interferon, a pegylated interferon or another anti-HCV agent.

In one embodiment, one or more different HCV inhibitor therapeutic agents is selected from a HCV inhibitor compound of the present invention or a form thereof.

In one embodiment, one or more different HCV inhibitor therapeutic agents is selected from a HCV inhibitor other than a HCV inhibitor compound of the present invention or a form thereof.

In one embodiment, one or more different therapeutic agents other than the HCV inhibitor compounds and forms thereof of the present invention is selected from HCV inhibitor compounds and forms thereof disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which is incorporated herein by reference in their entirety and for all purposes.

In one embodiment, one or more different HCV protease inhibitor therapeutic agents is selected from a NS2 protease inhibitor, a NS3 protease inhibitor, a peptide or dipeptide NS3 protease inhibitor or a NS4a protease cofactor inhibitor.

In one embodiment, one or more different HCV protease inhibitor therapeutic agents is selected from a HCV protease inhibitor or a form thereof of the present invention.

In one embodiment, one or more different HCV protease inhibitor therapeutic agents is selected from a HCV protease inhibitor or a form thereof other than the HCV protease inhibitor or forms thereof of the present invention.

In one embodiment, one or more different nucleoside or non-nucleoside HCV polymerase inhibitor therapeutic agents is selected from a NS5b polymerase inhibitor.

In one embodiment, one or more different therapeutic agents is selected from a NS4b inhibitor, NS5a inhibitor, IRES inhibitor, p7 inhibitor, entry inhibitor, fusion inhibitor, helicase inhibitor, ribavirin or a ribavirin analogue.

An embodiment of the present invention includes one or more different therapeutic agents selected from a TLR agonist, cyclophilin inhibitor, caspase or pancaspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH inhibitor, glycosidase inhibitor, glucosidase inhibitor, HCV therapeutic vaccine, A3 adenosine receptor (AR) agonist, polypeptide eglin c analog inhibitor, human pancreatic secretory trypsin and minibody repertoire inhibitor or a monoclonal antibody and fragment thereof.

An embodiment of the present invention includes one or more different therapeutic agents selected from a HIV inhibitor, HBV inhibitor, RNA inhibitor, RNAi, anti-phospholipid therapy, protein therapeutic, interferon replacement agent, botanical or non-specific pharmaceutical.

In one embodiment, the NS3 HCV protease inhibitor or one or more different NS3 HCV protease inhibitor therapeutic agents is selected from ACH-1625 (Achillion Pharmaceuticals, Inc.), BI 201335 (Boehringer Ingelheim Pharma), boceprevir (also referred to as SCH-503034, Schering-Plough Corporation), ciluprevir (also referred to as BILN-2061, Boehringer Ingelheim Pharma), IDX136 (Idenix Pharmaceuticals, Inc.), IDX316 (Idenix Pharmaceuticals, Inc.), ITMN-191 (also referred to as R-7227, InterMune/Roche Pharmaceuticals), MK-7009 (Merck), PHX1766 (Phenomix), SCH-6 (Schering-Plough Corporation), SCH-900518 (also referred to as SCH-518, Schering-Plough Corporation), telaprevir (also referred to as VX 950, Vertex Pharmaceuticals, Inc.), TMC435350 (also referred to as TMC435, Medivir/Tibotec), VBY-376 and VBY-106 (Virobay), VP50406 (ViroPharma, Inc.), VX-500 (Vertex Pharmaceuticals, Inc.), VX 550 (Vertex Pharmaceuticals, Inc.) or VX-813 (Vertex Pharmaceuticals, Inc.).

In one embodiment, the HCV NS4a protease cofactor inhibitor or one or more different HCV NS4a protease cofactor inhibitor therapeutic agents is selected from ACH-806 (also referred to as GS-9132, Achillion/Gilead) or ACH-1095 (also known as GS-9525, Gilead/Achillion.

In one embodiment, the one or more different nucleoside or non-nucleoside NS5b polymerase inhibitor therapeutic agents is selected from A-837093 (Abbott Laboratories), A-848837 (Abbott Laboratories), ABT-333 (Abbott Laboratories), AG-021541 (Pfizer Pharmaceuticals), ANA598 (Anadys Pharmaceuticals, Inc.), BILN-1941 (Boehringer Ingelheim Pharma), GL-59728 (Genelabs), GL-60667 (Genelabs), GS-9190 (Gilead), GSK-625433 (GlaxoSmithKline), HCV-796 (Wyeth/Viropharma, Inc.), HCV-896 (ViroPharma, Inc.), IDX102 (Idenix Pharmaceuticals, Inc.), IDX184 (Idenix Pharmaceuticals, Inc.), IDX375 (Idenix Pharmaceuticals, Inc.), JDK-003 (Akros Pharmaceuticals), MK-0608 (Merck), MK-3281 (Merck), NM107 (active moiety of valopicitabine, Idenix/Novartis), PF-00868554 (also referred to as PF-868554 or PF-868,554, Pfizer Pharmaceuticals), PSI-6130 (Pharmasset), PSI-7851 (Pharmasset), R1626 (a prodrug of R1479, Roche Pharmaceuticals), R7128 (a prodrug of PSI-6130, Pharmasset/Roche Pharmaceuticals), valopicitabine (also referred to as NM-283, Idenix/Novartis), VBY-708 (Virobay), VCH-222 (Virochem), VCH-759 (Virochem), VCH-916 (Virochem) or XTL-2125 (also referred to as BC2125, XTL Biopharmaceuticals, Ltd.).

In one embodiment, the one or more different NS4b inhibitor therapeutic agents is selected from anguizole (Genelabs/GSKNiropharma, Inc.), clemizole (Eiger BioPharmaceuticals, Inc./Stanford University) or Compound A (BMS).

In one embodiment, the one or more different NS5a inhibitor therapeutic agents is selected from A-689 (also referred to as AZD7295, Arrow Therapeutics, Ltd./AstraZeneca), A-831 (also referred to as AZD2836, Arrow Therapeutics, Ltd./AstraZeneca), BMS-790052 (Bristol-Myers Squibb).

In one embodiment, the one or more different IRES inhibitor therapeutic agents is selected from a steroid, a ribozyme, miRNA, sRNA or an antisense RNA.

In one embodiment, the one or more different IRES inhibitor steroid therapeutic agents is mifepristone (also referred to as VGX-410C, VGX Pharmaceuticals).

In one embodiment, the one or more different IRES inhibitor ribozyme, miRNA, siRNA or antisense RNA therapeutic agents is selected from an antisense oligonucleotide ISIS-14803 (Isis Pharmaceuticals), a ribozyme such as HEFTAZYME®, (a synthetic ribozyme, Ribozyme Pharmaceuticals, Inc.), a RNAi such as TT033 (Benitec/Tacere Bio/Pfizer) or SIRNA-034 (Sirna Therapeutics), a miRNA such as SPC3649 (LNA-antimiR™-122 brand, Santaris Pharma) or an anti-miR-122 miRNA (Regulus Therapeutics), sRNA, In one embodiment, one or more different p7 inhibitor therapeutic agents is selected from BIT225 (Biotron Limited), and one or more different viral entry inhibitor therapeutic agents is selected from ITX5061 (iTherX Pharmaceuticals, Inc.), PRO206 (Progenics), an SP-30 entry inhibitor (Samaritan Pharmaceuticals) or a broad spectrum entry inhibitor therapeutic agent selected from REP 9AC (an amphipathic DNA polymer, REPLICor, Inc.).

In one embodiment, one or more different ribavirin therapeutic agents is selected from ribavirin (VIRAZOLE® and VILONA® brands, ICN Pharmaceuticals), ribavirin for oral administration (REBETOL® brand, Schering-Plough Corporation), ribavirin tablets (COPEGUS® brand, Roche Pharmaceuticals), ribavirin capsules (RIBASPHERE® brand, Three Rivers Pharmaceuticals, LLC), In one embodiment, one or more different ribavirin analogue therapeutic agents is selected from levovirin (L-isomer of ribavirin, Valeant Pharmaceuticals), R1518 (a prodrug of levovirin, also referred to as levovirin valinate, Roche Pharmaceuticals) or taribavirin (an oral prodrug of ribavirin, also referred to as viramidine, Valeant Pharmaceuticals).

An embodiment of the present invention includes one or more different therapeutic agents selected from ribavirin and at least one or more of a nonpegylated interferon or a pegylated interferon.

In one embodiment, the one or more different non-pegylated interferon therapeutic agent optionally adiministered with ribavirin is selected from interferon alfa-2a (ROFERON®-A brand, Roche Pharmaceuticals), interferon alfa-2b (INTRON® A brand, Schering-Plough Corporation), interferon alfa-2c (BEROFOR® brand, Boehringer Ingelheim), interferon-alpha variant GEA007.1 (GenOdyssee SA), interferon-alpha for low dose oral administration (Amarillo Biosciences, Inc./CytoPharm, Inc.), interferon-alpha for oral administration (BELEROFON® brand, Nautilus Biotech), long-acting interferon-alpha (LOCTERON® brand, also referred to as BLX-883, Biolex Therapeutics/OctoPlus), long-acting albuminfusion interferon alfa-2b (ALBUFERON® brand, also referred to as albinterferon alfa-2b, Human Genome Sciences), purified multi-subtype human leukocyte interferon-alpha (MULTIFERON® brand, Swedish Orphan International), interferon beta-1a (REBIF® brand, Merck Serono), interferon omega (also referred to as leukocycle (II) interferon, Intarcia Therapeutics), interferon omega (VIRBAGEN OMEGA® brand, Virbac), interferon omega (OMEGA INTERFERON® brand, Biomedicines), consensus interferon (INFERGEN® brand, also referred to as interferon alfacon-1, Three Rivers Pharma), medusa interferon (MEDUSA INTERFERON® brand, Flamel Technologies).

In one embodiment, the one or more different pegylated interferon therapeutic agent optionally administered with ribavirin is selected from Peginterferon alfa-2a (PEGASYS® brand, Roche Pharmaceuticals), Peginterferon alfa-2b (PEGINTRON® brand, Schering-Plough Corporation), Peginterferon alfacon-1 (pegylated form of interferon alfacon-1, also referred to as PEG-Alfacon, InterMune), Peg-Interferon Lambda IL-29 (Zymogenetics/Bristol-Myers Squibb).

In one embodiment, the one or more different therapeutic agents are a TLR agonist selected from ANA773 (Anadys Pharmaceuticals, Inc.), a TLR-7 agonist selected from isatoribine (also referred to as ANA245, Anadys Pharmaceuticals, Inc.), ANA-971 (a prodrug of TLR-7 agonist isatoribine, Anadys Pharmaceuticals, Inc.), ANA975 (a prodrug of TLR-7 agonist isatoribine, Anadys Pharmaceuticals, Inc.), a TLR9 agonist selected from IMO-2125 (Idera Pharmaceuticals), a TLR9 agonist (Actilon brand, Coley), a cyclophilin B inhibitor selected from Debio 025 (Debiopharm Group) or SCY-635 (Scynexis) or a cyclosporin A analog selected from NIM811 (Novartis), a pancaspase inhibitor selected from PF-03491390 (also referred to as IDN-6556, Pfizer Pharmaceuticals), an interleukin-7 immunomodulator selected from CYT107 (Cytheris SA), NOV-205 (Novelos Therapeutics), oglufanide disodium (Implicit Bioscience) or thymosin alpha 1 (also referred to as thymalfasin, ZADAXIN® brand, SciClone Pharmaceuticals), a immunomodulator/antiinflammatory selected from NOV205 (Novelos Therapeutics, Inc.), an antiinflammatory selected from CTS-1027, a matrix metalloproteinase selected from a (MMP) inhibitor (Conatus) or CF102, an A3AR agonist (Can-Fite BioPharma, Ltd.), an antiinflammatory/antifibrotic selected from mitoquinone (MitoQ® brand, Antipodean Pharmaceuticals) or PYN17 (Phynova), a broad spectrum immune stimulator selected from SCV-07 (SciClone), an immune regulator selected from ECH18 (Enzo BioChem/Therapeutics), an antifibrotic selected from JKB-122 (Jenken Biosciences), a tumor necrosis factor α inhibitor antifibrotic selected from ENBREL® brand (Wyeth), a phospholipid antifibrotic for oral administration selected from IP-501 (Indevus Pharmaceuticals), a hemopurifier (Aethion Medical), an IMPDH inhibitor selected from merimepodib (also referred to as VX-497, Vertex Pharmaceuticals, Inc.), a glucosidase inhibitor selected from celgosivir, an alpha-glucosidase I inhibitor selected from MX-3253 (Migenix), a HCV therapeutic vaccine selected from a DNA vaccine (ChronVac-C® brand, lnovio/Tripep AB), a MVA virus vaccine carrying and expressing HCV non-structural proteins (NS3, NS4 and NS5b) selected from TG4040 (Transgene) or (Inovio/Tripep AB), an antiviral vaccine selected from GNI-103 (GENimmune), a virosome-based combination vaccine of synthetic HCV'peptide antigens (Pevion Biotect), an E1 vaccine (Innogenetics), a HCV E1/E2/MF59 vaccine (Chiron/Novartis), a vaccine selected from CSL123 (Chiron/CSL), a targeted molecular immunogen vaccine selected from GI-5005 (GlobeImmune), a vaccine having a combination of five synthetic peptides selected from IC-41 (Intercell AG/Novartis), an antiviral vaccine (AMANTADINE® brand, Endo Labs), a monoclonal antibody selected from 170® (also referred to as HCV-AB$^{XTL}$ 68 or HCV-AB, Biochem Therapeutics/OSI Pharmaceuticals), an immune globulin polyclonal antibody selected from intravenous human immune globulin (CIVACIR® brand, NABI), a humanized Y-90 labeled antibody (Immunomedics, Inc.) an anti-PD1 antibody selected from MDX-1106 (also referred to as ONO-4538, Medarex, Inc./Ono Pharmaceutical), an anti-CD20 monoclonal antibody (RITUXIMAB® brand, Genentech), a monoclonal antibody selected from XTL-6865 or XTL-002 (XTL Biopharmaceuticals, Ltd.), a HIV fusion inhibitor selected from enfuvirtide (FUZEON® brand, Trimeris/Roche Pharmaceuticals), an anti-phospholipid therapy selected from bavituximab (formerly TARVACIN® brand, Peregrine Pharmaceuticals, Inc.), a protein therapeutic or interferon replacement agent selected from oligoadenylate synthetase stimulant CB-183,872 (Cubist Pharmaceuticals, also referred to as IB657 from Illumigen Biosciences), a botanical selected from an antiviral botanical extract PYN18 (Phynova) or a non-specific pharmaceutical selected from the cholesterol-lowering agent fluvastatin (Oklahoma University Health Sciences Center), atorvastatin (Okayama University, Japan), lovastatin (Okayama University, Japan) or simvastatin (Okayama University, Japan), a thiazolide analog selected from nitazoxanide (ALINIA™brand, Romark Pharmaceuticals), photo-sensitized methylene blue (SUVUS® brand, Bioenvision), a synthetic phytochemical selected from KPE02003002 (Kemin Pharma) or KPE00001133 (Kemin Pharma), an antiviral agent selected from CB5300 (Canopus BioPharma, Inc.) or a tyrosine phosphatase inhibitor selected from sodium stibogluconate (LENOCTA™ brand, VioQuest Pharmaceuticals).

In one embodiment, one or more different therapeutic agents is selected from histamine dihydrochloride (CEPLENE® and MAXAMINE® brands, Maxim Pharmaceuticals), an immunosuppressive agent selected from mycophenolate mofetil (Roche Pharmaceuticals), mycophenolic acid (Roche Pharmaceuticals), or α1-antichymotrypsin.

The present invention is also directed to a method for treating or ameliorating HCV infection or disorders or symptoms associated therewith in a subject in need thereof comprising, administering an effective amount of a combination product to the subject, wherein the combination product is a HCV inhibitor and one or more therapeutic agents selected from either or both a HCV protease inhibitor and one or more different therapeutic agents administered in combination to the subject.

An embodiment of the present invention includes the use of a combination product comprising, a HCV inhibitor and one or more therapeutic agents selected from either or both a HCV protease inhibitor and one or more different therapeutic agents in the preparation of a medicament, pharmaceutical composition or pharmaceutical kit for treating or ameliorating HCV infection or disorders or symptoms associated therewith in a subject in need thereof.

An effective amount of the combination product used in the method of the present invention includes an amount of a HCV inhibitor, an amount of a HCV protease inhibitor and an amount of one or more different therapeutic agents that, when administered in combination to the subject is effective to inhibit viral replication.

An embodiment of the method of the present invention includes one or more different therapeutic agents selected from ribavirin and at least one or more of a nonpegylated interferon or a pegylated interferon.

Similarly, a therapeutically effective amount of the combination product used in the method of the present invention is an amount effective against HCV infection to produce the desired therapeutic effect in a suitable human subject.

As used herein, the term "treating or ameliorating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "subject" and "human".

The term "effective amount" or "therapeutically effective amount" is meant to describe an amount of the combination product of the present invention, wherein the combination product includes an amount of a HCV inhibitor, an amount of a HCV protease inhibitor and an amount of one or more different therapeutic agents that, when administered in combination to the subject is effective to inhibit viral replication and produce the desired therapeutic or ameliorative effect in a suitable human subject.

The therapeutic effect of the combination product used in the method of the present invention can be determined by analyzing (1) the presence of HCV RNA; (2) the presence of anti-HCV antibodies; (3) the level of serum alanine aminotransferase (ALT) and aspartate aminotransferase (AST) (ALT and AST are elevated in patients chronically infected with HCV); or (4) hepatocellular damage or any combination thereof. The precise effective amount for a subject will depend upon the subject's body weight, size and health. Therapeutically effective amounts for a given patient can be determined by routine experimentation that is within the skill and judgment of the clinician.

For a HCV inhibitor and one or more therapeutic agents selected from either or both a HCV protease inhibitor and one or more different therapeutic agents administered in combination to the subject, as used in the method described herein, the therapeutically effective amount can be estimated initially either in cell culture assays, including the HCV replicon and HCV infectious system (HCVcc), or in relevant animal models, such as the chimeric SCID-beige/Alb-uPA mouse model or in chimpanzees, marmosets and tamarins. The animal model may also be used to determine the appropriate concentration range and route of administration. Such information can then be used to determine useful doses and routes for administration in humans.

Therapeutic efficacy and toxicity may be determined by standard pharmaceutical procedures in cell cultures or experimental animals, e.g. $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. A combination product as used in the method described herein that exhibits a large therapeutic index is preferred. The dosage contained in such a combination product is preferably within a range of circulating concentrations that include an $ED_{50}$ with little or no toxicity. The dosage may vary within this range depending upon the dosage form employed, therapeutic sensitivity of the patient, use of prior anti-viral therapies and the route of administration.

More specifically, the concentration-biological effect relationships observed with regard to use of a combination product indicates an initial target plasma concentration ranging from approximately 0.1 μg/mL to approximately 500 μg/mL, or from approximately 0.1 ng/mL to approximately 250 μg/mL, or from approximately 0.1 μg/mL to approximately 50 μg/mL, or from approximately 0.5 pg/mL to approximately 50 pg/mL, or from approximately 1.0 μg/mL to approximately 25 μg/mL.

To achieve such plasma concentrations, the effective amount of the combination product comprising a HCV inhibitor and one or more therapeutic agents selected from either or both a HCV protease inhibitor and one or more different therapeutic agents administered in combination to the subject, as used in the method described herein, may each be administered at doses that vary from about 0.1 μg to about 3,600 mg, depending upon the route of administration. Guidance as to particular dosages and methods of delivery is provided in the literature and is generally available to practitioners in the art. In general, the dose for each may be in the range of from about 0.1 μg/day to about 4.5 g/day, about 1 mg/day to about 3 g/day, or from about 0.1 g/day to about 3 g/day, or from about 0.3 g/day to about 3 g/day, or from about 0.5 g/day to about 2 g/day, in single, divided, or continuous doses for a patient weighing between about 40 to about 100 kg (which dose may be adjusted for patients above or below this weight range, particularly for children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time, and frequency of administration, drug combination(s), reaction sensitivities, and tolerance/response to therapy. Long-acting medicaments or pharmaceutical compositions may be administered every 3 to 4 days, every week, or once every two weeks depending on half-life and clearance rate of the particular formulation.

In one embodiment, the combination product comprising a HCV inhibitor and one or more therapeutic agents selected from either or both a HCV protease inhibitor and one or more different therapeutic agents administered in combination to the subject, as used in the method described herein, may each be administered at a dosage range of from about 0.1 pg to about 3600 mg per day (e.g., at a dose selected from 0.1 mg, 1 mg, 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000-mg, 3050 mg, 3100 mg, 3150 mg, 3200 mg, 3250 mg, 3300 mg, 3350 mg, 3400 mg, 3450 mg, 3500 mg, 3550 mg or 3600 mg per day).

In one embodiment, a HCV inhibitor and one or more therapeutic agents selected from either or both a HCV protease inhibitor and one or more different therapeutic agents administered in combination to the subject, as used in the method described herein, may each be administered at a dosage range of from about 0.1 mg to about 2500 mg per day.

In another embodiment, a HCV inhibitor and one or more therapeutic agents selected from either or both a HCV protease inhibitor and one or more different therapeutic agents administered in combination to the subject, as used in the method described herein, may each be administered as a single dose (i.e., QD) or divided over 2-4 doses (i.e., BID, TID, or QID) per day. In another embodiment, a HCV inhibitor and one or more therapeutic agents selected from either or both a HCV protease inhibitor and one or more different therapeutic agents may each be administered in combination either concurrently or consecutively to the subject, as used in the method described herein.

In one embodiment, a HCV inhibitor and one or more therapeutic agents selected from either or both a HCV protease inhibitor and one or more different therapeutic agents administered in combination to the subject, as used in the method described herein, may each be administered orally.

In one embodiment, a HCV inhibitor and one or more therapeutic agents selected from either or both a HCV protease inhibitor and one or more different therapeutic agents administered in combination to the subject, as used in the method described herein, may each be administered at a dosage range of from about 1.0 mg to about 2400 mg per day.

In another embodiment, the HCV protease inhibitor may be administered at a dosage of about 1200 mg per day, administered as a dosage of about 400 mg TID.

In another embodiment, the HCV protease inhibitor may be administered at a dosage of about 800 mg, 1600 mg, or 2400 mg per day administered as a dosage of about 800 mg QD, BID or TID, respectively.

In one embodiment, the present invention includes a combination product comprising, a HCV inhibitor and one or more therapeutic agents selected from either or both a HCV protease inhibitor and one or more different therapeutic agents for use in the preparation of a medicament for treating or ameliorating HCV infection or disorders or symptoms associated therewith in a subject in need thereof.

In one embodiment, the present invention includes a combination product comprising, a HCV inhibitor and one or more therapeutic agents selected from either or both a HCV protease inhibitor and one or more different therapeutic agents for use in the preparation of a pharmaceutical composition comprising the combination product in admixture with a pharmaceutically acceptable carrier.

In one embodiment, the present invention includes a combination product comprising, a HCV inhibitor and one or more therapeutic agents selected from either or both a HCV protease inhibitor and one or more different therapeutic agents for use in the preparation of a pharmaceutical kit comprising the combination product and instructions for administering the combination product for treating or ameliorating HCV infection or disorders or symptoms associated therewith in a subject in need thereof.

In one embodiment, the subject is treatment naive. In another embodiment, the subject is not treatment naive.

Pharmaceutical Compositions

Embodiments of the present invention include pharmaceutical compositions and combinations of the present invention useful for treating subjects having any HCV genotype. HCV genotypes and subtypes may differ in their antigenicity, level of viremia, severity of disease produced, and response to interferon therapy (see, Holland, J, et al., HCV genotyping by direct sequencing of the product from the Roche Amplicor Test: methodology and application to a South Australian population, *Pathology,* 1998, 30:192-195). The nomenclature of HCV classification (see, Simmonds, P. et al., Classification of HCV into six major genotypes and a series of subtypes by phylogenetic analysis of the NS5 region, *J. Gen. Virol.,* 1993, 74:2391-9) is widely used and classifies HCV isolates into six major genotypes, 1 through 6, with two or more related subtypes, e.g., 1a, 1b. Additional genotypes 7-11 have been proposed, however the phylogenetic basis on which this classification is based has been questioned, and thus types 7, 8, 9 and 11 isolates have been reassigned as type 6, and type 10 isolates as type 3 (see, Lamballerie, et al., Classification of HCV variants in six major types based on analysis of the envelope 1 and nonstructural 5B genome regions and complete polyprotein sequences, *J. Gen. Virol.,* 1997, 78:45-51). The major genotypes have been defined as having sequence similarities of between 55 and 72% (mean 64.5%), and subtypes within types as having 75%-86% similarity (mean 80%) when sequenced in the NS5 region (see, P Simmonds, et al., Identification of genotypes of HCV by sequence comparisons in the core, E1 and NS5 regions, *J. Gen. Virol.,* 1994, 75:1053-61).

In one embodiment, a dosage for the administration of a combination product, medicament, pharmaceutical composition or pharmaceutical kit of the present invention is from about 0.001 to about 500 mg/kg of body weight/day; or, from about 0.01 to about 25 mg/kg of body weight/day.

As used herein, the term "composition" means a product comprising the specified ingredients in the specified amounts, as well as any product which results, directly or indirectly, from combination of the specified ingredients in the specified amounts.

For administration of pharmaceutically acceptable salts of the compounds, the weights indicated above refer to the weight of the acid equivalent or the base equivalent of the therapeutic compound derived from the salt.

When administering an effective amount of a combination product to the subject in need thereof, wherein the combination product is a HCV inhibitor and one or more therapeutic agents selected from either or both a HCV protease inhibitor and one or more different therapeutic agents administered in combination either concurrently or consecutively to the subject, the term "either concurrently or consecutively" refers to administering the HCV inhibitor and one or more therapeutic agents selected from either or both the HCV protease inhibitor and one or more different therapeutic agents in any order such as, for example, simultaneously, sequentially, in alternation, concurrently, in parallel, or by any other combination therapy regimen known in the art.

When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

The amounts of the various active ingredients in a combination therapy may be administered in different amounts (i.e., different dosage amounts) or in the same amount (i.e., the same dosage amount). Thus, for illustration purposes, a HCV inhibitor compound of the present invention and one or more therapeutic agents selected from either or both a HCV protease inhibitor and one or more different therapeutic agents may each be present in fixed amounts (dosage amounts) in a single dosage unit (e.g., a capsule, a tablet and the like). If formulated as a fixed dose, such a combination product may employ the HCV inhibitor compounds of the present invention within the dosage range described herein and one or more therapeutic agents selected from either or both a HCV protease inhibitor and one or more different therapeutic agents within the dosage range recommended for each HCV inhibitor and/or HCV protease inhibitor and/or different therapeutic agent. HCV inhibitor compounds of the present invention may also be administered sequentially with one or more known therapeutic agents selected from either or both a HCV protease inhibitor and one or more different therapeutic agents when a combination formulation is inappropriate. The invention is not limited in the sequence of administration; the HCV inhibitor compounds of the present invention may also be administered either prior to or after administration of one or more of the known therapeutic agent selected from either or both a HCV protease inhibitor and one or more different therapeutic agents. Such techniques are within the skills of persons skilled in the art as well as attending physicians and clinicians.

The pharmacological properties of the active ingredients in the combination product comprising a HCV inhibitor and one or more therapeutic agents selected from either or both a HCV protease inhibitor and one or more different therapeutic agents used in the preparation of a medicament, pharmaceutical composition or pharmaceutical kit for treating or ameliorating HCV infection or disorders or symptoms associated therewith in a subject in need thereof may be confirmed by any number of pharmacological assays for measuring inhibition of viral replication such as are well known to those skilled in the art.

While it is possible for each of the active ingredients of the present invention to be administered alone, it is preferable to administer the active ingredients as a combination product. The combination product comprising a HCV inhibitor and one or more therapeutic agents selected from either or both a HCV protease inhibitor and one or more different therapeutic agents may also comprise at least the HCV inhibitor and one or more therapeutic agents selected from either or both a HCV protease inhibitor and one or more different therapeutic agents, as defined above, together with one or more acceptable carriers, adjuvants or vehicles thereof and optionally other adjuvant therapeutic agents. Each carrier, adjuvant or vehicle must be acceptable in the sense of being compatible with the other ingredients of the composition and pharmaceutically acceptable for use in a combination product for use in a subject in need of such treatment.

Accordingly, the invention also relates to pharmaceutical compositions of the active ingredients in the combination product comprising at least one HCV inhibitor compound and one or more therapeutic agents selected from either or both a HCV protease inhibitor and one or more different therapeutic agents as utilized in the presently claimed methods, and at least one pharmaceutically acceptable carrier, adjuvant or vehicle.

In yet another embodiment, the present invention discloses methods for preparing pharmaceutical compositions of the combination product comprising the HCV inhibitor compounds and one or more therapeutic agents selected from either or both a HCV protease inhibitor and one or more different therapeutic agents as active ingredients. In the combination product and methods of the present invention, the active ingredients may typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active HCV inhibitor compounds and one or more therapeutic agents selected from either or both a HCV protease inhibitor and one or more different therapeutic agents may, be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Powders and tablets of the active ingredients in the combination product may be comprised of from about 5 to about 95 percent of said active ingredients. Surfactants may be present in the pharmaceutical compositions of the combination product of the present invention in an amount of from about 0.1 to about 10% by weight or from about 1 to about 5% by weight. Acidifying agents may be present in the pharmaceutical formulations of the present invention in a total amount of from about 0.1 to about 10% by weight or from about 1 to about 5% by weight.

Suitable binders may be included where appropriate and include starch, gelatin, natural sugars, corn sweeteners, or natural and synthetic gums such as acacia, sodium alginate, carboxymethylcellulose, polyethylene glycol and waxes.

Suitable lubricants may be included where appropriate and include boric acid, sodium benzoate, sodium acetate, sodium chloride, and the like. Disintegrants may be included where appropriate and include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the active ingredients in the combination product of the present invention may be formulated in sustained release form to provide a controlled release rate of any one or more of the components or active ingredients to optimize the therapeutic effects, i.e. HCV inhibitory activity. Suitable dosage forms for sustained release include layered tablets containing layers of varying disintegration rates or controlled release polymeric matrices impregnated with the active ingredients in the combination product and shaped in tablet form or capsules containing such impregnated or encapsulated porous polymeric matrices.

Liquid form preparations for active ingredients in the combination product include solutions, suspensions and emulsions. As an example, such forms include those in a water or water-propylene glycol solution for use as a parenteral injection. The liquid form preparation may also include the addition of sweeteners and pacifiers for oral solutions, suspensions and emulsions. Liquid form preparations may also include solutions for intranasal administration.

Aerosol preparations for active ingredients in the combination product suitable for inhalation may include solutions and solids in powder form, which may be in combination with a pharmaceutically acceptable carrier such as inert compressed gas, e.g. nitrogen.

For preparing suppositories of active ingredients in the combination product, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations for active ingredients in the combination product which are intended to be converted, shortly before use, to liquid form preparations for either oral or parenteral administration. Such resulting liquid forms include solutions, suspensions and emulsions.

The active ingredients in a combination product of the present invention may also be deliverable transdermally. The transdermal compositions may take the form of creams, lotions, aerosols and/or emulsions and can be included in a transdermal patch of the matrix or reservoir type as are conventional in the art for this purpose.

Preferably the active ingredients in a combination product are administered orally, intravenously, intrathecally or subcutaneously, parenteraly, transdermally or by any combination of such methods.

Preferably, the combination product is in a unit dosage form. In such form, the product is subdivided into suitably sized unit doses containing appropriate quantities of the active components, e.g., an effective amount to achieve the desired purpose. Other useful dosage forms include solid tablets, lyophilized wafers, capsules, powder, oral gels and the like.

Tablets for active ingredients in the combination product include compressed or molded solid dosage forms containing the active ingredients in admixture with suitable excipients.

The tablet can be prepared by compression of mixtures or granulations obtained by wet granulation, dry granulation or by compaction.

Lyophilized wafers for active ingredients in the combination product include mouth-soluble, freeze-dried, taste-masked solid dosage forms containing the active ingredients in admixture with suitable excipients. The wafer can be prepared by freeze drying suspensions or solutions containing the active ingredients and optional excipients, Capsule forms of active ingredients in the combination product may include capsules made of methyl cellulose, polyvinyl alcohol, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Powders for active ingredients in the combination product may include powder blends containing the active ingredients and suitable diluents for reconstitution or suspension in water or juices.

Oral gels for active ingredients in the combination product include active ingredients dispersed or solubilized in a hydrophilic semi-solid matrix.

Suitable excipients for use in the combination product are those substances that usually make up the major portion of the composition or dosage form, including sugars such as lactose, sucrose, mannitol and sorbitol; starches derived from wheat, corn, rice and potato; and celluloses such as microcrystalline cellulose. The amount of excipient in the pharmaceutical composition of the combination product can range from about 10 to about 90% by weight of the total composition, or from about 25 to about 75%, or from about 30 to about 60% by weight, or from about 12 to about 60%.

Suitable disintegrants are those materials added to the pharmaceutical composition of the combination product to help the composition to break apart (disintegrate) and release the active ingredients, including "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the pharmaceutical composition of the combination product can range from about 2 to about 15% by weight of the composition, or from about 4 to about 10% by weight.

Suitable binders are those substances that bind or "glue" powders together and make them cohesive by forming granules, thus serving as the "adhesive" in the pharmaceutical composition and further adding cohesive strength already available in the diluent or bulking agent, including sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the pharmaceutical composition can range from about 2 to about 20% by weight of the composition, or from about 3 to about 10% by weight, or from about 3 to about 6% by weight.

Suitable lubricants are those substances added to the pharmaceutical composition to enable the tablet, granules, etc., after they have been compressed, to release from the mold or die by reducing friction or wear, including metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and D-leucine or L-leucine. Lubricants are usually added at the very last step before compression, since they must be present on the surfaces of the granules and in between them and the parts of the tablet press. The amount of lubricant in the pharmaceutical composition can range from about 0.2 to about 5% by weight of the composition, or from about 0.5 to about 2%, or from about 0.3 to about 1.5% by weight.

Suitable glidents are those materials that prevent caking and improve the flow characteristics of granulations, so that flow is smooth and uniform, including silicon dioxide and talc. The amount of glident in the pharmaceutical composition can range from about 0.1% to about 5% by weight of the total composition, or from about 0.5 to about 2% by weight.

Suitable coloring agents are those excipients that provide coloration to the composition or the dosage form, including food grade dyes and food grade dyes adsorbed onto a suitable adsorbent such as clay or aluminum oxide. The amount of the coloring agent can vary from about 0.1 to about 5% by weight of the composition, or from about 0.1 to about 1%.

The term "bioavailability" refers to the rate at and extent to which the active ingredient of the combination product is absorbed into the systemic circulation from an administered dose as compared to a standard or control.

Conventional methods for preparing tablet forms of the active ingredients are known. Such methods include dry methods such as direct compression and compression of granulation produced by compaction, or wet methods or other special procedures. Conventional methods for making other forms of the active ingredients for administration such as, for example, capsules, suppositories and the like are also well known.

For preparing pharmaceutical compositions of the combination product comprising, a HCV inhibitor and one or more therapeutic agents selected from either or both a HCV protease inhibitor and one or more different therapeutic agents described herein, the combination product active ingredients are intimately admixed with inert, pharmaceutically acceptable carriers that can be either solid or liquid. Solid form preparations include powders (including sachets or packets thereof), dispersible granules (including sachets or packets thereof), tablets, capsules and suppositories. The powders and tablets may be comprised of from about 5 to about 95 percent of the active ingredient. Suitable solid carriers are known in the art, e.g., magnesium carbonate, magnesium stearate, talc, sugar or lactose.

Tablets, powders (including sachets or packets thereof), dispersible granules (including sachets or packets thereof) and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The term "pharmaceutical composition" is also intended to encompass both the bulk composition and individual dosage units comprised of more than one (e.g., two) pharmaceutically active agents such as, for example, a HCV inhibitor and one or more therapeutic agents selected from either or both a HCV protease inhibitor and one or more different therapeutic agents, as described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a subject by administering a pharmaceutical composition of the active ingredients in the combination product of the present invention is also intended to encompass the administration of the afore-said bulk composition and individual dosage units.

In one embodiment, the pharmaceutical composition of the active ingredients in the combination product is administered orally, intravenously or subcutaneously as a unit dosage form subdivided into suitably sized unit doses containing appropriate quantities of the active ingredients, e.g., an effective amount to achieve the desired therapeutic purpose. The actual dosage employed may be varied depending upon the requirements of the patient and the severity of the condition being treated. Determination of the proper dosage regimen for a particular situation is within the skill of the art. For convenience, the total daily dosage of the active ingredients in the combination product may be divided and administered in portions during the day as required.

The pharmaceutical composition(s) of the active ingredients in the combination product of the present invention may be administered in an amount effective to reduce the concentration of HCV RNA per milliliter of plasma to a level of less than about 29 IU/mL. The term "concentration of less than 29 International Units of HCV RNA per milliliter of plasma (29 IU/mL)" in the context of the present invention means that there are fewer than 29 IU/mL of HCV RNA, which translates into fewer than 100 copies of HCV-RNA per mL of plasma of the patient as measured by quantitative, multi-cycle reverse transcriptase PCR methodology.

HCV-RNA is preferably measured in the present invention by research-based RT-PCR methodology well known to the skilled clinician. This methodology is referred to herein as HCV-RNA/qPCR. The lower limit of detection of HCV-RNA is 29 IU/mL or 100 copies/mL. Serum HCV-RNA/qPCR testing and HCV genotype testing will be performed by a central laboratory (see, J G McHutchinson, et al., *N. Engl. J. Med.,* 1998, 339:1485-1492; and, G L. Davis, et al., *N. Engl. J. Med.,* 1998, 339:1493-1499).

BIOLOGICAL EXAMPLES

Among other assays known to those skilled in the art for determining inhibition of viral replication, the following example demonstrates the effect on HCV replicon RNA response after treatment with an embodiment of the combination product of the present invention.

Example 1

Combination of HCV Inhibitor and HCV Therapeutic Agents

Replicon Response to Antiviral Agent(s)

Replicon cells were seeded at 5000 cells/well in 96-well plates and were treated with a HCV inhibitor and/or a HCV therapeutic agent for three days. The growth medium consisted of a final concentration of 0.5% DMSO and 10% fetal bovine serum.

The HCV therapeutic agents, an interferon-α, a NS5b HCV polymerase inhibitor Compound 1p and a NS3/NS4a HCV protease inhibitor Compound 2p in the compound treatment samples were each serially diluted to the concentration ratios indicated in Table 1. Replicon cells in the untreated control were not treated with a HCV inhibitor or therapeutic agent. To each concentration of therapeutic agent, the HCV inhibitor Compound 661 was titrated. After three days, Bright Glo agent was used to detect luciferase activity. The activity of the medium without cells was measured as the background control. Replicon inhibition was calculated using the following formula:

$$\%\ \text{Inhibition} = 100 \times \left[1 - \left(\frac{\text{Luciferase count of compound treatment sample} - \text{background control}}{\text{Luciferase count of untreated control} - \text{background control)}}\right)\right]$$

The combination index results for various combination ratios at various levels of maximal inhibitory concentration ($IC_{50}$, $IC_{75}$, $IC_{90}$) for representative embodiments of the combination product of the present invention shown in Table 1 demonstrate the inhibition of replicon replication after treatment, wherein the embodiments of the combination product comprise a HCV inhibitor Compound 661, representative of compounds described herein, in combination with a therapeutic agent selected from interferon-α, a NS5b HCV polymerase inhibitor Compound 1p, or a NS3/NS4a HCV protease inhibitor Compound 2p.

TABLE 1

| Cpd 661 (μM) | Combination ratio | Combination Index | | |
|---|---|---|---|---|
| Combinations | (Cpd 661:agent) | $IC_{50}$ | $IC_{75}$ | $IC_{90}$ |
| Interferon-α (U/mL) | 0.031:1 to 0.5:1 | 0.36-0.84 | 0.42-0.78 | 0.35-0.72 |
| Cpd 1p (μM) | 0.019:1 to 0.3:1 | 0.19-0.94 | 0.13-0.61 | 0.09-0.4 |
| Cpd 2p (μM) | 18.75:1 to 300:1 | 0.26-0.91 | 0.27-0.66 | 0.29-0.48 |

The summary of results for the combination products in Table 1 show reduced replicon RNA levels after replicon cells were treated for three days with embodiments of the combination product of the present invention.

The results of Example 1 demonstrate that the combination of a therapeutic agent and a HCV inhibitor is more efficacious in inhibiting HCV RNA replication in replicon cells than either the HCV inhibitor or therapeutic agent alone.

It will be appreciated by those skilled in the art that changes could be made to the embodiments described above without departing from the broad inventive concept thereof. It is understood, therefore, that this invention is not limited to the particular embodiments disclosed herein, but it is intended to cover modifications that are within the spirit and scope of the invention, as defined by the appended claims.

Each document (including granted patents, published patent applications, and nonpatent publications such as journal articles) referred to in this application is incorporated herein in its entirety by reference for all purposes. Citation of or reference to any application or publication herein is not an admission that such document is available as prior art to the present invention.

What is claimed:

1. A combination product for treating or ameliorating HCV (hepatitis C virus) infection or disorders or symptoms associated therewith in a subject in need thereof comprising a HCV inhibitor selected from:

1
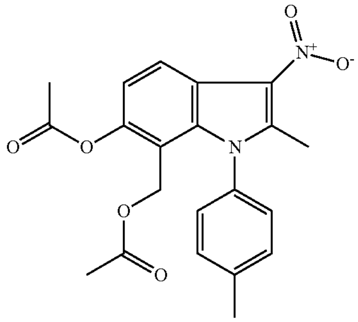
2
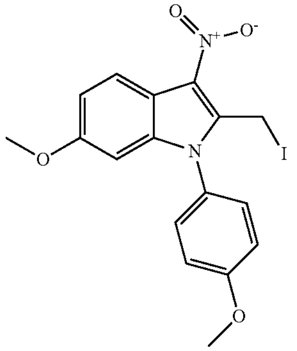
3
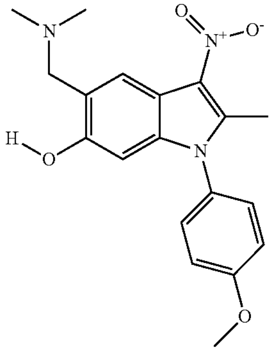
4
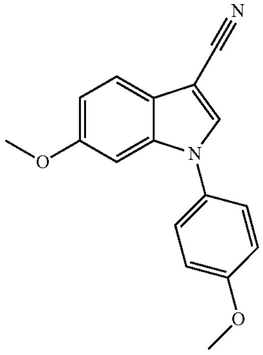
5
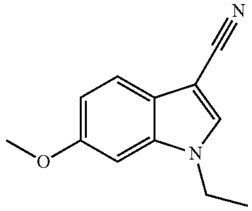
-continued
6
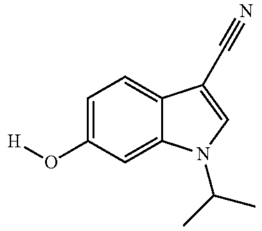
7
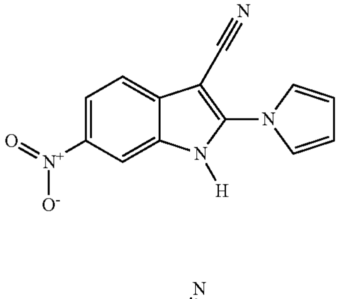
8
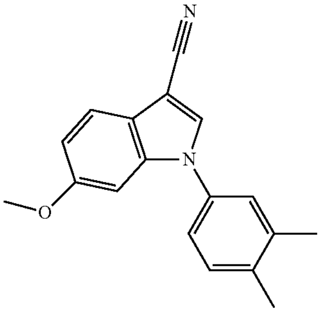
9
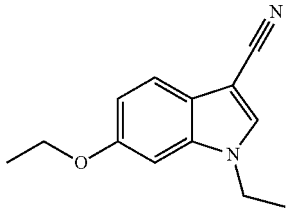
10
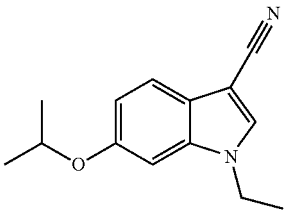
11
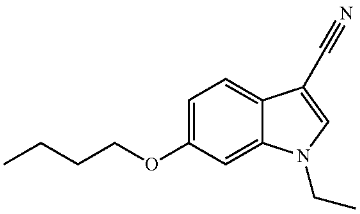

-continued
12
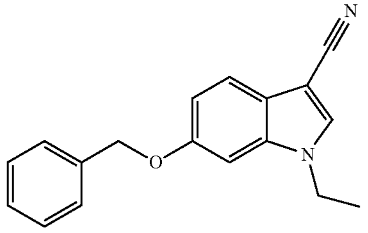
13
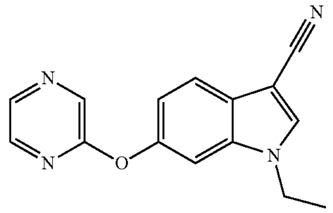
14
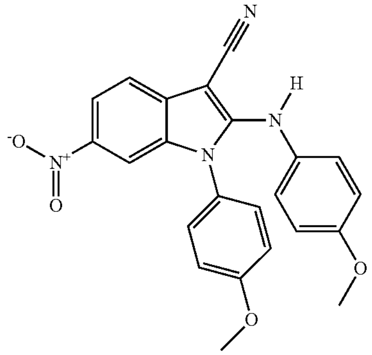
15
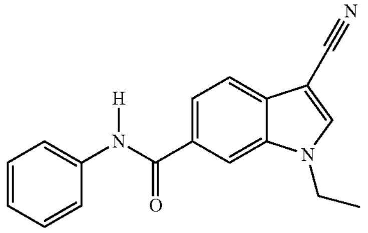
16
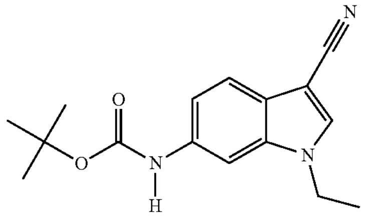
17
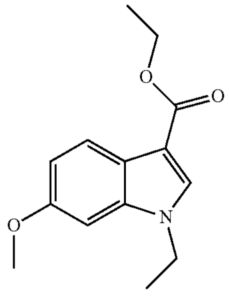
-continued
18
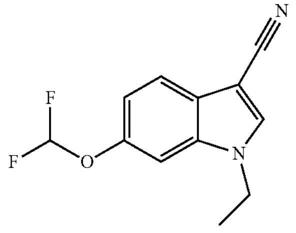
19
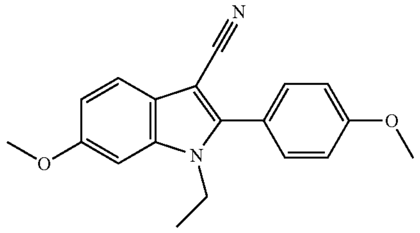
20
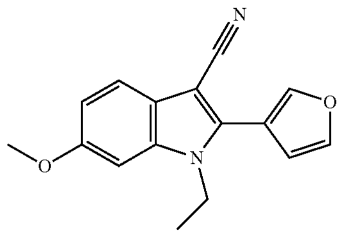
21
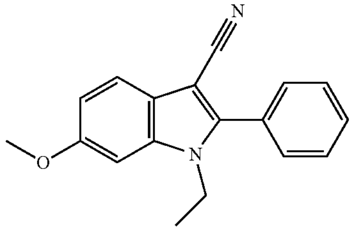
22
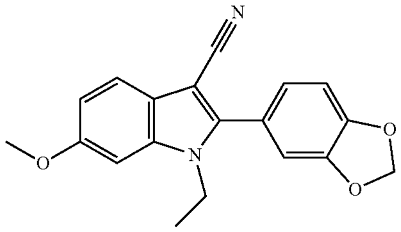
23
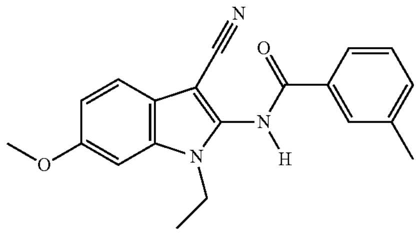

24
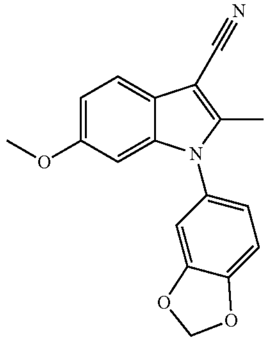
25
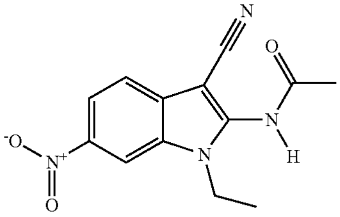
26
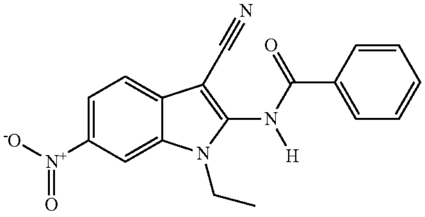
27
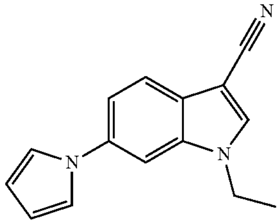
28
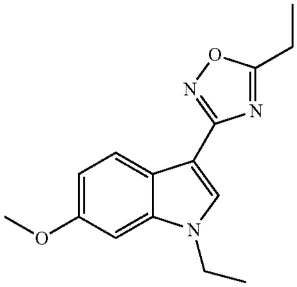
29
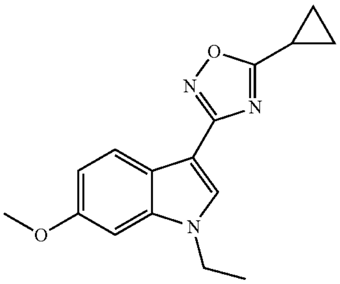
30
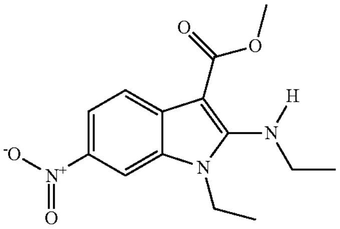
31
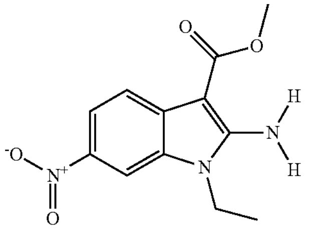
32
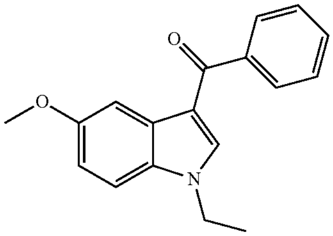
33
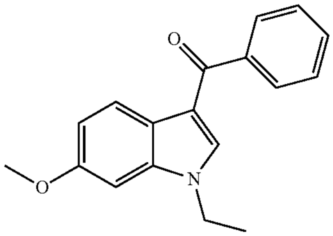
34
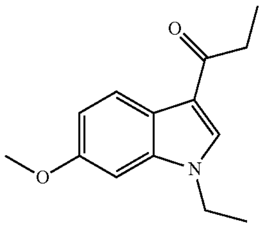
35
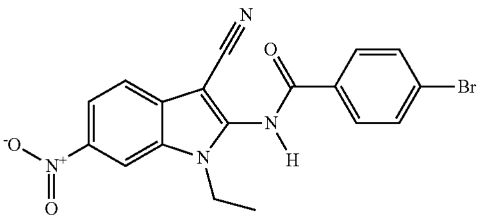

-continued
36
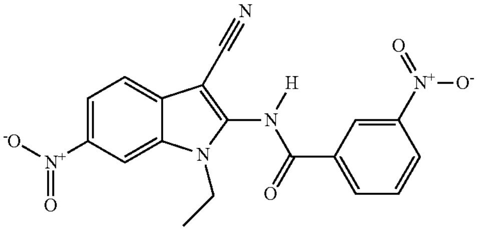
37
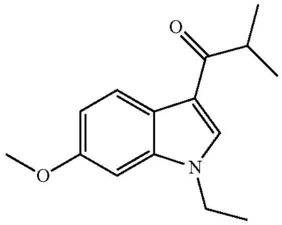
38
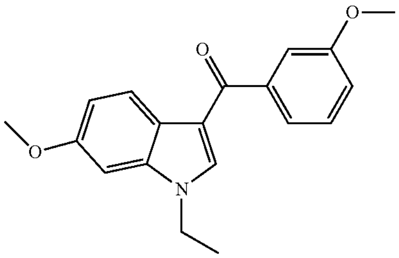
39
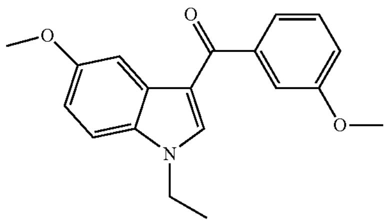
40
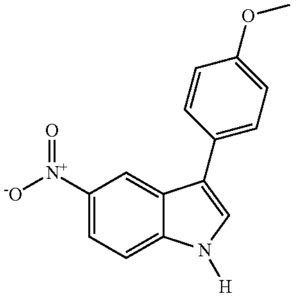
41
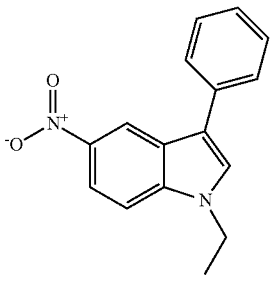
-continued
42
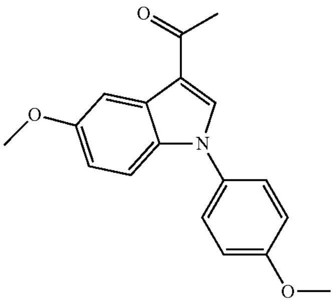
43
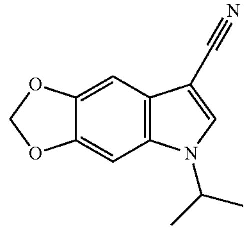
44
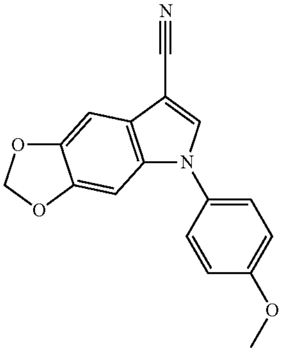
45
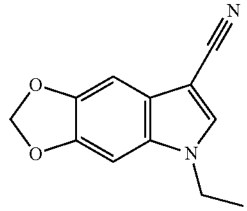
46
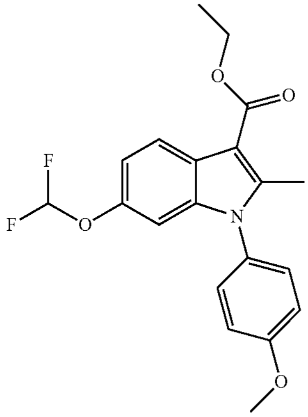

-continued
47
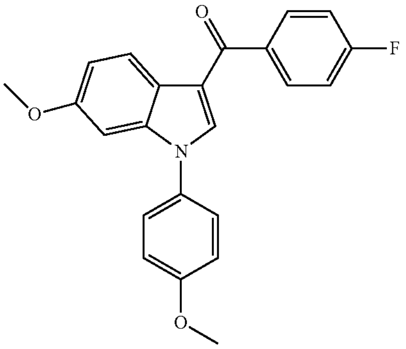
48
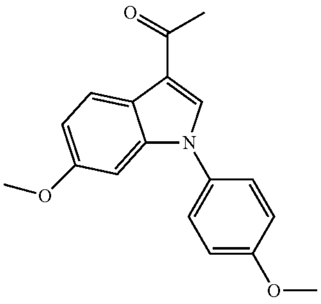
49
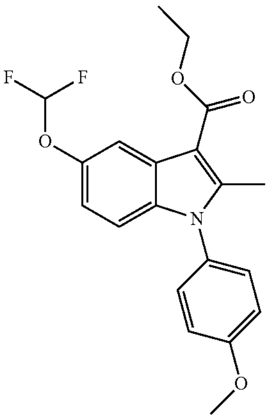
50
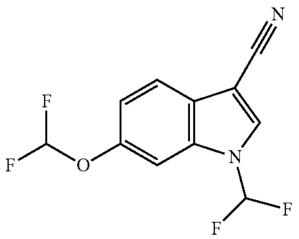
51
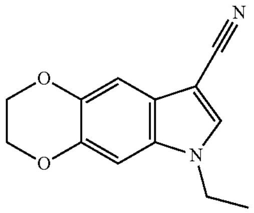
-continued
52
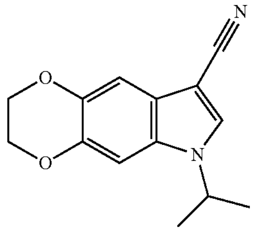
53
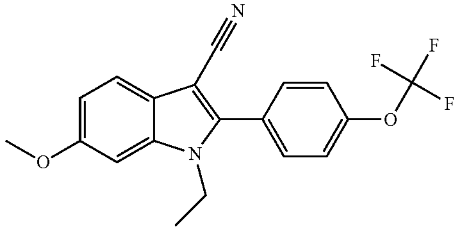
54
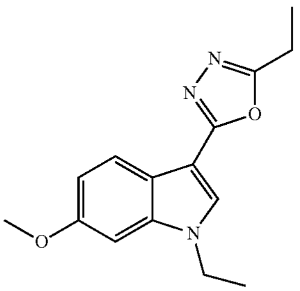
55
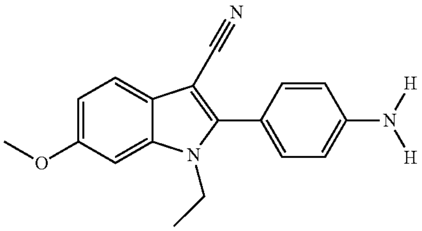
56
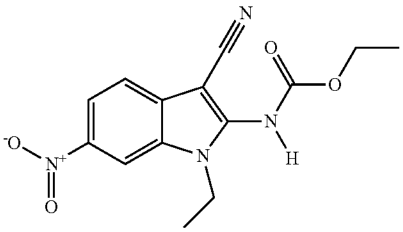
57
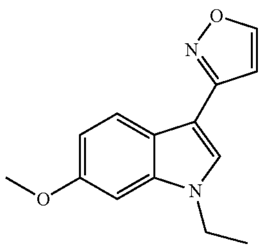

-continued
58
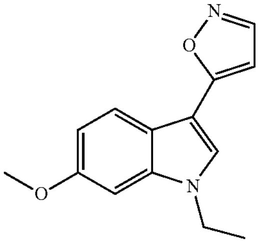
59
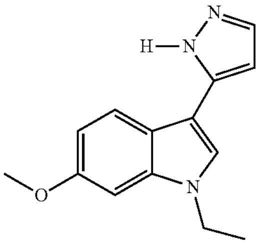
60
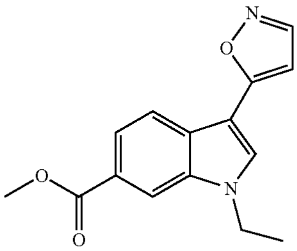
61
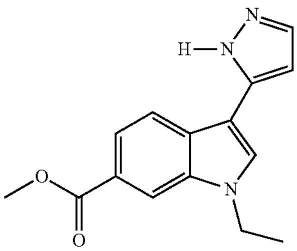
62
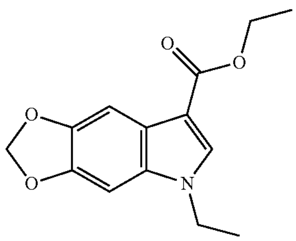
63
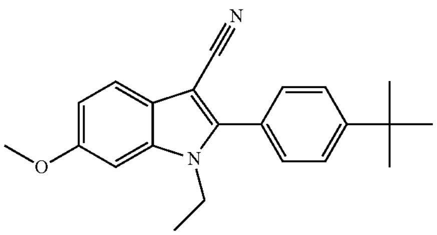
-continued
64
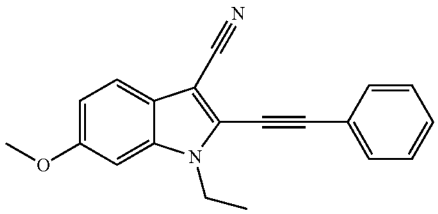
65
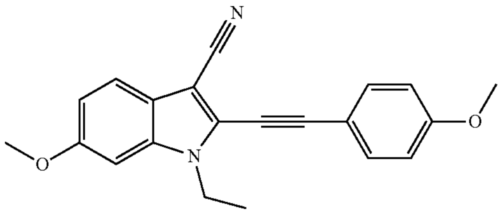
66
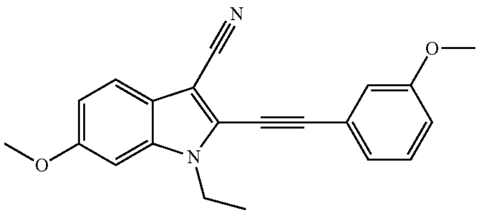
67
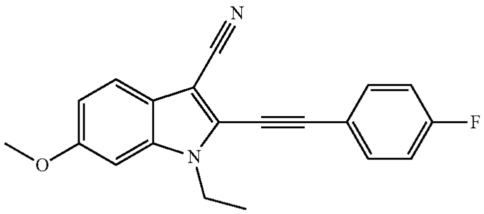
68
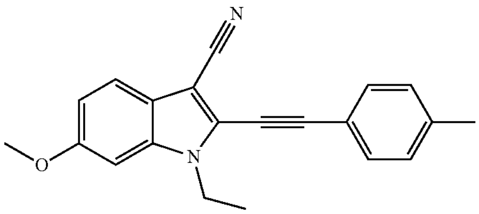
69
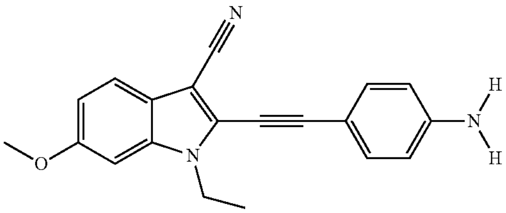
70
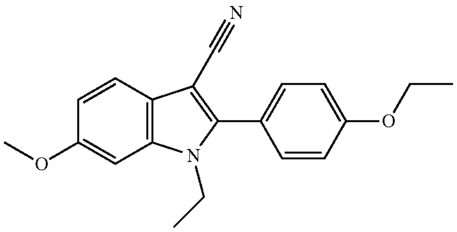

-continued
71
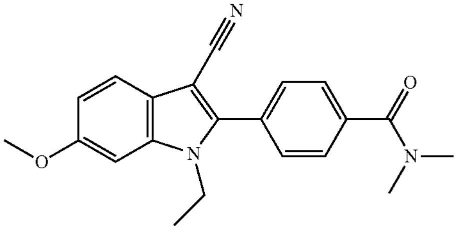
72
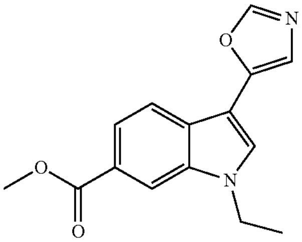
73
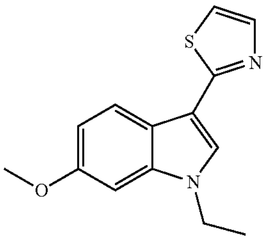
74
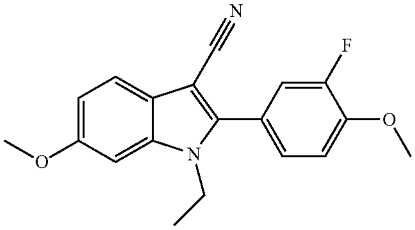
75
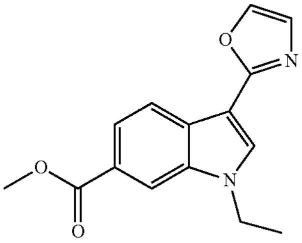
76
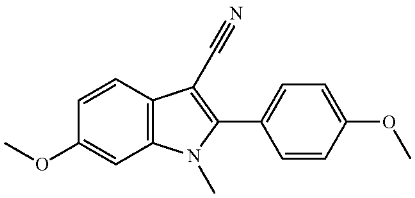
77
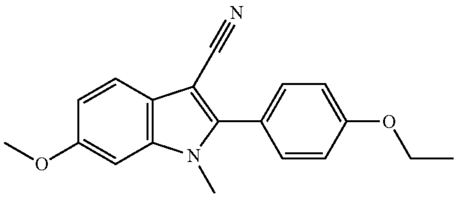
-continued
78
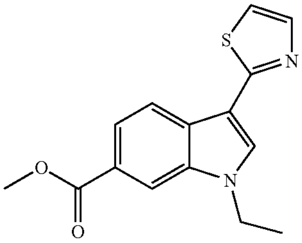
79
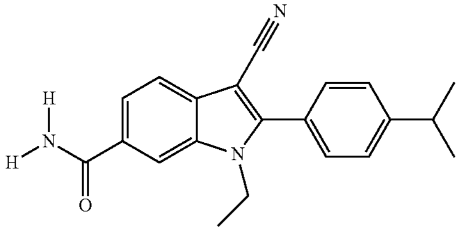
80
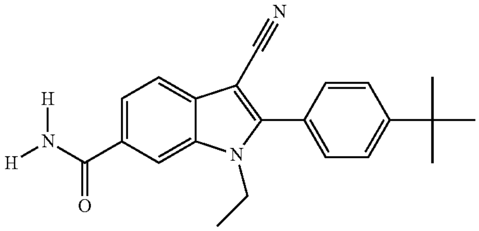
81
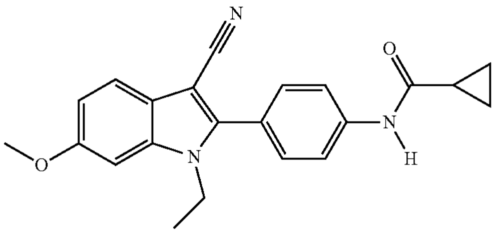
82
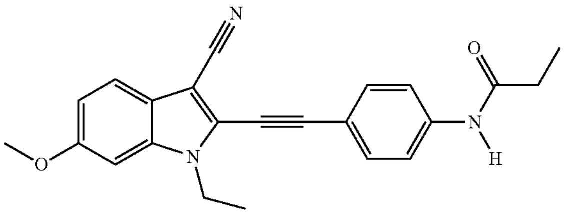
83
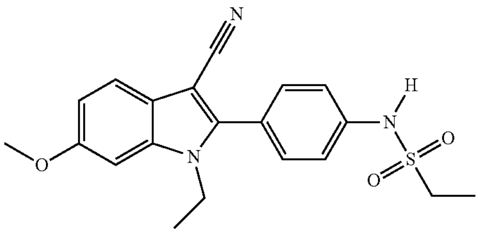

-continued
84
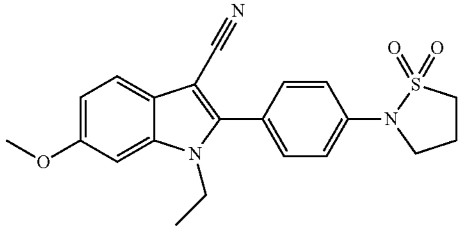
85
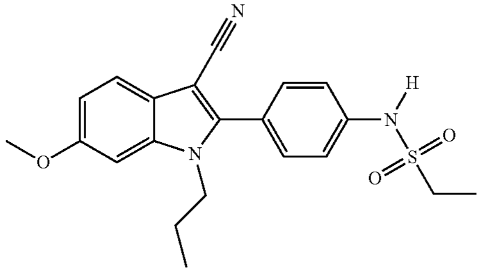
86
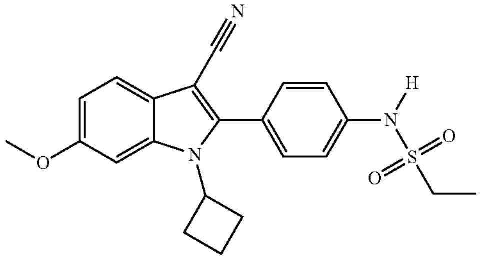
87
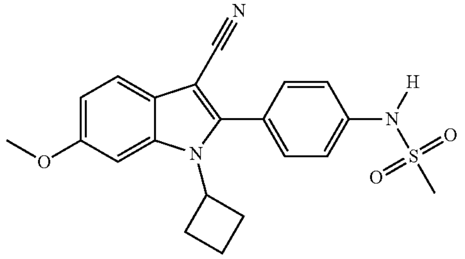
88
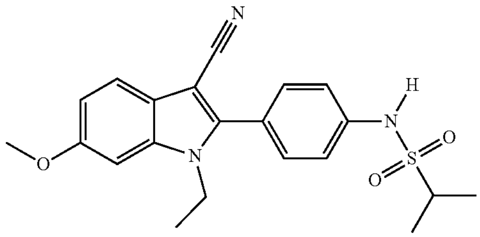
89
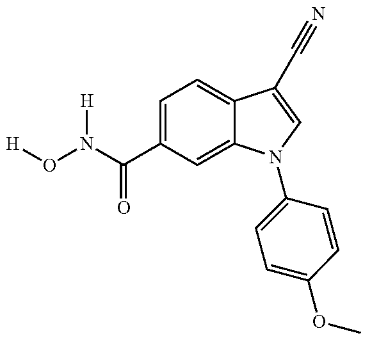
-continued
90
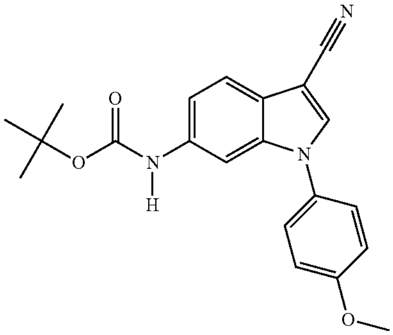
91
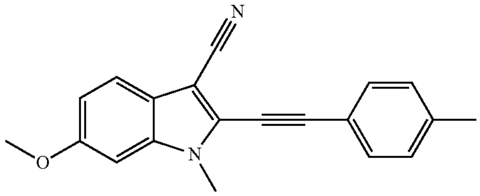
92
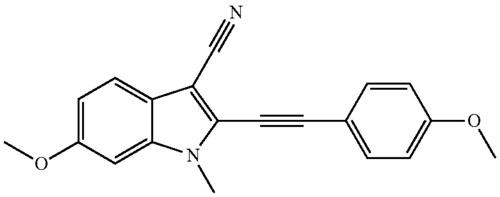
93
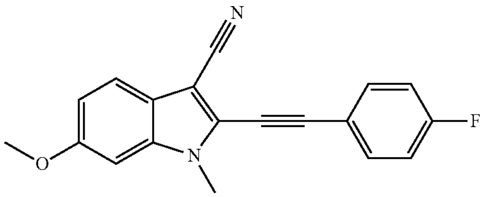
94
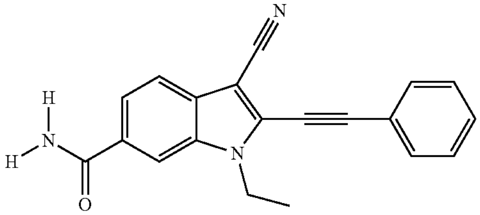
95
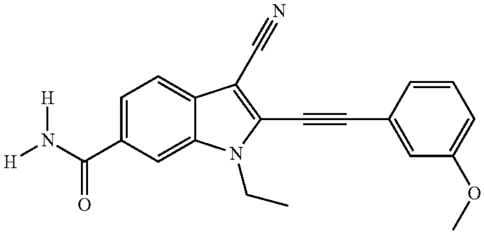

-continued
96
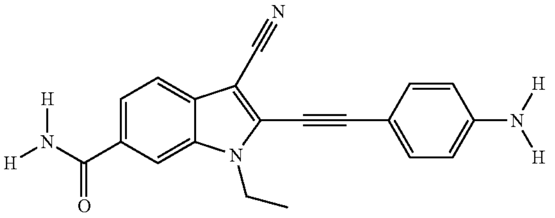
97
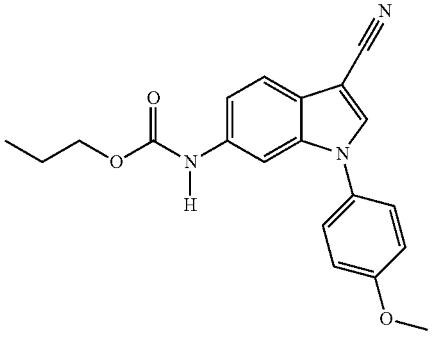
98
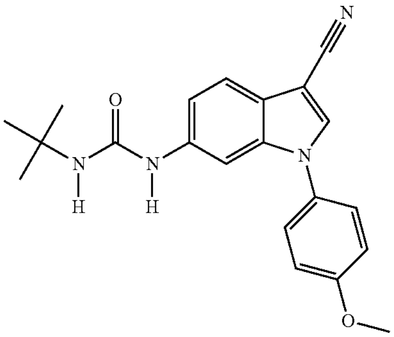
99
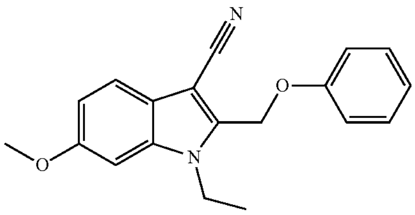
100
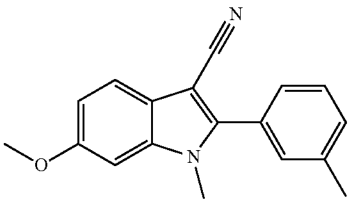
-continued
101
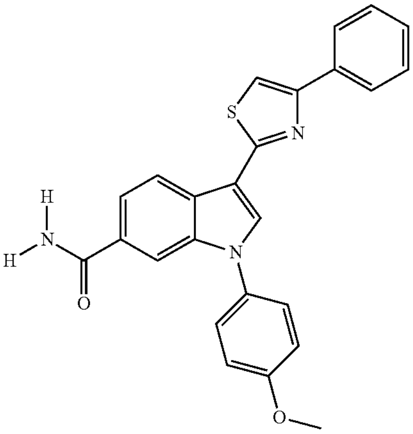
102
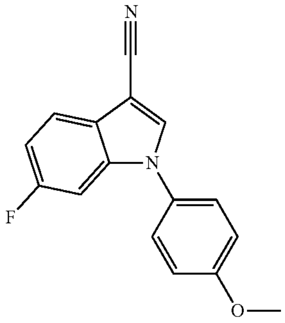
103
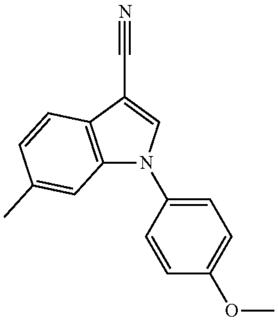
104
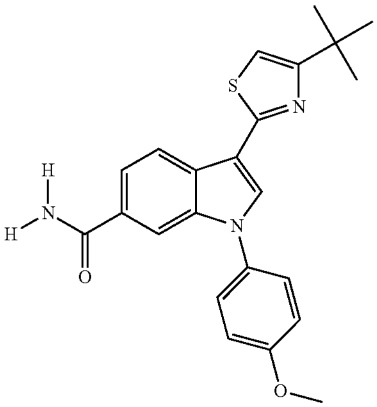

105
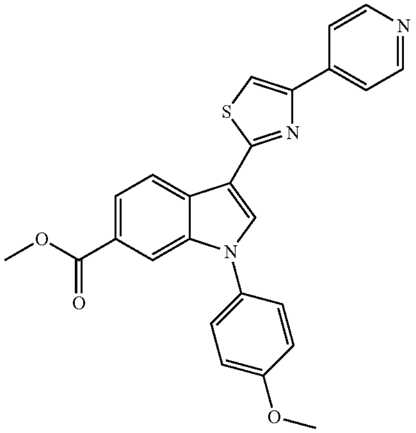
106
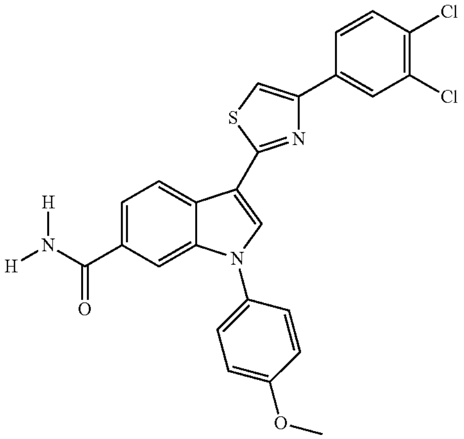
107
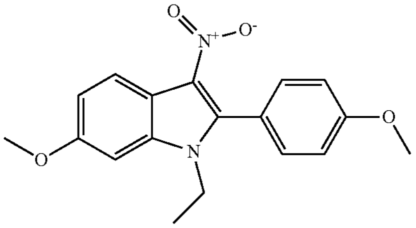
108
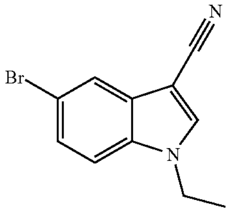
109
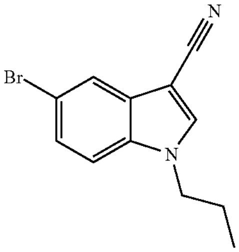
110
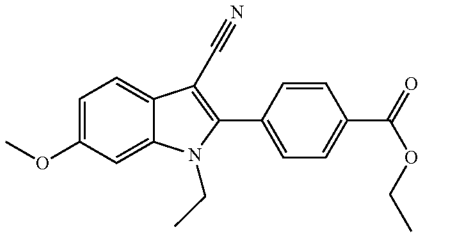
111
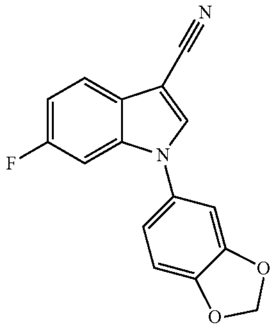
112
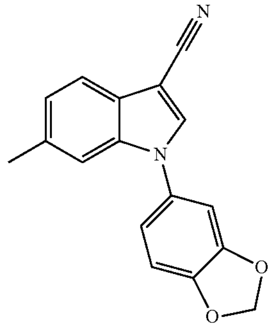
113
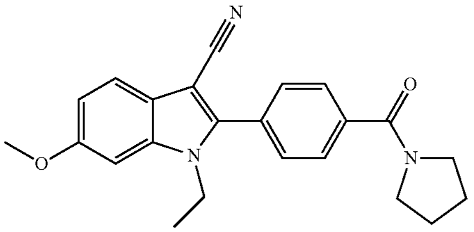
114
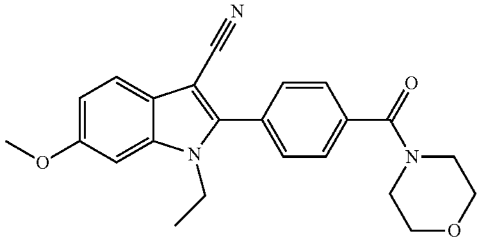
115
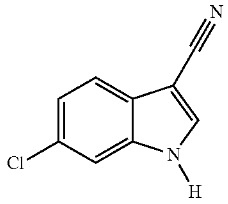

-continued
116
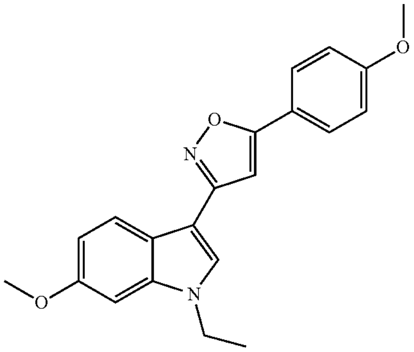
117
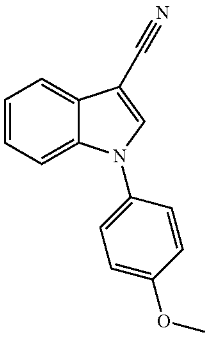
118
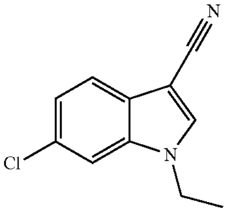
119
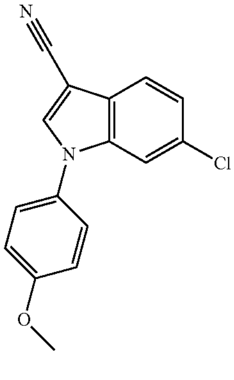
120
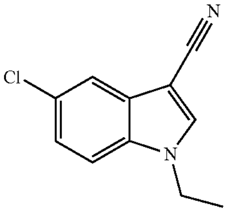
-continued
121
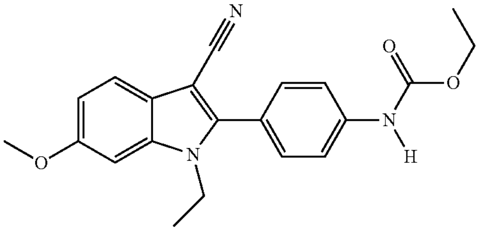
122
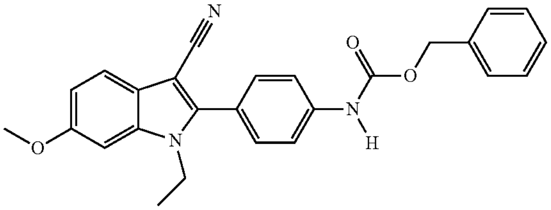
123
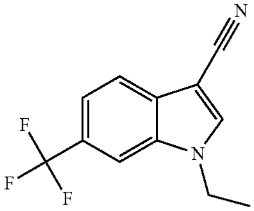
124
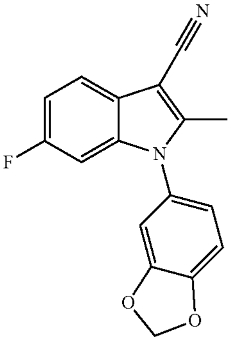
125
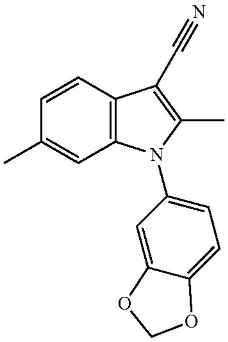
126
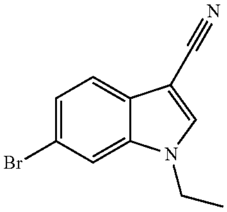

127
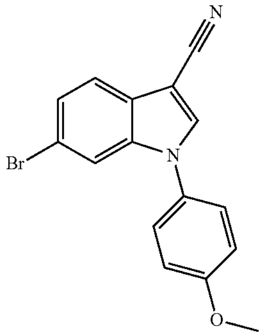
128
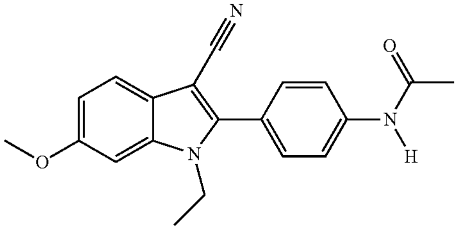
129
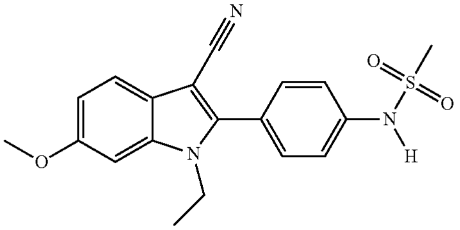
130
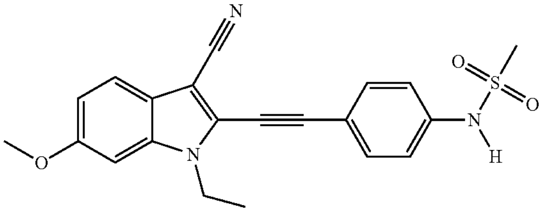
131
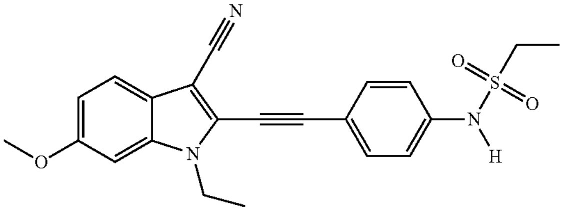
132
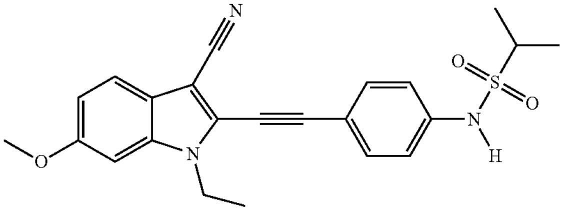
133
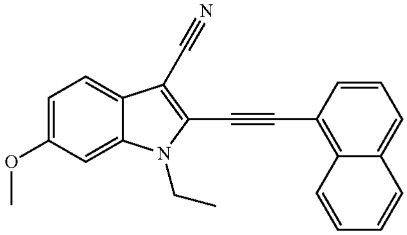
134
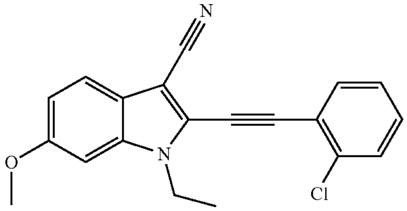
135
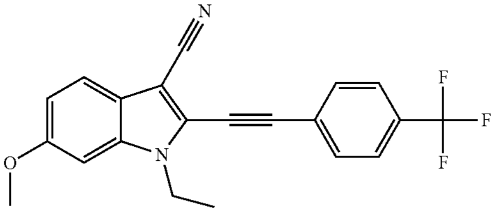
136
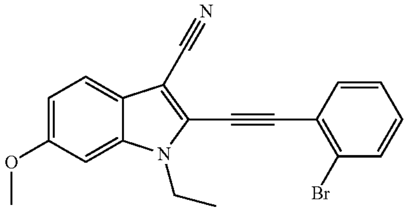
137
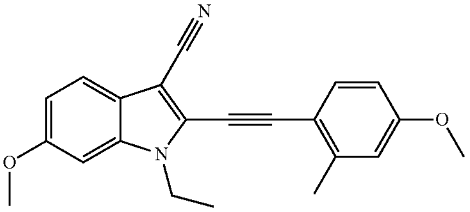
138
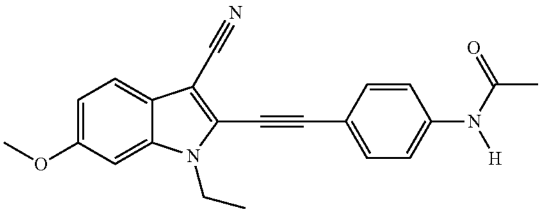
139
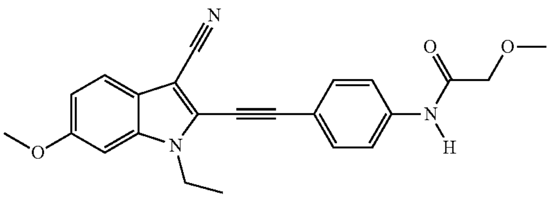

-continued
140
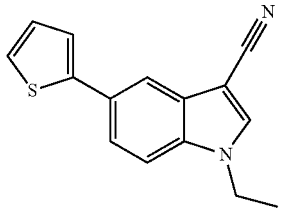
141
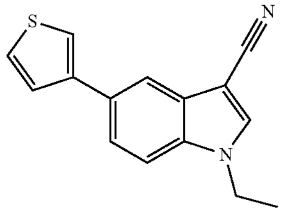
142
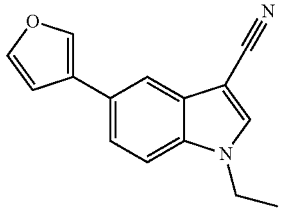
143
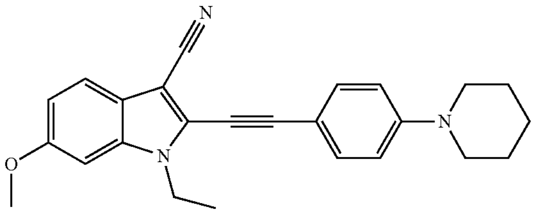
144
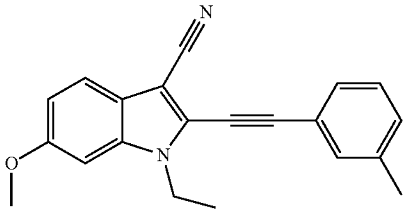
145
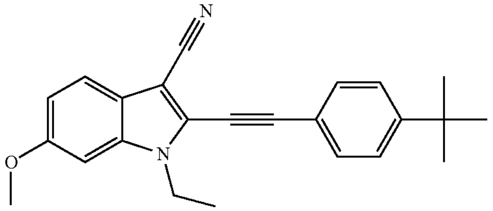
146
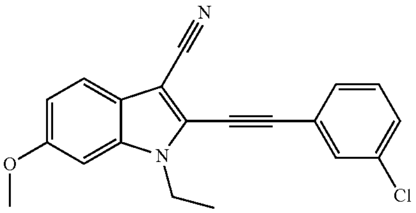
-continued
147
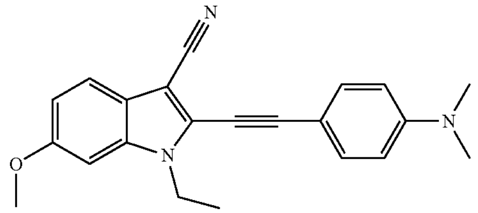
148
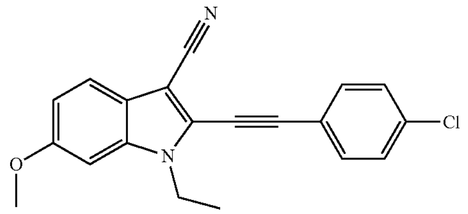
149
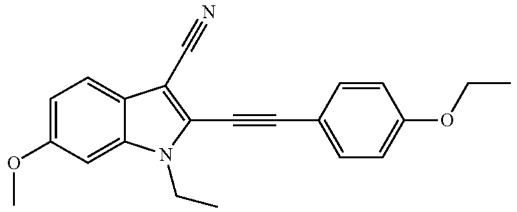
150
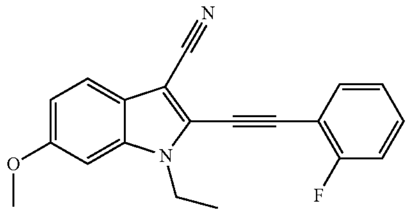
151
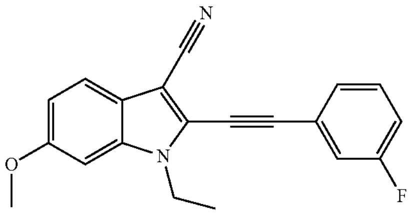
152
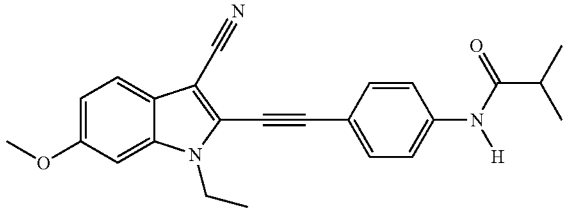
153
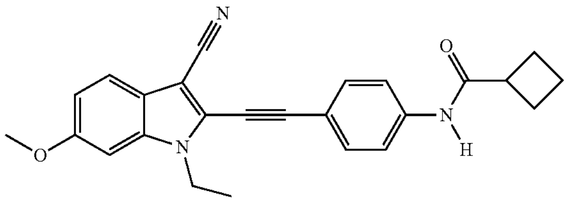

-continued
154
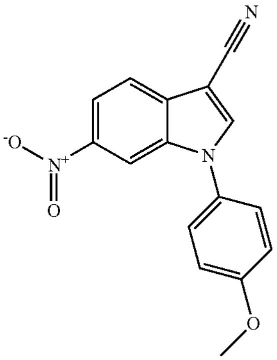
155
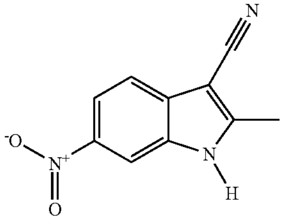
156
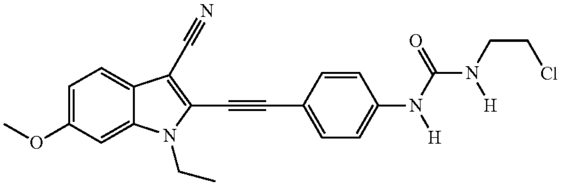
157
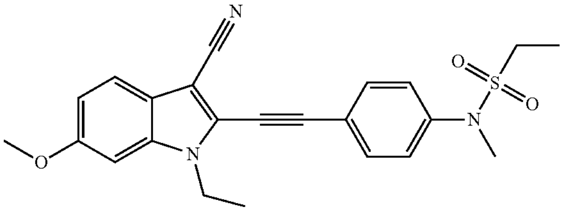
158
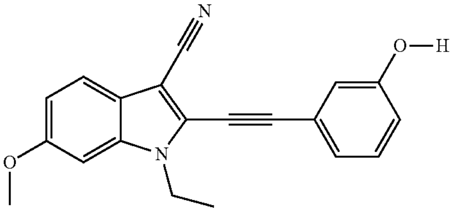
159
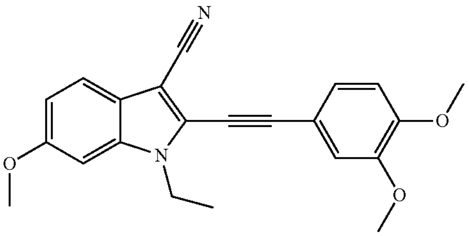
-continued
160
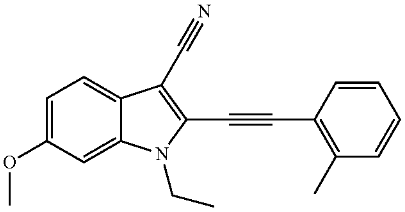
161
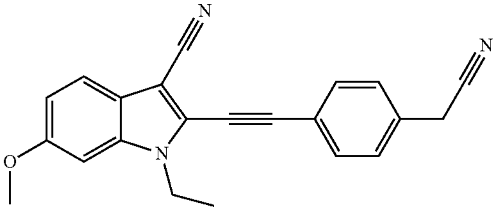
162
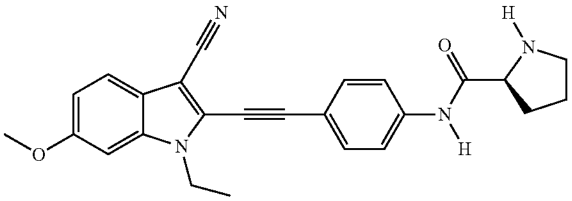
163
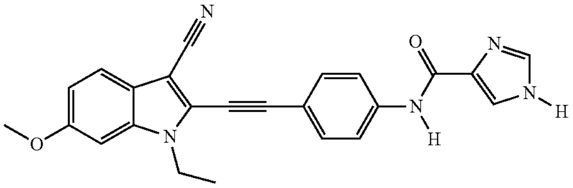
164
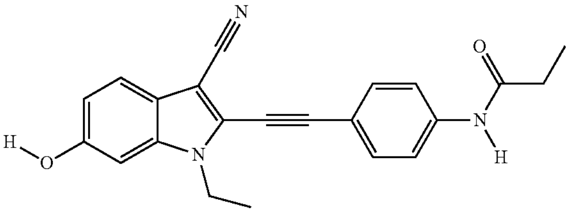
165
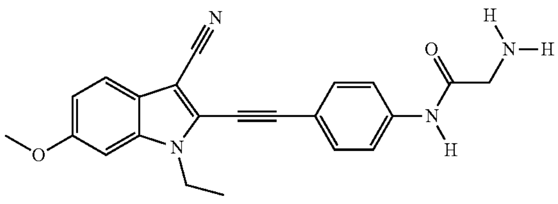
166
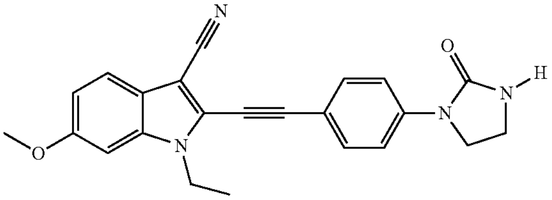

-continued
167
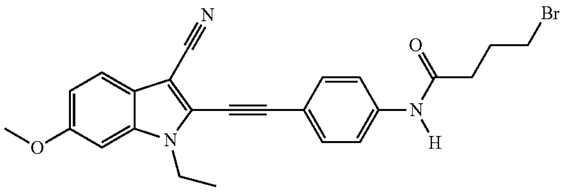
168
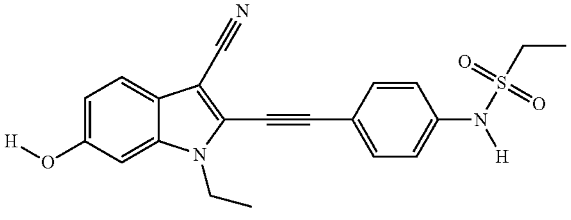
169
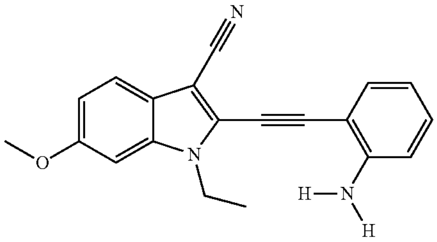
170
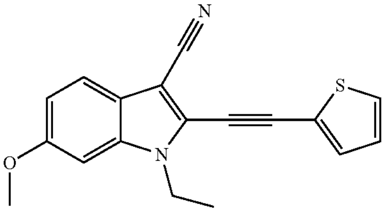
171
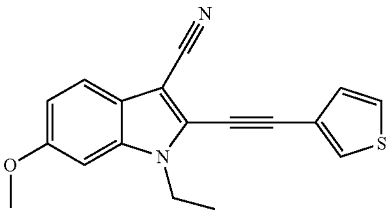
172
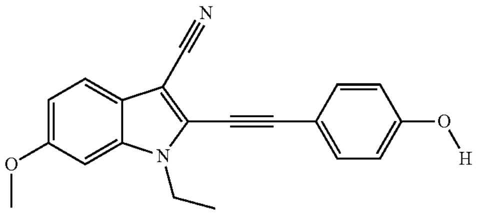
173
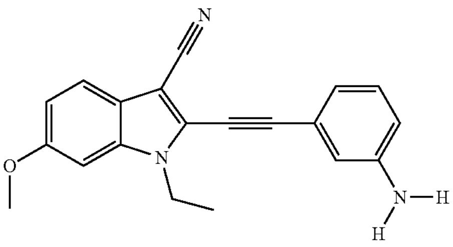
-continued
174
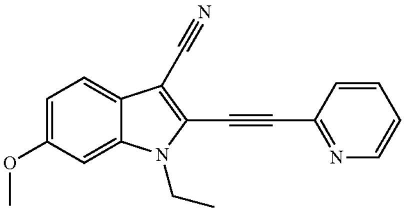
175
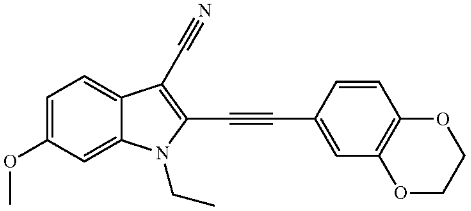
176
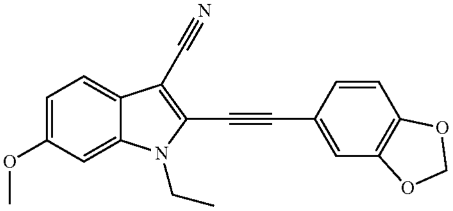
177
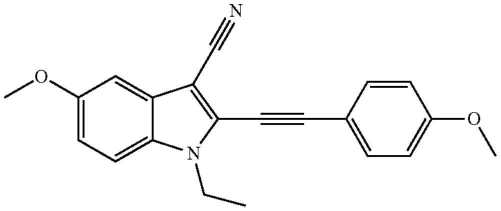
178
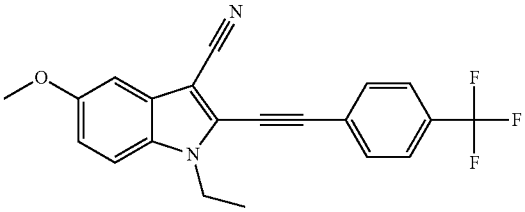
179
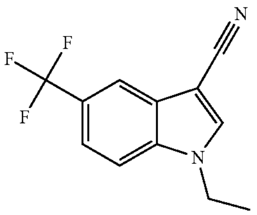
180
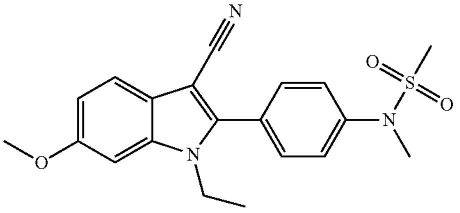

-continued
181
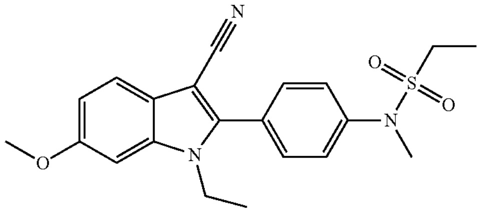
182
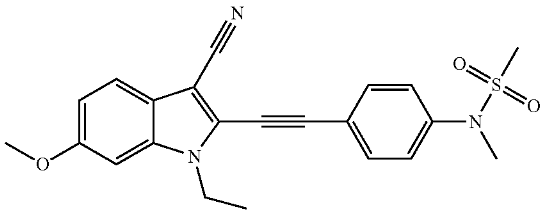
183
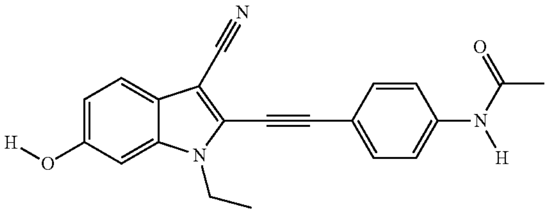
184
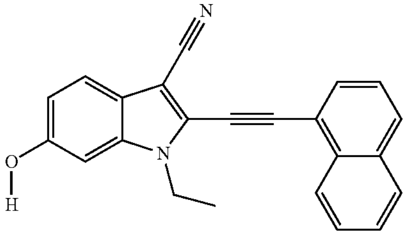
185
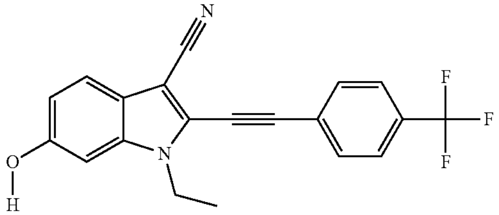
186
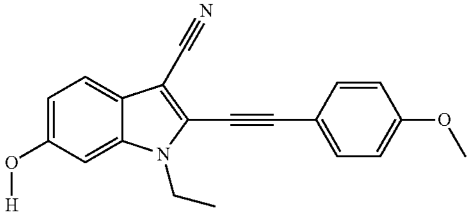
187
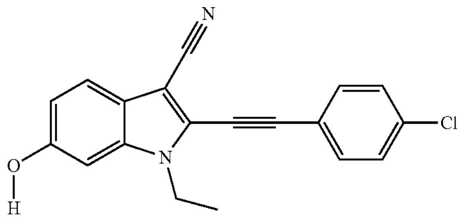
-continued
188
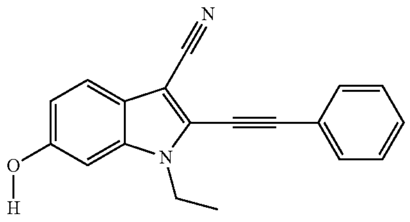
189
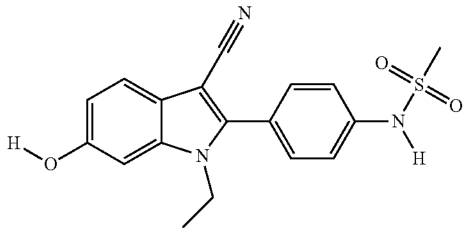
190
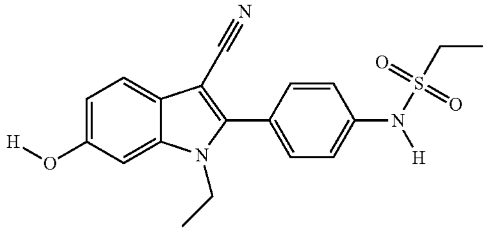
191
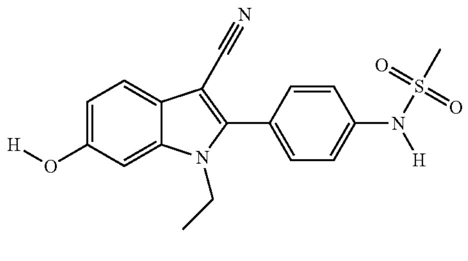
192
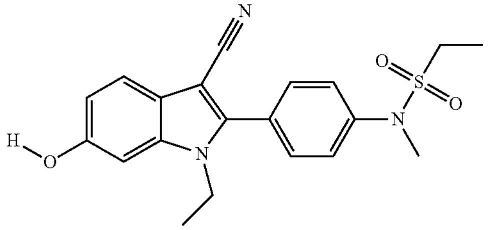
193
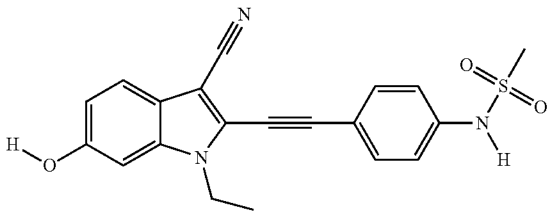

-continued
194
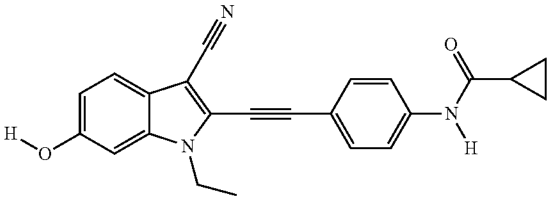
195
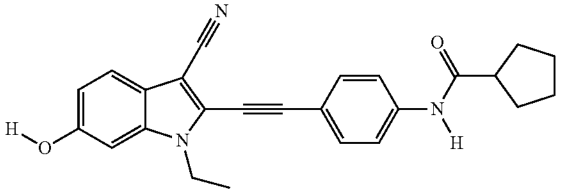
196
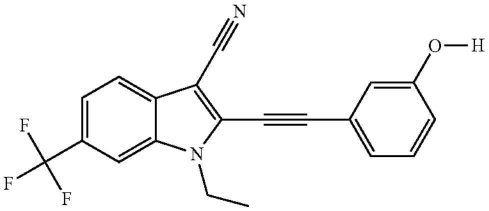
197
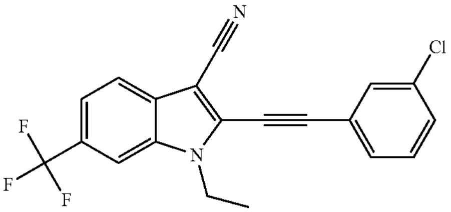
198
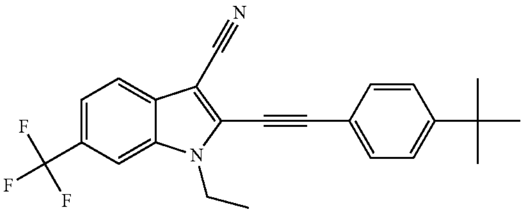
199
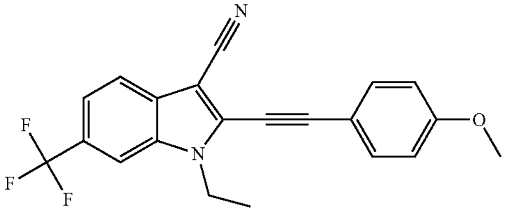
200
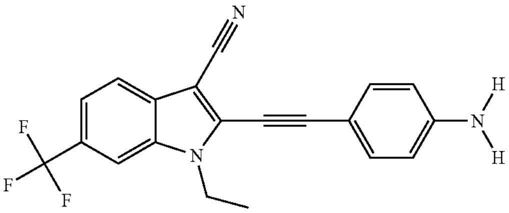
-continued
201
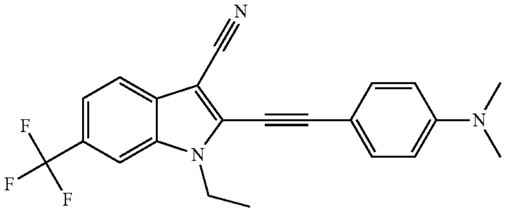
202
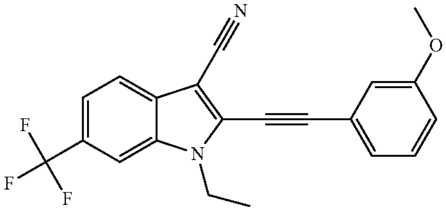
203
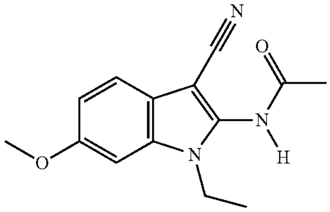
204
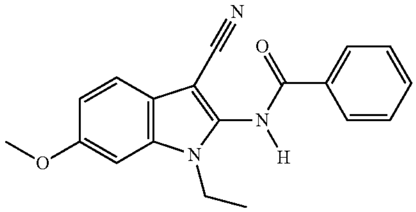
205
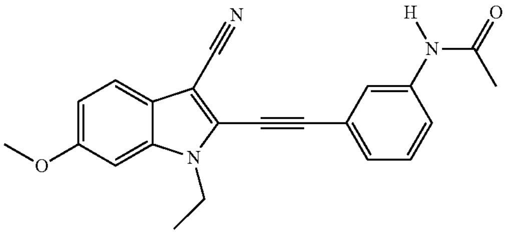
206
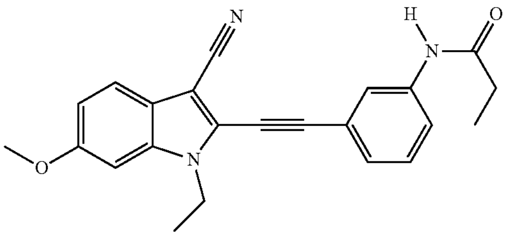
207
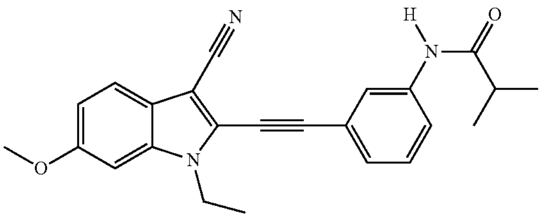

-continued
208
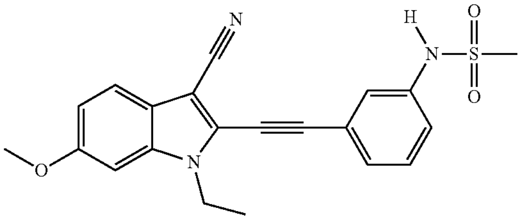
209
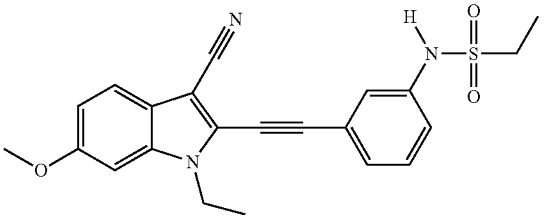
210
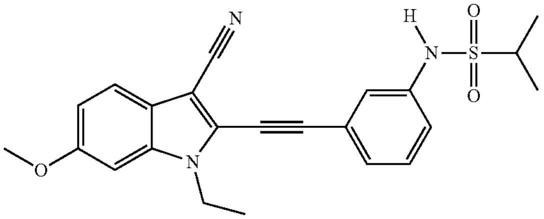
211
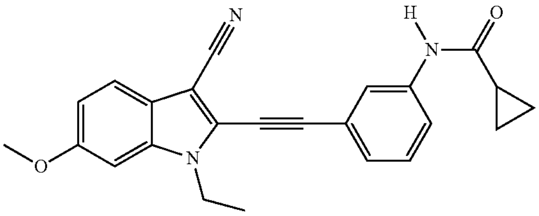
212
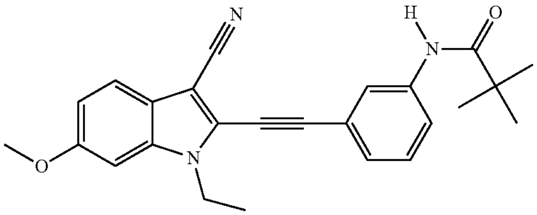
213
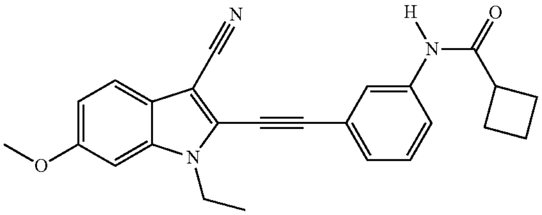
-continued
214
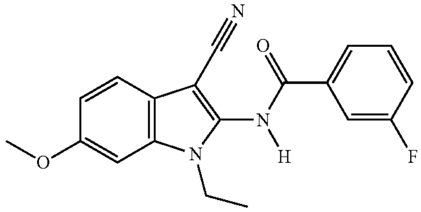
215
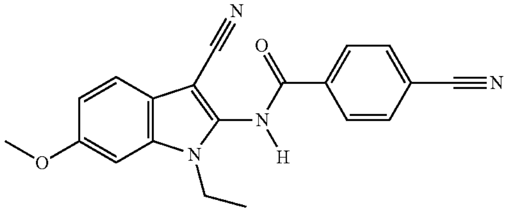
216
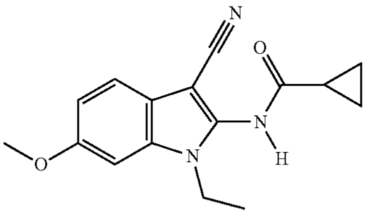
217
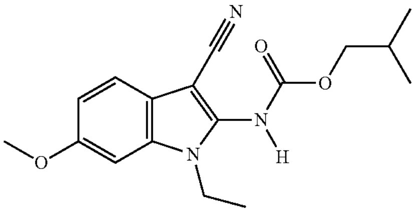
218
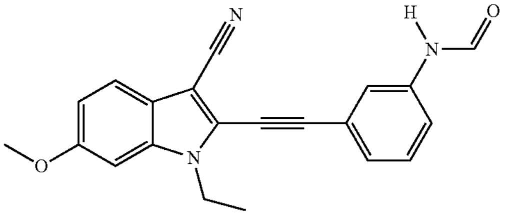
219
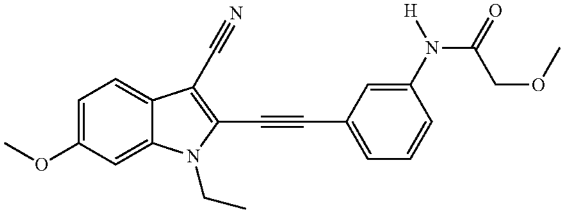
220
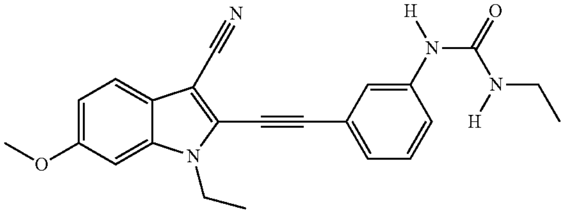

-continued
221
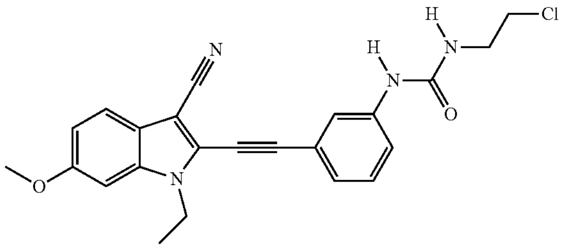
222
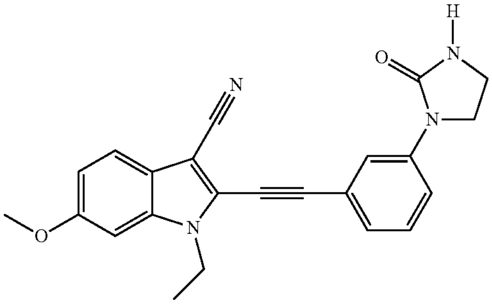
223
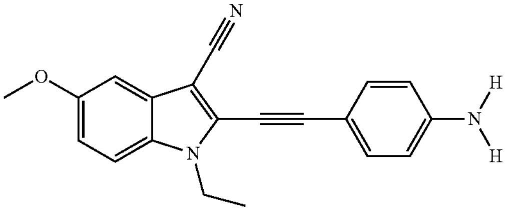
224
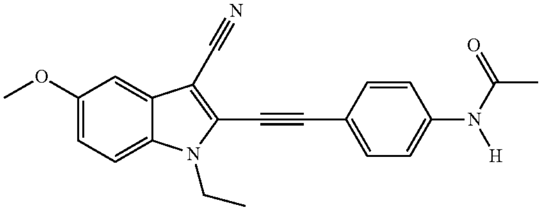
225
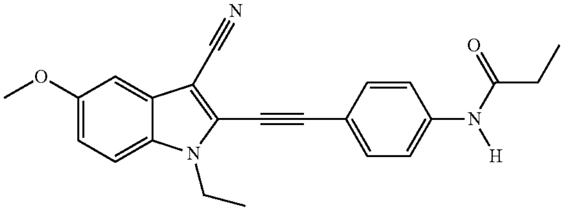
226
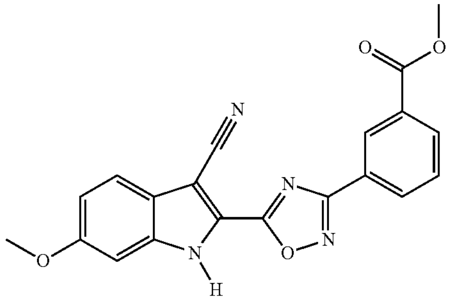
-continued
227
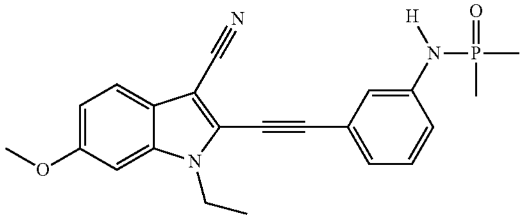
228
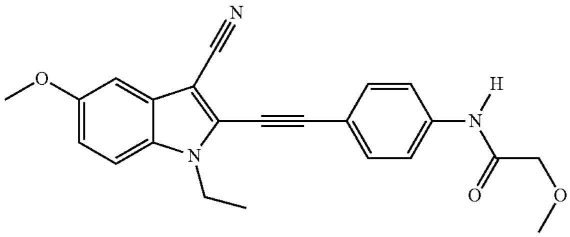
229
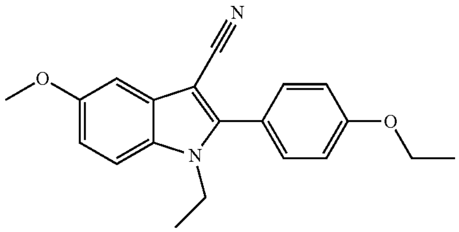
230
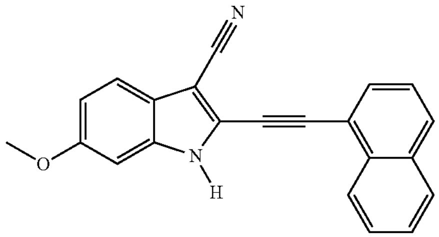
231
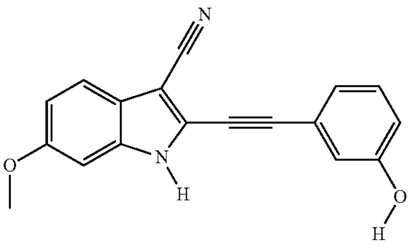
232
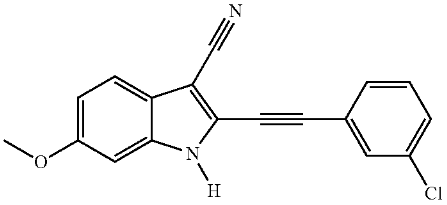

-continued
233
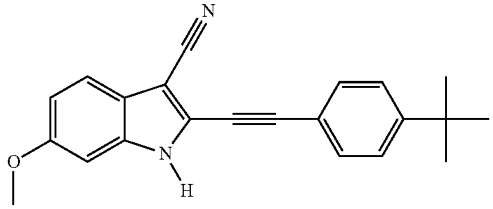
234
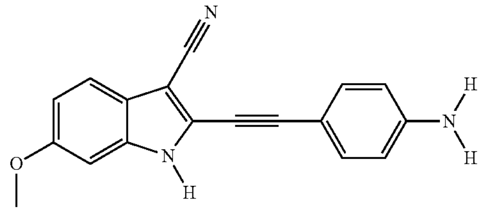
235
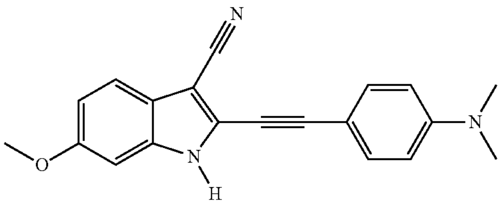
236
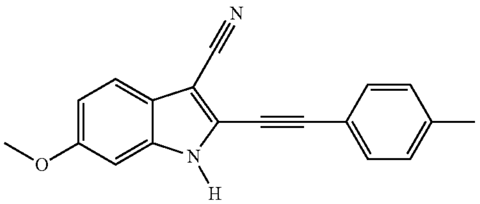
237
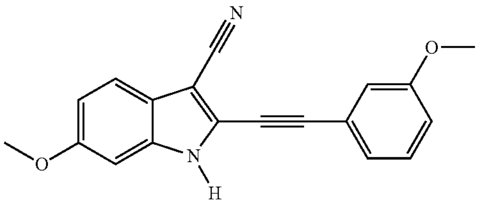
238
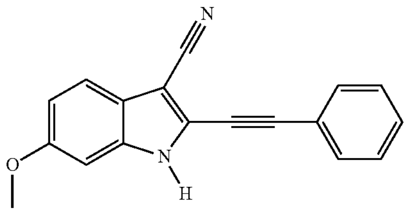
239
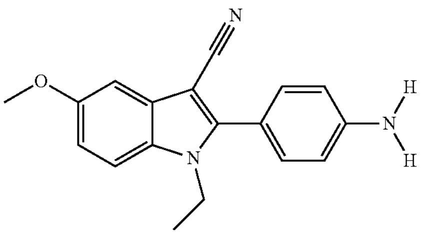
-continued
240
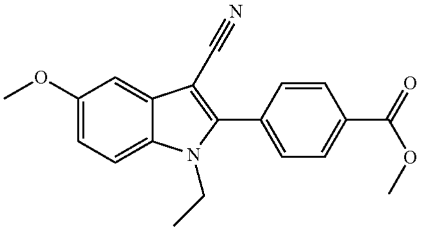
241
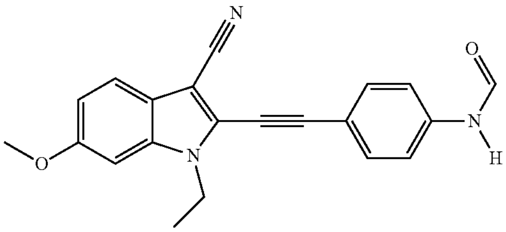
242
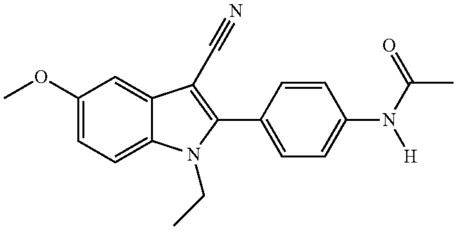
243
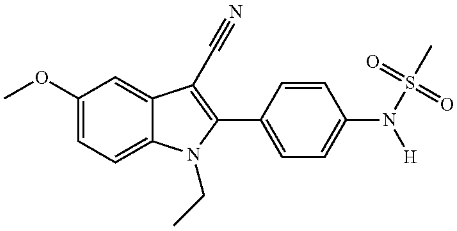
244
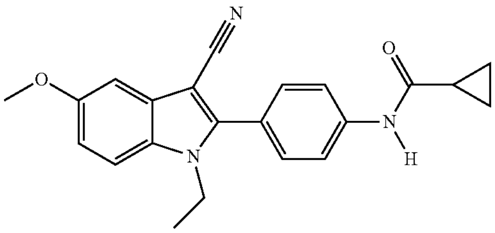
245
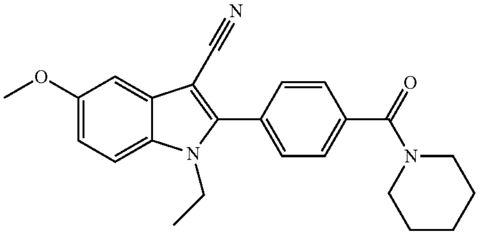

-continued
246
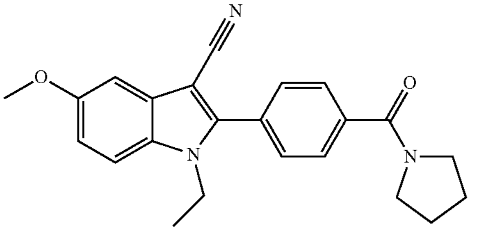
247
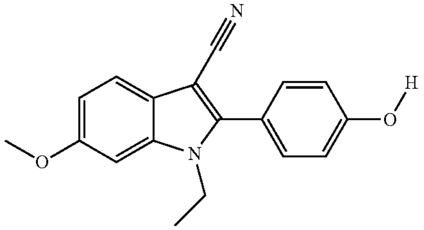
248
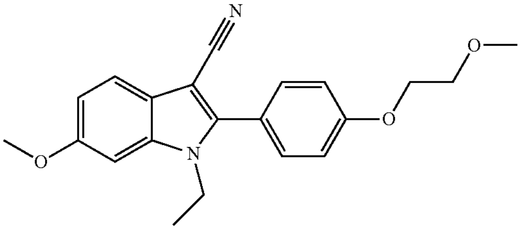
249
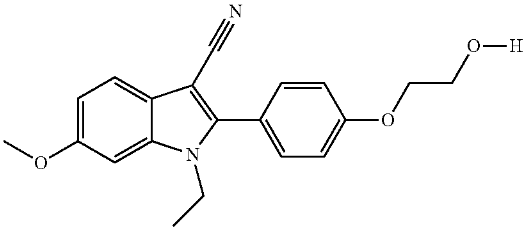
250
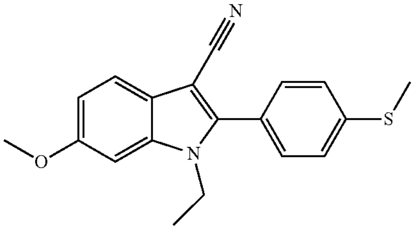
251
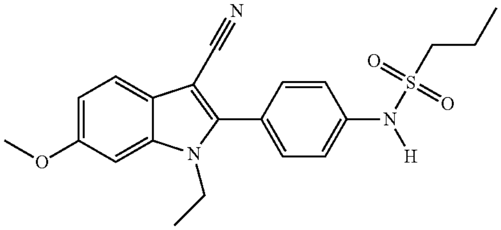
-continued
252
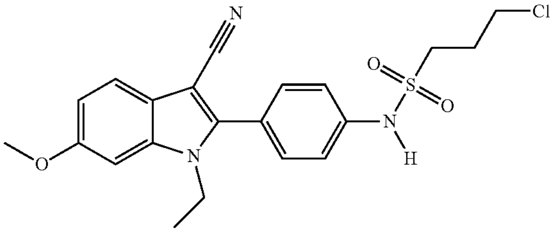
253
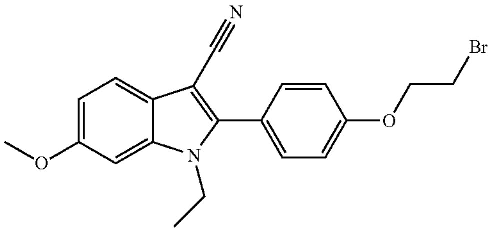
254
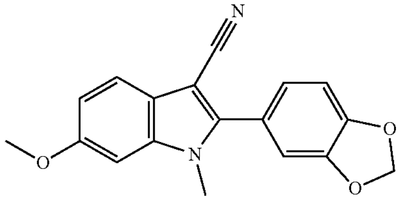
255
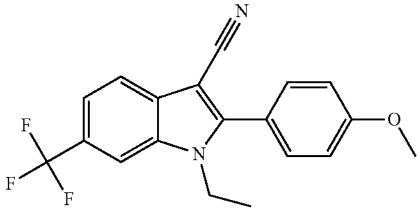
256
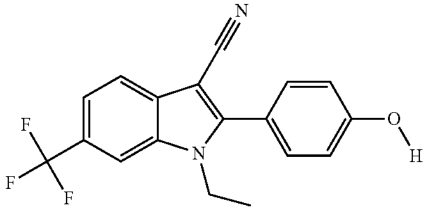
257
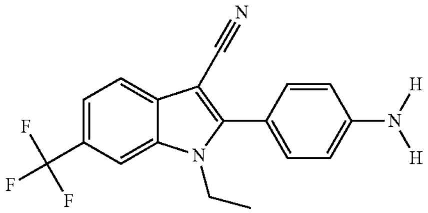
258
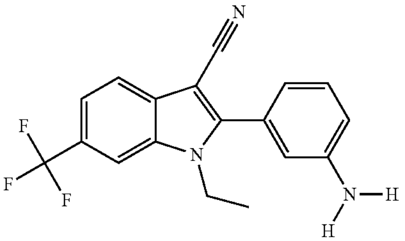

-continued
259
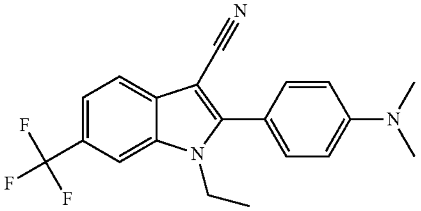
260
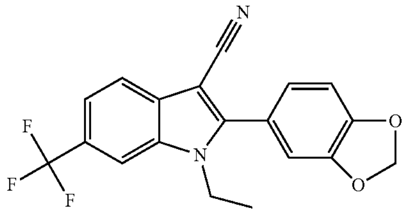
261
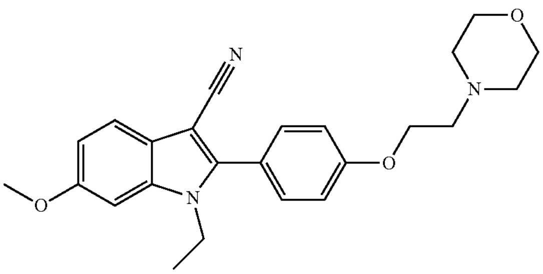
262
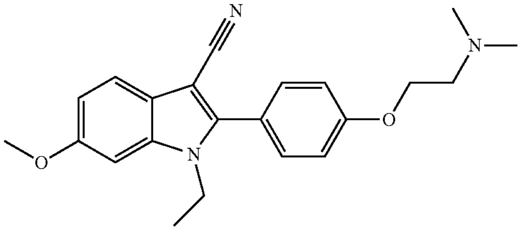
263
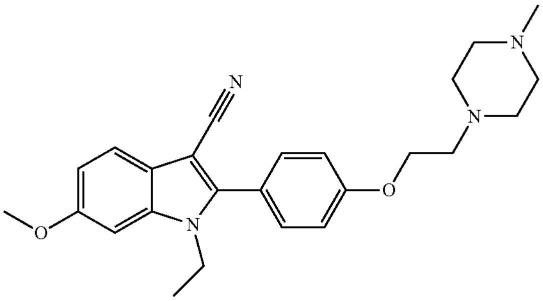
264
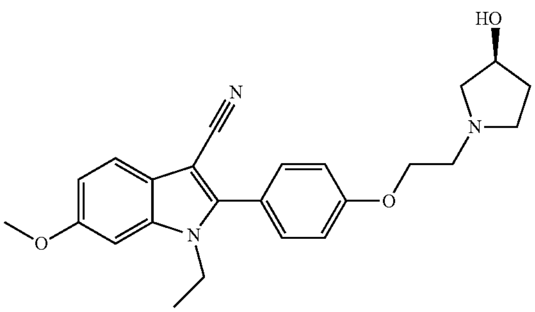
-continued
265
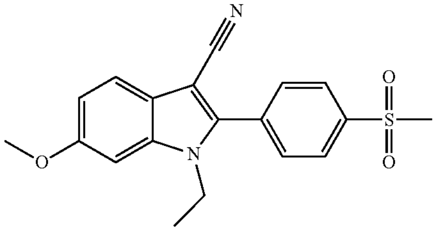
266
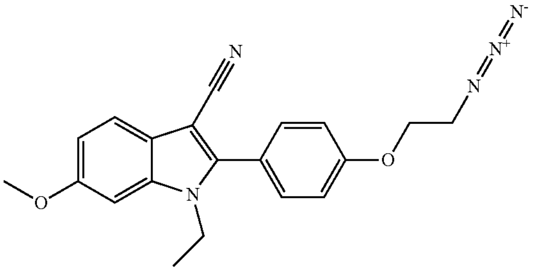
267
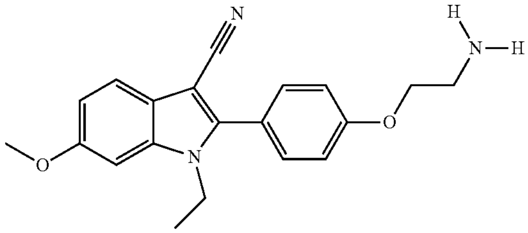
268
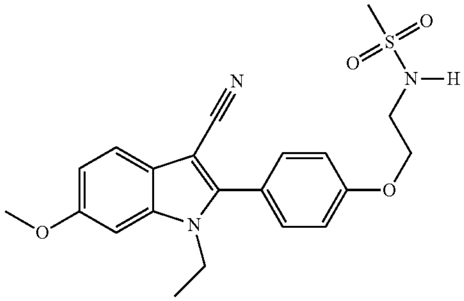
269
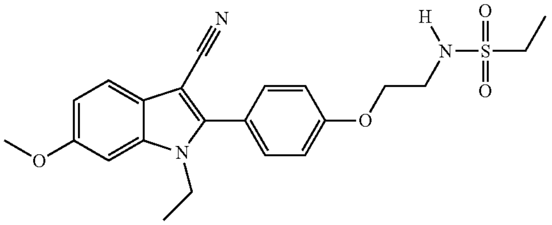
270
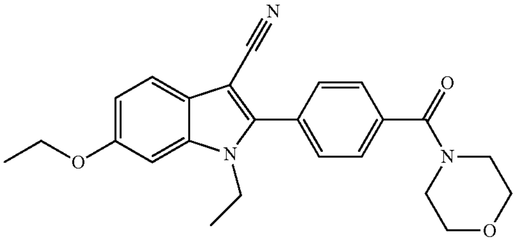

-continued
271
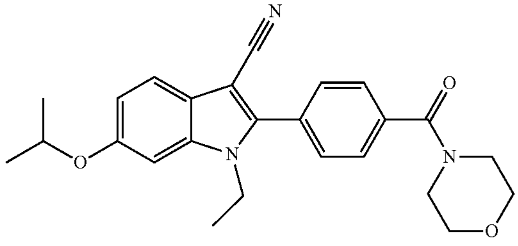
272
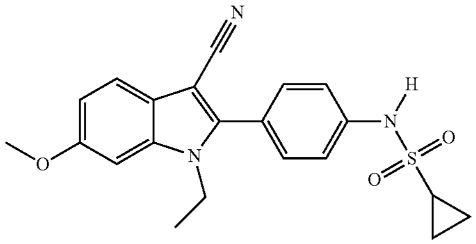
273
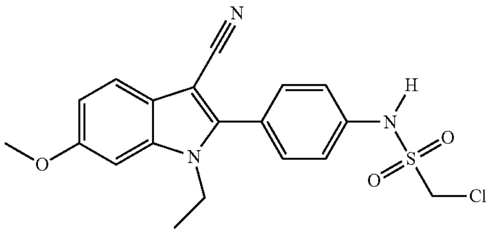
274
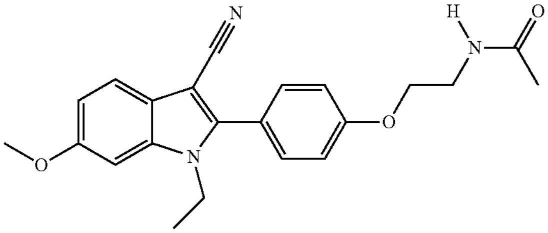
275
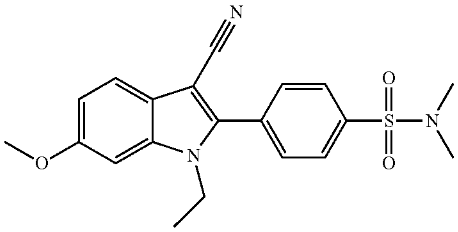
276
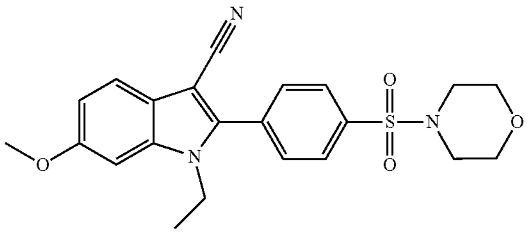
-continued
277
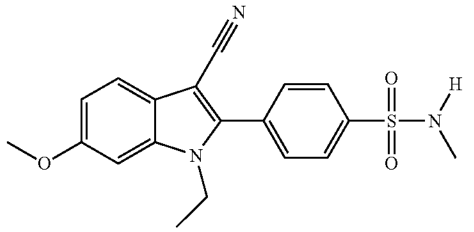
278
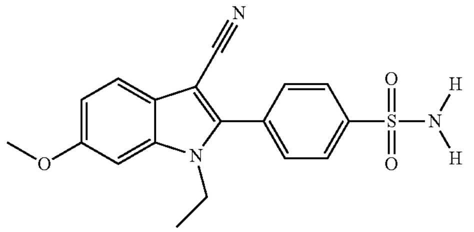
279
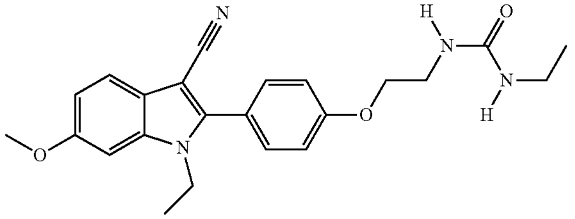
280
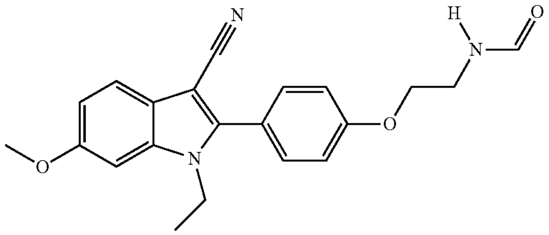
281
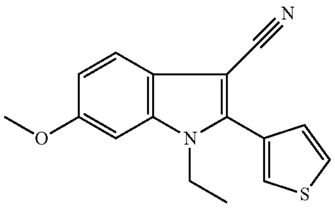
282
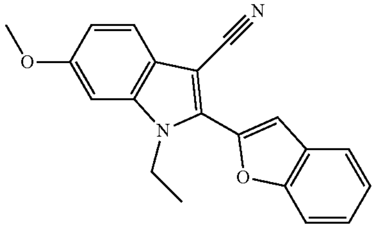

-continued
283
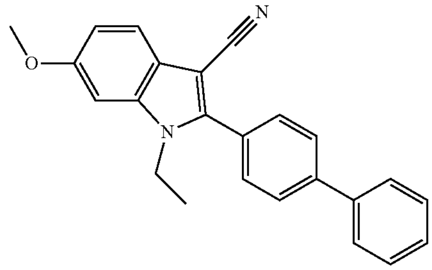
284
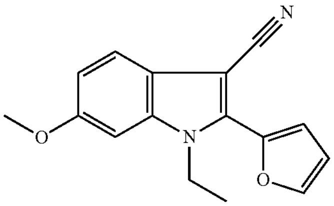
285
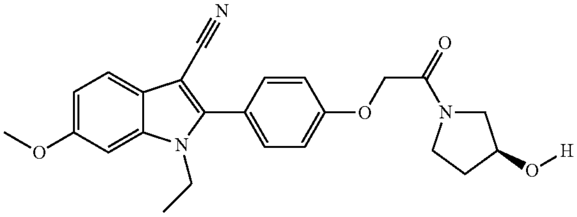
286
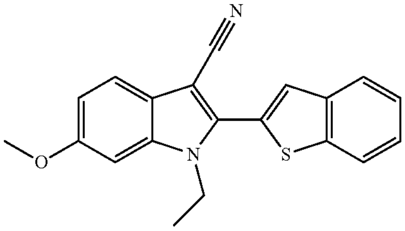
287
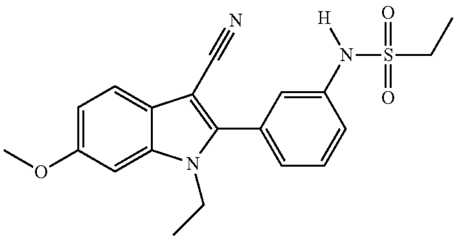
288
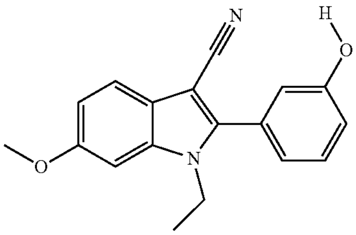
-continued
289
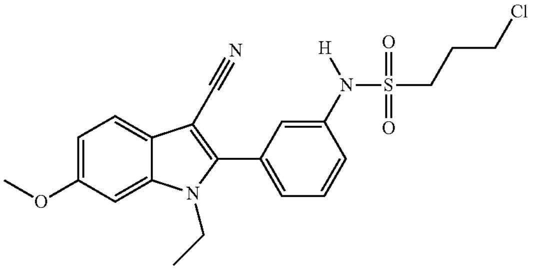
290
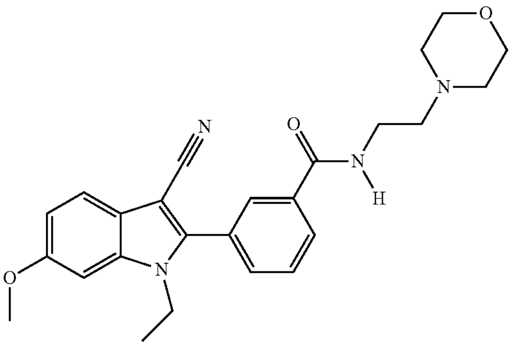
291
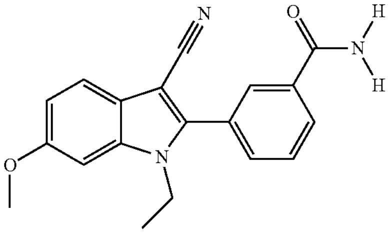
292
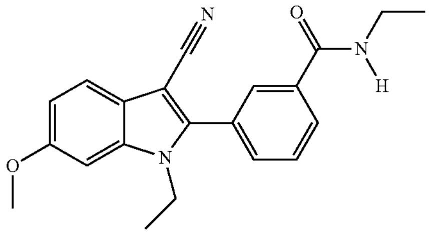
293
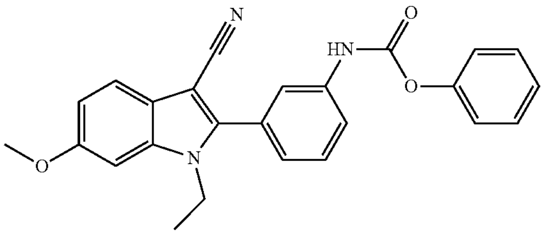
294
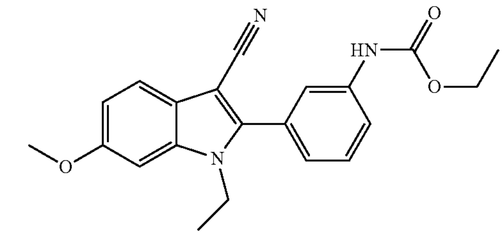

-continued
295
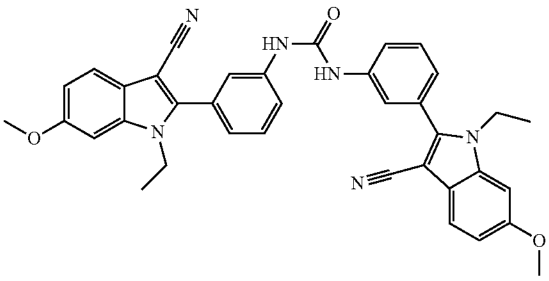
296
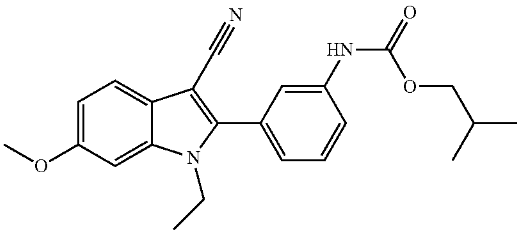
297
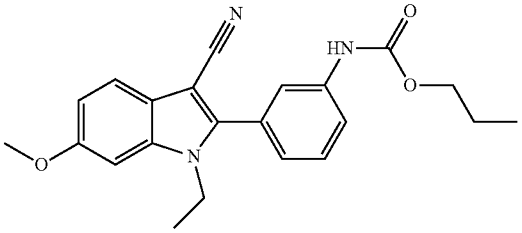
298
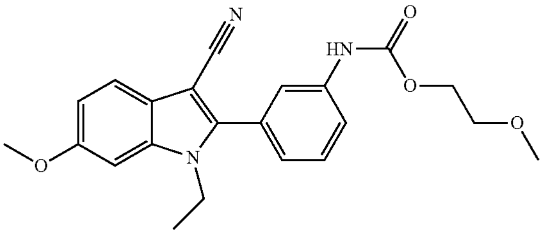
299
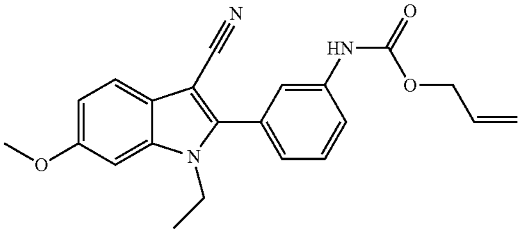
300
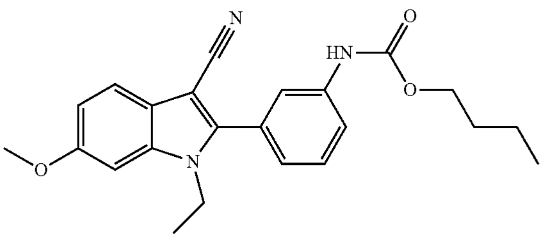
-continued
301
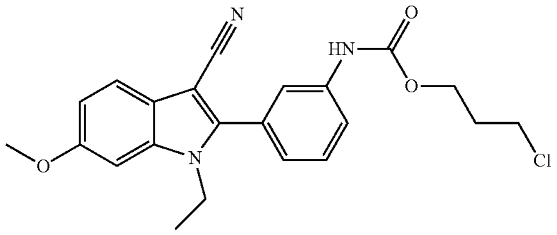
302
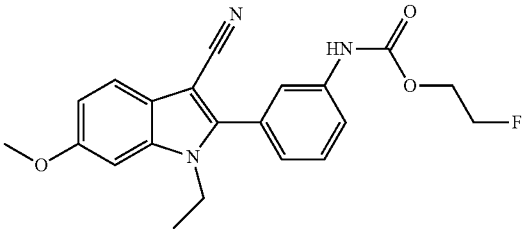
303
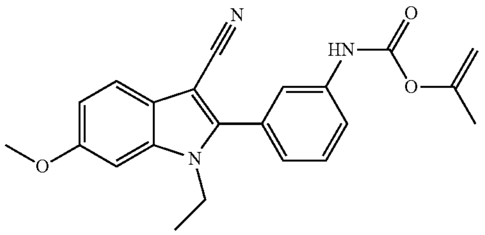
304
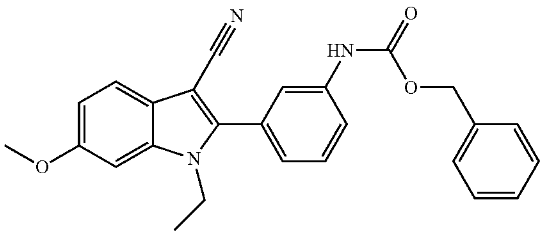
305
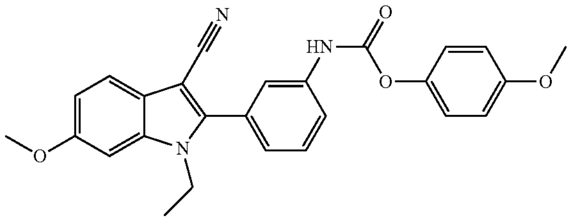
306
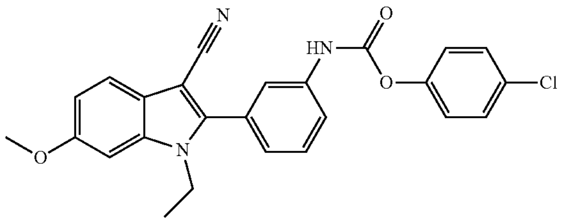

-continued
307
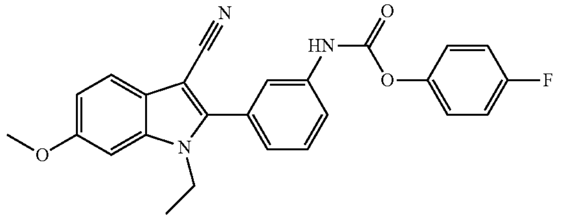
308
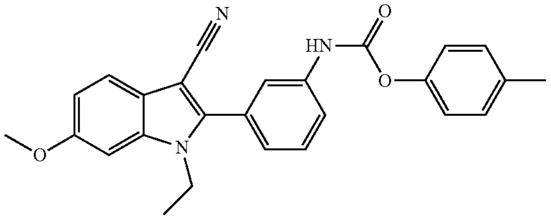
309
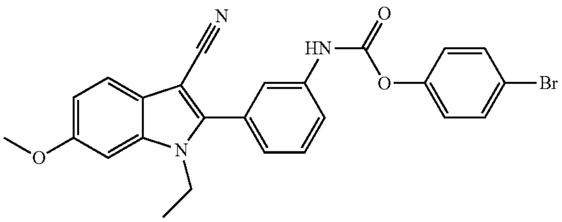
310
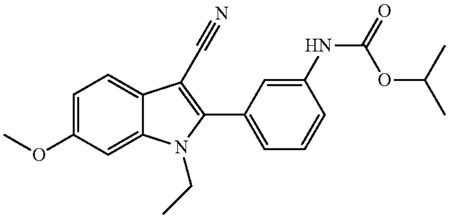
311
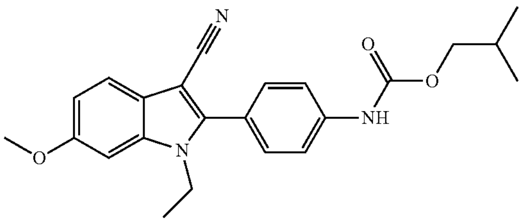
312
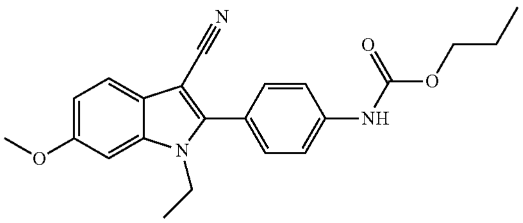
-continued
313
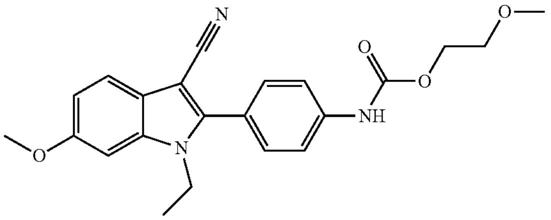
314
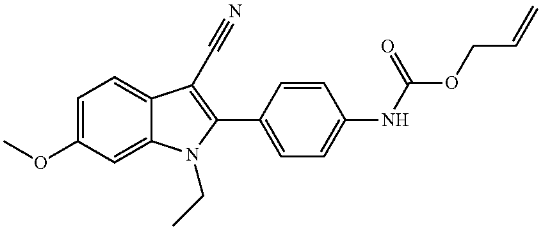
315
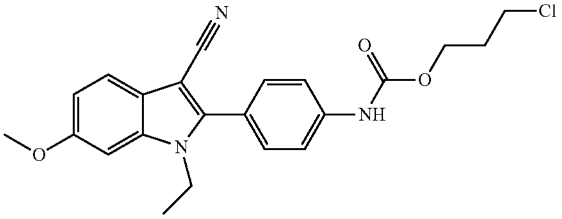
316
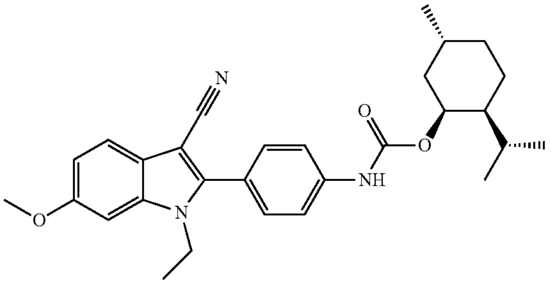
317
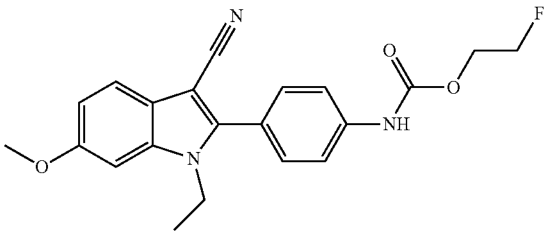

-continued
318
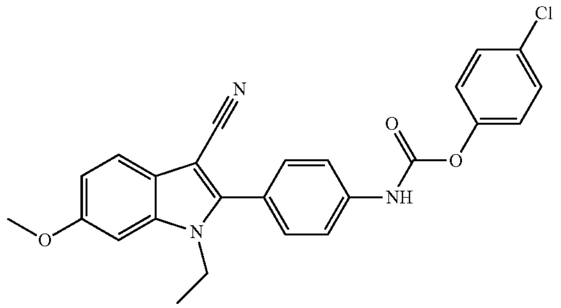
319
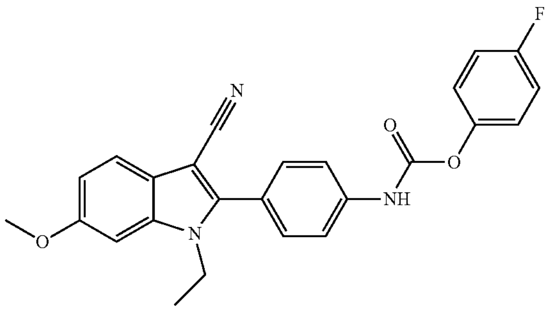
320
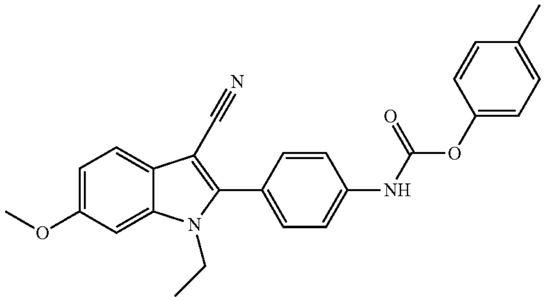
321
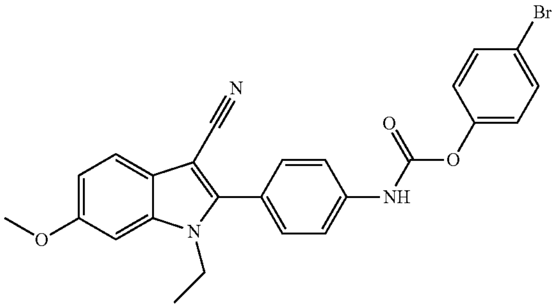
322
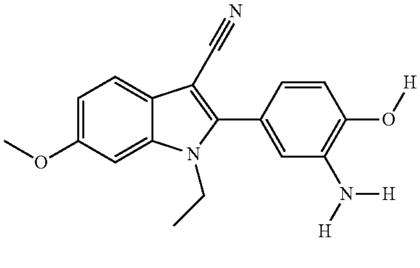
-continued
323
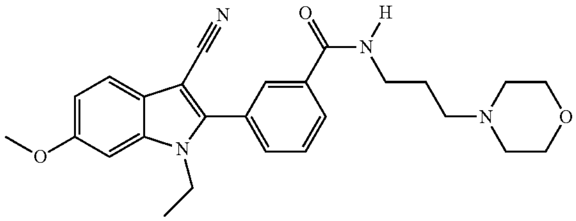
324
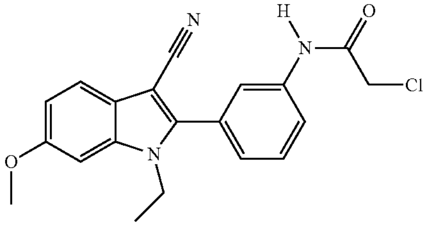
325
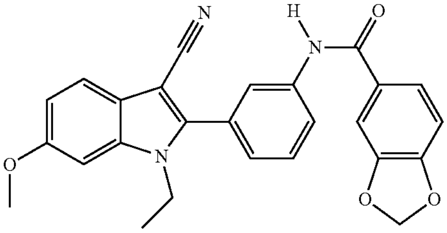
326
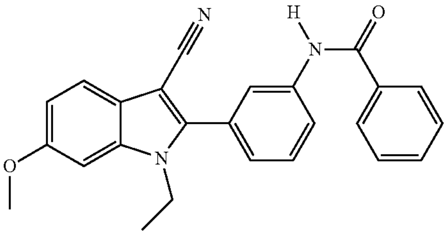
327
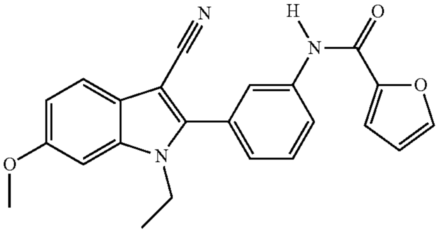
328
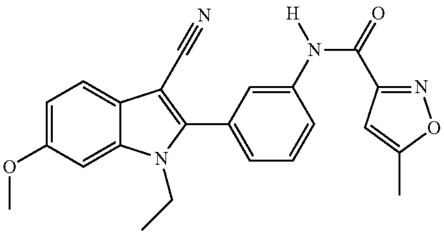

-continued
329
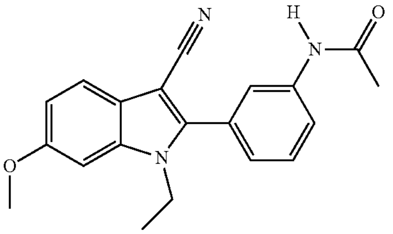
330
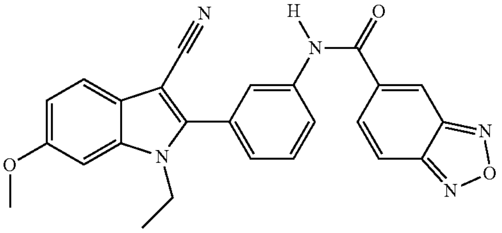
331
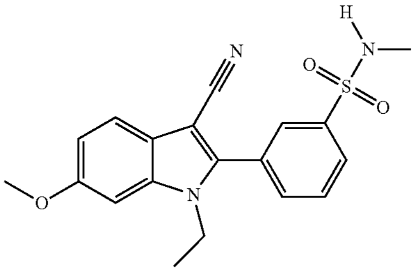
332
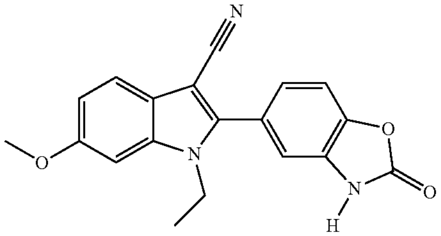
333
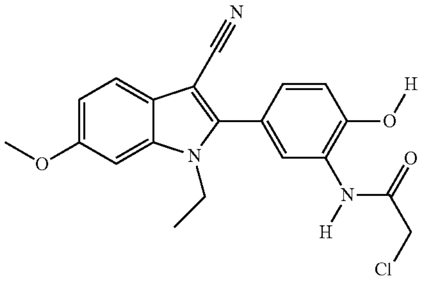
334
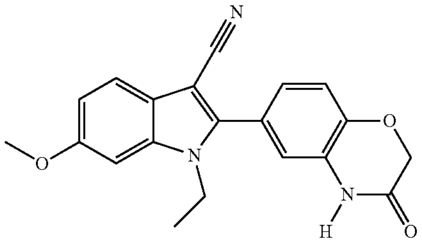
-continued
335
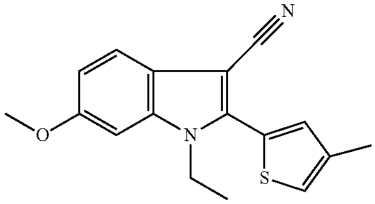
336
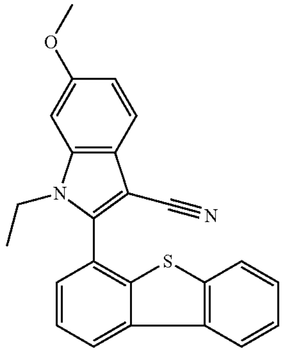
337
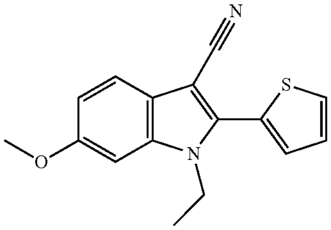
338
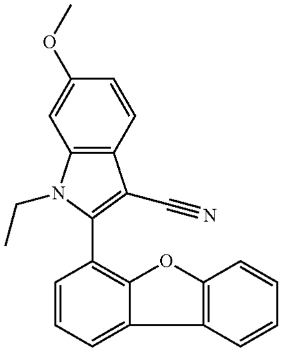
339
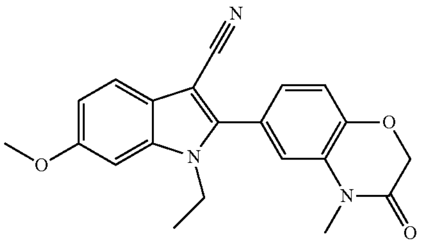

-continued
340
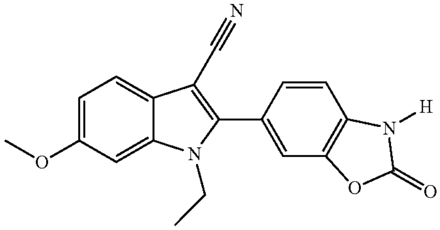
341
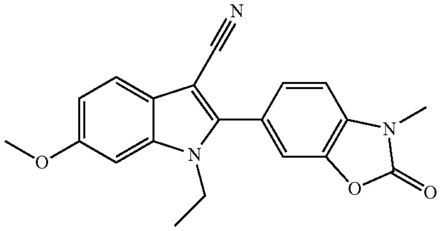
342
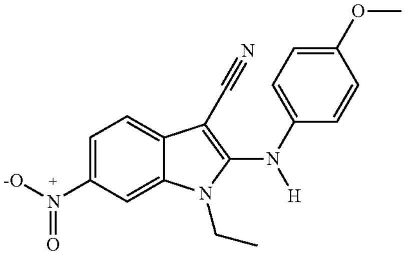
343
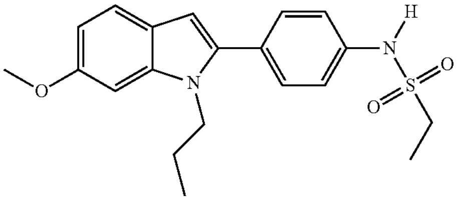
344
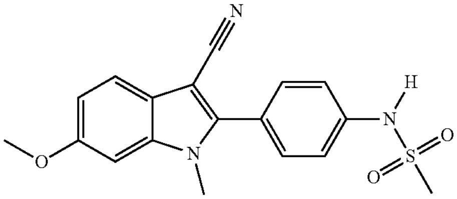
345
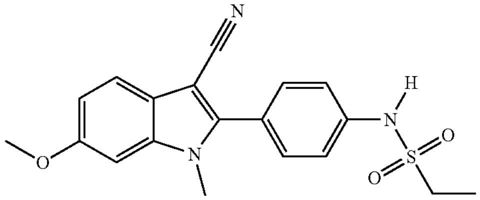
346
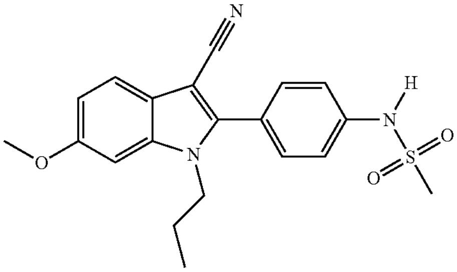
-continued
347
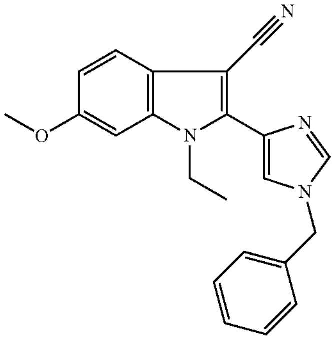
348
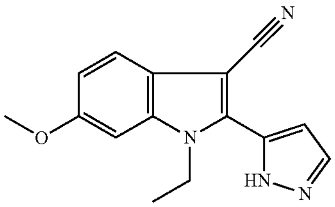
349
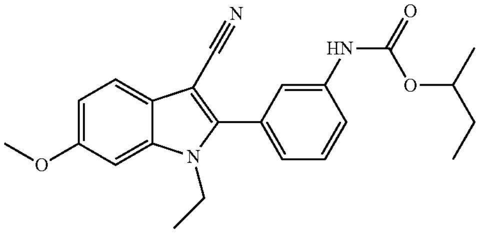
350
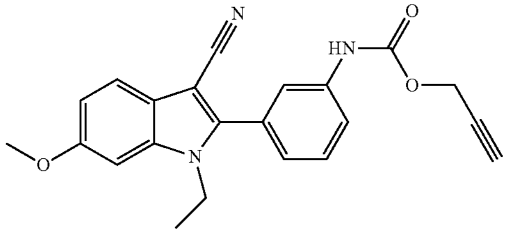
351
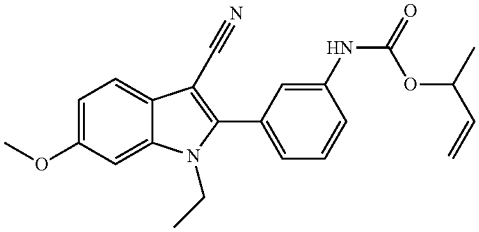
352
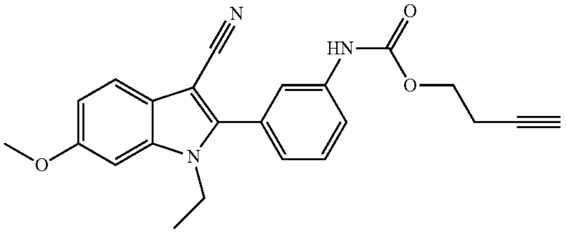

-continued
353
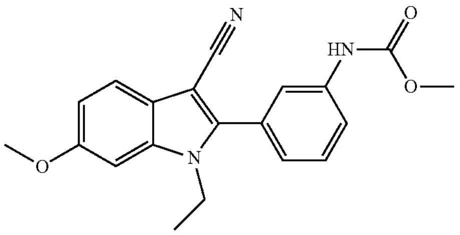
354
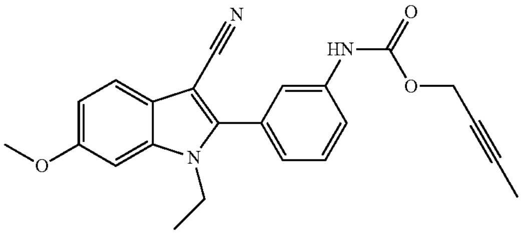
355
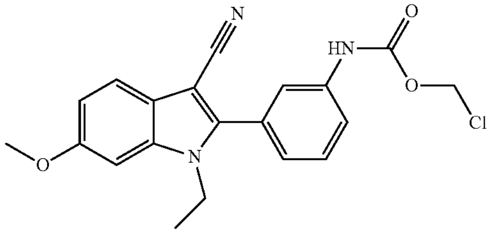
356
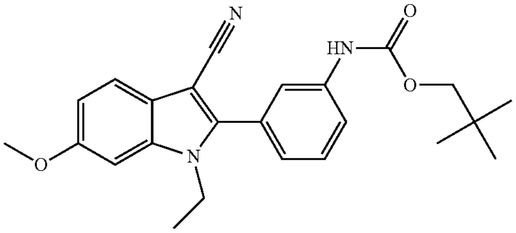
357
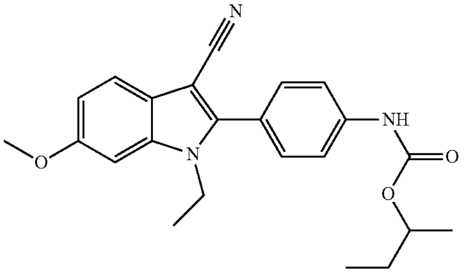
358
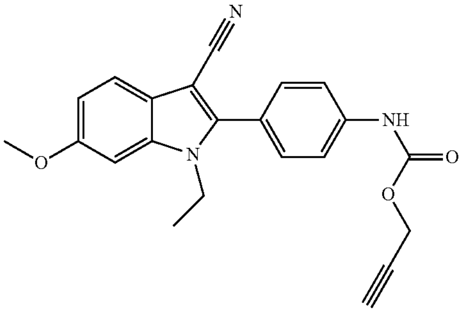
359
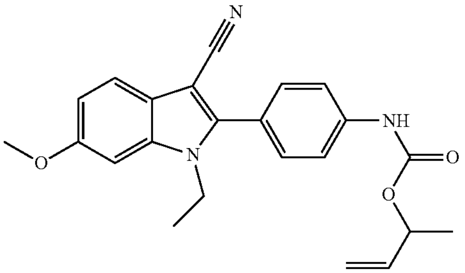
360
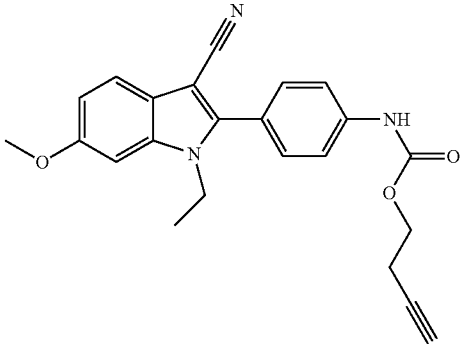
361
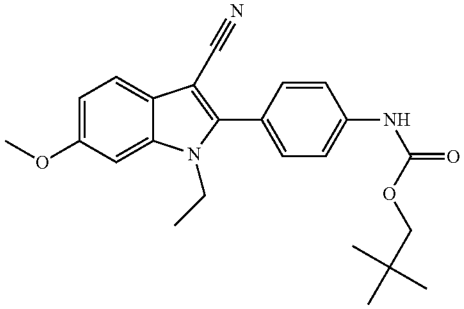
362
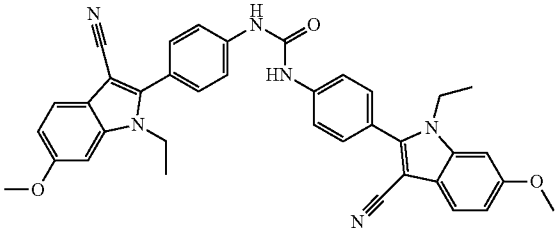
363
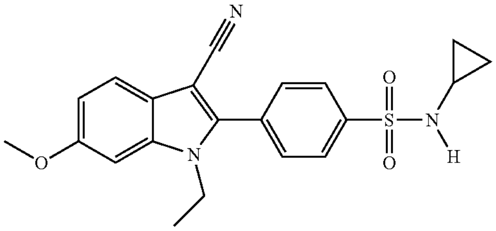

-continued
364
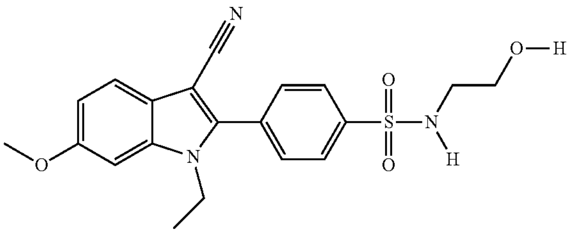
365
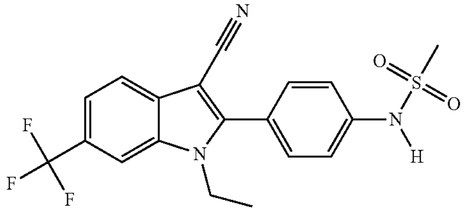
366
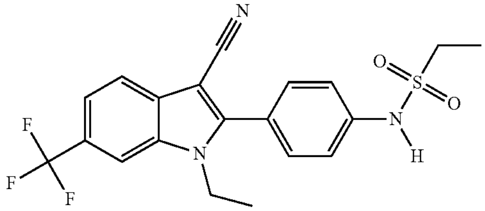
367
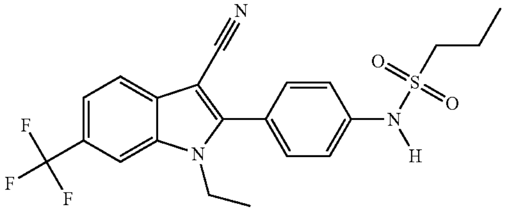
368
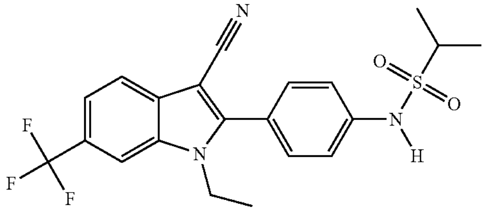
369
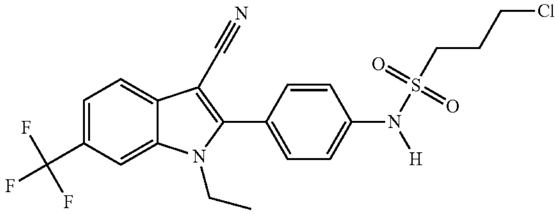
370
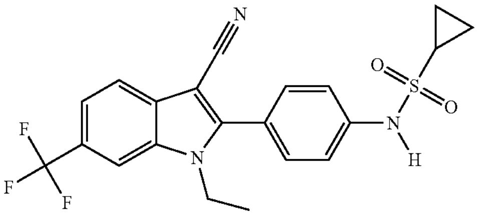
-continued
371
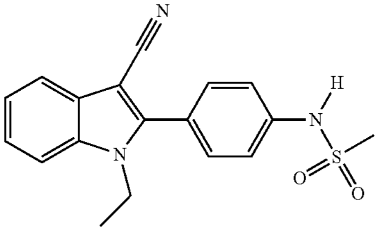
372
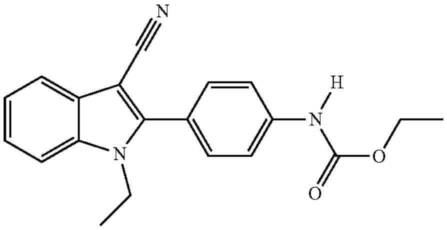
373
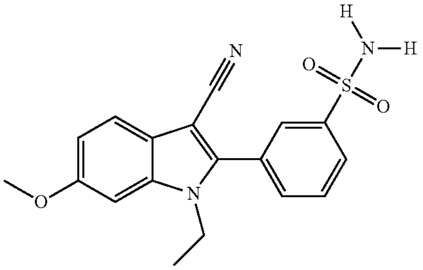
374
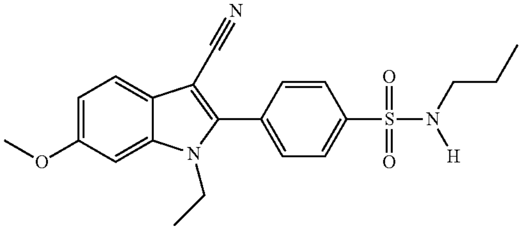
375
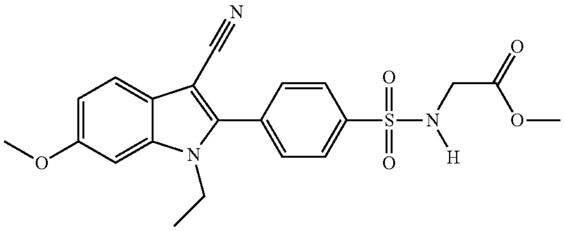
376
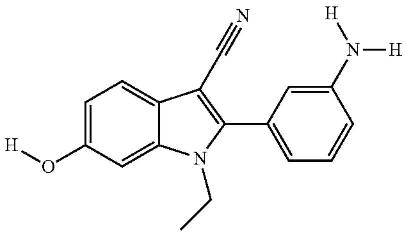

-continued
377
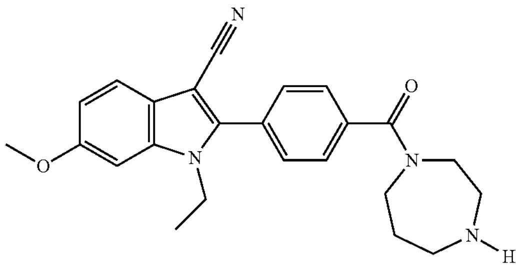
378
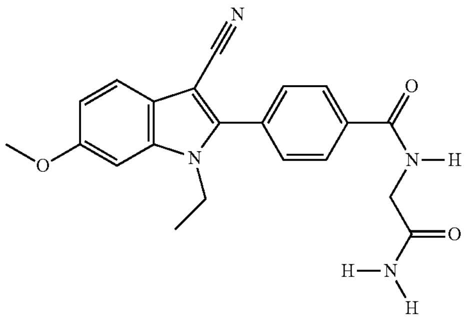
379
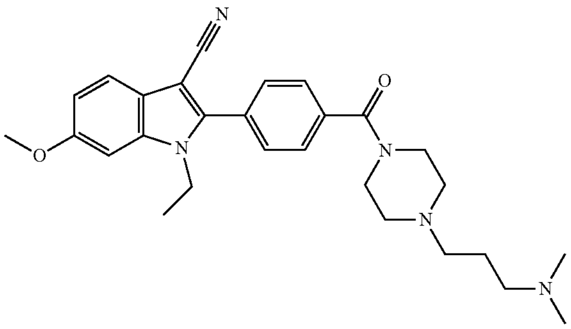
380
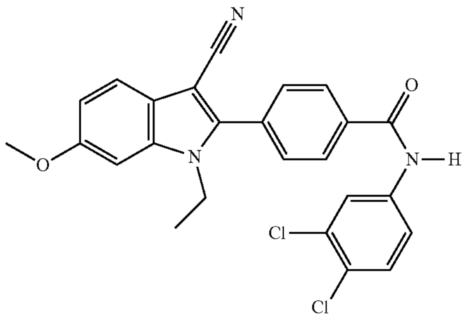
381
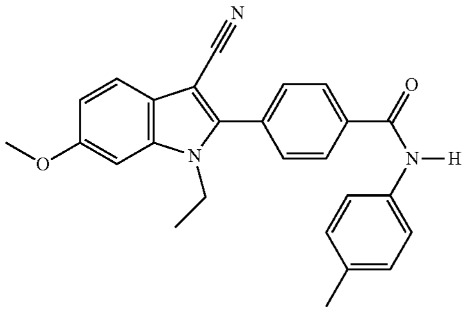
-continued
382
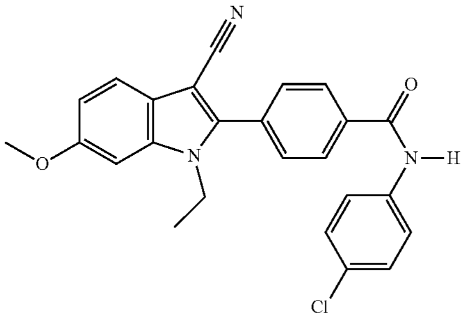
383
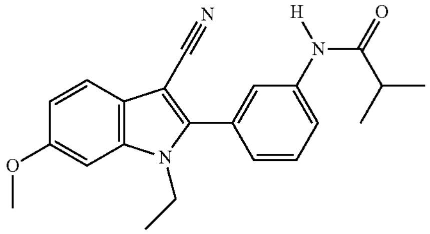
384
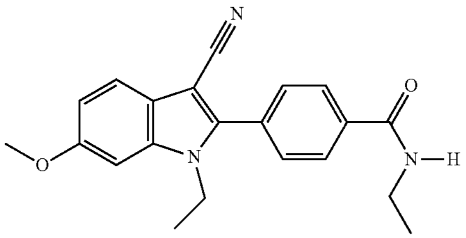
385
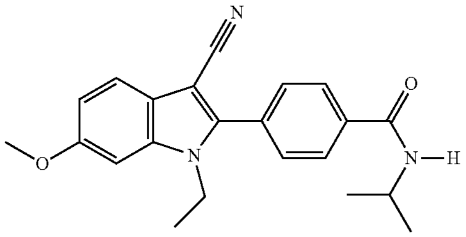
386
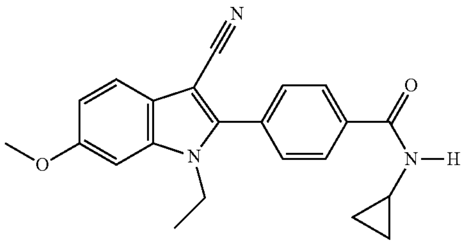
387
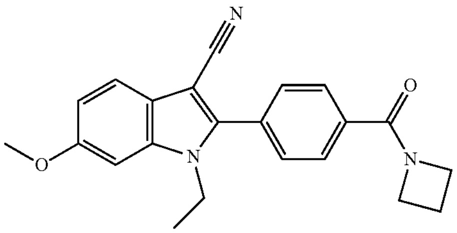

-continued
388
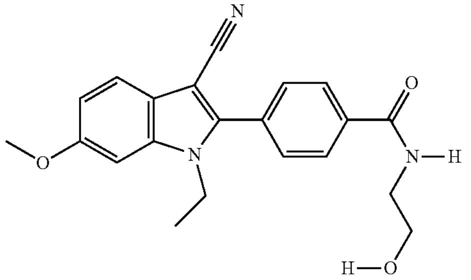
389
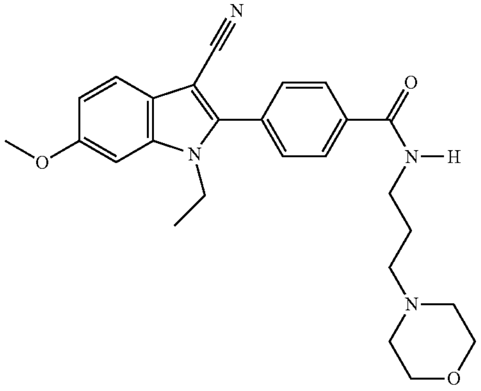
390
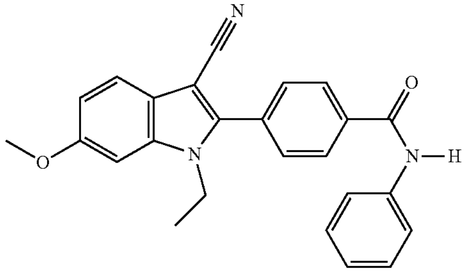
391
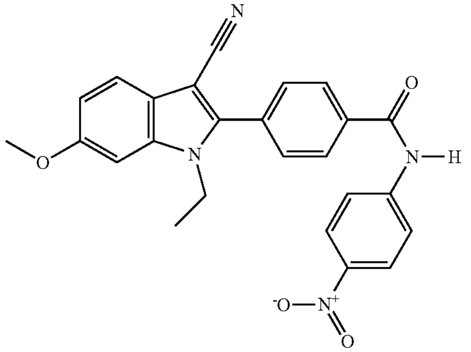
392
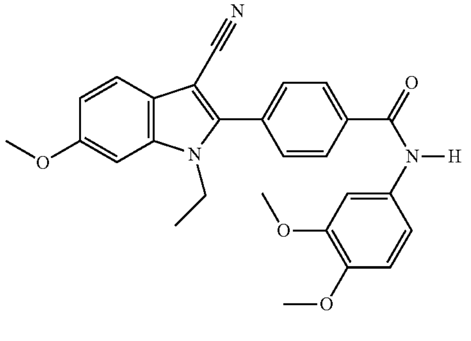
-continued
393
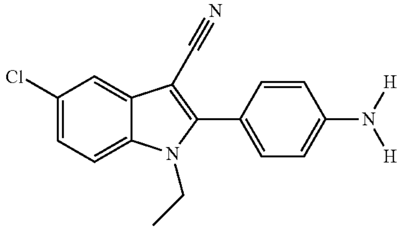
394
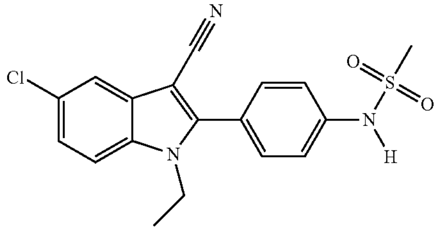
395
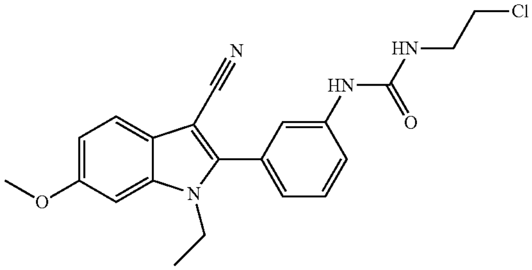
396
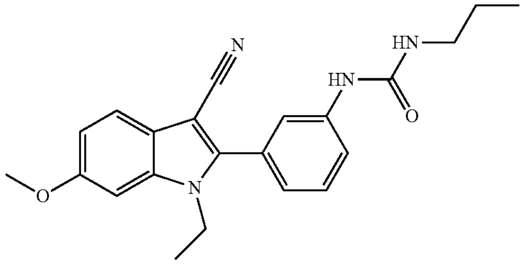
397
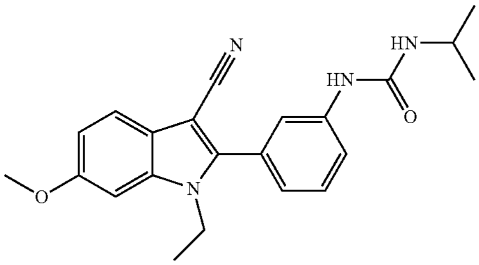
398
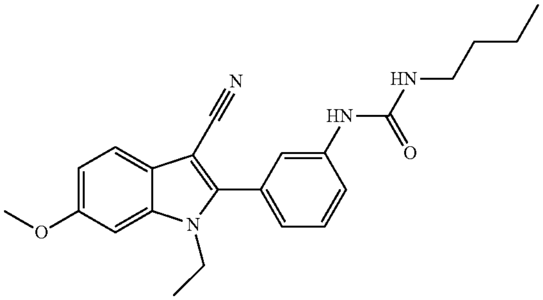

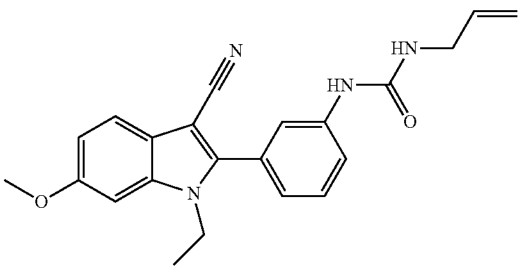
399
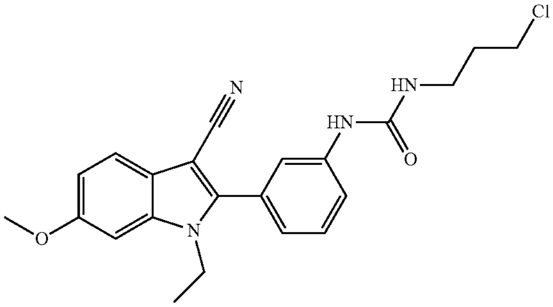
400
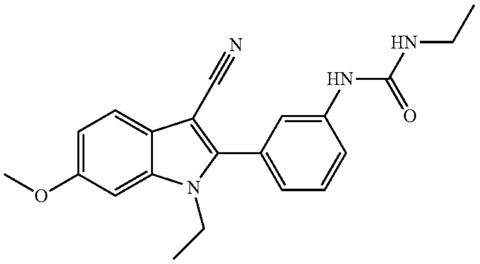
401
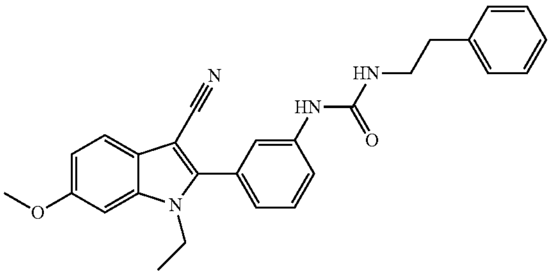
402
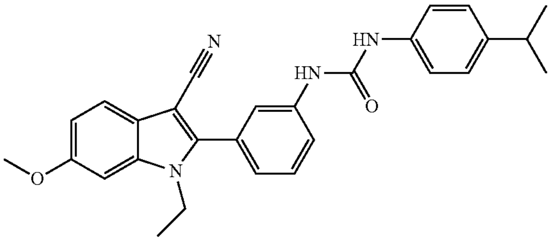
403
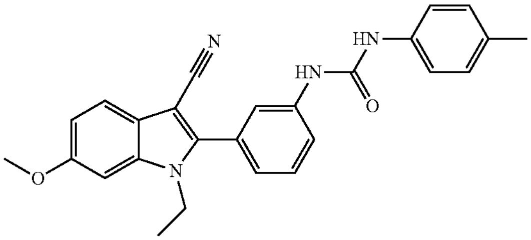
404
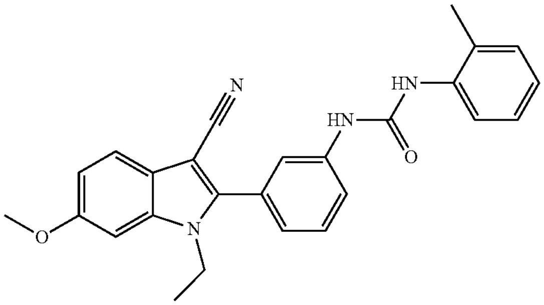
405
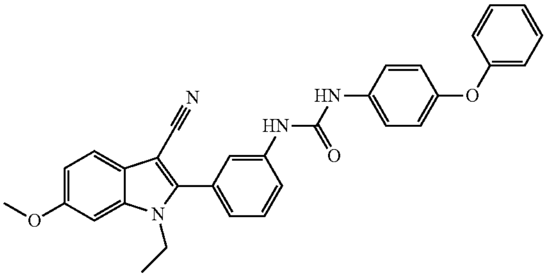
406
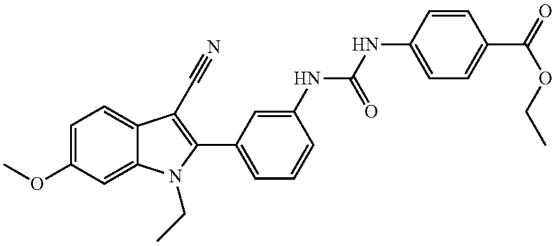
407
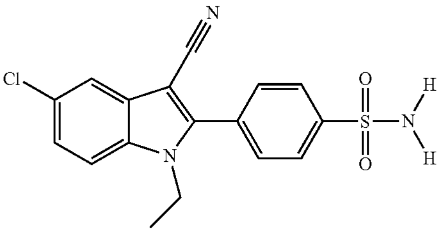
408

-continued
409
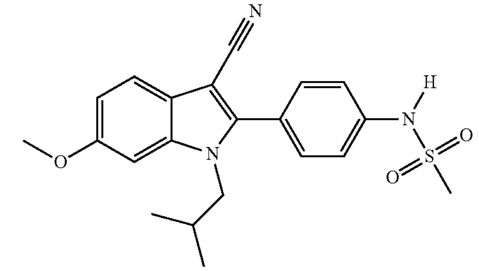
410
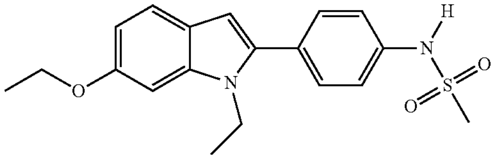
411
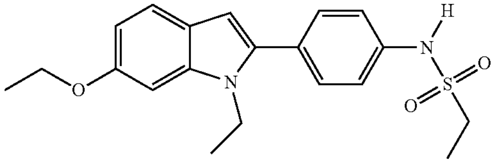
412
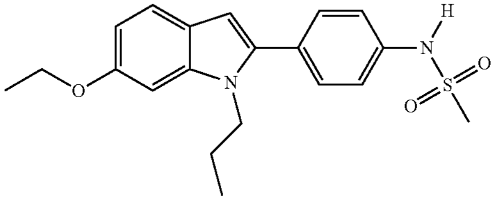
413
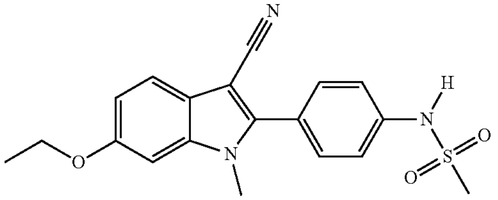
414
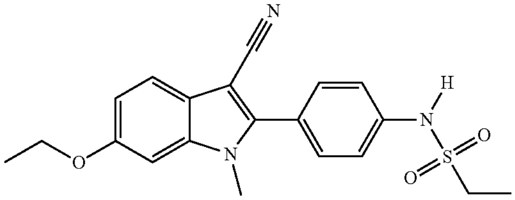
415
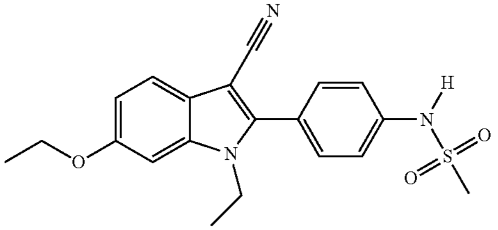
-continued
416
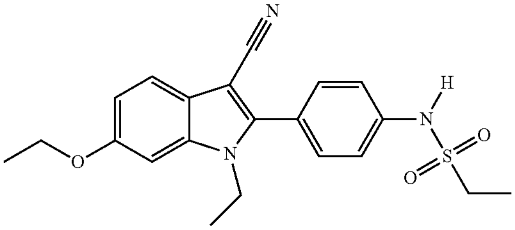
417
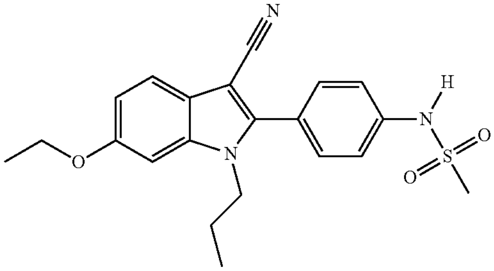
418
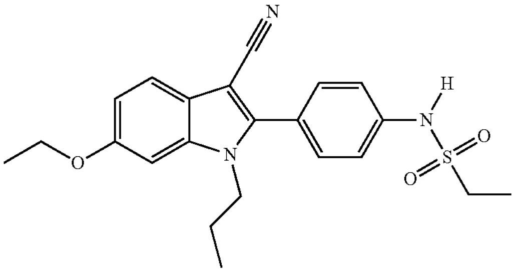
419
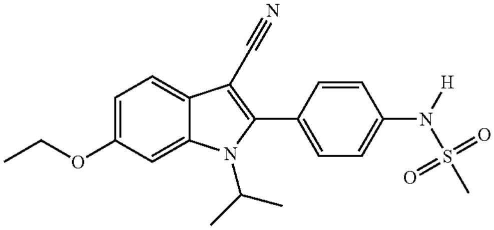
420
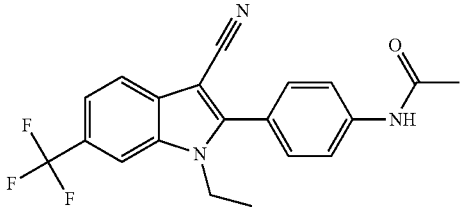
421
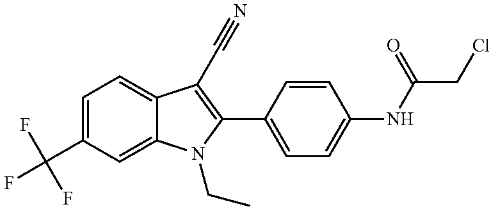

422
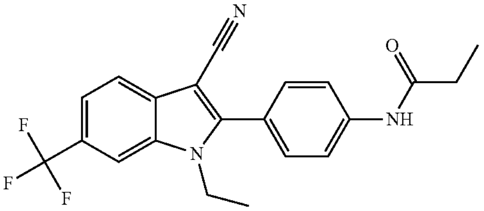
423
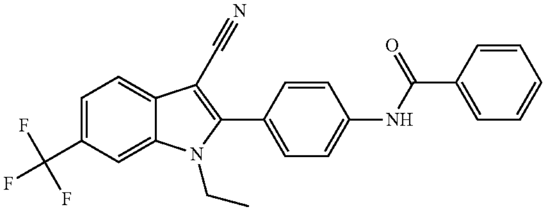
424
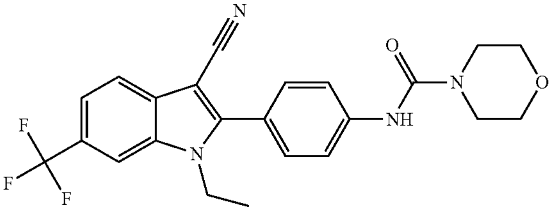
425
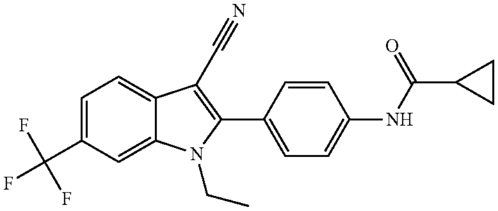
426
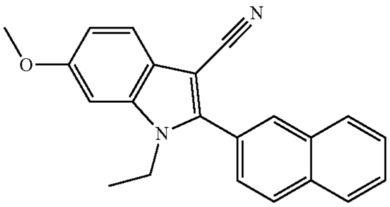
427
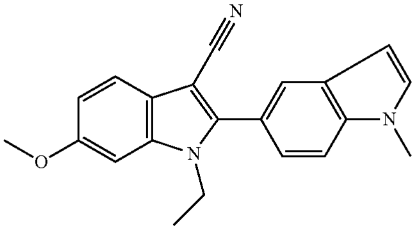
428
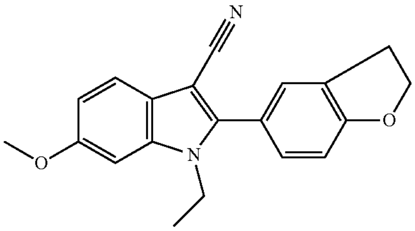
429
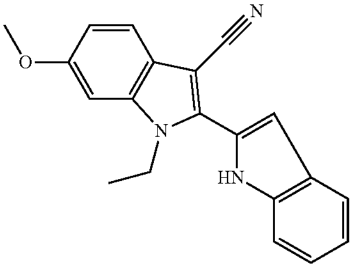
430
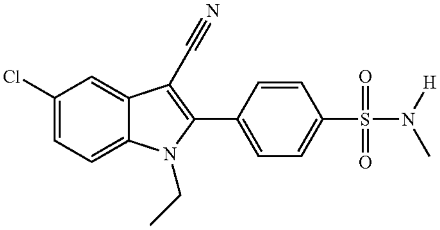
431
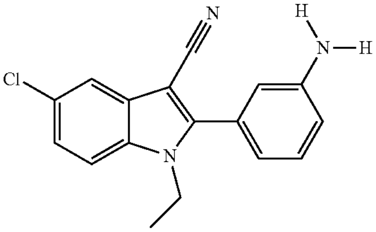
432
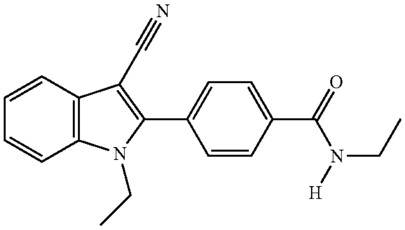
433
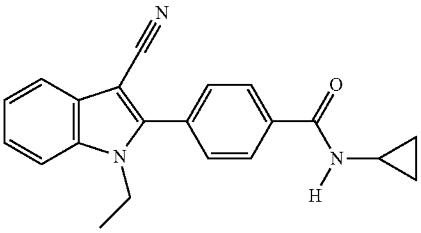
434
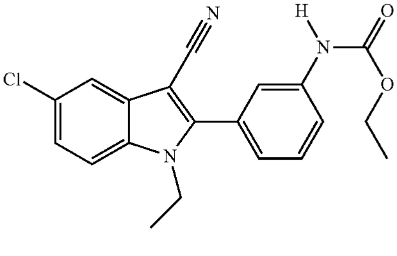

-continued
435
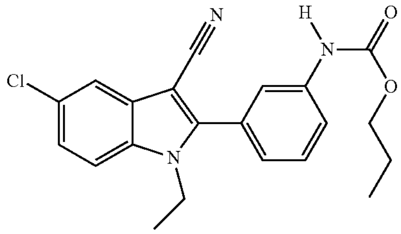
436
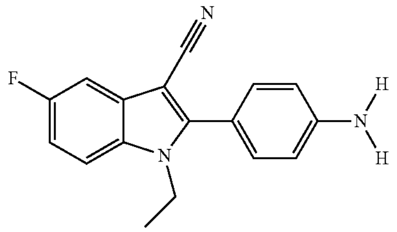
437
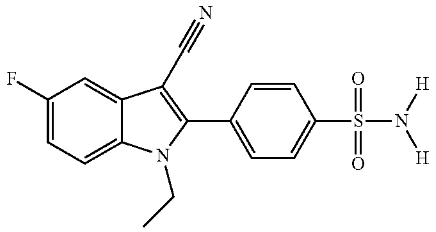
438
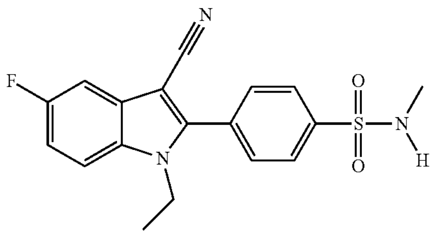
439
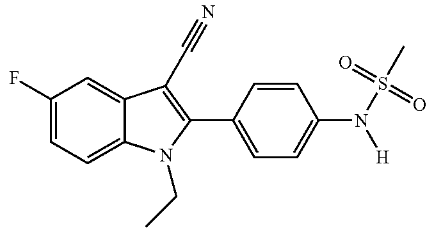
440
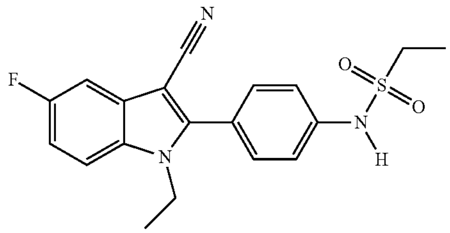
-continued
441
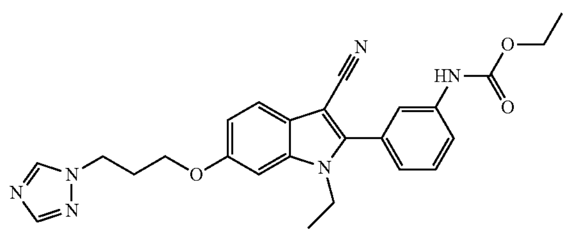
442
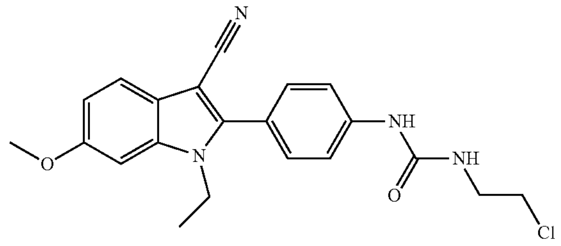
443
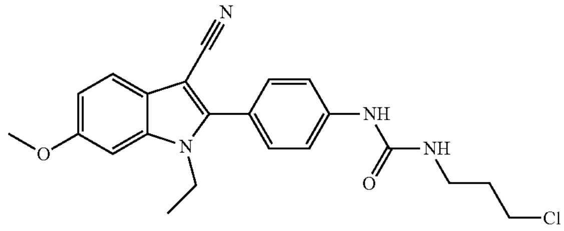
444
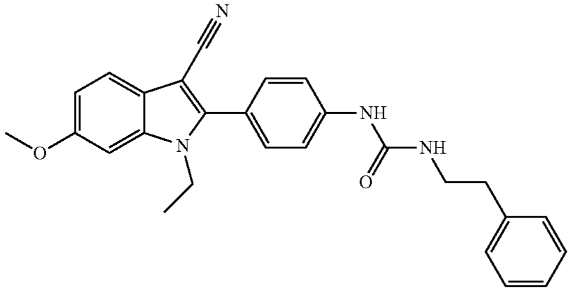
445
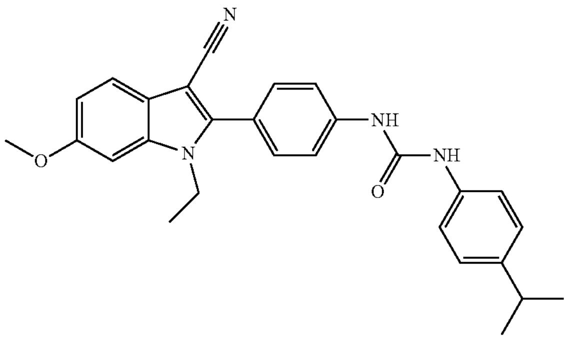

-continued
446
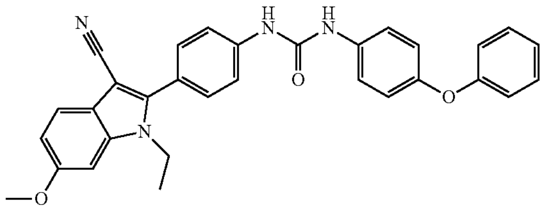
447
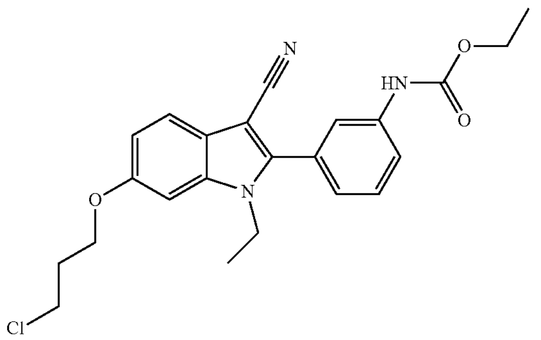
448
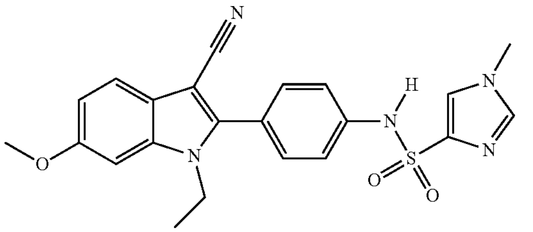
449
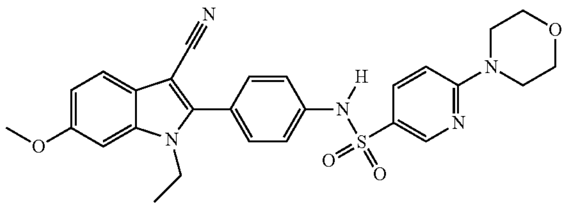
450
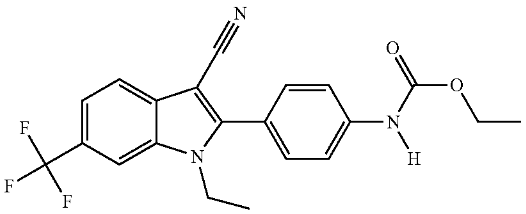
451
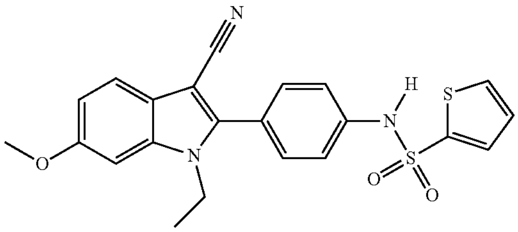
-continued
452
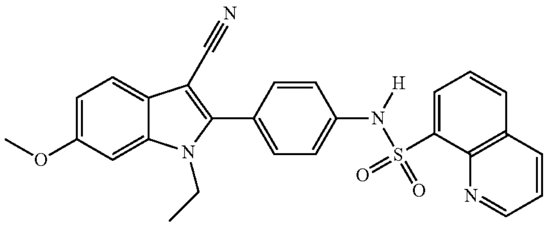
453
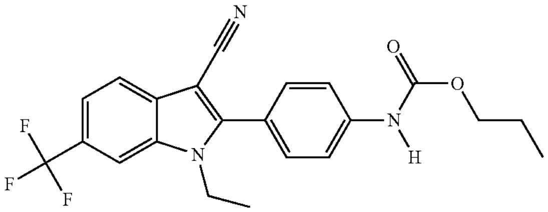
454
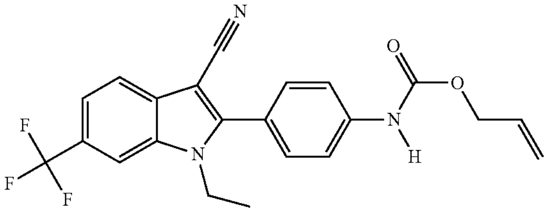
455
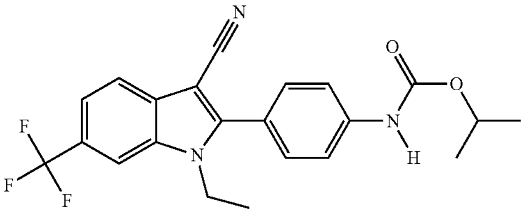
456
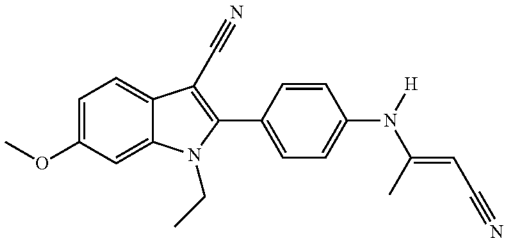
457
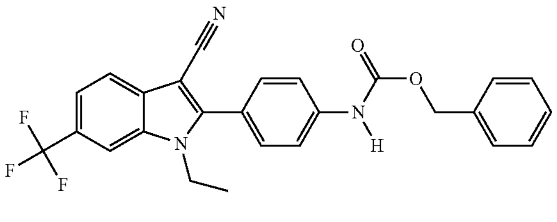

458
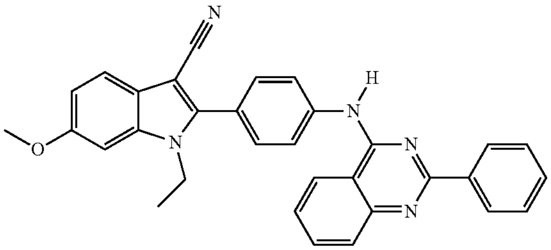
459
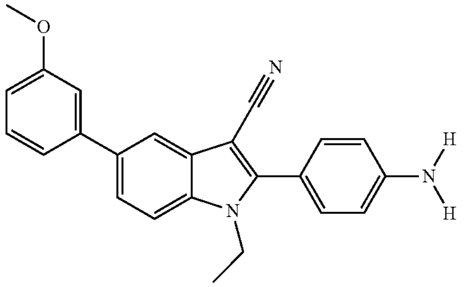
460
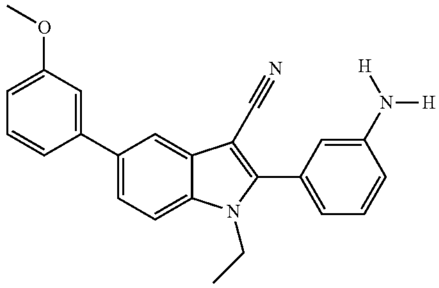
461
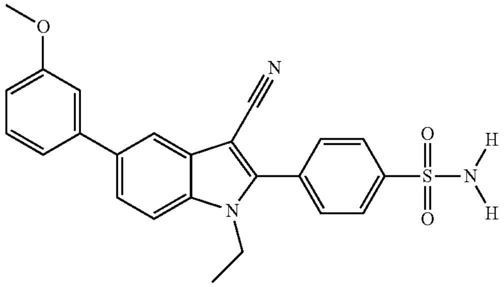
462
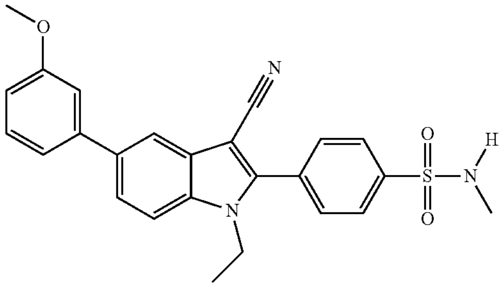
463
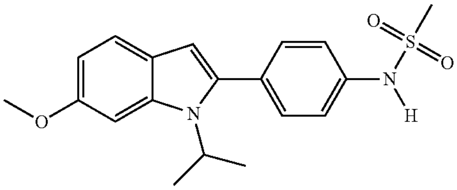
464
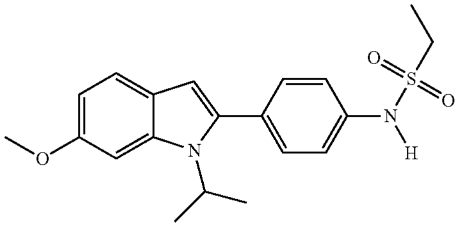
465
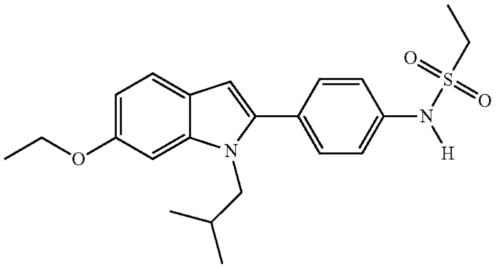
466
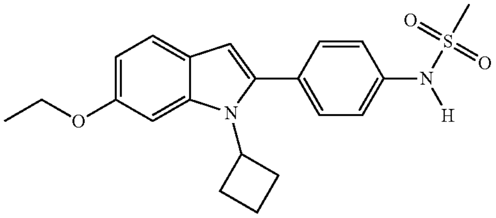
467
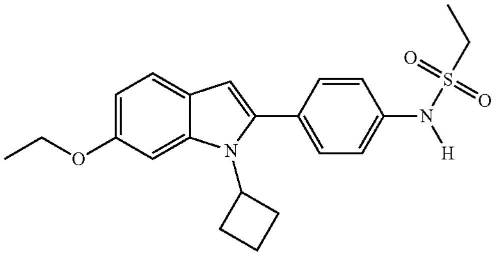
468
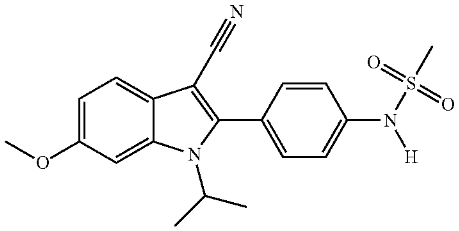
469
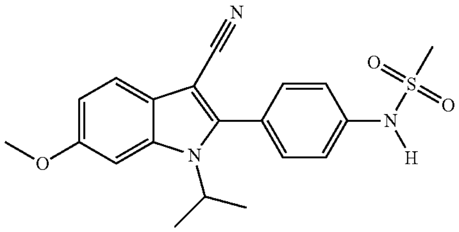

-continued
470
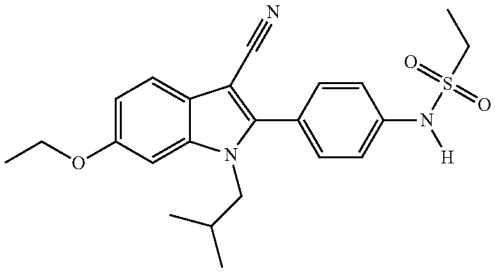
471
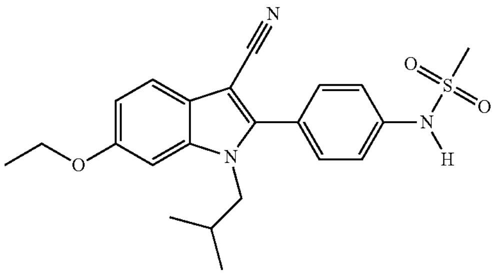
472
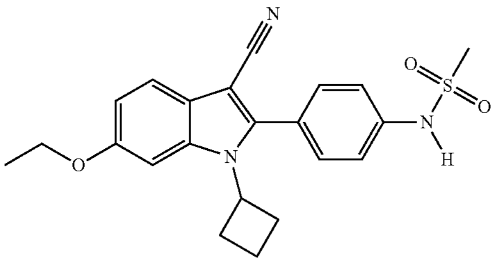
473
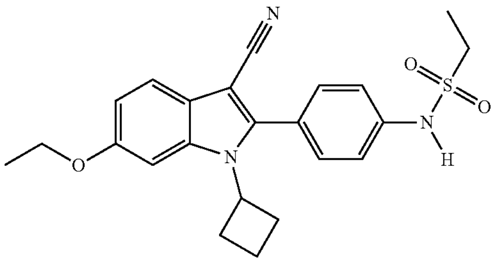
474
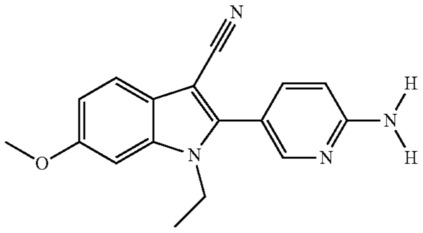
475
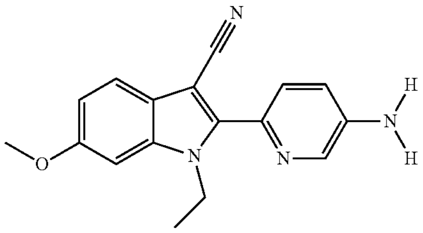
-continued
476
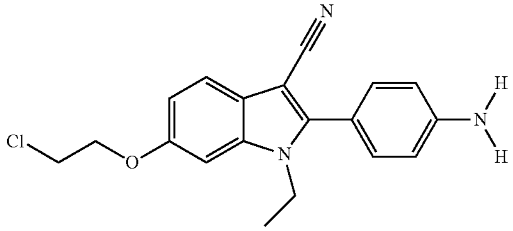
477
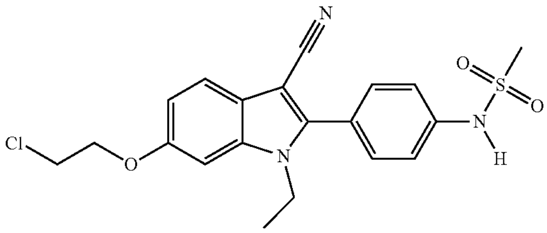
478
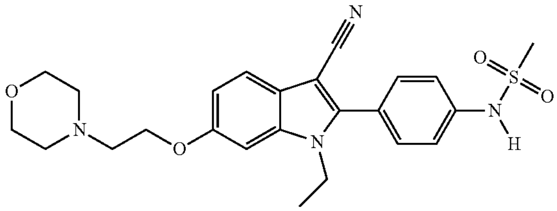
479
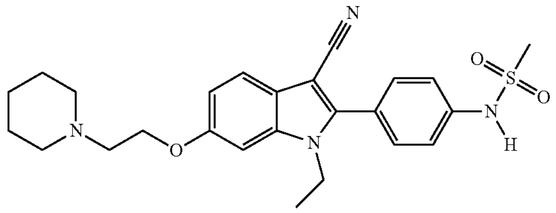
480
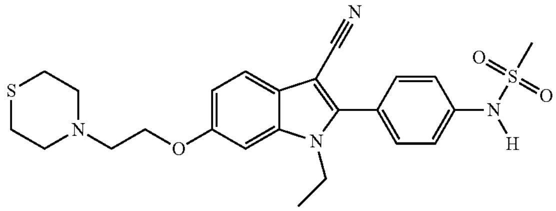
481
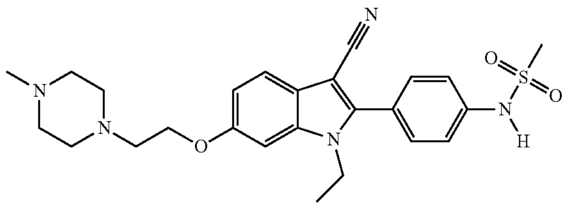

-continued
482
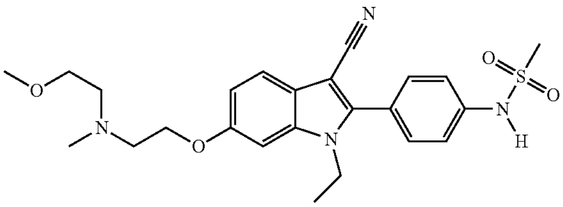
483
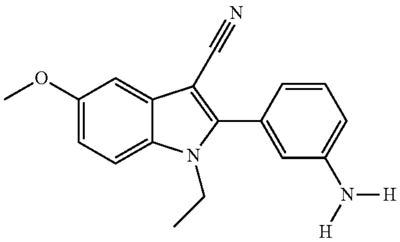
484
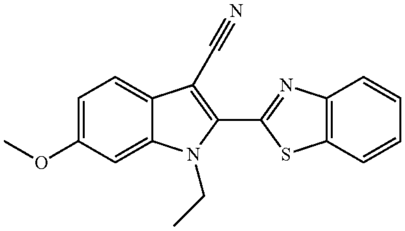
485
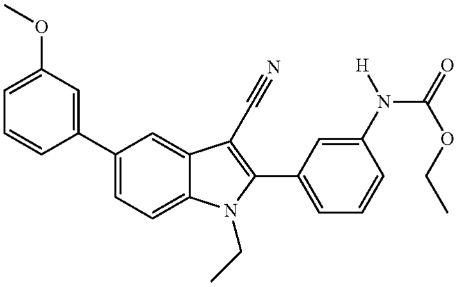
486
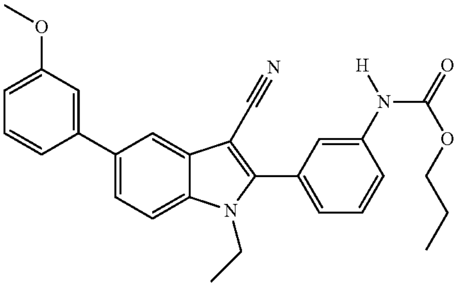
487
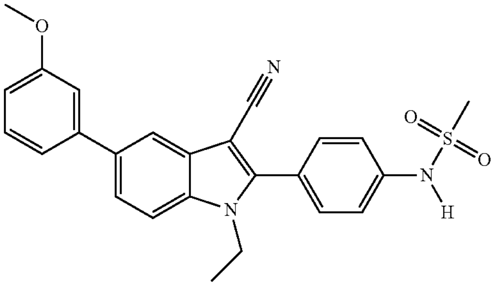
-continued
488
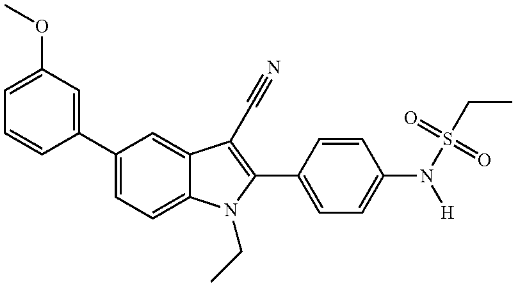
489
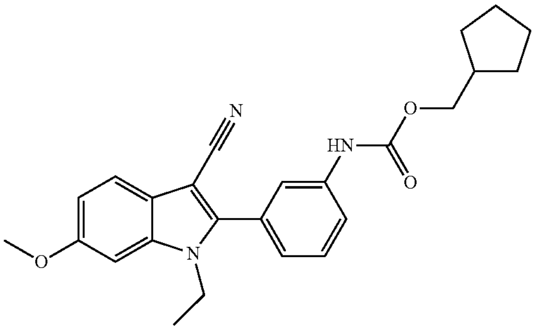
490
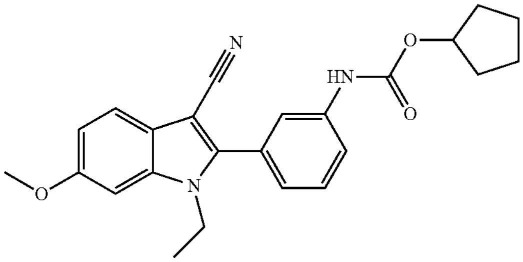
491
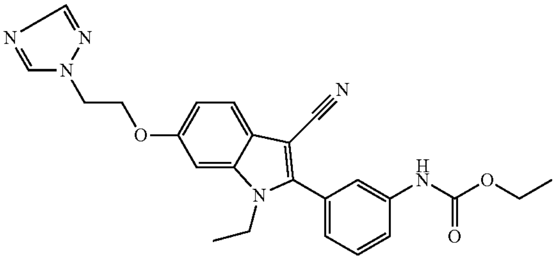
492
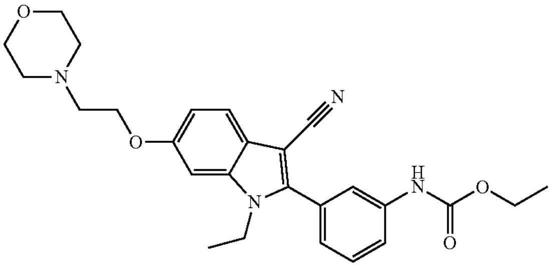

-continued
493
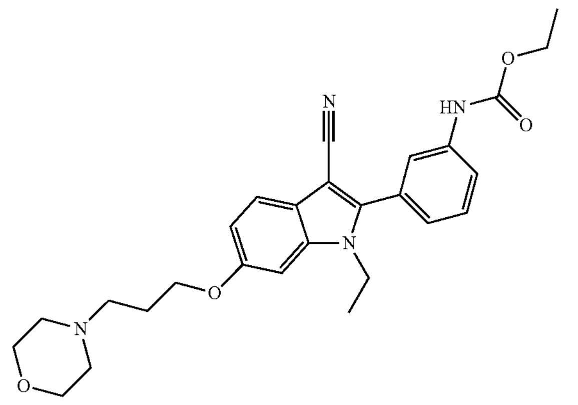
494
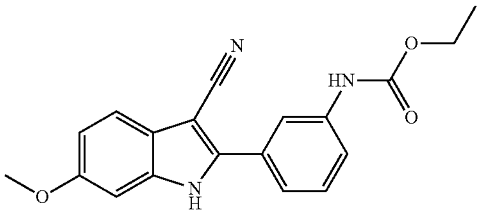
495
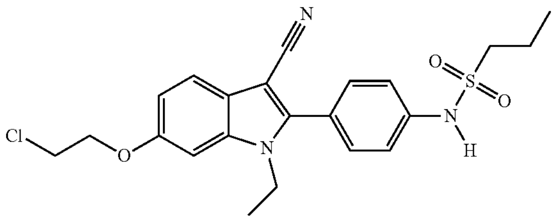
496
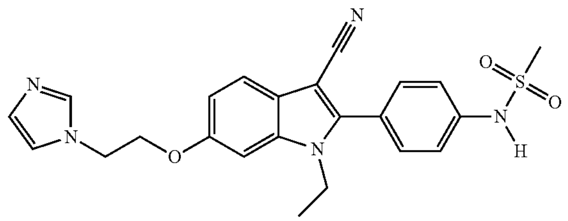
497
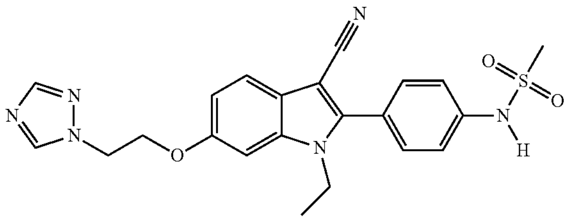
498
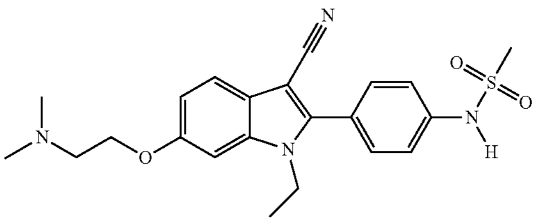
-continued
499
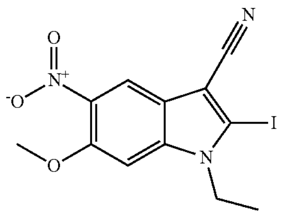
500
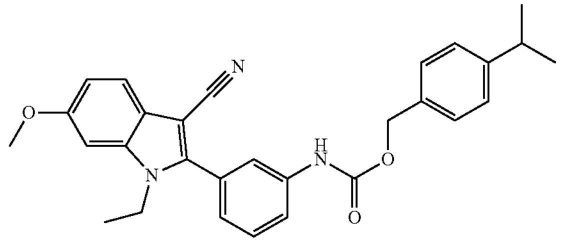
501
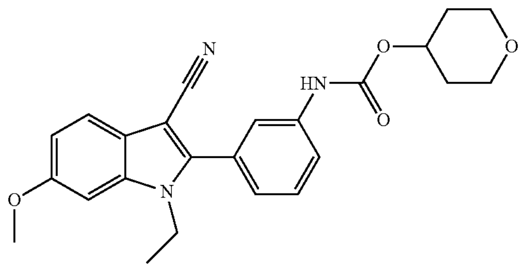
502
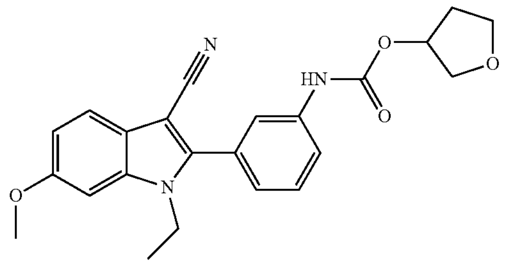
503
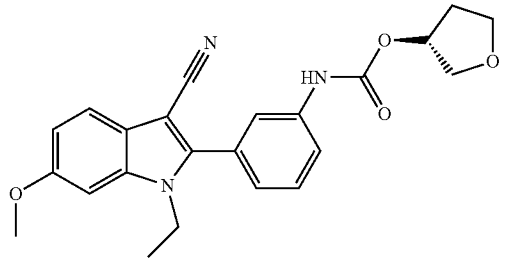
504
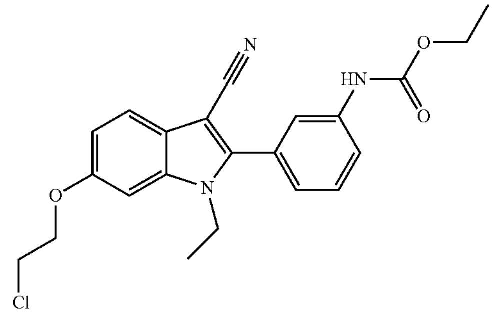

-continued
505
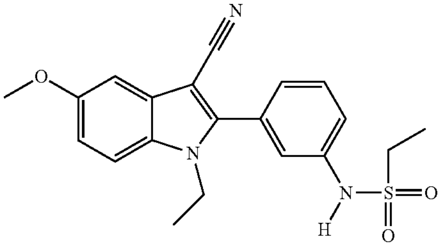
506
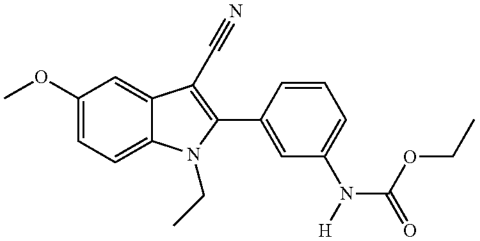
507
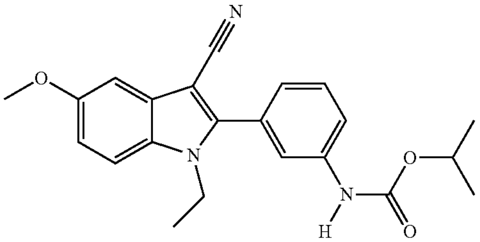
508
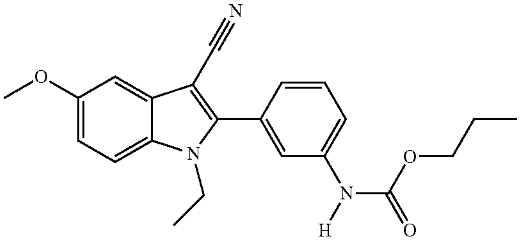
509
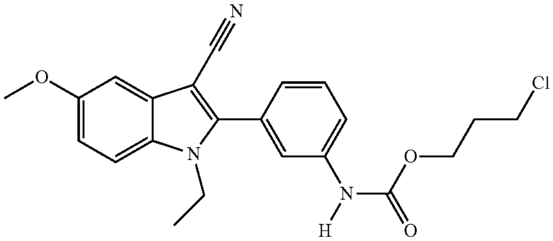
510
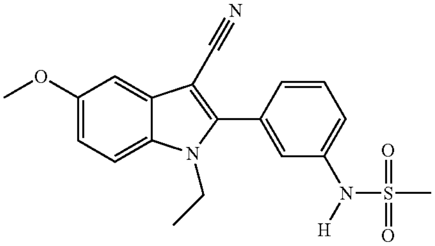
-continued
511
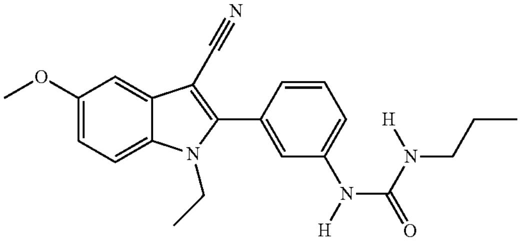
512
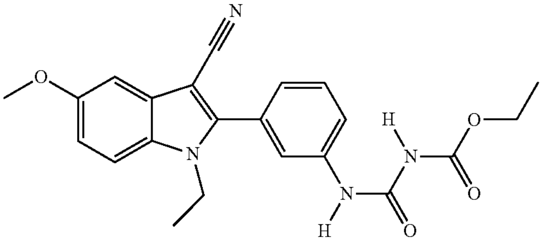
513
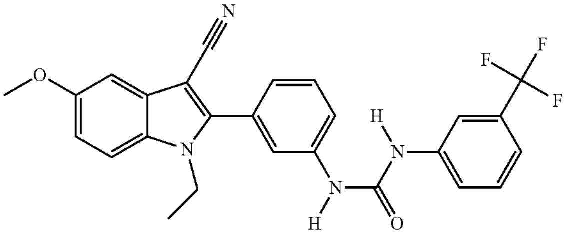
514
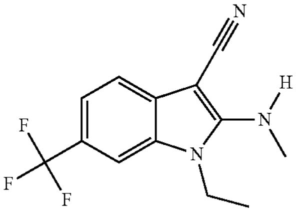
515
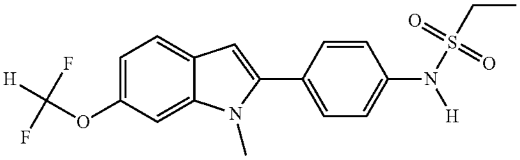
516
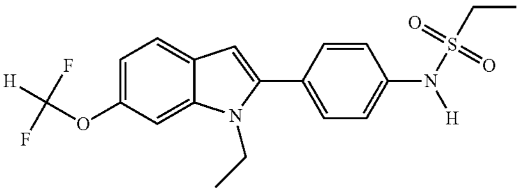
517
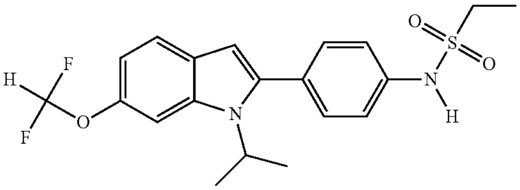

-continued
518
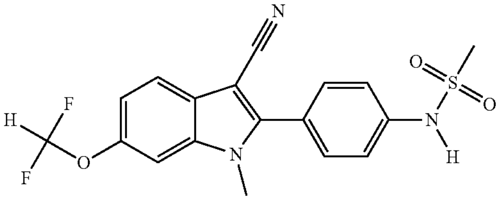
519
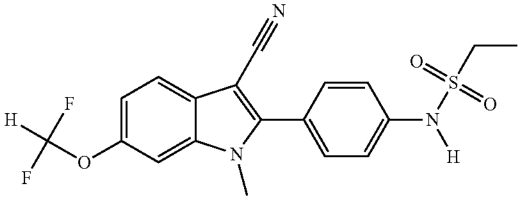
520
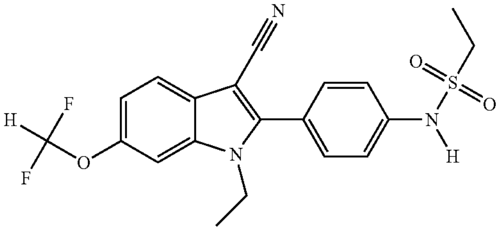
521
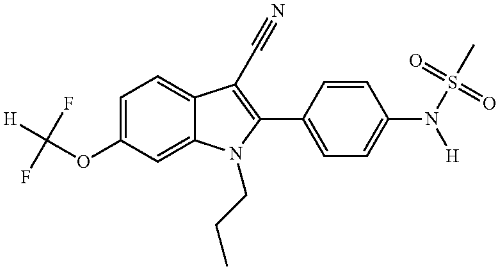
522
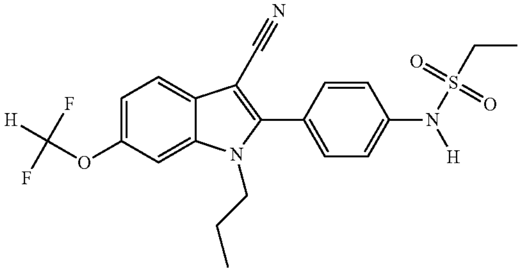
523
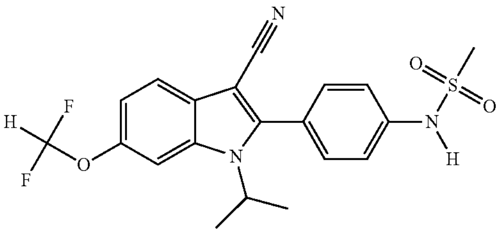
-continued
524
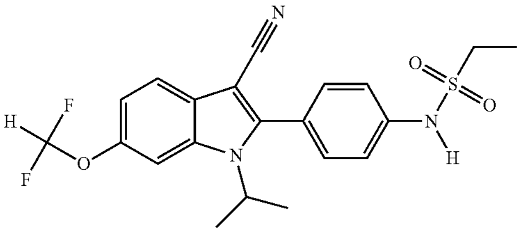
525
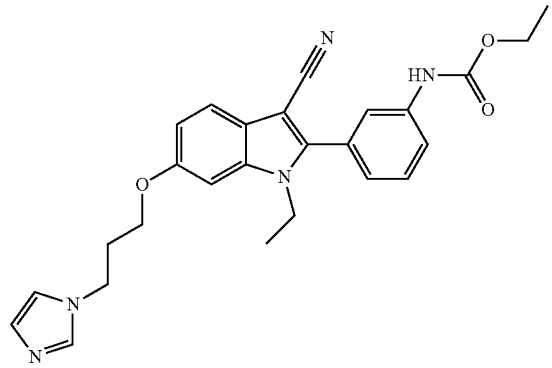
526
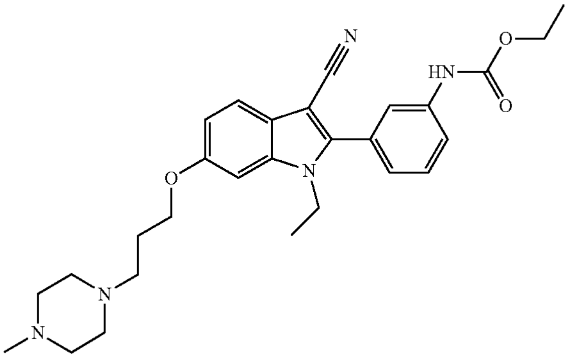
527
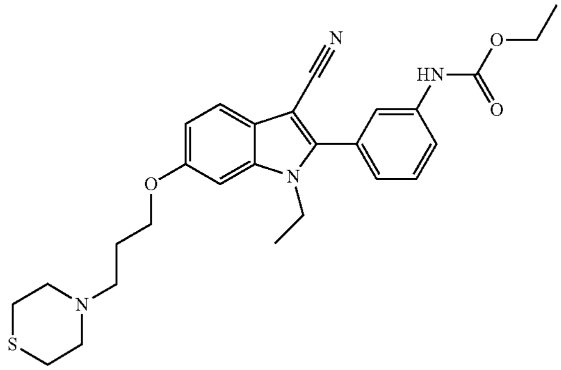

-continued
528
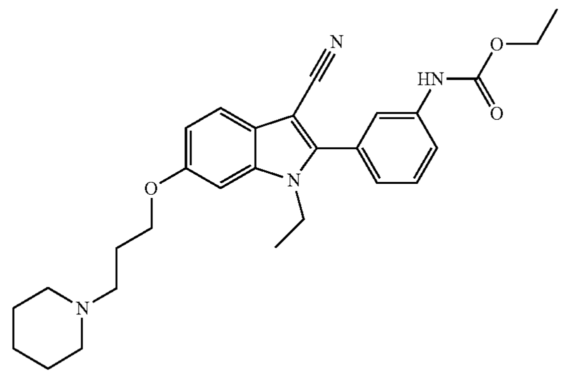
529
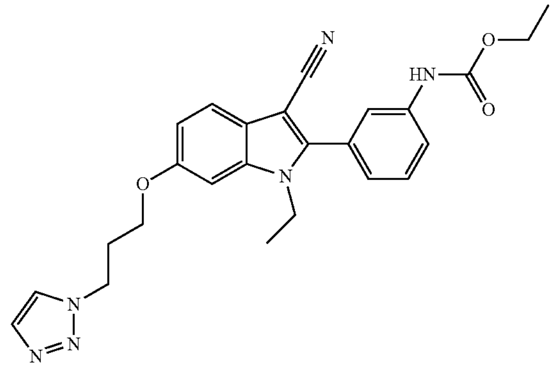
530
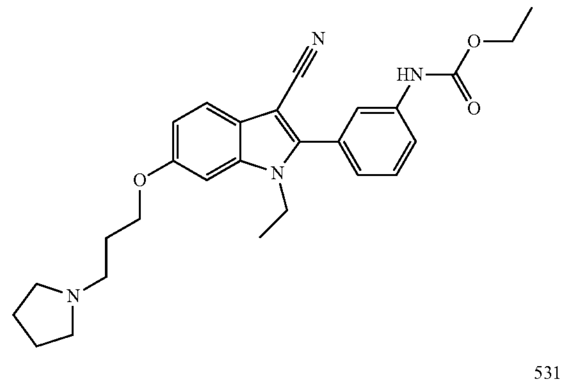
531
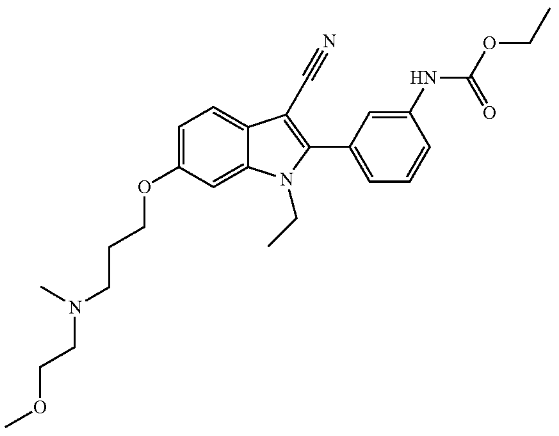
-continued
532
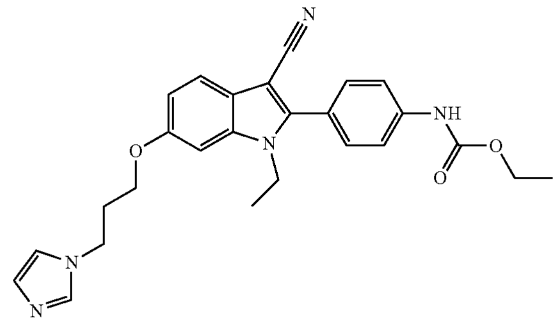
533
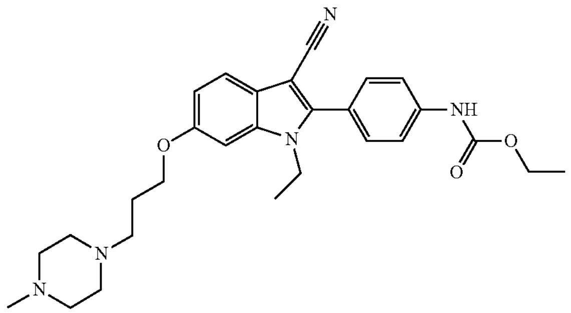
534
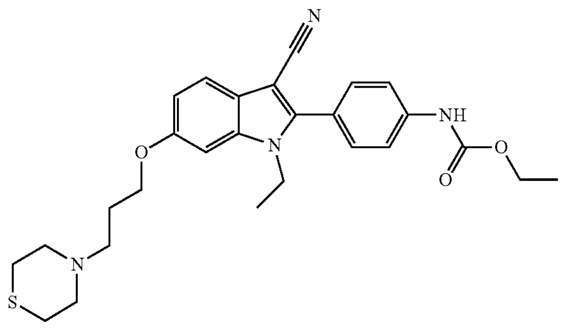
535
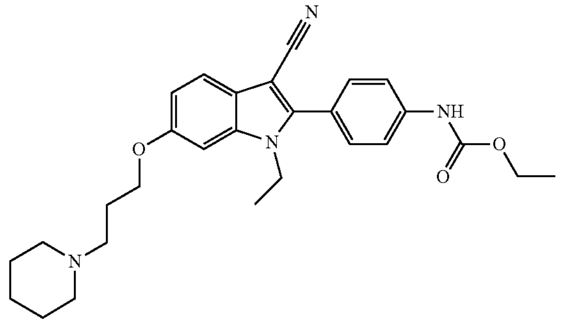

-continued
536
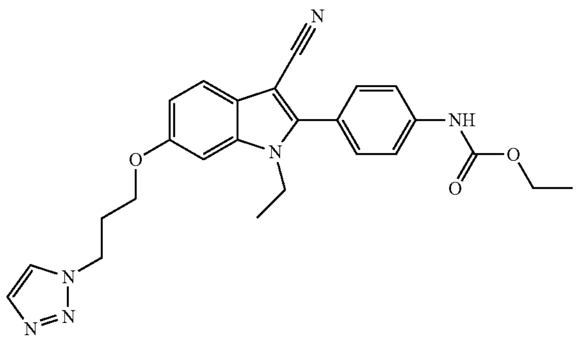
537
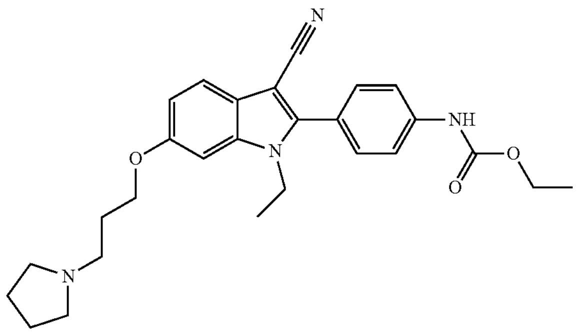
538
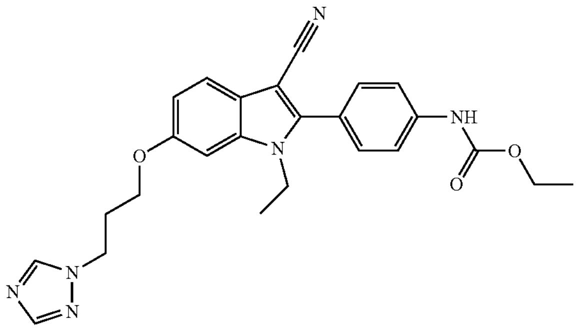
539
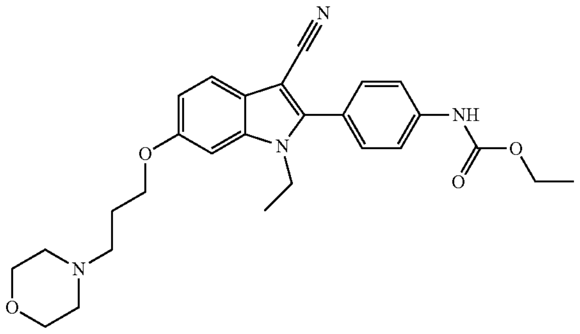
-continued
540
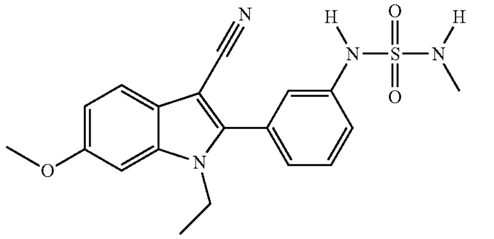
541
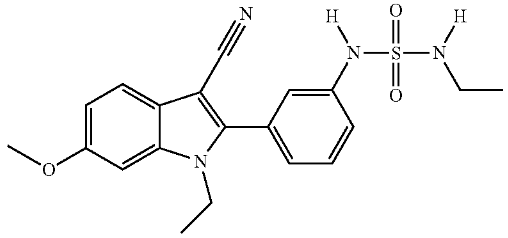
542
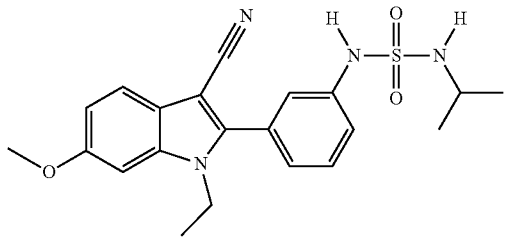
543
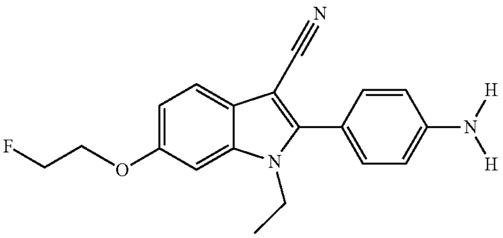
544
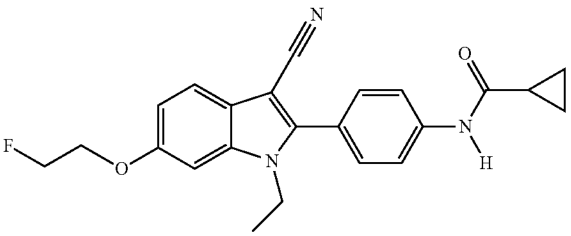
545
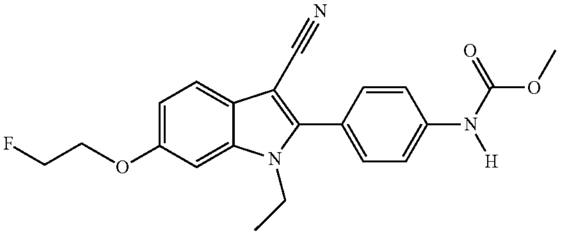

-continued
546
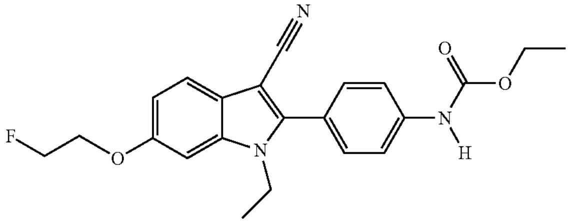
547
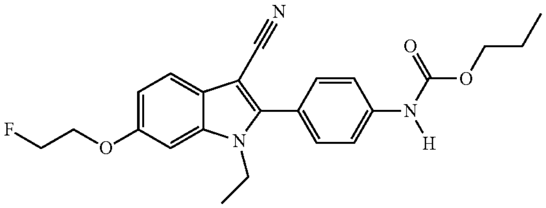
548
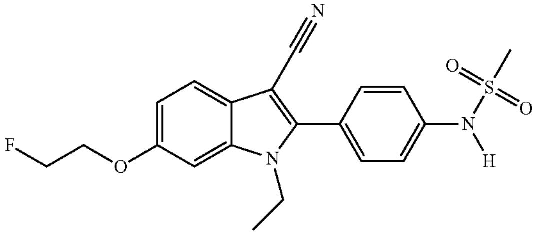
549
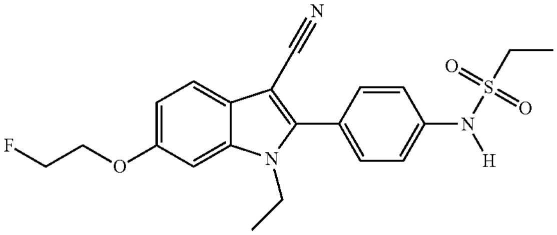
550
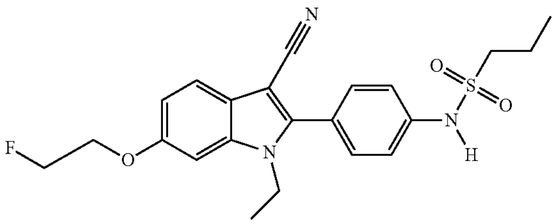
551
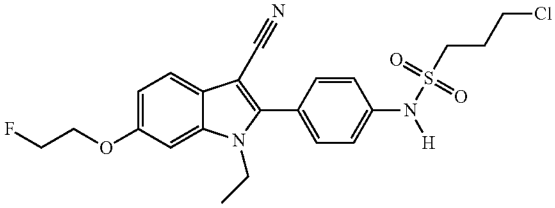
-continued
552
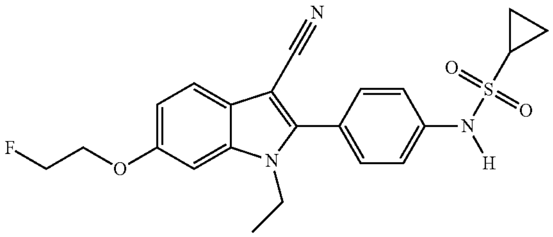
553
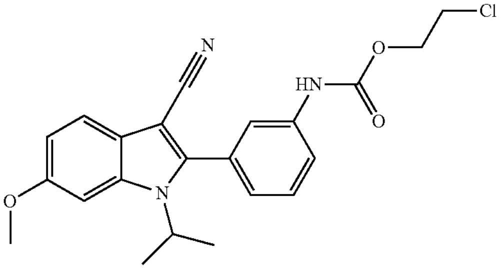
554
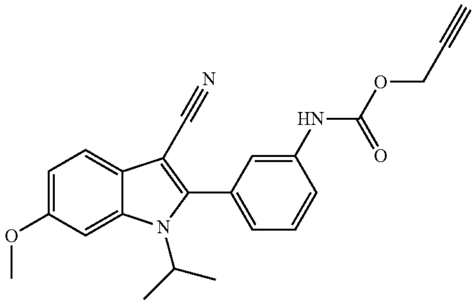
555
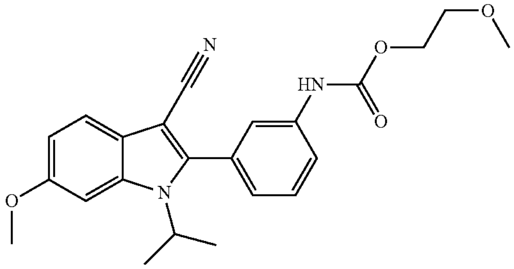
556
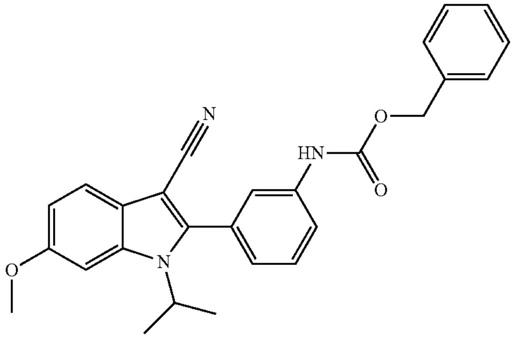

-continued
557
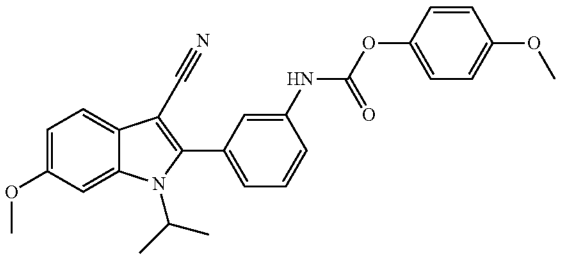
558
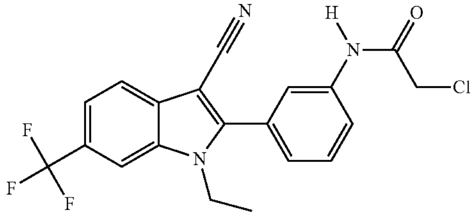
559
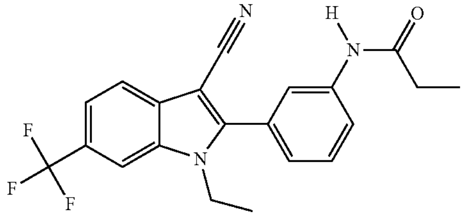
560
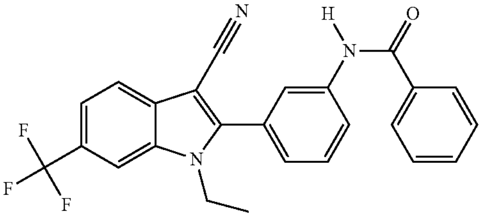
561
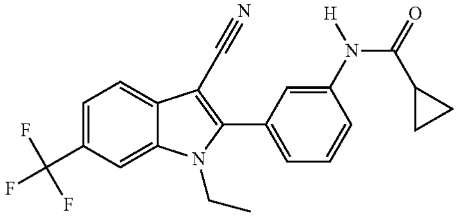
562
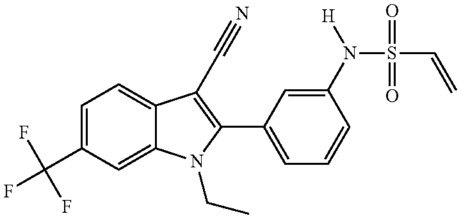
563
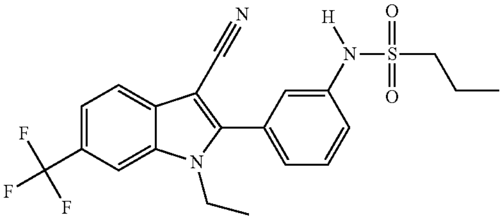
-continued
564
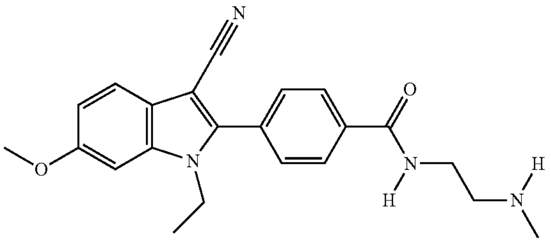
565
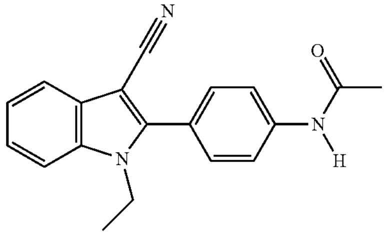
566
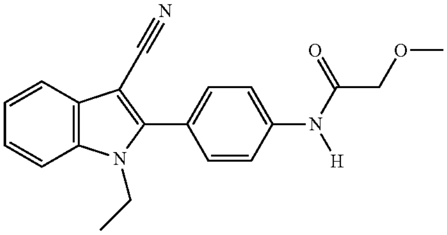
567
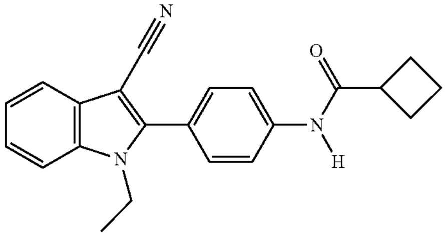
568
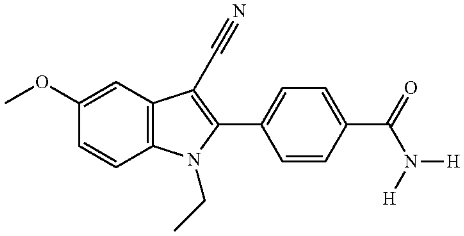
569
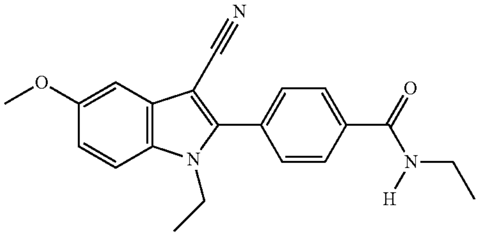

-continued
570
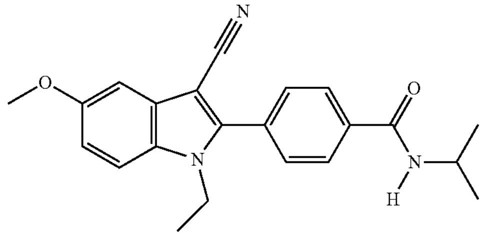
571
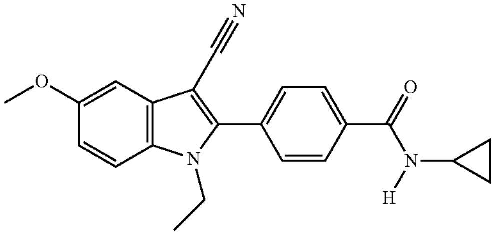
572
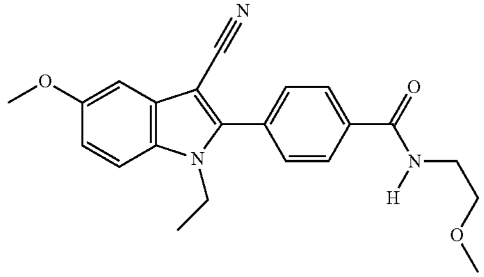
573
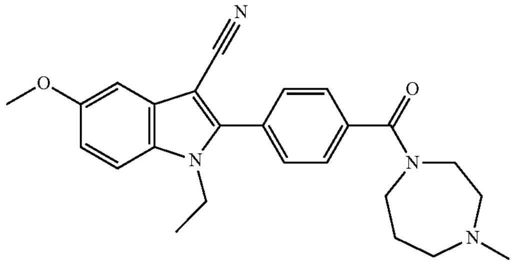
574
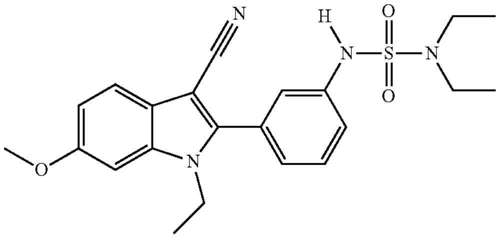
575
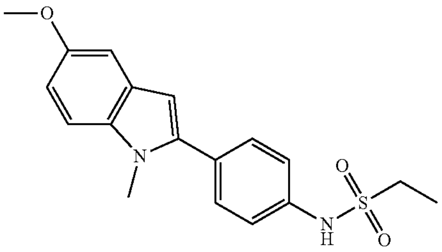
-continued
576
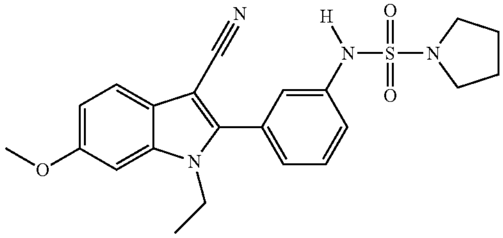
577
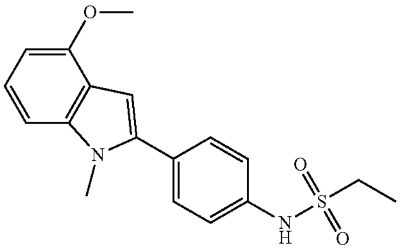
578
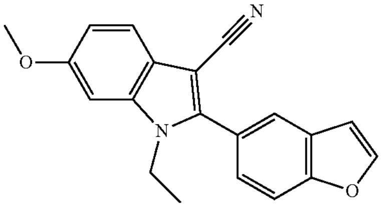
579
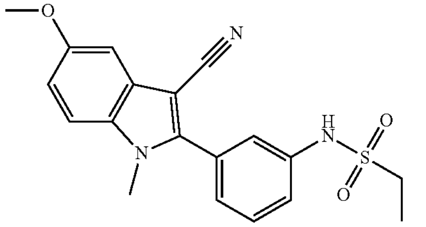
580
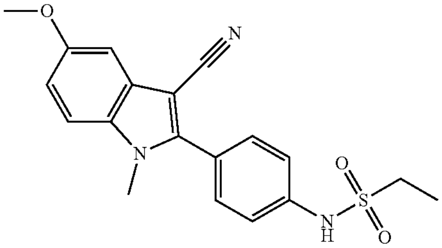
581
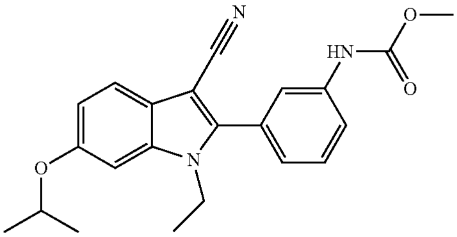

-continued
582
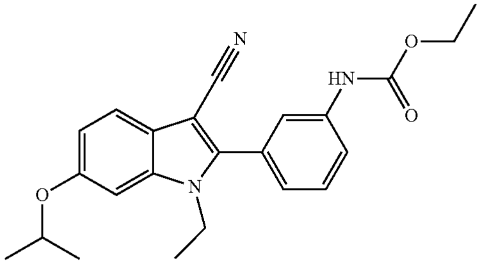
583
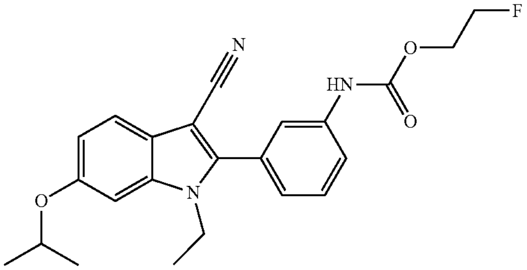
584
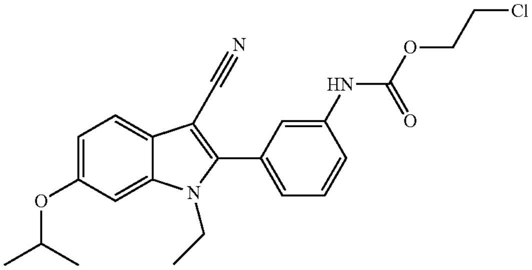
585
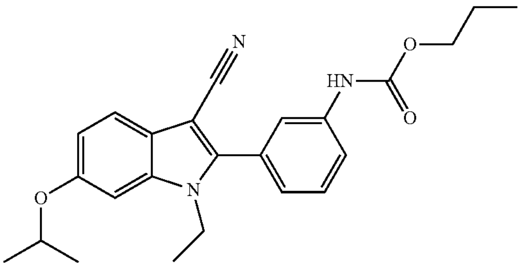
586
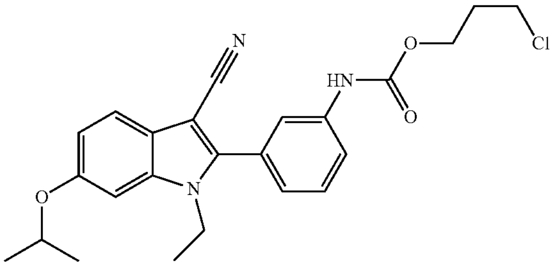
-continued
587
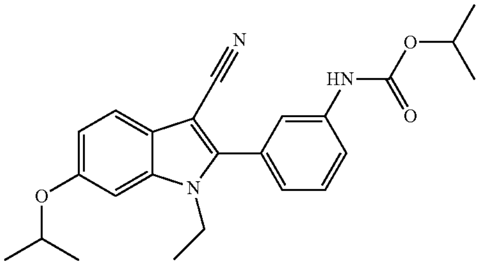
588
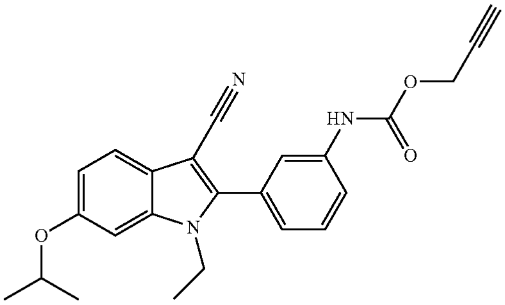
589
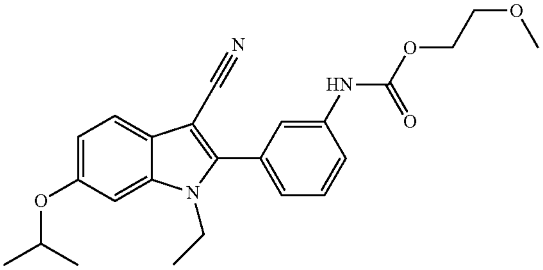
590
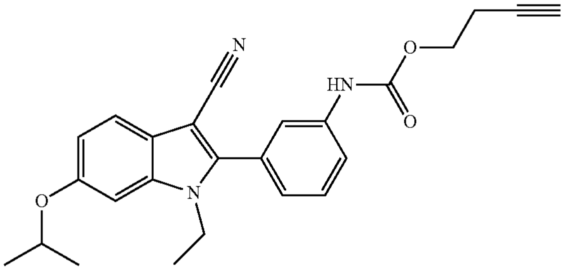
591
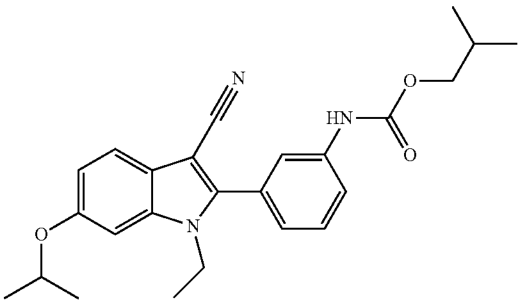

-continued
592
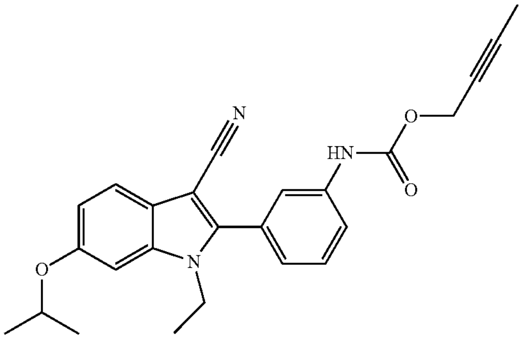
593
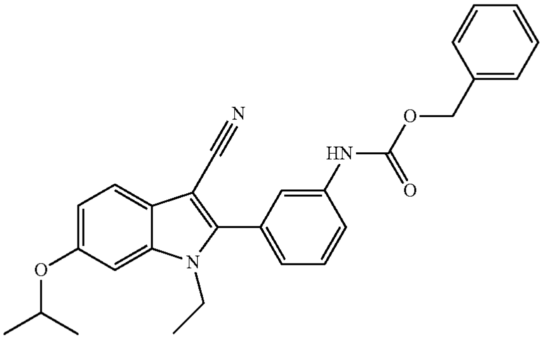
594
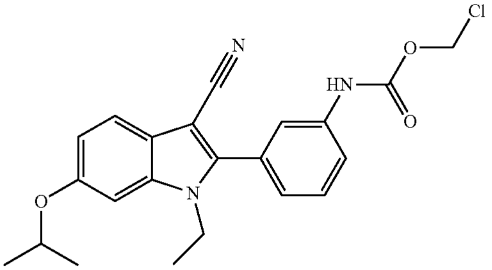
595
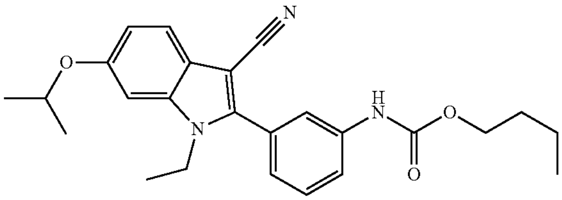
596
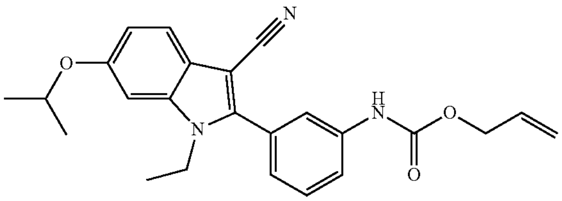
-continued
597
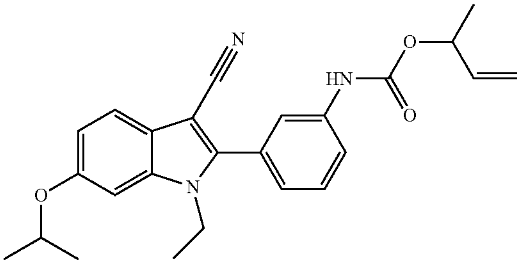
598
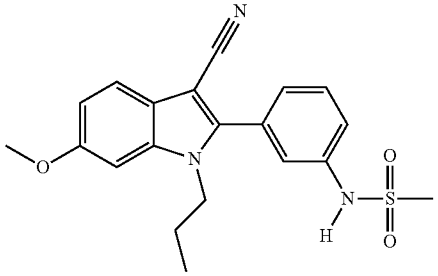
599
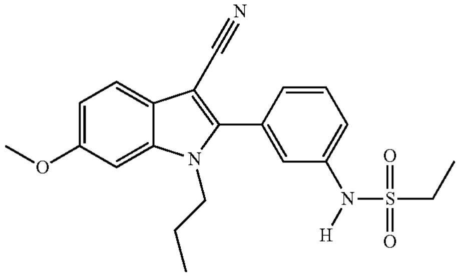
600
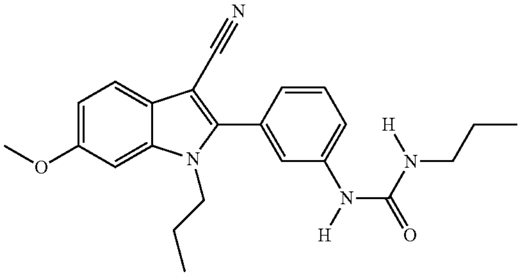
601
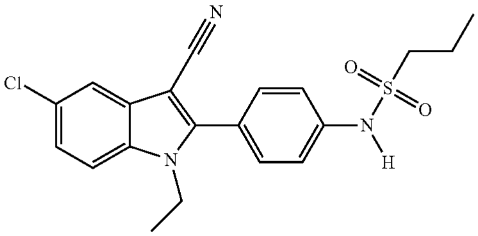
602
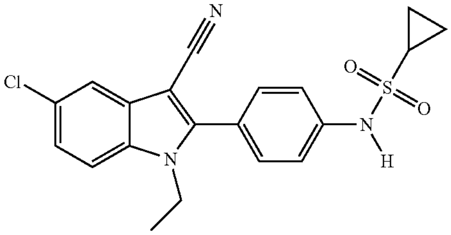

-continued
603
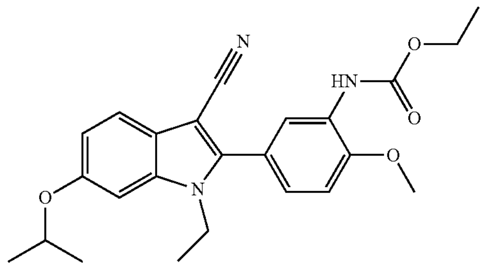
604
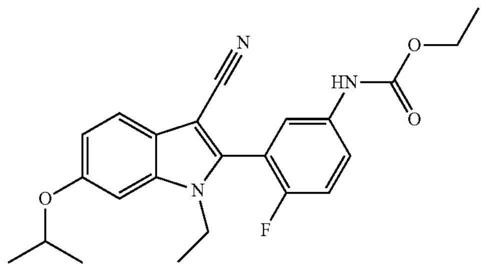
605
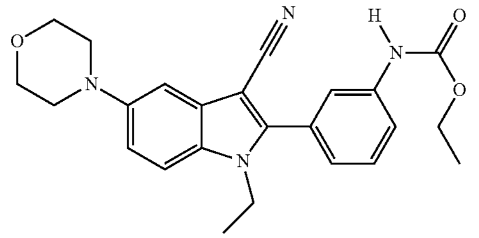
606
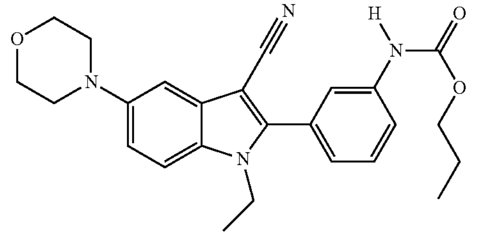
607
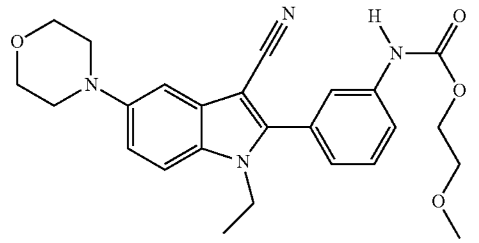
608
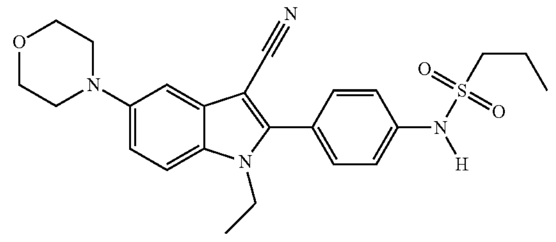
-continued
609
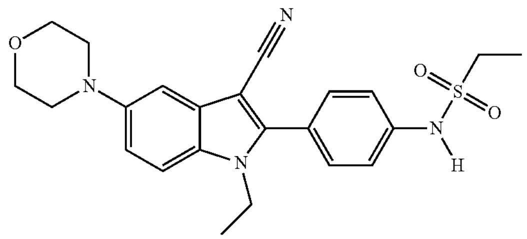
610
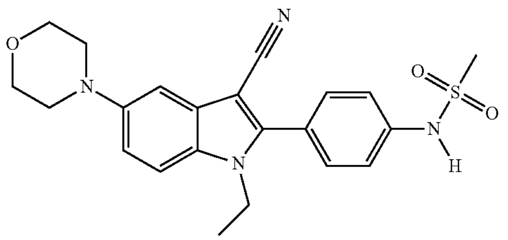
611
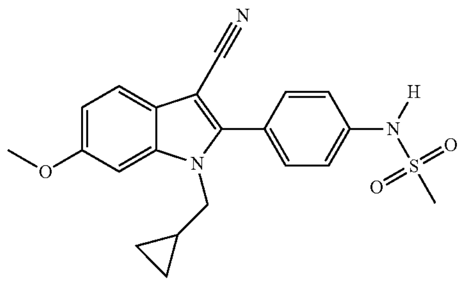
612
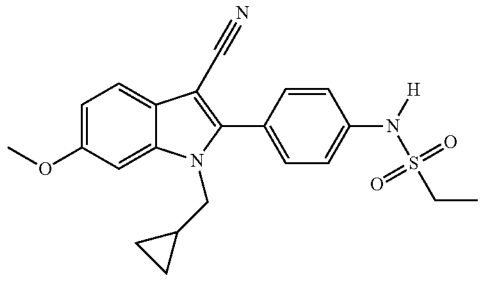
613
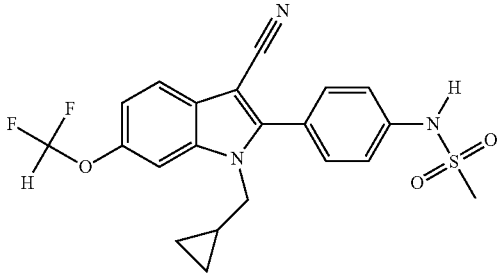

-continued
614
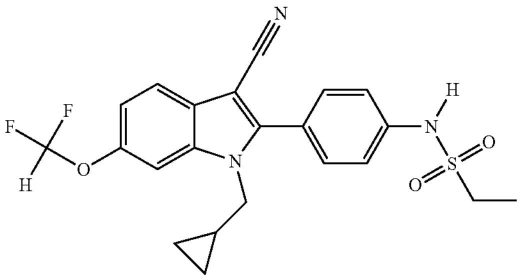
615
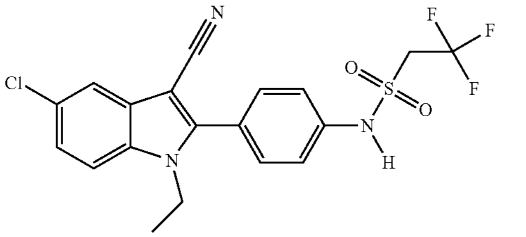
616
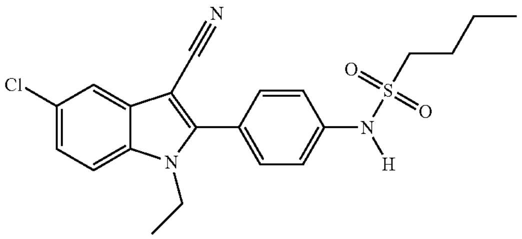
617
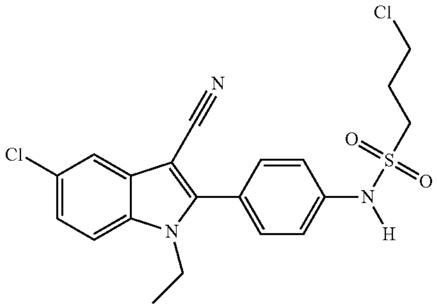
618
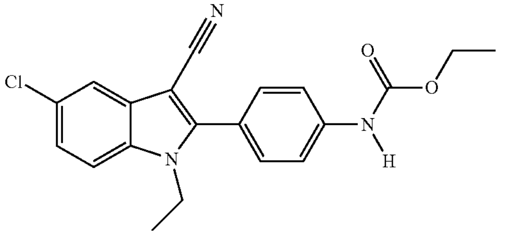
619
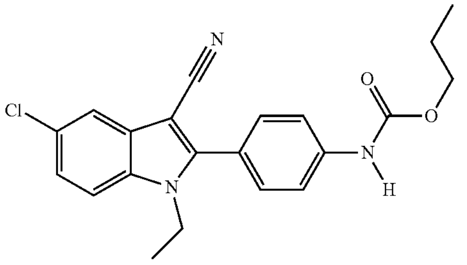
-continued
620
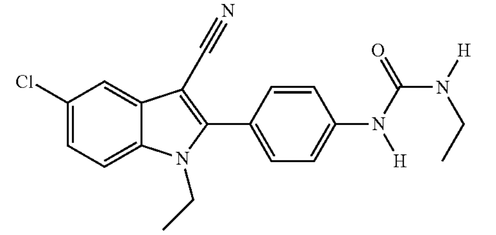
621
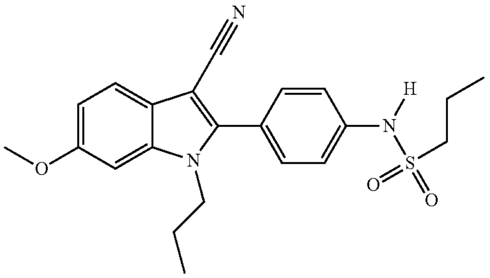
622
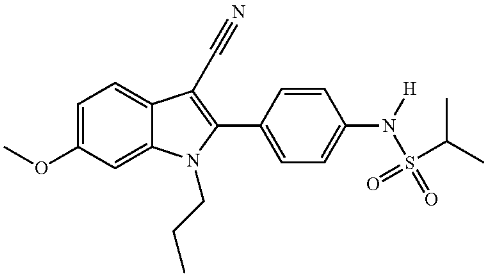
623
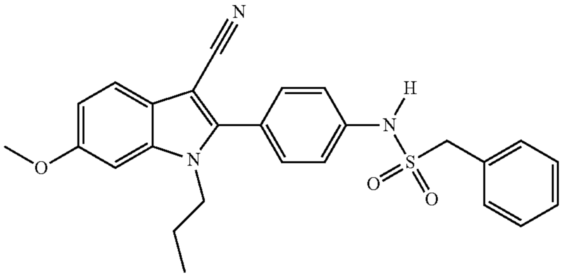
624
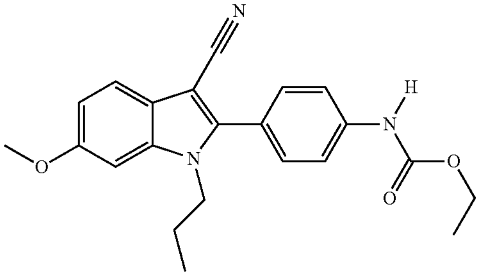

625
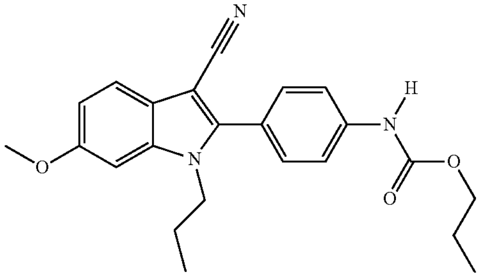
626
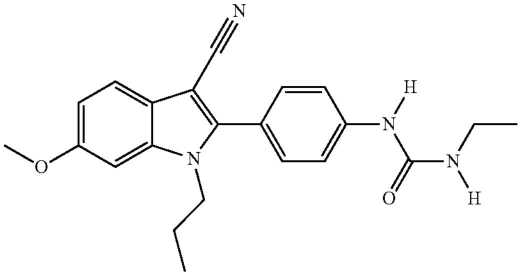
627
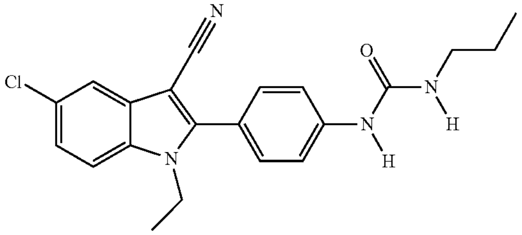
628
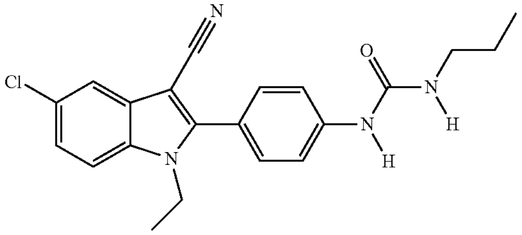
629
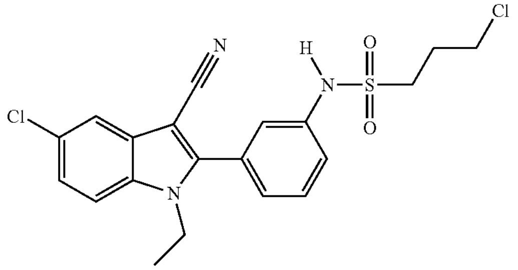
630
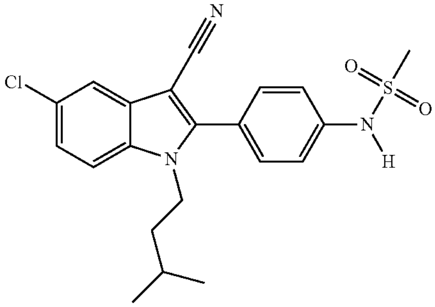
631
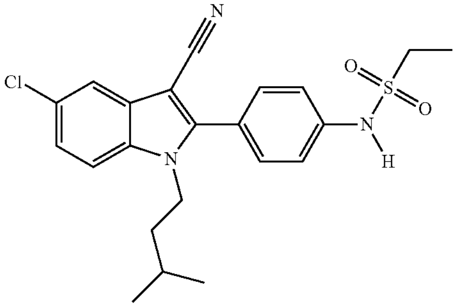
632
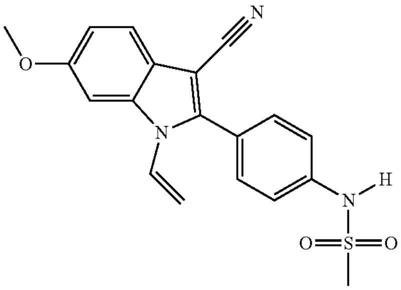
633
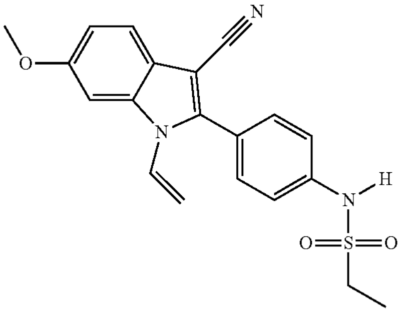
634
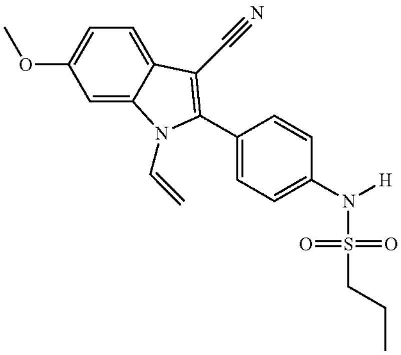

-continued
635
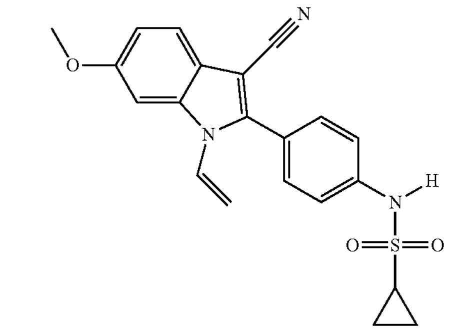
636
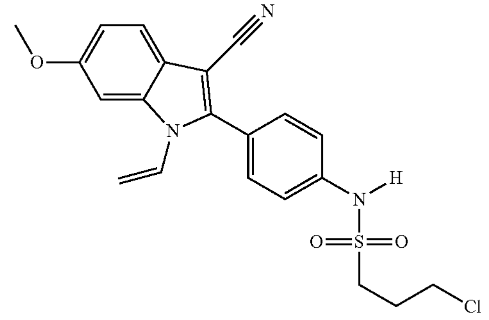
637
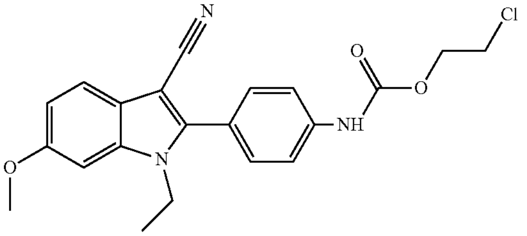
638
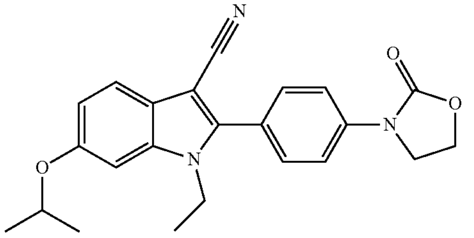
639
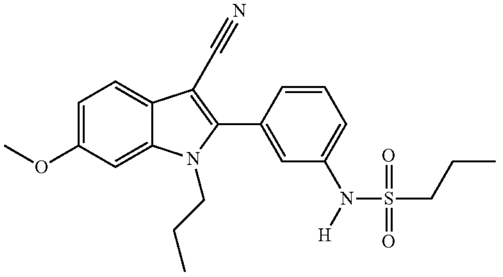
-continued
640
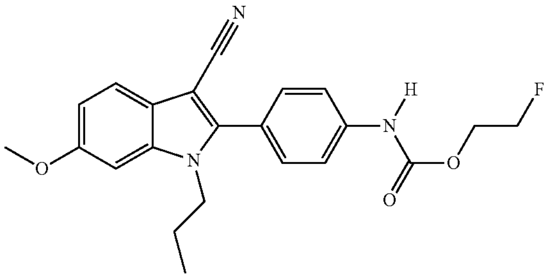
641
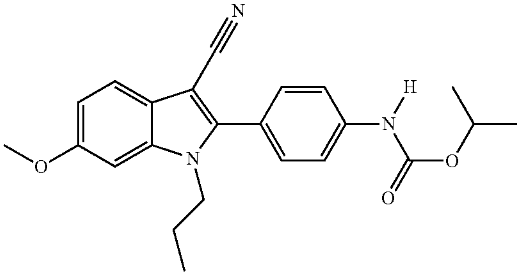
642
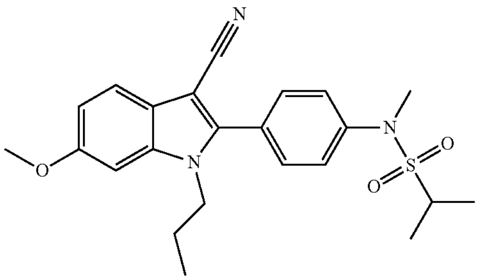
643
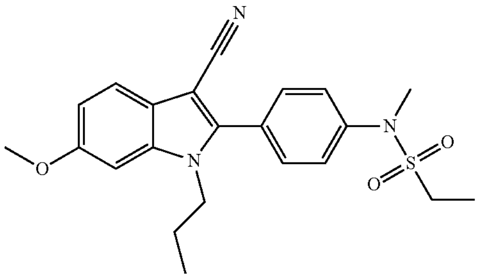
644
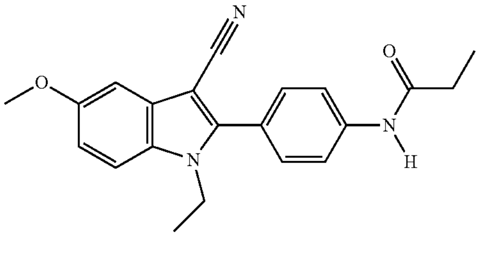

645
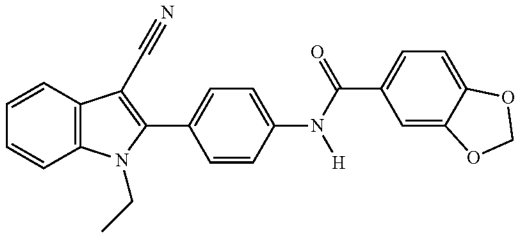
646
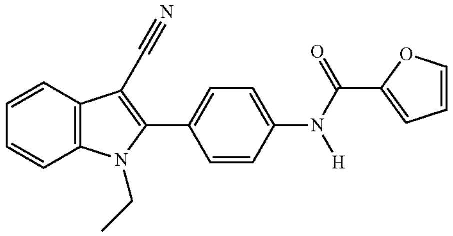
647
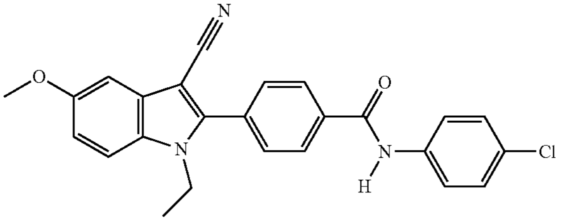
648
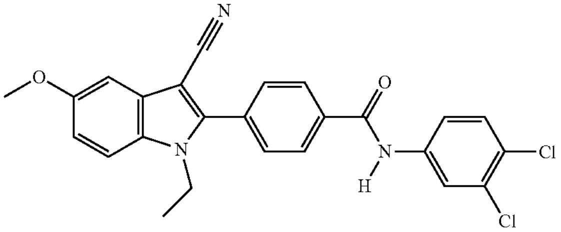
649
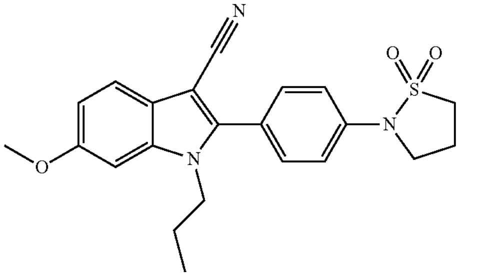
650
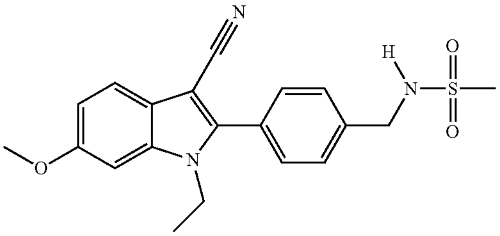
651
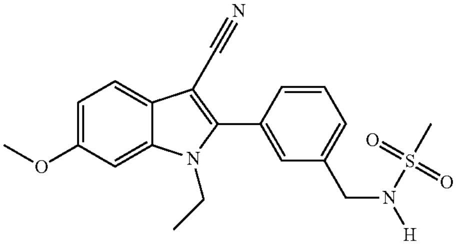
652
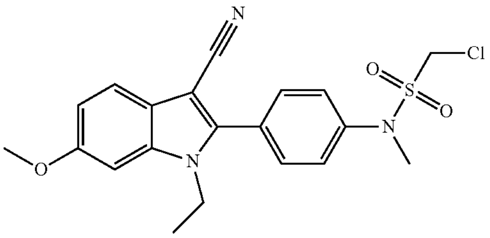
653
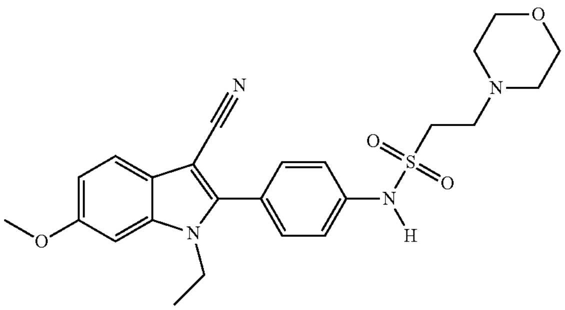
654
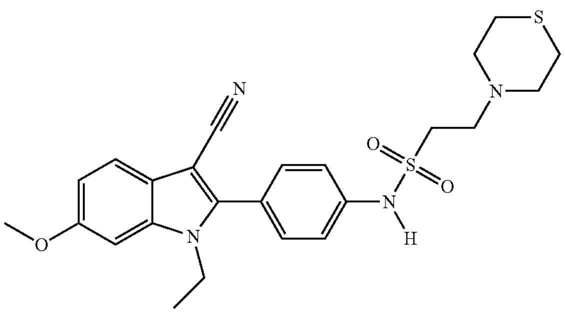
655
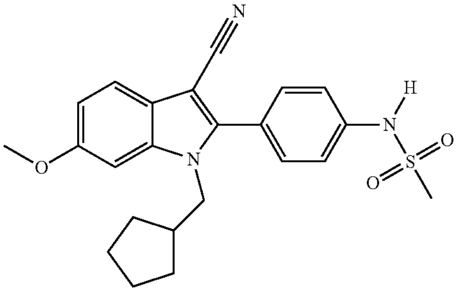

-continued
656
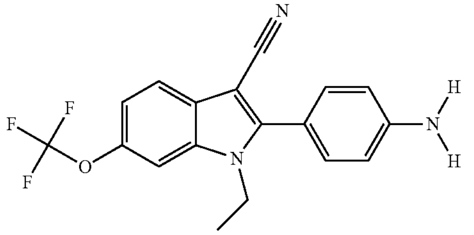
657
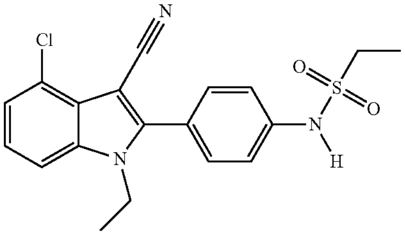
658
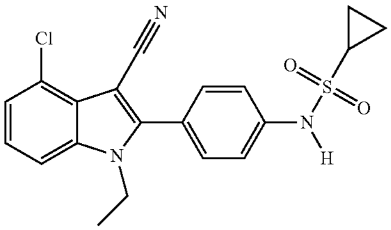
659
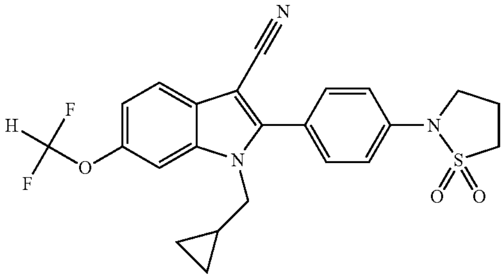
660
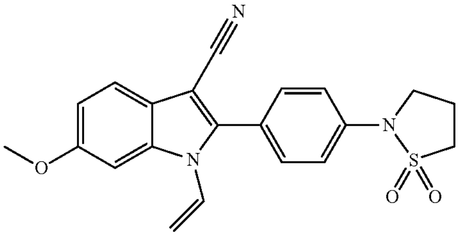
661
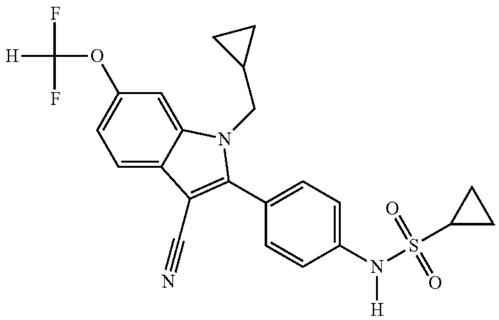
-continued
662
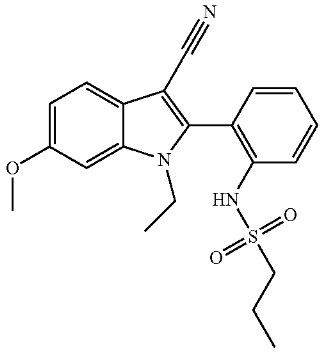
663
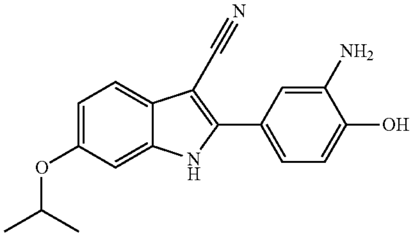
664
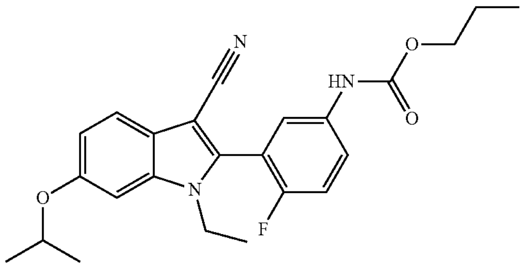
665
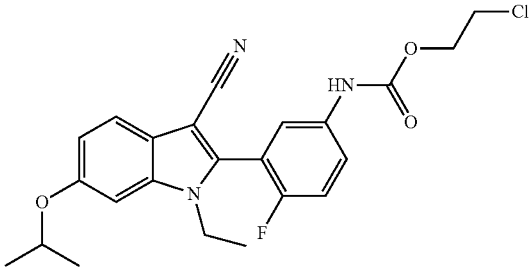
666
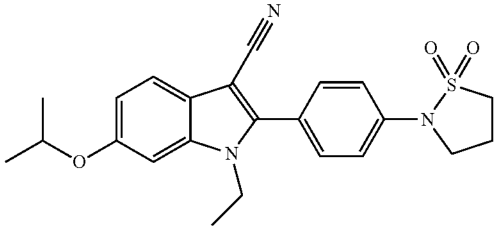

-continued
667
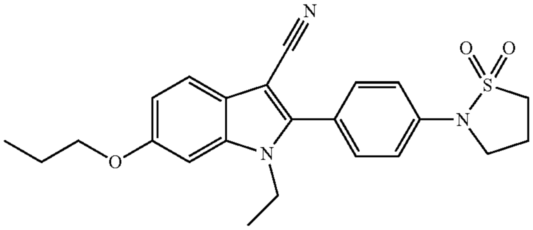
668
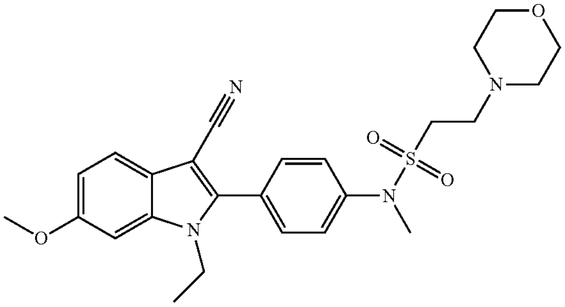
669
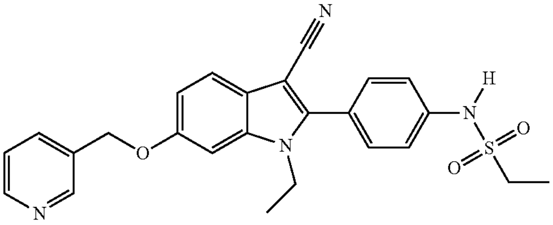
670
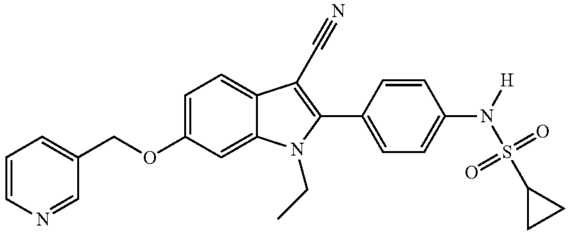
671
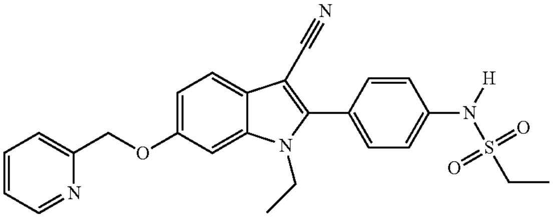
672
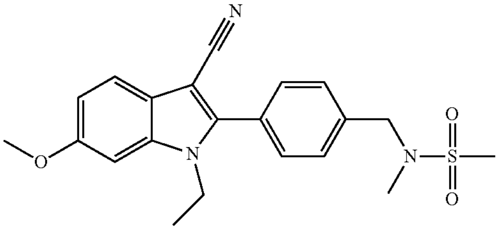
-continued
673
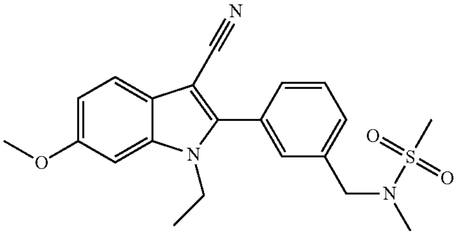
674
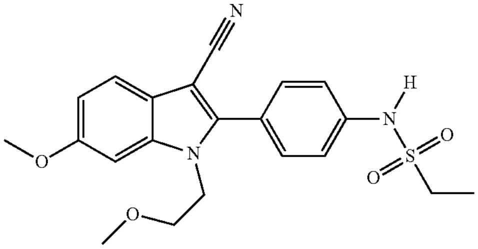
675
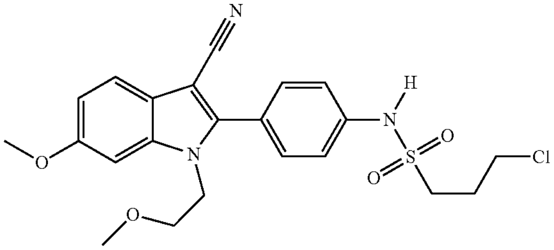
676
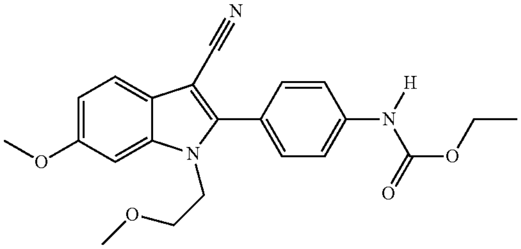
677
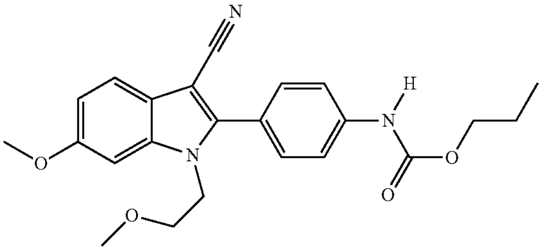
678
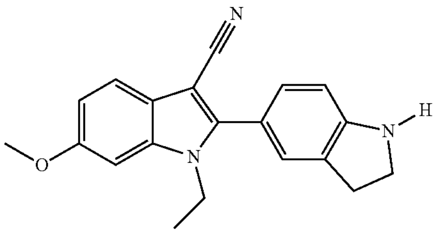

-continued
679
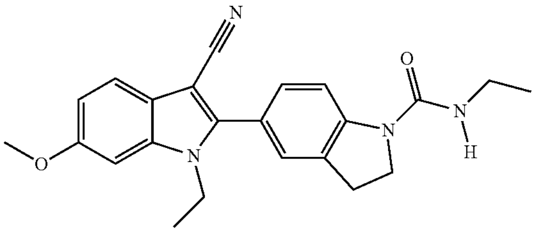
680
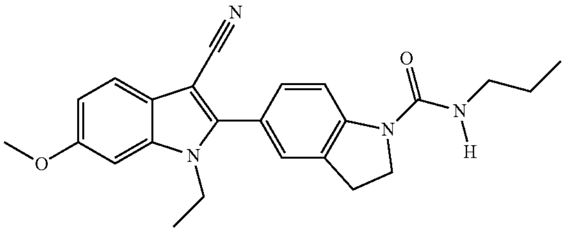
681
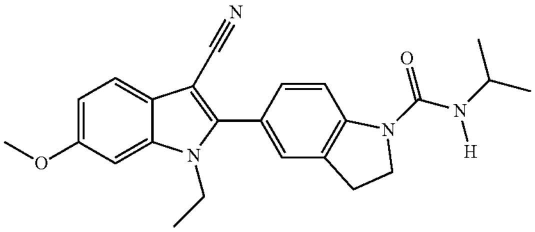
682
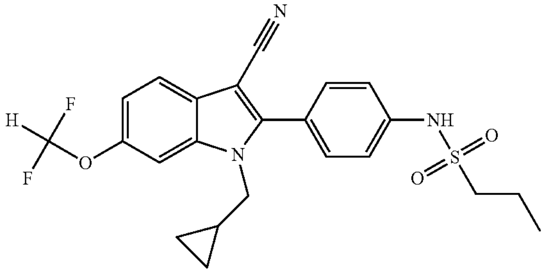
683
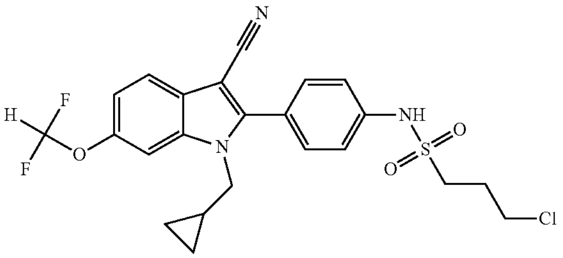
684
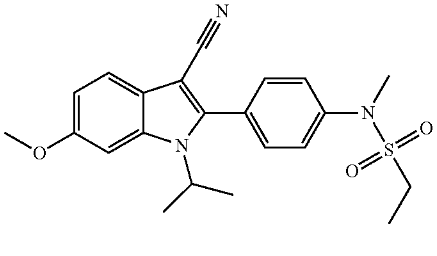
-continued
685
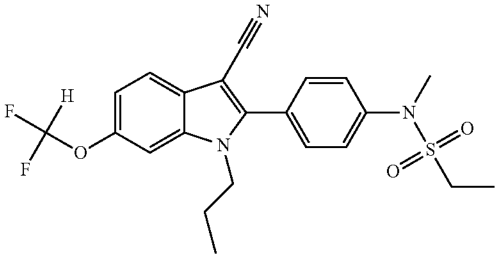
686
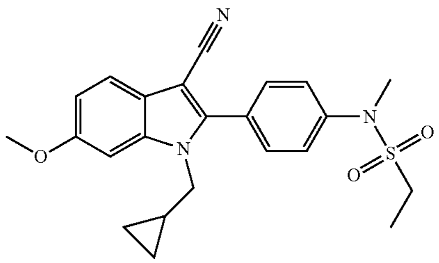
687
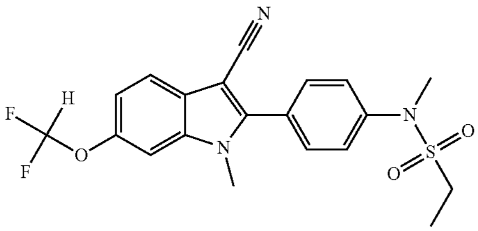
688
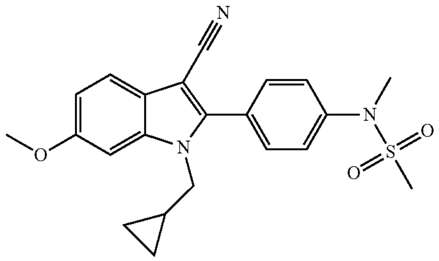
689
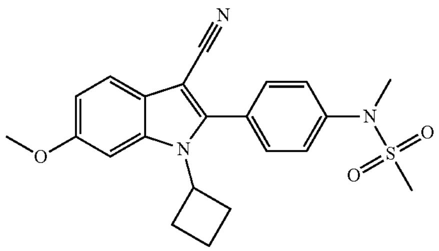
690
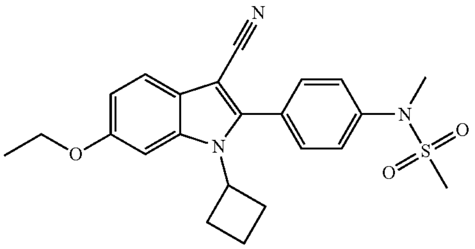

-continued
691
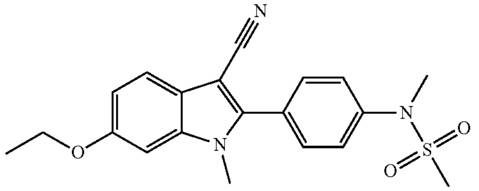
692
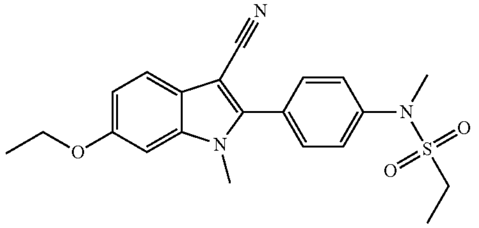
693
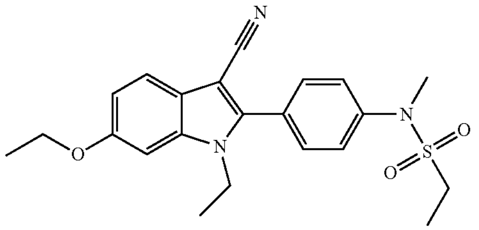
694
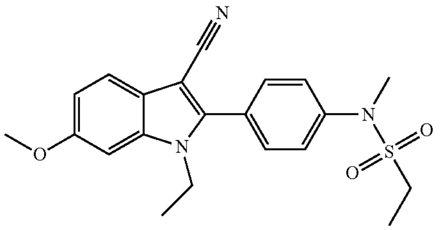
695
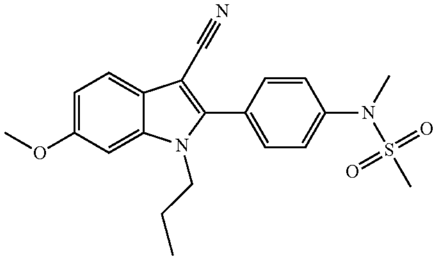
696
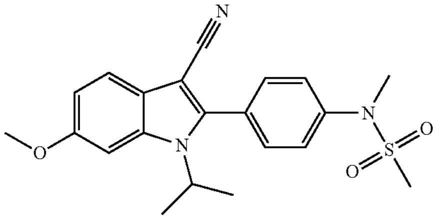
-continued
697
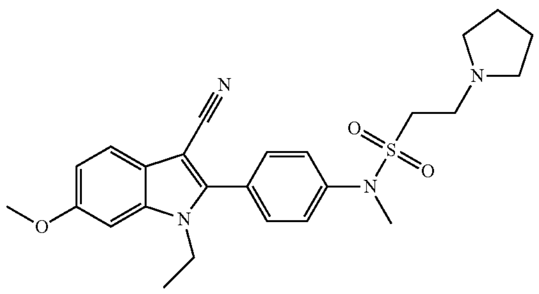
698
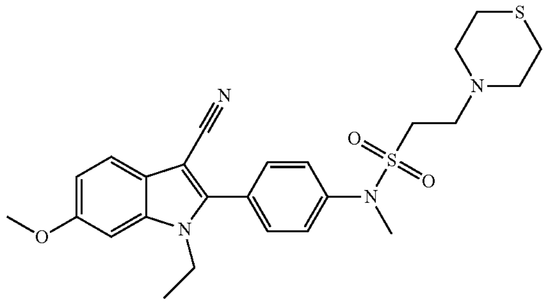
699
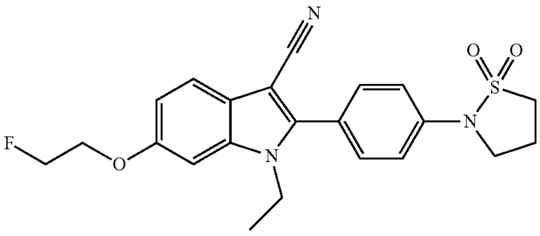
701
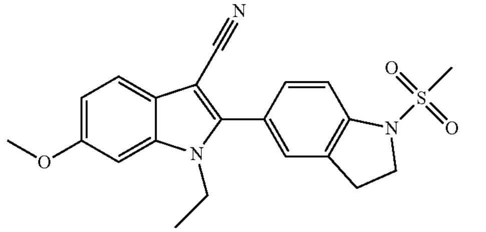
702
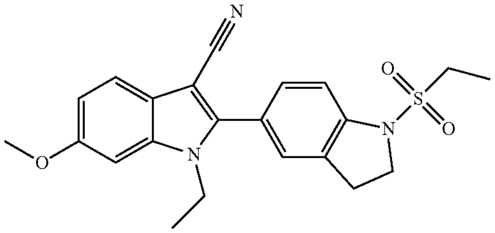
703
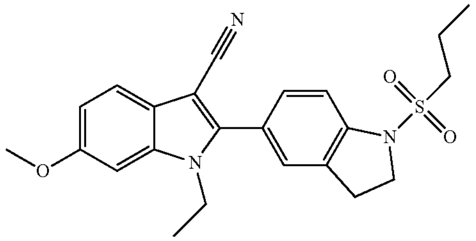

-continued
704
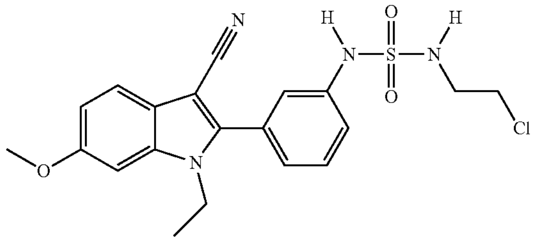
705
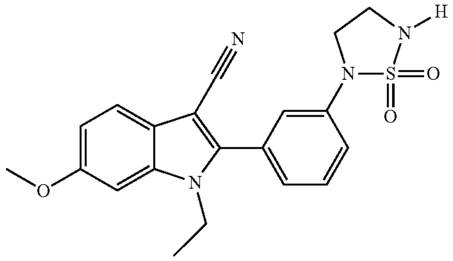
706
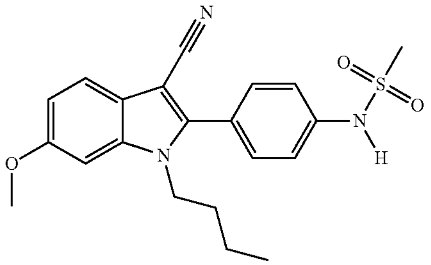
707
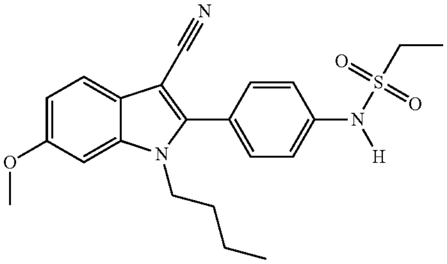
708
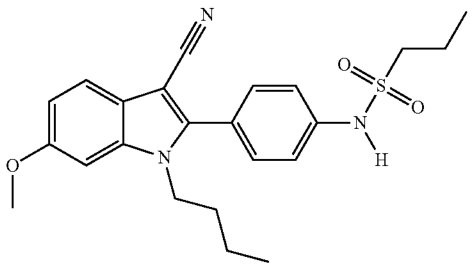
709
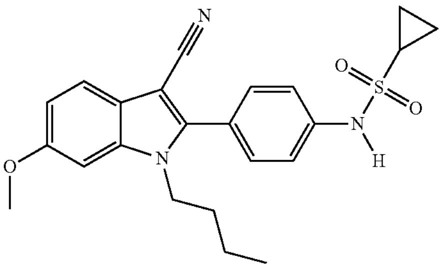
-continued
710
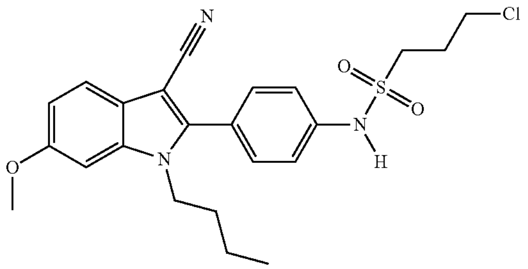
711
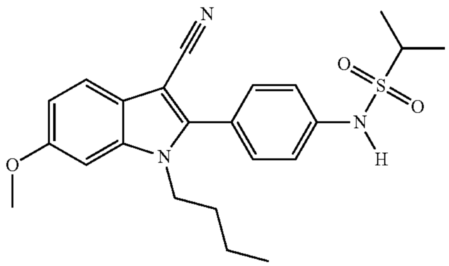
712
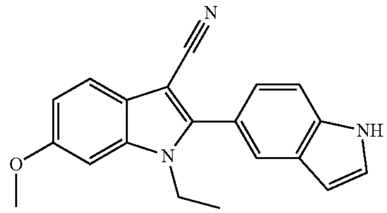
713
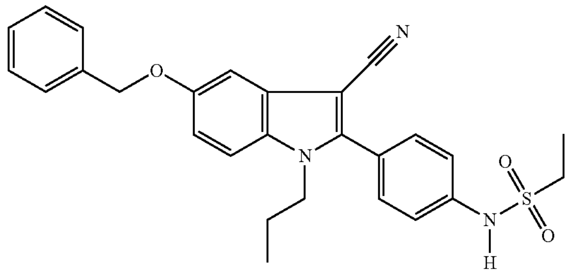
714
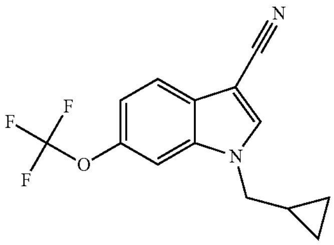
715
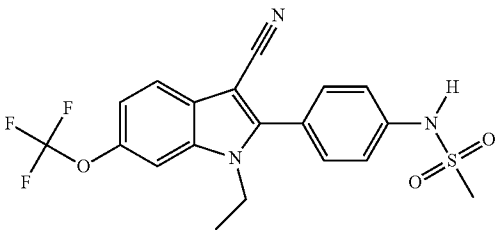

-continued
716
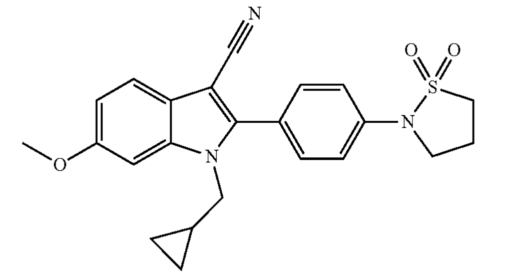
717
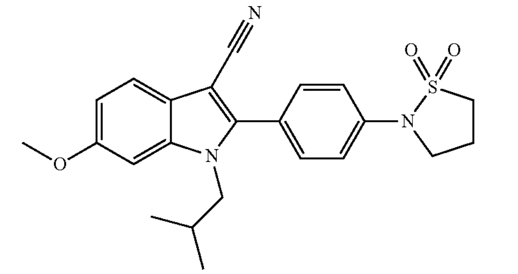
718
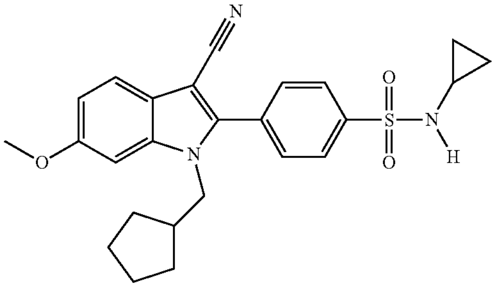
719
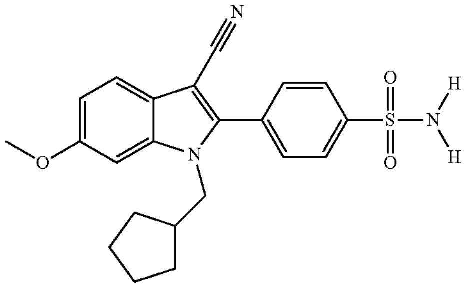
720
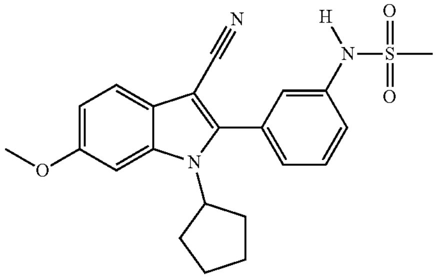
-continued
721
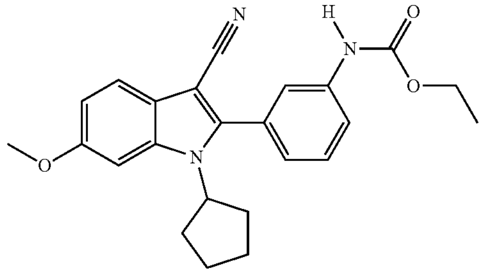
722
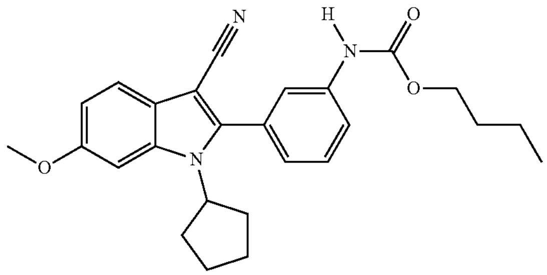
723
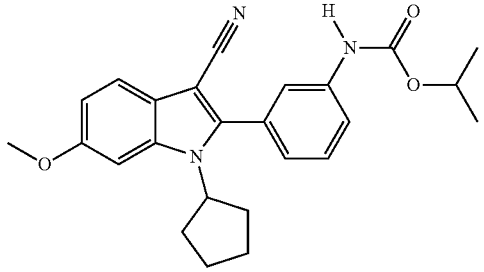
724
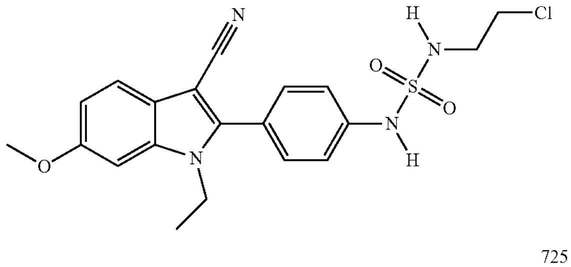
725
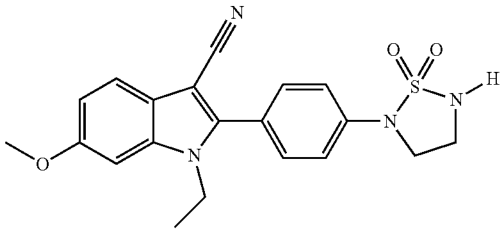
726
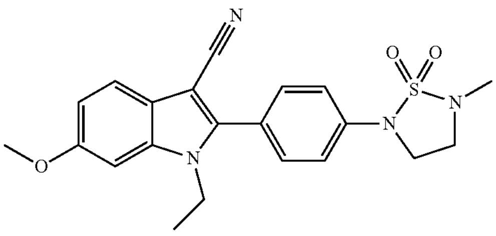

-continued
727
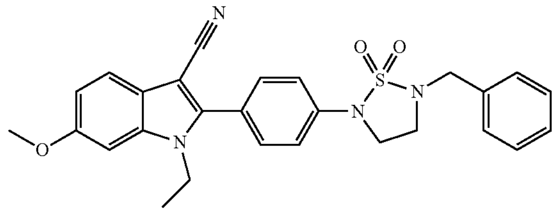
728
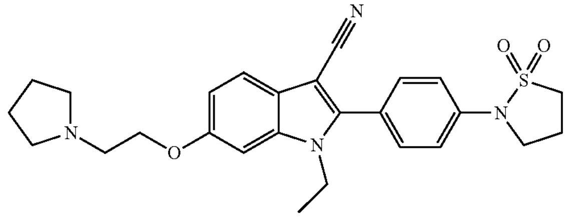
729
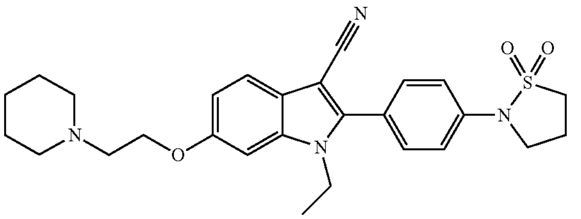
730
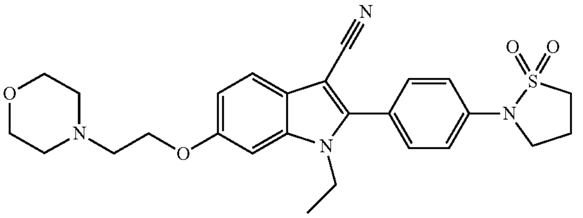
731
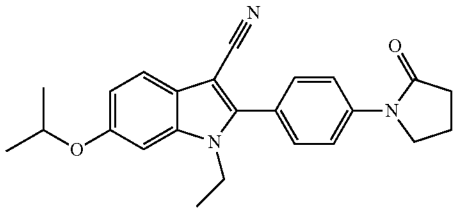
732
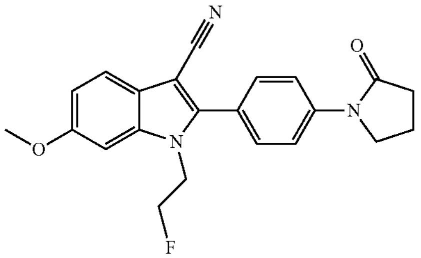
-continued
733
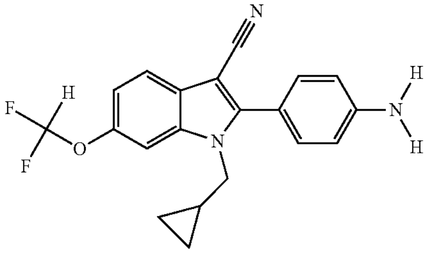
734
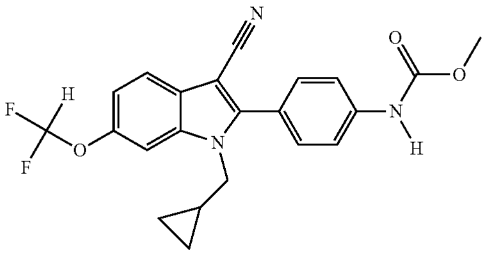
735
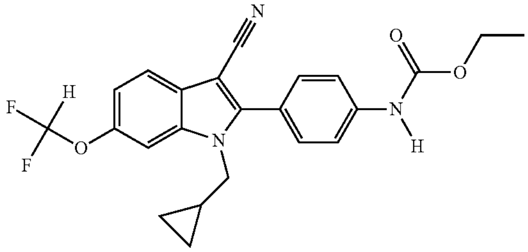
736
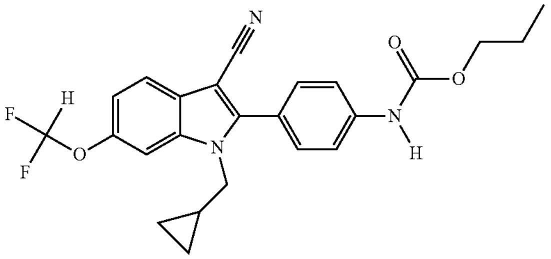
737
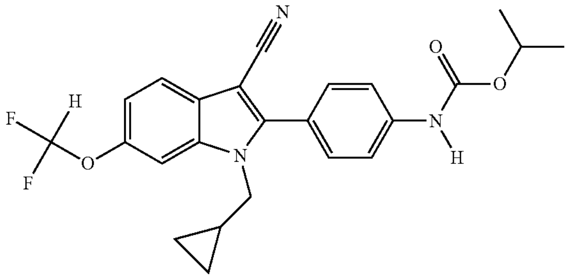

-continued
738
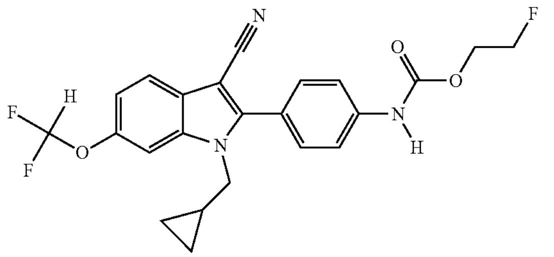
739
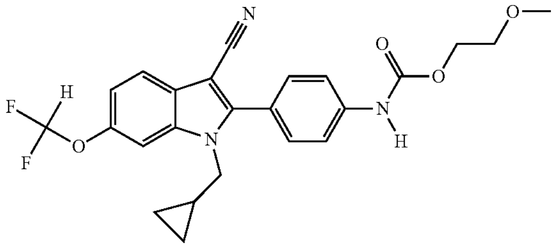
740
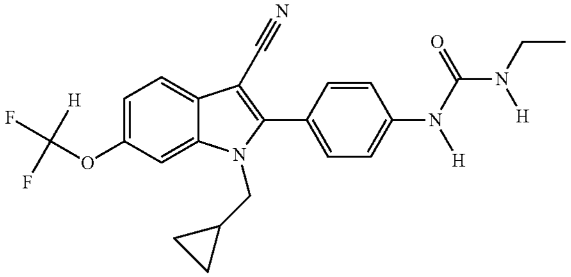
741
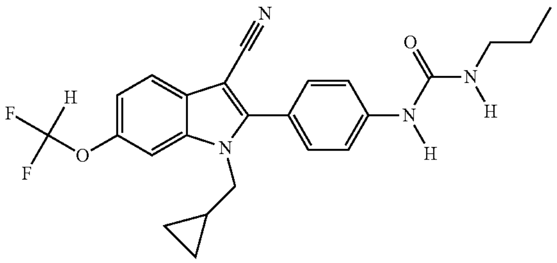
742
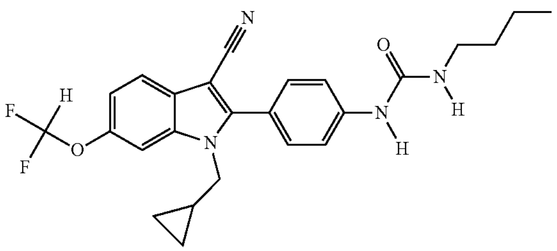
-continued
743
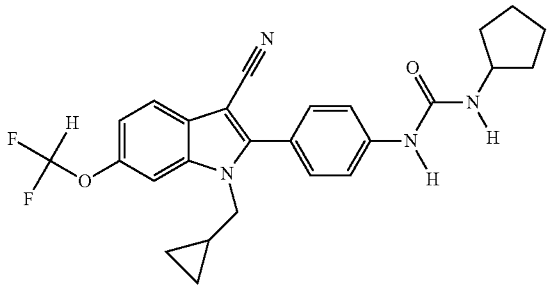
744
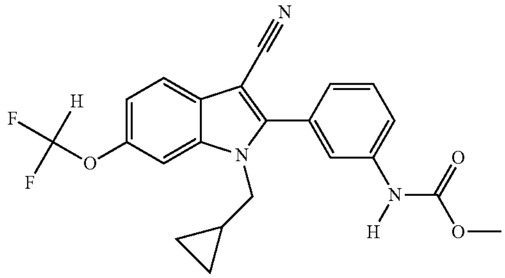
745
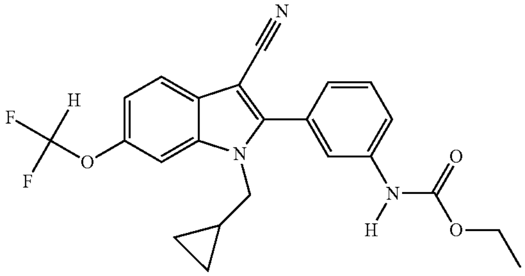
746
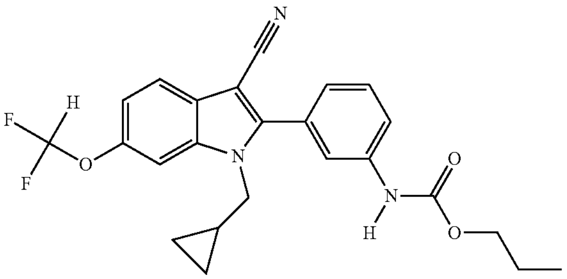
747
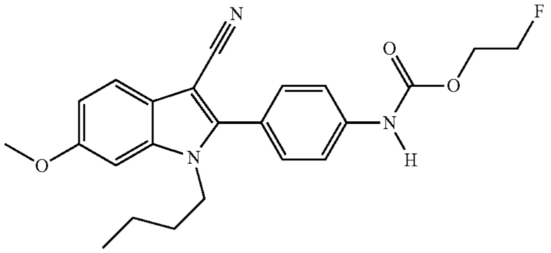

-continued
748
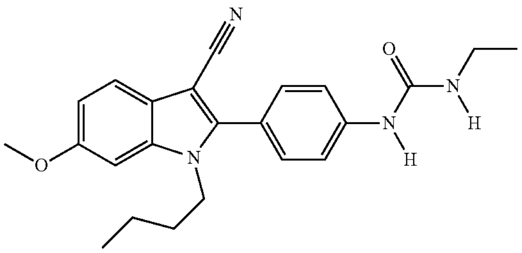
749
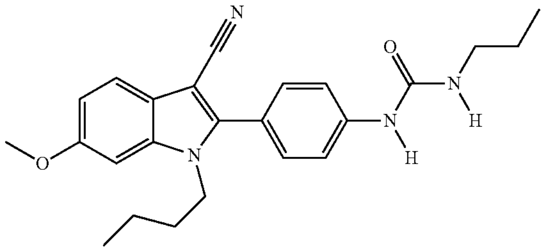
750
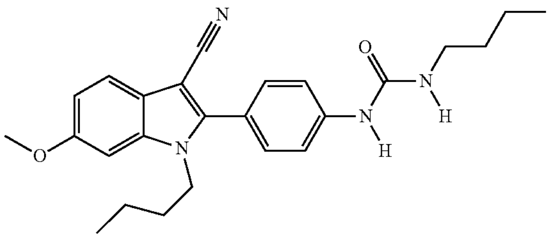
751
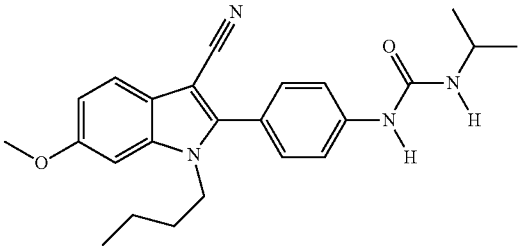
752
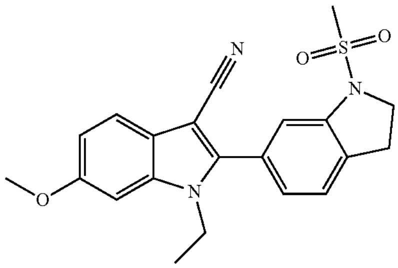
-continued
753
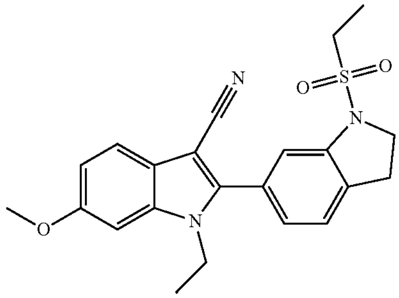
754
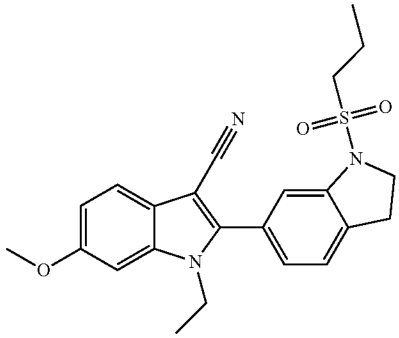
755
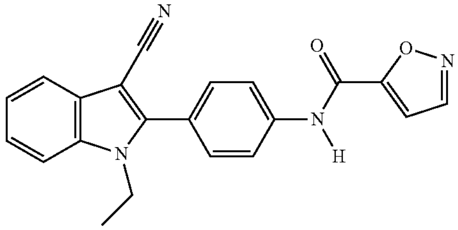
756
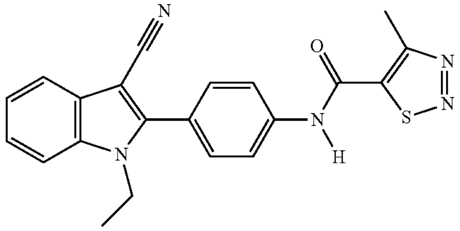
757
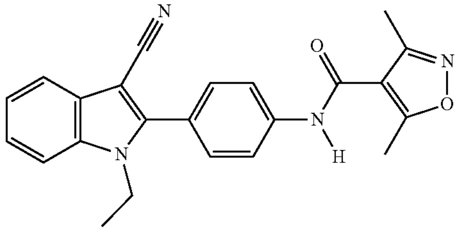
758
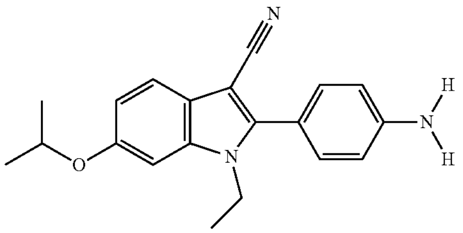

759
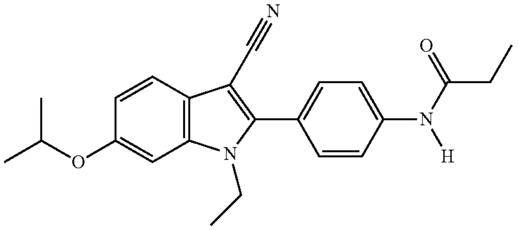
760
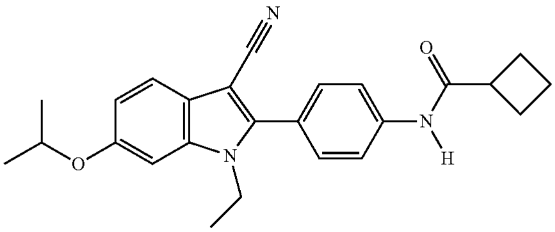
761
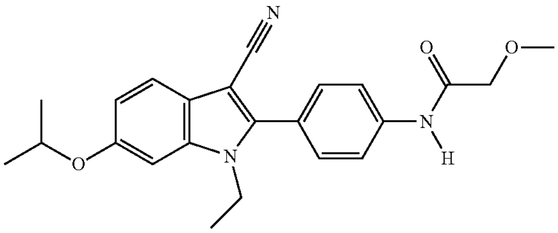
762
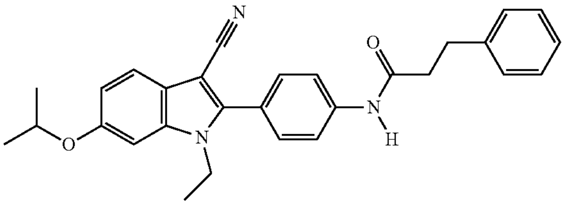
763
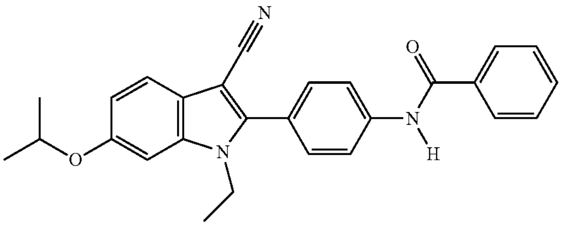
764
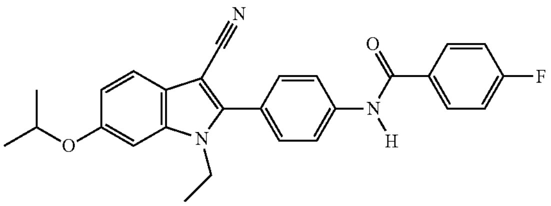
765
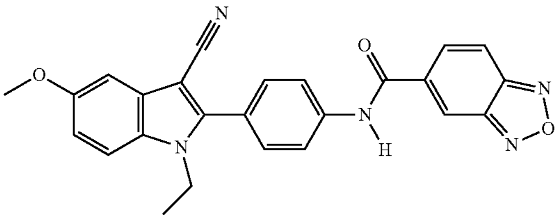
766
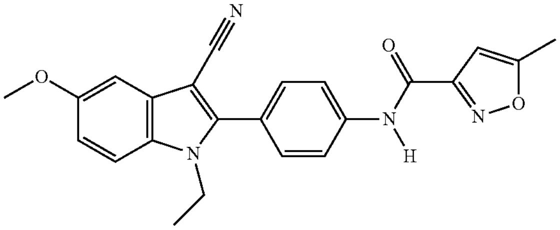
767
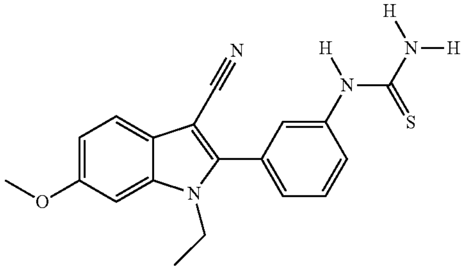
768
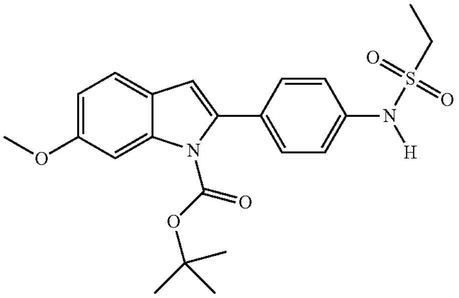
769
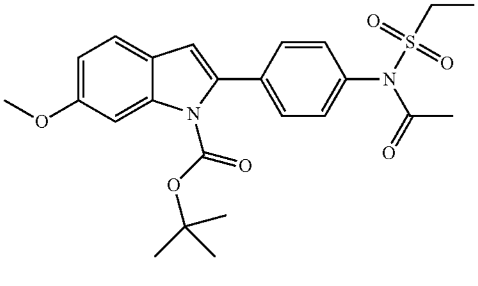
770
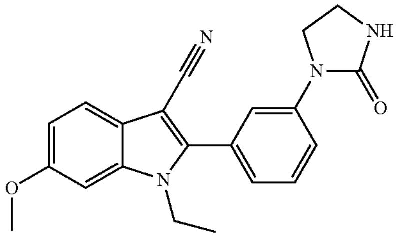

771
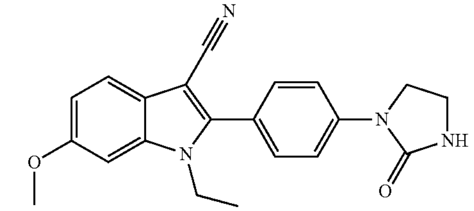
772
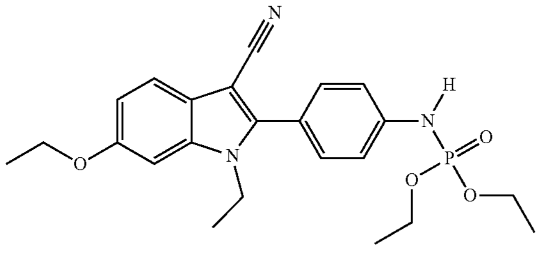
773
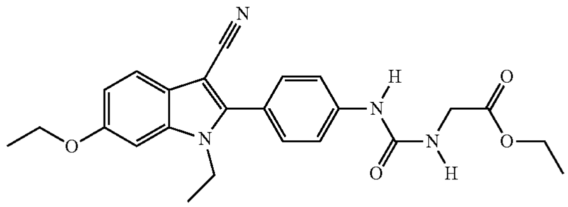
774
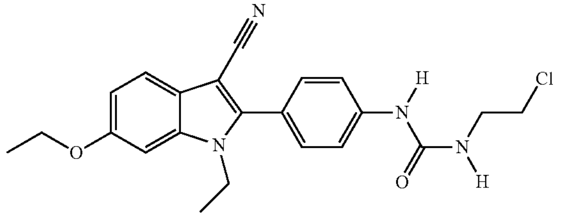
775
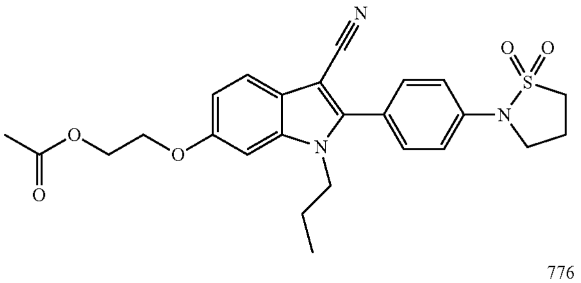
776
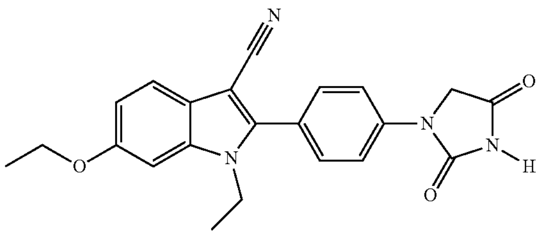
777
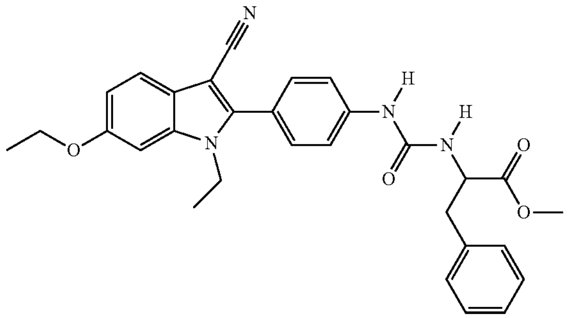
778
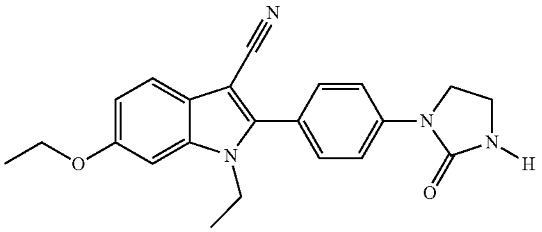
779
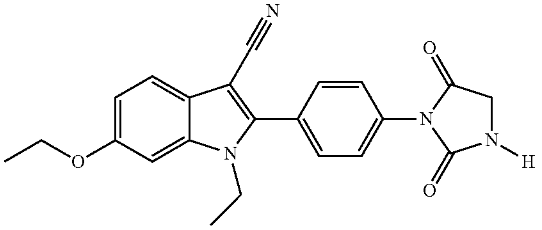
780
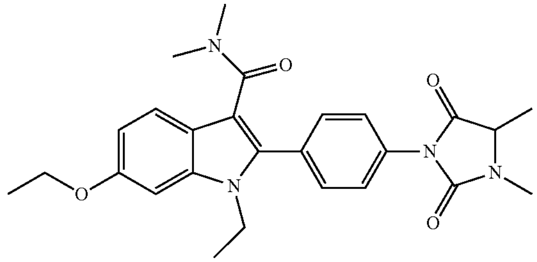
781
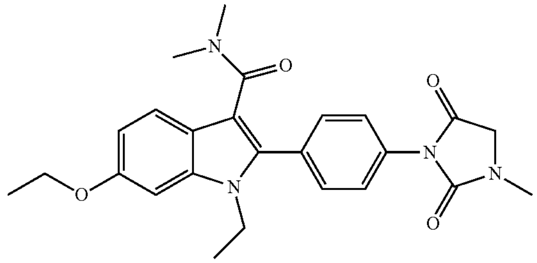

-continued
782
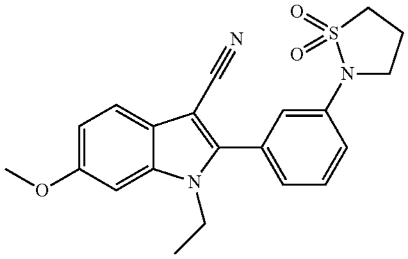
783
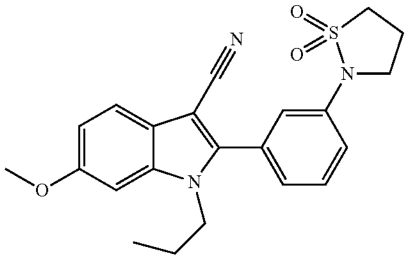
784
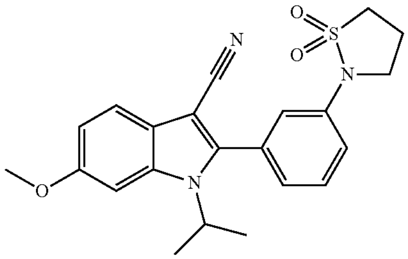
785
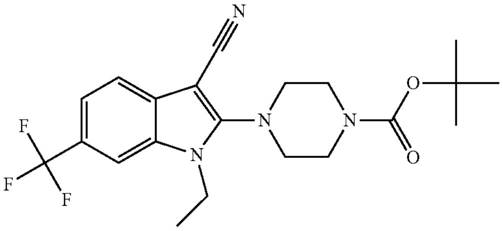
786
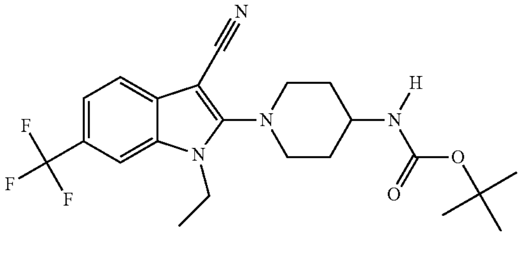
787
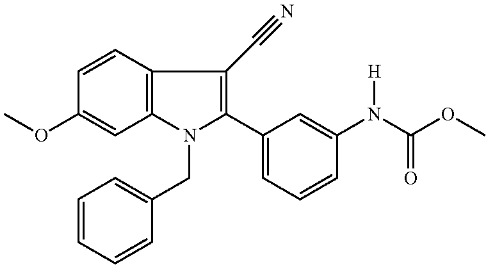
-continued
788
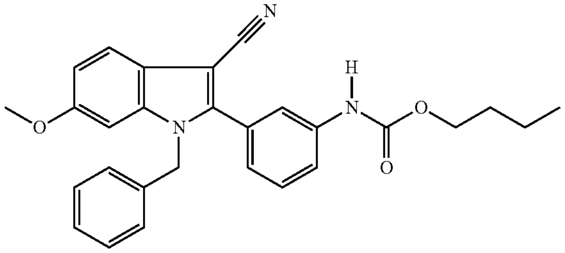
789
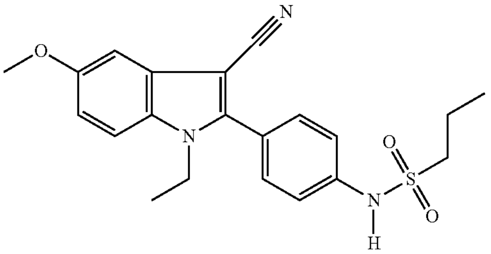
790
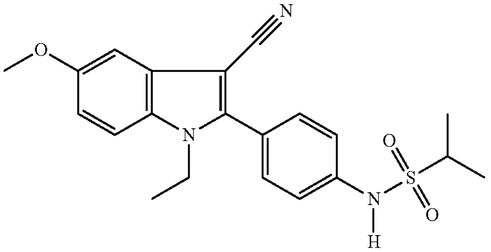
791
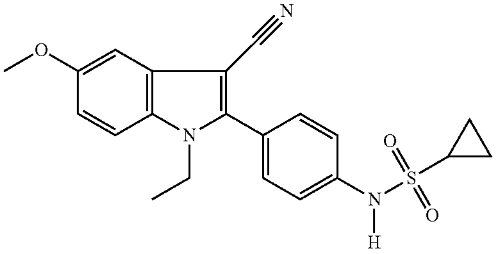
792
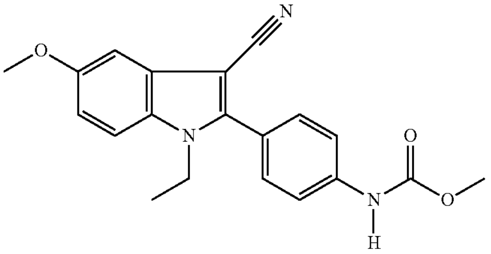
793
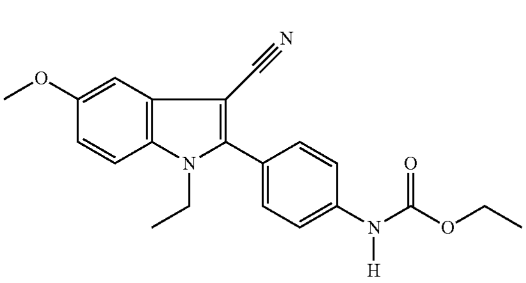

-continued
794
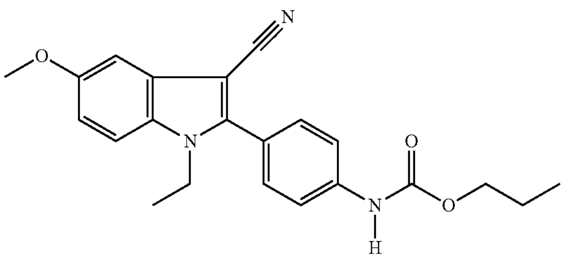
795
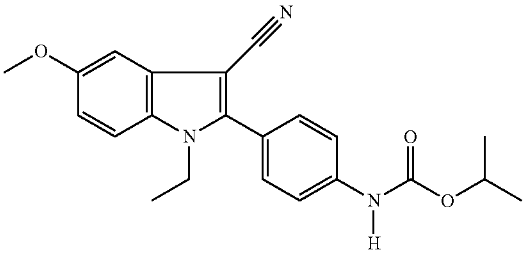
796
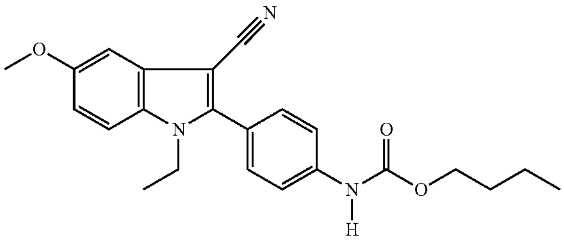
797
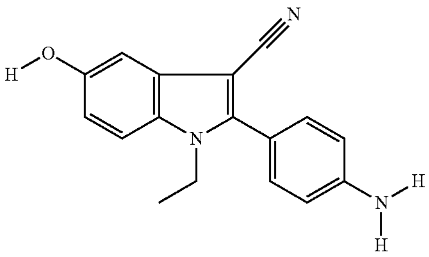
798
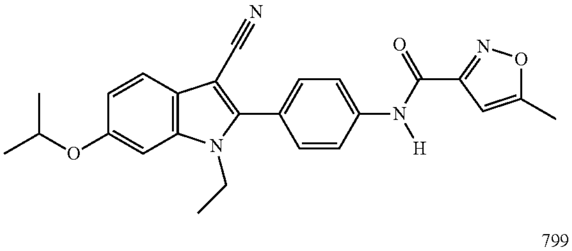
799
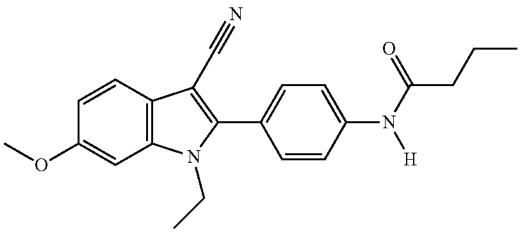
-continued
801
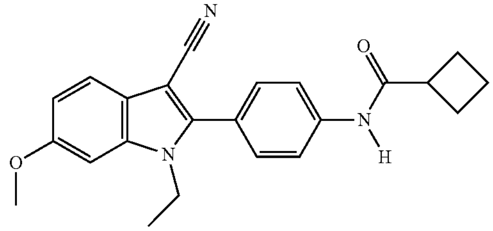
802
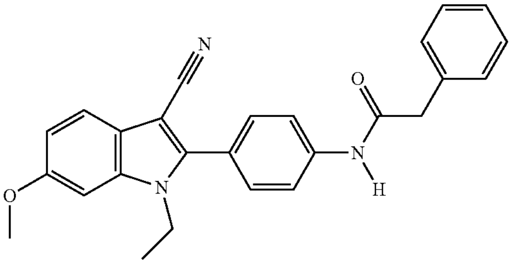
803
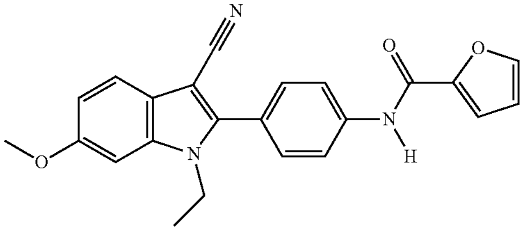
804
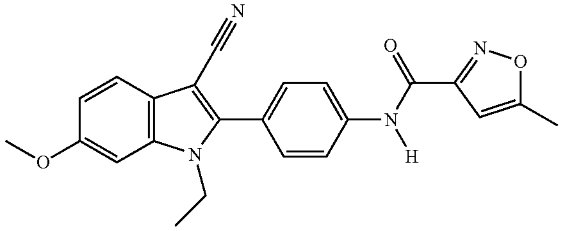
805
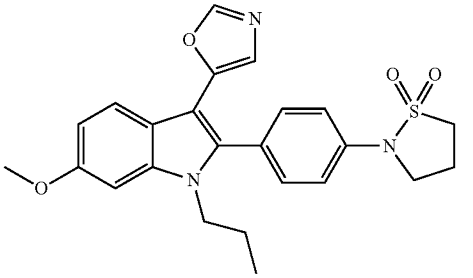
806
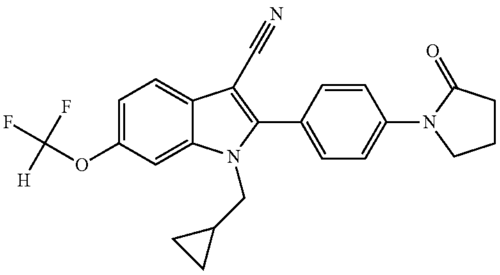

-continued
807
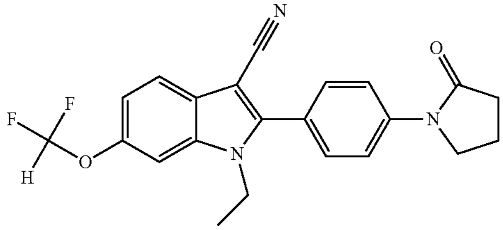
808
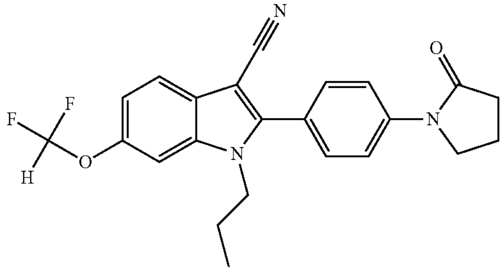
809
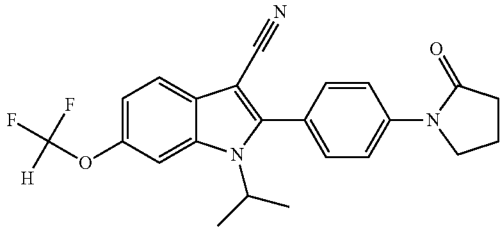
810
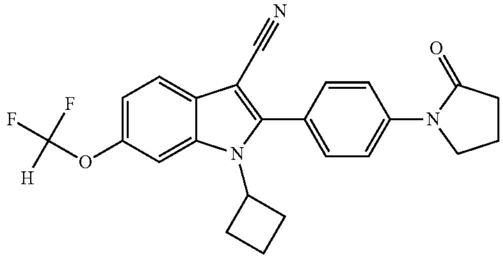
811
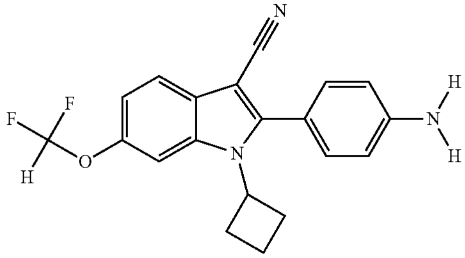
812
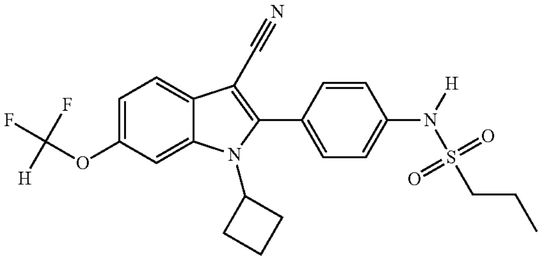
-continued
813
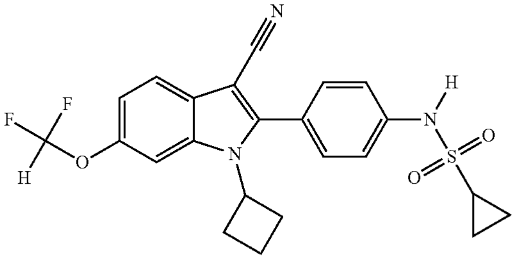
814
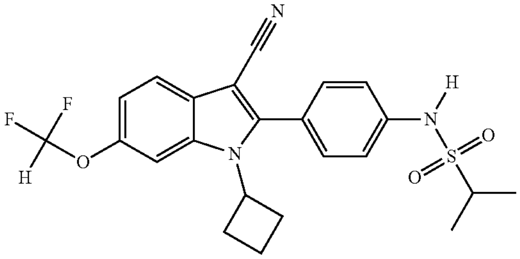
815
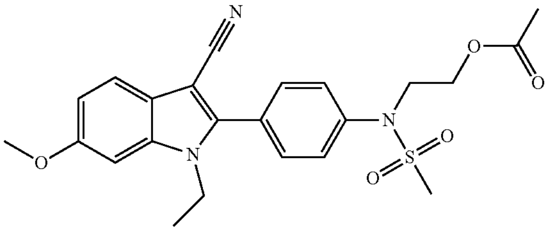
816
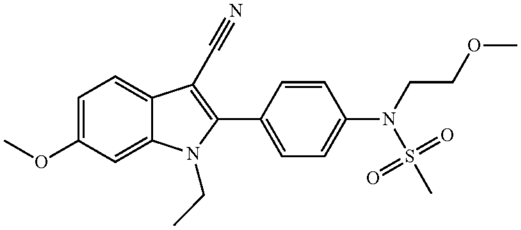
817
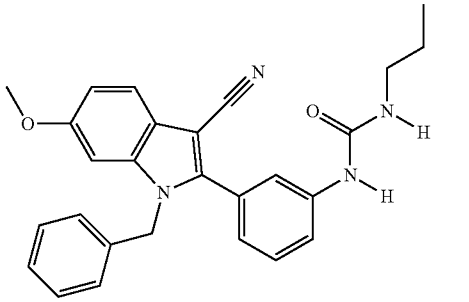

-continued
818
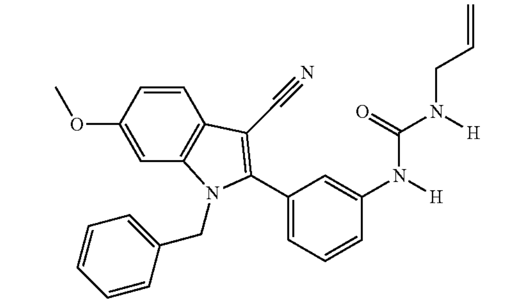
819
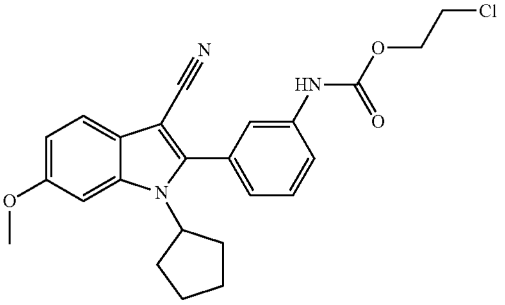
820
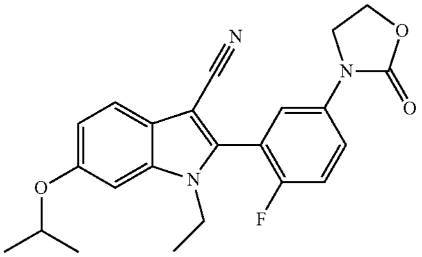
821
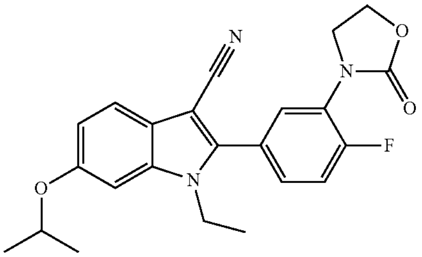
822
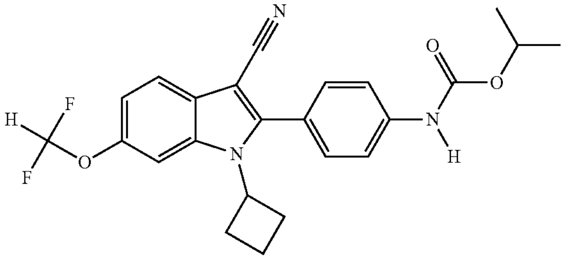
-continued
823
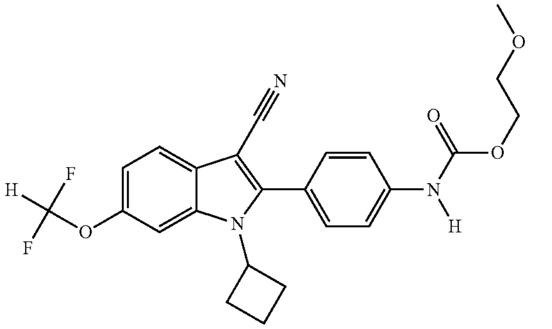
824
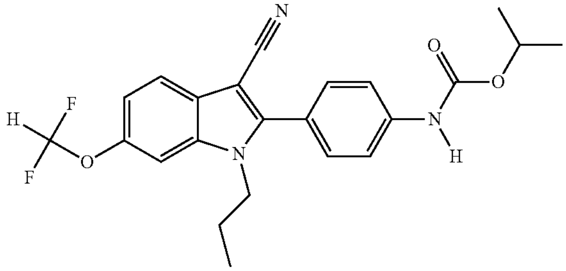
825
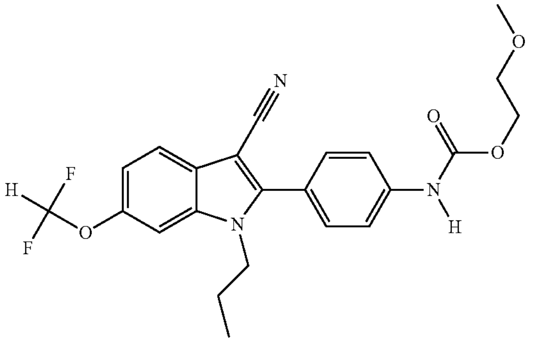
826
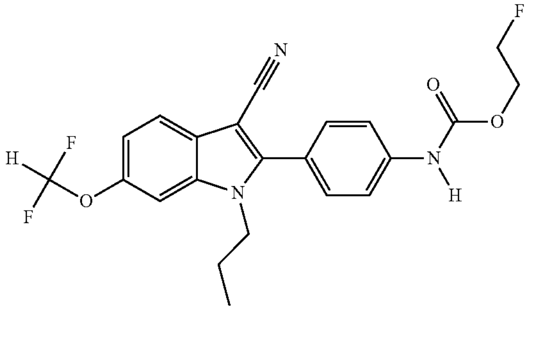

-continued
827
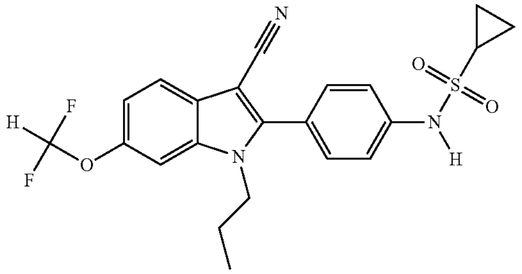
828
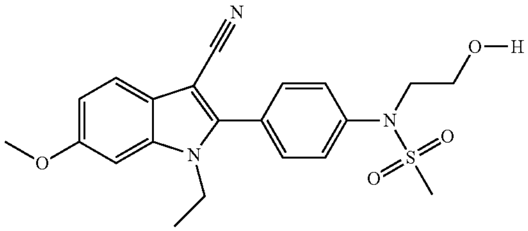
829
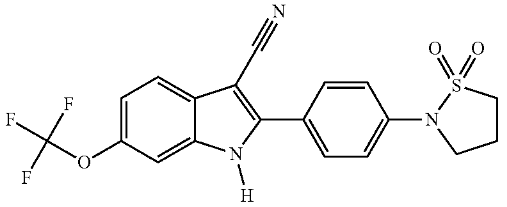
830
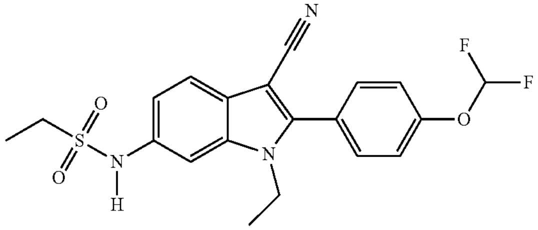
831
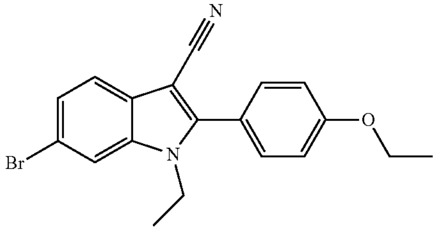
832
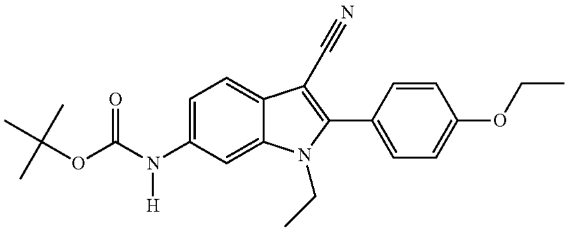
-continued
833
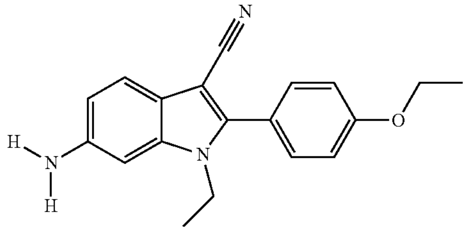
834
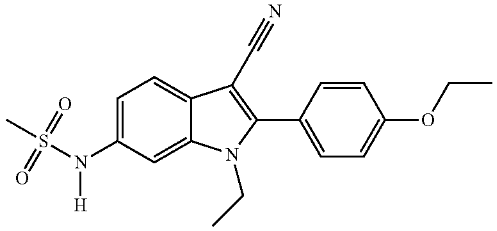
835
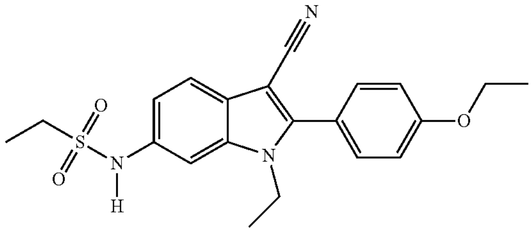
836
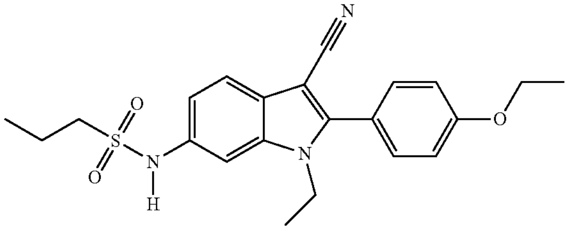
837
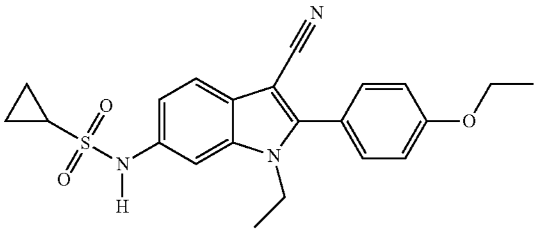
838
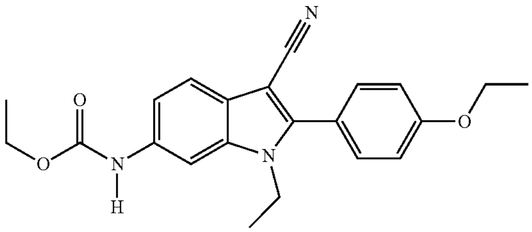

-continued
839
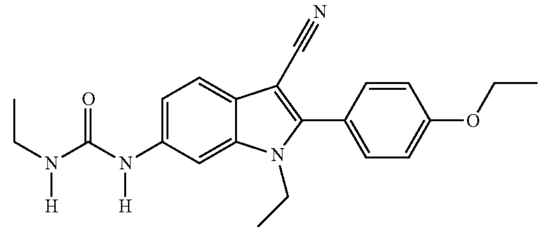
840
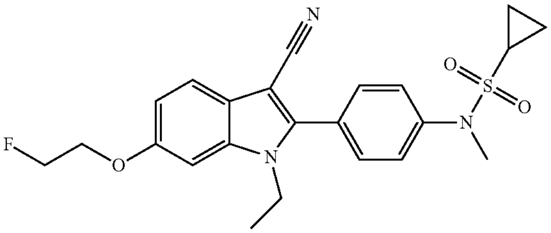
841
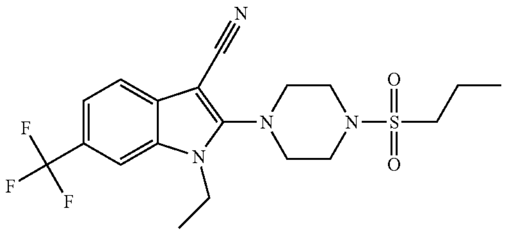
842
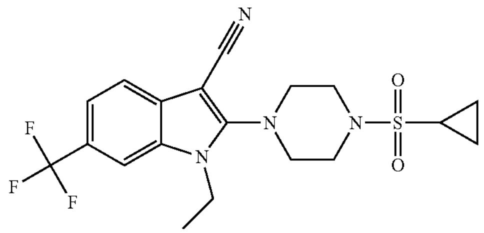
843
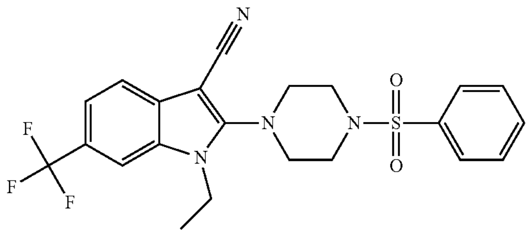
844
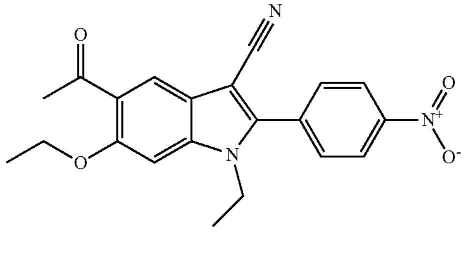
-continued
845
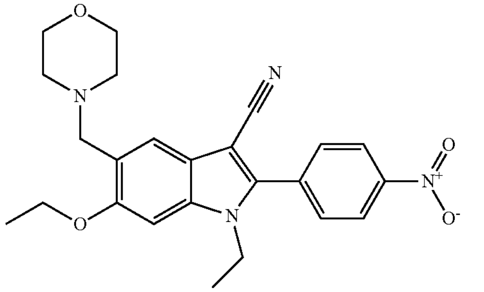
846
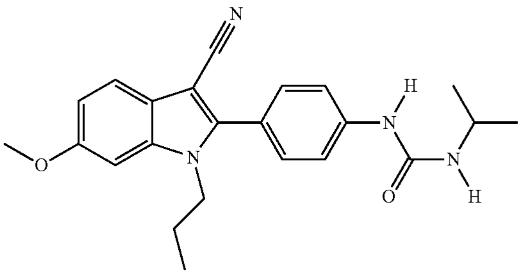
847
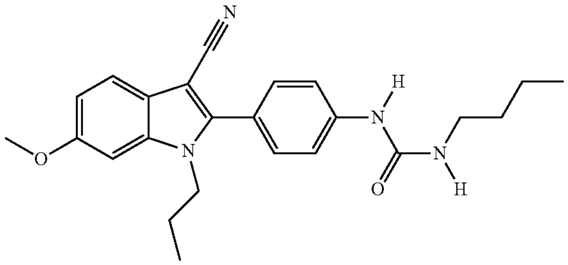
848
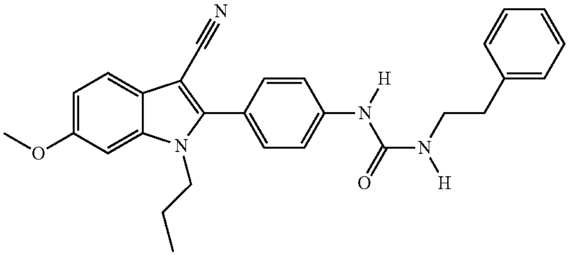
849
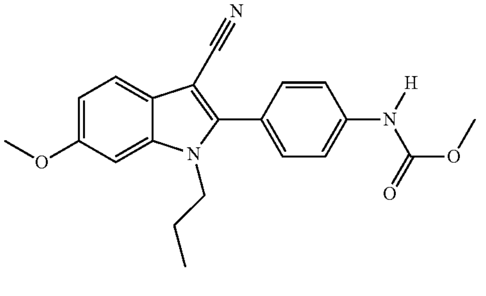

-continued
850
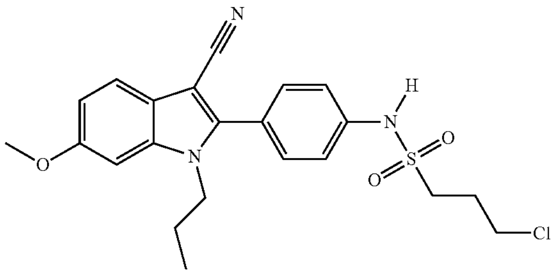
851
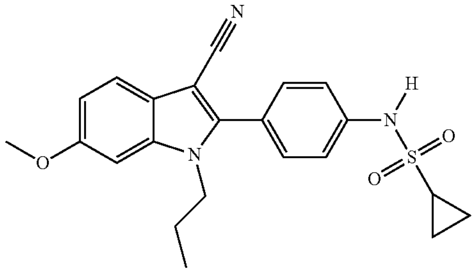
852
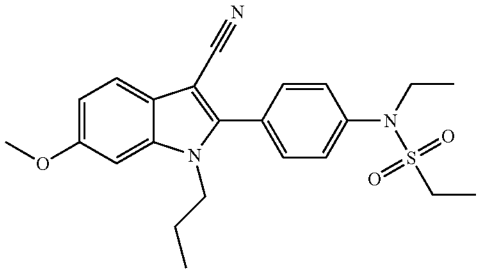
853
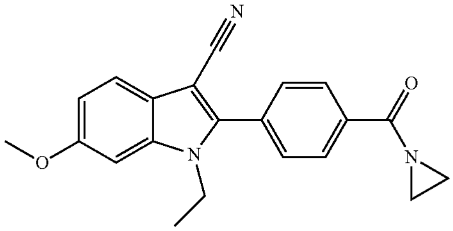
854
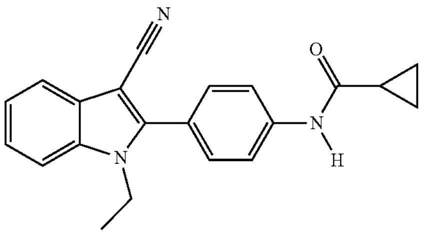
855
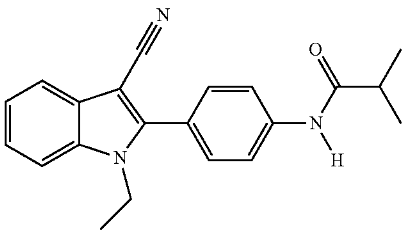
-continued
856
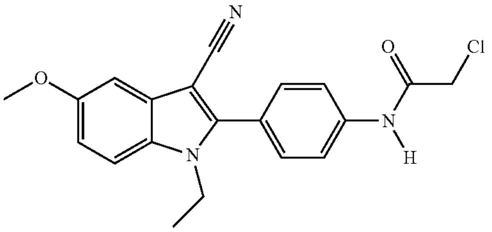
857
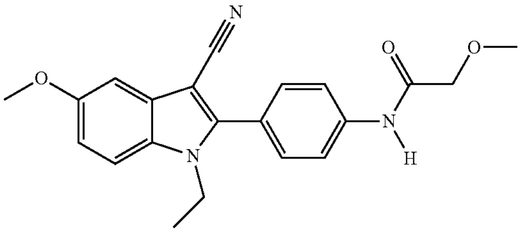
858
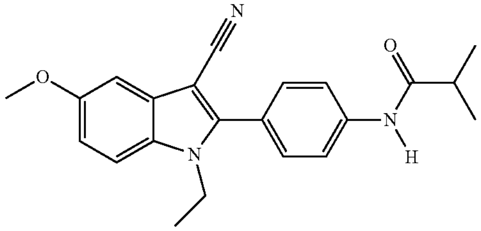
859
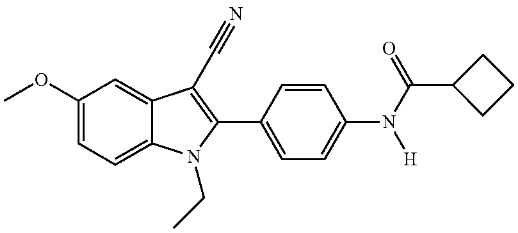
860
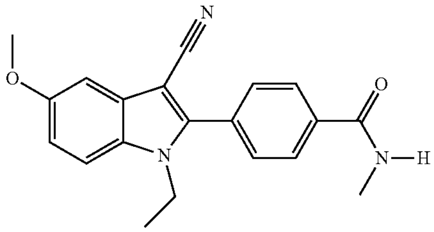
861
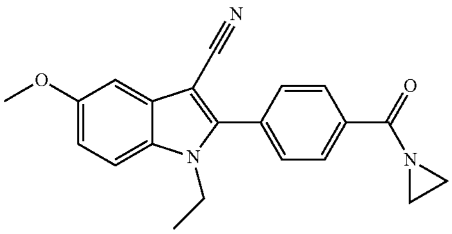

-continued

862

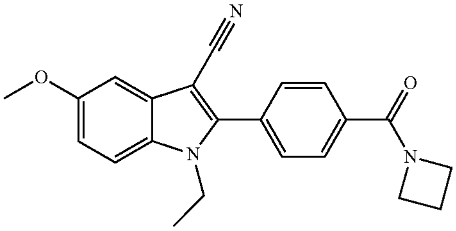

863

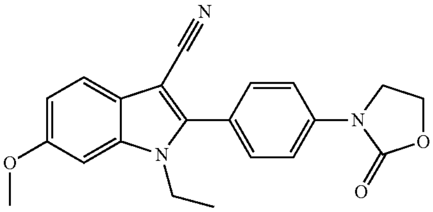

864

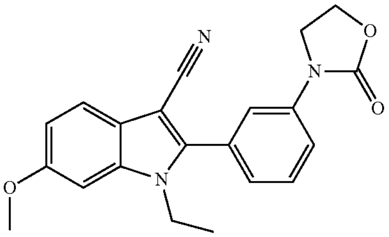

-continued

865

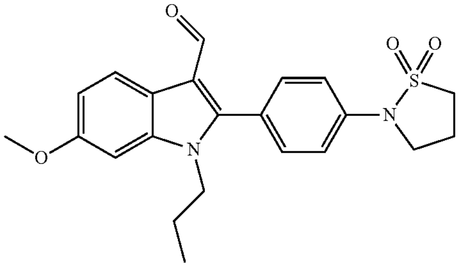

or an enantiomer, steroisomer, diastereomer, racemic, tautomeric, ester, solvate, hydrate, isotopologue or salt form thereof and an HCV protease inhibitor which is:

N-(tert-butoxycarbonyl)-3-methyl-L-valyl-(4R)-N-{(1S, 2R)-1-[(cyclopropylsulfonyl)carbamoyl]-2-ethenylcyclopropyl}-4-[(7-methoxy-2-phenylquinolin-4-yl)oxy]-L-prolinamide.

2. The product of claim 1, further comprising one or more different therapeutic agents selected from a HCV inhibitor, a HCV protease inhibitor, a nucleoside or non-nucleoside HCV polymerase inhibitor, a nonpegylated interferon, a pegylated interferon or another anti-HCV agent.

3. The product of claim 2, wherein the one or more different HCV protease inhibitor therapeutic agents is selected from a NS2 protease inhibitor, a NS3 protease inhibitor, a peptide or dipeptide NS3 protease inhibitor or a NS4a protease cofactor inhibitor.

4. The product of claim 2, wherein the effective amount of each of the HCV inhibitor and one or more therapeutic agents is in a range of from about 0.1 μg to about 4.5 g per day.

* * * * *

UNITED STATES PATENT AND TRADEMARK OFFICE

CERTIFICATE OF CORRECTION

PATENT NO. : 8,927,576 B2
APPLICATION NO. : 13/259627
DATED : January 6, 2015
INVENTOR(S) : Zhengxian Gu It is certified that error appears in the above-identified patent and that said Letters Patent is hereby corrected as shown below:

On the Title Page, item (74) Attorney, Agent, or Firm, replace "Hoffman & Baron, LLP" with --Hoffmann & Baron, LLP--.

In the Specification
Column 1, line 8, replace "filed Apr. 5, 2010" with --filed Apr. 6, 2010--.

Column 334, line 36, replace "both the and trans-forms" with --both the cis- and trans-forms--.

Signed and Sealed this
Sixth Day of October, 2015

Michelle K. Lee
*Director of the United States Patent and Trademark Office*